(12) United States Patent  
Iwase et al.

(10) Patent No.: US 10,894,798 B2  
(45) Date of Patent: Jan. 19, 2021

(54) SUBSTITUTED DIHYDROPYRROLOPYRAZOLE DERIVATIVE

(71) Applicant: UBE INDUSTRIES, LTD., Ube (JP)

(72) Inventors: Noriaki Iwase, Ube (JP); Yasuhiro Aga, Ube (JP); Shigeru Ushiyama, Ube (JP); Shigeyuki Kono, Ube (JP); Hidetoshi Sunamoto, Ube (JP); Takashi Matsushita, Ube (JP); Sayaka Ogi, Ube (JP); Satoshi Umezaki, Ube (JP); Masahiro Kojima, Ube (JP); Kazuhiro Onuma, Ube (JP); Yusuke Shiraishi, Ube (JP); Makoto Okudo, Ube (JP); Tomio Kimura, Tokyo (JP)

(73) Assignee: UBE INDUSTRIES, LTD., Yamaguchi (JP)

(*) Notice: Subject to any disclaimer, the term of this patent is extended or adjusted under 35 U.S.C. 154(b) by 0 days.

(21) Appl. No.: 16/373,840

(22) Filed: Apr. 3, 2019

(65) Prior Publication Data

US 2019/0256531 A1  Aug. 22, 2019

Related U.S. Application Data

(62) Division of application No. 15/736,677, filed as application No. PCT/JP2016/067703 on Jun. 14, 2016, now Pat. No. 10,273,252.

(30) Foreign Application Priority Data

Jun. 15, 2015 (JP) ................. 2015-120372  
Apr. 28, 2016 (JP) ................. 2016-091128

(51) Int. Cl.
| | |
|---|---|
| *C07F 7/08* | (2006.01) |
| *C07F 7/10* | (2006.01) |
| *C07F 7/12* | (2006.01) |
| *A61K 31/695* | (2006.01) |
| *A61P 35/00* | (2006.01) |
| *A61K 45/06* | (2006.01) |

(52) U.S. Cl.
CPC .......... *C07F 7/0812* (2013.01); *A61K 31/695* (2013.01); *A61K 45/06* (2013.01); *A61P 35/00* (2018.01); *C07F 7/10* (2013.01); *C07F 7/12* (2013.01)

(58) Field of Classification Search
CPC ............. C07F 7/0812; C07F 7/12; C07F 7/10  
See application file for complete search history.

(56) References Cited

FOREIGN PATENT DOCUMENTS

| | | | |
|---|---|---|---|
| EA | 200701257 | A1 | 12/2007 |
| EP | 3214086 | A1 | 9/2017 |
| JP | 2006-514026 | A | 4/2006 |
| JP | 2006-516266 | A | 6/2006 |
| JP | 2008-526826 | A | 7/2008 |
| JP | 2009-520805 | A | 5/2009 |
| JP | 2010-505905 | A | 2/2010 |
| JP | 2010-523643 | A | 7/2010 |
| JP | 2013-533854 | A | 8/2013 |
| WO | 02/12242 | A2 | 2/2002 |
| WO | 2004/056827 | A2 | 7/2004 |
| WO | 2004/062662 | A1 | 7/2004 |
| WO | 2004/080457 | A1 | 9/2004 |
| WO | 2005/005427 | A1 | 1/2005 |
| WO | 2006/072831 | A1 | 7/2006 |
| WO | 2007/068637 | A1 | 6/2007 |
| WO | 2007/072153 | A2 | 6/2007 |
| WO | 2007/099171 | A2 | 9/2007 |
| WO | 2008/043745 | A1 | 4/2008 |
| WO | 2008/125945 | A2 | 10/2008 |
| WO | 2008/151304 | A1 | 12/2008 |
| WO | 2011/044264 | A2 | 4/2011 |
| WO | 2011/151368 | A2 | 12/2011 |
| WO | 2013/128028 | A1 | 9/2013 |
| WO | 2013/128029 | A1 | 9/2013 |

(Continued)

OTHER PUBLICATIONS

Malumbres et al., "Cell cycle, CDKs and cancer: a changing paradigm", Nature, 2009, 9, p. 153-p. 166.

(Continued)

*Primary Examiner* — Amanda L. Aguirre  
(74) *Attorney, Agent, or Firm* — Oliff PLC

(57) ABSTRACT

The present invention provides a compound represented by the general formula (Ia) or a pharmacologically acceptable salt thereof. In the general formula (Ia), two R moieties each independently represent a $C_{1-3}$ alkyl group or the like; and $R^1$, $R^2$ and $R^3$ each independently represent an optionally substituted linear or branched $C_{1-4}$ alkyl group.

[Chemical Formula 1]

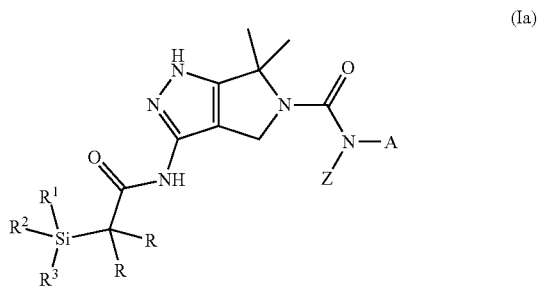

(Ia)

14 Claims, No Drawings

(56) References Cited

FOREIGN PATENT DOCUMENTS

| WO | 2014/063068 | A1 | | 4/2014 | |
|---|---|---|---|---|---|
| WO | 2015/058126 | A1 | | 4/2015 | |
| WO | 2015/058140 | A1 | | 4/2015 | |
| WO | 2015/058163 | A2 | | 4/2015 | |
| WO | 2015/124941 | A1 | | 8/2015 | |
| WO | 2015/154022 | A1 | | 10/2015 | |
| WO | 2015/154038 | A1 | | 10/2015 | |
| WO | 2015/154039 | A2 | | 10/2015 | |
| WO | 2016/068287 | A1 | | 5/2016 | |
| WO | WO-2016068287 | A1 | * | 5/2016 | ............... C07F 7/10 |
| WO | 2017-188357 | A1 | | 11/2017 | |
| WO | WO-2017188357 | A1 | * | 11/2017 | ........... A61K 31/519 |
| WO | WO-2017188358 | A1 | * | 11/2017 | ........... A61K 31/695 |
| WO | WO-2017188369 | A1 | * | 11/2017 | ........... A61K 31/695 |

OTHER PUBLICATIONS

Fisher, Robert P., "Secrets of a double agent: CDK7 in cell-cycle control and transcription", Journal of Cell Science, 2005, 118(22), p. 5171-p. 5180.

Svejstrup, Jesper Q., "The RNA polymerase II transcription cycle: cycling through chromatin", Biochim Biophys Acta, 2004, p. 64-p. 73.

Ali et al., "The development of a selective cyclin-dependent kinase inhibitor which demonstrates anti-tumor activity", Cancer Res, 2009, p. 1-16.

Guo et al., "Discovery of Pyrroloaminopyrazoles as Novel PAK Inhibitors", Journal of Medicinal Chemistry, 2012, p. 4728-p. 4739.

Brasca et al., "Optimization of 6,6-dimethyl pyrrolo[3,4-c]pyrazoles: Identification of PHA-793887, a potent CDK inhibitor suitable for intravenous dosing", Bioorganic & Medicinal Chemistry, 2010, p. 1844-p. 1853.

Brasca et al., "6-Substituted Pyrrolo[3,4-c]pyrazoles: An Improved Class of CDK2 Inhibitors", ChemMedChem, 2007, p. 841-p. 852.

Krystof et al., "Cyclin-Dependent Kinase Inhibitors as Anticancer Drugs", Current Drug Targets, 2010, p. 291-p. 302.

Farahi et al., "Effects of the cyclin-dependent kinase inhibitor R-roscovitine on eosinophil survival and clearance", Clinical & Experimental Allergy, 2011, p. 673-p. 687.

Inoshima et al., "Induction of CDK inhibitor p21 gene as a new therapeuticstrategy against pulmonary fibrosis", Am J Physiol Lung Cell Mol Physiol, 2004, p. L727-p. L733.

Jul. 6, 20416 International Search Report issued in International Application No. PCT/JP2016/067703.

Dec. 28, 2017 International Preliminary Report on Patentability issued in International Application No. PCT/JP2016/067703.

Jun. 27, 2018 Office Action issued in U.S. Appl. No. 15/736,677.

Kwiatkowski et al., "Targeting transcription regulation in cancer with a covalent CDK7 inhibitor," Nature, 511, Jul. 2014, pp. 616-620.

Fuente et al., "Pharmacological Cyclin-Dependent Kinase Inhibitors as HIV-1 Antiviral Therapeutics," Current HIV Research, 1(2), Apr. 2003, pp. 131-152.

Abdellatif et al., "A Ras-Dependent Pathway Regulates RNA Polymerase II Phosphorylation in Cardiac Myocytes: Implications for Cardiac Hypertrophy," Molecular and Cellular Biology, 18(11), Nov. 1998, pp. 6279-6736.

Miracco et al., "Cyclin D1, B and A expression and cell turnover in psoriatic skin lesions before and after cyclosporin treatment," British Journal of Dermatology, 14(5), Nov. 2000, pp. 950-956.

Yoshida et al., "CDK inhibitors suppress Th17 and promote iTreg differentiation, and ameliorate experimental autoimmune encephalomyelitis in mice," Biochemical and Biophysical Research Communications, 435(3), May 2013, pp. 378-384.

Zhu et al., "Neuronal CDK7 in hippocampus is related to aging and Alzheimer disease," Neurobiology of Aging, 21(6), Nov. 2000, pp. 807-813.

Farahi et al., "Effects of the cyclin-dependent kinase inhibitor R-roscovitine on eosinophil survival and clearance," clinical & Experimental Allergy, 41, Jan. 2011, pp. 673-687.

Leitch et al., "Cyclin-dependent kinases 7 and 9 specifically regulate neutrophil transcription and their inhibition drives apoptosis to promote resolution of inflammation," Cell Death and Differentiation, 19, Jun. 2012, pp. 1950-1961.

Wasilewska et al., "Interleukin-17 inhibitors. A new era in treatment of psoriasis and other skin diseases," Advances in Dermatology and Allergology, 33(4), Aug. 2016, pp. 247-252.

Cao et al., "Inhibit Globally, Act Locally: CDK7 Inhibitors in Cancer Therapy," Cancer Cell, 26, Aug. 2014, pp. 158-159.

Xia et al., "Selective inhibition of CDK7 ameliorates experimental arthritis in mice," Clinical and Experimental Medicine, 15(3), Aug. 2014, pp. 269-275.

Kapasi et al., "Inhibition of the Cyclin-Dependent Kinases at the Beginning of Human Cytomegalovirus Infection Specifically Alters the Levels and Localization of the RNA Polymerase II Carboxyl-Terminal Domain Kinases cdk9 and cdk7 at the Viral Transcriptosome," Journal of Virology, 82(1), Jan. 2008, pp. 394-407.

Pippin et al., "Direct in vivo Inhibition of the Nuclear Cell Cycle Cascade in Experimental Mesangial Proliferative Glomerulonephritis with Roscovitine, a Novel Cyclin-dependent Kinase Antagonist," The Journal of Clinical Investigation, 100(19), Nov. 1997, pp. 2512-2520.

Sano et al., "Activation and function of cyclin T-Cdk9 (positive transcription elongation factor-b) in cardiac muscle-cell hypertrophy," Nature Medicine, 8(11), Nov. 2002, pp. 1310-1317.

Rossi et al., "Cyclin-dependent kinase inhibitors enhance the resolution of inflammation by promoting inflammatory cell apoptosis," Nature Medicine, 12(9), Sep. 2006, pp. 1056-1064.

Steinman et al., "Antifibrotic Effects of Roscovitine in Normal and Scleroderma Fibroblasts," PLoS One, 7(11), Nov. 2012, e48560, 7 pages.

Sun et al., "Regulation of NF-kB in Autoimmunity," Trends in Immunology, 34(6), Jun. 2013, pp. 282-289.

Dec. 12, 2018 extended European Search Report issued in Application No. 168116275.

Jul. 19, 2016 International Search Report issued in International Patent Application No. PCT/JP2016/067703.

* cited by examiner

SUBSTITUTED DIHYDROPYRROLOPYRAZOLE DERIVATIVE

This is a Divisional of application Ser. No. 15/736,677 filed Dec. 14, 2017, which is a National Stage Application of PCT/JP2016/067703 filed Jun. 14, 2016. The entire disclosures of the prior applications are hereby incorporated by reference herein their entirety.

The present invention relates to a substituted dihydropyrrolopyrazole compound or a pharmacologically acceptable salt thereof which has excellent CDK7 inhibitory activity and is useful as a medicament (e.g., a medicament for the treatment or prevention of a cancer, an inflammatory disease, an allergic disease or a chronic respiratory disease).

TECHNICAL FIELD

Background Art

CDKs (cyclin-dependent kinases) are cell growth control factors that are involved in entry to DNA synthesis (S phase) of the cell cycle and a mitotic phase (M phase), etc., and many types of CDKs are known. Also, the activation of CDK is controlled in multiple stages through the phosphorylation or dephosphorylation of the threonine residue of active loop (T loop) in its three-dimensional structure. When the particular threonine residue of CDK is phosphorylated, it forms a complex with a particular cyclin and is activated. This complex, which is important for cell cycle control, includes CDK1, CDK2/cyclin A, CDK1/cyclins B1 to B3 and CDK2, CDK4, CDK5, CDK6/cyclin D1 to D3, and CDK2/cyclin E, which are respectively involved in the particular periods of the cell cycle. CDK7 forms a CDK-activating kinase (CAK) together with cyclin H and MAT1 in metazoans and participates in the phosphorylation of CDKs (e.g., CDK1, CDK2, CDK4, and CDK6) necessary for the progression of the cell cycle (see Non Patent Literature 1).

Cell overgrowth by the abnormal activation of CDKs is a common feature in many cancers, and it is known that this is associated with a loss of checkpoint functions involved in the cell cycle control of cancer cells (see Non Patent Literature 2). Also, CDKs are known to have functions other than cell cycle control, and CDK7 is known to promote the binding of RNA polymerase II (RNAPII) to DNA and elongation thereof to positively control the transcription through the phosphorylation of serine in the COOH-terminal domain of the RNAPII (see Non Patent Literature 3).

CDK7 inhibitors exhibit effects in cell growth tests of various cancer cells and cancer-bearing mouse models, and the inhibition is expected to be useful as anticancer agents (see Non Patent Literatures 4 and 5).

Furthermore, it has been reported that in collagen-induced rheumatism mouse models, amelioration of clinical scores or tissue damage, decrease in the levels of inflammation-induced cytokines such as IL-6, IL-1β, and IL-17, and anti-CII-IgG2α, and decrease in the proportion of Th17 cells are attained by inhibiting CDK7 (see Non Patent Literature 6).

The CDK7 inhibitors, which play an important role in the progression of the cell cycle, are further expected to also have effects on the suppression of infection by viruses such as HIV, EBV, and HCV, and cardiomegaly (see Non Patent Literatures 7 and 8). Examples of diseases for which the CDK7 inhibitors seem to be useful, in addition to those described above, include autoimmune diseases typified by psoriasis and multiple sclerosis; neurodegenerative diseases such as Alzheimer's disease, etc.; allergic diseases typified by atopic dermatitis; etc.; chronic respiratory diseases typified by chronic obstructive pulmonary disease (COPD), etc.; and fibrosis typified by idiopathic pulmonary fibrosis, etc. (see Non Patent Literatures 9 to 11 and Non Patent Literatures 16 to 18).

Although the development of many CDK inhibitors is currently underway, there are not many compounds having an excellent CDK7 inhibitory effect (see Non Patent Literature 15).

CITATION LIST

Patent Literature

Patent Literature 1: WO 2002/012242
Patent Literature 2: WO 2004/056827
Patent Literature 3: WO 2004/080457
Patent Literature 4: WO 2007/068637
Patent Literature 5: WO 2007/072153
Patent Literature 6: WO 2007/099171
Patent Literature 7: WO 2008/043745
Patent Literature 8: WO 2008/125945
Patent Literature 9: WO 2011/044264
Patent Literature 10: WO 2008/151304
Patent Literature 11: WO 2013/128028
Patent Literature 12: WO 2013/128029
Patent Literature 13: WO 2014/063068
Patent Literature 14: WO 2015/058126
Patent Literature 15: WO 2015/058140
Patent Literature 16: WO 2015/058163
Patent Literature 17: WO 2015/124941
Patent Literature 18: WO 2015/154022
Patent Literature 19: WO 2015/154038
Patent Literature 20: WO 2015/154039

Non Patent Literature

Non Patent Literature 1: Journal of Cell Science 2005, 118 (20), 5171-5180
Non Patent Literature 2: Nature Reviews Cancer 2009, 9, 153-166
Non Patent Literature 3: Biochim Biophys Acta 2004, 1677, 64-73
Non Patent Literature 4: Nature 2014, 511, 616-620
Non Patent Literature 5: Cancer Res 2009, 69, 6208-6215
Non Patent Literature 6: Clin. Exp. Med. 2015, 15, 269-275
Non Patent Literature 7: Curr HIV Res 2003, 1 (2), 131-152
Non Patent Literature 8: Mol Cell Biol 1998, 18 (11), 6729-6736
Non Patent Literature 9: Br J Dermatol 2000, 143 (5), 950-956
Non Patent Literature 10: Biochem Biophys Res Commun 2013, 435 (3), 378-384
Non Patent Literature 11: Neurobiol Aging 2000, 6, 807-813
Non Patent Literature 12: Journal of Medicinal Chemistry 2012, 55 (10), 4728-4739
Non Patent Literature 13: Bioorganic & Medicinal Chemistry 2010, 18 (5), 1844-1853
Non Patent Literature 14: Chem Med Chem 2007, 2, 841-852
Non Patent Literature 15: Current Drug Targets, 2010, 11, 291-302
Non Patent Literature 16: Clinical & Experimental Allergy, 2011, 41, 673-687

Non Patent Literature 17: Cell Death and Differentiation, 2012, 19, 1950-1961

Non Patent Literature 18: Am. J. Physiol. Lung Cell Mol, 2004, 286, 727-733

SUMMARY OF INVENTION

Technical Problem

The present inventors have conducted studies on novel substituted dihydropyrrolopyrazole compounds with the aim of developing excellent CDK7 inhibitors and completed the present invention by finding that a novel substituted dihydropyrrolopyrazole compound having a particular structure or a pharmacologically acceptable salt thereof has excellent CDK7 inhibitory activity and is useful as a medicament (e.g., a medicament for the treatment or prevention of cancers, inflammatory diseases, allergic diseases or chronic respiratory diseases).

Patent Literatures 1 to 9 and Non Patent Literatures 12 to 14 describe a compound having a 6,6-dimethyl-4,6-dihydropyrrolo[3,4-c]pyrazole skeleton, but do not disclose the compound according to the present invention or the pharmacologically acceptable salt thereof.

As compounds inhibiting CDK7, pyrazolopyrimidine derivatives are disclosed in Patent Literature 10, pyrazolotriazine derivatives are disclosed in Patent Literatures 11 and 12, phenyl derivatives are disclosed in Patent Literature 13 and Non Patent Literature 4, and heterocyclic compounds are disclosed in Patent Literatures 14 to 20; however, a compound having a 4,6-dihydropyrrolo[3,4-c]pyrazole skeleton is not disclosed.

Solution to Problem

The present invention provides a novel substituted dihydropyrrolopyrazole compound or a pharmacologically acceptable salt thereof which has excellent CDK7 inhibitory activity;
a pharmaceutical composition, preferably a pharmaceutical composition for the treatment or prevention of cancers, benign tumor, angiogenesis, inflammatory diseases (e.g., autoimmune diseases), infection by viruses (HIV, EBV, HCV, etc.), neurodegenerative diseases (e.g., Alzheimer's disease), allergic diseases (e.g., atopic dermatitis), chronic respiratory diseases (e.g., chronic obstructive pulmonary disease (COPD)), fibrosis (e.g., idiopathic pulmonary fibrosis), circulatory diseases such as cardiomegaly, or impotence, comprising the substituted dihydropyrrolopyrazole compound or the pharmacologically acceptable salt thereof as an active ingredient; use of the substituted dihydropyrrolopyrazole compound or the pharmacologically acceptable salt thereof for the production of a pharmaceutical composition for the treatment or prevention (preferably, treatment) of diseases (preferably, the diseases described above);
a method for treating or preventing (preferably, treating) diseases (preferably, the diseases described above) by administering a pharmaceutically effective amount of the substituted dihydropyrrolopyrazole compound or the pharmacologically acceptable salt thereof to a warm-blooded animal (preferably, a human); and a method for producing the substituted dihydropyrrolopyrazole compound or the pharmacologically acceptable salt thereof, or an intermediate thereof.

Examples of the cancers include urinary bladder cancer, breast cancer, large intestine cancer (e.g., colorectal cancer, for example, colon adenocarcinoma and colon adenoma), kidney cancer, epidermal cancer, liver cancer, lung cancer (e.g., adenocarcinoma, small-cell lung cancer, and non-small cell lung cancer), esophageal cancer, gallbladder cancer, ovary cancer, pancreatic cancer (e.g., exocrine pancreatic tumor), gastric cancer, cervical cancer, endometrial cancer, thyroid gland cancer, cancer of the nose, head and neck cancer, prostate cancer, skin cancer (e.g., squamous cell cancer), hematopoietic organ tumors of the lymphatic system (e.g., leukemia, acute lymphatic leukemia, chronic lymphatic leukemia, B cell lymphoma (e.g., diffuse large B cell lymphoma), T cell lymphoma, multiple myeloma, Hodgkin's lymphoma, non-Hodgkin's lymphoma, hairy cell lymphoma, and Burkitt's lymphoma), hematopoietic organ tumors of the myeloid system (e.g., acute or chronic myeloid leukemia, myelodysplastic syndrome, and promyelocytic leukemia), follicular carcinoma of thyroid, mesenchymal tumors (e.g., fibrosarcoma, Ewing's sarcoma, and rhabdomyosarcoma), tumors of the central or peripheral nervous system (e.g., astrocytoma, neuroblastoma, glioma, brain tumor, and schwannoma), melanoma, seminoma, teratoma, osteosarcoma, xeroderma pigmentosum, keratoacanthoma, follicular carcinoma of thyroid, and Kaposi's sarcoma.

Examples of the autoimmune diseases include multiple sclerosis, Guillain-Barre syndrome, myasthenia gravis, chronic atrophic gastritis, autoimmune hepatitis, primary biliary cirrhosis, ulcerative colitis, Crohn's disease, primary sclerosing cholangitis, autoimmune pancreatitis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Graves' disease, Hashimoto disease, primary hypothyroidism, idiopathic Addison's disease, type 1 diabetes mellitus, circumscribed scleroderma, epidermolysis bullosa acquisita, vitiligo vulgaris, autoimmune optic neuropathy, autoimmune inner ear disorder, idiopathic azoospermia, rheumatoid arthritis, systemic lupus erythematosus, drug-induced lupus erythematosus, Sjogren's syndrome, polymyositis, psoriasis, dermatomyositis, scleroderma, vasculitis syndrome, mixed connective-tissue disease, and inflammatory bowel disease. In this context, the inflammatory bowel disease (IBD) is a generic name for diseases that cause chronic inflammation or ulcer in the large intestinal or small intestinal mucosa, and examples thereof include Crohn disease and ulcerative colitis.

According to one aspect, the present invention provides the following [1] to [79]:

[1] A compound represented by the formula (Ia) or a pharmacologically acceptable salt thereof:

[Chemical Formula 1]

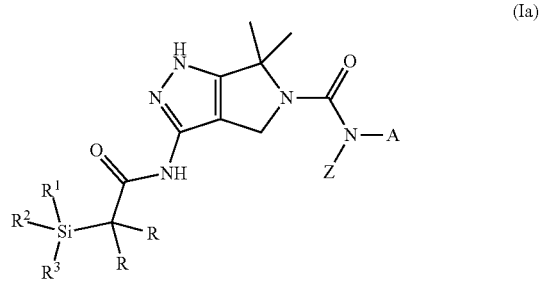

(Ia)

wherein
two R moieties each independently are a $C_{1-3}$ alkyl group or are groups bonded to each other to form a $C_{2-5}$ alkylene group;
A is an optionally substituted $C_{6-10}$ aryl group or an optionally substituted heteroaryl group, and Z is a hydrogen atom or an optionally substituted $C_{1-6}$ alkyl group, or a group represented by Z—N-A forms an optionally substituted bicyclic fused heterocyclic group through the bonding between A and Z; and
$R^1$, $R^2$ and $R^3$ each independently are an optionally substituted linear or branched $C_{1-4}$ alkyl group.

[2] A compound represented by the formula (I) or a pharmacologically acceptable salt thereof:

[Chemical Formula 2]

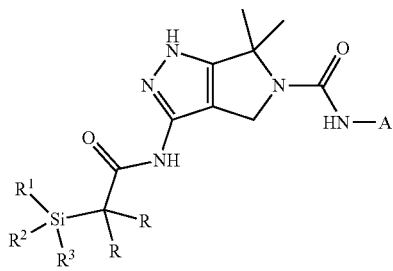

(I)

wherein
two R moieties each independently are a $C_{1-3}$ alkyl group or are groups bonded to each other to form a $C_{2-5}$ alkylene group;
A is an optionally substituted $C_{6-10}$ aryl group or an optionally substituted heteroaryl group; and
$R^1$, $R^2$ and $R^3$ each independently are an optionally substituted linear or branched $C_{1-4}$ alkyl group.

[3] A compound represented by the formula (IIa) or a pharmacologically acceptable salt thereof:

[Chemical Formula 3]

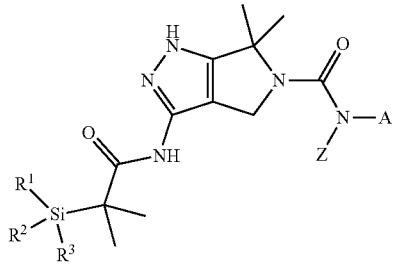

(IIa)

wherein
A is an optionally substituted $C_{6-10}$ aryl group or an optionally substituted heteroaryl group, and Z is a hydrogen atom or an optionally substituted $C_{1-6}$ alkyl group, or a group represented by Z—N-A forms an optionally substituted bicyclic fused heterocyclic group through the bonding between A and Z; and
$R^1$, $R^2$ and $R^3$ each independently are an optionally substituted linear or branched $C_{1-4}$ alkyl group.

[4] A compound represented by the formula (II) or a pharmacologically acceptable salt thereof:

[Chemical Formula 4]

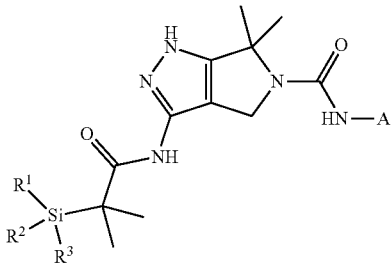

(II)

wherein
A is an optionally substituted $C_{6-10}$ aryl group or an optionally substituted heteroaryl group; and
$R^1$, $R^2$ and $R^3$ each independently are an optionally substituted linear or branched $C_{1-4}$ alkyl group.

[5] A compound represented by the formula (IIIa) or a pharmacologically acceptable salt thereof:

[Chemical Formula 5]

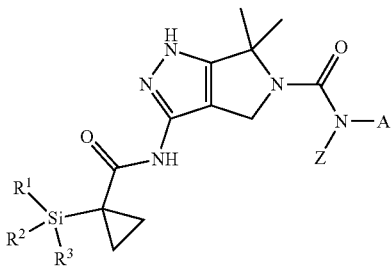

(IIIa)

wherein
A is an optionally substituted $C_{6-10}$ aryl group or an optionally substituted heteroaryl group, and Z is a hydrogen atom or an optionally substituted $C_{1-6}$ alkyl group, or a group represented by Z—N-A forms an optionally substituted bicyclic fused heterocyclic group through the bonding between A and Z; and
$R^1$, $R^2$ and $R^3$ each independently are an optionally substituted linear or branched $C_{1-4}$ alkyl group.

[6] A compound represented by the formula (III) or a pharmacologically acceptable salt thereof:

[Chemical Formula 6]

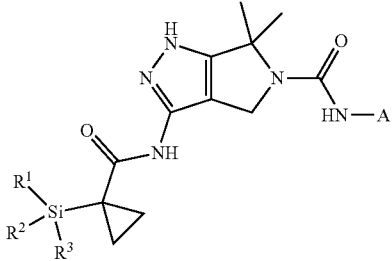

(III)

wherein
A is an optionally substituted $C_{6-10}$ aryl group or an optionally substituted heteroaryl group; and R¹, R² and R³ each independently are an optionally substituted linear or branched $C_{1-4}$ alkyl group.

[7] A compound represented by the formula (IVa) or a pharmacologically acceptable salt thereof:

[Chemical Formula 7]

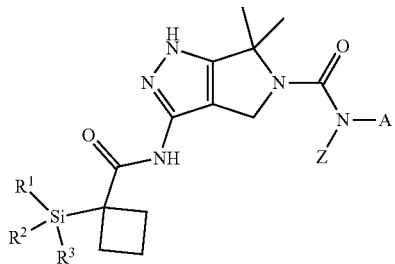

(IVa)

wherein

A is an optionally substituted $C_{6-10}$ aryl group or an optionally substituted heteroaryl group, and Z is a hydrogen atom or an optionally substituted $C_{1-6}$ alkyl group, or a group represented by Z—N-A forms an optionally substituted bicyclic fused heterocyclic group through the bonding between A and Z; and R¹, R² and R³ each independently are an optionally substituted linear or branched $C_{1-4}$ alkyl group.

[8] A compound represented by the formula (IV) or a pharmacologically acceptable salt thereof:

[Chemical Formula 8]

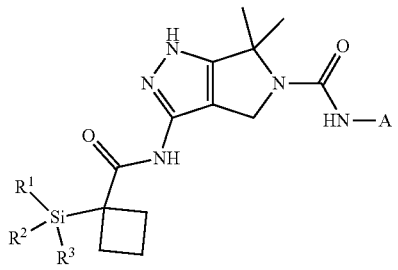

(IV)

wherein

A is an optionally substituted $C_{6-10}$ aryl group or an optionally substituted heteroaryl group; and R¹, R² and R³ each independently are an optionally substituted linear or branched $C_{1-4}$ alkyl group.

[9] A compound selected from the compound group consisting of 6,6-Dimethyl-N-phenyl-3-[1-(trimethylsilyl)cyclobutanecarboxamido]-4,6-dihydropyrrolo[3,4-c]pyrazole-5 (1H)-carboxamide, 6,6-Dimethyl-N-(p-tolyl)-3-[1-(trimethylsilyl)cyclobutanecarboxamido]-4,6-dihydro pyrrolo[3,4-c]pyrazole-5 (1H)-carboxamide, N-(4-methoxyphenyl)-6,6-dimethyl-3-[1-(trimethylsilyl)cyclobutanecarboxamido]-4,6-dihydropyrrolo[3,4-c]pyrazole-5(1H)-carboxamide, N-(4-fluorophenyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(pyridin-3-yl)-3-[1-(trimethylsilyl)cyclobutanecarboxamido]-4,6-di hydropyrrolo[3,4-c]pyrazole-5 (1H)-carboxamide, N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(o-tolyl)-3-[1-(trimethylsilyl)cyclobutanecarboxamido]-4,6-dihydro pyrrolo[3,4-c]pyrazole-5 (1H)-carboxamide, 6,6-Dimethyl-N-(m-tolyl)-3-[1-(trimethylsilyl)cyclobutanecarboxamido]-4,6-dihydropyrrolo[3,4-c]pyrazole-5 (1H)-carboxamide, N-([1,1'-biphenyl]-3-yl)-6,6-dimethyl-3-[1-(trimethylsilyl)cyclobutanecarboxamido]-4,6-dihydropyrrolo[3,4-c]pyrazole-5(1H)-carboxamide, N-(3-fluorophenyl)-6,6-dimethyl-3-[1-(trimethylsilyl)cyclobutanecarboxamido]-4,6-dihydropyrrolo[3,4-c]pyrazole-5(1H)-carboxamide, N-(3-chlorophenyl)-6,6-dimethyl-3-[1-(trimethylsilyl)cyclobutanecarboxamido]-4,6-dihydropyrrolo[3,4-c]pyrazole-5(1H)-carboxamide, N-(2-methoxyphenyl)-6,6-dimethyl-3-[1-(trimethylsilyl)cyclobutanecarboxamido]-4,6-dihydropyrrolo[3,4-c]pyrazole-5(1H)-carboxamide, N-(2-chlorophenyl)-6,6-dimethyl-3-[1-(trimethylsilyl)cyclobutanecarboxamido]-4,6-dihydropyrrolo[3,4-c]pyrazole-5(1H)-carboxamide, N-([1,1'-biphenyl]-2-yl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(pyridin-2-yl)-3-[1-(trimethylsilyl)cyclobutanecarboxamido]-4,6-di hydropyrrolo[3,4-c]pyrazole-5 (1H)-carboxamide, N-(2-ethylphenyl)-6,6-dimethyl-3-[1-(trimethylsilyl)cyclobutanecarboxamido]-4,6-dihydropyrrolo[3,4-c]pyrazole-5(1H)-carboxamide, N-(2,6-dimethylphenyl)-6,6-dimethyl-3-[1-(trimethylsilyl)cyclobutanecarboxamido]-4,6-dihydropyrrolo[3,4-c]pyrazole-5(1H)-carboxamide, N-(2,3-difluorophenyl)-6,6-dimethyl-3-[1-(trimethylsilyl)cyclobutanecarboxamido]-4,6-dihydropyrrolo[3,4-c]pyrazole-5(1H)-carboxamide, N-(2,3-dimethylphenyl)-6,6-dimethyl-3-[1-(trimethylsilyl)cyclobutanecarboxamido]-4,6-dihydropyrrolo[3,4-c]pyrazole-5(1H)-carboxamide, N-(2-fluoro-6-methylphenyl)-6,6-dimethyl-3-[1-(trimethylsilyl)cyclobutanecarboxamido]-4,6-dihydropyrrolo[3,4-c]pyrazole-5(1H)-carboxamide, N-[2-(difluoromethoxy)phenyl]-6,6-dimethyl-3-[1-(trimethylsilyl)cyclobutanecarboxamido]-4,6-dihydropyrrolo[3,4-c]pyrazole-5(1H)-carboxamide, N-(2-ethoxyphenyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-[2-(trifluoromethoxy)phenyl]-3-[1-(trimethylsilyl)cyclobutanecarboxamido]-4,6-dihydropyrrolo[3,4-c]pyrazole-5(1H)-carboxamide, N-(2-fluoro-4-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2,6-difluorophenyl)-6,6-dimethyl-3-[1-(trimethylsilyl)cyclobutanecarboxamido]-4,6-dihydropyrrolo[3,4-c]pyrazole-5(1H)-carboxamide, N-[2-(tert-butyl)phenyl]-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-[2-(trifluoromethyl)phenyl]-3-[1-(trimethylsilyl)cyclobutanecarboxamido]-4,6-dihydropyrrolo[3,4-c]pyrazole-5(1H)-carboxamide, N-(3-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-cyanophenyl)-6,6-dimethyl-3-[1-(trimethylsilyl)cyclobutanecarboxamido]-4,6-dihydropyrrolo[3,4-c]pyrazole-5(1H)-carboxamide, N-(4-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-fluoro-5-methylphenyl)-6,6-dimethyl-3-[1-(trimethylsilyl)cyclobutanecarboxamido]-4,6-dihydropyrrolo[3,4-c]pyrazole-5(1H)-carboxamide, N-(5-fluoro-2-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2,4-difluorophenyl)-6,6-dimethyl-3-[1-(trimethylsilyl)cyclobutanecarboxamido]-4,6-dihydropyrrolo[3,4-c]pyrazole-5(1H)-carboxamide, N-(2,5-difluorophenyl)-6,6-dimethyl-3-[1-(trimethylsilyl)cyclobutanecarboxamido]-4,6-dihydropyrrolo[3,4-c]pyrazole-5(1H)-carboxamide, N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide, N-(2-chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide, N-(2,4-dimethylphenyl)-6,6-dimethyl-3-[1-(trimethylsilyl)cyclobutanecarboxamido]-4,6-dihydropyrrolo[3,4-c]pyrazole-5(1H)-carboxamide, 3-[1-(Ethyldimethylsilyl)cyclobutanecarboxamido]-N-(2-fluorophenyl)-6,6-dimethyl-4,6-dihydropyrrolo[3,4-c]pyrazole-5(1H)-carboxamide, 6,6-Dimethyl-N-(3-methylisothiazol-4-yl)-3-[1-(trimethylsilyl)cyclobutanecarboxamido]-4,6-dihydropyrrolo[3,4-c]pyrazole-5(1H)-carboxamide, 6,6-Dimethyl-N-(thiophen-2-yl)-3-[1-(trimethylsilyl)cyclobutanecarboxamido]-2,6-dihydropyrrolo[3,4-c]pyrazole-5(1H)-carboxamide, 6,6-Dimethyl-N-(thiophen-3-yl)-3-[1-(trimethylsilyl)cyclobutanecarboxamido]-2,6-dihydropyrrolo[3,4-c]pyrazole-5(1H)-carboxamide, N-(2,6-difluoro-4-methoxyphenyl)-6,6-dimethyl-3-[1-(trimethylsilyl)cyclobutanecarboxamido]-4,6-dihydropyrrolo[3,4-c]pyrazole-5(1H)-carboxamide, N-(2-fluoro-6-methoxyphenyl)-6,6-dimethyl-3-[1-(trimethylsilyl)cyclobutanecarboxamido]-4,6-dihydropyrrolo[3,4-c]pyrazole-5(1H)-carboxamide, N-[2-fluoro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide, N-(5-chloro-2-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2,5-dichlorophenyl)-6,6-dimethyl-3-[1-(trimethylsilyl)cyclobutanecarboxamido]-4,6-dihydropyrrolo[3,4-c]pyrazole-5(1H)-carboxamide, N-(2-cyclopropylphenyl)-6,6-dimethyl-3-[1-(trimethylsilyl)cyclobutanecarboxamido]-4,6-dihydropyrrolo[3,4-c]pyrazole-5(1H)-carboxamide, N-(2,6-dichlorophenyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(2,4,6-trifluorophenyl)-3-[1-(trimethylsilyl)cyclobutanecarboxamido]-4,6-dihydropyrrolo[3,4-c]pyrazole-5(1H)-carboxamide, N-(2-ethyl-6-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-bromophenyl)-6,6-dimethyl-3-[1-(trimethylsilyl)cyclobutanecarboxamido]-4,6-dihydropyrrolo[3,4-c]pyrazole-5(1H)-carboxamide, N-(2-chloro-5-fluorophenyl)-6,6-dimethyl-3-[1-(trimethylsilyl)cyclobutanecarboxamido]-4,6-dihydropyrrolo[3,4-c]pyrazole-5(1H)-carboxamide, N-(5-chloro-2-fluorophenyl)-6,6-dimethyl-3-[1-(trimethylsilyl)cyclobutanecarboxamido]-4,6-dihydropyrrolo[3,4-c]pyrazole-5(1H)-carboxamide, 6,6-Dimethyl-N-(2,3,6-trifluorophenyl)-3-[1-(trimethylsilyl)cyclobutanecarboxamido]-4,6-dihydropyrrolo[3,4-c]pyrazole-5(1H)-carboxamide, N-(2-chloro-6-methoxyphenyl)-6,6-dimethyl-3-[1-(trimethylsilyl)cyclobutanecarboxamido]-4,6-dihydropyrrolo[3,4-c]pyrazole-5(1H)-carboxamide, N-[2-(1,1-difluoroethyl)phenyl]-6,6-dimethyl-3-[1-(trimethylsilyl)cyclobutanecarboxamido]-4,6-dihydropyrrolo[3,4-c]pyrazole-5(1H)-carboxamide, N-(6-chloro-2-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-fluoro-6-(methoxy-d3)phenyl)-6,6-dimethyl-3-[1-(trimethylsilyl)cyclobutanecarboxamido]-4,6-dihydropyrrolo[3,4-c]pyrazole-5(1H)-carboxamide, N-[2-chloro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide, N-(2-fluoro-6-methoxy-3-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2,6-difluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide, N-[2-(difluoromethoxy)-6-fluorophenyl]-6,6-dimethyl-3-[1-(trimethylsilyl)cyclobutanecarboxamido]-4,6-dihydropyrrolo[3,4-c]pyrazole-5(1H)-carboxamide, N-(2-bromo-6-chlorophenyl)-6,6-dimethyl-3-[1-(trimethylsilyl)cyclobutanecarboxamido]-4,6-dihydropyrrolo[3,4-c]pyrazole-5(1H)-carboxamide, N-(2-chloro-6-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-ethyl-6-fluorophenyl)-6,6-dimethyl-3-[1-(trimethylsilyl)cyclobutanecarboxamido]-4,6-dihydropyrrolo[3,4-c]pyrazole-5 (1H)-carboxamide, N-(2-bromo-6-fluorophenyl)-6,6-dimethyl-3-[1-(trimethylsilyl)cyclobutanecarboxamido]-4,6-dihydropyrrolo[3,4-c]pyrazole-5(1H)-carboxamide, N-(2-bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide, N-(2-chloro-5-methylphenyl)-6,6-dimethyl-3-[1-(trimethylsilyl)cyclobutanecarboxamido]-4,6-dihydropyrrolo[3,4-c]pyrazole-5(1H)-carboxamide, N-(6-fluoro-2,3-dihydrobenzofuran-7-yl)-6,6-dimethyl-3-[1-(trimethylsilyl)cyclobutanecarboxamido]-4,6-dihydropyrrolo[3,4-c]pyrazole-5(1H)-carboxamide,
N-(2-cyano-6-fluorophenyl)-6,6-dimethyl-3-[1-(trimethylsilyl)cyclobutanecarboxamido]-4,6-dihydropyrrolo[3,4-c]pyrazole-5(1H)-carboxamide,
N-(2-chloro-6-cyclopropylphenyl)-6,6-dimethyl-3-[1-(trimethylsilyl)cyclobutanecarboxamido]-4,6-dihydropyrrolo[3,4-c]pyrazole-5(1H)-carboxamide,
N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide,
N-(6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide,
N-(2-chloro-3-fluoro-6-methylphenyl)-6,6-dimethyl-3-[1-(trimethylsilyl)cyclobutanecarboxamido]-4,6-dihydropyrrolo[3,4-c]pyrazole-5(1H)-carboxamide,
N-[2-(difluoromethoxy)-6-fluorophenyl]-6,6-dimethyl-3-[1-(trimethylsilyl)cyclopropanecarboxamido]-4,6-dihydropyrrolo[3,4-c]pyrazole-5(1H)-carboxamide,
N-(2,6-dichlorophenyl)-6,6-dimethyl-3-[1-(trimethylsilyl)cyclopropanecarboxamido]-4,6-dihydropyrrolo[3,4-c]pyrazole-5(1H)-carboxamide,
N-(2,6-dichlorophenyl)-6,6-dimethyl-3-[2-methyl-2-(trimethylsilyl)propaneamido]-4,6-dihydropyrrolo[3,4-c]pyrazole-5(1H)-carboxamide,
N-[2-(difluoromethoxy)-6-fluorophenyl]-6,6-dimethyl-3-[2-methyl-2-(trimethylsilyl)propaneamido]-4,6-dihydropyrrolo[3,4-c]pyrazole-5(1H)-carboxamide,
N-(2,6-dichloro-4-fluorophenyl)-6,6-dimethyl-3-[1-(trimethyl silyl)cyclobutanecarboxamido]-4,6-dihydropyrrolo[3,4-c]pyrazole-5(1H)-carboxamide,
N-(2-ethyl-6-fluorophenyl)-6,6-dimethyl-3-[1-(trimethylsilyl)cyclopropanecarboxamido]-4,6-dihydropyrrolo[3,4-c]pyrazole-5(1H)-carboxamide,
N-(2-bromo-6-methylphenyl)-6,6-dimethyl-3-[1-(trimethylsilyl)cyclopropanecarboxamido]-4,6-dihydropyrrolo[3,4-c]pyrazole-5(1H)-carboxamide,
N-(2-chloro-5-methoxyphenyl)-6,6-dimethyl-3-[1-(trimethylsilyl)cyclobutanecarboxamido]-4,6-dihydropyrrolo[3,4-c]pyrazole-5(1H)-carboxamide,
N-(2-ethyl-6-fluorophenyl)-6,6-dimethyl-3-[2-methyl-2-(trimethylsilyl)propaneamido]-4,6-dihydropyrrolo[3,4-c]pyrazole-5(1H)-carboxamide,
N-(2-bromo-6-methylphenyl)-6,6-dimethyl-3-[2-methyl-2-(trimethylsilyl)propaneamido]-4,6-dihydropyrrolo[3,4-c]pyrazole-5(1H)-carboxamide,
N-(6-fluorobenzofuran-7-yl)-6,6-dimethyl-3-[2-methyl-2-(trimethylsilyl)propaneamido]-4,6-dihydropyrrolo[3,4-c]pyrazole-5(1H)-carboxamide,
N-(6-fluorobenzofuran-7-yl)-6,6-dimethyl-3-[1-(trimethylsilyl)cyclopropanecarboxamido]-4,6-dihydropyrrolo[3,4-c]pyrazole-5(1H)-carboxamide,
N,6,6-trimethyl-N-phenyl-3-[1-(trimethylsilyl)cyclobutanecarboxamido]-4,6-dihydropyrrolo[3,4-c]pyrazole-5(1H)-carboxamide,
N-(6-fluoro-3-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide,
N-(2-chloro-6-fluorobenzofuran-7-yl)-6,6-dimethyl-3-[1-(trimethylsilyl)cyclobutane carboxamido]-4,6-dihydropyrrolo[3,4-c]pyrazole-5(1H)-carboxamide,
N-[5-(indoline-1-carbonyl)-6,6-dimethyl-1,4,5,6-tetrahydropyrrolo[3,4-c]pyrazol-3-yl]-1-(trimethylsilyl)cyclobutanecarboxamide,
N-[5-(3,4-dihydro-2H-benzo[b][1,4]oxazine-4-carbonyl)-6,6-dimethyl-1,4,5,6-tetrahydropyrrolo[3,4-c]pyrazol-3-yl]-1-(trimethylsilyl)cyclobutanecarboxamide,
N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide, and
N-[5-(1H-indole-1-carbonyl)-6,6-dimethyl-1,4,5,6-tetrahydropyrrolo[3,4-c]pyrazol-3-yl]-1-(trimethylsilyl)cyclobutanecarboxamide or a pharmacologically acceptable salt thereof.

[10]
N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[11]
6,6-Dimethyl-N-(o-tolyl)-3-[1-(trimethylsilyl)cyclobutanecarboxamido]-4,6-dihydropyrrolo[3,4-c]pyrazole-5(1H)-carboxamide or a pharmacologically acceptable salt thereof.

[12]
N-(2-chloro-6-methylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[13]
N-(5-fluoro-2-methylphenyl)-6,6-dimethyl-3-[1-(trimethylsilyl)cyclobutane carboxamido]-4,6-dihydropyrrolo[3,4-c]pyrazole-5(1H)-carboxamide or a pharmacologically acceptable salt thereof.

[14]
N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[15]
N-(2-chloro-6-fluorophenyl)-6,6-dimethyl-3-[1-(trimethylsilyl)cyclobutane carboxamido]-4,6-dihydropyrrolo[3,4-c]pyrazole-5(1H)-carboxamide or a pharmacologically acceptable salt thereof.

[16]
N-(2-bromo-6-methylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[17]
N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[18]
N-(6-fluorobenzofuran-7-yl)-6,6-dimethyl-3-[1-(trimethylsilyl)cyclobutane carboxamido]-4,6-dihydropyrrolo[3,4-c]pyrazole-5(1H)-carboxamide or a pharmacologically acceptable salt thereof.

[19]
N-(2-chloro-6-fluorobenzofuran-7-yl)-6,6-dimethyl-3-[1-(trimethyl silyl)cyclobutanecarboxamido]-4,6-dihydropyrrolo[3,4-c]pyrazole-5(1H)-carboxamide or a pharmacologically acceptable salt thereof.

[20]
N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide or a pharmacologically acceptable salt thereof.

[21] A pharmaceutical composition comprising a compound or a pharmacologically acceptable salt thereof according to any of [1] to [20].

[22] The pharmaceutical composition according to [21], wherein the pharmaceutical composition is a CDK7 inhibitor.

[23] The pharmaceutical composition according to [21] or [22], wherein the pharmaceutical composition is for the treatment or prevention of a cancer, an inflammatory disease, an allergic disease or a chronic respiratory disease.

[24] The pharmaceutical composition according to [23], wherein the cancer is a blood cancer or a solid cancer.

[25] The pharmaceutical composition according to [24], wherein the blood cancer is multiple myeloma, chronic myelogenous leukemia, blood tumor, hematological malignancy, childhood leukemia, childhood lymphoma, Hodgkin's disease, lymphocytic lymphoma, cutaneous lymphoma, acute leukemia, chronic leukemia, acute lymphoblastic leukemia, acute myeloid leukemia, chronic myelogenous leukemia, plasma cell neoplasm, lymphoid neoplasm or AIDS-related cancer.

[26] The pharmaceutical composition according to [24], wherein the solid cancer is bladder cancer, breast cancer, colon cancer, kidney cancer, liver cancer, lung cancer, small-cell lung cancer, non-small cell lung cancer, head and neck cancer, esophageal cancer, gallbladder cancer, ovarian cancer, pancreatic cancer, stomach cancer, uterine cervical cancer, thyroid cancer, prostate cancer, skin cancer including squamous cell carcinoma, fibrosarcoma, rhabdomyosarcoma, astrocytoma, neuroblastoma, glioma and neurilemmoma, melanoma, seminoma, teratocarcinoma, osteosarcoma, xeroderma pigmentosum, keratoacanthoma, follicular thyroid cancer or Kaposi's sarcoma.

[27] The pharmaceutical composition according to [23], wherein the inflammatory disease is an autoimmune disease.

[28] The pharmaceutical composition according to [27], wherein the autoimmune disease is rheumatoid arthritis.

[29] The pharmaceutical composition according to [27], wherein the autoimmune disease is psoriasis.

[30] The pharmaceutical composition according to [27], wherein the autoimmune disease is multiple sclerosis.

[31] The pharmaceutical composition according to [27], wherein the autoimmune disease is inflammatory bowel disease.

[32] The pharmaceutical composition according to [23], wherein the chronic respiratory disease is chronic obstructive pulmonary disease.

[33] The pharmaceutical composition according to [23], wherein the allergic disease is atopic dermatitis.

[34]. The pharmaceutical composition according to any of [21] to [33], wherein the pharmaceutical composition is administered in combination with one or more additional drug(s) selected from the group consisting of anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease and drugs for the treatment of atopic dermatitis.

[35] The pharmaceutical composition according to any of [21] to [33], wherein the pharmaceutical composition is administered at the same time with or at a different time from a composition comprising, as an active ingredient, one or more additional drug(s) selected from the group consisting of anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease and drugs for the treatment of atopic dermatitis.

[36] The pharmaceutical composition according to any of [21] to [33], further comprising, as an active ingredient, one or more additional drug(s) selected from the group consisting of anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease and drugs for the treatment of atopic dermatitis.

[37] The pharmaceutical composition according to any of [34] to [36], wherein the additional drug is selected from the group consisting of tyrosine kinase inhibitors, immune checkpoint inhibitors, DNA alkylating agents, DNA synthesis inhibitors, platinum-containing drugs, antimetabolites, topoisomerase I inhibitors, topoisomerase II inhibitors, tubulin activator, hormone antagonists, aromatase inhibitors, differentiation inducers, proteosome inhibitors, phospholipid kinase inhibitors, adenosine deaminase inhibitors, anti-angiogenic agents, histone deacetylase (HDAC) inhibitors, BET bromodomain inhibitors, histone demethylase inhibitors, histone methyltransferase inhibitors, matrix metalloprotease inhibitors, farnesyltransferase inhibitors, bisphosphonate preparations, Hsp90 inhibitors, kinesin Eg5 inhibitors, serine threonine kinase inhibitors, anticytokine agents, immunosuppressants, immunomodulators, active form of vitamin D3 external agent, S1P1 receptor antagonists, interferon preparations, anticholinergic drugs, leukotriene antagonists, PDE4 inhibitors, PGD2 receptor antagonists, neutrophil elastase inhibitors, antihistamine agents, classical non-steroidal anti-inflammatory drugs, cyclooxygenase inhibitors, nitric oxide-releasing non-steroidal anti-inflammatory drugs, gold preparations, penicillamine, aminosalicylic acid preparations, antimalarial drugs, pyrimidine synthesis inhibitors, TNF inhibitors, interleukin inhibitors, interleukin receptor antagonists, interleukin drugs, B-cell activation inhibitors, costimulatory molecule-related protein preparations, MAPK inhibitors, gene regulation drugs, cytokine production inhibitors, TNF-α-converting enzyme inhibitors, interleukin-1β-converting enzyme inhibitors, chemokine antagonists, therapeutic vaccine, gene therapy, antisense compounds, proteasome inhibitors, JAK inhibitors, T cell inhibitors, inosine monophosphate dehydrogenase (IMPDH) inhibitors, adhesion molecule inhibitors, thalidomide, cathepsin inhibitors, glucose-6-phosphate dehydrogenase inhibitors, dihydroorotate dehydrogenase (DHODH) inhibitors, phospholipase A2 inhibitors, iNOS inhibitors, microtubule stimulants, anti-microtubule agents, MHC class II antagonists, CD4 antagonists, CD23 antagonists, leukotriene B4 receptor antagonists, 5-lipoxygenase inhibitors, cathepsin B inhibitors, osteogenesis stimulators, dipeptidyl peptidase inhibitors, collagen agonists, capsaicin creams, sulfa drugs, hyaluronic acid derivatives, glucosamine sulfate, amiprilose, CD20 inhibitors, CD52 inhibitors, antiasthmatic drugs, drugs for the treatment of atopic dermatitis, drugs for the treatment of allergic rhinitis, opioid receptor agonists, immunoglobulins, glatiramer acetate, T cell receptor vaccines, adhesion molecule inhibitors, muscle relaxants, local anesthetics, ketamine, short-acting or long-acting muscarine receptor antagonists, short-acting and long-acting β receptor agonists, inhaled steroids, oral steroids, combination drugs of β receptor agonists and inhaled steroids, vitamin derivatives and adrenocortical steroids.

[38] The pharmaceutical composition according to any of [34] to [36], wherein the additional drug is selected from the group consisting of cisplatin, doxorubicin, Taxotere, Taxol, etoposide, irinotecan, topotecan, paclitaxel, docetaxel, epothilone, tamoxifen, 5-fluorouracil, fingolimod, methotrexate, temozolomide, cyclophosphamide, SCH 66336, R115777, L778,123, BMS 214662, gefitinib, erlotinib, panitumumab, afatinib, dasatinib, bosutinib, vandetanib, sunitinib, axitinib, pazopanib, lenvatinib, lapatinib, nintedanib, nilotinib, crizotinib, ceritinib, alectinib, ibrutinib, imatinib, sorafenib, vemurafenib, dabrafenib, trametinib, palbociclib, interferon alpha-2b, cytarabine, adriamycin, Cytoxan, gemcitabine, uracil mustard, chlormethine, ifosfamide, melphalan, chlorambucil, pipobroman, triethylenemelamine, triethylenethiophosphoramine, ofatumumab, busulfan, carmustine, lomustine, streptozocin, dacarbazine, floxuridine, 6-mercaptopurine, 6-thioguanine, regorafenib, ramucirumab, fludarabine phosphate, oxaliplatin, folinate, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, drostanolone propionate, testolactone, megestrol acetate, methylprednisolone, methyltestosterone, prednisolone, chlorotrianisene, hydroxyprogesterone, aminoglutethimide, estramustine, medroxyprogesterone acetate, leuprolide acetate, flutamide, toremifene, goserelin, carboplatin, hydroxyurea, amsacrine, procarbazine, mitotane, mitoxantrone, levamisole, Navelbine, anastrozole, letrozole, capecitabine, reloxafine, droloxifene, hexamethylmelamine, bevacizumab, omalizumab, mepolizumab, gemtuzumab ozogamicin, mogamulizumab, pertuzumab, ocrelizumab, alemtuzumab, inotuzumab, tositumomab, bortezomib, ibritumomab tiuxetan, diarsenic trioxide, vinorelbine, porfimer sodium, thiotepa, altretamine, trastuzumab, letrozole, fulvestrant, exemestane, rituximab, cetuximab, basiliximab, nivolumab, ipilimumab, pembrolizumab, durvalumab, atezolizumab, avelumab, alcofenac, aceclofenac, sulindac, tolmetin, etodolac, fenoprofen, tiaprofenic acid, meclofenamic acid, meloxicam, tenoxicam, lornoxicam, nabumetone, acetaminophen, phenacetin, ethenzamide, sulpyrine, antipyrine, migrenin, aspirin, mefenamic acid, flufenamic acid, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesilate, camostat mesilate, ulinastatin, colchicine, probenecid, sulfinpyrazone, benzbromarone, allopurinol, brentuximab vedotin, gold sodium thiomalate, sodium hyaluronate, atropine, scopolamine, morphine or salts thereof, pethidine, levorphanol, oxymorphone, celecoxib, etoricoxib, valdecoxib, loxoprofen, auranofin, D-penicillamine, sulfasalazine, mesalazine, olsalazine, balsalazide, chloroquine, leflunomide, tacrolimus, infliximab, etanercept, adalimumab, certolizumab pegol, golimumab, PASSTNF-α, soluble TNF-α receptor, TNF-α-binding protein, anti-TNF-α antibodies, denosumab, anakinra, antibodies against soluble interleukin-1 receptor, tocilizumab, anti-interleukin-6 antibodies, interleukin-10, ustekinumab, briakinumab, secukinumab (AIN-457), ixekizumab (LY-2439821), AMG827, Rituxan, belimumab, abatacept, BMS-582949, inhibitors of molecules involved in signal transduction, MAPK inhibitors, salicylic acid ointments, urea ointments, iguratimod, tetomilast, belnacasan, HMPL-004, IL-8 antagonists, CXCR1-CXCR2 dual antagonists, reparixin, CCR9 antagonists, denileukin diftitox, CCX025, N-{4-chloro-2-[(1-oxidopyridin-4-yl)carbonyl]phenyl}-4-(propan-2-yloxy)benzenesulfonamide, MCP-1 antagonists, irbesartan, TNF-α vaccines, ISIS-104838, natalizumab, vedolizumab, AJM300, TRK-170, E6007, MX-68, BMS-188667, CKD-461, rimexolone, cyclosporine A, mizoribine, gusperimus, sirolimus, temsirolimus, everolimus, antilymphocyte serum, freeze-dried sulfonated normal immunoglobulin, erythropoietin, colony-stimulating factors, atiprimod dihydrochloride, azathioprine, interferon α, interferon β-1b, interferon β-1a, tofacitinib, baricitinib, carfilzomib, ruxolitinib, dexamethasone, hexestrol, methimazole, betamethasone, triamcinolone acetonide, fluocinonide, fluocinolone acetonide, cortisone acetate, hydrocortisone, fluorometholone, beclomethasone propionate, estriol, mycophenolate mofetil, alicaforsen sodium, selectin inhibitors, ELAM-1 inhibitors, VCAM-1 inhibitors, ICAM-1 inhibitors, V-85546, roflumilast, apremilast, VAS203, reumacon, zanolimumab, DW-1350, zileuton, Tyk2 inhibitors, Synvisc (hylan G-F 20), Orthovisc, atacicept, blisibimod, tizanidine, eperisone, afloqualone, baclofen, diazepam, dantrolene sodium, vitamin D3 derivatives, vitamin D2 derivatives, isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, ozagrel hydrochloride, pranlukast hydrate, seratrodast, ciclesonide, chlorpheniramine maleate, alimemazine tartrate, clemastine fumarate, homochlorcyclizine hydrochloride, fexofenadine, ketotifen fumarate, cetirizine hydrochloride, oxatomide, ebastine, epinastine hydrochloride, loratadine, tramadol, promethazine, hydroxyzine, homochlorcyclizine, cyproheptadine, mequitazine, emedastine fumarate, pseudoephedrine, bepotastine besilate, levocetirizine, olopatadine hydrochloride, mycophenolate mofetil, daclizumab, galiximab, metformin hydrochloride, visilizumab, aminopterin, pazopanib hydrochloride, fezakinumab, ruxolitinib phosphate, ixekizumab, guselkumab, SLx-2119, PRX-167700, lidocaine, tiotropium bromide, salmeterol xinafoate, formoterol fumarate, fluticasone propionate, beclometasone propionate, budesonide, and combination drugs of salmeterol xinafoate and fluticasone propionate.

[39] The pharmaceutical composition according to any of [34] to [36], wherein the additional drug is 5-fluorouracil.

[40] The pharmaceutical composition according to any of [34] to [36], wherein the additional drug is oxaliplatin.

[41] The pharmaceutical composition according to any of [34] to [36], wherein the additional drug is irinotecan.

[42] A method for treating or preventing a cancer, an inflammatory disease, an allergic disease or a chronic respiratory disease, comprising administering a compound or a pharmacologically acceptable salt thereof according to any of [1] to [20] to a subject in need thereof.

[43] The method according to [42], wherein the cancer is a blood cancer or a solid cancer.

[44] The method according to [43], wherein the blood cancer is selected from the group consisting of multiple myeloma, chronic myeloid leukemia, blood tumor, hematological malignancy, childhood leukemia, childhood lymphoma, Hodgkin's disease, lymphocytic lymphoma, cutaneous lymphoma, acute leukemia, chronic leukemia, acute lymphoblastic leukemia, acute myeloid leukemia, chronic myelogenous leukemia, plasma cell neoplasm, lymphoid neoplasm and AIDS-related cancer.

[45] The method according to [43], wherein the solid cancer is selected from the group consisting of bladder cancer, breast cancer, colon cancer, kidney cancer, liver cancer, lung cancer, small-cell lung cancer, non-small cell lung cancer, head and neck cancer, esophageal cancer, gallbladder cancer, ovarian cancer, pancreatic cancer, stomach cancer, uterine cervical cancer, thyroid gland cancer, prostate cancer, skin cancer including squamous cell carcinoma, fibrosarcoma, rhabdomyosarcoma, astrocytoma, neuroblastoma, glioma and neurilemmoma, melanoma, seminoma, teratocarcinoma, osteosarcoma, xeroderma pigmentosum, keratoacanthoma, follicular thyroid cancer and Kaposi's sarcoma.

[46] The method according to [42], wherein the inflammatory disease is an autoimmune disease.

[47] The method according to [46], wherein the autoimmune disease is rheumatoid arthritis.

[48] The method according to [46], wherein the autoimmune disease is psoriasis.

[49] The method according to [46], wherein the autoimmune disease is multiple sclerosis.

[50] The method according to [46], wherein the autoimmune disease is inflammatory bowel disease.

[51] The method according to [42], wherein the chronic respiratory disease is chronic obstructive pulmonary disease.

[52] The method according to [42], wherein the allergic disease is atopic dermatitis.

[53] The method according to any of [42] to [52], wherein the compound or the pharmacologically acceptable salt thereof is administered in combination with one or more additional drug(s) selected from the group consisting of anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease and drugs for the treatment of atopic dermatitis.

[54] The method according to any of [42] to [52], wherein the compound or the pharmacologically acceptable salt thereof is administered at the same time with or at a different time from a composition containing, as an active ingredient, one or more additional drug(s) selected from the group consisting of anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease and drugs for the treatment of atopic dermatitis.

[55] The method according to any of [42] to [52], wherein the administration of the compound or the pharmacologically acceptable salt thereof is the administration of a composition containing, as active ingredients, the compound or the pharmacologically acceptable salt thereof and one or more additional drug(s) selected from the group consisting of anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease and drugs for the treatment of atopic dermatitis.

[56] The method according to any of [53] to [55], wherein the additional drug is selected from the group consisting of tyrosine kinase inhibitors, immune checkpoint inhibitors, DNA alkylating agents, DNA synthesis inhibitors, platinum-containing drugs, antimetabolites, topoisomerase I inhibitors, topoisomerase II inhibitors, tubulin activator, hormone antagonists, aromatase inhibitors, differentiation inducers, proteosome inhibitors, phospholipid kinase inhibitors, adenosine deaminase inhibitors, antiangiogenic agents, histone deacetylase (HDAC) inhibitors, BET bromodomain inhibitors, histone demethylase inhibitors, histone methyltransferase inhibitors, matrix metalloprotease inhibitors, farnesyltransferase inhibitors, bisphosphonate preparations, Hsp90 inhibitors, kinesin Eg5 inhibitors, serine threonine kinase inhibitors, anticytokine agents, immunosuppressants, immunomodulators, active form of vitamin D3 external agent, S1P1 receptor antagonists, interferon preparations, anticholinergic drugs, leukotriene antagonists, PDE4 inhibitors, PGD2 receptor antagonists, neutrophil elastase inhibitors, antihistamine agents, classical non-steroidal anti-inflammatory drugs, cyclooxygenase inhibitors, nitric oxide-releasing non-steroidal anti-inflammatory drugs, gold drugs, penicillamine, aminosalicylic acid preparations, antimalarial drugs, pyrimidine synthesis inhibitors, TNF inhibitors, interleukin inhibitors, interleukin receptor antagonists, interleukin drugs, B-cell activation inhibitors, costimulatory molecule-related protein preparations, MAPK inhibitors, gene regulation drugs, cytokine production inhibitors, TNF-α-converting enzyme inhibitors, interleukin-1β-converting enzyme inhibitors, chemokine antagonists, therapeutic vaccine, gene therapy, antisense compounds, proteasome inhibitors, JAK inhibitors, T cell inhibitors, inosine monophosphate dehydrogenase (IMPDH) inhibitors, adhesion molecule inhibitors, thalidomide, cathepsin inhibitors, glucose-6-phosphate dehydrogenase inhibitors, dihydroorotate dehydrogenase (DHODH) inhibitors, phospholipase A2 inhibitors, iNOS inhibitors, microtubule stimulants, anti-microtubule agents, MHC class II antagonists, CD4 antagonists, CD23 antagonists, leukotriene B4 receptor antagonists, 5-lipoxygenase inhibitors, cathepsin B inhibitors, osteogenesis stimulators, dipeptidyl peptidase inhibitors, collagen agonists, capsaicin creams, sulfa drugs, hyaluronic acid derivatives, glucosamine sulfate, amiprilose, CD20 inhibitors, CD52 inhibitors, antiasthmatic drugs, drugs for the treatment of atopic dermatitis, drugs for the treatment of allergic rhinitis, opioid receptor agonists, immunoglobulins, glatiramer acetate, T cell receptor vaccines, adhesion molecule inhibitors, muscle relaxants, local anesthetics, ketamine, short-acting and long-acting muscarine receptor antagonists, short-acting and long-acting β receptor agonists, inhaled steroids, oral steroids, combination drugs of β receptor agonists and inhaled steroids, vitamin derivatives and adrenocortical steroids.

[57] The method according to any of [53] to [55], wherein the additional drug is selected from the group consisting of cisplatin, doxorubicin, Taxotere, Taxol, etoposide, irinotecan, topotecan, paclitaxel, docetaxel, epothilone, tamoxifen, 5-fluorouracil, fingolimod, methotrexate, temozolomide, cyclophosphamide, SCH 66336, R115777, L778,123, BMS 214662, gefitinib, erlotinib, panitumumab, afatinib, dasatinib, bosutinib, vandetanib, sunitinib, axitinib, pazopanib, lenvatinib, lapatinib, nintedanib, nilotinib, crizotinib, ceritinib, alectinib, ibrutinib, imatinib, sorafenib, vemurafenib, dabrafenib, trametinib, palbociclib, interferon alpha-2b, cytarabine, adriamycin, Cytoxan, gemcitabine, uracil mustard, chlormethine, ifosfamide, melphalan, chlorambucil, pipobroman, triethylenemelamine, triethylenethiophosphoramine, ofatumumab, busulfan, carmustine, lomustine, streptozocin, dacarbazine, floxuridine, 6-mercaptopurine, 6-thioguanine, regorafenib, ramucirumab, fludarabine phosphate, oxaliplatin, folinate, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, drostanolone propionate, testolactone, megestrol acetate, methylprednisolone, methyltestosterone, prednisolone, chlorotrianisene, hydroxyprogesterone, aminoglutethimide, estramustine, medroxyprogesterone acetate, leuprolide acetate, flutamide, toremifene, goserelin, carboplatin, hydroxyurea, amsacrine, procarbazine, mitotane, mitoxantrone, levamisole, Navelbine, anastrozole, letrozole, capecitabine, reloxafine, droloxifene, hexamethylmelamine, bevacizumab, omalizumab, mepolizumab, gemtuzumab ozogamicin, mogamulizumab, pertuzumab, ocrelizumab, alemtuzumab, inotuzumab, tositumomab, bortezomib, ibritumomab tiuxetan, diarsenic trioxide, vinorelbine, porfimer sodium, thiotepa, altretamine, trastuzumab, letrozole, fulvestrant, exemestane, rituximab, cetuximab, basiliximab, nivolumab, ipilimumab, pembrolizumab, durvalumab, atezolizumab, avelumab, alcofenac, aceclofenac, sulindac, tolmetin, etodolac, fenoprofen, tiaprofenic acid, meclofenamic acid, meloxicam, tenoxicam, lornoxicam, nabumetone, acetaminophen, phenacetin, ethenzamide, sulpyrine, antipyrine, migrenin, aspirin, mefenamic acid, flufenamic acid, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesilate, camostat mesilate, ulinastatin, colchicine, probenecid, sulfinpyrazone, benzbromarone, allopurinol, brentuximab vedotin, gold sodium thiomalate, sodium hyaluronate, atropine, scopolamine, morphine or salts thereof, pethidine, levorphanol, oxymorphone, celecoxib, etoricoxib, valdecoxib, loxoprofen, auranofin, D-penicillamine, sulfasalazine, mesalazine, olsalazine, balsalazide, chloroquine, leflunomide, tacrolimus, infliximab, etanercept, adalimumab, certolizumab pegol, golimumab, PASSTNF-α, soluble TNF-α receptor, TNF-α-binding protein, anti-TNF-α antibodies, denosumab, anakinra, antibodies against soluble interleukin-1 receptor, tocilizumab, anti-interleukin-6 antibodies, interleukin-10, ustekinumab, briakinumab, secukinumab (AIN-457), ixekizumab (LY-2439821), AMG827, Rituxan, belimumab, abatacept, BMS-582949, inhibitors of molecules involved in signal transduction, MAPK inhibitors, salicylic acid ointments, urea ointments, iguratimod, tetomilast, belnacasan, HMPL-004, IL-8 antagonists, CXCR1-CXCR2 dual antagonists, reparixin, CCR9 antagonists, denileukin diftitox, CCX025, N-{4-chloro-2-[(1-oxidopyridin-4-yl)carbonyl]phenyl}-4-(propan-2-yloxy)benzenesulfonamide, MCP-1 antagonists, irbesartan, TNF-α vaccines, ISIS-104838, natalizumab, vedolizumab, AJM300, TRK-170, E6007, MX-68, BMS-188667, CKD-461, rimexolone, cyclosporine A, mizoribine, gusperimus, sirolimus, temsirolimus, everolimus, antilymphocyte serum, freeze-dried sulfonated normal immunoglobulin, erythropoietin, colony-stimulating factors, atiprimod dihydrochloride, azathioprine, interferon α, interferon β-1b, interferon β3-1a, tofacitinib, baricitinib, carfilzomib, ruxolitinib, dexamethasone, hexestrol, methimazole, betamethasone, triamcinolone acetonide, fluocinonide, fluocinolone acetonide, cortisone acetate, hydrocortisone, fluorometholone, beclomethasone propionate, estriol, mycophenolate mofetil, alicaforsen sodium, selectin inhibitors, ELAM-1 inhibitors, VCAM-1 inhibitors, ICAM-1 inhibitors, V-85546, roflumilast, apremilast, VAS203, reumacon, zanolimumab, DW-1350, zileuton, Tyk2 inhibitors, Synvisc (hylan G-F 20), Orthovisc, atacicept, blisibimod, tizanidine, eperisone, afloqualone, baclofen, diazepam, dantrolene sodium, vitamin D3 derivatives, vitamin D2 derivatives, isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, ozagrel hydrochloride, pranlukast hydrate, seratrodast, ciclesonide, chlorpheniramine maleate, alimemazine tartrate, clemastine fumarate, homochlorcyclizine hydrochloride, fexofenadine, ketotifen fumarate, cetirizine hydrochloride, oxatomide, ebastine, epinastine hydrochloride, loratadine, tramadol, promethazine, hydroxyzine, homochlorcyclizine, cyproheptadine, mequitazine, emedastine fumarate, pseudoephedrine, bepotastine besilate, levocetirizine, olopatadine hydrochloride, mycophenolate mofetil, daclizumab, galiximab, metformin hydrochloride, visilizumab, aminopterin, pazopanib hydrochloride, fezakinumab, ruxolitinib phosphate, ixekizumab, guselkumab, SLx-2119, PRX-167700, lidocaine, tiotropium bromide, salmeterol xinafoate, formoterol fumarate, fluticasone propionate, beclometasone propionate, budesonide, and combination drugs of salmeterol xinafoate and fluticasone propionate.

[58] The method according to any of [53] to [55], wherein the additional drug is 5-fluorouracil.

[59] The method according to any of [53] to [55], wherein the additional drug is oxaliplatin.

[60] The method according to any of [53] to [55], wherein the additional drug is irinotecan.

[61] Use of a compound or a pharmacologically acceptable salt thereof according to any of [1] to [20] for the production of a pharmaceutical composition which is a CDK7 inhibitor.

[62] Use of a compound or a pharmacologically acceptable salt thereof according to any of [1] to [20] for the inhibition of CDK7.

[63] Use of a compound or a pharmacologically acceptable salt thereof according to any of [1] to [20] for the treatment or prevention of a cancer, an inflammatory disease, an allergic disease, or a chronic respiratory disease.

[64] The use according to [63], wherein the cancer is a blood cancer or a solid cancer.

[65] The use according to [64], wherein the blood cancer is selected from the group consisting of multiple myeloma, chronic myeloid leukemia, blood tumor, hematological malignancy, childhood leukemia, childhood lymphoma, Hodgkin's disease, lymphocytic lymphoma, cutaneous lymphoma, acute leukemia, chronic leukemia, acute lymphoblastic leukemia, acute myeloid leukemia, chronic myelogenous leukemia, plasma cell neoplasm, lymphoid neoplasm and AIDS-related cancer.

[66] The use according to [64], wherein the solid cancer is selected from the group consisting of bladder cancer, breast cancer, colon cancer, kidney cancer, liver cancer, lung cancer, small-cell lung cancer, non-small cell lung cancer, head and neck cancer, esophageal cancer, gallbladder cancer, ovarian cancer, pancreatic cancer, stomach cancer, uterine cervical cancer, thyroid cancer, prostate cancer, skin cancer including squamous cell carcinoma, fibrosarcoma, rhabdomyosarcoma, astrocytoma, neuroblastoma, glioma and neurilemmoma, melanoma, seminoma, teratocarcinoma, osteosarcoma, xeroderma pigmentosum, keratoacanthoma, follicular thyroid cancer and Kaposi's sarcoma.

[67] The use according to [63], wherein the inflammatory disease is an autoimmune disease.

[68] The use according to [67], wherein the autoimmune disease is rheumatoid arthritis.

[69] The use according to [67], wherein the autoimmune disease is psoriasis.

[70] The use according to [67], wherein the autoimmune disease is multiple sclerosis.

[71] The use according to [67], wherein the autoimmune disease is inflammatory bowel disease.

[72] The use according to [63], wherein the chronic respiratory disease is chronic obstructive pulmonary disease.
[73] The use according to [63], wherein the allergic disease is atopic dermatitis.
[74] The compound or a pharmacologically acceptable salt thereof according to any of [1] to [20] for use as an active ingredient in a pharmaceutical composition.
[75] The compound or a pharmacologically acceptable salt thereof according to [74], wherein the pharmaceutical composition is a pharmaceutical composition for the treatment of a cancer, an inflammatory disease, an allergic disease or a chronic respiratory disease.
[76] The compound or a pharmacologically acceptable salt thereof according to [75], wherein the cancer is a blood cancer or a solid cancer.
[77] The compound or a pharmacologically acceptable salt thereof according to [75], wherein the blood cancer is selected from the group consisting of multiple myeloma, chronic myeloid leukemia, blood tumor, hematological malignancy, childhood leukemia, childhood lymphoma, Hodgkin's disease, lymphocytic lymphoma, cutaneous lymphoma, acute leukemia, chronic leukemia, acute lymphoblastic leukemia, acute myeloid leukemia, chronic myelogenous leukemia, plasma cell neoplasm, lymphoid neoplasm and AIDS-related cancer.
[78] The compound or a pharmacologically acceptable salt thereof according to [75], wherein the solid cancer is selected from the group consisting of bladder cancer, breast cancer, colon cancer, kidney cancer, liver cancer, lung cancer, small-cell lung cancer, non-small cell lung cancer, head and neck cancer, esophageal cancer, gallbladder cancer, ovarian cancer, pancreatic cancer, stomach cancer, uterine cervical cancer, thyroid cancer, prostate cancer, skin cancer including squamous cell carcinoma, fibrosarcoma, rhabdomyosarcoma, astrocytoma, neuroblastoma, glioma and neurilemmoma, melanoma, seminoma, teratocarcinoma, osteosarcoma, xeroderma pigmentosum, keratoacanthoma, follicular thyroid cancer and Kaposi's sarcoma.
[79] The compound or a pharmacologically acceptable salt thereof according to [75], wherein the inflammatory disease is an autoimmune disease.
[80] The compound or a pharmacologically acceptable salt thereof according to [79], wherein the autoimmune disease is rheumatoid arthritis.
[81] The compound or a pharmacologically acceptable salt thereof according to [79], wherein the autoimmune disease is psoriasis.
[82] The compound or a pharmacologically acceptable salt thereof according to [79], wherein the autoimmune disease is multiple sclerosis.
[83] The compound or a pharmacologically acceptable salt thereof according to [79], wherein the autoimmune disease is inflammatory bowel disease.
[84] The compound or a pharmacologically acceptable salt thereof according to [75], wherein the chronic respiratory disease is chronic obstructive pulmonary disease.
[85] The compound or a pharmacologically acceptable salt thereof according to [75], wherein the allergic disease is atopic dermatitis.

Specific examples of the compound represented by the general formula (I) of the present invention can include compounds as shown in Tables 1 to 49 below. In Tables 1 to 49 below, D represents deuterium, Br represents a bromine atom, Cl represents a chlorine atom, F represents a fluorine atom, Me represents a methyl group, Et represents an ethyl group, nPr represents a n-propyl group, iPr represents an isopropyl group, cPr represents a cyclopropyl group, tBu represents a tert-butyl group, Ph represents a phenyl group, and MeO represents a methoxy group. As specific examples, "CF$_3$" represents a trifluoromethyl group, "CHF$_2$O" represents a difluoromethoxy group, "CD$_3$" represents a group in which three hydrogen atoms constituting the methyl group are replaced with deuterium atoms, "1,1-diF-Et" means a group in which the ethyl group is substituted at position 1 by two fluorine atoms, i.e., a 1,1,-difluoroethyl group, "2,6-diF-Ph" means a group in which the phenyl group is substituted at positions 2 and 6 by fluorine atoms, respectively, i.e., a 2,6-difluorophenyl group, "2,4-diCl-6-Me-Ph" means a group in which the phenyl group is substituted at positions 2 and 4 by chlorine atoms, respectively, and substituted at position 6 by a methyl group, i.e., a 2,4-dichloro-6-methylphenyl group, and "CH$_2$CH$_2$CH$_2$CH$_2$" means a 1,4-butylene group formed by bonding two R moieties to each other.

TABLE 1

(I)

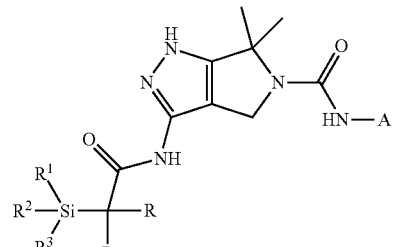

| Comp. No. | R$^1$ | R$^2$ | R$^3$ | R | R | A |
|---|---|---|---|---|---|---|
| I-1 | Me | Me | Me | Me | Et | Ph |
| I-2 | Me | Me | Me | Me | nPr | Ph |
| I-3 | Me | Me | Me | Me | iPr | Ph |
| I-4 | Me | Me | Me | Et | Et | Ph |
| I-5 | Me | Me | Me | Et | nPr | Ph |
| I-6 | Me | Me | Me | nPr | nPr | Ph |
| I-7 | Me | Me | Me | CH$_2$CH$_2$CH$_2$ | | Ph |
| I-8 | Me | Me | Me | CH$_2$CH$_2$CH$_2$CH$_2$ | | Ph |
| I-9 | Me | Me | Me | Me | Et | 2-F—Ph |
| I-10 | Me | Me | Me | Me | nPr | 2-F—Ph |
| I-11 | Me | Me | Me | Me | iPr | 2-F—Ph |
| I-12 | Me | Me | Me | Et | Et | 2-F—Ph |
| I-13 | Me | Me | Me | Et | nPr | 2-F—Ph |
| I-14 | Me | Me | Me | nPr | nPr | 2-F—Ph |
| I-15 | Me | Me | Me | CH$_2$CH$_2$CH$_2$ | | 2-F—Ph |
| I-16 | Me | Me | Me | CH$_2$CH$_2$CH$_2$CH$_2$ | | 2-F—Ph |
| I-17 | Me | Me | Me | Me | Et | 3-F—Ph |
| I-18 | Me | Me | Me | Me | nPr | 3-F—Ph |
| I-19 | Me | Me | Me | Me | iPr | 3-F—Ph |
| I-20 | Me | Me | Me | Et | Et | 3-F—Ph |
| I-21 | Me | Me | Me | Et | nPr | 3-F—Ph |
| I-22 | Me | Me | Me | nPr | nPr | 3-F—Ph |
| I-23 | Me | Me | Me | CH$_2$CH$_2$CH$_2$ | | 3-F—Ph |
| I-24 | Me | Me | Me | CH$_2$CH$_2$CH$_2$CH$_2$ | | 3-F—Ph |
| I-25 | Me | Me | Me | Me | Et | 4-F—Ph |
| I-26 | Me | Me | Me | Me | nPr | 4-F—Ph |
| I-27 | Me | Me | Me | Me | iPr | 4-F—Ph |
| I-28 | Me | Me | Me | Et | Et | 4-F—Ph |
| I-29 | Me | Me | Me | Et | nPr | 4-F—Ph |
| I-30 | Me | Me | Me | nPr | nPr | 4-F—Ph |
| I-31 | Me | Me | Me | CH$_2$CH$_2$CH$_2$ | | 4-F—Ph |
| I-32 | Me | Me | Me | CH$_2$CH$_2$CH$_2$CH$_2$ | | 4-F—Ph |
| I-33 | Me | Me | Me | Me | Et | 2-Cl—Ph |
| I-34 | Me | Me | Me | Me | nPr | 2-Cl—Ph |
| I-35 | Me | Me | Me | Me | iPr | 2-Cl—Ph |
| I-36 | Me | Me | Me | Et | Et | 2-Cl—Ph |
| I-37 | Me | Me | Me | Et | nPr | 2-Cl—Ph |
| I-38 | Me | Me | Me | nPr | nPr | 2-Cl—Ph |
| I-39 | Me | Me | Me | CH$_2$CH$_2$CH$_2$ | | 2-Cl—Ph |
| I-40 | Me | Me | Me | CH$_2$CH$_2$CH$_2$CH$_2$ | | 2-Cl—Ph |
| I-41 | Me | Me | Me | Me | Et | 3-Cl—Ph |

TABLE 1-continued

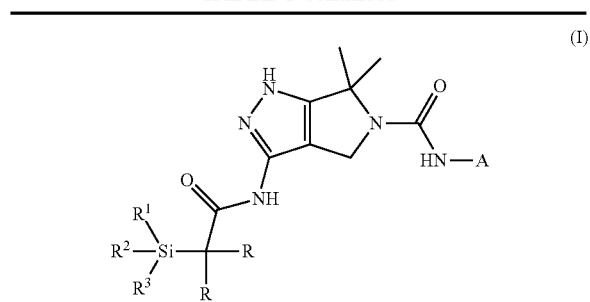
(I)

| Comp. No. | R¹ | R² | R³ | R | R | A |
|---|---|---|---|---|---|---|
| I-42 | Me | Me | Me | Me | nPr | 3-Cl—Ph |
| I-43 | Me | Me | Me | Me | iPr | 3-Cl—Ph |
| I-44 | Me | Me | Me | Et | Et | 3-Cl—Ph |
| I-45 | Me | Me | Me | Et | nPr | 3-Cl—Ph |
| I-46 | Me | Me | Me | nPr | nPr | 3-Cl—Ph |
| I-47 | Me | Me | Me | CH₂CH₂CH₂CH₂ | | 3-Cl—Ph |
| I-48 | Me | Me | Me | CH₂CH₂CH₂CH₂CH₂ | | 3-Cl—Ph |
| I-49 | Me | Me | Me | Me | Et | 4-Cl—Ph |
| I-50 | Me | Me | Me | Me | nPr | 4-Cl—Ph |
| I-51 | Me | Me | Me | Me | iPr | 4-Cl—Ph |
| I-52 | Me | Me | Me | Et | Et | 4-Cl—Ph |
| I-53 | Me | Me | Me | Et | nPr | 4-Cl—Ph |
| I-54 | Me | Me | Me | nPr | nPr | 4-Cl—Ph |
| I-55 | Me | Me | Me | CH₂CH₂CH₂CH₂ | | 4-Cl—Ph |
| I-56 | Me | Me | Me | CH₂CH₂CH₂CH₂CH₂ | | 4-Cl—Ph |
| I-57 | Me | Me | Me | Me | Et | 2-Br—Ph |
| I-58 | Me | Me | Me | Me | nPr | 2-Br—Ph |
| I-59 | Me | Me | Me | Me | iPr | 2-Br—Ph |
| I-60 | Me | Me | Me | Et | Et | 2-Br—Ph |
| I-61 | Me | Me | Me | Et | nPr | 2-Br—Ph |
| I-62 | Me | Me | Me | nPr | nPr | 2-Br—Ph |
| I-63 | Me | Me | Me | CH₂CH₂CH₂CH₂ | | 2-Br—Ph |
| I-64 | Me | Me | Me | CH₂CH₂CH₂CH₂CH₂ | | 2-Br—Ph |
| I-65 | Me | Me | Me | Me | Et | 3-Br—Ph |
| I-66 | Me | Me | Me | Me | nPr | 3-Br—Ph |
| I-67 | Me | Me | Me | Me | iPr | 3-Br—Ph |
| I-68 | Me | Me | Me | Et | Et | 3-Br—Ph |
| I-69 | Me | Me | Me | Et | nPr | 3-Br—Ph |
| I-70 | Me | Me | Me | nPr | nPr | 3-Br—Ph |
| I-71 | Me | Me | Me | CH₂CH₂CH₂CH₂ | | 3-Br—Ph |
| I-72 | Me | Me | Me | CH₂CH₂CH₂CH₂CH₂ | | 3-Br—Ph |
| I-73 | Me | Me | Me | Me | Et | 4-Br—Ph |
| I-74 | Me | Me | Me | Me | nPr | 4-Br—Ph |
| I-75 | Me | Me | Me | Me | iPr | 4-Br—Ph |
| I-76 | Me | Me | Me | Et | Et | 4-Br—Ph |
| I-77 | Me | Me | Me | Et | nPr | 4-Br—Ph |
| I-78 | Me | Me | Me | nPr | nPr | 4-Br—Ph |
| I-79 | Me | Me | Me | CH₂CH₂CH₂CH₂ | | 4-Br—Ph |
| I-80 | Me | Me | Me | CH₂CH₂CH₂CH₂CH₂ | | 4-Br—Ph |
| I-81 | Me | Me | Me | Me | Et | 2-Me—Ph |
| I-82 | Me | Me | Me | Me | nPr | 2-Me—Ph |
| I-83 | Me | Me | Me | Me | iPr | 2-Me—Ph |
| I-84 | Me | Me | Me | Et | Et | 2-Me—Ph |
| I-85 | Me | Me | Me | Et | nPr | 2-Me—Ph |
| I-86 | Me | Me | Me | nPr | nPr | 2-Me—Ph |
| I-87 | Me | Me | Me | CH₂CH₂CH₂CH₂ | | 2-Me—Ph |
| I-88 | Me | Me | Me | CH₂CH₂CH₂CH₂CH₂ | | 2-Me—Ph |
| I-89 | Me | Me | Me | Me | Et | 3-Me—Ph |
| I-90 | Me | Me | Me | Me | nPr | 3-Me—Ph |
| I-91 | Me | Me | Me | Me | iPr | 3-Me—Ph |
| I-92 | Me | Me | Me | Et | Et | 3-Me—Ph |
| I-93 | Me | Me | Me | Et | nPr | 3-Me—Ph |
| I-94 | Me | Me | Me | nPr | nPr | 3-Me—Ph |
| I-95 | Me | Me | Me | CH₂CH₂CH₂CH₂ | | 3-Me—Ph |
| I-96 | Me | Me | Me | CH₂CH₂CH₂CH₂CH₂ | | 3-Me—Ph |
| I-97 | Me | Me | Me | Me | Et | 4-Me—Ph |
| I-98 | Me | Me | Me | Me | nPr | 4-Me—Ph |
| I-99 | Me | Me | Me | Me | iPr | 4-Me—Ph |
| I-100 | Me | Me | Me | Et | Et | 4-Me—Ph |

TABLE 2

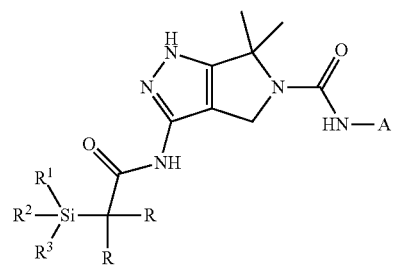
(I)

| Comp. No. | R¹ | R² | R³ | R | R | A |
|---|---|---|---|---|---|---|
| I-101 | Me | Me | Me | Et | nPr | 4-Me—Ph |
| I-102 | Me | Me | Me | nPr | nPr | 4-Me—Ph |
| I-103 | Me | Me | Me | CH₂CH₂CH₂CH₂ | | 4-Me—Ph |
| I-104 | Me | Me | Me | CH₂CH₂CH₂CH₂CH₂ | | 4-Me—Ph |
| I-105 | Me | Me | Me | Me | Et | 2-Et—Ph |
| I-106 | Me | Me | Me | Me | nPr | 2-Et—Ph |
| I-107 | Me | Me | Me | Me | iPr | 2-Et—Ph |
| I-108 | Me | Me | Me | Et | Et | 2-Et—Ph |
| I-109 | Me | Me | Me | Et | nPr | 2-Et—Ph |
| I-110 | Me | Me | Me | nPr | nPr | 2-Et—Ph |
| I-111 | Me | Me | Me | CH₂CH₂CH₂CH₂ | | 2-Et—Ph |
| I-112 | Me | Me | Me | CH₂CH₂CH₂CH₂CH₂ | | 2-Et—Ph |
| I-113 | Me | Me | Me | Me | Et | 3-Et—Ph |
| I-114 | Me | Me | Me | Me | nPr | 3-Et—Ph |
| I-115 | Me | Me | Me | Me | iPr | 3-Et—Ph |
| I-116 | Me | Me | Me | Et | Et | 3-Et—Ph |
| I-117 | Me | Me | Me | Et | nPr | 3-Et—Ph |
| I-118 | Me | Me | Me | nPr | nPr | 3-Et—Ph |
| I-119 | Me | Me | Me | CH₂CH₂CH₂CH₂ | | 3-Et—Ph |
| I-120 | Me | Me | Me | CH₂CH₂CH₂CH₂CH₂ | | 3-Et—Ph |
| I-121 | Me | Me | Me | Me | Et | 4-Et—Ph |
| I-122 | Me | Me | Me | Me | nPr | 4-Et—Ph |
| I-123 | Me | Me | Me | Me | iPr | 4-Et—Ph |
| I-124 | Me | Me | Me | Et | Et | 4-Et—Ph |
| I-125 | Me | Me | Me | Et | nPr | 4-Et—Ph |
| I-126 | Me | Me | Me | nPr | nPr | 4-Et—Ph |
| I-127 | Me | Me | Me | CH₂CH₂CH₂CH₂ | | 4-Et—Ph |
| I-128 | Me | Me | Me | CH₂CH₂CH₂CH₂CH₂ | | 4-Et—Ph |
| I-129 | Me | Me | Me | Me | Et | 2-cPr—Ph |
| I-130 | Me | Me | Me | Me | nPr | 2-cPr—Ph |
| I-131 | Me | Me | Me | Me | iPr | 2-cPr—Ph |
| I-132 | Me | Me | Me | Et | Et | 2-cPr—Ph |
| I-133 | Me | Me | Me | Et | nPr | 2-cPr—Ph |
| I-134 | Me | Me | Me | nPr | nPr | 2-cPr—Ph |
| I-135 | Me | Me | Me | CH₂CH₂CH₂CH₂ | | 2-cPr—Ph |
| I-136 | Me | Me | Me | CH₂CH₂CH₂CH₂CH₂ | | 2-cPr—Ph |
| I-137 | Me | Me | Me | Me | Et | 2-CF₃—Ph |
| I-138 | Me | Me | Me | Me | nPr | 2-CF₃—Ph |
| I-139 | Me | Me | Me | Me | iPr | 2-CF₃—Ph |
| I-140 | Me | Me | Me | Et | Et | 2-CF₃—Ph |
| I-141 | Me | Me | Me | Et | nPr | 2-CF₃—Ph |
| I-142 | Me | Me | Me | nPr | nPr | 2-CF₃—Ph |
| I-143 | Me | Me | Me | CH₂CH₂CH₂CH₂ | | 2-CF₃—Ph |
| I-144 | Me | Me | Me | CH₂CH₂CH₂CH₂CH₂ | | 2-CF₃—Ph |
| I-145 | Me | Me | Me | Me | Et | 2-NC—Ph |
| I-146 | Me | Me | Me | Me | nPr | 2-NC—Ph |
| I-147 | Me | Me | Me | Me | iPr | 2-NC—Ph |
| I-148 | Me | Me | Me | Et | Et | 2-NC—Ph |
| I-149 | Me | Me | Me | Et | nPr | 2-NC—Ph |
| I-150 | Me | Me | Me | nPr | nPr | 2-NC—Ph |
| I-151 | Me | Me | Me | CH₂CH₂CH₂CH₂ | | 2-NC—Ph |
| I-152 | Me | Me | Me | CH₂CH₂CH₂CH₂CH₂ | | 2-NC—Ph |
| I-153 | Me | Me | Me | Me | Et | 2-MeO—Ph |
| I-154 | Me | Me | Me | Me | nPr | 2-MeO—Ph |
| I-155 | Me | Me | Me | Me | iPr | 2-MeO—Ph |
| I-156 | Me | Me | Me | Et | Et | 2-MeO—Ph |
| I-157 | Me | Me | Me | Et | nPr | 2-MeO—Ph |
| I-158 | Me | Me | Me | nPr | nPr | 2-MeO—Ph |
| I-159 | Me | Me | Me | CH₂CH₂CH₂CH₂ | | 2-MeO—Ph |
| I-160 | Me | Me | Me | CH₂CH₂CH₂CH₂CH₂ | | 2-MeO—Ph |
| I-161 | Me | Me | Me | Me | Et | 3-MeO—Ph |
| I-162 | Me | Me | Me | Me | nPr | 3-MeO—Ph |

TABLE 2-continued

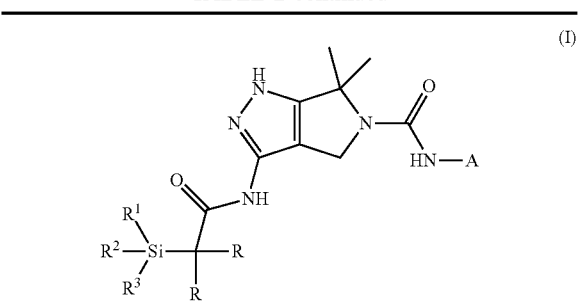

(I)

| Comp. No. | R¹ | R² | R³ | R | R | A |
|---|---|---|---|---|---|---|
| I-163 | Me | Me | Me | Me | iPr | 3-MeO—Ph |
| I-164 | Me | Me | Me | Et | Et | 3-MeO—Ph |
| I-165 | Me | Me | Me | Et | nPr | 3-MeO—Ph |
| I-166 | Me | Me | Me | nPr | nPr | 3-MeO—Ph |
| I-167 | Me | Me | Me | CH$_2$CH$_2$CH$_2$CH$_2$ | | 3-MeO—Ph |
| I-168 | Me | Me | Me | CH$_2$CH$_2$CH$_2$CH$_2$CH$_2$ | | 3-MeO—Ph |
| I-169 | Me | Me | Me | Me | Et | 4-MeO—Ph |
| I-170 | Me | Me | Me | Me | nPr | 4-MeO—Ph |
| I-171 | Me | Me | Me | Me | iPr | 4-MeO—Ph |
| I-172 | Me | Me | Me | Et | Et | 4-MeO—Ph |
| I-173 | Me | Me | Me | Et | nPr | 4-MeO—Ph |
| I-174 | Me | Me | Me | nPr | nPr | 4-MeO—Ph |
| I-175 | Me | Me | Me | CH$_2$CH$_2$CH$_2$CH$_2$ | | 4-MeO—Ph |
| I-176 | Me | Me | Me | CH$_2$CH$_2$CH$_2$CH$_2$CH$_2$ | | 4-MeO—Ph |
| I-177 | Me | Me | Me | Me | Et | 2,3-diF—Ph |
| I-178 | Me | Me | Me | Me | nPr | 2,3-diF—Ph |
| I-179 | Me | Me | Me | Me | iPr | 2,3-diF—Ph |
| I-180 | Me | Me | Me | Et | Et | 2,3-diF—Ph |
| I-181 | Me | Me | Me | Et | nPr | 2,3-diF—Ph |
| I-182 | Me | Me | Me | nPr | nPr | 2,3-diF—Ph |
| I-183 | Me | Me | Me | CH$_2$CH$_2$CH$_2$CH$_2$ | | 2,3-diF—Ph |
| I-184 | Me | Me | Me | CH$_2$CH$_2$CH$_2$CH$_2$CH$_2$ | | 2,3-diF—Ph |
| I-185 | Me | Me | Me | Me | Et | 2,4-diF—Ph |
| I-186 | Me | Me | Me | Me | nPr | 2,4-diF—Ph |
| I-187 | Me | Me | Me | Me | iPr | 2,4-diF—Ph |
| I-188 | Me | Me | Me | Et | Et | 2,4-diF—Ph |
| I-189 | Me | Me | Me | Et | nPr | 2,4-diF—Ph |
| I-190 | Me | Me | Me | nPr | nPr | 2,4-diF—Ph |
| I-191 | Me | Me | Me | CH$_2$CH$_2$CH$_2$CH$_2$ | | 2,4-diF—Ph |
| I-192 | Me | Me | Me | CH$_2$CH$_2$CH$_2$CH$_2$CH$_2$ | | 2,4-diF—Ph |
| I-193 | Me | Me | Me | Me | Et | 2,5-diF—Ph |
| I-194 | Me | Me | Me | Me | nPr | 2,5-diF—Ph |
| I-195 | Me | Me | Me | Me | iPr | 2,5-diF—Ph |
| I-196 | Me | Me | Me | Et | Et | 2,5-diF—Ph |
| I-197 | Me | Me | Me | Et | nPr | 2,5-diF—Ph |
| I-198 | Me | Me | Me | nPr | nPr | 2,5-diF—Ph |
| I-199 | Me | Me | Me | CH$_2$CH$_2$CH$_2$CH$_2$ | | 2,5-diF—Ph |
| I-200 | Me | Me | Me | CH$_2$CH$_2$CH$_2$CH$_2$CH$_2$ | | 2,5-diF—Ph |

TABLE 3

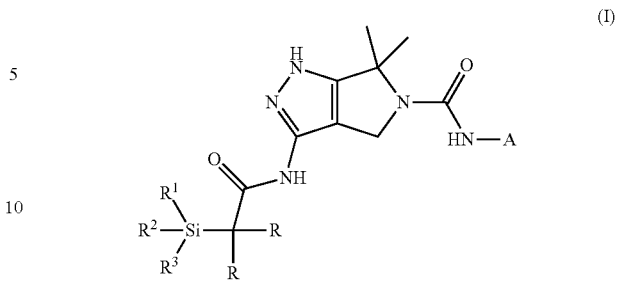

(I)

| Comp. No. | R¹ | R² | R³ | R | R | A |
|---|---|---|---|---|---|---|
| I-201 | Me | Me | Me | Me | Et | 2,6-diF—Ph |
| I-202 | Me | Me | Me | Me | nPr | 2,6-diF—Ph |
| I-203 | Me | Me | Me | Me | iPr | 2,6-diF—Ph |
| I-204 | Me | Me | Me | Et | Et | 2,6-diF—Ph |
| I-205 | Me | Me | Me | Et | nPr | 2,6-diF—Ph |
| I-206 | Me | Me | Me | nPr | nPr | 2,6-diF—Ph |
| I-207 | Me | Me | Me | CH$_2$CH$_2$CH$_2$CH$_2$ | | 2,6-diF—Ph |
| I-208 | Me | Me | Me | CH$_2$CH$_2$CH$_2$CH$_2$CH$_2$ | | 2,6-diF—Ph |
| I-209 | Me | Me | Me | Me | Et | 2-F-3-Cl—Ph |
| I-210 | Me | Me | Me | Me | nPr | 2-F-3-Cl—Ph |
| I-211 | Me | Me | Me | Me | iPr | 2-F-3-Cl—Ph |
| I-212 | Me | Me | Me | Et | Et | 2-F-3-Cl—Ph |
| I-213 | Me | Me | Me | Et | nPr | 2-F-3-Cl—Ph |
| I-214 | Me | Me | Me | nPr | nPr | 2-F-3-Cl—Ph |
| I-215 | Me | Me | Me | CH$_2$CH$_2$CH$_2$CH$_2$ | | 2-F-3-Cl—Ph |
| I-216 | Me | Me | Me | CH$_2$CH$_2$CH$_2$CH$_2$CH$_2$ | | 2-F-3-Cl—Ph |
| I-217 | Me | Me | Me | Me | Et | 2-F-4-Cl—Ph |
| I-218 | Me | Me | Me | Me | nPr | 2-F-4-Cl—Ph |
| I-219 | Me | Me | Me | Me | iPr | 2-F-4-Cl—Ph |
| I-220 | Me | Me | Me | Et | Et | 2-F-4-Cl—Ph |
| I-221 | Me | Me | Me | Et | nPr | 2-F-4-Cl—Ph |
| I-222 | Me | Me | Me | nPr | nPr | 2-F-4-Cl—Ph |
| I-223 | Me | Me | Me | CH$_2$CH$_2$CH$_2$CH$_2$ | | 2-F-4-Cl—Ph |
| I-224 | Me | Me | Me | CH$_2$CH$_2$CH$_2$CH$_2$CH$_2$ | | 2-F-4-Cl—Ph |
| I-225 | Me | Me | Me | Me | Et | 2-F-5-Cl—Ph |
| I-226 | Me | Me | Me | Me | nPr | 2-F-5-Cl—Ph |
| I-227 | Me | Me | Me | Me | iPr | 2-F-5-Cl—Ph |
| I-228 | Me | Me | Me | Et | Et | 2-F-5-Cl—Ph |
| I-229 | Me | Me | Me | Et | nPr | 2-F-5-Cl—Ph |
| I-230 | Me | Me | Me | nPr | nPr | 2-F-5-Cl—Ph |
| I-231 | Me | Me | Me | CH$_2$CH$_2$CH$_2$CH$_2$ | | 2-F-5-Cl—Ph |
| I-232 | Me | Me | Me | CH$_2$CH$_2$CH$_2$CH$_2$CH$_2$ | | 2-F-5-Cl—Ph |
| I-233 | Me | Me | Me | Me | Et | 2-F-6-Cl—Ph |
| I-234 | Me | Me | Me | Me | nPr | 2-F-6-Cl—Ph |
| I-235 | Me | Me | Me | Me | iPr | 2-F-6-Cl—Ph |
| I-236 | Me | Me | Me | Et | Et | 2-F-6-Cl—Ph |
| I-237 | Me | Me | Me | Et | nPr | 2-F-6-Cl—Ph |
| I-238 | Me | Me | Me | nPr | nPr | 2-F-6-Cl—Ph |
| I-239 | Me | Me | Me | CH$_2$CH$_2$CH$_2$CH$_2$ | | 2-F-6-Cl—Ph |
| I-240 | Me | Me | Me | CH$_2$CH$_2$CH$_2$CH$_2$CH$_2$ | | 2-F-6-Cl—Ph |
| I-241 | Me | Me | Me | Me | Et | 2-F-3-Me—Ph |
| I-242 | Me | Me | Me | Me | nPr | 2-F-3-Me—Ph |
| I-243 | Me | Me | Me | Me | iPr | 2-F-3-Me—Ph |
| I-244 | Me | Me | Me | Et | Et | 2-F-3-Me—Ph |
| I-245 | Me | Me | Me | Et | nPr | 2-F-3-Me—Ph |
| I-246 | Me | Me | Me | nPr | nPr | 2-F-3-Me—Ph |
| I-247 | Me | Me | Me | CH$_2$CH$_2$CH$_2$CH$_2$ | | 2-F-3-Me—Ph |
| I-248 | Me | Me | Me | CH$_2$CH$_2$CH$_2$CH$_2$CH$_2$ | | 2-F-3-Me—Ph |
| I-249 | Me | Me | Me | Me | Et | 2-F-4-Me—Ph |
| I-250 | Me | Me | Me | Me | nPr | 2-F-4-Me—Ph |
| I-251 | Me | Me | Me | Me | iPr | 2-F-4-Me—Ph |
| I-252 | Me | Me | Me | Et | Et | 2-F-4-Me—Ph |
| I-253 | Me | Me | Me | Et | nPr | 2-F-4-Me—Ph |
| I-254 | Me | Me | Me | nPr | nPr | 2-F-4-Me—Ph |
| I-255 | Me | Me | Me | CH$_2$CH$_2$CH$_2$CH$_2$ | | 2-F-4-Me—Ph |
| I-256 | Me | Me | Me | CH$_2$CH$_2$CH$_2$CH$_2$CH$_2$ | | 2-F-4-Me—Ph |
| I-257 | Me | Me | Me | Me | Et | 2-F-5-Me—Ph |
| I-258 | Me | Me | Me | Me | nPr | 2-F-5-Me—Ph |
| I-259 | Me | Me | Me | Me | iPr | 2-F-5-Me—Ph |
| I-260 | Me | Me | Me | Et | Et | 2-F-5-Me—Ph |
| I-261 | Me | Me | Me | Et | nPr | 2-F-5-Me—Ph |
| I-262 | Me | Me | Me | nPr | nPr | 2-F-5-Me—Ph |
| I-263 | Me | Me | Me | CH$_2$CH$_2$CH$_2$CH$_2$ | | 2-F-5-Me—Ph |
| I-264 | Me | Me | Me | CH$_2$CH$_2$CH$_2$CH$_2$CH$_2$ | | 2-F-5-Me—Ph |

TABLE 3-continued

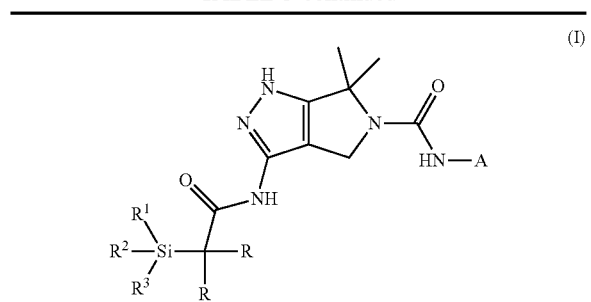

(I)

| Comp. No. | R¹ | R² | R³ | R | R | A |
|---|---|---|---|---|---|---|
| I-265 | Me | Me | Me | Me | Et | 2-F-6-Me—Ph |
| I-266 | Me | Me | Me | Me | nPr | 2-F-6-Me—Ph |
| I-267 | Me | Me | Me | Me | iPr | 2-F-6-Me—Ph |
| I-268 | Me | Me | Me | Et | Et | 2-F-6-Me—Ph |
| I-269 | Me | Me | Me | Et | nPr | 2-F-6-Me—Ph |
| I-270 | Me | Me | Me | nPr | nPr | 2-F-6-Me—Ph |
| I-271 | Me | Me | Me | CH₂CH₂CH₂CH₂ | | 2-F-6-Me—Ph |
| I-272 | Me | Me | Me | CH₂CH₂CH₂CH₂CH₂ | | 2-F-6-Me—Ph |
| I-273 | Me | Me | Me | Me | Et | 2-F-3-CF₃—Ph |
| I-274 | Me | Me | Me | Me | nPr | 2-F-3-CF₃—Ph |
| I-275 | Me | Me | Me | Me | iPr | 2-F-3-CF₃—Ph |
| I-276 | Me | Me | Me | Et | Et | 2-F-3-CF₃—Ph |
| I-277 | Me | Me | Me | Et | nPr | 2-F-3-CF₃—Ph |
| I-278 | Me | Me | Me | nPr | nPr | 2-F-3-CF₃—Ph |
| I-279 | Me | Me | Me | CH₂CH₂CH₂CH₂ | | 2-F-3-CF₃—Ph |
| I-280 | Me | Me | Me | CH₂CH₂CH₂CH₂CH₂ | | 2-F-3-CF₃—Ph |
| I-281 | Me | Me | Me | Me | Et | 2-F-4-CF₃—Ph |
| I-282 | Me | Me | Me | Me | nPr | 2-F-4-CF₃—Ph |
| I-283 | Me | Me | Me | Me | iPr | 2-F-4-CF₃—Ph |
| I-284 | Me | Me | Me | Et | Et | 2-F-4-CF₃—Ph |
| I-285 | Me | Me | Me | Et | nPr | 2-F-4-CF₃—Ph |
| I-286 | Me | Me | Me | nPr | nPr | 2-F-4-CF₃—Ph |
| I-287 | Me | Me | Me | CH₂CH₂CH₂CH₂ | | 2-F-4-CF₃—Ph |
| I-288 | Me | Me | Me | CH₂CH₂CH₂CH₂CH₂ | | 2-F-4-CF₃—Ph |
| I-289 | Me | Me | Me | Me | Et | 2-F-5-CF₃—Ph |
| I-290 | Me | Me | Me | Me | nPr | 2-F-5-CF₃—Ph |
| I-291 | Me | Me | Me | Me | iPr | 2-F-5-CF₃—Ph |
| I-292 | Me | Me | Me | Et | Et | 2-F-5-CF₃—Ph |
| I-293 | Me | Me | Me | Et | nPr | 2-F-5-CF₃—Ph |
| I-294 | Me | Me | Me | nPr | nPr | 2-F-5-CF₃—Ph |
| I-295 | Me | Me | Me | CH₂CH₂CH₂CH₂ | | 2-F-5-CF₃—Ph |
| I-296 | Me | Me | Me | CH₂CH₂CH₂CH₂CH₂ | | 2-F-5-CF₃—Ph |
| I-297 | Me | Me | Me | Me | Et | 2-F-6-CF₃—Ph |
| I-298 | Me | Me | Me | Me | nPr | 2-F-6-CF₃—Ph |
| I-299 | Me | Me | Me | Me | iPr | 2-F-6-CF₃—Ph |
| I-300 | Me | Me | Me | Et | Et | 2-F-6-CF₃—Ph |

TABLE 4

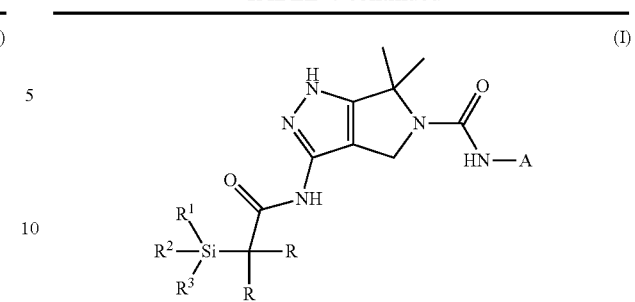

(I)

| Comp. No. | R¹ | R² | R³ | R | R | A |
|---|---|---|---|---|---|---|
| I-301 | Me | Me | Me | Et | nPr | 2-F-6-CF₃—Ph |
| I-302 | Me | Me | Me | nPr | nPr | 2-F-6-CF₃—Ph |
| I-303 | Me | Me | Me | CH₂CH₂CH₂CH₂ | | 2-F-6-CF₃—Ph |
| I-304 | Me | Me | Me | CH₂CH₂CH₂CH₂CH₂ | | 2-F-6-CF₃—Ph |

TABLE 4-continued

| Comp. No. | R¹ | R² | R³ | R | R | A |
|---|---|---|---|---|---|---|
| I-305 | Me | Me | Me | Me | Et | 2-F-3-MeO—Ph |
| I-306 | Me | Me | Me | Me | nPr | 2-F-3-MeO—Ph |
| I-307 | Me | Me | Me | Me | iPr | 2-F-3-MeO—Ph |
| I-308 | Me | Me | Me | Et | Et | 2-F-3-MeO—Ph |
| I-309 | Me | Me | Me | Et | nPr | 2-F-3-MeO—Ph |
| I-310 | Me | Me | Me | nPr | nPr | 2-F-3-MeO—Ph |
| I-311 | Me | Me | Me | CH₂CH₂CH₂CH₂ | | 2-F-3-MeO—Ph |
| I-312 | Me | Me | Me | CH₂CH₂CH₂CH₂CH₂ | | 2-F-3-MeO—Ph |
| I-313 | Me | Me | Me | Me | Et | 2-F-4-MeO—Ph |
| I-314 | Me | Me | Me | Me | nPr | 2-F-4-MeO—Ph |
| I-315 | Me | Me | Me | Me | iPr | 2-F-4-MeO—Ph |
| I-316 | Me | Me | Me | Et | Et | 2-F-4-MeO—Ph |
| I-317 | Me | Me | Me | Et | nPr | 2-F-4-MeO—Ph |
| I-318 | Me | Me | Me | nPr | nPr | 2-F-4-MeO—Ph |
| I-319 | Me | Me | Me | CH₂CH₂CH₂CH₂ | | 2-F-4-MeO—Ph |
| I-320 | Me | Me | Me | CH₂CH₂CH₂CH₂CH₂ | | 2-F-4-MeO—Ph |
| I-321 | Me | Me | Me | Me | Et | 2-F-5-MeO—Ph |
| I-322 | Me | Me | Me | Me | nPr | 2-F-5-MeO—Ph |
| I-323 | Me | Me | Me | Me | iPr | 2-F-5-MeO—Ph |
| I-324 | Me | Me | Me | Et | Et | 2-F-5-MeO—Ph |
| I-325 | Me | Me | Me | Et | nPr | 2-F-5-MeO—Ph |
| I-326 | Me | Me | Me | nPr | nPr | 2-F-5-MeO—Ph |
| I-327 | Me | Me | Me | CH₂CH₂CH₂CH₂ | | 2-F-5-MeO—Ph |
| I-328 | Me | Me | Me | CH₂CH₂CH₂CH₂CH₂ | | 2-F-5-MeO—Ph |
| I-329 | Me | Me | Me | Me | Et | 2-F-6-MeO—Ph |
| I-330 | Me | Me | Me | Me | nPr | 2-F-6-MeO—Ph |
| I-331 | Me | Me | Me | Me | iPr | 2-F-6-MeO—Ph |
| I-332 | Me | Me | Me | Et | Et | 2-F-6-MeO—Ph |
| I-333 | Me | Me | Me | Et | nPr | 2-F-6-MeO—Ph |
| I-334 | Me | Me | Me | nPr | nPr | 2-F-6-MeO—Ph |
| I-335 | Me | Me | Me | CH₂CH₂CH₂CH₂ | | 2-F-6-MeO—Ph |
| I-336 | Me | Me | Me | CH₂CH₂CH₂CH₂CH₂ | | 2-F-6-MeO—Ph |
| I-337 | Me | Me | Me | Me | Et | 2-F-3-CHF₂O—Ph |
| I-338 | Me | Me | Me | Me | nPr | 2-F-3-CHF₂O—Ph |
| I-339 | Me | Me | Me | Me | iPr | 2-F-3-CHF₂O—Ph |
| I-340 | Me | Me | Me | Et | Et | 2-F-3-CHF₂O—Ph |
| I-341 | Me | Me | Me | Et | nPr | 2-F-3-CHF₂O—Ph |
| I-342 | Me | Me | Me | nPr | nPr | 2-F-3-CHF₂O—Ph |
| I-343 | Me | Me | Me | CH₂CH₂CH₂CH₂ | | 2-F-3-CHF₂O—Ph |
| I-344 | Me | Me | Me | CH₂CH₂CH₂CH₂CH₂ | | 2-F-3-CHF₂O—Ph |
| I-345 | Me | Me | Me | Me | Et | 2-F-4-CHF₂O—Ph |
| I-346 | Me | Me | Me | Me | nPr | 2-F-4-CHF₂O—Ph |
| I-347 | Me | Me | Me | Me | iPr | 2-F-4-CHF₂O—Ph |
| I-348 | Me | Me | Me | Et | Et | 2-F-4-CHF₂O—Ph |
| I-349 | Me | Me | Me | Et | nPr | 2-F-4-CHF₂O—Ph |
| I-350 | Me | Me | Me | nPr | nPr | 2-F-4-CHF₂O—Ph |
| I-351 | Me | Me | Me | CH₂CH₂CH₂CH₂ | | 2-F-4-CHF₂O—Ph |
| I-352 | Me | Me | Me | CH₂CH₂CH₂CH₂CH₂ | | 2-F-4-CHF₂O—Ph |
| I-353 | Me | Me | Me | Me | Et | 2-F-5-CHF₂O—Ph |
| I-354 | Me | Me | Me | Me | nPr | 2-F-5-CHF₂O—Ph |
| I-355 | Me | Me | Me | Me | iPr | 2-F-5-CHF₂O—Ph |
| I-356 | Me | Me | Me | Et | Et | 2-F-5-CHF₂O—Ph |
| I-35+ | Me | Me | Me | Et | nPr | 2-F-5-CHF₂O—Ph |
| I-358 | Me | Me | Me | nPr | nPr | 2-F-5-CHF₂O—Ph |
| I-359 | Me | Me | Me | CH₂CH₂CH₂CH₂ | | 2-F-5-CHF₂O—Ph |
| I-360 | Me | Me | Me | CH₂CH₂CH₂CH₂CH₂ | | 2-F-5-CHF₂O—Ph |
| I-361 | Me | Me | Me | Me | Et | 2-F-6-CHF₂O—Ph |
| I-362 | Me | Me | Me | Me | nPr | 2-F-6-CHF₂O—Ph |
| I-363 | Me | Me | Me | Me | iPr | 2-F-6-CHF₂O—Ph |
| I-364 | Me | Me | Me | Et | Et | 2-F-6-CHF₂O—Ph |
| I-365 | Me | Me | Me | Et | nPr | 2-F-6-CHF₂O—Ph |
| I-366 | Me | Me | Me | nPr | nPr | 2-F-6-CHF₂O—Ph |

TABLE 4-continued

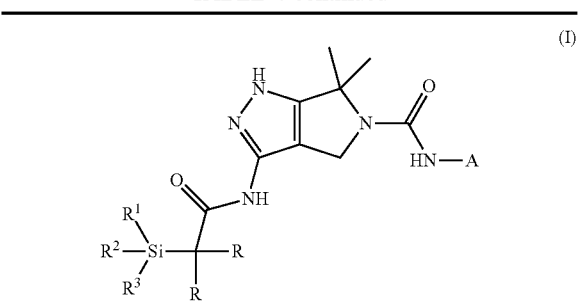

(I)

| Comp. No. | R¹ | R² | R³ | R | R | A |
|---|---|---|---|---|---|---|
| I-36+ | Me | Me | Me | CH₂CH₂CH₂CH₂ | | 2-F-6-CHF₂O—Ph |
| I-368 | Me | Me | Me | CH₂CH₂CH₂CH₂CH₂ | | 2-F-6-CHF₂O—Ph |
| I-369 | Me | Me | Me | Me | Et | 2-F-3-CD₃O—Ph |
| I-370 | Me | Me | Me | Me | nPr | 2-F-3-CD₃O—Ph |
| I-371 | Me | Me | Me | Me | iPr | 2-F-3-CD₃O—Ph |
| I-372 | Me | Me | Me | Et | Et | 2-F-3-CD₃O—Ph |
| I-373 | Me | Me | Me | Et | nPr | 2-F-3-CD₃O—Ph |
| I-374 | Me | Me | Me | nPr | nPr | 2-F-3-CD₃O—Ph |
| I-375 | Me | Me | Me | CH₂CH₂CH₂CH₂ | | 2-F-3-CD₃O—Ph |
| I-376 | Me | Me | Me | CH₂CH₂CH₂CH₂CH₂ | | 2-F-3-CD₃O—Ph |
| I-377 | Me | Me | Me | Me | Et | 2-F-4-CD₃O—Ph |
| I-378 | Me | Me | Me | Me | nPr | 2-F-4-CD₃O—Ph |
| I-379 | Me | Me | Me | Me | iPr | 2-F-4-CD₃O—Ph |
| I-380 | Me | Me | Me | Et | Et | 2-F-4-CD₃O—Ph |
| I-381 | Me | Me | Me | Et | nPr | 2-F-4-CD₃O—Ph |
| I-382 | Me | Me | Me | nPr | nPr | 2-F-4-CD₃O—Ph |
| I-383 | Me | Me | Me | CH₂CH₂CH₂CH₂ | | 2-F-4-CD₃O—Ph |
| I-384 | Me | Me | Me | CH₂CH₂CH₂CH₂CH₂ | | 2-F-4-CD₃O—Ph |
| I-385 | Me | Me | Me | Me | Et | 2-F-5-CD₃O—Ph |
| I-386 | Me | Me | Me | Me | nPr | 2-F-5-CD₃O—Ph |
| I-387 | Me | Me | Me | Me | iPr | 2-F-5-CD₃O—Ph |
| I-388 | Me | Me | Me | Et | Et | 2-F-5-CD₃O—Ph |
| I-389 | Me | Me | Me | Et | nPr | 2-F-5-CD₃O—Ph |
| I-390 | Me | Me | Me | nPr | nPr | 2-F-5-CD₃O—Ph |
| I-391 | Me | Me | Me | CH₂CH₂CH₂CH₂ | | 2-F-5-CD₃O—Ph |
| I-392 | Me | Me | Me | CH₂CH₂CH₂CH₂CH₂ | | 2-F-5-CD₃O—Ph |
| I-393 | Me | Me | Me | Me | Et | 2-F-6-CD₃O—Ph |
| I-394 | Me | Me | Me | Me | nPr | 2-F-6-CD₃O—Ph |
| I-395 | Me | Me | Me | Me | iPr | 2-F-6-CD₃O—Ph |
| I-396 | Me | Me | Me | Et | Et | 2-F-6-CD₃O—Ph |
| I-397 | Me | Me | Me | Et | nPr | 2-F-6-CD₃O—Ph |
| I-398 | Me | Me | Me | nPr | nPr | 2-F-6-CD₃O—Ph |
| I-399 | Me | Me | Me | CH₂CH₂CH₂CH₂ | | 2-F-6-CD₃O—Ph |
| I-400 | Me | Me | Me | CH₂CH₂CH₂CH₂CH₂ | | 2-F-6-CD₃O—Ph |

TABLE 5

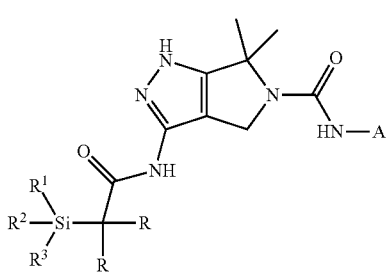

(I)

| Comp. No. | R¹ | R² | R³ | R | R | A |
|---|---|---|---|---|---|---|
| I-401 | Me | Me | Me | Me | Et | 2-Cl-3-F—Ph |
| I-402 | Me | Me | Me | Me | nPr | 2-Cl-3-F—Ph |
| I-403 | Me | Me | Me | Me | iPr | 2-Cl-3-F—Ph |
| I-404 | Me | Me | Me | Et | Et | 2-Cl-3-F—Ph |
| I-405 | Me | Me | Me | Et | nPr | 2-Cl-3-F—Ph |
| I-406 | Me | Me | Me | nPr | nPr | 2-Cl-3-F—Ph |

TABLE 5-continued

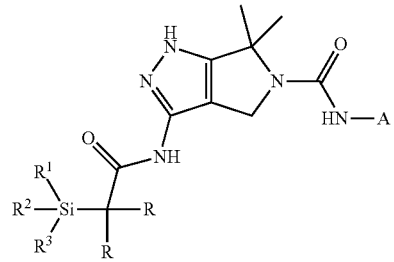

(I)

| Comp. No. | R¹ | R² | R³ | R | R | A |
|---|---|---|---|---|---|---|
| I-407 | Me | Me | Me | CH₂CH₂CH₂CH₂ | | 2-Cl-3-F—Ph |
| I-408 | Me | Me | Me | CH₂CH₂CH₂CH₂CH₂ | | 2-Cl-3-F—Ph |
| I-409 | Me | Me | Me | Me | Et | 2-Cl-4-F—Ph |
| I-410 | Me | Me | Me | Me | nPr | 2-Cl-4-F—Ph |
| I-411 | Me | Me | Me | Me | iPr | 2-Cl-4-F—Ph |
| I-412 | Me | Me | Me | Et | Et | 2-Cl-4-F—Ph |
| I-413 | Me | Me | Me | Et | nPr | 2-Cl-4-F—Ph |
| I-414 | Me | Me | Me | nPr | nPr | 2-Cl-4-F—Ph |
| I-415 | Me | Me | Me | CH₂CH₂CH₂CH₂ | | 2-Cl-4-F—Ph |
| I-416 | Me | Me | Me | CH₂CH₂CH₂CH₂CH₂ | | 2-Cl-4-F—Ph |
| I-417 | Me | Me | Me | Me | Et | 2-Cl-5-F—Ph |
| I-418 | Me | Me | Me | Me | nPr | 2-Cl-5-F—Ph |
| I-419 | Me | Me | Me | Me | iPr | 2-Cl-5-F—Ph |
| I-420 | Me | Me | Me | Et | Et | 2-Cl-5-F—Ph |
| I-421 | Me | Me | Me | Et | nPr | 2-Cl-5-F—Ph |
| I-422 | Me | Me | Me | nPr | nPr | 2-Cl-5-F—Ph |
| I-423 | Me | Me | Me | CH₂CH₂CH₂CH₂ | | 2-Cl-5-F—Ph |
| I-424 | Me | Me | Me | CH₂CH₂CH₂CH₂CH₂ | | 2-Cl-5-F—Ph |
| I-425 | Me | Me | Me | Me | Et | 2,3-diCl—Ph |
| I-426 | Me | Me | Me | Me | nPr | 2,3-diCl—Ph |
| I-427 | Me | Me | Me | Me | iPr | 2,3-diCl—Ph |
| I-428 | Me | Me | Me | Et | Et | 2,3-diCl—Ph |
| I-429 | Me | Me | Me | Et | nPr | 2,3-diCl—Ph |
| I-430 | Me | Me | Me | nPr | nPr | 2,3-diCl—Ph |
| I-431 | Me | Me | Me | CH₂CH₂CH₂CH₂ | | 2,3-diCl—Ph |
| I-432 | Me | Me | Me | CH₂CH₂CH₂CH₂CH₂ | | 2,3-diCl—Ph |
| I-433 | Me | Me | Me | Me | Et | 2,4-diCl—Ph |
| I-434 | Me | Me | Me | Me | nPr | 2,4-diCl—Ph |
| I-435 | Me | Me | Me | Me | iPr | 2,4-diCl—Ph |
| I-436 | Me | Me | Me | Et | Et | 2,4-diCl—Ph |
| I-437 | Me | Me | Me | Et | nPr | 2,4-diCl—Ph |
| I-438 | Me | Me | Me | nPr | nPr | 2,4-diCl—Ph |
| I-439 | Me | Me | Me | CH₂CH₂CH₂CH₂ | | 2,4-diCl—Ph |
| I-440 | Me | Me | Me | CH₂CH₂CH₂CH₂CH₂ | | 2,4-diCl—Ph |
| I-441 | Me | Me | Me | Me | Et | 2,5-diCl—Ph |
| I-442 | Me | Me | Me | Me | nPr | 2,5-diCl—Ph |
| I-443 | Me | Me | Me | Me | iPr | 2,5-diCl—Ph |
| I-444 | Me | Me | Me | Et | Et | 2,5-diCl—Ph |
| I-445 | Me | Me | Me | Et | nPr | 2,5-diCl—Ph |
| I-446 | Me | Me | Me | nPr | nPr | 2,5-diCl—Ph |
| I-447 | Me | Me | Me | CH₂CH₂CH₂CH₂ | | 2,5-diCl—Ph |
| I-448 | Me | Me | Me | CH₂CH₂CH₂CH₂CH₂ | | 2,5-diCl—Ph |
| I-449 | Me | Me | Me | Me | Et | 2,6-diCl—Ph |
| I-450 | Me | Me | Me | Me | nPr | 2,6-diCl—Ph |
| I-451 | Me | Me | Me | Me | iPr | 2,6-diCl—Ph |
| I-452 | Me | Me | Me | Et | Et | 2,6-diCl—Ph |
| I-453 | Me | Me | Me | Et | nPr | 2,6-diCl—Ph |
| I-454 | Me | Me | Me | nPr | nPr | 2,6-diCl—Ph |
| I-455 | Me | Me | Me | CH₂CH₂CH₂CH₂ | | 2,6-diCl—Ph |
| I-456 | Me | Me | Me | CH₂CH₂CH₂CH₂CH₂ | | 2,6-diCl—Ph |
| I-457 | Me | Me | Me | Me | Et | 2-Cl-3-Br—Ph |
| I-458 | Me | Me | Me | Me | nPr | 2-Cl-3-Br—Ph |
| I-459 | Me | Me | Me | Me | iPr | 2-Cl-3-Br—Ph |
| I-460 | Me | Me | Me | Et | Et | 2-Cl-3-Br—Ph |
| I-461 | Me | Me | Me | Et | nPr | 2-Cl-3-Br—Ph |
| I-462 | Me | Me | Me | nPr | nPr | 2-Cl-3-Br—Ph |
| I-463 | Me | Me | Me | CH₂CH₂CH₂CH₂ | | 2-Cl-3-Br—Ph |
| I-464 | Me | Me | Me | CH₂CH₂CH₂CH₂CH₂ | | 2-Cl-3-Br—Ph |
| I-465 | Me | Me | Me | Me | Et | 2-Cl-4-Br—Ph |
| I-466 | Me | Me | Me | Me | nPr | 2-Cl-4-Br—Ph |
| I-467 | Me | Me | Me | Me | iPr | 2-Cl-4-Br—Ph |
| I-468 | Me | Me | Me | Et | Et | 2-Cl-4-Br—Ph |

TABLE 5-continued (I)

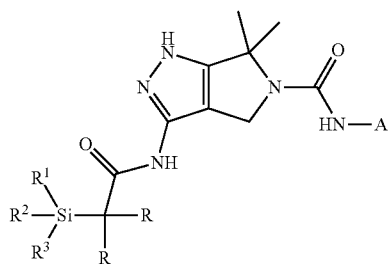

| Comp. No. | R¹ | R² | R³ | R | R | A |
|---|---|---|---|---|---|---|
| I-469 | Me | Me | Me | Et | nPr | 2-Cl-4-Br—Ph |
| I-470 | Me | Me | Me | nPr | nPr | 2-Cl-4-Br—Ph |
| I-471 | Me | Me | Me | CH₂CH₂CH₂CH₂ | | 2-Cl-4-Br—Ph |
| I-472 | Me | Me | Me | CH₂CH₂CH₂CH₂CH₂ | | 2-Cl-4-Br—Ph |
| I-473 | Me | Me | Me | Me | Et | 2-Cl-5-Br—Ph |
| I-474 | Me | Me | Me | Me | nPr | 2-Cl-5-Br—Ph |
| I-475 | Me | Me | Me | Me | iPr | 2-Cl-5-Br—Ph |
| I-476 | Me | Me | Me | Et | Et | 2-Cl-5-Br—Ph |
| I-477 | Me | Me | Me | Et | nPr | 2-Cl-5-Br—Ph |
| I-478 | Me | Me | Me | nPr | nPr | 2-Cl-5-Br—Ph |
| I-479 | Me | Me | Me | CH₂CH₂CH₂CH₂ | | 2-Cl-5-Br—Ph |
| I-480 | Me | Me | Me | CH₂CH₂CH₂CH₂CH₂ | | 2-Cl-5-Br—Ph |
| I-481 | Me | Me | Me | Me | Et | 2-Cl-6-Br—Ph |
| I-482 | Me | Me | Me | Me | nPr | 2-Cl-6-Br—Ph |
| I-483 | Me | Me | Me | Me | iPr | 2-Cl-6-Br—Ph |
| I-484 | Me | Me | Me | Et | Et | 2-Cl-6-Br—Ph |
| I-485 | Me | Me | Me | Et | nPr | 2-Cl-6-Br—Ph |
| I-486 | Me | Me | Me | nPr | nPr | 2-Cl-6-Br—Ph |
| I-487 | Me | Me | Me | CH₂CH₂CH₂CH₂ | | 2-Cl-6-Br—Ph |
| I-488 | Me | Me | Me | CH₂CH₂CH₂CH₂CH₂ | | 2-Cl-6-Br—Ph |
| I-489 | Me | Me | Me | Me | Et | 2-Cl-3-Me—Ph |
| I-490 | Me | Me | Me | Me | nPr | 2-Cl-3-Me—Ph |
| I-491 | Me | Me | Me | Me | iPr | 2-Cl-3-Me—Ph |
| I-492 | Me | Me | Me | Et | Et | 2-Cl-3-Me—Ph |
| I-493 | Me | Me | Me | Et | nPr | 2-Cl-3-Me—Ph |
| I-494 | Me | Me | Me | nPr | nPr | 2-Cl-3-Me—Ph |
| I-495 | Me | Me | Me | CH₂CH₂CH₂CH₂ | | 2-Cl-3-Me—Ph |
| I-496 | Me | Me | Me | CH₂CH₂CH₂CH₂CH₂ | | 2-Cl-3-Me—Ph |
| I-497 | Me | Me | Me | Me | Et | 2-Cl-4-Me—Ph |
| I-498 | Me | Me | Me | Me | nPr | 2-Cl-4-Me—Ph |
| I-499 | Me | Me | Me | Me | iPr | 2-Cl-4-Me—Ph |
| I-500 | Me | Me | Me | Et | Et | 2-Cl-4-Me—Ph |

TABLE 6

(I)

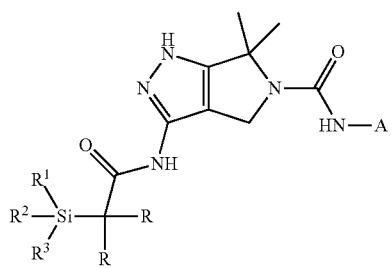

| Comp. No. | R¹ | R² | R³ | R | R | A |
|---|---|---|---|---|---|---|
| I-501 | Me | Me | Me | Et | nPr | 2-Cl-4-Me—Ph |
| I-502 | Me | Me | Me | nPr | nPr | 2-Cl-4-Me—Ph |
| I-503 | Me | Me | Me | CH₂CH₂CH₂CH₂ | | 2-Cl-4-Me—Ph |
| I-504 | Me | Me | Me | CH₂CH₂CH₂CH₂CH₂ | | 2-Cl-4-Me—Ph |
| I-505 | Me | Me | Me | Me | Et | 2-Cl-5-Me—Ph |
| I-506 | Me | Me | Me | Me | nPr | 2-Cl-5-Me—Ph |
| I-507 | Me | Me | Me | Me | iPr | 2-Cl-5-Me—Ph |
| I-508 | Me | Me | Me | Et | Et | 2-Cl-5-Me—Ph |

TABLE 6-continued (I)

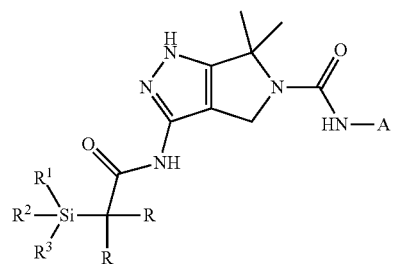

| Comp. No. | R¹ | R² | R³ | R | R | A |
|---|---|---|---|---|---|---|
| I-509 | Me | Me | Me | Et | nPr | 2-Cl-5-Me—Ph |
| I-510 | Me | Me | Me | nPr | nPr | 2-Cl-5-Me—Ph |
| I-511 | Me | Me | Me | CH₂CH₂CH₂CH₂ | | 2-Cl-5-Me—Ph |
| I-512 | Me | Me | Me | CH₂CH₂CH₂CH₂CH₂ | | 2-Cl-5-Me—Ph |
| I-513 | Me | Me | Me | Me | Et | 2-Cl-6-Me—Ph |
| I-514 | Me | Me | Me | Me | nPr | 2-Cl-6-Me—Ph |
| I-515 | Me | Me | Me | Me | iPr | 2-Cl-6-Me—Ph |
| I-516 | Me | Me | Me | Et | Et | 2-Cl-6-Me—Ph |
| I-517 | Me | Me | Me | Et | nPr | 2-Cl-6-Me—Ph |
| I-518 | Me | Me | Me | nPr | nPr | 2-Cl-6-Me—Ph |
| I-519 | Me | Me | Me | CH₂CH₂CH₂CH₂ | | 2-Cl-6-Me—Ph |
| I-520 | Me | Me | Me | CH₂CH₂CH₂CH₂CH₂ | | 2-Cl-6-Me—Ph |
| I-521 | Me | Me | Me | Me | Et | 2-Cl-3-Et—Ph |
| I-522 | Me | Me | Me | Me | nPr | 2-Cl-3-Et—Ph |
| I-523 | Me | Me | Me | Me | iPr | 2-Cl-3-Et—Ph |
| I-524 | Me | Me | Me | Et | Et | 2-Cl-3-Et—Ph |
| I-525 | Me | Me | Me | Et | nPr | 2-Cl-3-Et—Ph |
| I-526 | Me | Me | Me | nPr | nPr | 2-Cl-3-Et—Ph |
| I-527 | Me | Me | Me | CH₂CH₂CH₂CH₂ | | 2-Cl-3-Et—Ph |
| I-528 | Me | Me | Me | CH₂CH₂CH₂CH₂CH₂ | | 2-Cl-3-Et—Ph |
| I-529 | Me | Me | Me | Me | Et | 2-Cl-4-Et—Ph |
| I-530 | Me | Me | Me | Me | nPr | 2-Cl-4-Et—Ph |
| I-531 | Me | Me | Me | Me | iPr | 2-Cl-4-Et—Ph |
| I-532 | Me | Me | Me | Et | Et | 2-Cl-4-Et—Ph |
| I-533 | Me | Me | Me | Et | nPr | 2-Cl-4-Et—Ph |
| I-534 | Me | Me | Me | nPr | nPr | 2-Cl-4-Et—Ph |
| I-535 | Me | Me | Me | CH₂CH₂CH₂CH₂ | | 2-Cl-4-Et—Ph |
| I-536 | Me | Me | Me | CH₂CH₂CH₂CH₂CH₂ | | 2-Cl-4-Et—Ph |
| I-537 | Me | Me | Me | Me | Et | 2-Cl-5-Et—Ph |
| I-538 | Me | Me | Me | Me | nPr | 2-Cl-5-Et—Ph |
| I-539 | Me | Me | Me | Me | iPr | 2-Cl-5-Et—Ph |
| I-540 | Me | Me | Me | Et | Et | 2-Cl-5-Et—Ph |
| I-541 | Me | Me | Me | Et | nPr | 2-Cl-5-Et—Ph |
| I-542 | Me | Me | Me | nPr | nPr | 2-Cl-5-Et—Ph |
| I-543 | Me | Me | Me | CH₂CH₂CH₂CH₂ | | 2-Cl-5-Et—Ph |
| I-544 | Me | Me | Me | CH₂CH₂CH₂CH₂CH₂ | | 2-Cl-5-Et—Ph |
| I-545 | Me | Me | Me | Me | Et | 2-Cl-6-Et—Ph |
| I-546 | Me | Me | Me | Me | nPr | 2-Cl-6-Et—Ph |
| I-547 | Me | Me | Me | Me | iPr | 2-Cl-6-Et—Ph |
| I-548 | Me | Me | Me | Et | Et | 2-Cl-6-Et—Ph |
| I-549 | Me | Me | Me | Et | nPr | 2-Cl-6-Et—Ph |
| I-550 | Me | Me | Me | nPr | nPr | 2-Cl-6-Et—Ph |
| I-551 | Me | Me | Me | CH₂CH₂CH₂CH₂ | | 2-Cl-6-Et—Ph |
| I-552 | Me | Me | Me | CH₂CH₂CH₂CH₂CH₂ | | 2-Cl-6-Et—Ph |
| I-553 | Me | Me | Me | Me | Et | 2-Cl-3-cPr—Ph |
| I-554 | Me | Me | Me | Me | nPr | 2-Cl-3-cPr—Ph |
| I-555 | Me | Me | Me | Me | iPr | 2-Cl-3-cPr—Ph |
| I-556 | Me | Me | Me | Et | Et | 2-Cl-3-cPr—Ph |
| I-557 | Me | Me | Me | Et | nPr | 2-Cl-3-cPr—Ph |
| I-558 | Me | Me | Me | nPr | nPr | 2-Cl-3-cPr—Ph |
| I-559 | Me | Me | Me | CH₂CH₂CH₂CH₂ | | 2-Cl-3-cPr—Ph |
| I-560 | Me | Me | Me | CH₂CH₂CH₂CH₂CH₂ | | 2-Cl-3-cPr—Ph |
| I-561 | Me | Me | Me | Me | Et | 2-Cl-4-cPr—Ph |
| I-562 | Me | Me | Me | Me | nPr | 2-Cl-4-cPr—Ph |
| I-563 | Me | Me | Me | Me | iPr | 2-Cl-4-cPr—Ph |
| I-564 | Me | Me | Me | Et | Et | 2-Cl-4-cPr—Ph |
| I-565 | Me | Me | Me | Et | nPr | 2-Cl-4-cPr—Ph |
| I-566 | Me | Me | Me | nPr | nPr | 2-Cl-4-cPr—Ph |
| I-567 | Me | Me | Me | CH₂CH₂CH₂CH₂ | | 2-Cl-4-cPr—Ph |
| I-568 | Me | Me | Me | CH₂CH₂CH₂CH₂CH₂ | | 2-Cl-4-cPr—Ph |
| I-569 | Me | Me | Me | Me | Et | 2-Cl-5-cPr—Ph |
| I-570 | Me | Me | Me | Me | nPr | 2-Cl-5-cPr—Ph |

TABLE 6-continued

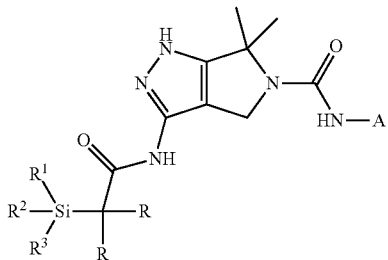

(I)

| Comp. No. | R¹ | R² | R³ | R | R | A |
|---|---|---|---|---|---|---|
| I-571 | Me | Me | Me | Me | iPr | 2-Cl-5-cPr—Ph |
| I-572 | Me | Me | Me | Et | Et | 2-Cl-5-cPr—Ph |
| I-573 | Me | Me | Me | Et | nPr | 2-Cl-5-cPr—Ph |
| I-574 | Me | Me | Me | nPr | nPr | 2-Cl-5-cPr—Ph |
| I-575 | Me | Me | Me | CH₂CH₂CH₂CH₂ | | 2-Cl-5-cPr—Ph |
| I-576 | Me | Me | Me | CH₂CH₂CH₂CH₂CH₂ | | 2-Cl-5-cPr—Ph |
| I-577 | Me | Me | Me | Me | Et | 2-Cl-6-cPr—Ph |
| I-578 | Me | Me | Me | Me | nPr | 2-Cl-6-cPr—Ph |
| I-579 | Me | Me | Me | Me | iPr | 2-Cl-6-cPr—Ph |
| I-580 | Me | Me | Me | Et | Et | 2-Cl-6-cPr—Ph |
| I-581 | Me | Me | Me | Et | nPr | 2-Cl-6-cPr—Ph |
| I-582 | Me | Me | Me | nPr | nPr | 2-Cl-6-cPr—Ph |
| I-583 | Me | Me | Me | CH₂CH₂CH₂CH₂ | | 2-Cl-6-cPr—Ph |
| I-584 | Me | Me | Me | CH₂CH₂CH₂CH₂CH₂ | | 2-Cl-6-cPr—Ph |
| I-585 | Me | Me | Me | Me | Et | 2-Cl-3-CF₃—Ph |
| I-586 | Me | Me | Me | Me | nPr | 2-Cl-3-CF₃—Ph |
| I-587 | Me | Me | Me | Me | iPr | 2-Cl-3-CF₃—Ph |
| I-588 | Me | Me | Me | Et | Et | 2-Cl-3-CF₃—Ph |
| I-589 | Me | Me | Me | Et | nPr | 2-Cl-3-CF₃—Ph |
| I-590 | Me | Me | Me | nPr | nPr | 2-Cl-3-CF₃—Ph |
| I-591 | Me | Me | Me | CH₂CH₂CH₂CH₂ | | 2-Cl-3-CF₃—Ph |
| I-592 | Me | Me | Me | CH₂CH₂CH₂CH₂CH₂ | | 2-Cl-3-CF₃—Ph |
| I-593 | Me | Me | Me | Me | Et | 2-Cl-4-CF₃—Ph |
| I-594 | Me | Me | Me | Me | nPr | 2-Cl-4-CF₃—Ph |
| I-595 | Me | Me | Me | Me | iPr | 2-Cl-4-CF₃—Ph |
| I-596 | Me | Me | Me | Et | Et | 2-Cl-4-CF₃—Ph |
| I-597 | Me | Me | Me | Et | nPr | 2-Cl-4-CF₃—Ph |
| I-598 | Me | Me | Me | nPr | nPr | 2-Cl-4-CF₃—Ph |
| I-599 | Me | Me | Me | CH₂CH₂CH₂CH₂ | | 2-Cl-4-CF₃—Ph |
| I-600 | Me | Me | Me | CH₂CH₂CH₂CH₂CH₂ | | 2-Cl-4-CF₃—Ph |

TABLE 7

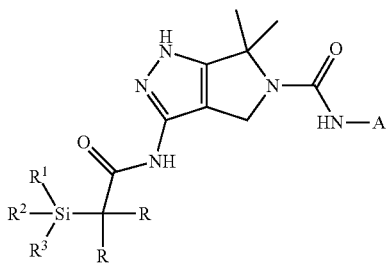

(I)

| Comp. No. | R¹ | R² | R³ | R | R | A |
|---|---|---|---|---|---|---|
| I-601 | Me | Me | Me | Me | Et | 2-Cl-5-CF₃—Ph |
| I-602 | Me | Me | Me | Me | nPr | 2-Cl-5-CF₃—Ph |
| I-603 | Me | Me | Me | Me | iPr | 2-Cl-5-CF₃—Ph |
| I-604 | Me | Me | Me | Et | Et | 2-Cl-5-CF₃—Ph |
| I-605 | Me | Me | Me | Et | nPr | 2-Cl-5-CF₃—Ph |
| I-606 | Me | Me | Me | nPr | nPr | 2-Cl-5-CF₃—Ph |
| I-607 | Me | Me | Me | CH₂CH₂CH₂CH₂ | | 2-Cl-5-CF₃—Ph |
| I-608 | Me | Me | Me | CH₂CH₂CH₂CH₂CH₂ | | 2-Cl-5-CF₃—Ph |
| I-609 | Me | Me | Me | Me | Et | 2-Cl-6-CF₃—Ph |
| I-610 | Me | Me | Me | Me | nPr | 2-Cl-6-CF₃—Ph |

TABLE 7-continued

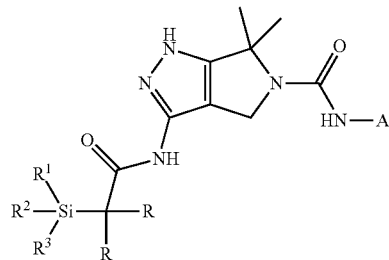

(I)

| Comp. No. | R¹ | R² | R³ | R | R | A |
|---|---|---|---|---|---|---|
| I-611 | Me | Me | Me | Me | iPr | 2-Cl-6-CF₃—Ph |
| I-612 | Me | Me | Me | Et | Et | 2-Cl-6-CF₃—Ph |
| I-613 | Me | Me | Me | Et | nPr | 2-Cl-6-CF₃—Ph |
| I-614 | Me | Me | Me | nPr | nPr | 2-Cl-6-CF₃—Ph |
| I-615 | Me | Me | Me | CH₂CH₂CH₂CH₂ | | 2-Cl-6-CF₃—Ph |
| I-616 | Me | Me | Me | CH₂CH₂CH₂CH₂CH₂ | | 2-Cl-6-CF₃—Ph |
| I-617 | Me | Me | Me | Me | Et | 2-Cl-3-MeO—Ph |
| I-618 | Me | Me | Me | Me | nPr | 2-Cl-3-MeO—Ph |
| I-619 | Me | Me | Me | Me | iPr | 2-Cl-3-MeO—Ph |
| I-620 | Me | Me | Me | Et | Et | 2-Cl-3-MeO—Ph |
| I-621 | Me | Me | Me | Et | nPr | 2-Cl-3-MeO—Ph |
| I-622 | Me | Me | Me | nPr | nPr | 2-Cl-3-MeO—Ph |
| I-623 | Me | Me | Me | CH₂CH₂CH₂CH₂ | | 2-Cl-3-MeO—Ph |
| I-624 | Me | Me | Me | CH₂CH₂CH₂CH₂CH₂ | | 2-Cl-3-MeO—Ph |
| I-625 | Me | Me | Me | Me | Et | 2-Cl-4-MeO—Ph |
| I-626 | Me | Me | Me | Me | nPr | 2-Cl-4-MeO—Ph |
| I-627 | Me | Me | Me | Me | iPr | 2-Cl-4-MeO—Ph |
| I-628 | Me | Me | Me | Et | Et | 2-Cl-4-MeO—Ph |
| I-629 | Me | Me | Me | Et | nPr | 2-Cl-4-MeO—Ph |
| I-630 | Me | Me | Me | nPr | nPr | 2-Cl-4-MeO—Ph |
| I-631 | Me | Me | Me | CH₂CH₂CH₂CH₂ | | 2-Cl-4-MeO—Ph |
| I-632 | Me | Me | Me | CH₂CH₂CH₂CH₂CH₂ | | 2-Cl-4-MeO—Ph |
| I-633 | Me | Me | Me | Me | Et | 2-Cl-5-MeO—Ph |
| I-634 | Me | Me | Me | Me | nPr | 2-Cl-5-MeO—Ph |
| I-635 | Me | Me | Me | Me | iPr | 2-Cl-5-MeO—Ph |
| I-636 | Me | Me | Me | Et | Et | 2-Cl-5-MeO—Ph |
| I-637 | Me | Me | Me | Et | nPr | 2-Cl-5-MeO—Ph |
| I-638 | Me | Me | Me | nPr | nPr | 2-Cl-5-MeO—Ph |
| I-639 | Me | Me | Me | CH₂CH₂CH₂CH₂ | | 2-Cl-5-MeO—Ph |
| I-640 | Me | Me | Me | CH₂CH₂CH₂CH₂CH₂ | | 2-Cl-5-MeO—Ph |
| I-641 | Me | Me | Me | Me | Et | 2-Cl-6-MeO—Ph |
| I-642 | Me | Me | Me | Me | nPr | 2-Cl-6-MeO—Ph |
| I-643 | Me | Me | Me | Me | iPr | 2-Cl-6-MeO—Ph |
| I-644 | Me | Me | Me | Et | Et | 2-Cl-6-MeO—Ph |
| I-645 | Me | Me | Me | Et | nPr | 2-Cl-6-MeO—Ph |
| I-646 | Me | Me | Me | nPr | nPr | 2-Cl-6-MeO—Ph |
| I-647 | Me | Me | Me | CH₂CH₂CH₂CH₂ | | 2-Cl-6-MeO—Ph |
| I-648 | Me | Me | Me | CH₂CH₂CH₂CH₂CH₂ | | 2-Cl-6-MeO—Ph |
| I-649 | Me | Me | Me | Me | Et | 2-Cl-3-CD₃O—Ph |
| I-650 | Me | Me | Me | Me | nPr | 2-Cl-3-CD₃O—Ph |
| I-651 | Me | Me | Me | Me | iPr | 2-Cl-3-CD₃O—Ph |
| I-652 | Me | Me | Me | Et | Et | 2-Cl-3-CD₃O—Ph |
| I-653 | Me | Me | Me | Et | nPr | 2-Cl-3-CD₃O—Ph |
| I-654 | Me | Me | Me | nPr | nPr | 2-Cl-3-CD₃O—Ph |
| I-655 | Me | Me | Me | CH₂CH₂CH₂CH₂ | | 2-Cl-3-CD₃O—Ph |
| I-656 | Me | Me | Me | CH₂CH₂CH₂CH₂CH₂ | | 2-Cl-3-CD₃O—Ph |
| I-657 | Me | Me | Me | Me | Et | 2-Cl-4-CD₃O—Ph |
| I-658 | Me | Me | Me | Me | nPr | 2-Cl-4-CD₃O—Ph |
| I-659 | Me | Me | Me | Me | iPr | 2-Cl-4-CD₃O—Ph |
| I-660 | Me | Me | Me | Et | Et | 2-Cl-4-CD₃O—Ph |
| I-661 | Me | Me | Me | Et | nPr | 2-Cl-4-CD₃O—Ph |
| I-662 | Me | Me | Me | nPr | nPr | 2-Cl-4-CD₃O—Ph |
| I-663 | Me | Me | Me | CH₂CH₂CH₂CH₂ | | 2-Cl-4-CD₃O—Ph |
| I-664 | Me | Me | Me | CH₂CH₂CH₂CH₂CH₂ | | 2-Cl-4-CD₃O—Ph |
| I-665 | Me | Me | Me | Me | Et | 2-Cl-5-CD₃O—Ph |
| I-666 | Me | Me | Me | Me | nPr | 2-Cl-5-CD₃O—Ph |
| I-667 | Me | Me | Me | Me | iPr | 2-Cl-5-CD₃O—Ph |
| I-668 | Me | Me | Me | Et | Et | 2-Cl-5-CD₃O—Ph |
| I-669 | Me | Me | Me | Et | nPr | 2-Cl-5-CD₃O—Ph |
| I-670 | Me | Me | Me | nPr | nPr | 2-Cl-5-CD₃O—Ph |
| I-671 | Me | Me | Me | CH₂CH₂CH₂CH₂ | | 2-Cl-5-CD₃O—Ph |
| I-672 | Me | Me | Me | CH₂CH₂CH₂CH₂CH₂ | | 2-Cl-5-CD₃O—Ph |

TABLE 7-continued (I) Structure with pyrazolo-pyrrole core, silyl-substituted amide, and HN—A urea group.

| Comp. No. | R¹ | R² | R³ | R | R | A |
|---|---|---|---|---|---|---|
| I-673 | Me | Me | Me | Me | Et | 2-Cl-6-CD₃O—Ph |
| I-674 | Me | Me | Me | Me | nPr | 2-Cl-6-CD₃O—Ph |
| I-675 | Me | Me | Me | Me | iPr | 2-Cl-6-CD₃O—Ph |
| I-676 | Me | Me | Me | Et | Et | 2-Cl-6-CD₃O—Ph |
| I-677 | Me | Me | Me | Et | nPr | 2-Cl-6-CD₃O—Ph |
| I-678 | Me | Me | Me | nPr | nPr | 2-Cl-6-CD₃O—Ph |
| I-679 | Me | Me | Me | CH₂CH₂CH₂CH₂ | | 2-Cl-6-CD₃O—Ph |
| I-680 | Me | Me | Me | CH₂CH₂CH₂CH₂CH₂ | | 2-Cl-6-CD₃O—Ph |
| I-681 | Me | Me | Me | Me | Et | 2-Me-3-F—Ph |
| I-682 | Me | Me | Me | Me | nPr | 2-Me-3-F—Ph |
| I-683 | Me | Me | Me | Me | iPr | 2-Me-3-F—Ph |
| I-684 | Me | Me | Me | Et | Et | 2-Me-3-F—Ph |
| I-685 | Me | Me | Me | Et | nPr | 2-Me-3-F—Ph |
| I-686 | Me | Me | Me | nPr | nPr | 2-Me-3-F—Ph |
| I-687 | Me | Me | Me | CH₂CH₂CH₂CH₂ | | 2-Me-3-F—Ph |
| I-688 | Me | Me | Me | CH₂CH₂CH₂CH₂CH₂ | | 2-Me-3-F—Ph |
| I-689 | Me | Me | Me | Me | Et | 2-Me-4-F—Ph |
| I-690 | Me | Me | Me | Me | nPr | 2-Me-4-F—Ph |
| I-691 | Me | Me | Me | Me | iPr | 2-Me-4-F—Ph |
| I-692 | Me | Me | Me | Et | Et | 2-Me-4-F—Ph |
| I-693 | Me | Me | Me | Et | nPr | 2-Me-4-F—Ph |
| I-694 | Me | Me | Me | nPr | nPr | 2-Me-4-F—Ph |
| I-695 | Me | Me | Me | CH₂CH₂CH₂CH₂ | | 2-Me-4-F—Ph |
| I-696 | Me | Me | Me | CH₂CH₂CH₂CH₂CH₂ | | 2-Me-4-F—Ph |
| I-697 | Me | Me | Me | Me | Et | 2-Me-5-F—Ph |
| I-698 | Me | Me | Me | Me | nPr | 2-Me-5-F—Ph |
| I-699 | Me | Me | Me | Me | iPr | 2-Me-5-F—Ph |
| I-700 | Me | Me | Me | Et | Et | 2-Me-5-F—Ph |

TABLE 8

(I) Structure with pyrazolo-pyrrole core, silyl-substituted amide, and HN—A urea group.

| Comp. No. | R¹ | R² | R³ | R | R | A |
|---|---|---|---|---|---|---|
| I-701 | Me | Me | Me | Et | nPr | 2-Me-5-F—Ph |
| I-702 | Me | Me | Me | nPr | nPr | 2-Me-5-F—Ph |
| I-703 | Me | Me | Me | CH₂CH₂CH₂CH₂ | | 2-Me-5-F—Ph |
| I-704 | Me | Me | Me | CH₂CH₂CH₂CH₂CH₂ | | 2-Me-5-F—Ph |
| I-705 | Me | Me | Me | Me | Et | 2,3-diMe—Ph |
| I-706 | Me | Me | Me | Me | nPr | 2,3-diMe—Ph |
| I-707 | Me | Me | Me | Me | iPr | 2,3-diMe—Ph |
| I-708 | Me | Me | Me | Et | Et | 2,3-diMe—Ph |
| I-709 | Me | Me | Me | Et | nPr | 2,3-diMe—Ph |
| I-710 | Me | Me | Me | nPr | nPr | 2,3-diMe—Ph |
| I-711 | Me | Me | Me | CH₂CH₂CH₂CH₂ | | 2,3-diMe—Ph |
| I-712 | Me | Me | Me | CH₂CH₂CH₂CH₂CH₂ | | 2,3-diMe—Ph |
| I-713 | Me | Me | Me | Me | Et | 2,5-diMe—Ph |
| I-714 | Me | Me | Me | Me | nPr | 2,5-diMe—Ph |
| I-715 | Me | Me | Me | Me | iPr | 2,5-diMe—Ph |
| I-716 | Me | Me | Me | Et | Et | 2,5-diMe—Ph |
| I-717 | Me | Me | Me | Et | nPr | 2,5-diMe—Ph |
| I-718 | Me | Me | Me | nPr | nPr | 2,5-diMe—Ph |
| I-719 | Me | Me | Me | CH₂CH₂CH₂CH₂ | | 2,5-diMe—Ph |
| I-720 | Me | Me | Me | CH₂CH₂CH₂CH₂CH₂ | | 2,5-diMe—Ph |
| I-721 | Me | Me | Me | Me | Et | 2,6-diMe—Ph |
| I-722 | Me | Me | Me | Me | nPr | 2,6-diMe—Ph |
| I-723 | Me | Me | Me | Me | iPr | 2,6-diMe—Ph |
| I-724 | Me | Me | Me | Et | Et | 2,6-diMe—Ph |
| I-725 | Me | Me | Me | Et | nPr | 2,6-diMe—Ph |
| I-726 | Me | Me | Me | nPr | nPr | 2,6-diMe—Ph |
| I-727 | Me | Me | Me | CH₂CH₂CH₂CH₂ | | 2,6-diMe—Ph |
| I-728 | Me | Me | Me | CH₂CH₂CH₂CH₂CH₂ | | 2,6-diMe—Ph |
| I-729 | Me | Me | Me | Me | Et | 2-Me-3-Et—Ph |
| I-730 | Me | Me | Me | Me | nPr | 2-Me-3-Et—Ph |
| I-731 | Me | Me | Me | Me | iPr | 2-Me-3-Et—Ph |
| I-732 | Me | Me | Me | Et | Et | 2-Me-3-Et—Ph |
| I-733 | Me | Me | Me | Et | nPr | 2-Me-3-Et—Ph |
| I-734 | Me | Me | Me | nPr | nPr | 2-Me-3-Et—Ph |
| I-735 | Me | Me | Me | CH₂CH₂CH₂CH₂ | | 2-Me-3-Et—Ph |
| I-736 | Me | Me | Me | CH₂CH₂CH₂CH₂CH₂ | | 2-Me-3-Et—Ph |
| I-737 | Me | Me | Me | Me | Et | 2-Me-4-Et—Ph |
| I-738 | Me | Me | Me | Me | nPr | 2-Me-4-Et—Ph |
| I-739 | Me | Me | Me | Me | iPr | 2-Me-4-Et—Ph |
| I-740 | Me | Me | Me | Et | Et | 2-Me-4-Et—Ph |
| I-741 | Me | Me | Me | Et | nPr | 2-Me-4-Et—Ph |
| I-742 | Me | Me | Me | nPr | nPr | 2-Me-4-Et—Ph |
| I-743 | Me | Me | Me | CH₂CH₂CH₂CH₂ | | 2-Me-4-Et—Ph |
| I-744 | Me | Me | Me | CH₂CH₂CH₂CH₂CH₂ | | 2-Me-4-Et—Ph |
| I-745 | Me | Me | Me | Me | Et | 2-Me-5-Et—Ph |
| I-746 | Me | Me | Me | Me | nPr | 2-Me-5-Et—Ph |
| I-747 | Me | Me | Me | Me | iPr | 2-Me-5-Et—Ph |
| I-748 | Me | Me | Me | Et | Et | 2-Me-5-Et—Ph |
| I-749 | Me | Me | Me | Et | nPr | 2-Me-5-Et—Ph |
| I-750 | Me | Me | Me | nPr | nPr | 2-Me-5-Et—Ph |
| I-751 | Me | Me | Me | CH₂CH₂CH₂CH₂ | | 2-Me-5-Et—Ph |
| I-752 | Me | Me | Me | CH₂CH₂CH₂CH₂CH₂ | | 2-Me-5-Et—Ph |
| I-753 | Me | Me | Me | Me | Et | 2-Me-6-Et—Ph |
| I-754 | Me | Me | Me | Me | nPr | 2-Me-6-Et—Ph |
| I-755 | Me | Me | Me | Me | iPr | 2-Me-6-Et—Ph |
| I-756 | Me | Me | Me | Et | Et | 2-Me-6-Et—Ph |
| I-757 | Me | Me | Me | Et | nPr | 2-Me-6-Et—Ph |
| I-758 | Me | Me | Me | nPr | nPr | 2-Me-6-Et—Ph |
| I-759 | Me | Me | Me | CH₂CH₂CH₂CH₂ | | 2-Me-6-Et—Ph |
| I-760 | Me | Me | Me | CH₂CH₂CH₂CH₂CH₂ | | 2-Me-6-Et—Ph |
| I-761 | Me | Me | Me | Me | Et | 2,3,6-triF—Ph |
| I-762 | Me | Me | Me | Me | nPr | 2,3,6-triF—Ph |
| I-763 | Me | Me | Me | Me | iPr | 2,3,6-triF—Ph |
| I-764 | Me | Me | Me | Et | Et | 2,3,6-triF—Ph |
| I-765 | Me | Me | Me | Et | nPr | 2,3,6-triF—Ph |
| I-766 | Me | Me | Me | nPr | nPr | 2,3,6-triF—Ph |
| I-767 | Me | Me | Me | CH₂CH₂CH₂CH₂ | | 2,3,6-triF—Ph |
| I-768 | Me | Me | Me | CH₂CH₂CH₂CH₂CH₂ | | 2,3,6-triF—Ph |
| I-769 | Me | Me | Me | Me | Et | 2,4,6-triF—Ph |
| I-770 | Me | Me | Me | Me | nPr | 2,4,6-triF—Ph |
| I-771 | Me | Me | Me | Me | iPr | 2,4,6-triF—Ph |
| I-772 | Me | Me | Me | Et | Et | 2,4,6-triF—Ph |
| I-773 | Me | Me | Me | Et | nPr | 2,4,6-triF—Ph |
| I-774 | Me | Me | Me | nPr | nPr | 2,4,6-triF—Ph |

TABLE 8-continued (I)

| Comp. No. | R¹ | R² | R³ | R | R | A |
|---|---|---|---|---|---|---|
| I-775 | Me | Me | Me | CH₂CH₂CH₂CH₂ | | 2,4,6-triF—Ph |
| I-776 | Me | Me | Me | CH₂CH₂CH₂CH₂CH₂ | | 2,4,6-triF—Ph |
| I-777 | Me | Me | Me | Me | Et | 2,6-diF-3-Me—Ph |
| I-778 | Me | Me | Me | Me | nPr | 2,6-diF-3-Me—Ph |
| I-779 | Me | Me | Me | Me | iPr | 2,6-diF-3-Me—Ph |
| I-780 | Me | Me | Me | Et | Et | 2,6-diF-3-Me—Ph |
| I-781 | Me | Me | Me | Et | nPr | 2,6-diF-3-Me—Ph |
| I-782 | Me | Me | Me | nPr | nPr | 2,6-diF-3-Me—Ph |
| I-783 | Me | Me | Me | CH₂CH₂CH₂CH₂ | | 2,6-diF-3-Me—Ph |
| I-784 | Me | Me | Me | CH₂CH₂CH₂CH₂CH₂ | | 2,6-diF-3-Me—Ph |
| I-785 | Me | Me | Me | Me | Et | 2,6-diF-3-MeO—Ph |
| I-786 | Me | Me | Me | Me | nPr | 2,6-diF-3-MeO—Ph |
| I-787 | Me | Me | Me | Me | iPr | 2,6-diF-3-MeO—Ph |
| I-788 | Me | Me | Me | Et | Et | 2,6-diF-3-MeO—Ph |
| I-789 | Me | Me | Me | Et | nPr | 2,6-diF-3-MeO—Ph |
| I-790 | Me | Me | Me | nPr | nPr | 2,6-diF-3-MeO—Ph |
| I-791 | Me | Me | Me | CH₂CH₂CH₂CH₂ | | 2,6-diF-3-MeO—Ph |
| I-792 | Me | Me | Me | CH₂CH₂CH₂CH₂CH₂ | | 2,6-diF-3-MeO—Ph |
| I-793 | Me | Me | Me | Me | Et | 2,6-diF-4-MeO—Ph |
| I-794 | Me | Me | Me | Me | nPr | 2,6-diF-4-MeO—Ph |
| I-795 | Me | Me | Me | Me | iPr | 2,6-diF-4-MeO—Ph |
| I-796 | Me | Me | Me | Et | Et | 2,6-diF-4-MeO—Ph |
| I-797 | Me | Me | Me | Et | nPr | 2,6-diF-4-MeO—Ph |
| I-798 | Me | Me | Me | nPr | nPr | 2,6-diF-4-MeO—Ph |
| I-799 | Me | Me | Me | CH₂CH₂CH₂CH₂ | | 2,6-diF-4-MeO—Ph |
| I-800 | Me | Me | Me | CH₂CH₂CH₂CH₂CH₂ | | 2,6-diF-4-MeO—Ph |

TABLE 9

(I)

| Comp. No. | R¹ | R² | R³ | R | R | A |
|---|---|---|---|---|---|---|
| I-801 | Me | Me | Me | Me | Et | 2-F-3-Br-6-Cl—Ph |
| I-802 | Me | Me | Me | Me | nPr | 2-F-3-Br-6-Cl—Ph |
| I-803 | Me | Me | Me | Me | iPr | 2-F-3-Br-6-Cl—Ph |
| I-804 | Me | Me | Me | Et | Et | 2-F-3-Br-6-Cl—Ph |
| I-805 | Me | Me | Me | Et | nPr | 2-F-3-Br-6-Cl—Ph |
| I-806 | Me | Me | Me | nPr | nPr | 2-F-3-Br-6-Cl—Ph |
| I-807 | Me | Me | Me | CH₂CH₂CH₂CH₂ | | 2-F-3-Br-6-Cl—Ph |
| I-808 | Me | Me | Me | CH₂CH₂CH₂CH₂CH₂ | | 2-F-3-Br-6-Cl—Ph |
| I-809 | Me | Me | Me | Me | Et | 2-F-3-Me-6-Cl—Ph |
| I-810 | Me | Me | Me | Me | nPr | 2-F-3-Me-6-Cl—Ph |
| I-811 | Me | Me | Me | Me | iPr | 2-F-3-Me-6-Cl—Ph |
| I-812 | Me | Me | Me | Et | Et | 2-F-3-Me-6-Cl—Ph |
| I-813 | Me | Me | Me | Et | nPr | 2-F-3-Me-6-Cl—Ph |
| I-814 | Me | Me | Me | nPr | nPr | 2-F-3-Me-6-Cl—Ph |

TABLE 9-continued (I)

| Comp. No. | R¹ | R² | R³ | R | R | A |
|---|---|---|---|---|---|---|
| I-815 | Me | Me | Me | CH₂CH₂CH₂CH₂ | | 2-F-3-Me-6-Cl—Ph |
| I-816 | Me | Me | Me | CH₂CH₂CH₂CH₂CH₂ | | 2-F-3-Me-6-Cl—Ph |
| I-817 | Me | Me | Me | Me | Et | 2-F-4-Me-6-Cl—Ph |
| I-818 | Me | Me | Me | Me | nPr | 2-F-4-Me-6-Cl—Ph |
| I-819 | Me | Me | Me | Me | iPr | 2-F-4-Me-6-Cl—Ph |
| I-820 | Me | Me | Me | Et | Et | 2-F-4-Me-6-Cl—Ph |
| I-821 | Me | Me | Me | Et | nPr | 2-F-4-Me-6-Cl—Ph |
| I-822 | Me | Me | Me | nPr | nPr | 2-F-4-Me-6-Cl—Ph |
| I-823 | Me | Me | Me | CH₂CH₂CH₂CH₂ | | 2-F-4-Me-6-Cl—Ph |
| I-824 | Me | Me | Me | CH₂CH₂CH₂CH₂CH₂ | | 2-F-4-Me-6-Cl—Ph |
| I-825 | Me | Me | Me | Me | Et | 2-Cl-3-Br-6-F—Ph |
| I-826 | Me | Me | Me | Me | nPr | 2-Cl-3-Br-6-F—Ph |
| I-827 | Me | Me | Me | Me | iPr | 2-Cl-3-Br-6-F—Ph |
| I-828 | Me | Me | Me | Et | Et | 2-Cl-3-Br-6-F—Ph |
| I-829 | Me | Me | Me | Et | nPr | 2-Cl-3-Br-6-F—Ph |
| I-830 | Me | Me | Me | nPr | nPr | 2-Cl-3-Br-6-F—Ph |
| I-831 | Me | Me | Me | CH₂CH₂CH₂CH₂ | | 2-Cl-3-Br-6-F—Ph |
| I-832 | Me | Me | Me | CH₂CH₂CH₂CH₂CH₂ | | 2-Cl-3-Br-6-F—Ph |
| I-833 | Me | Me | Me | Me | Et | 2-Cl-3-Me-6-F—Ph |
| I-834 | Me | Me | Me | Me | nPr | 2-Cl-3-Me-6-F—Ph |
| I-835 | Me | Me | Me | Me | iPr | 2-Cl-3-Me-6-F—Ph |
| I-836 | Me | Me | Me | Et | Et | 2-Cl-3-Me-6-F—Ph |
| I-837 | Me | Me | Me | Et | nPr | 2-Cl-3-Me-6-F—Ph |
| I-838 | Me | Me | Me | nPr | nPr | 2-Cl-3-Me-6-F—Ph |
| I-839 | Me | Me | Me | CH₂CH₂CH₂CH₂ | | 2-Cl-3-Me-6-F—Ph |
| I-840 | Me | Me | Me | CH₂CH₂CH₂CH₂CH₂ | | 2-Cl-3-Me-6-F—Ph |
| I-841 | Me | Me | Me | Me | Et | 2-Cl-3-MeO-6-F—Ph |
| I-842 | Me | Me | Me | Me | nPr | 2-Cl-3-MeO-6-F—Ph |
| I-843 | Me | Me | Me | Me | iPr | 2-Cl-3-MeO-6-F—Ph |
| I-844 | Me | Me | Me | Et | Et | 2-Cl-3-MeO-6-F—Ph |
| I-845 | Me | Me | Me | Et | nPr | 2-Cl-3-MeO-6-F—Ph |
| I-846 | Me | Me | Me | nPr | nPr | 2-Cl-3-MeO-6-F—Ph |
| I-847 | Me | Me | Me | CH₂CH₂CH₂CH₂ | | 2-Cl-3-MeO-6-F—Ph |
| I-848 | Me | Me | Me | CH₂CH₂CH₂CH₂CH₂ | | 2-Cl-3-MeO-6-F—Ph |
| I-849 | Me | Me | Me | Me | Et | 2-Cl-3-F-6-Me—Ph |
| I-850 | Me | Me | Me | Me | nPr | 2-Cl-3-F-6-Me—Ph |
| I-851 | Me | Me | Me | Me | iPr | 2-Cl-3-F-6-Me—Ph |
| I-852 | Me | Me | Me | Et | Et | 2-Cl-3-F-6-Me—Ph |
| I-853 | Me | Me | Me | Et | nPr | 2-Cl-3-F-6-Me—Ph |
| I-854 | Me | Me | Me | nPr | nPr | 2-Cl-3-F-6-Me—Ph |
| I-855 | Me | Me | Me | CH₂CH₂CH₂CH₂ | | 2-Cl-3-F-6-Me—Ph |
| I-856 | Me | Me | Me | CH₂CH₂CH₂CH₂CH₂ | | 2-Cl-3-F-6-Me—Ph |
| I-857 | Me | Me | Me | Me | Et | 2-Cl-4-F-6-Me—Ph |
| I-858 | Me | Me | Me | Me | nPr | 2-Cl-4-F-6-Me—Ph |
| I-859 | Me | Me | Me | Me | iPr | 2-Cl-4-F-6-Me—Ph |
| I-860 | Me | Me | Me | Et | Et | 2-Cl-4-F-6-Me—Ph |
| I-861 | Me | Me | Me | Et | nPr | 2-Cl-4-F-6-Me—Ph |
| I-862 | Me | Me | Me | nPr | nPr | 2-Cl-4-F-6-Me—Ph |
| I-863 | Me | Me | Me | CH₂CH₂CH₂CH₂ | | 2-Cl-4-F-6-Me—Ph |
| I-864 | Me | Me | Me | CH₂CH₂CH₂CH₂CH₂ | | 2-Cl-4-F-6-Me—Ph |
| I-865 | Me | Me | Me | Me | Et | 2,3-diCl-6-Me—Ph |
| I-866 | Me | Me | Me | Me | nPr | 2,3-diCl-6-Me—Ph |
| I-867 | Me | Me | Me | Me | iPr | 2,3-diCl-6-Me—Ph |
| I-868 | Me | Me | Me | Et | Et | 2,3-diCl-6-Me—Ph |
| I-869 | Me | Me | Me | Et | nPr | 2,3-diCl-6-Me—Ph |
| I-870 | Me | Me | Me | nPr | nPr | 2,3-diCl-6-Me—Ph |
| I-871 | Me | Me | Me | CH₂CH₂CH₂CH₂ | | 2,3-diCl-6-Me—Ph |
| I-872 | Me | Me | Me | CH₂CH₂CH₂CH₂CH₂ | | 2,3-diCl-6-Me—Ph |
| I-873 | Me | Me | Me | Me | Et | 2,4-diCl-6-Me—Ph |
| I-874 | Me | Me | Me | Me | nPr | 2,4-diCl-6-Me—Ph |
| I-875 | Me | Me | Me | Me | iPr | 2,4-diCl-6-Me—Ph |
| I-876 | Me | Me | Me | Et | Et | 2,4-diCl-6-Me—Ph |

TABLE 9-continued

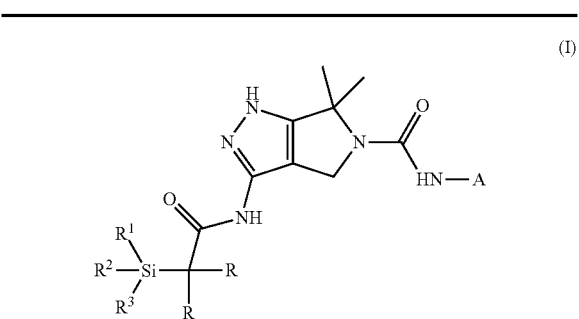

(I)

| Comp. No. | R¹ | R² | R³ | R | R | A |
|---|---|---|---|---|---|---|
| I-877 | Me | Me | Me | Et | nPr | 2,4-diCl-6-Me—Ph |
| I-878 | Me | Me | Me | nPr | nPr | 2,4-diCl-6-Me—Ph |
| I-879 | Me | Me | Me | CH₂CH₂CH₂CH₂ | | 2,4-diCl-6-Me—Ph |
| I-880 | Me | Me | Me | CH₂CH₂CH₂CH₂CH₂ | | 2,4-diCl-6-Me—Ph |
| I-881 | Me | Me | Me | Me | Et | 2-Cl-3-Br-6-Me—Ph |
| I-882 | Me | Me | Me | Me | nPr | 2-Cl-3-Br-6-Me—Ph |
| I-883 | Me | Me | Me | Me | iPr | 2-Cl-3-Br-6-Me—Ph |
| I-884 | Me | Me | Me | Et | Et | 2-Cl-3-Br-6-Me—Ph |
| I-885 | Me | Me | Me | Et | nPr | 2-Cl-3-Br-6-Me—Ph |
| I-886 | Me | Me | Me | nPr | nPr | 2-Cl-3-Br-6-Me—Ph |
| I-887 | Me | Me | Me | CH₂CH₂CH₂CH₂ | | 2-Cl-3-Br-6-Me—Ph |
| I-888 | Me | Me | Me | CH₂CH₂CH₂CH₂CH₂ | | 2-Cl-3-Br-6-Me—Ph |
| I-889 | Me | Me | Me | Me | Et | 2-Cl-3,6-diMe—Ph |
| I-890 | Me | Me | Me | Me | nPr | 2-Cl-3,6-diMe—Ph |
| I-891 | Me | Me | Me | Me | iPr | 2-Cl-3,6-diMe—Ph |
| I-892 | Me | Me | Me | Et | Et | 2-Cl-3,6-diMe—Ph |
| I-893 | Me | Me | Me | Et | nPr | 2-Cl-3,6-diMe—Ph |
| I-894 | Me | Me | Me | nPr | nPr | 2-Cl-3,6-diMe—Ph |
| I-895 | Me | Me | Me | CH₂CH₂CH₂CH₂ | | 2-Cl-3,6-diMe—Ph |
| I-896 | Me | Me | Me | CH₂CH₂CH₂CH₂CH₂ | | 2-Cl-3,6-diMe—Ph |
| I-897 | Me | Me | Me | Me | Et | 2-Cl-4,6-diMe—Ph |
| I-898 | Me | Me | Me | Me | nPr | 2-Cl-4,6-diMe—Ph |
| I-899 | Me | Me | Me | Me | iPr | 2-Cl-4,6-diMe—Ph |
| I-900 | Me | Me | Me | Et | Et | 2-Cl-4,6-diMe—Ph |

TABLE 10

(I)

| Comp. No. | R¹ | R² | R³ | R | R | A |
|---|---|---|---|---|---|---|
| I-901 | Me | Me | Me | Et | nPr | 2-Cl-4,6-diMe—Ph |
| I-902 | Me | Me | Me | nPr | nPr | 2-Cl-4,6-diMe—Ph |
| I-903 | Me | Me | Me | CH₂CH₂CH₂CH₂ | | 2-Cl-4,6-diMe—Ph |
| I-904 | Me | Me | Me | CH₂CH₂CH₂CH₂CH₂ | | 2-Cl-4,6-diMe—Ph |

TABLE 11

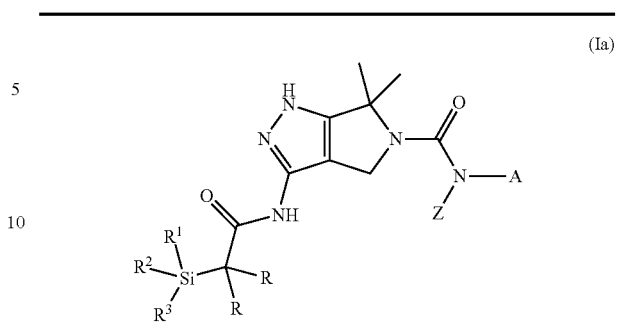

(Ia)

| Comp. No. | R¹ | R² | R³ | R | R | A | Z |
|---|---|---|---|---|---|---|---|
| I-905 | Me | Me | Me | Me | Me | Ph | Me |
| I-906 | Me | Me | Me | Me | Me | 2-F—Ph | Me |
| I-907 | Me | Me | Me | Me | Me | 2-Me—Ph | Me |
| I-908 | Me | Me | Me | Me | Me | 2-Cl-6-Me—Ph | Me |
| I-909 | Me | Me | Me | Me | Me | 2-Me-6-F—Ph | Me |
| I-910 | Me | Me | Me | Me | Me | 2,5-diMe—Ph | Me |
| I-911 | Me | Me | Me | Me | Me | 2-Cl-6-F—Ph | Me |
| I-912 | Me | Me | Me | Me | Me | 2-Br-6-Me—Ph | Me |
| I-913 | Me | Me | Me | Me | Me | 2-F-3,6-diMe—Ph | Me |
| I-914 | Me | Me | Me | Me | Me | 6-F-benzofuran-7-yl | Me |
| I-915 | Me | Me | Me | Me | Me | Ph | Et |
| I-916 | Me | Me | Me | Me | Me | 2-F—Ph | Et |
| I-917 | Me | Me | Me | Me | Me | 2-Me—Ph | Et |
| I-918 | Me | Me | Me | Me | Me | 2-Cl-6-Me—Ph | Et |
| I-919 | Me | Me | Me | Me | Me | 2-Me-6-F—Ph | Et |
| I-920 | Me | Me | Me | Me | Me | 2,5-diMe—Ph | Et |
| I-921 | Me | Me | Me | Me | Me | 2-Cl-6-F—Ph | Et |
| I-922 | Me | Me | Me | Me | Me | 2-Br-6-Me—Ph | Et |
| I-923 | Me | Me | Me | Me | Me | 2-F-3,6-diMe—Ph | Et |
| I-924 | Me | Me | Me | Me | Me | 6-F-benzofuran-7-yl | Et |
| I-925 | Me | Me | Me | Me | Me | Ph | iPr |
| I-926 | Me | Me | Me | Me | Me | 2-F—Ph | iPr |
| I-927 | Me | Me | Me | Me | Me | 2-Me—Ph | iPr |
| I-928 | Me | Me | Me | Me | Me | 2-Cl-6-Me—Ph | iPr |
| I-929 | Me | Me | Me | Me | Me | 2-Me-6-F—Ph | iPr |
| I-930 | Me | Me | Me | Me | Me | 2,5-diMe—Ph | iPr |
| I-931 | Me | Me | Me | Me | Me | 2-Cl-6-F—Ph | iPr |
| I-932 | Me | Me | Me | Me | Me | 2-Br-6-Me—Ph | iPr |
| I-933 | Me | Me | Me | Me | Me | 2-F-3,6-diMe—Ph | iPr |
| I-934 | Me | Me | Me | Me | Me | 6-F-benzofuran-7-yl | iPr |
| I-935 | Me | Me | Me | CH₂CH₂ | | Ph | Me |
| I-936 | Me | Me | Me | CH₂CH₂ | | 2-F—Ph | Me |
| I-937 | Me | Me | Me | CH₂CH₂ | | 2-Me—Ph | Me |
| I-938 | Me | Me | Me | CH₂CH₂ | | 2-Cl-6-Me—Ph | Me |
| I-939 | Me | Me | Me | CH₂CH₂ | | 2-Me-6-F—Ph | Me |
| I-940 | Me | Me | Me | CH₂CH₂ | | 2,5-diMe—Ph | Me |
| I-941 | Me | Me | Me | CH₂CH₂ | | 2-Cl-6-F—Ph | Me |
| I-942 | Me | Me | Me | CH₂CH₂ | | 2-Br-6-Me—Ph | Me |
| I-943 | Me | Me | Me | CH₂CH₂ | | 2-F-3,6-diMe—Ph | Me |
| I-944 | Me | Me | Me | CH₂CH₂ | | 6-F-benzofuran-7-yl | Me |
| I-945 | Me | Me | Me | CH₂CH₂ | | Ph | Et |
| I-946 | Me | Me | Me | CH₂CH₂ | | 2-F—Ph | Et |
| I-947 | Me | Me | Me | CH₂CH₂ | | 2-Me—Ph | Et |
| I-948 | Me | Me | Me | CH₂CH₂ | | 2-Cl-6-Me—Ph | Et |
| I-949 | Me | Me | Me | CH₂CH₂ | | 2-Me-6-F—Ph | Et |

TABLE 12

(Ia)

| Comp. No. | R¹ | R² | R³ | R | R | A | Z |
|---|---|---|---|---|---|---|---|
| I-950 | Me | Me | Me | CH₂CH₂ | | 2,5-diMe—Ph | Et |
| I-951 | Me | Me | Me | CH₂CH₂ | | 2-Cl-6-F—Ph | Et |
| I-952 | Me | Me | Me | CH₂CH₂ | | 2-Br-6-Me—Ph | Et |
| I-953 | Me | Me | Me | CH₂CH₂ | | 2-F-3,6-diMe—Ph | Et |
| I-954 | Me | Me | Me | CH₂CH₂ | | 6-F-benzofuran-7-yl | Et |
| I-955 | Me | Me | Me | CH₂CH₂ | | Ph | iPr |
| I-956 | Me | Me | Me | CH₂CH₂ | | 2-F—Ph | iPr |
| I-957 | Me | Me | Me | CH₂CH₂ | | 2-Me—Ph | iPr |
| I-958 | Me | Me | Me | CH₂CH₂ | | 2-Cl-6-Me—Ph | iPr |
| I-959 | Me | Me | Me | CH₂CH₂ | | 2-Me-6-F—Ph | iPr |
| I-960 | Me | Me | Me | CH₂CH₂ | | 2,5-diMe—Ph | iPr |
| I-961 | Me | Me | Me | CH₂CH₂ | | 2-Cl-6-F—Ph | iPr |
| I-962 | Me | Me | Me | CH₂CH₂ | | 2-Br-6-Me—Ph | iPr |
| I-963 | Me | Me | Me | CH₂CH₂ | | 2-F-3,6-diMe—Ph | iPr |
| I-964 | Me | Me | Me | CH₂CH₂ | | 6-F-benzofuran-7-yl | iPr |
| I-965 | Me | Me | Me | CH₂CH₂CH₂ | | Ph | Me |
| I-966 | Me | Me | Me | CH₂CH₂CH₂ | | 2-F—Ph | Me |
| I-967 | Me | Me | Me | CH₂CH₂CH₂ | | 2-Me—Ph | Me |
| I-968 | Me | Me | Me | CH₂CH₂CH₂ | | 2-Cl-6-Me—Ph | Me |
| I-969 | Me | Me | Me | CH₂CH₂CH₂ | | 2-Me-6-F—Ph | Me |
| I-970 | Me | Me | Me | CH₂CH₂CH₂ | | 2,5-diMe—Ph | Me |
| I-971 | Me | Me | Me | CH₂CH₂CH₂ | | 2-Cl-6-F—Ph | Me |
| I-972 | Me | Me | Me | CH₂CH₂CH₂ | | 2-Br-6-Me—Ph | Me |
| I-973 | Me | Me | Me | CH₂CH₂CH₂ | | 2-F-3,6-diMe—Ph | Me |
| I-974 | Me | Me | Me | CH₂CH₂CH₂ | | 6-F-benzofuran-7-yl | Me |
| I-975 | Me | Me | Me | CH₂CH₂CH₂ | | Ph | Et |
| I-976 | Me | Me | Me | CH₂CH₂CH₂ | | 2-F—Ph | Et |
| I-977 | Me | Me | Me | CH₂CH₂CH₂ | | 2-Me—Ph | Et |
| I-978 | Me | Me | Me | CH₂CH₂CH₂ | | 2-Cl-6-Me—Ph | Et |
| I-979 | Me | Me | Me | CH₂CH₂CH₂ | | 2-Me-6-F—Ph | Et |
| I-980 | Me | Me | Me | CH₂CH₂CH₂ | | 2,5-diMe—Ph | Et |
| I-981 | Me | Me | Me | CH₂CH₂CH₂ | | 2-Cl-6-F—Ph | Et |
| I-982 | Me | Me | Me | CH₂CH₂CH₂ | | 2-Br-6-Me—Ph | Et |
| I-983 | Me | Me | Me | CH₂CH₂CH₂ | | 2-F-3,6-diMe—Ph | Et |
| I-984 | Me | Me | Me | CH₂CH₂CH₂ | | 6-F-benzofuran-7-yl | Et |
| I-985 | Me | Me | Me | CH₂CH₂CH₂ | | Ph | iPr |
| I-986 | Me | Me | Me | CH₂CH₂CH₂ | | 2-F—Ph | iPr |
| I-987 | Me | Me | Me | CH₂CH₂CH₂ | | 2-Me—Ph | iPr |
| I-988 | Me | Me | Me | CH₂CH₂CH₂ | | 2-Cl-6-Me—Ph | iPr |
| I-989 | Me | Me | Me | CH₂CH₂CH₂ | | 2-Me-6-F—Ph | iPr |
| I-990 | Me | Me | Me | CH₂CH₂CH₂ | | 2,5-diMe—Ph | iPr |
| I-991 | Me | Me | Me | CH₂CH₂CH₂ | | 2-Cl-6-F—Ph | iPr |
| I-992 | Me | Me | Me | CH₂CH₂CH₂ | | 2-Br-6-Me—Ph | iPr |
| I-993 | Me | Me | Me | CH₂CH₂CH₂ | | 2-F-3,6-diMe—Ph | iPr |
| I-994 | Me | Me | Me | CH₂CH₂CH₂ | | 6-F-benzofuran-7-yl | iPr |

TABLE 13

(Ia)

| Comp. No. | R¹ | R² | R³ | R | R | ⸺N(Z)—A |
|---|---|---|---|---|---|---|
| I-995 | Me | Me | Me | Me | Me | indol-1-yl |
| I-996 | Me | Me | Me | CH₂CH₂ | | indol-1-yl |
| I-997 | Me | Me | Me | CH₂CH₂CH₂ | | indol-1-yl |
| I-998 | Me | Me | Me | Me | Me | indolin-1-yl |
| I-999 | Me | Me | Me | CH₂CH₂ | | indolin-1-yl |
| I-1000 | Me | Me | Me | CH₂CH₂CH₂ | | indolin-1-yl |
| I-1001 | Me | Me | Me | Me | Me | 7-Cl-indolin-1-yl |
| I-1002 | Me | Me | Me | CH₂CH₂ | | 7-Cl-indolin-1-yl |

TABLE 13-continued (Ia)

| Comp. No. | R¹ | R² | R³ | R | R | N–A / Z group |
|---|---|---|---|---|---|---|
| I-1003 | Me | Me | Me | CH₂CH₂CH₂ | | 7-Cl-indolin-1-yl |
| I-1004 | Me | Me | Me | Me | Me | 7-Br-indolin-1-yl |
| I-1005 | Me | Me | Me | CH₂CH₂ | | 7-Br-indolin-1-yl |
| I-1006 | Me | Me | Me | CH₂CH₂CH₂ | | 7-Br-indolin-1-yl |
| I-1007 | Me | Me | Me | Me | Me | 6-F-indolin-1-yl |
| I-1008 | Me | Me | Me | CH₂CH₂ | | 6-F-indolin-1-yl |
| I-1009 | Me | Me | Me | CH₂CH₂CH₂ | | 6-F-indolin-1-yl |
| I-1010 | Me | Me | Me | Me | Me | 6-Me-indolin-1-yl |
| I-1011 | Me | Me | Me | CH₂CH₃ | | 6-Me-indolin-1-yl |
| I-1012 | Me | Me | Me | CH₂CH₂CH₂ | | 6-Me-indolin-1-yl |
| I-1013 | Me | Me | Me | Me | Me | 7-F-6-Me-indolin-1-yl |
| I-1014 | Me | Me | Me | CH₂CH₂ | | 7-F-6-Me-indolin-1-yl |
| I-1015 | Me | Me | Me | CH₂CH₂CH₂ | | 7-F-6-Me-indolin-1-yl |
| I-1016 | Me | Me | Me | Me | Me | 1,2,3,4-tetrahydroquinolin-1-yl |

TABLE 13-continued (Ia)

| Comp. No. | R¹ | R² | R³ | R | R | N-A / Z |
|---|---|---|---|---|---|---|
| I-1017 | Me | Me | Me | CH₂CH₂ | | 1,2,3,4-tetrahydroquinolin-1-yl |
| I-1018 | Me | Me | Me | CH₂CH₂CH₂ | | 1,2,3,4-tetrahydroquinolin-1-yl |
| I-1019 | Me | Me | Me | Me | Me | 8-Cl-1,2,3,4-tetrahydroquinolin-1-yl |
| I-1020 | Me | Me | Me | CH₂CH₂ | | 8-Cl-1,2,3,4-tetrahydroquinolin-1-yl |
| I-1021 | Me | Me | Me | CH₂CH₂CH₂ | | 8-Cl-1,2,3,4-tetrahydroquinolin-1-yl |
| I-1022 | Me | Me | Me | Me | Me | 8-Br-1,2,3,4-tetrahydroquinolin-1-yl |
| I-1023 | Me | Me | Me | CH₂CH₂ | | 8-Br-1,2,3,4-tetrahydroquinolin-1-yl |
| I-1024 | Me | Me | Me | CH₂CH₂CH₂ | | 8-Br-1,2,3,4-tetrahydroquinolin-1-yl |
| I-1025 | Me | Me | Me | Me | Me | 7-F-1,2,3,4-tetrahydroquinolin-1-yl |
| I-1026 | Me | Me | Me | CH₂CH₂ | | 7-F-1,2,3,4-tetrahydroquinolin-1-yl |
| I-1027 | Me | Me | Me | CH₂CH₂CH₂ | | 7-F-1,2,3,4-tetrahydroquinolin-1-yl |
| I-1028 | Me | Me | Me | Me | Me | 7-Me-1,2,3,4-tetrahydroquinolin-1-yl |
| I-1029 | Me | Me | Me | CH₂CH₃ | | 7-Me-1,2,3,4-tetrahydroquinolin-1-yl |
| I-1030 | Me | Me | Me | CH₂CH₂CH₂ | | 7-Me-1,2,3,4-tetrahydroquinolin-1-yl |

TABLE 13-continued
(Ia)
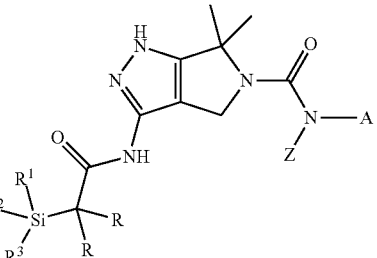
| Comp. No. | R¹ | R² | R³ | R | R | N(Z)-A |
|---|---|---|---|---|---|---|
| I-1031 | Me | Me | Me | Me | Me | 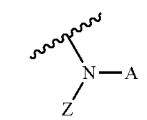 |
| I-1032 | Me | Me | Me | CH₂CH₂ | | 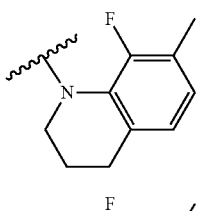 |
| I-1033 | Me | Me | Me | CH₂CH₂CH₂ | | 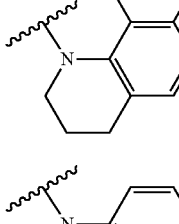 |
| I-1034 | Me | Me | Me | Me | Me | 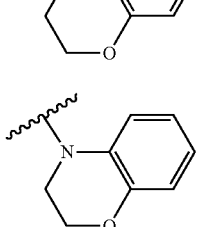 |
| I-1035 | Me | Me | Me | CH₂CH₂ | | 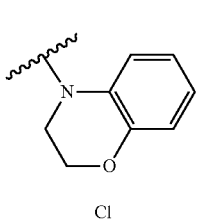 |
| I-1036 | Me | Me | Me | CH₂CH₂CH₂ | | 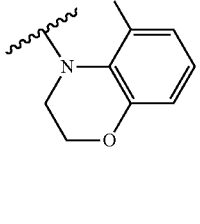 |
| I-1037 | Me | Me | Me | Me | Me | 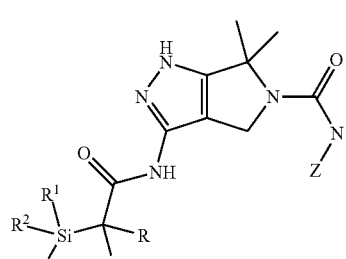 |
TABLE 13-continued
(Ia)
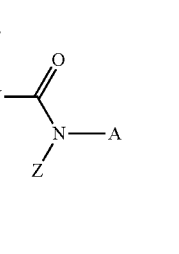
| Comp. No. | R¹ | R² | R³ | R | R | N(Z)-A |
|---|---|---|---|---|---|---|
| I-1038 | Me | Me | Me | CH₂CH₃ | | 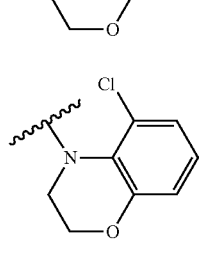 |
| I-1039 | Me | Me | Me | CH₂CH₂CH₂ | | 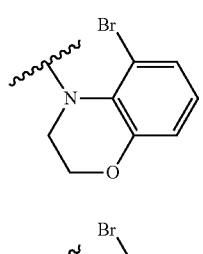 |
| I-1040 | Me | Me | Me | Me | Me | 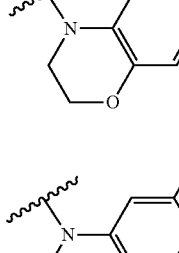 |
| I-1041 | Me | Me | Me | CH₂CH₂ | | 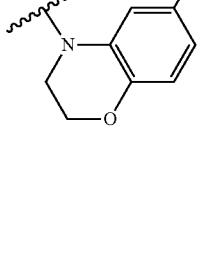 |
| I-1042 | Me | Me | Me | CH₂CH₂CH₂ | | |
| I-1043 | Me | Me | Me | Me | Me | |

TABLE 13-continued (Ia)

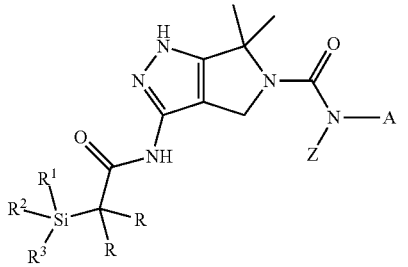

| Comp. No. | R¹ | R² | R³ | R | R | N-A / Z |
|---|---|---|---|---|---|---|
| I-1044 | Me | Me | Me | CH₂CH₂ | | 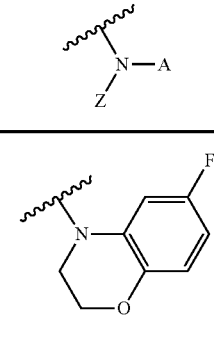 |
| I-1045 | Me | Me | Me | CH₂CH₂CH₂ | | 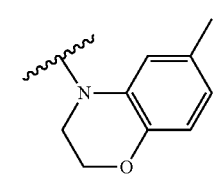 |
| I-1046 | Me | Me | Me | Me | Me | 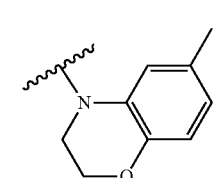 |
| I-1047 | Me | Me | Me | CH₂CH₂ | | 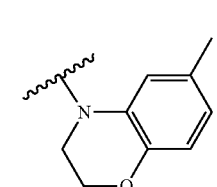 [SMILES: *N1CCCc2ccc(C)cc21] |
| I-1048 | Me | Me | Me | CH₂CH₂CH₂ | | 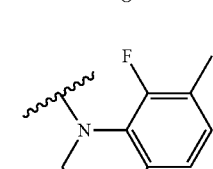 |
| I-1049 | Me | Me | Me | Me | Me | 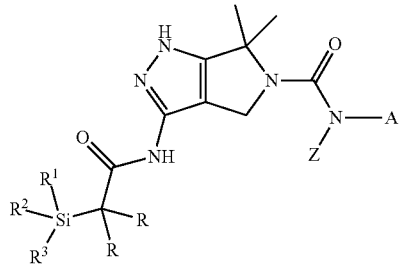 |

TABLE 13-continued (Ia)

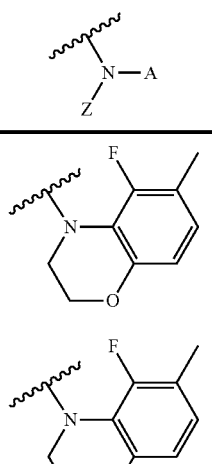

| Comp. No. | R¹ | R² | R³ | R | R | N-A / Z |
|---|---|---|---|---|---|---|
| I-1050 | Me | Me | Me | CH₂CH₂ | | (5-F, 6-Me benzoxazine) |
| I-1051 | Me | Me | Me | CH₂CH₂CH₂ | | (5-F, 6-Me benzoxazine) |

TABLE 14

(II)

| Comp. No. | R¹ | R² | R³ | A |
|---|---|---|---|---|
| II-1 | Me | Me | Me | Ph |
| II-2 | Me | Et | Me | Ph |
| II-3 | Me | Me | Me | 2-F—Ph |
| II-4 | Me | Et | Me | 2-F—Ph |
| II-5 | Me | Me | Me | 3-F—Ph |
| II-6 | Me | Et | Me | 3-F—Ph |
| II-7 | Me | Me | Me | 4-F—Ph |
| II-8 | Me | Et | Me | 4-F—Ph |
| II-9 | Me | Me | Me | 2-Cl—Ph |
| II-10 | Me | Et | Me | 2-Cl—Ph |
| II-11 | Me | Me | Me | 3-Cl—Ph |
| II-12 | Me | Et | Me | 3-Cl—Ph |
| II-13 | Me | Me | Me | 4-Cl—Ph |
| II-14 | Me | Et | Me | 4-Cl—Ph |
| II-15 | Me | Me | Me | 2-Br—Ph |
| II-16 | Me | Et | Me | 2-Br—Ph |
| II-17 | Me | Me | Me | 3-Br—Ph |
| II-18 | Me | Et | Me | 3-Br—Ph |
| II-19 | Me | Me | Me | 4-Br—Ph |
| II-20 | Me | Et | Me | 4-Br—Ph |
| II-21 | Me | Me | Me | 2-Me—Ph |

TABLE 14-continued

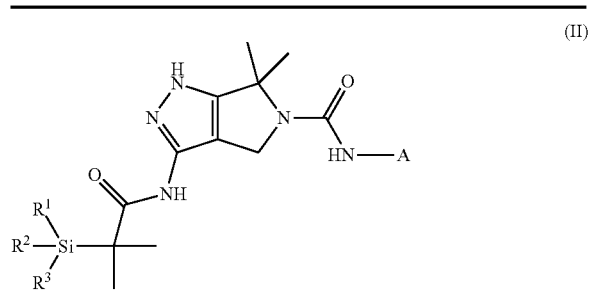

(II)

| Comp. No. | R¹ | R² | R³ | A |
|---|---|---|---|---|
| II-22 | Me | Et | Me | 2-Me—Ph |
| II-23 | Me | Me | Me | 3-Me—Ph |
| II-24 | Me | Et | Me | 3-Me—Ph |
| II-25 | Me | Me | Me | 4-Me—Ph |
| II-26 | Me | Et | Me | 4-Me—Ph |
| II-27 | Me | Me | Me | 2-Et—Ph |
| II-28 | Me | Et | Me | 2-Et—Ph |
| II-29 | Me | Me | Me | 3-Et—Ph |
| II-30 | Me | Et | Me | 3-Et—Ph |
| II-31 | Me | Me | Me | 4-Et—Ph |
| II-32 | Me | Et | Me | 4-Et—Ph |
| II-33 | Me | Me | Me | 2-iPr—Ph |
| II-34 | Me | Et | Me | 2-iPr—Ph |
| II-35 | Me | Me | Me | 3-iPr—Ph |
| II-36 | Me | Et | Me | 3-iPr—Ph |
| II-37 | Me | Me | Me | 4-iPr—Ph |
| II-38 | Me | Et | Me | 4-iPr—Ph |
| II-39 | Me | Me | Me | 2-cPr—Ph |
| II-40 | Me | Et | Me | 2-cPr—Ph |
| II-41 | Me | Me | Me | 3-cPr—Ph |
| II-42 | Me | Et | Me | 3-cPr—Ph |
| II-43 | Me | Me | Me | 4-cPr—Ph |
| II-44 | Me | Et | Me | 4-cPr—Ph |
| II-45 | Me | Me | Me | 2-(1,1-diF—Et)—Ph |
| II-46 | Me | Et | Me | 2-(1,1-diF—Et)—Ph |
| II-47 | Me | Me | Me | 3-(1,1-diF—Et)—Ph |
| II-48 | Me | Et | Me | 3-(1,1-diF—Et)—Ph |
| II-49 | Me | Me | Me | 4-(1,1-diF—Et)—Ph) |
| II-50 | Me | Et | Me | 4-(1,1-diF—Et)—Ph) |
| II-51 | Me | Me | Me | 2-CF₃—Ph |
| II-52 | Me | Et | Me | 2-CF₃—Ph |
| II-53 | Me | Me | Me | 3-CF₃—Ph |
| II-54 | Me | Et | Me | 3-CF₃—Ph |
| II-55 | Me | Me | Me | 4-CF₃—Ph |
| II-56 | Me | Et | Me | 4-CF₃—Ph |
| II-57 | Me | Me | Me | 2-tBu—Ph |
| II-58 | Me | Et | Me | 2-tBu—Ph |
| II-59 | Me | Me | Me | 3-tBu—Ph |
| II-60 | Me | Et | Me | 3-tBu—Ph |
| II-61 | Me | Me | Me | 4-tBu—Ph |
| II-62 | Me | Et | Me | 4-tBu—Ph |
| II-63 | Me | Me | Me | 2-NC—Ph |
| II-64 | Me | Et | Me | 2-NC—Ph |
| II-65 | Me | Me | Me | 3-NC—Ph |
| II-66 | Me | Et | Me | 3-NC—Ph |
| II-67 | Me | Me | Me | 4-NC—Ph |
| II-68 | Me | Et | Me | 4-NC—Ph |
| II-69 | Me | Me | Me | 2-Ph—Ph |
| II-70 | Me | Et | Me | 2-Ph—Ph |
| II-71 | Me | Me | Me | 3-Ph—Ph |
| II-72 | Me | Et | Me | 3-Ph—Ph |
| II-73 | Me | Me | Me | 4-Ph—Ph |
| II-74 | Me | Et | Me | 4-Ph—Ph |
| II-75 | Me | Me | Me | 2-MeO—Ph |
| II-76 | Me | Et | Me | 2-MeO—Ph |
| II-77 | Me | Me | Me | 3-MeO—Ph |
| II-78 | Me | Et | Me | 3-MeO—Ph |
| II-79 | Me | Me | Me | 4-MeO—Ph |
| II-80 | Me | Et | Me | 4-MeO—Ph |
| II-81 | Me | Me | Me | 2-EtO—Ph |
| II-82 | Me | Et | Me | 2-EtO—Ph |
| II-83 | Me | Me | Me | 3-EtO—Ph |
| II-84 | Me | Et | Me | 3-EtO—Ph |
| II-85 | Me | Me | Me | 4-EtO—Ph |

TABLE 14-continued

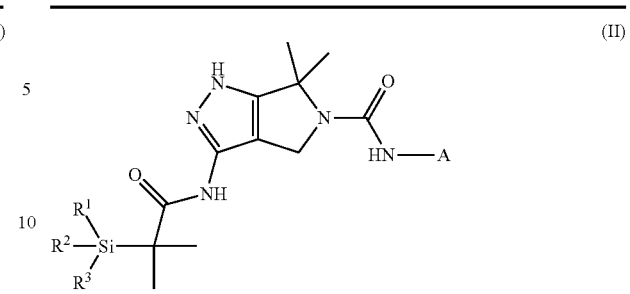

(II)

| Comp. No. | R¹ | R² | R³ | A |
|---|---|---|---|---|
| II-86 | Me | Et | Me | 4-EtO—Ph |
| II-87 | Me | Me | Me | 2-CHF₂O—Ph |
| II-88 | Me | Et | Me | 2-CHF₂O—Ph |
| II-89 | Me | Me | Me | 3-CHF₂O—Ph |
| II-90 | Me | Et | Me | 3-CHF₂O—Ph |
| II-91 | Me | Me | Me | 4-CHF₂O—Ph |
| II-92 | Me | Et | Me | 4-CHF₂O—Ph |
| II-93 | Me | Me | Me | 2-CF₃O—Ph |
| II-94 | Me | Et | Me | 2-CF₃O—Ph |
| II-95 | Me | Me | Me | 3-CF₃O—Ph |
| II-96 | Me | Et | Me | 3-CF₃O—Ph |
| II-97 | Me | Me | Me | 4-CF₃O—Ph |
| II-98 | Me | Et | Me | 4-CF₃O—Ph |
| II-99 | Me | Me | Me | 2,3-diF—Ph |
| II-100 | Me | Et | Me | 2,3-diF—Ph |

TABLE 15

(II)

| Comp. No. | R¹ | R² | R³ | A |
|---|---|---|---|---|
| II-101 | Me | Me | Me | 2,4-diF—Ph |
| II-102 | Me | Et | Me | 2,4-diF—Ph |
| II-103 | Me | Me | Me | 2,5,-diF—Ph |
| II-104 | Me | Et | Me | 2,5,-diF—Ph |
| II-105 | Me | Me | Me | 2,6-diF—Ph |
| II-106 | Me | Et | Me | 2,6-diF—Ph |
| II-107 | Me | Me | Me | 2-F-3-Cl—Ph |
| II-108 | Me | Et | Me | 2-F-3-Cl—Ph |
| II-109 | Me | Me | Me | 2-F-4-Cl—Ph |
| II-110 | Me | Et | Me | 2-F-4-Cl—Ph |
| II-111 | Me | Me | Me | 2-F-5-Cl—Ph |
| II-112 | Me | Et | Me | 2-F-5-Cl—Ph |
| II-113 | Me | Me | Me | 2-F-6-Cl—Ph |
| II-114 | Me | Et | Me | 2-F-6-Cl—Ph |
| II-115 | Me | Me | Me | 2-F-3-Br—Ph |
| II-116 | Me | Et | Me | 2-F-3-Br—Ph |
| II-117 | Me | Me | Me | 2-F-4-Br—Ph |
| II-118 | Me | Et | Me | 2-F-4-Br—Ph |
| II-119 | Me | Me | Me | 2-F-5-Br—Ph |
| II-120 | Me | Et | Me | 2-F-5-Br—Ph |
| II-121 | Me | Me | Me | 2-F-6-Br—Ph |
| II-122 | Me | Et | Me | 2-F-6-Br—Ph |
| II-123 | Me | Me | Me | 2-F-3-Me—Ph |
| II-124 | Me | Et | Me | 2-F-3-Me—Ph |
| II-125 | Me | Me | Me | 2-F-4-Me—Ph |
| II-126 | Me | Et | Me | 2-F-4-Me—Ph |
| II-127 | Me | Me | Me | 2-F-5-Me—Ph |

TABLE 15-continued (II)

| Comp. No. | R¹ | R² | R³ | A |
|---|---|---|---|---|
| II-128 | Me | Et | Me | 2-F-5-Me—Ph |
| II-129 | Me | Me | Me | 2-F-6-Me—Ph |
| II-130 | Me | Et | Me | 2-F-6-Me—Ph |
| II-131 | Me | Me | Me | 2-F-3-Et—Ph |
| II-132 | Me | Et | Me | 2-F-3-Et—Ph |
| II-133 | Me | Me | Me | 2-F-4-Et—Ph |
| II-134 | Me | Et | Me | 2-F-4-Et—Ph |
| II-135 | Me | Me | Me | 2-F-5-Et—Ph |
| II-136 | Me | Et | Me | 2-F-5-Et—Ph |
| II-137 | Me | Me | Me | 2-F-6-Et—Ph |
| II-138 | Me | Et | Me | 2-F-6-Et—Ph |
| II-139 | Me | Me | Me | 2-F-3-cPr—Ph |
| II-140 | Me | Et | Me | 2-F-3-cPr—Ph |
| II-141 | Me | Me | Me | 2-F-4-cPr—Ph |
| II-142 | Me | Et | Me | 2-F-4-cPr—Ph |
| II-143 | Me | Me | Me | 2-F-5-cPr—Ph |
| II-144 | Me | Et | Me | 2-F-5-cPr—Ph |
| II-145 | Me | Me | Me | 2-F-6-cPr—Ph |
| II-146 | Me | Et | Me | 2-F-6-cPr—Ph |
| II-147 | Me | Me | Me | 2-F-3-CF₃—Ph |
| II-148 | Me | Et | Me | 2-F-3-CF₃—Ph |
| II-149 | Me | Me | Me | 2-F-4-CF₃—Ph |
| II-150 | Me | Et | Me | 2-F-4-CF₃—Ph |
| II-151 | Me | Me | Me | 2-F-5-CF3—Ph |
| II-152 | Me | Et | Me | 2-F-5-CF3—Ph |
| II-153 | Me | Me | Me | 2-F-6-CF3—Ph |
| II-154 | Me | Et | Me | 2-F-6-CF3—Ph |
| II-155 | Me | Me | Me | 2-F-3-MeO—Ph |
| II-156 | Me | Et | Me | 2-F-3-MeO—Ph |
| II-157 | Me | Me | Me | 2-F-4-MeO—Ph |
| II-158 | Me | Et | Me | 2-F-4-MeO—Ph |
| II-159 | Me | Me | Me | 2-F-5-MeO—Ph |
| II-160 | Me | Et | Me | 2-F-5-MeO—Ph |
| II-161 | Me | Me | Me | 2-F-6-MeO—Ph |
| II-162 | Me | Et | Me | 2-F-6-MeO—Ph |
| II-163 | Me | Me | Me | 2-F-3-CHF₂O—Ph |
| II-164 | Me | Et | Me | 2-F-3-CHF₂O—Ph |
| II-165 | Me | Me | Me | 2-F-4-CHF₂O—Ph |
| II-166 | Me | Et | Me | 2-F-4-CHF₂O—Ph |
| II-167 | Me | Me | Me | 2-F-5-CHF₂O—Ph |
| II-168 | Me | Et | Me | 2-F-5-CHF₂O—Ph |
| II-169 | Me | Me | Me | 2-F-6-CHF₂O—Ph |
| II-170 | Me | Et | Me | 2-F-6-CHF₂O—Ph |
| II-171 | Me | Me | Me | 2-F-3-CD₃O—Ph |
| II-172 | Me | Et | Me | 2-F-3-CD₃O—Ph |
| II-173 | Me | Me | Me | 2-F-4-CD₃O—Ph |
| II-174 | Me | Et | Me | 2-F-4-CD₃O—Ph |
| II-175 | Me | Me | Me | 2-F-5-CD₃O—Ph |
| II-176 | Me | Et | Me | 2-F-5-CD₃O—Ph |
| II-177 | Me | Me | Me | 2-F-6-CD₃O—Ph |
| II-178 | Me | Et | Me | 2-F-6-CD₃O—Ph |
| II-179 | Me | Me | Me | 2-F-3-NC—Ph |
| II-180 | Me | Et | Me | 2-F-3-NC—Ph |
| II-181 | Me | Me | Me | 2-F-4-NC—Ph |
| II-182 | Me | Et | Me | 2-F-4-NC—Ph |
| II-183 | Me | Me | Me | 2-F-5-NC—Ph |
| II-184 | Me | Et | Me | 2-F-5-NC—Ph |
| II-185 | Me | Me | Me | 2-F-6-NC—Ph |
| II-186 | Me | Et | Me | 2-F-6-NC—Ph |
| II-187 | Me | Me | Me | 2-Cl-3-F—Ph |
| II-188 | Me | Et | Me | 2-Cl-3-F—Ph |
| II-189 | Me | Me | Me | 2-Cl-4-F—Ph |
| II-190 | Me | Et | Me | 2-Cl-4-F—Ph |
| II-191 | Me | Me | Me | 2-Cl-5-F—Ph |
| II-192 | Me | Et | Me | 2-Cl-5-F—Ph |
| II-193 | Me | Me | Me | 2,3-diCl—Ph |
| II-194 | Me | Et | Me | 2,3-diCl—Ph |
| II-195 | Me | Me | Me | 2,4-diCl—Ph |
| II-196 | Me | Et | Me | 2,4-diCl—Ph |
| II-197 | Me | Me | Me | 2,5-diCl—Ph |
| II-198 | Me | Et | Me | 2,5-diCl—Ph |
| II-199 | Me | Me | Me | 2,6-diCl—Ph |
| II-200 | Me | Et | Me | 2,6-diCl—Ph |

TABLE 16

(II)

| Comp. No. | R¹ | R² | R³ | A |
|---|---|---|---|---|
| II-201 | Me | Me | Me | 2-Cl-3-Br—Ph |
| II-202 | Me | Et | Me | 2-Cl-3-Br—Ph |
| II-203 | Me | Me | Me | 2-Cl-4-Br—Ph |
| II-204 | Me | Et | Me | 2-Cl-4-Br—Ph |
| II-205 | Me | Me | Me | 2-Cl-5-Br—Ph |
| II-206 | Me | Et | Me | 2-Cl-5-Br—Ph |
| II-207 | Me | Me | Me | 2-Cl-6-Br—Ph |
| II-208 | Me | Et | Me | 2-Cl-6-Br—Ph |
| II-209 | Me | Me | Me | 2-Cl-3-Me—Ph |
| II-210 | Me | Et | Me | 2-Cl-3-Me—Ph |
| II-211 | Me | Me | Me | 2-Cl-4-Me—Ph |
| II-212 | Me | Et | Me | 2-Cl-4-Me—Ph |
| II-213 | Me | Me | Me | 2-Cl-5-Me—Ph |
| II-214 | Me | Et | Me | 2-Cl-5-Me—Ph |
| II-215 | Me | Me | Me | 2-Cl-6-Me—Ph |
| II-216 | Me | Et | Me | 2-Cl-6-Me—Ph |
| II-217 | Me | Me | Me | 2-Cl-3-Et—Ph |
| II-218 | Me | Et | Me | 2-Cl-3-Et—Ph |
| II-219 | Me | Me | Me | 2-Cl-4-Et—Ph |
| II-220 | Me | Et | Me | 2-Cl-4-Et—Ph |
| II-221 | Me | Me | Me | 2-Cl-5-Et—Ph |
| II-222 | Me | Et | Me | 2-Cl-5-Et—Ph |
| II-223 | Me | Me | Me | 2-Cl-6-Et—Ph |
| II-224 | Me | Et | Me | 2-Cl-6-Et—Ph |
| II-225 | Me | Me | Me | 2-Cl-3-cPr—Ph |
| II-226 | Me | Et | Me | 2-Cl-3-cPr—Ph |
| II-227 | Me | Me | Me | 2-Cl-4-cPr—Ph |
| II-228 | Me | Et | Me | 2-Cl-4-cPr—Ph |
| II-229 | Me | Me | Me | 2-Cl-5-cPr—Ph |
| II-230 | Me | Et | Me | 2-Cl-5-cPr—Ph |
| II-231 | Me | Me | Me | 2-Cl-6-cPr—Ph |
| II-232 | Me | Et | Me | 2-Cl-6-cPr—Ph |
| II-233 | Me | Me | Me | 2-Cl-3-CF₃—Ph |
| II-234 | Me | Et | Me | 2-Cl-3-CF₃—Ph |

TABLE 16-continued (II)

| Comp. No. | R¹ | R² | R³ | A |
|---|---|---|---|---|
| II-235 | Me | Me | Me | 2-Cl-4-CF$_3$—Ph |
| II-236 | Me | Et | Me | 2-Cl-4-CF$_3$—Ph |
| II-237 | Me | Me | Me | 2-Cl-5-CF$_3$—Ph |
| II-238 | Me | Et | Me | 2-Cl-5-CF$_3$—Ph |
| II-239 | Me | Me | Me | 2-Cl-6-CF$_3$—Ph |
| II-240 | Me | Et | Me | 2-Cl-6-CF$_3$—Ph |
| II-241 | Me | Me | Me | 2-Cl-3-MeO—Ph |
| II-242 | Me | Et | Me | 2-Cl-3-MeO—Ph |
| II-243 | Me | Me | Me | 2-Cl-4-MeO—Ph |
| II-244 | Me | Et | Me | 2-Cl-4-MeO—Ph |
| II-245 | Me | Me | Me | 2-Cl-5-MeO—Ph |
| II-246 | Me | Et | Me | 2-Cl-5-MeO—Ph |
| II-247 | Me | Me | Me | 2-Cl-6-MeO—Ph |
| II-248 | Me | Et | Me | 2-Cl-6-MeO—Ph |
| II-249 | Me | Me | Me | 2-Cl-3-CHF$_2$O—Ph |
| II-250 | Me | Et | Me | 2-Cl-3-CHF$_2$O—Ph |
| II-251 | Me | Me | Me | 2-Cl-4-CHF$_2$O—Ph |
| II-252 | Me | Et | Me | 2-Cl-4-CHF$_2$O—Ph |
| II-253 | Me | Me | Me | 2-Cl-5-CHF$_2$O—Ph |
| II-254 | Me | Et | Me | 2-Cl-5-CHF$_2$O—Ph |
| II-255 | Me | Me | Me | 2-Cl-6-CHF$_2$O—Ph |
| II-256 | Me | Et | Me | 2-Cl-6-CHF$_2$O—Ph |
| II-257 | Me | Me | Me | 2-Cl-3-CD$_3$O—Ph |
| II-258 | Me | Et | Me | 2-Cl-3-CD$_3$O—Ph |
| II-259 | Me | Me | Me | 2-Cl-4-CD$_3$O—Ph |
| II-260 | Me | Et | Me | 2-Cl-4-CD$_3$O—Ph |
| II-261 | Me | Me | Me | 2-Cl-5-CD$_3$O—Ph |
| II-262 | Me | Et | Me | 2-Cl-5-CD$_3$O—Ph |
| II-263 | Me | Me | Me | 2-Cl-6-CD$_3$O—Ph |
| II-264 | Me | Et | Me | 2-Cl-6-CD$_3$O—Ph |
| II-265 | Me | Me | Me | 2-Cl-3-NC—Ph |
| II-266 | Me | Et | Me | 2-Cl-3-NC—Ph |
| II-267 | Me | Me | Me | 2-Cl-4-NC—Ph |
| II-268 | Me | Et | Me | 2-Cl-4-NC—Ph |
| II-269 | Me | Me | Me | 2-Cl-5-NC—Ph |
| II-270 | Me | Et | Me | 2-Cl-5-NC—Ph |
| II-271 | Me | Me | Me | 2-Cl-6-NC—Ph |
| II-272 | Me | Et | Me | 2-Cl-6-NC—Ph |
| II-273 | Me | Me | Me | 2-Br-3-F—Ph |
| II-274 | Me | Et | Me | 2-Br-3-F—Ph |
| II-275 | Me | Me | Me | 2-Br-4-F—Ph |
| II-276 | Me | Et | Me | 2-Br-4-F—Ph |
| II-277 | Me | Me | Me | 2-Br-5-F—Ph |
| II-278 | Me | Et | Me | 2-Br-5-F—Ph |
| II-279 | Me | Me | Me | 2-Br-3-Cl—Ph |
| II-280 | Me | Et | Me | 2-Br-3-Cl—Ph |
| II-281 | Me | Me | Me | 2-Br-4-Cl—Ph |
| II-282 | Me | Et | Me | 2-Br-4-Cl—Ph |
| II-283 | Me | Me | Me | 2-Br-5-Cl—Ph |
| II-284 | Me | Et | Me | 2-Br-5-Cl—Ph |
| II-285 | Me | Me | Me | 2,3-diBr—Ph |
| II-286 | Me | Et | Me | 2,3-diBr—Ph |
| II-287 | Me | Me | Me | 2,4-diBr—Ph |
| II-288 | Me | Et | Me | 2,4-diBr—Ph |
| II-289 | Me | Me | Me | 2,5-diBr—Ph |
| II-290 | Me | Et | Me | 2,5-diBr—Ph |
| II-291 | Me | Me | Me | 2,6-diBr—Ph |
| II-292 | Me | Et | Me | 2,6-diBr—Ph |
| II-293 | Me | Me | Me | 2-Br-3-Me—Ph |
| II-294 | Me | Et | Me | 2-Br-3-Me—Ph |
| II-295 | Me | Me | Me | 2-Br-4-Me—Ph |
| II-296 | Me | Et | Me | 2-Br-4-Me—Ph |
| II-297 | Me | Me | Me | 2-Br-5-Me—Ph |
| II-298 | Me | Et | Me | 2-Br-5-Me—Ph |
| II-299 | Me | Me | Me | 2-Br-6-Me—Ph |
| II-300 | Me | Et | Me | 2-Br-6-Me—Ph |

TABLE 17

(II)

| Comp. No. | R¹ | R² | R³ | A |
|---|---|---|---|---|
| II-301 | Me | Me | Me | 2-Br-3-Et—Ph |
| II-302 | Me | Et | Me | 2-Br-3-Et—Ph |
| II-303 | Me | Me | Me | 2-Br-4-Et—Ph |
| II-304 | Me | Et | Me | 2-Br-4-Et—Ph |
| II-305 | Me | Me | Me | 2-Br-5-Et—Ph |
| II-306 | Me | Et | Me | 2-Br-5-Et—Ph |
| II-307 | Me | Me | Me | 2-Br-6-Et—Ph |
| II-308 | Me | Et | Me | 2-Br-6-Et—Ph |
| II-309 | Me | Me | Me | 2-Br-3-cPr—Ph |
| II-310 | Me | Et | Me | 2-Br-3-cPr—Ph |
| II-311 | Me | Me | Me | 2-Br-4-cPr—Ph |
| II-312 | Me | Et | Me | 2-Br-4-cPr—Ph |
| II-313 | Me | Me | Me | 2-Br-5-cPr—Ph |
| II-314 | Me | Et | Me | 2-Br-5-cPr—Ph |
| II-315 | Me | Me | Me | 2-Br-6-cPr—Ph |
| II-316 | Me | Et | Me | 2-Br-6-cPr—Ph |
| II-317 | Me | Me | Me | 2-Br-3-CF$_3$—Ph |
| II-318 | Me | Et | Me | 2-Br-3-CF$_3$—Ph |
| II-319 | Me | Me | Me | 2-Br-4-CF$_3$—Ph |
| II-320 | Me | Et | Me | 2-Br-4-CF$_3$—Ph |
| II-321 | Me | Me | Me | 2-Br-5-CF$_3$—Ph |
| II-322 | Me | Et | Me | 2-Br-5-CF$_3$—Ph |
| II-323 | Me | Me | Me | 2-Br-6-CF$_3$—Ph |
| II-324 | Me | Et | Me | 2-Br-6-CF$_3$—Ph |
| II-325 | Me | Me | Me | 2-Br-3-MeO—Ph |
| II-326 | Me | Et | Me | 2-Br-3-MeO—Ph |
| II-327 | Me | Me | Me | 2-Br-4-MeO—Ph |
| II-328 | Me | Et | Me | 2-Br-4-MeO—Ph |
| II-329 | Me | Me | Me | 2-Br-5-MeO—Ph |
| II-330 | Me | Et | Me | 2-Br-5-MeO—Ph |
| II-331 | Me | Me | Me | 2-Br-6-MeO—Ph |
| II-332 | Me | Et | Me | 2-Br-6-MeO—Ph |
| II-333 | Me | Me | Me | 2-Br-3-CHF$_2$O—Ph |
| II-334 | Me | Et | Me | 2-Br-3-CHF$_2$O—Ph |
| II-335 | Me | Me | Me | 2-Br-4-CHF$_2$O—Ph |
| II-336 | Me | Et | Me | 2-Br-4-CHF$_2$O—Ph |
| II-337 | Me | Me | Me | 2-Br-5-CHF$_2$O—Ph |
| II-338 | Me | Et | Me | 2-Br-5-CHF$_2$O—Ph |
| II-339 | Me | Me | Me | 2-Br-6-CHF$_2$O—Ph |
| II-340 | Me | Et | Me | 2-Br-6-CHF$_2$O—Ph |
| II-341 | Me | Me | Me | 2-Br-3-CD$_3$O—Ph |

TABLE 17-continued (II)

| Comp. No. | R¹ | R² | R³ | A |
|---|---|---|---|---|
| II-342 | Me | Et | Me | 2-Br-3-CD$_3$O—Ph |
| II-343 | Me | Me | Me | 2-Br-4-CD$_3$O—Ph |
| II-344 | Me | Et | Me | 2-Br-4-CD$_3$O—Ph |
| II-345 | Me | Me | Me | 2-Br-5-CD$_3$O—Ph |
| II-346 | Me | Et | Me | 2-Br-5-CD$_3$O—Ph |
| II-347 | Me | Me | Me | 2-Br-6-CD$_3$O—Ph |
| II-348 | Me | Et | Me | 2-Br-6-CD$_3$O—Ph |
| II-349 | Me | Me | Me | 2-Br-3-NC—Ph |
| II-350 | Me | Et | Me | 2-Br-3-NC—Ph |
| II-351 | Me | Me | Me | 2-Br-4-NC—Ph |
| II-352 | Me | Et | Me | 2-Br-4-NC—Ph |
| II-353 | Me | Me | Me | 2-Br-5-NC—Ph |
| II-354 | Me | Et | Me | 2-Br-5-NC—Ph |
| II-355 | Me | Me | Me | 2-Br-6-NC—Ph |
| II-356 | Me | Et | Me | 2-Br-6-NC—Ph |
| II-357 | Me | Me | Me | 2-Me-3-F—Ph |
| II-358 | Me | Et | Me | 2-Me-3-F—Ph |
| II-359 | Me | Me | Me | 2-Me-4-F—Ph |
| II-360 | Me | Et | Me | 2-Me-4-F—Ph |
| II-361 | Me | Me | Me | 2-Me-5-F—Ph |
| II-362 | Me | Et | Me | 2-Me-5-F—Ph |
| II-363 | Me | Me | Me | 2-Me-3-Cl—Ph |
| II-364 | Me | Et | Me | 2-Me-3-Cl—Ph |
| II-365 | Me | Me | Me | 2-Me-4-Cl—Ph |
| II-366 | Me | Et | Me | 2-Me-4-Cl—Ph |
| II-367 | Me | Me | Me | 2-Me-5-Cl—Ph |
| II-368 | Me | Et | Me | 2-Me-5-Cl—Ph |
| II-369 | Me | Me | Me | 2-Me-3-Br—Ph |
| II-370 | Me | Et | Me | 2-Me-3-Br—Ph |
| II-371 | Me | Me | Me | 2-Me-4-Br—Ph |
| II-372 | Me | Et | Me | 2-Me-4-Br—Ph |
| II-373 | Me | Me | Me | 2-Me-5-Br—Ph |
| II-374 | Me | Et | Me | 2-Me-5-Br—Ph |
| II-375 | Me | Me | Me | 2,3-diMe—Ph |
| II-376 | Me | Et | Me | 2,3-diMe—Ph |
| II-377 | Me | Me | Me | 2,4-diMe—Ph |
| II-378 | Me | Et | Me | 2,4-diMe—Ph |
| II-379 | Me | Me | Me | 2,5-diMe—Ph |
| II-380 | Me | Et | Me | 2,5-diMe—Ph |
| II-381 | Me | Me | Me | 2,6-diMe—Ph |
| II-382 | Me | Et | Me | 2,6-diMe—Ph |
| II-383 | Me | Me | Me | 2-Me-3-Et—Ph |
| II-384 | Me | Et | Me | 2-Me-3-Et—Ph |
| II-385 | Me | Me | Me | 2-Me-4-Et—Ph |
| II-386 | Me | Et | Me | 2-Me-4-Et—Ph |
| II-387 | Me | Me | Me | 2-Me-5-Et—Ph |
| II-388 | Me | Et | Me | 2-Me-5-Et—Ph |
| II-389 | Me | Me | Me | 2-Me-6-Et—Ph |
| II-390 | Me | Et | Me | 2-Me-6-Et—Ph |
| II-391 | Me | Me | Me | 2-Me-3-cPr—Ph |
| II-392 | Me | Et | Me | 2-Me-3-cPr—Ph |
| II-393 | Me | Me | Me | 2-Me-4-cPr—Ph |
| II-394 | Me | Et | Me | 2-Me-4-cPr—Ph |
| II-395 | Me | Me | Me | 2-Me-5-cPr—Ph |
| II-396 | Me | Et | Me | 2-Me-5-cPr—Ph |
| II-397 | Me | Me | Me | 2-Me-6-cPr—Ph |
| II-398 | Me | Et | Me | 2-Me-6-cPr—Ph |
| II-399 | Me | Me | Me | 2-Me-3-CF$_3$—Ph |
| II-400 | Me | Et | Me | 2-Me-3-CF$_3$—Ph |

TABLE 18

(II)

| Comp. No. | R¹ | R² | R³ | A |
|---|---|---|---|---|
| II-401 | Me | Me | Me | 2-Me-4-CF$_3$—Ph |
| II-402 | Me | Et | Me | 2-Me-4-CF$_3$—Ph |
| II-403 | Me | Me | Me | 2-Me-5-CF$_3$—Ph |
| II-404 | Me | Et | Me | 2-Me-5-CF$_3$—Ph |
| II-405 | Me | Me | Me | 2-Me-6-CF$_3$—Ph |
| II-406 | Me | Et | Me | 2-Me-6-CF$_3$—Ph |
| II-407 | Me | Me | Me | 2-Me-3-MeO—Ph |
| II-408 | Me | Et | Me | 2-Me-3-MeO—Ph |
| II-409 | Me | Me | Me | 2-Me-4-MeO—Ph |
| II-410 | Me | Et | Me | 2-Me-4-MeO—Ph |
| II-411 | Me | Me | Me | 2-Me-5-MeO—Ph |
| II-412 | Me | Et | Me | 2-Me-5-MeO—Ph |
| II-413 | Me | Me | Me | 2-Me-6-MeO—Ph |
| II-414 | Me | Et | Me | 2-Me-6-MeO—Ph |
| II-415 | Me | Me | Me | 2-Me-3-CHF$_2$O—Ph |
| II-416 | Me | Et | Me | 2-Me-3-CHF$_2$O—Ph |
| II-417 | Me | Me | Me | 2-Me-4-CHF$_2$O—Ph |
| II-418 | Me | Et | Me | 2-Me-4-CHF$_2$O—Ph |
| II-419 | Me | Me | Me | 2-Me-5-CHF$_2$O—Ph |
| II-420 | Me | Et | Me | 2-Me-5-CHF$_2$O—Ph |
| II-421 | Me | Me | Me | 2-Me-6-CHF$_2$O—Ph |
| II-422 | Me | Et | Me | 2-Me-6-CHF$_2$O—Ph |
| II-423 | Me | Me | Me | 2-Me-3-CD$_3$O—Ph |
| II-424 | Me | Et | Me | 2-Me-3-CD$_3$O—Ph |
| II-425 | Me | Me | Me | 2-Me-4-CD$_3$O—Ph |
| II-426 | Me | Et | Me | 2-Me-4-CD$_3$O—Ph |
| II-427 | Me | Me | Me | 2-Me-5-CD$_3$O—Ph |
| II-428 | Me | Et | Me | 2-Me-5-CD$_3$O—Ph |
| II-429 | Me | Me | Me | 2-Me-6-CD$_3$O—Ph |
| II-430 | Me | Et | Me | 2-Me-6-CD$_3$O—Ph |
| II-431 | Me | Me | Me | 2-Me-3-NC—Ph |
| II-432 | Me | Et | Me | 2-Me-3-NC—Ph |
| II-433 | Me | Me | Me | 2-Me-4-NC—Ph |
| II-434 | Me | Et | Me | 2-Me-4-NC—Ph |
| II-435 | Me | Me | Me | 2-Me-5-NC—Ph |
| II-436 | Me | Et | Me | 2-Me-5-NC—Ph |
| II-437 | Me | Me | Me | 2-Me-6-NC—Ph |
| II-438 | Me | Et | Me | 2-Me-6-NC—Ph |
| II-439 | Me | Me | Me | 2-Et-3-F—Ph |
| II-440 | Me | Et | Me | 2-Et-3-F—Ph |
| II-441 | Me | Me | Me | 2-Et-4-F—Ph |
| II-442 | Me | Et | Me | 2-Et-4-F—Ph |
| II-443 | Me | Me | Me | 2-Et-5-F—Ph |
| II-444 | Me | Et | Me | 2-Et-5-F—Ph |
| II-445 | Me | Me | Me | 2-Et-3-Cl—Ph |
| II-446 | Me | Et | Me | 2-Et-3-Cl—Ph |
| II-447 | Me | Me | Me | 2-Et-4-Cl—Ph |
| II-448 | Me | Et | Me | 2-Et-4-Cl—Ph |
| II-449 | Me | Me | Me | 2-Et-5-Cl—Ph |
| II-450 | Me | Et | Me | 2-Et-5-Cl—Ph |
| II-451 | Me | Me | Me | 2-Et-3-Br—Ph |
| II-452 | Me | Et | Me | 2-Et-3-Br—Ph |
| II-453 | Me | Me | Me | 2-Et-4-Br—Ph |
| II-454 | Me | Et | Me | 2-Et-4-Br—Ph |
| II-455 | Me | Me | Me | 2-Et-5-Br—Ph |
| II-456 | Me | Et | Me | 2-Et-5-Br—Ph |
| II-457 | Me | Me | Me | 2-Et-3-Me—Ph |
| II-458 | Me | Et | Me | 2-Et-3-Me—Ph |
| II-459 | Me | Me | Me | 2-Et-4-Me—Ph |
| II-460 | Me | Et | Me | 2-Et-4-Me—Ph |
| II-461 | Me | Me | Me | 2-Et-5-Me—Ph |
| II-462 | Me | Et | Me | 2-Et-5-Me—Ph |
| II-463 | Me | Me | Me | 2,3-diEt—Ph |
| II-464 | Me | Et | Me | 2,3-diEt—Ph |

TABLE 18-continued (II)

| Comp. No. | R¹ | R² | R³ | A |
|---|---|---|---|---|
| II-465 | Me | Me | Me | 2,4-diEt—Ph |
| II-466 | Me | Et | Me | 2,4-diEt—Ph |
| II-467 | Me | Me | Me | 2,5-diEt—Ph |
| II-468 | Me | Et | Me | 2,5-diEt—Ph |
| II-469 | Me | Me | Me | 2,6-diEt—Ph |
| II-470 | Me | Et | Me | 2,6-diEt—Ph |
| II-471 | Me | Me | Me | 2-Et-3-cPr—Ph |
| II-472 | Me | Et | Me | 2-Et-3-cPr—Ph |
| II-473 | Me | Me | Me | 2-Et-4-cPr—Ph |
| II-474 | Me | Et | Me | 2-Et-4-cPr—Ph |
| II-475 | Me | Me | Me | 2-Et-5-cPr—Ph |
| II-476 | Me | Et | Me | 2-Et-5-cPr—Ph |
| II-477 | Me | Me | Me | 2-Et-6-cPr—Ph |
| II-478 | Me | Et | Me | 2-Et-6-cPr—Ph |
| II-479 | Me | Me | Me | 2-Et-3-CF₃—Ph |
| II-480 | Me | Et | Me | 2-Et-3-CF₃—Ph |
| II-481 | Me | Me | Me | 2-Et-4-CF₃—Ph |
| II-482 | Me | Et | Me | 2-Et-4-CF₃—Ph |
| II-483 | Me | Me | Me | 2-Et-5-CF₃—Ph |
| II-484 | Me | Et | Me | 2-Et-5-CF₃—Ph |
| II-485 | Me | Me | Me | 2-Et-6-CF₃—Ph |
| II-486 | Me | Et | Me | 2-Et-6-CF₃—Ph |
| II-487 | Me | Me | Me | 2-Et-3-MeO—Ph |
| II-488 | Me | Et | Me | 2-Et-3-MeO—Ph |
| II-489 | Me | Me | Me | 2-Et-4-MeO—Ph |
| II-490 | Me | Et | Me | 2-Et-4-MeO—Ph |
| II-491 | Me | Me | Me | 2-Et-5-MeO—Ph |
| II-492 | Me | Et | Me | 2-Et-5-MeO—Ph |
| II-493 | Me | Me | Me | 2-Et-6-MeO—Ph |
| II-494 | Me | Et | Me | 2-Et-6-MeO—Ph |
| II-495 | Me | Me | Me | 2-Et-3-CHF₂O—Ph |
| II-496 | Me | Et | Me | 2-Et-3-CHF₂O—Ph |
| II-497 | Me | Me | Me | 2-Et-4-CHF₂O—Ph |
| II-498 | Me | Et | Me | 2-Et-4-CHF₂O—Ph |
| II-499 | Me | Me | Me | 2-Et-5-CHF₂O—Ph |
| II-500 | Me | Et | Me | 2-Et-5-CHF₂O—Ph |

TABLE 19

(II)

| Comp. No. | R¹ | R² | R³ | A |
|---|---|---|---|---|
| II-501 | Me | Me | Me | 2-Et-6-CHF₂O—Ph |
| II-502 | Me | Et | Me | 2-Et-6-CHF₂O—Ph |
| II-503 | Me | Me | Me | 2-Et-3-CD₃O—Ph |
| II-504 | Me | Et | Me | 2-Et-3-CD₃O—Ph |
| II-505 | Me | Me | Me | 2-Et-4-CD₃O—Ph |
| II-506 | Me | Et | Me | 2-Et-4-CD₃O—Ph |

TABLE 19-continued (II)

| Comp. No. | R¹ | R² | R³ | A |
|---|---|---|---|---|
| II-507 | Me | Me | Me | 2-Et-5-CD₃O—Ph |
| II-508 | Me | Et | Me | 2-Et-5-CD₃O—Ph |
| II-509 | Me | Me | Me | 2-Et-6-CD₃O—Ph |
| II-510 | Me | Et | Me | 2-Et-6-CD₃O—Ph |
| II-511 | Me | Me | Me | 2-Et-3-NC—Ph |
| II-512 | Me | Et | Me | 2-Et-3-NC—Ph |
| II-513 | Me | Me | Me | 2-Et-4-NC—Ph |
| II-514 | Me | Et | Me | 2-Et-4-NC—Ph |
| II-515 | Me | Me | Me | 2-Et-5-NC—Ph |
| II-516 | Me | Et | Me | 2-Et-5-NC—Ph |
| II-517 | Me | Me | Me | 2-Et-6-NC—Ph |
| II-518 | Me | Et | Me | 2-Et-6-NC—Ph |
| II-519 | Me | Me | Me | 2-MeO-3-F—Ph |
| II-520 | Me | Et | Me | 2-MeO-3-F—Ph |
| II-521 | Me | Me | Me | 2-MeO-4-F—Ph |
| II-522 | Me | Et | Me | 2-MeO-4-F—Ph |
| II-523 | Me | Me | Me | 2-MeO-5-F—Ph |
| II-524 | Me | Et | Me | 2-MeO-5-F—Ph |
| II-525 | Me | Me | Me | 2-MeO-3-Cl—Ph |
| II-526 | Me | Et | Me | 2-MeO-3-Cl—Ph |
| II-527 | Me | Me | Me | 2-MeO-4-Cl—Ph |
| II-528 | Me | Et | Me | 2-MeO-4-Cl—Ph |
| II-529 | Me | Me | Me | 2-MeO-5-Cl—Ph |
| II-530 | Me | Et | Me | 2-MeO-5-Cl—Ph |
| II-531 | Me | Me | Me | 2-MeO-3-Br—Ph |
| II-532 | Me | Et | Me | 2-MeO-3-Br—Ph |
| II-533 | Me | Me | Me | 2-MeO-4-Br—Ph |
| II-534 | Me | Et | Me | 2-MeO-4-Br—Ph |
| II-535 | Me | Me | Me | 2-MeO-5-Br—Ph |
| II-536 | Me | Et | Me | 2-MeO-5-Br—Ph |
| II-537 | Me | Me | Me | 2-MeO-3-Me—Ph |
| II-538 | Me | Et | Me | 2-MeO-3-Me—Ph |
| II-539 | Me | Me | Me | 2-MeO-4-Me—Ph |
| II-540 | Me | Et | Me | 2-MeO-4-Me—Ph |
| II-541 | Me | Me | Me | 2-MeO-5-Me—Ph |
| II-542 | Me | Et | Me | 2-MeO-5-Me—Ph |
| II-543 | Me | Me | Me | 2-MeO-3-Et—Ph |
| II-544 | Me | Et | Me | 2-MeO-3-Et—Ph |
| II-545 | Me | Me | Me | 2-MeO-4-Et—Ph |
| II-546 | Me | Et | Me | 2-MeO-4-Et—Ph |
| II-547 | Me | Me | Me | 2-MeO-5-Et—Ph |
| II-548 | Me | Et | Me | 2-MeO-5-Et—Ph |
| II-549 | Me | Me | Me | 2-MeO-3-cPr—Ph |
| II-550 | Me | Et | Me | 2-MeO-3-cPr—Ph |
| II-551 | Me | Me | Me | 2-MeO-4-cPr—Ph |
| II-552 | Me | Et | Me | 2-MeO-4-cPr—Ph |
| II-553 | Me | Me | Me | 2-MeO-5-cPr—Ph |
| II-554 | Me | Et | Me | 2-MeO-5-cPr—Ph |
| II-555 | Me | Me | Me | 2-MeO-6-cPr—Ph |
| II-556 | Me | Et | Me | 2-MeO-6-cPr—Ph |
| II-557 | Me | Me | Me | 2-MeO-3-CF₃—Ph |
| II-558 | Me | Et | Me | 2-MeO-3-CF₃—Ph |
| II-559 | Me | Me | Me | 2-MeO-4-CF₃—Ph |
| II-560 | Me | Et | Me | 2-MeO-4-CF₃—Ph |
| II-561 | Me | Me | Me | 2-MeO-5-CF₃—Ph |
| II-562 | Me | Et | Me | 2-MeO-5-CF₃—Ph |
| II-563 | Me | Me | Me | 2-MeO-6-CF₃—Ph |
| II-564 | Me | Et | Me | 2-MeO-6-CF₃—Ph |
| II-565 | Me | Me | Me | 2,3-diMeO—Ph |
| II-566 | Me | Et | Me | 2,3-diMeO—Ph |
| II-567 | Me | Me | Me | 2,4-diMeO—Ph |
| II-568 | Me | Et | Me | 2,4-diMeO—Ph |
| II-569 | Me | Me | Me | 2,5-diMeO—Ph |
| II-570 | Me | Et | Me | 2,5-diMeO—Ph |

TABLE 19-continued (II)

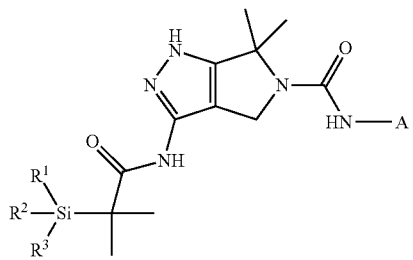

| Comp. No. | R¹ | R² | R³ | A |
|---|---|---|---|---|
| II-571 | Me | Me | Me | 2,6-diMeO—Ph |
| II-572 | Me | Et | Me | 2,6-diMeO—Ph |
| II-573 | Me | Me | Me | 2-MeO-3-CHF₂O—Ph |
| II-574 | Me | Et | Me | 2-MeO-3-CHF₂O—Ph |
| II-575 | Me | Me | Me | 2-MeO-4-CHF₂O—Ph |
| II-576 | Me | Et | Me | 2-MeO-4-CHF₂O—Ph |
| II-577 | Me | Me | Me | 2-MeO-5-CHF₂O—Ph |
| II-578 | Me | Et | Me | 2-MeO-5-CHF₂O—Ph |
| II-579 | Me | Me | Me | 2-MeO-6-CHF₂O—Ph |
| II-580 | Me | Et | Me | 2-MeO-6-CHF₂O—Ph |
| II-581 | Me | Me | Me | 2-MeO-3-CD₃O—Ph |
| II-582 | Me | Et | Me | 2-MeO-3-CD₃O—Ph |
| II-583 | Me | Me | Me | 2-MeO-4-CD₃O—Ph |
| II-584 | Me | Et | Me | 2-MeO-4-CD₃O—Ph |
| II-585 | Me | Me | Me | 2-MeO-5-CD₃O—Ph |
| II-586 | Me | Et | Me | 2-MeO-5-CD₃O—Ph |
| II-587 | Me | Me | Me | 2-MeO-6-CD₃O—Ph |
| II-588 | Me | Et | Me | 2-MeO-6-CD₃O—Ph |
| II-589 | Me | Me | Me | 2-MeO-3-NC—Ph |
| II-590 | Me | Et | Me | 2-MeO-3-NC—Ph |
| II-591 | Me | Me | Me | 2-MeO-4-NC—Ph |
| II-592 | Me | Et | Me | 2-MeO-4-NC—Ph |
| II-593 | Me | Me | Me | 2-MeO-5-NC—Ph |
| II-594 | Me | Et | Me | 2-MeO-5-NC—Ph |
| II-595 | Me | Me | Me | 2-MeO-6-NC—Ph |
| II-596 | Me | Et | Me | 2-MeO-6-NC—Ph |
| II-597 | Me | Me | Me | 2,3,6-triF—Ph |
| II-598 | Me | Et | Me | 2,3,6-triF—Ph |
| II-599 | Me | Me | Me | 2,4,6-triF—Ph |
| II-600 | Me | Et | Me | 2,4,6-triF—Ph |

TABLE 20

(II)

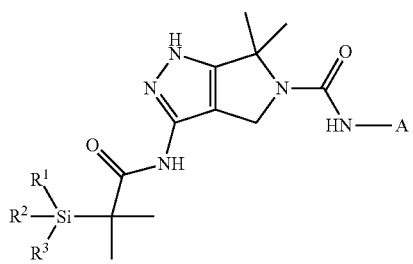

| Comp. No. | R¹ | R² | R³ | A |
|---|---|---|---|---|
| II-601 | Me | Me | Me | 2,6-diF-3-Cl—Ph |
| II-602 | Me | Et | Me | 2,6-diF-3-Cl—Ph |
| II-603 | Me | Me | Me | 2,6-diF-4-Cl—Ph |
| II-604 | Me | Et | Me | 2,6-diF-4-Cl—Ph |
| II-605 | Me | Me | Me | 2,6-diF-3-Br—Ph |
| II-606 | Me | Et | Me | 2,6-diF-3-Br—Ph |
| II-607 | Me | Me | Me | 2,6-diF-4-Br—Ph |
| II-608 | Me | Et | Me | 2,6-diF-4-Br—Ph |
| II-609 | Me | Me | Me | 2,6-diF-3-Me—Ph |
| II-610 | Me | Et | Me | 2,6-diF-3-Me—Ph |
| II-611 | Me | Me | Me | 2,6-diF-4-Me—Ph |
| II-612 | Me | Et | Me | 2,6-diF-4-Me—Ph |

TABLE 20-continued (II)

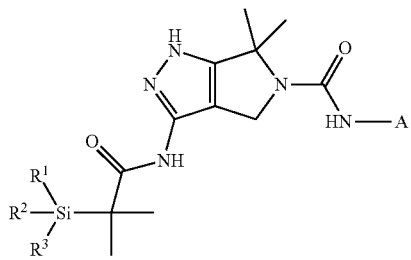

| Comp. No. | R¹ | R² | R³ | A |
|---|---|---|---|---|
| II-613 | Me | Me | Me | 2,6-diF-3-MeO—Ph |
| II-614 | Me | Et | Me | 2,6-diF-3-MeO—Ph |
| II-615 | Me | Me | Me | 2,6-diF-4-MeO—Ph |
| II-616 | Me | Et | Me | 2,6-diF-4-MeO—Ph |
| II-617 | Me | Me | Me | 2,3-diF-6-Cl—Ph |
| II-618 | Me | Et | Me | 2,3-diF-6-Cl—Ph |
| II-619 | Me | Me | Me | 2,4-diF-6-Cl—Ph |
| II-620 | Me | Et | Me | 2,4-diF-6-Cl—Ph |
| II-621 | Me | Me | Me | 2-F-3,6-diCl—Ph |
| II-622 | Me | Et | Me | 2-F-3,6-diCl—Ph |
| II-623 | Me | Me | Me | 2-F-4,6-diCl—Ph |
| II-624 | Me | Et | Me | 2-F-4,6-diCl—Ph |
| II-625 | Me | Me | Me | 2-F-3-Br-6-Cl—Ph |
| II-626 | Me | Et | Me | 2-F-3-Br-6-Cl—Ph |
| II-627 | Me | Me | Me | 2-F-4-Br-6-Cl—Ph |
| II-628 | Me | Et | Me | 2-F-4-Br-6-Cl—Ph |
| II-629 | Me | Me | Me | 2-F-3-Me-6-Cl—Ph |
| II-630 | Me | Et | Me | 2-F-3-Me-6-Cl—Ph |
| II-631 | Me | Me | Me | 2-F-4-Me-6-Cl—Ph |
| II-632 | Me | Et | Me | 2-F-4-Me-6-Cl—Ph |
| II-633 | Me | Me | Me | 2-F-3-MeO-6-Cl—Ph |
| II-634 | Me | Et | Me | 2-F-3-MeO-6-Cl—Ph |
| II-635 | Me | Me | Me | 2-F-4-MeO-6-Cl—Ph |
| II-636 | Me | Et | Me | 2-F-4-MeO-6-Cl—Ph |
| II-637 | Me | Me | Me | 2,3-diF-6-Br—Ph |
| II-638 | Me | Et | Me | 2,3-diF-6-Br—Ph |
| II-639 | Me | Me | Me | 2,4-diF-6-Br—Ph |
| II-640 | Me | Et | Me | 2,4-diF-6-Br—Ph |
| II-641 | Me | Me | Me | 2-F-3-Cl-6-Br—Ph |
| II-642 | Me | Et | Me | 2-F-3-Cl-6-Br—Ph |
| II-643 | Me | Me | Me | 2-F-4-Cl-6-Br—Ph |
| II-644 | Me | Et | Me | 2-F-4-Cl-6-Br—Ph |
| II-645 | Me | Me | Me | 2-F-3,6-diBr—Ph |
| II-646 | Me | Et | Me | 2-F-3,6-diBr—Ph |
| II-647 | Me | Me | Me | 2-F-4,6-diBr—Ph |
| II-648 | Me | Et | Me | 2-F-4,6-diBr—Ph |
| II-649 | Me | Me | Me | 2-F-3-Me-6-Br—Ph |
| II-650 | Me | Et | Me | 2-F-3-Me-6-Br—Ph |
| II-651 | Me | Me | Me | 2-F-4-Me-6-Br—Ph |
| II-652 | Me | Et | Me | 2-F-4-Me-6-Br—Ph |
| II-653 | Me | Me | Me | 2-F-3-MeO-6-Br—Ph |
| II-654 | Me | Et | Me | 2-F-3-MeO-6-Br—Ph |
| II-655 | Me | Me | Me | 2-F-4-MeO-6-Br—Ph |
| II-656 | Me | Et | Me | 2-F-4-MeO-6-Br—Ph |
| II-657 | Me | Me | Me | 2,3-diF-6-Me—Ph |
| II-658 | Me | Et | Me | 2,3-diF-6-Me—Ph |
| II-659 | Me | Me | Me | 2,4-diF-6-Me—Ph |
| II-660 | Me | Et | Me | 2,4-diF-6-Me—Ph |
| II-661 | Me | Me | Me | 2-F-3-Cl-6-Me—Ph |
| II-662 | Me | Et | Me | 2-F-3-Cl-6-Me—Ph |
| II-663 | Me | Me | Me | 2-F-4-Cl-6-Me—Ph |
| II-664 | Me | Et | Me | 2-F-4-Cl-6-Me—Ph |
| II-665 | Me | Me | Me | 2-F-3-Br-6-Me—Ph |
| II-666 | Me | Et | Me | 2-F-3-Br-6-Me—Ph |
| II-667 | Me | Me | Me | 2-F-4-Br-6-Me—Ph |
| II-668 | Me | Et | Me | 2-F-4-Br-6-Me—Ph |
| II-669 | Me | Me | Me | 2-F-3,6-diMe—Ph |
| II-670 | Me | Et | Me | 2-F-3,6-diMe—Ph |
| II-671 | Me | Me | Me | 2-F-4,6-diMe—Ph |
| II-672 | Me | Et | Me | 2-F-4,6-diMe—Ph |
| II-673 | Me | Me | Me | 2-F-3-MeO-6-Me—Ph |
| II-674 | Me | Et | Me | 2-F-3-MeO-6-Me—Ph |
| II-675 | Me | Me | Me | 2-F-4-MeO-6-Me—Ph |
| II-676 | Me | Et | Me | 2-F-4-MeO-6-Me—Ph |

TABLE 20-continued

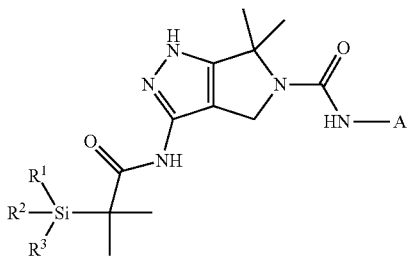

(II)

| Comp. No. | R¹ | R² | R³ | A |
|---|---|---|---|---|
| II-677 | Me | Me | Me | 2,3-diF-6-MeO—Ph |
| II-678 | Me | Et | Me | 2,3-diF-6-MeO—Ph |
| II-679 | Me | Me | Me | 2,4-diF-6-MeO—Ph |
| II-680 | Me | Et | Me | 2,4-diF-6-MeO—Ph |
| II-681 | Me | Me | Me | 2-F-3-Cl-6-MeO—Ph |
| II-682 | Me | Et | Me | 2-F-3-Cl-6-MeO—Ph |
| II-683 | Me | Me | Me | 2-F-4-Cl-6-MeO—Ph |
| II-684 | Me | Et | Me | 2-F-4-Cl-6-MeO—Ph |
| II-685 | Me | Me | Me | 2-F-3-Br-6-MeO—Ph |
| II-686 | Me | Et | Me | 2-F-3-Br-6-MeO—Ph |
| II-687 | Me | Me | Me | 2-F-4-Br-6-MeO—Ph |
| II-688 | Me | Et | Me | 2-F-4-Br-6-MeO—Ph |
| II-689 | Me | Me | Me | 2-F-3-Me-6-MeO—Ph |
| II-690 | Me | Et | Me | 2-F-3-Me-6-MeO—Ph |
| II-691 | Me | Me | Me | 2-F-4-Me-6-MeO—Ph |
| II-692 | Me | Et | Me | 2-F-4-Me-6-MeO—Ph |
| II-693 | Me | Me | Me | 2-F-3,6-diMeO—Ph |
| II-694 | Me | Et | Me | 2-F-3,6-diMeO—Ph |
| II-695 | Me | Me | Me | 2-F-4,6-diMeO—Ph |
| II-696 | Me | Et | Me | 2-F-4,6-diMeO—Ph |
| II-697 | Me | Me | Me | 2-Cl-3,6-diF—Ph |
| II-698 | Me | Et | Me | 2-Cl-3,6-diF—Ph |
| II-699 | Me | Me | Me | 2,3-diCl-6-F—Ph |
| II-700 | Me | Et | Me | 2,3-diCl-6-F—Ph |

TABLE 21

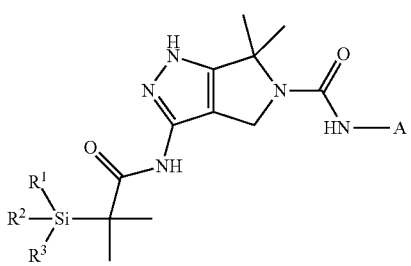

(II)

| Comp. No. | R¹ | R² | R³ | A |
|---|---|---|---|---|
| II-701 | Me | Me | Me | 2-Cl-3-Br-6-F—Ph |
| II-702 | Me | Et | Me | 2-Cl-3-Br-6-F—Ph |
| II-703 | Me | Me | Me | 2-Cl-3-Me-6-F—Ph |
| II-704 | Me | Et | Me | 2-Cl-3-Me-6-F—Ph |
| II-705 | Me | Me | Me | 2-Cl-3-MeO-6-F-Ph |
| II-706 | Me | Et | Me | 2-Cl-3-MeO-6-F-Ph |
| II-707 | Me | Me | Me | 2,6-diCl-3-F-Ph |
| II-708 | Me | Et | Me | 2,6-diCl-3-F-Ph |
| II-709 | Me | Me | Me | 2,6-diCl-4-F-Ph |
| II-710 | Me | Et | Me | 2,6-diCl-4-F-Ph |
| II-711 | Me | Me | Me | 2,3,6-triCl—Ph |
| II-712 | Me | Et | Me | 2,3,6-triCl—Ph |
| II-713 | Me | Me | Me | 2,4,6-triCl—Ph |
| II-714 | Me | Et | Me | 2,4,6-triCl—Ph |
| II-715 | Me | Me | Me | 2,6-diCl-3-Br—Ph |
| II-716 | Me | Et | Me | 2,6-diCl-3-Br—Ph |
| II-717 | Me | Me | Me | 2,6-diCl-4-Br—Ph |
| II-718 | Me | Et | Me | 2,6-diCl-4-Br—Ph |

TABLE 21-continued

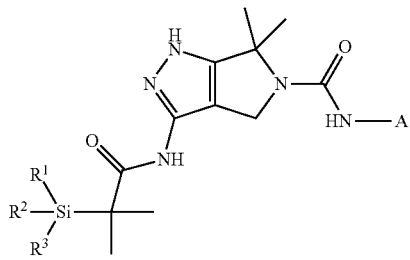

(II)

| Comp. No. | R¹ | R² | R³ | A |
|---|---|---|---|---|
| II-719 | Me | Me | Me | 2,6-diCl-3-Me—Ph |
| II-720 | Me | Et | Me | 2,6-diCl-3-Me—Ph |
| II-721 | Me | Me | Me | 2,6-diCl-4-Me—Ph |
| II-722 | Me | Et | Me | 2,6-diCl-4-Me—Ph |
| II-723 | Me | Me | Me | 2,6-diCl-3-MeO—Ph |
| II-724 | Me | Et | Me | 2,6-diCl-3-MeO—Ph |
| II-725 | Me | Me | Me | 2,6-diCl-4-MeO—Ph |
| II-726 | Me | Et | Me | 2,6-diCl-4-MeO—Ph |
| II-727 | Me | Me | Me | 2-Cl-3-F-6-Br—Ph |
| II-728 | Me | Et | Me | 2-Cl-3-F-6-Br—Ph |
| II-729 | Me | Me | Me | 2-Cl-4-F-6-Br—Ph |
| II-730 | Me | Et | Me | 2-Cl-4-F-6-Br—Ph |
| II-731 | Me | Me | Me | 2,3-diCl-6-Br—Ph |
| II-732 | Me | Et | Me | 2,3-diCl-6-Br—Ph |
| II-733 | Me | Me | Me | 2,4-diCl-6-Br—Ph |
| II-734 | Me | Et | Me | 2,4-diCl-6-Br—Ph |
| II-735 | Me | Me | Me | 2-Cl-3,6-diBr—Ph |
| II-736 | Me | Et | Me | 2-Cl-3,6-diBr—Ph |
| II-737 | Me | Me | Me | 2-Cl-4,6-diBr—Ph |
| II-738 | Me | Et | Me | 2-Cl-4,6-diBr—Ph |
| II-739 | Me | Me | Me | 2-Cl-3-Me-6-Br—Ph |
| II-740 | Me | Et | Me | 2-Cl-3-Me-6-Br—Ph |
| II-741 | Me | Me | Me | 2-Cl-4-Me-6-Br—Ph |
| II-742 | Me | Et | Me | 2-Cl-4-Me-6-Br—Ph |
| II-743 | Me | Me | Me | 2-Cl-3-MeO-6-Br—Ph |
| II-744 | Me | Et | Me | 2-Cl-3-MeO-6-Br—Ph |
| II-745 | Me | Me | Me | 2-Cl-4-MeO-6-Br—Ph |
| II-746 | Me | Et | Me | 2-Cl-4-MeO-6-Br—Ph |
| II-747 | Me | Me | Me | 2-Cl-3-F-6-Me—Ph |
| II-748 | Me | Et | Me | 2-Cl-3-F-6-Me—Ph |
| II-749 | Me | Me | Me | 2-Cl-4-F-6-Me—Ph |
| II-750 | Me | Et | Me | 2-Cl-4-F-6-Me—Ph |
| II-751 | Me | Me | Me | 2,3-diCl-6-Me—Ph |
| II-752 | Me | Et | Me | 2,3-diCl-6-Me—Ph |
| II-753 | Me | Me | Me | 2,4-diCl-6-Me—Ph |
| II-754 | Me | Et | Me | 2,4-diCl-6-Me—Ph |
| II-755 | Me | Me | Me | 2-Cl-3-Br-6-Me—Ph |
| II-756 | Me | Et | Et | 2-Cl-3-Br-6-Me—Ph |
| II-757 | Me | Me | Me | 2-Cl-4-Br-6-Me—Ph |
| II-758 | Me | Et | Me | 2-Cl-4-Br-6-Me—Ph |
| II-759 | Me | Me | Me | 2-Cl-3,6-diMe—Ph |
| II-760 | Me | Et | Me | 2-Cl-3,6-diMe—Ph |
| II-761 | Me | Me | Me | 2-Cl-4,6-diMe—Ph |
| II-762 | Me | Et | Me | 2-Cl-4,6-diMe—Ph |
| II-763 | Me | Me | Me | 2-Cl-3-MeO-6-Me—Ph |
| II-764 | Me | Et | Me | 2-Cl-3-MeO-6-Me—Ph |
| II-765 | Me | Me | Me | 2-Cl-4-MeO-6-Me—Ph |
| II-766 | Me | Et | Me | 2-Cl-4-MeO-6-Me—Ph |
| II-767 | Me | Me | Me | 2-Cl-3-F-6-MeO—Ph |
| II-768 | Me | Et | Me | 2-Cl-3-F-6-MeO—Ph |
| II-769 | Me | Me | Me | 2-Cl-4-F-6-MeO—Ph |
| II-770 | Me | Et | Me | 2-Cl-4-F-6-MeO—Ph |
| II-771 | Me | Me | Me | 2,3-diCl-6-MeO—Ph |
| II-772 | Me | Et | Me | 2,3-diCl-6-MeO—Ph |
| II-773 | Me | Me | Me | 2,4-diCl-6-MeO—Ph |
| II-774 | Me | Et | Me | 2,4-diCl-6-MeO—Ph |
| II-775 | Me | Me | Me | 2-Cl-3-Br-6-MeO—Ph |
| II-776 | Me | Et | Me | 2-Cl-3-Br-6-MeO—Ph |
| II-777 | Me | Me | Me | 2-Cl-4-Br-6-MeO—Ph |
| II-778 | Me | Et | Me | 2-Cl-4-Br-6-MeO—Ph |
| II-779 | Me | Me | Me | 2-Cl-3-Me-6-MeO—Ph |
| II-780 | Me | Et | Me | 2-Cl-3-Me-6-MeO—Ph |
| II-781 | Me | Me | Me | 2-Cl-4-Me-6-MeO—Ph |
| II-782 | Me | Et | Me | 2-Cl-4-Me-6-MeO—Ph |

TABLE 21-continued

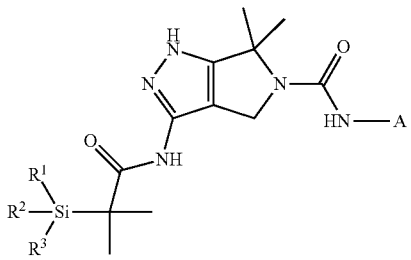

(II)

| Comp. No. | R¹ | R² | R³ | A |
|---|---|---|---|---|
| II-783 | Me | Me | Me | 2-Cl-3,6-diMeO—Ph |
| II-784 | Me | Et | Me | 2-Cl-3,6-diMeO—Ph |
| II-785 | Me | Me | Me | 2-Cl-4,6-diMeO—Ph |
| II-786 | Me | Et | Me | 2-Cl-4,6-diMeO—Ph |
| II-787 | Me | Me | Me | 2-Br-3,6-diF—Ph |
| II-788 | Me | Et | Me | 2-Br-3,6-diF—Ph |
| II-789 | Me | Me | Me | 2-Br-3-Cl-6-F—Ph |
| II-790 | Me | Et | Me | 2-Br-3-Cl-6-F—Ph |
| II-791 | Me | Me | Me | 2,3-diBr-6-F—Ph |
| II-792 | Me | Et | Me | 2,3-diBr-6-F—Ph |
| II-793 | Me | Me | Me | 2-Br-3-Me-6-F—Ph |
| II-794 | Me | Et | Me | 2-Br-3-Me-6-F—Ph |
| II-795 | Me | Me | Me | 2-Br-3-MeO-6-F—Ph |
| II-796 | Me | Et | Me | 2-Br-3-MeO-6-F—Ph |
| II-797 | Me | Me | Me | 2-Br-3-F-6-Cl—Ph |
| II-798 | Me | Et | Me | 2-Br-3-F-6-Cl—Ph |
| II-799 | Me | Me | Me | 2-Br-3,6-diCl—Ph |
| II-800 | Me | Et | Me | 2-Br-3,6-diCl—Ph |

TABLE 22

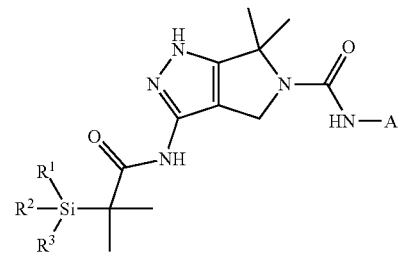

(II)

| Comp. No. | R¹ | R² | R³ | A |
|---|---|---|---|---|
| II-801 | Me | Me | Me | 2,3-diBr-6-Cl—Ph |
| II-802 | Me | Et | Me | 2,3-diBr-6-Cl—Ph |
| II-803 | Me | Me | Me | 2 Br-3-Me-6-Cl—Ph |
| II-804 | Me | Et | Me | 2 Br-3-Me-6-Cl—Ph |
| II-805 | Me | Me | Me | 2-Br-3-MeO-6-Cl—Ph |
| II-806 | Me | Et | Me | 2-Br-3-MeO-6-Cl—Ph |
| II-807 | Me | Me | Me | 2,6-diBr-3-F—Ph |
| II-808 | Me | Et | Me | 2,6-diBr-3-F—Ph |
| II-809 | Me | Me | Me | 2,6-diBr-4-F—Ph |
| II-810 | Me | Et | Me | 2,6-diBr-4-F—Ph |
| II-811 | Me | Me | Me | 2,6-diBr-3-Cl—Ph |
| II-812 | Me | Et | Me | 2,6-diBr-3-Cl—Ph |
| II-813 | Me | Me | Me | 2,6-diBr-4-Cl—Ph |
| II-814 | Me | Et | Me | 2,6-diBr-4-Cl—Ph |
| II-815 | Me | Me | Me | 2,3,6-triBr—Ph |
| II-816 | Me | Et | Me | 2,3,6-triBr—Ph |
| II-817 | Me | Me | Me | 2,4,6-triBr—Ph |
| II-818 | Me | Et | Me | 2,4,6-triBr—Ph |
| II-819 | Me | Me | Me | 2,6-diBr-3-Me—Ph |
| II-820 | Me | Et | Me | 2,6-diBr-3-Me—Ph |
| II-821 | Me | Me | Me | 2,6-diBr-4-Me—Ph |
| II-822 | Me | Et | Me | 2,6-diBr-4-Me—Ph |
| II-823 | Me | Me | Me | 2,6-diBr-3-MeO-Ph |
| II-824 | Me | Et | Me | 2,6-diBr-3-MeO—Ph |
| II-825 | Me | Me | Me | 2,6-diBr-4-MeO—Ph |

TABLE 22-continued

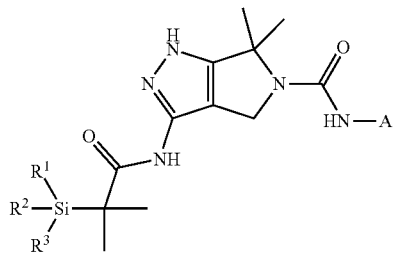

(II)

| Comp. No. | R¹ | R² | R³ | A |
|---|---|---|---|---|
| II-826 | Me | Et | Me | 2,6-diBr-4-MeO—Ph |
| II-827 | Me | Me | Me | 2-Br-3-F-6-Me—Ph |
| II-828 | Me | Et | Me | 2-Br-3-F-6-Me—Ph |
| II-829 | Me | Me | Me | 2-Br-4-F-6-Me—Ph |
| II-830 | Me | Et | Me | 2-Br-4-F-6-Me—Ph |
| II-831 | Me | Me | Me | 2-Br-3-Cl-6-Me—Ph |
| II-832 | Me | Et | Me | 2-Br-3-Cl-6-Me—Ph |
| II-833 | Me | Me | Me | 2-Br-4-Cl-6-Me—Ph |
| II-834 | Me | Et | Me | 2-Br-4-Cl-6-Me—Ph |
| II-835 | Me | Me | Me | 2,3-diBr-6-Me—Ph |
| II-836 | Me | Et | Me | 2,3-diBr-6-Me—Ph |
| II-837 | Me | Me | Me | 2,4-diBr-6-Me—Ph |
| II-838 | Me | Et | Me | 2,4-diBr-6-Me—Ph |
| II-839 | Me | Me | Me | 2-Br-3,6-diMe—Ph |
| II-840 | Me | Et | Me | 2-Br-3,6-diMe—Ph |
| II-841 | Me | Me | Me | 2-Br-4,6-diMe—Ph |
| II-842 | Me | Et | Me | 2-Br-4,6-diMe—Ph |
| II-843 | Me | Me | Me | 2-Br-3-MeO-6-Me—Ph |
| II-844 | Me | Et | Me | 2-Br-3-MeO-6-Me—Ph |
| II-845 | Me | Me | Me | 2-Br-4-MeO-6-Me—Ph |
| II-846 | Me | Et | Me | 2-Br-4-MeO-6-Me—Ph |
| II-847 | Me | Me | Me | 2-Br-3-F-6-MeO—Ph |
| II-848 | Me | Et | Me | 2-Br-3-F-6-MeO—Ph |
| II-849 | Me | Me | Me | 2-Br-4-F-6-MeO—Ph |
| II-850 | Me | Et | Me | 2-Br-4-F-6-MeO—Ph |
| II-851 | Me | Me | Me | 2-Br-3-Cl-6-MeO—Ph |
| II-852 | Me | Et | Me | 2-Br-3-Cl-6-MeO—Ph |
| II-853 | Me | Me | Me | 2-Br-4-Cl-6-MeO—Ph |
| II-854 | Me | Et | Me | 2-Br-4-Cl-6-MeO—Ph |
| II-855 | Me | Me | Me | 2,3-diBr-6-MeO—Ph |
| II-856 | Me | Et | Me | 2,3-diBr-6-MeO—Ph |
| II-857 | Me | Me | Me | 2,4-diBr-6-MeO—Ph |
| II-858 | Me | Et | Me | 2,4-diBr-6-MeO—Ph |
| II-859 | Me | Me | Me | 2-Br-3-Me-6-MeO—Ph |
| II-860 | Me | Et | Me | 2-Br-3-Me-6-MeO—Ph |
| II-861 | Me | Me | Me | 2-Br-4-Me-6-MeO—Ph |
| II-862 | Me | Et | Me | 2-Br-4-Me-6-MeO—Ph |
| II-863 | Me | Me | Me | 2-Br-3,6-diMeO—Ph |
| II-864 | Me | Et | Me | 2-Br-3,6-diMeO—Ph |
| II-865 | Me | Me | Me | 2-Br-4,6-diMeO—Ph |
| II-866 | Me | Et | Me | 2-Br-4,6-diMeO—Ph |
| II-867 | Me | Me | Me | 2-Me-3,6-diF—Ph |
| II-868 | Me | Et | Me | 2-Me-3,6-diF—Ph |
| II-869 | Me | Me | Me | 2-Me-3-Cl-6-F—Ph |
| II-870 | Me | Et | Me | 2-Me-3-Cl-6-F—Ph |
| II-871 | Me | Me | Me | 2-Me-3-Br-6-F—Ph |
| II-872 | Me | Et | Me | 2-Me-3-Br-6-F—Ph |
| II-873 | Me | Me | Me | 2,3-diMe-6-F—Ph |
| II-874 | Me | Et | Me | 2,3-diMe-6-F—Ph |
| II-875 | Me | Me | Me | 2,4-diMe-6-F—Ph |
| II-876 | Me | Et | Me | 2,4-diMe-6-F—Ph |
| II-877 | Me | Me | Me | 2-Me-3-MeO-6-F—Ph |
| II-878 | Me | Et | Me | 2-Me-3-MeO-6-F—Ph |
| II-879 | Me | Me | Me | 2-Me-4-MeO-6-F—Ph |
| II-880 | Me | Et | Me | 2-Me-4-MeO-6-F—Ph |
| II-881 | Me | Me | Me | 2-Me-3-F-6-Cl—Ph |
| II-882 | Me | Et | Me | 2-Me-3-F-6-Cl—Ph |
| II-883 | Me | Me | Me | 2-Me-3,6-diCl—Ph |
| II-884 | Me | Et | Me | 2-Me-3,6-diCl—Ph |
| II-885 | Me | Me | Me | 2-Me-3-Br-6-Cl—Ph |
| II-886 | Me | Et | Me | 2-Me-3-Br-6-Cl—Ph |
| II-887 | Me | Me | Me | 2,3-diMe-6-Cl—Ph |
| II-888 | Me | Et | Me | 2,3-diMe-6-Cl—Ph |
| II-889 | Me | Me | Me | 2,4-diMe-6-Cl—Ph |

TABLE 22-continued (II)

| Comp. No. | R¹ | R² | R³ | A |
|---|---|---|---|---|
| II-890 | Me | Et | Me | 2,4-diMe-6-Cl—Ph |
| II-891 | Me | Me | Me | 2-Me-3-MeO-6-Cl—Ph |
| II-892 | Me | Et | Me | 2-Me-3-MeO-6-Cl—Ph |
| II-893 | Me | Me | Me | 2-Me-4-MeO-6-Cl—Ph |
| II-894 | Me | Et | Me | 2-Me-4-MeO-6-Cl—Ph |
| II-895 | Me | Me | Me | 2-Me-3-F-6-Br—Ph |
| II-896 | Me | Et | Me | 2-Me-3-F-6-Br—Ph |
| II-897 | Me | Me | Me | 2-Me-3-Cl-6-Br—Ph |
| II-898 | Me | Et | Me | 2-Me-3-Cl-6-Br—Ph |
| II-899 | Me | Me | Me | 2-Me-3,6-diBr—Ph |
| II-900 | Me | Et | Me | 2-Me-3,6-diBr—Ph |

TABLE 23

(II)

| Comp. No. | R¹ | R² | R³ | A |
|---|---|---|---|---|
| II-901 | Me | Me | Me | 2,3-diMe-6-Br—Ph |
| II-902 | Me | Et | Me | 2,3-diMe-6-Br—Ph |
| II-903 | Me | Me | Me | 2,4-diMe-6-Br—Ph |
| II-904 | Me | Et | Me | 2,4-diMe-6-Br—Ph |
| II-905 | Me | Me | Me | 2-Me-3-MeO-6-Br—Ph |
| II-906 | Me | Et | Me | 2-Me-3-MeO-6-Br—Ph |
| II-907 | Me | Me | Me | 2-Me-4-MeO-6-Br—Ph |
| II-908 | Me | Et | Me | 2-Me-4-MeO-6-Br—Ph |
| II-909 | Me | Me | Me | 2-Me-3-F-6-Me—Ph |
| II-910 | Me | Et | Me | 2-Me-3-F-6-Me—Ph |
| II-911 | Me | Me | Me | 2-Me-3-Cl-6-Me—Ph |
| II-912 | Me | Et | Me | 2-Me-3-Cl-6-Me—Ph |
| II-913 | Me | Me | Me | 2-Me-3-Br-6-Me—Ph |
| II-914 | Me | Et | Me | 2-Me-3-Br-6-Me—Ph |
| II-915 | Me | Me | Me | 2,3,6-triMe—Ph |
| II-916 | Me | Et | Me | 2,3,6-triMe—Ph |
| II-917 | Me | Me | Me | 2,4,6-triMe—Ph |
| II-918 | Me | Et | Me | 2,4,6-triMe—Ph |
| II-919 | Me | Me | Me | 2-Me-3-MeO-6-Me—Ph |
| II-920 | Me | Et | Me | 2-Me-3-MeO-6-Me—Ph |
| II-921 | Me | Me | Me | 2-Me-4-MeO-6-Me—Ph |
| II-922 | Me | Et | Me | 2-Me-4-MeO-6-Me—Ph |
| II-923 | Me | Me | Me | 2-Me-3-F-6-MeO—Ph |
| II-924 | Me | Et | Me | 2-Me-3-F-6-MeO—Ph |
| II-925 | Me | Me | Me | 2-Me-3-Cl-6-MeO—Ph |
| II-926 | Me | Et | Me | 2-Me-3-Cl-6-MeO—Ph |
| II-927 | Me | Me | Me | 2-Me-3-Br-6-MeO—Ph |
| II-928 | Me | Et | Me | 2-Me-3-Br-6-MeO—Ph |
| II-929 | Me | Me | Me | 2,3-diMe-6-MeO—Ph |
| II-930 | Me | Et | Me | 2,3-diMe-6-MeO—Ph |
| II-931 | Me | Me | Me | 2,4-diMe-6-MeO—Ph |
| II-932 | Me | Et | Me | 2,4-diMe-6-MeO—Ph |

TABLE 23-continued (II)

| Comp. No. | R¹ | R² | R³ | A |
|---|---|---|---|---|
| II-933 | Me | Me | Me | 2-Me-3,6-diMeO—Ph |
| II-934 | Me | Et | Me | 2-Me-3,6-diMeO—Ph |
| II-935 | Me | Me | Me | 2-Me-4,6-diMeO—Ph |
| II-936 | Me | Et | Me | 2-Me-4,6-diMeO—Ph |
| II-937 | Me | Me | Me | 2-MeO-3,6-diF—Ph |
| II-938 | Me | Et | Me | 2-MeO-3,6-diF—Ph |
| II-939 | Me | Me | Me | 2-MeO-3-Cl-6 F—Ph |
| II-940 | Me | Et | Me | 2-MeO-3-Cl-6 F—Ph |
| II-941 | Me | Me | Me | 2-MeO-3-Br-6-F—Ph |
| II-942 | Me | Et | Me | 2-MeO-3-Br-6-F—Ph |
| II-943 | Me | Me | Me | 2-MeO-3-Me-6-F—Ph |
| II-944 | Me | Et | Me | 2-MeO-3-Me-6-F—Ph |
| II-945 | Me | Me | Me | 2,3-diMeO-6-F—Ph |
| II-946 | Me | Et | Me | 2,3-diMeO-6-F—Ph |
| II-947 | Me | Me | Me | 2,4-diMeO-6-F—Ph |
| II-948 | Me | Et | Me | 2,4-diMeO-6-F—Ph |
| II-949 | Me | Me | Me | 2-MeO-3-F-6-Cl—Ph |
| II-950 | Me | Et | Me | 2-MeO-3-F-6-Cl—Ph |
| II-951 | Me | Me | Me | 2-MeO-3,6-Cl—Ph |
| II-952 | Me | Et | Me | 2-MeO-3,6-Cl—Ph |
| II-953 | Me | Me | Me | 2-MeO-3-Br-6-Cl—Ph |
| II-954 | Me | Et | Me | 2-MeO-3-Br-6-Cl—Ph |
| II-955 | Me | Me | Me | 2-MeO-3-Me-6-Cl—Ph |
| II-956 | Me | Et | Me | 2-MeO-3-Me-6-Cl—Ph |
| II-957 | Me | Me | Me | 2,3-diMeO-6-Cl—Ph |
| II-958 | Me | Et | Me | 2,3-diMeO-6-Cl—Ph |
| II-959 | Me | Me | Me | 2,4-diMeO-6-Cl—Ph |
| II-960 | Me | Et | Me | 2,4-diMeO-6-Cl—Ph |
| II-961 | Me | Me | Me | 2-MeO-3-F-6-Br—Ph |
| II-962 | Me | Et | Me | 2-MeO-3-F-6-Br—Ph |
| II-963 | Me | Me | Me | 2-MeO-3-Cl-6-Br—Ph |
| II-964 | Me | Et | Me | 2-MeO-3-Cl-6-Br—Ph |
| II-965 | Me | Me | Me | 2-MeO-3,6-diBr—Ph |
| II-966 | Me | Et | Me | 2-MeO-3,6-diBr—Ph |
| II-967 | Me | Me | Me | 2-MeO-3-Me-6-Br—Ph |
| II-968 | Me | Et | Me | 2-MeO-3-Me-6-Br—Ph |
| II-969 | Me | Me | Me | 2,3-diMeO-6-Br—Ph |
| II-970 | Me | Et | Me | 2,3-diMeO-6-Br—Ph |
| II-971 | Me | Me | Me | 2,4-diMeO-6-Br—Ph |
| II-972 | Me | Et | Me | 2,4-diMeO-6-Br—Ph |
| II-973 | Me | Me | Me | 2-MeO-3-F-6-Me—Ph |
| II-974 | Me | Et | Me | 2-MeO-3-F-6-Me—Ph |
| II-975 | Me | Me | Me | 2-MeO-3-Cl-6-Me—Ph |
| II-976 | Me | Et | Me | 2-MeO-3-Cl-6-Me—Ph |
| II-977 | Me | Me | Me | 2-MeO-3-Br-6-Me—Ph |
| II-978 | Me | Et | Me | 2-MeO-3-Br-6-Me—Ph |
| II-979 | Me | Me | Me | 2-MeO-3,6-diMe—Ph |
| II-980 | Me | Et | Me | 2-MeO-3,6-diMe—Ph |
| II-981 | Me | Me | Me | 2,3-diMeO-6-Me—Ph |
| II-982 | Me | Et | Me | 2,3-diMeO-6-Me—Ph |
| II-983 | Me | Me | Me | 2,4-diMeO-6-Me—Ph |
| II-984 | Me | Et | Me | 2,4-diMeO-6-Me—Ph |
| II-985 | Me | Me | Me | 2,6-di-MeO-3-F—Ph |
| II-986 | Me | Et | Me | 2,6-di-MeO-3-F—Ph |
| II-987 | Me | Me | Me | 2,6-di-MeO-3-Cl—Ph |
| II-988 | Me | Et | Me | 2,6-di-MeO-3-Cl—Ph |
| II-989 | Me | Me | Me | 2,6-di-MeO-3-Br—Ph |
| II-990 | Me | Et | Me | 2,6-di-MeO-3-Br—Ph |
| II-991 | Me | Me | Me | 2,6-di-MeO-3-Me—Ph |
| II-992 | Me | Et | Me | 2,6-di-MeO-3-Me—Ph |
| II-993 | Me | Me | Me | 2,3,6-triMeO—Ph |

TABLE 23-continued (II)

| Comp. No. | R¹ | R² | R³ | A |
|---|---|---|---|---|
| II-994 | Me | Et | Me | 2,3,6-triMeO—Ph |
| II-995 | Me | Me | Me | 2,4,6-triMeO—Ph |
| II-996 | Me | Et | Me | 2,4,6-triMeO—Ph |

TABLE 24

(II)

| Comp. No. | R¹ | R² | R³ | A |
|---|---|---|---|---|
| II-997 | Me | Me | Me | 6-F-2,3-dihydrobenzofuran-7-yl |
| II-998 | Me | Et | Me | 6-F-2,3-dihydrobenzofuran-7-yl |
| II-999 | Me | Me | Me | 6-Cl-2,3-dihydrobenzofuran-7-yl |
| II-1000 | Me | Et | Me | 6-Cl-2,3-dihydrobenzofuran-7-yl |
| II-1001 | Me | Me | Me | 6-Br-2,3-dihydrobenzofuran-7-yl |
| II-1002 | Me | Et | Me | 6-Br-2,3-dihydrobenzofuran-7-yl |
| II-1003 | Me | Me | Me | 6-Me-2,3-dihydrobenzofuran-7-yl |
| II-1004 | Me | Et | Me | 6-Me-2,3-dihydrobenzofuran-7-yl |
| II-1005 | Me | Me | Me | 6-MeO-2,3-dihydrobenzofuran-7-yl |
| II-1006 | Me | Et | Me | 6-MeO-2,3-dihydrobenzofuran-7-yl |
| II-1007 | Me | Me | Me | pyridin-2-yl |
| II-1008 | Me | Et | Me | pyridin-2-yl |
| II-1009 | Me | Me | Me | 3-F-pyridin-2-yl |
| II-1010 | Me | Et | Me | 3-F-pyridin-2-yl |
| II-1011 | Me | Me | Me | 3-Cl-pyridin-2-yl |
| II-1012 | Me | Et | Me | 3-Cl-pyridin-2-yl |
| II-1013 | Me | Me | Me | 3-Br-pyridin-2-yl |
| II-1014 | Me | Et | Me | 3-Br-pyridin-2-yl |
| II-1015 | Me | Me | Me | 3-Me-pyridin-2-yl |
| II-1016 | Me | Et | Me | 3-Me-pyridin-2-yl |
| II-1017 | Me | Me | Me | 3-MeO-pyridin-2-yl |
| II-1018 | Me | Et | Me | 3-MeO-pyridin-2-yl |
| II-1019 | Me | Me | Me | pyridin-3-yl |
| II-1020 | Me | Et | Me | pyridin-3-yl |
| II-1021 | Me | Me | Me | 2-F-pyridin-3-yl |
| II-1022 | Me | Et | Me | 2-F-pyridin-3-yl |
| II-1023 | Me | Me | Me | 2-Cl-pyridin-3-yl |
| II-1024 | Me | Et | Me | 2-Cl-pyridin-3-yl |
| II-1025 | Me | Me | Me | 2-Br-pyridin-3-yl |
| II-1026 | Me | Et | Me | 2-Br-pyridin-3-yl |
| II-1027 | Me | Me | Me | 2-MeO-pyridin-3-yl |
| II-1028 | Me | Et | Me | 2-MeO-pyridin-3-yl |
| II-1029 | Me | Me | Me | pyridin-4-yl |
| II-1030 | Me | Et | Me | pyridin-4-yl |
| II-1031 | Me | Me | Me | 3-F-isothiazol-4-yl |
| II-1032 | Me | Et | Me | 3-F-isothiazol-4-yl |
| II-1033 | Me | Me | Me | 3-Cl-isothiazol-4-yl |
| II-1034 | Me | Et | Me | 3-Cl-isothiazol-4-yl |
| II-1035 | Me | Me | Me | 3-Me-isothiazol-4-yl |
| II-1036 | Me | Et | Me | 3-Me-isothiazol-4-yl |

TABLE 24-continued (II)

| Comp. No. | R¹ | R² | R³ | A |
|---|---|---|---|---|
| II-1037 | Me | Me | Me | 3-F-isoxazol-4-yl |
| II-1038 | Me | Et | Me | 3-F-isoxazol-4-yl |
| II-1039 | Me | Me | Me | 3-Cl-isoxazol-4-yl |
| II-1040 | Me | Et | Me | 3-Cl-isoxazol-4-yl |
| II-1041 | Me | Me | Me | 3-Me-isoxazol-4-yl |
| II-1042 | Me | Et | Me | 3-Me-isoxazol-4-yl |
| II-1043 | Me | Me | Me | thiophen-2-yl |
| II-1044 | Me | Et | Me | thiophen-2-yl |
| II-1045 | Me | Me | Me | thiophen-3-yl |
| II-1046 | Me | Et | Me | thiophen-3-yl |

TABLE 25

(II)

| Comp. No. | R¹ | R² | R³ | A |
|---|---|---|---|---|
| II-1047 | Me | Me | Me | benzofuran-7-yl |
| II-1048 | Me | Et | Me | benzofuran-7-yl |
| II-1049 | Me | Me | Me | 6-F-benzofuran-yl |
| II-1050 | Me | Et | Me | 6-F-benzofuran-yl |
| II-1051 | Me | Me | Me | 6-Cl-benzofuran-yl |
| II-1052 | Me | Et | Me | 6-Cl-benzofuran-yl |
| II-1053 | Me | Me | Me | 6-Br-benzofuran-yl |
| II-1054 | Me | Et | Me | 6-Br-benzofuran-yl |
| II-1055 | Me | Me | Me | 6-Me-benzofuran-yl |
| II-1056 | Me | Et | Me | 6-Me-benzofuran-yl |
| II-1057 | Me | Me | Me | 6-MeO-benzofuran-yl |
| II-1058 | Me | Et | Me | 6-MeO-benzofuran-yl |
| II-1059 | Me | Me | Me | 2-Me-6-F-benzofuran-7-yl |
| II-1060 | Me | Et | Me | 2-Me-6-F-benzofuran-7-yl |
| II-1061 | Me | Me | Me | 3-Me-6-F-benzofuran-7-yl |
| II-1062 | Me | Et | Me | 3-Me-6-F-benzofuran-7-yl |
| II-1063 | Me | Me | Me | 2-Cl-6-F-benzofuran-7-yl |
| II-1064 | Me | Et | Me | 2-Cl-6-F-benzofuran-7-yl |
| II-1065 | Me | Me | Me | 3-Cl-6-F-benzofuran-7-yl |
| II-1066 | Me | Et | Me | 3-Cl-6-F-benzofuran-7-yl |
| II-1067 | Me | Me | Me | 2-Me-6-Cl-benzofuran-7-yl |
| II-1068 | Me | Et | Me | 2-Me-6-Cl-benzofuran-7-yl |
| II-1069 | Me | Me | Me | 3-Me-6-Cl-benzofuran-7-yl |
| II-1070 | Me | Et | Me | 3-Me-6-Cl-benzofuran-7-yl |
| II-1071 | Me | Me | Me | 2-Cl-6-Cl-benzofuran-7-yl |
| II-1072 | Me | Et | Me | 2-Cl-6-Cl-benzofuran-7-yl |
| II-1073 | Me | Me | Me | 3-Cl-6-Cl-benzofuran-7-yl |
| II-1074 | Me | Et | Me | 3-Cl-6-Cl-benzofuran-7-yl |

TABLE 26

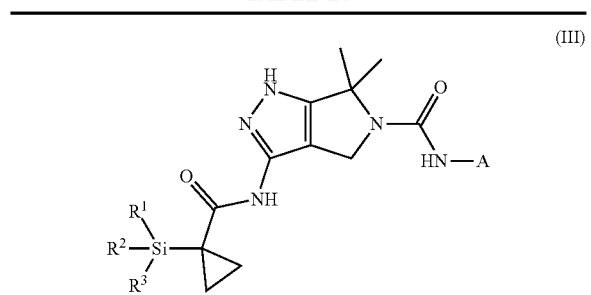

(III)

| Comp. No. | R¹ | R² | R³ | A |
|---|---|---|---|---|
| III-1 | Me | Me | Me | Ph |
| III-2 | Me | Et | Me | Ph |
| III-3 | Me | Me | Me | 2-F—Ph |
| III-4 | Me | Et | Me | 2-F—Ph |
| III-5 | Me | Me | Me | 3-F—Ph |
| III-6 | Me | Et | Me | 3-F—Ph |
| III-7 | Me | Me | Me | 4-F—Ph |
| III-8 | Me | Et | Me | 4-F—Ph |
| III-9 | Me | Me | Me | 2-Cl—Ph |
| III-10 | Me | Et | Me | 2-Cl—Ph |
| III-11 | Me | Me | Me | 3-Cl—Ph |
| III-12 | Me | Et | Me | 3-Cl—Ph |
| III-13 | Me | Me | Me | 4-Cl—Ph |
| III-14 | Me | Et | Me | 4-Cl—Ph |
| III-15 | Me | Me | Me | 2-Br—Ph |
| III-16 | Me | Et | Me | 2-Br—Ph |
| III-17 | Me | Me | Me | 3-Br—Ph |
| III-18 | Me | Et | Me | 3-Br—Ph |
| III-19 | Me | Me | Me | 4-Br—Ph |
| III-20 | Me | Et | Me | 4-Br—Ph |
| III-21 | Me | Me | Me | 2-Me—Ph |
| III-22 | Me | Et | Me | 2-Me—Ph |
| III-23 | Me | Me | Me | 3-Me—Ph |
| III-24 | Me | Et | Me | 3-Me—Ph |
| III-25 | Me | Me | Me | 4-Me—Ph |
| III-26 | Me | Et | Me | 4-Me—Ph |
| III-27 | Me | Me | Me | 2-Et—Ph |
| III-28 | Me | Et | Me | 2-Et—Ph |
| III-29 | Me | Me | Me | 3-Et—Ph |
| III-30 | Me | Et | Me | 3-Et—Ph |
| III-31 | Me | Me | Me | 4-Et—Ph |
| III-32 | Me | Et | Me | 4-Et—Ph |
| III-33 | Me | Me | Me | 2-iPr—Ph |
| III-34 | Me | Et | Me | 2-iPr—Ph |
| III-35 | Me | Me | Me | 3-iPr—Ph |
| III-36 | Me | Et | Me | 3-iPr—Ph |
| III-37 | Me | Me | Me | 4-iPr—Ph |
| III-38 | Me | Et | Me | 4-iPr—Ph |
| III-39 | Me | Me | Me | 2-cPr—Ph |
| III-40 | Me | Et | Me | 2-cPr—Ph |
| III-41 | Me | Me | Me | 3-cPr—Ph |
| III-42 | Me | Et | Me | 3-cPr—Ph |
| III-43 | Me | Me | Me | 4-cPr—Ph |
| III-44 | Me | Et | Me | 4-cPr—Ph |
| III-45 | Me | Me | Me | 2-(1,1-diF—Et)—Ph |
| III-46 | Me | Et | Me | 2-(1,1-diF—Et)—Ph |
| III-47 | Me | Me | Me | 3-(1,1-diF—Et)—Ph |
| III-48 | Me | Et | Me | 3-(1,1-diF—Et)—Ph |
| III-49 | Me | Me | Me | 4-(1,1-diF—Et)—Ph |
| III-50 | Me | Et | Me | 4-(1,1-diF—Et)—Ph |
| III-51 | Me | Me | Me | 2-CF₃—Ph |
| III-52 | Me | Et | Me | 2-CF₃—Ph |
| III-53 | Me | Me | Me | 3-CF₃—Ph |
| III-54 | Me | Et | Me | 3-CF₃—Ph |
| III-55 | Me | Me | Me | 4-CF₃—Ph |
| III-56 | Me | Et | Me | 4-CF₃—Ph |
| III-57 | Me | Me | Me | 2-tBu—Ph |
| III-58 | Me | Et | Me | 2-tBu—Ph |
| III-59 | Me | Me | Me | 3-tBu—Ph |
| III-60 | Me | Et | Me | 3-tBu—Ph |
| III-61 | Me | Me | Me | 4-tBu—Ph |
| III-62 | Me | Et | Me | 4-tBu—Ph |
| III-63 | Me | Me | Me | 2-NC—Ph |
| III-64 | Me | Et | Me | 2-NC—Ph |

TABLE 26-continued

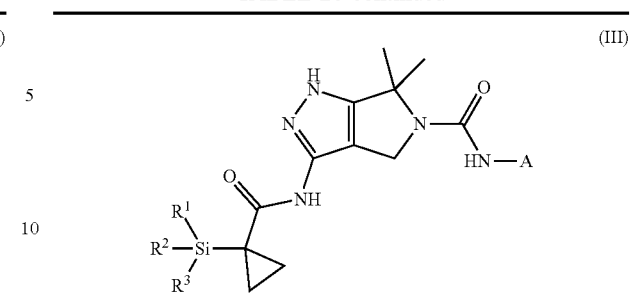

(III)

| Comp. No. | R¹ | R² | R³ | A |
|---|---|---|---|---|
| III-65 | Me | Me | Me | 3-NC—Ph |
| III-66 | Me | Et | Me | 3-NC—Ph |
| III-67 | Me | Me | Me | 4-NC—Ph |
| III-68 | Me | Et | Me | 4-NC—Ph |
| III-69 | Me | Me | Me | 2-Ph—Ph |
| III-70 | Me | Et | Me | 2-Ph—Ph |
| III-71 | Me | Me | Me | 3-Ph—Ph |
| III-72 | Me | Et | Me | 3-Ph—Ph |
| III-73 | Me | Me | Me | 4-Ph—Ph |
| III-74 | Me | Et | Me | 4-Ph—Ph |
| III-75 | Me | Me | Me | 2-MeO—Ph |
| III-76 | Me | Et | Me | 2-MeO—Ph |
| III-77 | Me | Me | Me | 3-MeO—Ph |
| III-78 | Me | Et | Me | 3-MeO—Ph |
| III-79 | Me | Me | Me | 4-MeO—Ph |
| III-80 | Me | Et | Me | 4-MeO—Ph |
| III-81 | Me | Me | Me | 2-EtO—Ph |
| III-82 | Me | Et | Me | 2-EtO—Ph |
| III-83 | Me | Me | Me | 3-EtO—Ph |
| III-84 | Me | Et | Me | 3-EtO—Ph |
| III-85 | Me | Me | Me | 4-EtO—Ph |
| III-86 | Me | Et | Me | 4-EtO—Ph |
| III-87 | Me | Me | Me | 2-CHF₂O—Ph |
| III-88 | Me | Et | Me | 2-CHF₂O—Ph |
| III-89 | Me | Me | Me | 3-CHF₂O—Ph |
| III-90 | Me | Et | Me | 3-CHF₂O—Ph |
| III-91 | Me | Me | Me | 4-CHF₂O—Ph |
| III-92 | Me | Et | Me | 4-CHF₂O—Ph |
| III-93 | Me | Me | Me | 2-CF₃O—Ph |
| III-94 | Me | Et | Me | 2-CF₃O—Ph |
| III-95 | Me | Me | Me | 3-CF₃O—Ph |
| III-96 | Me | Et | Me | 3-CF₃O—Ph |
| III-97 | Me | Me | Me | 4-CF₃O—Ph |
| III-98 | Me | Et | Me | 4-CF₃O—Ph |
| III-99 | Me | Me | Me | 2,3-diF—Ph |
| III-100 | Me | Et | Me | 2,3-diF—Ph |

TABLE 27

(III)

| Comp. No. | R¹ | R² | R³ | A |
|---|---|---|---|---|
| III-101 | Me | Me | Me | 2,4-diF—Ph |
| III-102 | Me | Et | Me | 2,4-diF—Ph |
| III-103 | Me | Me | Me | 2,5,-diF—Ph |
| III-104 | Me | Et | Me | 2,5,-diF—Ph |
| III-105 | Me | Me | Me | 2,6-diF—Ph |
| III-106 | Me | Et | Me | 2,6-diF—Ph |
| III-107 | Me | Me | Me | 2-F-3-Cl—Ph |

TABLE 27-continued

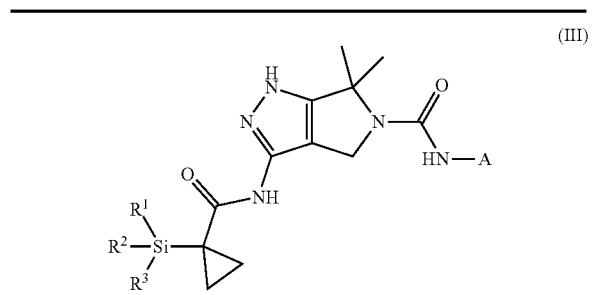

(III)

| Comp. No. | R¹ | R² | R³ | A |
|---|---|---|---|---|
| III-108 | Me | Et | Me | 2-F-3-Cl—Ph |
| III-109 | Me | Me | Me | 2-F-4-Cl—Ph |
| III-110 | Me | Et | Me | 2-F-4-Cl—Ph |
| Ill-111 | Me | Me | Me | 2-F-5-Cl—Ph |
| III-112 | Me | Et | Me | 2-F-5-Cl—Ph |
| III-113 | Me | Me | Me | 2-F-6-Cl—Ph |
| III-114 | Me | Et | Me | 2-F-6-Cl—Ph |
| III-115 | Me | Me | Me | 2-F-3-Br—Ph |
| III-116 | Me | Et | Me | 2-F-3-Br—Ph |
| III-117 | Me | Me | Me | 2-F-4-Br—Ph |
| III-118 | Me | Et | Me | 2-F-4-Br—Ph |
| III-119 | Me | Me | Me | 2-F-5-Br—Ph |
| III-120 | Me | Et | Me | 2-F-5-Br—Ph |
| III-121 | Me | Me | Me | 2-F-6-Br—Ph |
| III-122 | Me | Et | Me | 2-F-6-Br—Ph |
| III-123 | Me | Me | Me | 2-F-3-Me—Ph |
| III-124 | Me | Et | Me | 2-F-3-Me—Ph |
| III-125 | Me | Me | Me | 2-F-4-Me—Ph |
| III-126 | Me | Et | Me | 2-F-4 Me—Ph |
| III-127 | Me | Me | Me | 2-F-5-Me—Ph |
| III-128 | Me | Et | Me | 2-F-5-Me—Ph |
| III-129 | Me | Me | Me | 2-F-6-Me—Ph |
| III-130 | Me | Et | Me | 2-F-6-Me—Ph |
| III-131 | Me | Me | Me | 2-F-3-Et—Ph |
| III-132 | Me | Et | Me | 2-F-3-Et—Ph |
| III-133 | Me | Me | Me | 2-F-4-Et—Ph |
| III-134 | Me | Et | Me | 2-F-4-Et—Ph |
| III-135 | Me | Me | Me | 2-F-5-Et—Ph |
| III-136 | Me | Et | Me | 2-F-5-Et—Ph |
| III-137 | Me | Me | Me | 2-F-6-Et—Ph |
| III-138 | Me | Et | Me | 2-F-6-Et—Ph |
| III-139 | Me | Me | Me | 2-F-3-cPr—Ph |
| III-140 | Me | Et | Me | 2-F-3-cPr—Ph |
| III-141 | Me | Me | Me | 2-F-4-cPr—Ph |
| III-142 | Me | Et | Me | 2-F-4-cPr—Ph |
| III-143 | Me | Me | Me | 2-F-5-cPr—Ph |
| III-144 | Me | Et | Me | 2-F-5-cPr—Ph |
| III-145 | Me | Me | Me | 2-F-6-cPr—Ph |
| III-146 | Me | Et | Me | 2-F-6-cPr—Ph |
| III-147 | Me | Me | Me | 2-F-3-CF₃—Ph |
| III-148 | Me | Et | Me | 2-F-3-CF₃—Ph |
| III-149 | Me | Me | Me | 2-F-4-CF₃—Ph |
| III-150 | Me | Et | Me | 2-F-4-CF₃—Ph |
| III-151 | Me | Me | Me | 2-F-5-CF₃—Ph |
| III-152 | Me | Et | Me | 2-F-5-CF₃—Ph |
| III-153 | Me | Me | Me | 2-F-6-CF₃—Ph |
| III-154 | Me | Et | Me | 2-F-6-CF₃—Ph |
| III-155 | Me | Me | Me | 2-F-3-MeO—Ph |
| III-156 | Me | Et | Me | 2-F-3-MeO—Ph |
| III-157 | Me | Me | Me | 2-F-4-MeO—Ph |
| III-158 | Me | Et | Me | 2-F-4-MeO—Ph |
| III-159 | Me | Me | Me | 2-F-5-MeO—Ph |
| III-160 | Me | Et | Me | 2-F-5-MeO—Ph |
| Ill-161 | Me | Me | Me | 2-F-6-MeO—Ph |
| III-162 | Me | Et | Me | 2-F-6-MeO—Ph |
| III-163 | Me | Me | Me | 2-F-3-CHF₂O—Ph |
| III-164 | Me | Et | Me | 2-F-3-CHF₂O—Ph |
| III-165 | Me | Me | Me | 2-F-4-CHF₂O—Ph |
| III-166 | Me | Et | Me | 2-F-4-CHF₂O—Ph |
| III-167 | Me | Me | Me | 2-F-5-CHF₂O—Ph |
| III-168 | Me | Et | Me | 2-F-5-CHF₂O—Ph |
| III-169 | Me | Me | Me | 2-F-6-CHF₂O—Ph |
| III-170 | Me | Et | Me | 2-F-6-CHF₂O—Ph |
| III-171 | Me | Me | Me | 2-F-3-CD₃O—Ph |

TABLE 27-continued

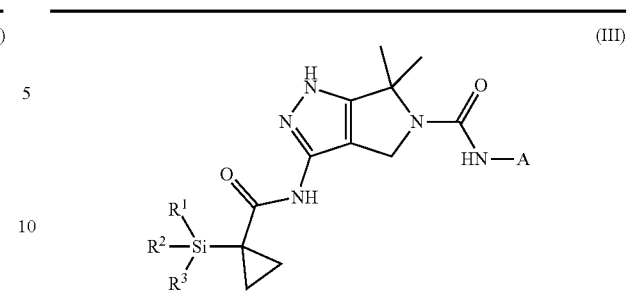

(III)

| Comp. No. | R¹ | R² | R³ | A |
|---|---|---|---|---|
| III-172 | Me | Et | Me | 2-F-3-CD₃O—Ph |
| III-173 | Me | Me | Me | 2-F-4-CD₃O—Ph |
| III-174 | Me | Et | Me | 2-F-4-CD₃O—Ph |
| III-175 | Me | Me | Me | 2-F-5-CD₃O—Ph |
| III-176 | Me | Et | Me | 2-F-5-CD₃O—Ph |
| III-177 | Me | Me | Me | 2-F-6-CD₃O—Ph |
| III-178 | Me | Et | Me | 2-F-6-CD₃O—Ph |
| III-179 | Me | Me | Me | 2-F-3-NC—Ph |
| III-180 | Me | Et | Me | 2-F-3-NC—Ph |
| III-181 | Me | Me | Me | 2-F-4-NC—Ph |
| III-182 | Me | Et | Me | 2-F-4-NC—Ph |
| III-183 | Me | Me | Me | 2-F-5-NC—Ph |
| III-184 | Me | Et | Me | 2-F-5-NC—Ph |
| III-185 | Me | Me | Me | 2-F-6-NC—Ph |
| III-186 | Me | Et | Me | 2-F-6-NC—Ph |
| III-187 | Me | Me | Me | 2-Cl-3-F—Ph |
| III-188 | Me | Et | Me | 2-Cl-3-F—Ph |
| III-189 | Me | Me | Me | 2-Cl-4-F—Ph |
| III-190 | Me | Et | Me | 2-Cl-4-F—Ph |
| III-191 | Me | Me | Me | 2-Cl-5-F—Ph |
| III-192 | Me | Et | Me | 2-Cl-5-F—Ph |
| III-193 | Me | Me | Me | 2,3-diCl—Ph |
| III-194 | Me | Et | Me | 2,3-diCl—Ph |
| III-195 | Me | Me | Me | 2,4-diCl—Ph |
| III-196 | Me | Et | Me | 2,4-diCl—Ph |
| III-197 | Me | Me | Me | 2,5-diCl—Ph |
| III-198 | Me | Et | Me | 2,5-diCl—Ph |
| III-199 | Me | Me | Me | 2,6-diCl—Ph |
| III-200 | Me | Et | Me | 2,6-diCl—Ph |

TABLE 28

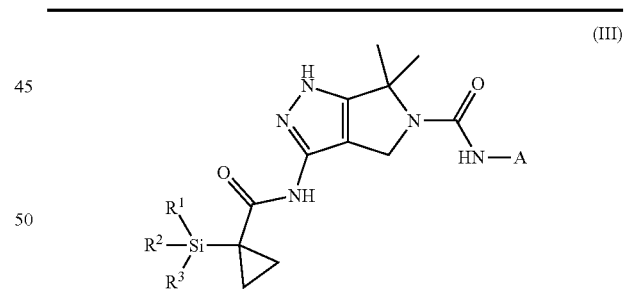

(III)

| Comp. No. | R¹ | R² | R³ | A |
|---|---|---|---|---|
| III-201 | Me | Me | Me | 2-Cl-3-Br—Ph |
| III-202 | Me | Et | Me | 2-Cl-3-Br—Ph |
| III-203 | Me | Me | Me | 2-Cl-4-Br—Ph |
| III-204 | Me | Et | Me | 2-Cl-4-Br—Ph |
| III-205 | Me | Me | Me | 2-Cl-5-Br—Ph |
| III-206 | Me | Et | Me | 2-Cl-5-Br—Ph |
| III-207 | Me | Me | Me | 2-Cl-6-Br—Ph |
| III-208 | Me | Et | Me | 2-Cl-6-Br—Ph |
| III-209 | Me | Me | Me | 2-Cl-3-Me—Ph |
| III-210 | Me | Et | Me | 2-Cl-3-Me—Ph |
| III-211 | Me | Me | Me | 2-Cl-4 Me—Ph |
| III-212 | Me | Et | Me | 2-Cl-4-Me—Ph |
| III-213 | Me | Me | Me | 2-Cl-5-Me—Ph |
| III-214 | Me | Et | Me | 2-Cl-5-Me—Ph |

TABLE 28-continued (III)

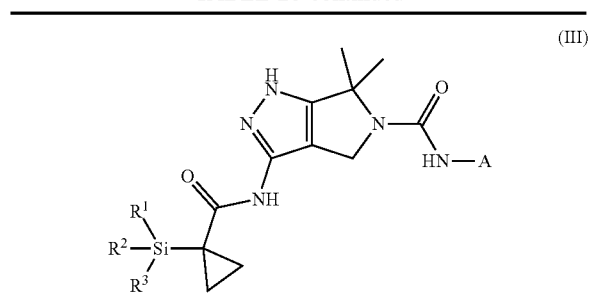

| Comp. No. | R¹ | R² | R³ | A |
|---|---|---|---|---|
| III-215 | Me | Me | Me | 2-Cl-6-Me—Ph |
| III-216 | Me | Et | Me | 2-Cl-6-Me—Ph |
| III-217 | Me | Me | Me | 2-Cl-3-Et—Ph |
| III-218 | Me | Et | Me | 2-Cl-3-Et—Ph |
| III-219 | Me | Me | Me | 2-Cl-4-Et—Ph |
| III-220 | Me | Et | Me | 2-Cl-4-Et—Ph |
| III-221 | Me | Me | Me | 2-Cl-5-Et—Ph |
| III-222 | Me | Et | Me | 2-Cl-5-Et—Ph |
| III-223 | Me | Me | Me | 2-Cl-6-Et—Ph |
| III-224 | Me | Et | Me | 2-Cl-6-Et—Ph |
| III-225 | Me | Me | Me | 2-Cl-3-cPr—Ph |
| III-226 | Me | Et | Me | 2-Cl-3-cPr—Ph |
| III-227 | Me | Me | Me | 2-Cl-4-cPr—Ph |
| III-228 | Me | Et | Me | 2-Cl-4-cPr—Ph |
| III-229 | Me | Me | Me | 2-Cl-5-cPr—Ph |
| III-230 | Me | Et | Me | 2-Cl-5-cPr—Ph |
| III-231 | Me | Me | Me | 2-Cl-6-cPr—Ph |
| III-232 | Me | Et | Me | 2-Cl-6-cPr—Ph |
| III-233 | Me | Me | Me | 2-Cl-3-CF₃—Ph |
| III-234 | Me | Et | Me | 2-Cl-3-CF₃—Ph |
| III-235 | Me | Me | Me | 2-Cl-4-CF₃—Ph |
| III-236 | Me | Et | Me | 2-Cl-4-CF₃—Ph |
| III-237 | Me | Me | Me | 2-Cl-5-CF₃—Ph |
| III-238 | Me | Et | Me | 2-Cl-5-CF₃—Ph |
| III-239 | Me | Me | Me | 2-Cl-6-CF₃—Ph |
| III-240 | Me | Et | Me | 2-Cl-6-CF₃—Ph |
| III-241 | Me | Me | Me | 2-Cl-3-MeO—Ph |
| III-242 | Me | Et | Me | 2-Cl-3-MeO—Ph |
| III-243 | Me | Me | Me | 2-Cl-4-MeO—Ph |
| III-244 | Me | Et | Me | 2-Cl-4-MeO—Ph |
| III-245 | Me | Me | Me | 2-Cl-5-MeO—Ph |
| III-246 | Me | Et | Me | 2-Cl-5-MeO—Ph |
| III-247 | Me | Me | Me | 2-Cl-6-MeO—Ph |
| III-248 | Me | Et | Me | 2-Cl-6-MeO—Ph |
| III-249 | Me | Me | Me | 2-Cl-3-CHF₂O—Ph |
| III-250 | Me | Et | Me | 2-Cl-3-CHF₂O—Ph |
| III-251 | Me | Me | Me | 2-Cl-4-CHF₂O—Ph |
| III-252 | Me | Et | Me | 2-Cl-4-CHF₂O—Ph |
| III-253 | Me | Me | Me | 2-Cl-5-CHF₂O—Ph |
| III-254 | Me | Et | Me | 2-Cl-5-CHF₂O—Ph |
| III-255 | Me | Me | Me | 2-Cl-6-CHF₂O—Ph |
| III-256 | Me | Et | Me | 2-Cl-6-CHF₂O—Ph |
| III-257 | Me | Me | Me | 2-Cl-3-CD₃O—Ph |
| III-258 | Me | Et | Me | 2-Cl-3-CD₃O—Ph |
| III-259 | Me | Me | Me | 2-Cl-4-CD₃O—Ph |
| III-260 | Me | Et | Me | 2-Cl-4-CD₃O—Ph |
| III-261 | Me | Me | Me | 2-Cl-5-CD₃O—Ph |
| III-262 | Me | Et | Me | 2-Cl-5-CD₃O—Ph |
| III-263 | Me | Me | Me | 2-Cl-6-CD₃O—Ph |
| III-264 | Me | Et | Me | 2-Cl-6-CD₃O—Ph |
| III-265 | Me | Me | Me | 2-Cl-3-NC—Ph |
| III-266 | Me | Et | Me | 2-Cl-3-NC—Ph |
| III-267 | Me | Me | Me | 2-Cl-4-NC—Ph |
| III-268 | Me | Et | Me | 2-Cl-4-NC—Ph |
| III-269 | Me | Me | Me | 2-Cl-5-NC—Ph |
| III-270 | Me | Et | Me | 2-Cl-5-NC—Ph |
| III-271 | Me | Me | Me | 2-Cl-6-NC—Ph |
| III-272 | Me | Et | Me | 2-Cl-6-NC—Ph |
| III-273 | Me | Me | Me | 2-Br-3-F—Ph |
| III-274 | Me | Et | Me | 2-Br-3-F—Ph |
| III-275 | Me | Me | Me | 2-Br-4-F—Ph |
| III-276 | Me | Et | Me | 2-Br-4-F—Ph |
| III-277 | Me | Me | Me | 2-Br-5-F—Ph |
| III-278 | Me | Et | Me | 2-Br-5-F—Ph |

TABLE 28-continued (III)

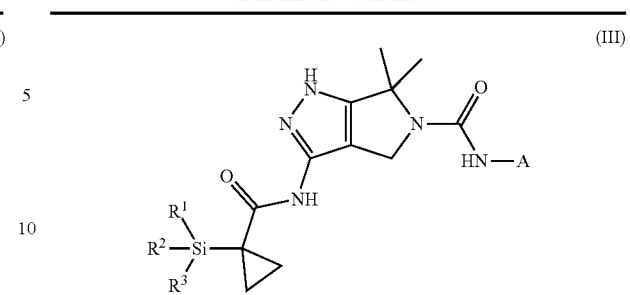

| Comp. No. | R¹ | R² | R³ | A |
|---|---|---|---|---|
| III-279 | Me | Me | Me | 2-Br-3-Cl—Ph |
| III-280 | Me | Et | Me | 2-Br-3-Cl—Ph |
| III-281 | Me | Me | Me | 2-Br-4-Cl—Ph |
| III-282 | Me | Et | Me | 2-Br-4-Cl—Ph |
| III-283 | Me | Me | Me | 2-Br-5-Cl—Ph |
| III-284 | Me | Et | Me | 2-Br-5-Cl—Ph |
| III-285 | Me | Me | Me | 2,3-diBr—Ph |
| III-286 | Me | Et | Me | 2,3-diBr—Ph |
| III-287 | Me | Me | Me | 2,4-diBr—Ph |
| III-288 | Me | Et | Me | 2,4-diBr—Ph |
| III-289 | Me | Me | Me | 2,5-diBr—Ph |
| III-290 | Me | Et | Me | 2,5-diBr—Ph |
| III-291 | Me | Me | Me | 2,6-diBr—Ph |
| III-292 | Me | Et | Me | 2,6-diBr—Ph |
| III-293 | Me | Me | Me | 2-Br-3-Me—Ph |
| III-294 | Me | Et | Me | 2-Br-3-Me—Ph |
| III-295 | Me | Me | Me | 2-Br-4-Me—Ph |
| III-296 | Me | Et | Me | 2-Br-4-Me—Ph |
| III-297 | Me | Me | Me | 2-Br-5-Me—Ph |
| III-298 | Me | Et | Me | 2-Br-5-Me—Ph |
| III-299 | Me | Me | Me | 2-Br-6-Me—Ph |
| III-300 | Me | Et | Me | 2-Br-6-Me—Ph |

TABLE 29

(III)

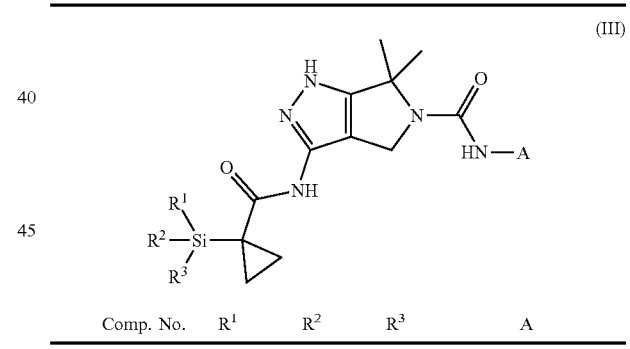

| Comp. No. | R¹ | R² | R³ | A |
|---|---|---|---|---|
| III-301 | Me | Me | Me | 2-Br-3-Et—Ph |
| III-302 | Me | Et | Me | 2-Br-3-Et—Ph |
| III-303 | Me | Me | Me | 2-Br-4-Et—Ph |
| III-304 | Me | Et | Me | 2-Br-4-Et—Ph |
| III-305 | Me | Me | Me | 2-Br-5-Et—Ph |
| III-306 | Me | Et | Me | 2-Br-5-Et—Ph |
| III-307 | Me | Me | Me | 2-Br-6-Et—Ph |
| III-308 | Me | Et | Me | 2-Br-6-Et—Ph |
| III-309 | Me | Me | Me | 2-Br-3-cPr—Ph |
| III-310 | Me | Et | Me | 2-Br-3-cPr—Ph |
| III-311 | Me | Me | Me | 2-Br-4-cPr—Ph |
| III-312 | Me | Et | Me | 2-Br-4-cPr—Ph |
| III-313 | Me | Me | Me | 2-Br-5-cPr—Ph |
| III-314 | Me | Et | Me | 2-Br-5-cPr—Ph |
| III-315 | Me | Me | Me | 2-Br-6-cPr—Ph |
| III-316 | Me | Et | Me | 2-Br-6-cPr—Ph |
| III-317 | Me | Me | Me | 2-Br-3-CF₃—Ph |
| III-318 | Me | Et | Me | 2-Br-3-CF₃—Ph |
| III-319 | Me | Me | Me | 2-Br-4-CF₃—Ph |
| III-320 | Me | Et | Me | 2-Br-4-CF₃—Ph |
| III-321 | Me | Me | Me | 2-Br-5-CF₃—Ph |

TABLE 29-continued (III)

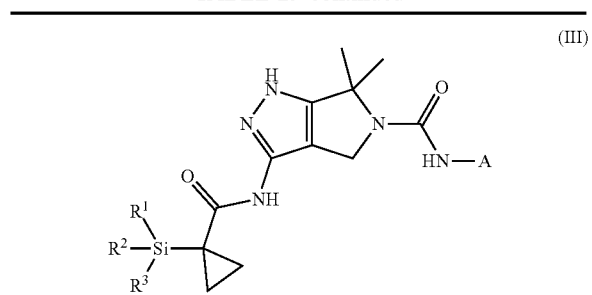

| Comp. No. | R¹ | R² | R³ | A |
|---|---|---|---|---|
| III-322 | Me | Et | Me | 2-Br-5-CF₃—Ph |
| III-323 | Me | Me | Me | 2-Br-6-CF₃—Ph |
| III-324 | Me | Et | Me | 2-Br-6-CF₃—Ph |
| III-325 | Me | Me | Me | 2-Br-3-MeO—Ph |
| III-326 | Me | Et | Me | 2-Br-3-MeO—Ph |
| III-327 | Me | Me | Me | 2-Br-4-MeO—Ph |
| III-328 | Me | Et | Me | 2-Br-4-MeO—Ph |
| III-329 | Me | Me | Me | 2-Br-5-MeO—Ph |
| III-330 | Me | Et | Me | 2-Br-5-MeO—Ph |
| III-331 | Me | Me | Me | 2-Br-6-MeO—Ph |
| III-332 | Me | Et | Me | 2-Br-6-MeO—Ph |
| III-333 | Me | Me | Me | 2-Br-3-CHF₂O—Ph |
| III-334 | Me | Et | Me | 2-Br-3-CHF₂O—Ph |
| III-335 | Me | Me | Me | 2-Br-4-CHF₂O—Ph |
| III-336 | Me | Et | Me | 2-Br-4-CHF₂O—Ph |
| III-337 | Me | Me | Me | 2-Br-5-CHF₂O—Ph |
| III-338 | Me | Et | Me | 2-Br-5-CHF₂O—Ph |
| III-339 | Me | Me | Me | 2-Br-6-CHF₂O—Ph |
| III-340 | Me | Et | Me | 2-Br-6-CHF₂O—Ph |
| III-341 | Me | Me | Me | 2-Br-3-CD₃O—Ph |
| III-342 | Me | Et | Me | 2-Br-3-CD₃O—Ph |
| III-343 | Me | Me | Me | 2-Br-4-CD₃O—Ph |
| III-344 | Me | Et | Me | 2-Br-4-CD₃O—Ph |
| III-345 | Me | Me | Me | 2-Br-5-CD₃O—Ph |
| III-346 | Me | Et | Me | 2-Br-5-CD₃O—Ph |
| III-347 | Me | Me | Me | 2-Br-6-CD₃O—Ph |
| III-348 | Me | Et | Me | 2-Br-6-CD₃O—Ph |
| III-349 | Me | Me | Me | 2-Br-3-NC—Ph |
| III-350 | Me | Et | Me | 2-Br-3-NC—Ph |
| III-351 | Me | Me | Me | 2-Br-4-NC—Ph |
| III-352 | Me | Et | Me | 2-Br-4-NC—Ph |
| III-353 | Me | Me | Me | 2-Br-5-NC—Ph |
| III-354 | Me | Et | Me | 2-Br-5-NC—Ph |
| III-355 | Me | Me | Me | 2-Br-6-NC—Ph |
| III-356 | Me | Et | Me | 2-Br-6-NC—Ph |
| III-357 | Me | Me | Me | 2-Me-3-F—Ph |
| III-358 | Me | Et | Me | 2-Me-3-F—Ph |
| III-359 | Me | Me | Me | 2-Me-4-F—Ph |
| III-360 | Me | Et | Me | 2-Me-4-F—Ph |
| III-361 | Me | Me | Me | 2-Me-5-F—Ph |
| III-362 | Me | Et | Me | 2-Me-5-F—Ph |
| III-363 | Me | Me | Me | 2-Me-3-Cl—Ph |
| III-364 | Me | Et | Me | 2-Me-3-Cl—Ph |
| III-365 | Me | Me | Me | 2-Me-4-Cl—Ph |
| III-366 | Me | Et | Me | 2-Me-4-Cl—Ph |
| III-367 | Me | Me | Me | 2-Me-5-Cl—Ph |
| III-368 | Me | Et | Me | 2-Me-5-Cl—Ph |
| III-369 | Me | Me | Me | 2-Me-3-Br—Ph |
| III-370 | Me | Et | Me | 2-Me-3-Br—Ph |
| III-371 | Me | Me | Me | 2-Me-4-Br—Ph |
| III-372 | Me | Et | Me | 2-Me-4-Br—Ph |
| III-373 | Me | Me | Me | 2-Me-5-Br—Ph |
| III-374 | Me | Et | Me | 2-Me-5-Br—Ph |
| III-375 | Me | Me | Me | 2,3-diMe—Ph |
| III-376 | Me | Et | Me | 2,3-diMe—Ph |
| III-377 | Me | Me | Me | 2,4-diMe—Ph |
| III-378 | Me | Et | Me | 2,4-diMe—Ph |
| III-379 | Me | Me | Me | 2,5-diMe—Ph |
| III-380 | Me | Et | Me | 2,5-diMe—Ph |
| III-381 | Me | Me | Me | 2,6-diMe—Ph |
| III-382 | Me | Et | Me | 2,6-diMe—Ph |
| III-383 | Me | Me | Me | 2-Me-3-Et—Ph |
| III-384 | Me | Et | Me | 2-Me-3-Et—Ph |
| III-385 | Me | Me | Me | 2-Me-4-Et—Ph |

TABLE 29-continued (III)

| Comp. No. | R¹ | R² | R³ | A |
|---|---|---|---|---|
| III-386 | Me | Et | Me | 2-Me-4-Et—Ph |
| III-387 | Me | Me | Me | 2-Me-5-Et—Ph |
| III-388 | Me | Et | Me | 2-Me-5-Et—Ph |
| III-389 | Me | Me | Me | 2-Me-6-Et—Ph |
| III-390 | Me | Et | Me | 2-Me-6-Et—Ph |
| III-391 | Me | Me | Me | 2-Me-3-cPr—Ph |
| III-392 | Me | Et | Me | 2-Me-3-cPr—Ph |
| III-393 | Me | Me | Me | 2-Me-4-cPr—Ph |
| III-394 | Me | Et | Me | 2-Me-4-cPr—Ph |
| III-395 | Me | Me | Me | 2-Me-5-cPr—Ph |
| III-396 | Me | Et | Me | 2-Me-5-cPr—Ph |
| III-397 | Me | Me | Me | 2-Me-6-cPr—Ph |
| III-398 | Me | Et | Me | 2-Me-6-cPr—Ph |
| III-399 | Me | Me | Me | 2-Me-3-CF₃—Ph |
| III-400 | Me | Et | Me | 2-Me-3-CF₃—Ph |

TABLE 30

(III)

| Comp. No. | R¹ | R² | R³ | A |
|---|---|---|---|---|
| III-401 | Me | Me | Me | 2-Me-4-CF₃—Ph |
| III-402 | Me | Et | Me | 2-Me-4-CF₃—Ph |
| III-403 | Me | Me | Me | 2-Me-5-CF₃—Ph |
| III-404 | Me | Et | Me | 2-Me-5-CF₃—Ph |
| III-405 | Me | Me | Me | 2-Me-6-CF₃—Ph |
| III-406 | Me | Et | Me | 2-Me-6-CF₃—Ph |
| III-407 | Me | Me | Me | 2-Me-3-MeO—Ph |
| III-408 | Me | Et | Me | 2-Me-3-MeO—Ph |
| III-409 | Me | Me | Me | 2-Me-4-MeO—Ph |
| III-410 | Me | Et | Me | 2-Me-4-MeO—Ph |
| III-411 | Me | Me | Me | 2-Me-5-MeO—Ph |
| III-412 | Me | Et | Me | 2-Me-5-MeO—Ph |
| III-413 | Me | Me | Me | 2-Me-6-MeO—Ph |
| III-414 | Me | Et | Me | 2-Me-6-MeO—Ph |
| III-415 | Me | Me | Me | 2-Me-3-CHF₂O—Ph |
| III-416 | Me | Et | Me | 2-Me-3-CHF₂O—Ph |
| III-417 | Me | Me | Me | 2-Me-4-CHF₂O—Ph |
| III-418 | Me | Et | Me | 2-Me-4-CHF₂O—Ph |
| III-419 | Me | Me | Me | 2-Me-5-CHF₂O—Ph |
| III-420 | Me | Et | Me | 2-Me-5-CHF₂O—Ph |
| III-421 | Me | Me | Me | 2-Me-6-CHF₂O—Ph |
| III-422 | Me | Et | Me | 2-Me-6-CHF₂O—Ph |
| III-423 | Me | Me | Me | 2-Me-3-CD₃O—Ph |
| III-424 | Me | Et | Me | 2-Me-3-CD₃O—Ph |
| III-425 | Me | Me | Me | 2-Me-4-CD₃O—Ph |
| III-426 | Me | Et | Me | 2-Me-4-CD₃O—Ph |
| III-427 | Me | Me | Me | 2-Me-5-CD₃O—Ph |
| III-428 | Me | Et | Me | 2-Me-5-CD₃O—Ph |

TABLE 30-continued

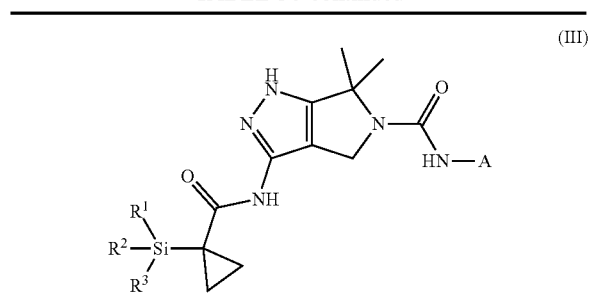

(III)

| Comp. No. | R¹ | R² | R³ | A |
|---|---|---|---|---|
| III-429 | Me | Me | Me | 2-Me-6-CD₃O—Ph |
| III-430 | Me | Et | Me | 2-Me-6-CD₃O—Ph |
| III-431 | Me | Me | Me | 2-Me-3-NC—Ph |
| III-432 | Me | Et | Me | 2-Me-3-NC—Ph |
| III-433 | Me | Me | Me | 2-Me-4-NC—Ph |
| III-434 | Me | Et | Me | 2-Me-4-NC—Ph |
| III-435 | Me | Me | Me | 2-Me-5-NC—Ph |
| III-436 | Me | Et | Me | 2-Me-5-NC—Ph |
| III-437 | Me | Me | Me | 2-Me-6-NC—Ph |
| III-438 | Me | Et | Me | 2-Me-6-NC—Ph |
| III-439 | Me | Me | Me | 2-Et-3-F—Ph |
| III-440 | Me | Et | Me | 2-Et-3-F—Ph |
| III-441 | Me | Me | Me | 2-Et-4-F—Ph |
| III-442 | Me | Et | Me | 2-Et-4-F—Ph |
| III-443 | Me | Me | Me | 2-Et-5-F—Ph |
| III-444 | Me | Et | Me | 2-Et-5-F—Ph |
| III-445 | Me | Me | Me | 2-Et-3-Cl—Ph |
| III-446 | Me | Et | Me | 2-Et-3-Cl—Ph |
| III-447 | Me | Me | Me | 2-Et-4-Cl—Ph |
| III-448 | Me | Et | Me | 2-Et-4-Cl—Ph |
| III-449 | Me | Me | Me | 2-Et-5-Cl—Ph |
| III-450 | Me | Et | Me | 2-Et-5-Cl—Ph |
| III-451 | Me | Me | Me | 2-Et-3-Br—Ph |
| III-452 | Me | Et | Me | 2-Et-3-Br—Ph |
| III-453 | Me | Me | Me | 2-Et-4-Br—Ph |
| III-454 | Me | Et | Me | 2-Et-4-Br—Ph |
| III-455 | Me | Me | Me | 2-Et-5-Br—Ph |
| III-456 | Me | Et | Me | 2-Et-5-Br—Ph |
| III-457 | Me | Me | Me | 2-Et-3-Me—Ph |
| III-458 | Me | Et | Me | 2-Et-3-Me—Ph |
| III-459 | Me | Me | Me | 2-Et-4-Me—Ph |
| III-460 | Me | Et | Me | 2-Et-4-Me—Ph |
| III-461 | Me | Me | Me | 2-Et-5-Me—Ph |
| III-462 | Me | Et | Me | 2-Et-5-Me—Ph |
| III-463 | Me | Me | Me | 2,3-diEt—Ph |
| III-464 | Me | Et | Me | 2,3-diEt—Ph |
| III-465 | Me | Me | Me | 2,4-diEt—Ph |
| III-466 | Me | Et | Me | 2,4-diEt—Ph |
| III-467 | Me | Me | Me | 2,5-diEt—Ph |
| III-468 | Me | Et | Me | 2,5-diEt—Ph |
| III-469 | Me | Me | Me | 2,6-diEt—Ph |
| III-470 | Me | Et | Me | 2,6-diEt—Ph |
| III-471 | Me | Me | Me | 2-Et-3-cPr—Ph |
| III-472 | Me | Et | Me | 2-Et-3-cPr—Ph |
| III-473 | Me | Me | Me | 2-Et-4-cPr—Ph |
| III-474 | Me | Et | Me | 2-Et-4-cPr—Ph |
| III-475 | Me | Me | Me | 2-Et-5-cPr—Ph |
| III-476 | Me | Et | Me | 2-Et-5-cPr—Ph |
| III-477 | Me | Me | Me | 2-Et-6-cPr—Ph |
| III-478 | Me | Et | Me | 2-Et-6-cPr—Ph |
| III-479 | Me | Me | Me | 2-Et-3-CF₃—Ph |
| III-480 | Me | Et | Me | 2-Et-3-CF₃—Ph |
| III-481 | Me | Me | Me | 2-Et-4-CF₃—Ph |
| III-482 | Me | Et | Me | 2-Et-4-CF₃—Ph |
| III-483 | Me | Me | Me | 2-Et-5-CF₃—Ph |
| III-484 | Me | Et | Me | 2-Et-5-CF₃—Ph |
| III-485 | Me | Me | Me | 2-Et-6-CF₃—Ph |
| III-486 | Me | Et | Me | 2-Et-6-CF₃—Ph |
| III-487 | Me | Me | Me | 2-Et-3-MeO—Ph |
| III-488 | Me | Et | Me | 2-Et-3-MeO—Ph |
| III-489 | Me | Me | Me | 2-Et-4-MeO—Ph |
| III-490 | Me | Et | Me | 2-Et-4-MeO—Ph |
| III-491 | Me | Me | Me | 2-Et-5-MeO—Ph |
| III-492 | Me | Et | Me | 2-Et-5-MeO—Ph |

TABLE 30-continued

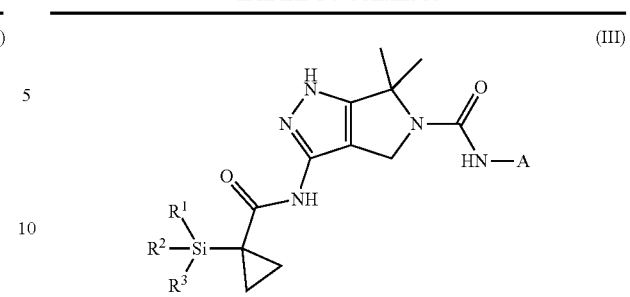

(III)

| Comp. No. | R¹ | R² | R³ | A |
|---|---|---|---|---|
| III-493 | Me | Me | Me | 2-Et-6-MeO—Ph |
| III-494 | Me | Et | Me | 2-Et-6-MeO—Ph |
| III-495 | Me | Me | Me | 2-Et-3-CHF₂O—Ph |
| III-496 | Me | Et | Me | 2-Et-3-CHF₂O—Ph |
| III-497 | Me | Me | Me | 2-Et-4-CHF₂O—Ph |
| III-498 | Me | Et | Me | 2-Et-4-CHF₂O—Ph |
| III-499 | Me | Me | Me | 2-Et-5-CHF₂O—Ph |
| III-500 | Me | Et | Me | 2-Et-5-CHF₂O—Ph |

TABLE 31

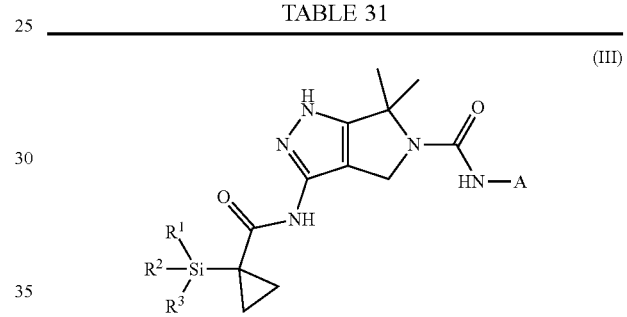

(III)

| Comp. No. | R¹ | R² | R³ | A |
|---|---|---|---|---|
| III-501 | Me | Me | Me | 2-Et-6-CHF₂O—Ph |
| III-502 | Me | Et | Me | 2-Et-6-CHF₂O—Ph |
| III-503 | Me | Me | Me | 2-Et-3-CD₃O—Ph |
| III-504 | Me | Et | Me | 2-Et-3-CD₃O—Ph |
| III-505 | Me | Me | Me | 2-Et-4-CD₃O—Ph |
| III-506 | Me | Et | Me | 2-Et-4-CD₃O—Ph |
| III-507 | Me | Me | Me | 2-Et-5-CD₃O—Ph |
| III-508 | Me | Et | Me | 2-Et-5-CD₃O—Ph |
| III-509 | Me | Me | Me | 2-Et-6-CD₃O—Ph |
| III-510 | Me | Et | Me | 2-Et-6-CD₃O—Ph |
| III-511 | Me | Me | Me | 2-Et-3-NC—Ph |
| III-512 | Me | Et | Me | 2-Et-3-NC—Ph |
| III-513 | Me | Me | Me | 2-Et-4-NC—Ph |
| III-514 | Me | Et | Me | 2-Et-4-NC—Ph |
| III-515 | Me | Me | Me | 2-Et-5-NC—Ph |
| III-516 | Me | Et | Me | 2-Et-5-NC—Ph |
| III-517 | Me | Me | Me | 2-Et-6-NC—Ph |
| III-518 | Me | Et | Me | 2-Et-6-NC—Ph |
| III-519 | Me | Me | Me | 2-MeO-3-F—Ph |
| III-520 | Me | Et | Me | 2-MeO-3-F—Ph |
| III-521 | Me | Me | Me | 2-MeO-4-F—Ph |
| III-522 | Me | Et | Me | 2-MeO-4-F—Ph |
| III-523 | Me | Me | Me | 2-MeO-5-F—Ph |
| III-524 | Me | Et | Me | 2-MeO-5-F—Ph |
| III-525 | Me | Me | Me | 2-MeO-3-Cl—Ph |
| III-526 | Me | Et | Me | 2-MeO-3-Cl—Ph |
| III-527 | Me | Me | Me | 2-MeO-4-Cl—Ph |
| III-528 | Me | Et | Me | 2-MeO-4-Cl—Ph |
| III-529 | Me | Me | Me | 2-MeO-5-Cl—Ph |
| III-530 | Me | Et | Me | 2-MeO-5-Cl—Ph |
| III-531 | Me | Me | Me | 2-MeO-3-Br—Ph |
| III-532 | Me | Et | Me | 2-MeO-3-Br—Ph |
| III-533 | Me | Me | Me | 2-MeO-4-Br—Ph |
| III-534 | Me | Et | Me | 2-MeO-4-Br—Ph |
| III-535 | Me | Me | Me | 2-MeO-5-Br—Ph |

TABLE 31-continued

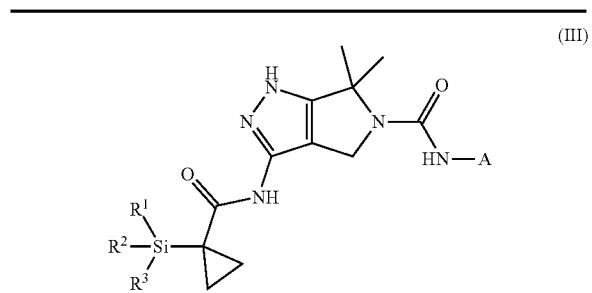

(III)

| Comp. No. | R¹ | R² | R³ | A |
|---|---|---|---|---|
| III-536 | Me | Et | Me | 2-MeO-5-Br—Ph |
| III-537 | Me | Me | Me | 2-MeO-3-Me—Ph |
| III-538 | Me | Et | Me | 2-MeO-3-Me—Ph |
| III-539 | Me | Me | Me | 2-MeO-4-Me—Ph |
| III-540 | Me | Et | Me | 2-MeO-4-Me—Ph |
| III-541 | Me | Me | Me | 2-MeO-5-Me—Ph |
| III-542 | Me | Et | Me | 2-MeO-5-Me—Ph |
| III-543 | Me | Me | Me | 2-MeO-3-Et—Ph |
| III-544 | Me | Et | Me | 2-MeO-3-Et—Ph |
| III-545 | Me | Me | Me | 2-MeO-4-Et—Ph |
| III-546 | Me | Et | Me | 2-MeO-4-Et—Ph |
| III-547 | Me | Me | Me | 2-MeO-5-Et—Ph |
| III-548 | Me | Et | Me | 2-MeO-5-Et—Ph |
| III-549 | Me | Me | Me | 2-MeO-3-cPr—Ph |
| III-550 | Me | Et | Me | 2-MeO-3-cPr—Ph |
| III-551 | Me | Me | Me | 2-MeO-4-cPr—Ph |
| III-552 | Me | Et | Me | 2-MeO-4-cPr—Ph |
| III-553 | Me | Me | Me | 2-MeO-5-cPr—Ph |
| III-554 | Me | Et | Me | 2-MeO-5-cPr—Ph |
| III-555 | Me | Me | Me | 2-MeO-6-cPr—Ph |
| III-556 | Me | Et | Me | 2-MeO-6-cPr—Ph |
| III-557 | Me | Me | Me | 2-MeO-3-CF₃—Ph |
| III-558 | Me | Et | Me | 2-MeO-3-CF₃—Ph |
| III-559 | Me | Me | Me | 2-MeO-4-CF₃—Ph |
| III-560 | Me | Et | Me | 2-MeO-4-CF₃—Ph |
| III-561 | Me | Me | Me | 2-MeO-5-CF₃—Ph |
| III-562 | Me | Et | Me | 2-MeO-5-CF₃—Ph |
| III-563 | Me | Me | Me | 2-MeO-6-CF₃—Ph |
| III-564 | Me | Et | Me | 2-MeO-6-CF₃—Ph |
| III-565 | Me | Me | Me | 2,3-diMeO—Ph |
| III-566 | Me | Et | Me | 2,3-diMeO—Ph |
| III-567 | Me | Me | Me | 2,4-diMeO—Ph |
| III-568 | Me | Et | Me | 2,4-diMeO—Ph |
| III-569 | Me | Me | Me | 2,5-diMeO—Ph |
| III-570 | Me | Et | Me | 2,5-diMeO—Ph |
| III-571 | Me | Me | Me | 2,6-diMeO—Ph |
| III-572 | Me | Et | Me | 2,6-diMeO—Ph |
| III-573 | Me | Me | Me | 2-MeO-3-CHF₂O—Ph |
| III-574 | Me | Et | Me | 2-MeO-3-CHF₂O—Ph |
| III-575 | Me | Me | Me | 2-MeO-4-CHF₂O—Ph |
| III-576 | Me | Et | Me | 2-MeO-4-CHF₂O—Ph |
| III-577 | Me | Me | Me | 2-MeO-5-CHF₂O—Ph |
| III-578 | Me | Et | Me | 2-MeO-5-CHF₂O—Ph |
| III-579 | Me | Me | Me | 2-MeO-6-CHF₂O—Ph |
| III-580 | Me | Et | Me | 2-MeO-6-CHF₂O—Ph |
| III-581 | Me | Me | Me | 2-MeO-3-CD₃O—Ph |
| III-582 | Me | Et | Me | 2-MeO-3-CD₃O—Ph |
| III-583 | Me | Me | Me | 2-MeO-4-CD₃O—Ph |
| III-584 | Me | Et | Me | 2-MeO-4-CD₃O—Ph |
| III-585 | Me | Me | Me | 2-MeO-5-CD₃O—Ph |
| III-586 | Me | Et | Me | 2-MeO-5-CD₃O—Ph |
| III-587 | Me | Me | Me | 2-MeO-6-CD₃O—Ph |
| III-588 | Me | Et | Me | 2-MeO-6-CD₃O—Ph |
| III-589 | Me | Me | Me | 2-MeO-3-NC—Ph |
| III-590 | Me | Et | Me | 2-MeO-3-NC—Ph |
| III-591 | Me | Me | Me | 2-MeO-4-NC—Ph |
| III-592 | Me | Et | Me | 2-MeO-4-NC—Ph |
| III-593 | Me | Me | Me | 2-MeO-5-NC—Ph |
| III-594 | Me | Et | Me | 2-MeO-5-NC—Ph |
| III-595 | Me | Me | Me | 2-MeO-6-NC—Ph |
| III-596 | Me | Et | Me | 2-MeO-6-NC—Ph |
| III-597 | Me | Me | Me | 2,3,6-triF—Ph |
| III-598 | Me | Et | Me | 2,3,6-triF—Ph |

TABLE 31-continued (III)

| Comp. No. | R¹ | R² | R³ | A |
|---|---|---|---|---|
| III-599 | Me | Me | Me | 2,4,6-triF—Ph |
| III-600 | Me | Et | Me | 2,4,6-triF—Ph |

TABLE 32

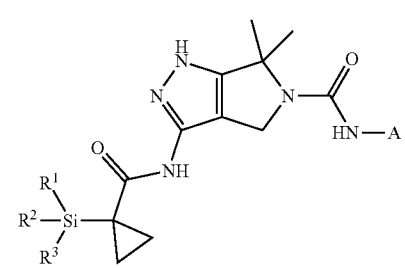

(III)

| Comp. No. | R¹ | R² | R³ | A |
|---|---|---|---|---|
| III-601 | Me | Me | Me | 2,6-diF-3-Cl—Ph |
| III-602 | Me | Et | Me | 2,6-diF-3-Cl—Ph |
| III-603 | Me | Me | Me | 2,6-diF-4-Cl—Ph |
| III-604 | Me | Et | Me | 2,6-diF-4-Cl—Ph |
| III-605 | Me | Me | Me | 2,6-diF-3-Br—Ph |
| III-606 | Me | Et | Me | 2,6-diF-3-Br—Ph |
| III-607 | Me | Me | Me | 2,6-diF-4-Br—Ph |
| III-608 | Me | Et | Me | 2,6-diF-4-Br—Ph |
| III-609 | Me | Me | Me | 2,6-diF-3-Me—Ph |
| III-610 | Me | Et | Me | 2,6-diF-3-Me—Ph |
| III-611 | Me | Me | Me | 2,6-diF-4-Me—Ph |
| III-612 | Me | Et | Me | 2,6-diF-4-Me—Ph |
| III-613 | Me | Me | Me | 2,6-diF-3-MeO—Ph |
| III-614 | Me | Et | Me | 2,6-diF-3-MeO—Ph |
| III-615 | Me | Me | Me | 2,6-diF-4-MeO—Ph |
| III-616 | Me | Et | Me | 2,6-diF-4-MeO—Ph |
| III-617 | Me | Me | Me | 2,3-diF-6-Cl—Ph |
| III-618 | Me | Et | Me | 2,3-diF-6-Cl—Ph |
| III-619 | Me | Me | Me | 2,4-diF-6-Cl—Ph |
| III-620 | Me | Et | Me | 2,4-diF-6-Cl—Ph |
| III-621 | Me | Me | Me | 2-F-3,6-diCl—Ph |
| III-622 | Me | Et | Me | 2-F-3,6-diCl—Ph |
| III-623 | Me | Me | Me | 2-F-4,6-diCl—Ph |
| III-624 | Me | Et | Me | 2-F-4,6-diCl—Ph |
| III-625 | Me | Me | Me | 2-F-3-Br-6-Cl—Ph |
| III-626 | Me | Et | Me | 2-F-3-Br-6-Cl—Ph |
| III-627 | Me | Me | Me | 2-F-4-Br-6-Cl—Ph |
| III-628 | Me | Et | Me | 2-F-4-Br-6-Cl—Ph |
| III-629 | Me | Me | Me | 2-F-3-Me-6-Cl—Ph |
| III-630 | Me | Et | Me | 2-F-3-Me-6-Cl—Ph |
| III-631 | Me | Me | Me | 2-F-4 Me-6-Cl—Ph |
| III-632 | Me | Et | Me | 2-F-4 Me-6-Cl—Ph |
| III-633 | Me | Me | Me | 2-F-3-MeO-6-Cl—Ph |
| III-634 | Me | Et | Me | 2 F-3-MeO-6-Cl—Ph |
| III-635 | Me | Me | Me | 2-F-4-MeO-6-Cl—Ph |
| III-636 | Me | Et | Me | 2-F-4-MeO-6-Cl—Ph |
| III-637 | Me | Me | Me | 2,3-diF-6-Br—Ph |
| III-638 | Me | Et | Me | 2,3-diF-6-Br—Ph |
| III-639 | Me | Me | Me | 2,4-diF-6-Br—Ph |
| III-640 | Me | Et | Me | 2,4-diF-6-Br—Ph |
| III-641 | Me | Me | Me | 2-F-3-Cl-6 Br—Ph |

TABLE 32-continued (III)

| Comp. No. | R¹ | R² | R³ | A |
|---|---|---|---|---|
| III-642 | Me | Et | Me | 2-F-3-Cl-6-Br—Ph |
| III-643 | Me | Me | Me | 2-F-4-Cl-6-Br—Ph |
| III-644 | Me | Et | Me | 2-F-4-Cl-6-Br—Ph |
| III-645 | Me | Me | Me | 2-F-3,6-diBr—Ph |
| III-646 | Me | Et | Me | 2-F-3,6-diBr—Ph |
| III-647 | Me | Me | Me | 2-F-4,6-diBr—Ph |
| III-648 | Me | Et | Me | 2-F-4,6-diBr—Ph |
| III-649 | Me | Me | Me | 2-F-3-Me-6-Br—Ph |
| III-650 | Me | Et | Me | 2-F-3-Me-6-Br—Ph |
| III-651 | Me | Me | Me | 2-F-4-Me-6-Br—Ph |
| III-652 | Me | Et | Me | 2-F-4-Me-6-Br—Ph |
| III-653 | Me | Me | Me | 2-F-3-MeO-6-Br—Ph |
| III-654 | Me | Et | Me | 2-F-3-MeO-6-Br—Ph |
| III-655 | Me | Me | Me | 2-F-4-MeO-6-Br—Ph |
| III-656 | Me | Et | Me | 2-F-4-MeO-6-Br—Ph |
| III-657 | Me | Me | Me | 2,3-diF-6-Me—Ph |
| III-658 | Me | Et | Me | 2,3-diF-6-Me—Ph |
| III-659 | Me | Me | Me | 2,4-diF-6-Me—Ph |
| III-660 | Me | Et | Me | 2,4-diF-6-Me—Ph |
| III-661 | Me | Me | Me | 2-F-3-Cl-6-Me—Ph |
| III-662 | Me | Et | Me | 2-F-3-Cl-6-Me—Ph |
| III-663 | Me | Me | Me | 2-F-4-Cl-6-Me—Ph |
| III-664 | Me | Et | Me | 2-F-4-Cl-6-Me—Ph |
| III-665 | Me | Me | Me | 2-F-3-Br-6-Me—Ph |
| III-666 | Me | Et | Me | 2-F-3-Br-6-Me—Ph |
| III-667 | Me | Me | Me | 2-F-4-Br-6-Me—Ph |
| III-668 | Me | Et | Me | 2-F-4-Br-6-Me—Ph |
| III-669 | Me | Me | Me | 2-F-3,6-diMe—Ph |
| III-670 | Me | Et | Me | 2-F-3,6-diMe—Ph |
| III-671 | Me | Me | Me | 2-F-4,6-diMe—Ph |
| III-672 | Me | Et | Me | 2-F-4,6-diMe—Ph |
| III-673 | Me | Me | Me | 2-F-3-MeO-6-Me—Ph |
| III-674 | Me | Et | Me | 2-F-3-MeO-6-Me—Ph |
| III-675 | Me | Me | Me | 2-F-4-MeO-6-Me—Ph |
| III-676 | Me | Et | Me | 2-F-4-MeO-6-Me—Ph |
| III-677 | Me | Me | Me | 2,3-diF-6-MeO—Ph |
| III-678 | Me | Et | Me | 2,3-diF-6-MeO—Ph |
| III-679 | Me | Me | Me | 2,4-diF-6-MeO—Ph |
| III-680 | Me | Et | Me | 2,4-diF-6-MeO—Ph |
| III-681 | Me | Me | Me | 2-F-3-Cl-6-MeO—Ph |
| III-682 | Me | Et | Me | 2-F-3-Cl-6-MeO—Ph |
| III-683 | Me | Me | Me | 2-F-4-Cl-6-MeO—Ph |
| III-684 | Me | Et | Me | 2-F-4-Cl-6-MeO—Ph |
| III-685 | Me | Me | Me | 2-F-3-Br-6-MeO—Ph |
| III-686 | Me | Et | Me | 2-F-3-Br-6-MeO—Ph |
| III-687 | Me | Me | Me | 2-F-4-Br-6-MeO—Ph |
| III-688 | Me | Et | Me | 2-F-4-Br-6-MeO—Ph |
| III-689 | Me | Me | Me | 2-F-3-Me-6-MeO—Ph |
| III-690 | Me | Et | Me | 2-F-3-Me-6-MeO—Ph |
| III-691 | Me | Me | Me | 2-F-4-Me-6-MeO—Ph |
| III-692 | Me | Et | Me | 2-F-4-Me-6-MeO—Ph |
| III-693 | Me | Me | Me | 2-F-3,6-diMeO—Ph |
| III-694 | Me | Et | Me | 2-F-3,6-diMeO—Ph |
| III-695 | Me | Me | Me | 2-F-4,6-diMeO—Ph |
| III-696 | Me | Et | Me | 2-F-4,6-diMeO—Ph |
| III-697 | Me | Me | Me | 2-Cl-3,6-diF—Ph |
| III-698 | Me | Et | Me | 2-Cl-3,6-diF—Ph |
| III-699 | Me | Me | Me | 2,3-diCl-6-F—Ph |
| III-700 | Me | Et | Me | 2,3-diCl-6-F—Ph |

TABLE 33

(III)

| Comp. No. | R¹ | R² | R³ | A |
|---|---|---|---|---|
| III-701 | Me | Me | Me | 2-Cl-3-Br-6-F—Ph |
| III-702 | Me | Et | Me | 2-Cl-3-Br-6-F—Ph |
| III-703 | Me | Me | Me | 2-Cl-3-Me-6-F—Ph |
| III-704 | Me | Et | Me | 2-Cl-3-Me-6-F—Ph |
| III-705 | Me | Me | Me | 2-Cl-3-MeO-6-F—Ph |
| III-706 | Me | Et | Me | 2-Cl-3-MeO-6-F—Ph |
| III-707 | Me | Me | Me | 2,6-diCl-3-F—Ph |
| III-708 | Me | Et | Me | 2,6-diCl-3-F—Ph |
| III-709 | Me | Me | Me | 2,6-diCl-4-F—Ph |
| III-710 | Me | Et | Me | 2,6-diCl-4-F—Ph |
| III-711 | Me | Me | Me | 2,3,6-triCl—Ph |
| III-712 | Me | Et | Me | 2,3,6-triCl—Ph |
| III-713 | Me | Me | Me | 2,4,6-triCl—Ph |
| III-714 | Me | Et | Me | 2,4,6-triCl—Ph |
| III-715 | Me | Me | Me | 2,6-diCl-3-Br—Ph |
| III-716 | Me | Et | Me | 2,6-diCl-3-Br—Ph |
| III-717 | Me | Me | Me | 2,6-diCl-4-Br—Ph |
| III-718 | Me | Et | Me | 2,6-diCl-4-Br—Ph |
| III-719 | Me | Me | Me | 2,6-diCl-3-Me—Ph |
| III-720 | Me | Et | Me | 2,6-diCl-3-Me—Ph |
| III-721 | Me | Me | Me | 2,6-diCl-4-Me—Ph |
| III-722 | Me | Et | Me | 2,6-diCl-4-Me—Ph |
| III-723 | Me | Me | Me | 2,6-diCl-3-MeO—Ph |
| III-724 | Me | Et | Me | 2,6-diCl-3-MeO—Ph |
| III-725 | Me | Me | Me | 2,6-diCl-4-MeO—Ph |
| III-726 | Me | Et | Me | 2,6-diCl-4-MeO—Ph |
| III-727 | Me | Me | Me | 2-Cl-3-F-6-Br—Ph |
| III-728 | Me | Et | Me | 2-Cl-3-F-6-Br—Ph |
| III-729 | Me | Me | Me | 2-Cl-4-F-6-Br—Ph |
| III-730 | Me | Et | Me | 2-Cl-4-F-6-Br—Ph |
| III-731 | Me | Me | Me | 2,3-diCl-6-Br—Ph |
| III-732 | Me | Et | Me | 2,3-diCl-6-Br—Ph |
| III-733 | Me | Me | Me | 2,4-diCl-6-Br—Ph |
| III-734 | Me | Et | Me | 2,4-diCl-6-Br—Ph |
| III-735 | Me | Me | Me | 2-Cl-3,6-diBr—Ph |
| III-736 | Me | Et | Me | 2-Cl-3,6-diBr—Ph |
| III-737 | Me | Me | Me | 2-Cl-4,6-diBr—Ph |
| III-738 | Me | Et | Me | 2-Cl-4,6-diBr—Ph |
| III-739 | Me | Me | Me | 2-Cl-3-Me-6-Br—Ph |
| III-740 | Me | Et | Me | 2-Cl-3-Me-6-Br—Ph |
| III-741 | Me | Me | Me | 2-Cl-4-Me-6-Br—Ph |
| III-742 | Me | Et | Me | 2-Cl-4-Me-6-Br—Ph |
| III-743 | Me | Me | Me | 2-Cl-3-MeO-6-Br—Ph |
| III-744 | Me | Et | Me | 2-Cl-3-MeO-6-Br—Ph |
| III-745 | Me | Me | Me | 2-Cl-4-MeO-6-Br—Ph |
| III-746 | Me | Et | Me | 2-Cl-4-MeO-6-Br—Ph |
| III-747 | Me | Me | Me | 2-Cl-3-F-6-Me—Ph |
| III-748 | Me | Et | Me | 2-Cl-3-F-6-Me—Ph |
| III-749 | Me | Me | Me | 2-Cl-4-F-6-Me—Ph |
| III-750 | Me | Et | Me | 2-Cl-4-F-6-Me—Ph |
| III-751 | Me | Me | Me | 2,3-diCl-6-Me—Ph |
| III-752 | Me | Et | Me | 2,3-diCl-6-Me—Ph |
| III-753 | Me | Me | Me | 2,4-diCl-6-Me—Ph |
| III-754 | Me | Et | Me | 2,4-diCl-6-Me—Ph |
| III-755 | Me | Me | Me | 2-Cl-3-Br-6-Me—Ph |
| III-756 | Me | Et | Me | 2-Cl-3-Br-6-Me—Ph |
| III-757 | Me | Me | Me | 2-Cl-4-Br-6-Me—Ph |
| III-758 | Me | Et | Me | 2-Cl-4-Br-6-Me—Ph |
| III-759 | Me | Me | Me | 2-Cl-3,6-diMe—Ph |
| III-760 | Me | Et | Me | 2-Cl-3,6-diMe—Ph |
| III-761 | Me | Me | Me | 2-Cl-4,6-diMe—Ph |
| III-762 | Me | Et | Me | 2-Cl-4,6-diMe—Ph |
| III-763 | Me | Me | Me | 2-Cl-3-MeO-6-Me—Ph |
| III-764 | Me | Et | Me | 2-Cl-3-MeO-6-Me—Ph |

TABLE 33-continued (III)

| Comp. No. | R¹ | R² | R³ | A |
|---|---|---|---|---|
| III-765 | Me | Me | Me | 2-Cl-4-MeO-6-Me—Ph |
| III-766 | Me | Et | Me | 2-Cl-4-MeO-6-Me—Ph |
| III-767 | Me | Me | Me | 2-Cl-3-F-6-MeO—Ph |
| III-768 | Me | Et | Me | 2-Cl-3-F-6-MeO—Ph |
| III-769 | Me | Me | Me | 2-Cl-4-F-6-MeO—Ph |
| III-770 | Me | Et | Me | 2-Cl-4-F-6-MeO—Ph |
| III-771 | Me | Me | Me | 2,3-diCl-6-MeO—Ph |
| III-772 | Me | Et | Me | 2,3-diCl-6-MeO—Ph |
| III-773 | Me | Me | Me | 2,4-diCl-6-MeO—Ph |
| III-774 | Me | Et | Me | 2,4-diCl-6-MeO—Ph |
| III-775 | Me | Me | Me | 2-Cl-3-Br-6-MeO—Ph |
| III-776 | Me | Et | Me | 2-Cl-3-Br-6-MeO—Ph |
| III-777 | Me | Me | Me | 2-Cl-4-Br-6-MeO—Ph |
| III-778 | Me | Et | Me | 2-Cl-4-Br-6-MeO—Ph |
| III-779 | Me | Me | Me | 2-Cl-3-Me-6-MeO—Ph |
| III-780 | Me | Et | Me | 2-Cl-3-Me-6-MeO—Ph |
| III-781 | Me | Me | Me | 2-Cl-4-Me-6-MeO—Ph |
| III-782 | Me | Et | Me | 2-Cl-4-Me-6-MeO—Ph |
| III-783 | Me | Me | Me | 2-Cl-3,6-diMeO—Ph |
| III-784 | Me | Et | Me | 2-Cl-3,6-diMeO—Ph |
| III-785 | Me | Me | Me | 2-Cl-4,6-diMeO—Ph |
| III-786 | Me | Et | Me | 2-Cl-4,6-diMeO—Ph |
| III-787 | Me | Me | Me | 2-Br-3,6-diF—Ph |
| III-788 | Me | Et | Me | 2-Br-3,6-diF—Ph |
| III-789 | Me | Me | Me | 2-Br-3-Cl-6-F—Ph |
| III-790 | Me | Et | Me | 2-Br-3-Cl-6-F—Ph |
| III-791 | Me | Me | Me | 2,3-diBr-6-F—Ph |
| III-792 | Me | Et | Me | 2,3-diBr-6-F—Ph |
| III-793 | Me | Me | Me | 2-Br-3-Me-6-F—Ph |
| III-794 | Me | Et | Me | 2-Br-3-Me-6-F—Ph |
| III-795 | Me | Me | Me | 2-Br-3-MeO-6-F—Ph |
| III-796 | Me | Et | Me | 2-Br-3-MeO-6-F—Ph |
| III-797 | Me | Me | Me | 2-Br-3-F-6-Cl—Ph |
| III-798 | Me | Et | Me | 2-Br-3-F-6-Cl—Ph |
| III-799 | Me | Me | Me | 2-Br-3,6-diCl—Ph |
| III-800 | Me | Et | Me | 2-Br-3,6-diCl—Ph |

TABLE 34

(III)

| Comp. No. | R¹ | R² | R³ | A |
|---|---|---|---|---|
| III-801 | Me | Me | Me | 2,3-diBr-6-Cl—Ph |
| III-802 | Me | Et | Me | 2,3-diBr-6-Cl—Ph |
| III-803 | Me | Me | Me | 2-Br-3-Me-6-Cl—Ph |
| III-804 | Me | Et | Me | 2-Br-3-Me-6-Cl—Ph |
| III-805 | Me | Me | Me | 2-Br-3-MeO-6-Cl—Ph |
| III-806 | Me | Et | Me | 2-Br-3-MeO-6-Cl—Ph |
| III-807 | Me | Me | Me | 2,6-diBr-3-F—Ph |

TABLE 34-continued (III)

| Comp. No. | R¹ | R² | R³ | A |
|---|---|---|---|---|
| III-808 | Me | Et | Me | 2,6-diBr-3-F—Ph |
| III-809 | Me | Me | Me | 2,6-diBr-4-F—Ph |
| III-810 | Me | Et | Me | 2,6-diBr-4-F—Ph |
| III-811 | Me | Me | Me | 2,6-diBr-3-Cl—Ph |
| III-812 | Me | Et | Me | 2,6-diBr-3-Cl—Ph |
| III-813 | Me | Me | Me | 2,6-diBr-4-Cl—Ph |
| III-814 | Me | Et | Me | 2,6-diBr-4-Cl—Ph |
| III-815 | Me | Me | Me | 2,3,6-triBr—Ph |
| III-816 | Me | Et | Me | 2,3,6-triBr—Ph |
| III-817 | Me | Me | Me | 2,4,6-triBr—Ph |
| III-818 | Me | Et | Me | 2,4,6-triBr—Ph |
| III-819 | Me | Me | Me | 2,6-diBr-3-Me—Ph |
| III-820 | Me | Et | Me | 2,6-diBr-3-Me—Ph |
| III-821 | Me | Me | Me | 2,6-diBr-4-Me—Ph |
| III-822 | Me | Et | Me | 2,6-diBr-4-Me—Ph |
| III-823 | Me | Me | Me | 2,6-diBr-3-MeO—Ph |
| III-824 | Me | Et | Me | 2,6-diBr-3-MeO—Ph |
| III-825 | Me | Me | Me | 2,6-diBr-4-MeO—Ph |
| III-826 | Me | Et | Me | 2,6-diBr-4-MeO—Ph |
| III-827 | Me | Me | Me | 2-Br-3-F-6-Me—Ph |
| III-828 | Me | Et | Me | 2-Br-3-F-6-Me—Ph |
| III-829 | Me | Me | Me | 2-Br-4-F-6-Me—Ph |
| III-830 | Me | Et | Me | 2-Br-4-F-6-Me—Ph |
| III-831 | Me | Me | Me | 2-Br-3-Cl-6-Me—Ph |
| III-832 | Me | Et | Me | 2-Br-3-Cl-6-Me—Ph |
| III-833 | Me | Me | Me | 2-Br-4-Cl-6-Me—Ph |
| III-834 | Me | Et | Me | 2-Br-4-Cl-6-Me—Ph |
| III-835 | Me | Me | Me | 2,3-diBr-6-Me—Ph |
| III-836 | Me | Et | Me | 2,3-diBr-6-Me—Ph |
| III-837 | Me | Me | Me | 2,4-diBr-6-Me—Ph |
| III-838 | Me | Et | Me | 2,4-diBr-6-Me—Ph |
| III-839 | Me | Me | Me | 2-Br-3,6-diMe—Ph |
| III-840 | Me | Et | Me | 2-Br-3,6-diMe—Ph |
| III-841 | Me | Me | Me | 2-Br-4,6-diMe—Ph |
| III-842 | Me | Et | Me | 2-Br-4,6-diMe—Ph |
| III-843 | Me | Me | Me | 2-Br-3-MeO-6-Me—Ph |
| III-844 | Me | Et | Me | 2-Br-3-MeO-6-Me—Ph |
| III-845 | Me | Me | Me | 2-Br-4-MeO-6-Me—Ph |
| III-846 | Me | Et | Me | 2-Br-4-MeO-6-Me—Ph |
| III-847 | Me | Me | Me | 2-Br-3-F-6-MeO—Ph |
| III-848 | Me | Et | Me | 2-Br-3-F-6-MeO—Ph |
| III-849 | Me | Me | Me | 2-Br-4-F-6-MeO—Ph |
| III-850 | Me | Et | Me | 2-Br-4-F-6-MeO—Ph |
| III-851 | Me | Me | Me | 2-Br-3-Cl-6-MeO—Ph |
| III-852 | Me | Et | Me | 2-Br-3-Cl-6-MeO—Ph |
| III-853 | Me | Me | Me | 2-Br-4-Cl-6-MeO—Ph |
| III-854 | Me | Et | Me | 2-Br-4-Cl-6-MeO—Ph |
| III-855 | Me | Me | Me | 2,3-diBr-6-MeO—Ph |
| III-856 | Me | Et | Me | 2,3-diBr-6-MeO—Ph |
| III-857 | Me | Me | Me | 2,4-diBr-6-MeO—Ph |
| III-858 | Me | Et | Me | 2,4-diBr-6-MeO—Ph |
| III-859 | Me | Me | Me | 2-Br-3-Me-6-MeO—Ph |
| III-860 | Me | Et | Me | 2-Br-3-Me-6-MeO—Ph |
| III-861 | Me | Me | Me | 2-Br-4-Me-6-MeO—Ph |
| III-862 | Me | Et | Me | 2-Br-4-Me-6-MeO—Ph |
| III-863 | Me | Me | Me | 2-Br-3,6-diMeO—Ph |
| III-864 | Me | Et | Me | 2-Br-3,6-diMeO—Ph |
| III-865 | Me | Me | Me | 2-Br-4,6-diMeO—Ph |
| III-866 | Me | Et | Me | 2-Br-4,6-diMeO—Ph |
| III-867 | Me | Me | Me | 2-Me-3,6-diF—Ph |
| III-868 | Me | Et | Me | 2-Me-3,6-diF—Ph |
| III-869 | Me | Me | Me | 2-Me-3-Cl-6-F—Ph |
| III-870 | Me | Et | Me | 2-Me-3-Cl-6-F—Ph |
| III-871 | Me | Me | Me | 2-Me-3-Br-6-F—Ph |

TABLE 34-continued (III)

| Comp. No. | R¹ | R² | R³ | A |
|---|---|---|---|---|
| III-872 | Me | Et | Me | 2-Me-3-Br-6-F—Ph |
| III-873 | Me | Me | Me | 2,3-diMe-6-F—Ph |
| III-874 | Me | Et | Me | 2,3-diMe-6-F—Ph |
| III-875 | Me | Me | Me | 2,4-diMe-6-F—Ph |
| III-876 | Me | Et | Me | 2,4-diMe-6-F—Ph |
| III-877 | Me | Me | Me | 2-Me-3-MeO-6-F—Ph |
| III-878 | Me | Et | Me | 2-Me-3-MeO-6-F—Ph |
| III-879 | Me | Me | Me | 2-Me-4-MeO-6-F—Ph |
| III-880 | Me | Et | Me | 2-Me-4-MeO-6-F—Ph |
| III-881 | Me | Me | Me | 2-Me-3-F-6-Cl—Ph |
| III-882 | Me | Et | Me | 2-Me-3-F-6-Cl—Ph |
| III-883 | Me | Me | Me | 2-Me-3,6-diCl—Ph |
| III-884 | Me | Et | Me | 2-Me-3,6-diCl—Ph |
| III-885 | Me | Me | Me | 2-Me-3-Br-6-Cl—Ph |
| III-886 | Me | Et | Me | 2-Me-3-Br-6-Cl—Ph |
| III-887 | Me | Me | Me | 2,3-diMe-6-Cl—Ph |
| III-888 | Me | Et | Me | 2,3-diMe-6-Cl—Ph |
| III-889 | Me | Me | Me | 2,4-diMe-6-Cl—Ph |
| III-890 | Me | Et | Me | 2,4-diMe-6-Cl—Ph |
| III-891 | Me | Me | Me | 2-Me-3-MeO-6-Cl—Ph |
| III-892 | Me | Et | Me | 2-Me-3-MeO-6-Cl—Ph |
| III-893 | Me | Me | Me | 2-Me-4-MeO-6-Cl—Ph |
| III-894 | Me | Et | Me | 2-Me-4-MeO-6-Cl—Ph |
| III-895 | Me | Me | Me | 2-Me-3-F-6-Br—Ph |
| III-896 | Me | Et | Me | 2-Me-3-F-6-Br—Ph |
| III-897 | Me | Me | Me | 2-Me-3-Cl-6-Br—Ph |
| III-898 | Me | Et | Me | 2-Me-3-Cl-6-Br—Ph |
| III-899 | Me | Me | Me | 2-Me-3,6-diBr—Ph |
| III-900 | Me | Et | Me | 2-Me-3,6-diBr—Ph |

TABLE 35

(III)

| Comp. No. | R¹ | R² | R³ | A |
|---|---|---|---|---|
| III-901 | Me | Me | Me | 2,3-diMe-6-Br—Ph |
| III-902 | Me | Et | Me | 2,3-diMe-6-Br—Ph |
| III-903 | Me | Me | Me | 2,4-diMe-6-Br—Ph |
| III-904 | Me | Et | Me | 2,4-diMe-6-Br—Ph |
| III-905 | Me | Me | Me | 2-Me-3-MeO-6-Br—Ph |
| III-906 | Me | Et | Me | 2-Me-3-MeO-6-Br—Ph |
| III-907 | Me | Me | Me | 2-Me-4-MeO-6-Br—Ph |
| III-908 | Me | Et | Me | 2-Me-4-MeO-6-Br—Ph |
| III-909 | Me | Me | Me | 2-Me-3-F-6-Me—Ph |
| III-910 | Me | Et | Me | 2-Me-3-F-6-Me—Ph |
| III-911 | Me | Me | Me | 2-Me-3-Cl-6-Me—Ph |
| III-912 | Me | Et | Me | 2-Me-3-Cl-6-Me—Ph |
| III-913 | Me | Me | Me | 2-Me-3-Br-6-Me—Ph |

TABLE 35-continued (III)

| Comp. No. | R¹ | R² | R³ | A |
|---|---|---|---|---|
| III-914 | Me | Et | Me | 2-Me-3-Br-6-Me—Ph |
| III-915 | Me | Me | Me | 2,3,6-triMe-Ph |
| III-916 | Me | Et | Me | 2,3,6-triMe-Ph |
| III-917 | Me | Me | Me | 2,4,6-triMe-Ph |
| III-918 | Me | Et | Me | 2,4,6-triMe-Ph |
| III-919 | Me | Me | Me | 2-Me-3-MeO-6-Me—Ph |
| III-920 | Me | Et | Me | 2-Me-3-MeO-6-Me—Ph |
| III-921 | Me | Me | Me | 2-Me-4-MeO-6-Me—Ph |
| III-922 | Me | Et | Me | 2-Me-4-MeO-6-Me—Ph |
| III-923 | Me | Me | Me | 2-Me-3-F-6-MeO—Ph |
| III-924 | Me | Et | Me | 2-Me-3-F-6-MeO—Ph |
| III-925 | Me | Me | Me | 2-Me-3-Cl-6-MeO—Ph |
| III-926 | Me | Et | Me | 2-Me-3-Cl-6-MeO—Ph |
| III-927 | Me | Me | Me | 2-Me-3-Br-6-MeO—Ph |
| III-928 | Me | Et | Me | 2-Me-3-Br-6-MeO—Ph |
| III-929 | Me | Me | Me | 2,3-diMe-6-MeO—Ph |
| III-930 | Me | Et | Me | 2,3-diMe-6-MeO—Ph |
| III-931 | Me | Me | Me | 2,4-diMe-6-MeO—Ph |
| III-932 | Me | Et | Me | 2,4-diMe-6-MeO—Ph |
| III-933 | Me | Me | Me | 2-Me-3,6-diMeO-Ph |
| III-934 | Me | Et | Me | 2-Me-3,6-diMeO-Ph |
| III-935 | Me | Me | Me | 2-Me-4,6-diMeO-Ph |
| III-936 | Me | Et | Me | 2-Me-4,6-diMeO-Ph |
| III-937 | Me | Me | Me | 2-MeO-3,6-diF-Ph |
| III-938 | Me | Et | Me | 2-MeO-3,6-diF-Ph |
| III-939 | Me | Me | Me | 2-MeO-3-Cl-6-F—Ph |
| III-940 | Me | Et | Me | 2-MeO-3-Cl-6-F—Ph |
| III-941 | Me | Me | Me | 2-MeO-3-Br-6-F—Ph |
| III-942 | Me | Et | Me | 2-MeO-3-Br-6-F—Ph |
| III-943 | Me | Me | Me | 2-MeO-3-Me-6-F—Ph |
| III-944 | Me | Et | Me | 2-MeO-3-Me-6-F—Ph |
| III-945 | Me | Me | Me | 2,3-diMeO-6-F—Ph |
| III-946 | Me | Et | Me | 2,3-diMeO-6-F—Ph |
| III-947 | Me | Me | Me | 2,4-diMeO-6-F—Ph |
| III-948 | Me | Et | Me | 2,4-diMeO-6-F—Ph |
| III-949 | Me | Me | Me | 2-MeO-3-F-6-Cl—Ph |
| III-950 | Me | Et | Me | 2-MeO-3-F-6-Cl—Ph |
| III-951 | Me | Me | Me | 2-MeO-3,6-Cl—Ph |
| III-952 | Me | Et | Me | 2-MeO-3,6-Cl—Ph |
| III-953 | Me | Me | Me | 2-MeO-3-Br-6-Cl—Ph |
| III-954 | Me | Et | Me | 2-MeO-3-Br-6-Cl—Ph |
| III-955 | Me | Me | Me | 2-MeO-3-Me-6-Cl—Ph |
| III-956 | Me | Et | Me | 2-MeO-3-Me-6-Cl—Ph |
| III-957 | Me | Me | Me | 2,3-diMeO-6-Cl—Ph |
| III-958 | Me | Et | Me | 2,3-diMeO-6-Cl—Ph |
| III-959 | Me | Me | Me | 2,4-diMeO-6-Cl—Ph |
| III-960 | Me | Et | Me | 2,4-diMeO-6-Cl—Ph |
| III-961 | Me | Me | Me | 2-MeO-3-F-6-Br—Ph |
| III-962 | Me | Et | Me | 2-MeO-3-F-6-Br—Ph |
| III-963 | Me | Me | Me | 2-MeO-3-Cl-6-Br—Ph |
| III-964 | Me | Et | Me | 2-MeO-3-Cl-6-Br—Ph |
| III-965 | Me | Me | Me | 2-MeO-3,6-diBr-Ph |
| III-966 | Me | Et | Me | 2-MeO-3,6-diBr-Ph |
| III-967 | Me | Me | Me | 2-MeO-3-Me-6-Br—Ph |
| III-968 | Me | Et | Me | 2-MeO-3-Me-6-Br—Ph |
| III-969 | Me | Me | Me | 2,3-diMeO-6-Br—Ph |
| III-970 | Me | Et | Me | 2,3-diMeO-6-Br—Ph |
| III-971 | Me | Me | Me | 2,4-diMeO-6-Br—Ph |
| III-972 | Me | Et | Me | 2,4-diMeO-6-Br—Ph |
| III-973 | Me | Me | Me | 2-MeO-3-F-6-Me—Ph |
| III-974 | Me | Et | Me | 2-MeO-3-F-6-Me—Ph |
| III-975 | Me | Me | Me | 2-MeO-3-Cl-6-Me—Ph |
| III-976 | Me | Et | Me | 2-MeO-3-Cl-6-Me—Ph |

TABLE 35-continued (III)

| Comp. No. | R¹ | R² | R³ | A |
|---|---|---|---|---|
| III-977 | Me | Me | Me | 2-MeO-3-Br-6-Me—Ph |
| III-978 | Me | Et | Me | 2-MeO-3-Br-6-Me—Ph |
| III-979 | Me | Me | Me | 2-MeO-3,6-diMe—Ph |
| III-980 | Me | Et | Me | 2-MeO-3,6-diMe—Ph |
| III-981 | Me | Me | Me | 2,3-diMeO-6-Me—Ph |
| III-982 | Me | Et | Me | 2,3-diMeO-6-Me—Ph |
| III-983 | Me | Me | Me | 2,4-diMeO-6-Me—Ph |
| III-984 | Me | Et | Me | 2,4-diMeO-6-Me—Ph |
| III-985 | Me | Me | Me | 2,6-di-MeO-3-F—Ph |
| III-986 | Me | Et | Me | 2,6-di-MeO-3-F—Ph |
| III-987 | Me | Me | Me | 2,6-di-MeO-3-Cl—Ph |
| III-988 | Me | Et | Me | 2,6-di-MeO-3-Cl—Ph |
| III-989 | Me | Me | Me | 2,6-di-MeO-3-Br—Ph |
| III-990 | Me | Et | Me | 2,6-di-MeO-3-Br—Ph |
| III-991 | Me | Me | Me | 2,6-di-MeO-3-Me—Ph |
| III-992 | Me | Et | Me | 2,6-di-MeO-3-Me—Ph |
| III-993 | Me | Me | Me | 2,3,6-triMeO-Ph |
| III-994 | Me | Et | Me | 2,3,6-triMeO-Ph |
| III-995 | Me | Me | Me | 2,4,6-triMeO-Ph |
| III-996 | Me | Et | Me | 2,4,6-triMeO-Ph |

TABLE 36

(III)

| Comp. No. | R¹ | R² | R³ | A |
|---|---|---|---|---|
| III-997 | Me | Me | Me | 6-F-2,3-dihydrobenzofuran-7-yl |
| III-998 | Me | Et | Me | 6-F-2,3-dihydrobenzofuran-7-yl |
| III-999 | Me | Me | Me | 6-Cl-2,3-dihydrobenzofuran-7-yl |
| III-1000 | Me | Et | Me | 6-Cl-2,3-dihydrobenzofuran-7-yl |
| III-1001 | Me | Me | Me | 6-Br-2,3-dihydrobenzofuran-7-yl |
| III-1002 | Me | Et | Me | 6-Br-2,3-dihydrobenzofuran-7-yl |
| III-1003 | Me | Me | Me | 6-Me-2,3-dihydrobenzofuran-7-yl |
| III-1004 | Me | Et | Me | 6-Me-2,3-dihydrobenzofuran-7-yl |
| III-1005 | Me | Me | Me | 6-MeO-2,3-dihydrobenzofuran-7-yl |
| III-1006 | Me | Et | Me | 6-MeO-2,3-dihydrobenzofuran-7-yl |
| III-1007 | Me | Me | Me | pyridin-2-yl |
| III-1008 | Me | Et | Me | pyridin-2-yl |
| III-1009 | Me | Me | Me | 3-F-pyridin-2-yl |
| III-1010 | Me | Et | Me | 3-F-pyridin-2-yl |
| III-1011 | Me | Me | Me | 3-Cl-pyridin-2-yl |
| III-1012 | Me | Et | Me | 3-Cl-pyridin-2-yl |
| III-1013 | Me | Me | Me | 3-Br-pyridin-2-yl |
| III-1014 | Me | Et | Me | 3-Br-pyridin-2-yl |
| III-1015 | Me | Me | Me | 3-Me-pyridin-2-yl |
| III-1016 | Me | Et | Me | 3-Me-pyridin-2-yl |
| III-1017 | Me | Me | Me | 3-MeO-pyridin-2-yl |
| III-1018 | Me | Et | Me | 3-MeO-pyridin-2-yl |

TABLE 36-continued (III)

| Comp. No. | R¹ | R² | R³ | A |
|---|---|---|---|---|
| III-1019 | Me | Me | Me | pyridin-3-yl |
| III-1020 | Me | Et | Me | pyridin-3-yl |
| III-1021 | Me | Me | Me | 2-F-pyridin-3-yl |
| III-1022 | Me | Et | Me | 2-F-pyridin-3-yl |
| III-1023 | Me | Me | Me | 2-Cl-pyridin-3-yl |
| III-1024 | Me | Et | Me | 2-Cl-pyridin-3-yl |
| III-1025 | Me | Me | Me | 2-Br-pyridin-3-yl |
| III-1026 | Me | Et | Me | 2-Br-pyridin-3-yl |
| III-1027 | Me | Me | Me | 2-MeO-pyridin-3-yl |
| III-1028 | Me | Et | Me | 2-MeO-pyridin-3-yl |
| III-1029 | Me | Me | Me | pyridin-4-yl |
| III-1030 | Me | Et | Me | pyridin-4-yl |
| III-1031 | Me | Me | Me | 3-F-isothiazol-4-yl |
| III-1032 | Me | Et | Me | 3-F-isothiazol-4-yl |
| III-1033 | Me | Me | Me | 3-Cl-isothiazol-4-yl |
| III-1034 | Me | Et | Me | 3-Cl-isothiazol-4-yl |
| III-1035 | Me | Me | Me | 3-Me-isothiazol-4-yl |
| III-1036 | Me | Et | Me | 3-Me-isothiazol-4-yl |
| III-1037 | Me | Me | Me | 3-F-isoxazol-4-yl |
| III-1038 | Me | Et | Me | 3-F-isoxazol-4-yl |
| III-1039 | Me | Me | Me | 3-Cl-isoxazol-4-yl |
| III-1040 | Me | Et | Me | 3-Cl-isoxazol-4-yl |
| III-1041 | Me | Me | Me | 3-Me-isoxazol-4-yl |
| III-1042 | Me | Et | Me | 3-Me-isoxazol-4-yl |
| III-1043 | Me | Me | Me | thiophen-2-yl |
| III-1044 | Me | Et | Me | thiophen-2-yl |
| III-1045 | Me | Me | Me | thiophen-3yl |
| III-1046 | Me | Et | Me | thiophen-3yl |

TABLE 37

(III)

| Comp. No. | R¹ | R² | R³ | A |
|---|---|---|---|---|
| III-1047 | Me | Me | Me | benzofuran-7-yl |
| III-1048 | Me | Et | Me | benzofuran-7-yl |
| III-1049 | Me | Me | Me | 6-F-benzofuran-7-yl |
| III-1050 | Me | Et | Me | 6-F-benzofuran-7-yl |
| III-1051 | Me | Me | Me | 6-Cl-benzofuran-7-yl |
| III-1052 | Me | Et | Me | 6-Cl-benzofuran-7-yl |
| III-1053 | Me | Me | Me | 6-Br-benzofuran-7-yl |
| III-1054 | Me | Et | Me | 6-Br-benzofuran-7-yl |
| III-1055 | Me | Me | Me | 6-Me-benzofuran-7-yl |
| III-1056 | Me | Et | Me | 6-Me-benzofuran-7-yl |
| III-1057 | Me | Me | Me | 6-MeO-benzofuran-7-yl |
| III-1058 | Me | Et | Me | 6-MeO-benzofuran-7-yl |
| III-1059 | Me | Me | Me | 2-Me-6-F-benzofuran-7-yl |
| III-1060 | Me | Et | Me | 2-Me-6-F-benzofuran-7-yl |

TABLE 37-continued (III)

| Comp. No. | R¹ | R² | R³ | A |
|---|---|---|---|---|
| III-1061 | Me | Me | Me | 3-Me-6-F-benzofuran-7-yl |
| III-1062 | Me | Et | Me | 3-Me-6-F-benzofuran-7-yl |
| III-1063 | Me | Me | Me | 2-Cl-6-F-benzofuran-7-yl |
| III-1064 | Me | Et | Me | 2-Cl-6-F-benzofuran-7-yl |
| III-1065 | Me | Me | Me | 3-Cl-6-F-benzofuran-7-yl |
| III-1066 | Me | Et | Me | 3-Cl-6-F-benzofuran-7-yl |
| III-1067 | Me | Me | Me | 2-Me-6-Cl-benzofuran-7-yl |
| III-1068 | Me | Et | Me | 2-Me-6-Cl-benzofuran-7-yl |
| III-1069 | Me | Me | Me | 3-Me-6-Cl-benzofuran-7-yl |
| III-1070 | Me | Et | Me | 3-Me-6-Cl-benzofuran-7-yl |
| III-1071 | Me | Me | Me | 2-Cl-6-Cl-benzofuran-7-yl |
| III-1072 | Me | Et | Me | 2-Cl-6-Cl-benzofuran-7-yl |
| III-1073 | Me | Me | Me | 3-Cl-6-Cl-benzofuran-7-yl |
| III-1074 | Me | Et | Me | 3-Cl-6-Cl-benzofuran-7-yl |

TABLE 38

(IV)

| Comp. No. | R¹ | R² | R³ | A |
|---|---|---|---|---|
| IV-1 | Me | Me | Me | Ph |
| IV-2 | Me | Et | Me | Ph |
| IV-3 | Me | Me | Me | 2-F—Ph |
| IV-4 | Me | Et | Me | 2-F—Ph |
| IV-5 | Me | Me | Me | 3-F—Ph |
| IV-6 | Me | Et | Me | 3-F—Ph |
| IV-7 | Me | Me | Me | 4-F—Ph |
| IV-8 | Me | Et | Me | 4-F—Ph |
| IV-9 | Me | Me | Me | 2-Cl—Ph |
| IV-10 | Me | Et | Me | 2-Cl—Ph |
| IV-11 | Me | Me | Me | 3-Cl—Ph |
| IV-12 | Me | Et | Me | 3-Cl—Ph |
| IV-13 | Me | Me | Me | 4-Cl—Ph |
| IV-14 | Me | Et | Me | 4-Cl—Ph |
| IV-15 | Me | Me | Me | 2-Br—Ph |
| IV-16 | Me | Et | Me | 2-Br—Ph |
| IV-17 | Me | Me | Me | 3-Br—Ph |
| IV-18 | Me | Et | Me | 3-Br—Ph |
| IV-19 | Me | Me | Me | 4-Br—Ph |
| IV-20 | Me | Et | Me | 4-Br—Ph |
| IV-21 | Me | Me | Me | 2-Me—Ph |
| IV-22 | Me | Et | Me | 2-Me—Ph |
| IV-23 | Me | Me | Me | 3-Me—Ph |
| IV-24 | Me | Et | Me | 3-Me—Ph |
| IV-25 | Me | Me | Me | 4-Me—Ph |
| IV-26 | Me | Et | Me | 4-Me—Ph |
| IV-27 | Me | Me | Me | 2-Et—Ph |
| IV-28 | Me | Et | Me | 2-Et—Ph |

TABLE 38-continued (IV)

| Comp. No. | R¹ | R² | R³ | A |
|---|---|---|---|---|
| IV-29 | Me | Me | Me | 3-Et—Ph |
| IV-30 | Me | Et | Me | 3-Et—Ph |
| IV-31 | Me | Me | Me | 4-Et—Ph |
| IV-32 | Me | Et | Me | 4-Et—Ph |
| IV-33 | Me | Me | Me | 2-iPr—Ph |
| IV-34 | Me | Et | Me | 2-iPr—Ph |
| IV-35 | Me | Me | Me | 3-iPr—Ph |
| IV-36 | Me | Et | Me | 3-iPr—Ph |
| IV-37 | Me | Me | Me | 4-iPr—Ph |
| IV-38 | Me | Et | Me | 4-iPr—Ph |
| IV-39 | Me | Me | Me | 2-cPr—Ph |
| IV-40 | Me | Et | Me | 2-cPr—Ph |
| IV-41 | Me | Me | Me | 3-cPr—Ph |
| IV-42 | Me | Et | Me | 3-cPr—Ph |
| IV-43 | Me | Me | Me | 4-cPr—Ph |
| IV-44 | Me | Et | Me | 4-cPr—Ph |
| IV-45 | Me | Me | Me | 2-(1,1-diF-Et)—Ph |
| IV-46 | Me | Et | Me | 2-(1,1-diF-Et)—Ph |
| IV-47 | Me | Me | Me | 3-(1,1-diF-Et)—Ph |
| IV-48 | Me | Et | Me | 3-(1,1-diF-Et)—Ph |
| IV-49 | Me | Me | Me | 4-(1,1-diF-Et)—Ph |
| IV-50 | Me | Et | Me | 4-(1,1-diF-Et)—Ph |
| IV-51 | Me | Me | Me | 2-$CF_3$—Ph |
| IV-52 | Me | Et | Me | 2-$CF_3$—Ph |
| IV-53 | Me | Me | Me | 3-$CF_3$—Ph |
| IV-54 | Me | Et | Me | 3-$CF_3$—Ph |
| IV-55 | Me | Me | Me | 4-$CF_3$—Ph |
| IV-56 | Me | Et | Me | 4-$CF_3$—Ph |
| IV-57 | Me | Me | Me | 2-tBu—Ph |
| IV-58 | Me | Et | Me | 2-tBu—Ph |
| IV-59 | Me | Me | Me | 3-tBu—Ph |
| IV-60 | Me | Et | Me | 3-tBu—Ph |
| IV-61 | Me | Me | Me | 4-tBu—Ph |
| IV-62 | Me | Et | Me | 4-tBu—Ph |
| IV-63 | Me | Me | Me | 2-NC—Ph |
| IV-64 | Me | Et | Me | 2-NC—Ph |
| IV-65 | Me | Me | Me | 3-NC—Ph |
| IV-66 | Me | Et | Me | 3-NC—Ph |
| IV-67 | Me | Me | Me | 4-NC—Ph |
| IV-68 | Me | Et | Me | 4-NC—Ph |
| IV-69 | Me | Me | Me | 2-Ph—Ph |
| IV-70 | Me | Et | Me | 2-Ph—Ph |
| IV-71 | Me | Me | Me | 3-Ph—Ph |
| IV-72 | Me | Et | Me | 3-Ph—Ph |
| IV-73 | Me | Me | Me | 4-Ph—Ph |
| IV-74 | Me | Et | Me | 4-Ph—Ph |
| IV-75 | Me | Me | Me | 2-MeO—Ph |
| IV-76 | Me | Et | Me | 2-MeO—Ph |
| IV-77 | Me | Me | Me | 3-MeO—Ph |
| IV-78 | Me | Et | Me | 3-MeO—Ph |
| IV-79 | Me | Me | Me | 4-MeO—Ph |
| IV-80 | Me | Et | Me | 4-MeO—Ph |
| IV-81 | Me | Me | Me | 2-EtO—Ph |
| IV-82 | Me | Et | Me | 2-EtO—Ph |
| IV-83 | Me | Me | Me | 3-EtO—Ph |
| IV-84 | Me | Et | Me | 3-EtO—Ph |
| IV-85 | Me | Me | Me | 4-EtO—Ph |
| IV-86 | Me | Et | Me | 4-EtO—Ph |
| IV-87 | Me | Me | Me | 2-$CHF_2$O—Ph |
| IV-88 | Me | Et | Me | 2-$CHF_2$O—Ph |
| IV-89 | Me | Me | Me | 3-$CHF_2$O—Ph |
| IV-90 | Me | Et | Me | 3-$CHF_2$O—Ph |
| IV-91 | Me | Me | Me | 4-$CHF_2$O—Ph |

TABLE 38-continued (IV)

| Comp. No. | R¹ | R² | R³ | A |
|---|---|---|---|---|
| IV-92 | Me | Et | Me | 4-CHF$_2$O—Ph |
| IV-93 | Me | Me | Me | 2-CF$_3$O—Ph |
| IV-94 | Me | Et | Me | 2-CF$_3$O—Ph |
| IV-95 | Me | Me | Me | 3-CF$_3$O—Ph |
| IV-96 | Me | Et | Me | 3-CF$_3$O—Ph |
| IV-97 | Me | Me | Me | 4-CF$_3$O—Ph |
| IV-98 | Me | Et | Me | 4-CF$_3$O—Ph |
| IV-99 | Me | Me | Me | 2,3-diF—Ph |
| IV-100 | Me | Et | Me | 2,3-diF—Ph |

TABLE 39

(IV)

| Comp. No. | R¹ | R² | R³ | A |
|---|---|---|---|---|
| IV-101 | Me | Me | Me | 2,4-diF—Ph |
| IV-102 | Me | Et | Me | 2,4-diF—Ph |
| IV-103 | Me | Me | Me | 2,5,-diF—Ph |
| IV-104 | Me | Et | Me | 2,5,-diF—Ph |
| IV-105 | Me | Me | Me | 2,6-diF—Ph |
| IV-106 | Me | Et | Me | 2,6-diF—Ph |
| IV-107 | Me | Me | Me | 2-F-3-Cl—Ph |
| IV-108 | Me | Et | Me | 2-F-3-Cl—Ph |
| IV-109 | Me | Me | Me | 2-F-4-Cl—Ph |
| IV-110 | Me | Et | Me | 2-F-4-Cl—Ph |
| IV-111 | Me | Me | Me | 2-F-5-Cl—Ph |
| IV-112 | Me | Et | Me | 2-F-5-Cl—Ph |
| IV-113 | Me | Me | Me | 2-F-6-Cl—Ph |
| IV-114 | Me | Et | Me | 2-F-6-Cl—Ph |
| IV-115 | Me | Me | Me | 2-F-3-Br—Ph |
| IV-116 | Me | Et | Me | 2-F-3-Br—Ph |
| IV-117 | Me | Me | Me | 2-F-4-Br—Ph |
| IV-118 | Me | Et | Me | 2-F-4-Br—Ph |
| IV-119 | Me | Me | Me | 2-F-5-Br—Ph |
| IV-120 | Me | Et | Me | 2-F-5-Br—Ph |
| IV-121 | Me | Me | Me | 2-F-6-Br—Ph |
| IV-122 | Me | Et | Me | 2-F-6-Br—Ph |
| IV-123 | Me | Me | Me | 2-F-3-Me—Ph |
| IV-124 | Me | Et | Me | 2-F-3-Me—Ph |
| IV-125 | Me | Me | Me | 2-F-4-Me—Ph |
| IV-126 | Me | Et | Me | 2-F-4-Me—Ph |
| IV-127 | Me | Me | Me | 2-F-5-Me—Ph |
| IV-128 | Me | Et | Me | 2-F-5-Me—Ph |
| IV-129 | Me | Me | Me | 2-F-6-Me—Ph |
| IV-130 | Me | Et | Me | 2-F-6-Me—Ph |
| IV-131 | Me | Me | Me | 2-F-3-Et—Ph |
| IV-132 | Me | Et | Me | 2-F-3-Et—Ph |
| IV-133 | Me | Me | Me | 2-F-4-Et—Ph |

TABLE 39-continued (IV)

| Comp. No. | R¹ | R² | R³ | A |
|---|---|---|---|---|
| IV-134 | Me | Et | Me | 2-F-4-Et—Ph |
| IV-135 | Me | Me | Me | 2-F-5-Et—Ph |
| IV-136 | Me | Et | Me | 2-F-5-Et—Ph |
| IV-137 | Me | Me | Me | 2-F-6-Et—Ph |
| IV-138 | Me | Et | Me | 2-F-6-Et—Ph |
| IV-139 | Me | Me | Me | 2-F-3-cPr—Ph |
| IV-140 | Me | Et | Me | 2-F-3-cPr—Ph |
| IV-141 | Me | Me | Me | 2-F-4-cPr—Ph |
| IV-142 | Me | Et | Me | 2-F-4-cPr—Ph |
| IV-143 | Me | Me | Me | 2-F-5-cPr—Ph |
| IV-144 | Me | Et | Me | 2-F-5-cPr—Ph |
| IV-145 | Me | Me | Me | 2-F-6-cPr—Ph |
| IV-146 | Me | Et | Me | 2-F-6-cPr—Ph |
| IV-147 | Me | Me | Me | 2-F-3-CF$_3$—Ph |
| IV-148 | Me | Et | Me | 2-F-3-CF$_3$—Ph |
| IV-149 | Me | Me | Me | 2-F-4-CF$_3$—Ph |
| IV-150 | Me | Et | Me | 2-F-4-CF$_3$—Ph |
| IV-151 | Me | Me | Me | 2-F-5-CF$_3$—Ph |
| IV-152 | Me | Et | Me | 2-F-5-CF$_3$—Ph |
| IV-153 | Me | Me | Me | 2-F-6-CF$_3$—Ph |
| IV-154 | Me | Et | Me | 2-F-6-CF$_3$—Ph |
| IV-155 | Me | Me | Me | 2-F-3-MeO—Ph |
| IV-156 | Me | Et | Me | 2-F-3-MeO—Ph |
| IV-157 | Me | Me | Me | 2-F-4-MeO—Ph |
| IV-158 | Me | Et | Me | 2-F-4-MeO—Ph |
| IV-159 | Me | Me | Me | 2-F-5-MeO—Ph |
| IV-160 | Me | Et | Me | 2-F-5-MeO—Ph |
| IV-161 | Me | Me | Me | 2-F-6-MeO—Ph |
| IV-162 | Me | Et | Me | 2-F-6-MeO—Ph |
| IV-163 | Me | Me | Me | 2-F-3-CHF$_2$—Ph |
| IV-164 | Me | Et | Me | 2-F-3-CHF$_2$—Ph |
| IV-165 | Me | Me | Me | 2-F-4-CHF$_2$—Ph |
| IV-166 | Me | Et | Me | 2-F-4-CHF$_2$—Ph |
| IV-167 | Me | Me | Me | 2-F-5-CHF$_2$—Ph |
| IV-168 | Me | Et | Me | 2-F-5-CHF$_2$—Ph |
| IV-169 | Me | Me | Me | 2-F-6-CHF$_2$—Ph |
| IV-170 | Me | Et | Me | 2-F-6-CHF$_2$—Ph |
| IV-171 | Me | Me | Me | 2-F-3-CD$_3$O—Ph |
| IV-172 | Me | Et | Me | 2-F-3-CD$_3$O—Ph |
| IV-173 | Me | Me | Me | 2-F-4-CD$_3$O—Ph |
| IV-174 | Me | Et | Me | 2-F-4-CD$_3$O—Ph |
| IV-175 | Me | Me | Me | 2-F-5-CD$_3$O—Ph |
| IV-176 | Me | Et | Me | 2-F-5-CD$_3$O—Ph |
| IV-177 | Me | Me | Me | 2-F-6-CD$_3$O—Ph |
| IV-178 | Me | Et | Me | 2-F-6-CD$_3$O—Ph |
| IV-179 | Me | Me | Me | 2-F-3-NC—Ph |
| IV-180 | Me | Et | Me | 2-F-3-NC—Ph |
| IV-181 | Me | Me | Me | 2-F-4-NC—Ph |
| IV-182 | Me | Et | Me | 2-F-4-NC—Ph |
| IV-183 | Me | Me | Me | 2-F-5-NC—Ph |
| IV-184 | Me | Et | Me | 2-F-5-NC—Ph |
| IV-185 | Me | Me | Me | 2-F-6-NC—Ph |
| IV-186 | Me | Et | Me | 2-F-6-NC—Ph |
| IV-187 | Me | Me | Me | 2-Cl-3-F—Ph |
| IV-188 | Me | Et | Me | 2-Cl-3-F—Ph |
| IV-189 | Me | Me | Me | 2-Cl-4-F—Ph |
| IV-190 | Me | Et | Me | 2-Cl-4-F—Ph |
| IV-191 | Me | Me | Me | 2-Cl-5-F—Ph |
| IV-192 | Me | Et | Me | 2-Cl-5-F—Ph |
| IV-193 | Me | Me | Me | 2,3-diCl—Ph |
| IV-194 | Me | Et | Me | 2,3-diCl—Ph |
| IV-195 | Me | Me | Me | 2,4-diCl—Ph |
| IV-196 | Me | Et | Me | 2,4-diCl—Ph |

TABLE 39-continued (IV)

| Comp. No. | R¹ | R² | R³ | A |
|---|---|---|---|---|
| IV-197 | Me | Me | Me | 2,5-diCl—Ph |
| IV-198 | Me | Et | Me | 2,5-diCl—Ph |
| IV-199 | Me | Me | Me | 2,6-diCl—Ph |
| IV-200 | Me | Et | Me | 2,6-diCl—Ph |

TABLE 40

(IV)

| Comp. No. | R¹ | R² | R³ | A |
|---|---|---|---|---|
| IV-201 | Me | Me | Me | 2-Cl-3-Br—Ph |
| IV-202 | Me | Et | Me | 2-Cl-3-Br—Ph |
| IV-203 | Me | Me | Me | 2-Cl-4-Br—Ph |
| IV-204 | Me | Et | Me | 2-Cl-4-Br—Ph |
| IV-205 | Me | Me | Me | 2-Cl-5-Br—Ph |
| IV-206 | Me | Et | Me | 2-Cl-5-Br—Ph |
| IV-207 | Me | Me | Me | 2-Cl-6-Br—Ph |
| IV-208 | Me | Et | Me | 2-Cl-6-Br—Ph |
| IV-209 | Me | Me | Me | 2-Cl-3-Me—Ph |
| IV-210 | Me | Et | Me | 2-Cl-3-Me—Ph |
| IV-211 | Me | Me | Me | 2-Cl-4-Me—Ph |
| IV-212 | Me | Et | Me | 2-Cl-4-Me—Ph |
| IV-213 | Me | Me | Me | 2-Cl-5-Me—Ph |
| IV-214 | Me | Et | Me | 2-Cl-5-Me—Ph |
| IV-215 | Me | Me | Me | 2-Cl-6-Me—Ph |
| IV-216 | Me | Et | Me | 2-Cl-6-Me—Ph |
| IV-217 | Me | Me | Me | 2-Cl-3-Et—Ph |
| IV-218 | Me | Et | Me | 2-Cl-3-Et—Ph |
| IV-219 | Me | Me | Me | 2-Cl-4-Et—Ph |
| IV-220 | Me | Et | Me | 2-Cl-4-Et—Ph |
| IV-221 | Me | Me | Me | 2-Cl-5-Et—Ph |
| IV-222 | Me | Et | Me | 2-Cl-5-Et—Ph |
| IV-223 | Me | Me | Me | 2-Cl-6-Et—Ph |
| IV-224 | Me | Et | Me | 2-Cl-6-Et—Ph |
| IV-225 | Me | Me | Me | 2-Cl-3-cPr—Ph |
| IV-226 | Me | Et | Me | 2-Cl-3-cPr—Ph |
| IV-227 | Me | Me | Me | 2-Cl-4-cPr—Ph |
| IV-228 | Me | Et | Me | 2-Cl-4-cPr—Ph |
| IV-229 | Me | Me | Me | 2-Cl-5-cPr—Ph |
| IV-230 | Me | Et | Me | 2-Cl-5-cPr—Ph |
| IV-231 | Me | Me | Me | 2-Cl-6-cPr—Ph |
| IV-232 | Me | Et | Me | 2-Cl-6-cPr—Ph |
| IV-233 | Me | Me | Me | 2-Cl-3-CF₃—Ph |
| IV-234 | Me | Et | Me | 2-Cl-3-CF₃—Ph |
| IV-235 | Me | Me | Me | 2-Cl-4-CF₃—Ph |
| IV-236 | Me | Et | Me | 2-Cl-4-CF₃—Ph |
| IV-237 | Me | Me | Me | 2-Cl-5-CF₃—Ph |
| IV-238 | Me | Et | Me | 2-Cl-5-CF₃—Ph |

TABLE 40-continued (IV)

| Comp. No. | R¹ | R² | R³ | A |
|---|---|---|---|---|
| IV-239 | Me | Me | Me | 2-Cl-6-CF₃—Ph |
| IV-240 | Me | Et | Me | 2-Cl-6-CF₃—Ph |
| IV-241 | Me | Me | Me | 2-Cl-3-MeO—Ph |
| IV-242 | Me | Et | Me | 2-Cl-3-MeO—Ph |
| IV-243 | Me | Me | Me | 2-Cl-4-MeO—Ph |
| IV-244 | Me | Et | Me | 2-Cl-4-MeO—Ph |
| IV-245 | Me | Me | Me | 2-Cl-5-MeO—Ph |
| IV-246 | Me | Et | Me | 2-Cl-5-MeO—Ph |
| IV-247 | Me | Me | Me | 2-Cl-6-MeO—Ph |
| IV-248 | Me | Et | Me | 2-Cl-6-MeO—Ph |
| IV-249 | Me | Me | Me | 2-Cl-3-CHF₂O—Ph |
| IV-250 | Me | Et | Me | 2-Cl-3-CHF₂O—Ph |
| IV-251 | Me | Me | Me | 2-Cl-4-CHF₂O—Ph |
| IV-252 | Me | Et | Me | 2-Cl-4-CHF₂O—Ph |
| IV-253 | Me | Me | Me | 2-Cl-5-CHF₂O—Ph |
| IV-254 | Me | Et | Me | 2-Cl-5-CHF₂O—Ph |
| IV-255 | Me | Me | Me | 2-Cl-6-CHF₂O—Ph |
| IV-256 | Me | Et | Me | 2-Cl-6-CHF₂O—Ph |
| IV-257 | Me | Me | Me | 2-Cl-3-CD₃O—Ph |
| IV-258 | Me | Et | Me | 2-Cl-3-CD₃O—Ph |
| IV-259 | Me | Me | Me | 2-Cl-4-CD₃O—Ph |
| IV-260 | Me | Et | Me | 2-Cl-4-CD₃O—Ph |
| IV-261 | Me | Me | Me | 2-Cl-5-CD₃O—Ph |
| IV-262 | Me | Et | Me | 2-Cl-5-CD₃O—Ph |
| IV-263 | Me | Me | Me | 2-Cl-6-CD₃O—Ph |
| IV-264 | Me | Et | Me | 2-Cl-6-CD₃O—Ph |
| IV-265 | Me | Me | Me | 2-Cl-3-NC—Ph |
| IV-266 | Me | Et | Me | 2-Cl-3-NC—Ph |
| IV-267 | Me | Me | Me | 2-Cl-4-NC—Ph |
| IV-268 | Me | Et | Me | 2-Cl-4-NC—Ph |
| IV-269 | Me | Me | Me | 2-Cl-5-NC—Ph |
| IV-270 | Me | Et | Me | 2-Cl-5-NC—Ph |
| IV-271 | Me | Me | Me | 2-Cl-6-NC—Ph |
| IV-272 | Me | Et | Me | 2-Cl-6-NC—Ph |
| IV-273 | Me | Me | Me | 2-Br-3-F—Ph |
| IV-274 | Me | Et | Me | 2-Br-3-F—Ph |
| IV-275 | Me | Me | Me | 2-Br-4-F—Ph |
| IV-276 | Me | Et | Me | 2-Br-4-F—Ph |
| IV-277 | Me | Me | Me | 2-Br-5-F—Ph |
| IV-278 | Me | Et | Me | 2-Br-5-F—Ph |
| IV-279 | Me | Me | Me | 2-Br-3-Cl—Ph |
| IV-280 | Me | Et | Me | 2-Br-3-Cl—Ph |
| IV-281 | Me | Me | Me | 2-Br-4-Cl—Ph |
| IV-282 | Me | Et | Me | 2-Br-4-Cl—Ph |
| IV-283 | Me | Me | Me | 2-Br-5-Cl—Ph |
| IV-284 | Me | Et | Me | 2-Br-5-Cl—Ph |
| IV-285 | Me | Me | Me | 2,3-diBr—Ph |
| IV-286 | Me | Et | Me | 2,3-diBr—Ph |
| IV-287 | Me | Me | Me | 2,4-diBr—Ph |
| IV-288 | Me | Et | Me | 2,4-diBr—Ph |
| IV-289 | Me | Me | Me | 2,5-diBr—Ph |
| IV-290 | Me | Et | Me | 2,5-diBr—Ph |
| IV-291 | Me | Me | Me | 2,6-diBr—Ph |
| IV-292 | Me | Et | Me | 2,6-diBr—Ph |
| IV-293 | Me | Me | Me | 2-Br-3-Me—Ph |
| IV-294 | Me | Et | Me | 2-Br-3-Me—Ph |
| IV-295 | Me | Me | Me | 2-Br-4-Me—Ph |
| IV-296 | Me | Et | Me | 2-Br-4-Me—Ph |
| IV-297 | Me | Me | Me | 2-Br-5-Me—Ph |
| IV-298 | Me | Et | Me | 2-Br-5-Me—Ph |
| IV-299 | Me | Me | Me | 2-Br-6-Me—Ph |
| IV-300 | Me | Et | Me | 2-Br-6-Me—Ph |

TABLE 41

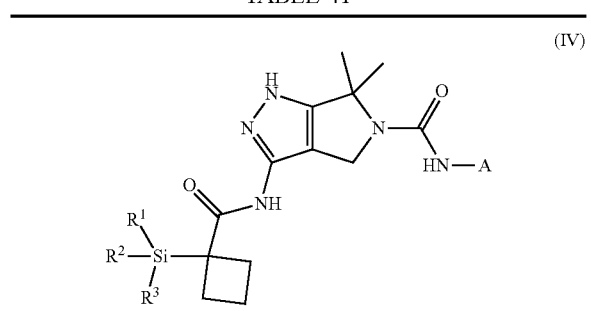

(IV)

| Comp. No. | R¹ | R² | R³ | A |
|---|---|---|---|---|
| IV-301 | Me | Me | Me | 2-Br-3-Et—Ph |
| IV-302 | Me | Et | Me | 2-Br-3-Et—Ph |
| IV-303 | Me | Me | Me | 2-Br-4-Et—Ph |
| IV-304 | Me | Et | Me | 2-Br-4-Et—Ph |
| IV-305 | Me | Me | Me | 2-Br-5-Et—Ph |
| IV-306 | Me | Et | Me | 2-Br-5-Et—Ph |
| IV-307 | Me | Me | Me | 2-Br-6-Et—Ph |
| IV-308 | Me | Et | Me | 2-Br-6-Et—Ph |
| IV-309 | Me | Me | Me | 2-Br-3-cPr—Ph |
| IV-310 | Me | Et | Me | 2-Br-3-cPr—Ph |
| IV-311 | Me | Me | Me | 2-Br-4-cPr—Ph |
| IV-312 | Me | Et | Me | 2-Br-4-cPr—Ph |
| IV-313 | Me | Me | Me | 2-Br-5-cPr—Ph |
| IV-314 | Me | Et | Me | 2-Br-5-cPr—Ph |
| IV-315 | Me | Me | Me | 2-Br-6-cPr—Ph |
| IV-316 | Me | Et | Me | 2-Br-6-cPr—Ph |
| IV-317 | Me | Me | Me | 2-Br-3-CF₃—Ph |
| IV-318 | Me | Et | Me | 2-Br-3-CF₃—Ph |
| IV-319 | Me | Me | Me | 2-Br-4-CF₃—Ph |
| IV-320 | Me | Et | Me | 2-Br-4-CF₃—Ph |
| IV-321 | Me | Me | Me | 2-Br-5-CF₃—Ph |
| IV-322 | Me | Et | Me | 2-Br-5-CF₃—Ph |
| IV-323 | Me | Me | Me | 2-Br-6-CF₃—Ph |
| IV-324 | Me | Et | Me | 2-Br-6-CF₃—Ph |
| IV-325 | Me | Me | Me | 2-Br-3-MeO—Ph |
| IV-326 | Me | Et | Me | 2-Br-3-MeO—Ph |
| IV-327 | Me | Me | Me | 2-Br-4-MeO—Ph |
| IV-328 | Me | Et | Me | 2-Br-4-MeO—Ph |
| IV-329 | Me | Me | Me | 2-Br-5-MeO—Ph |
| IV-330 | Me | Et | Me | 2-Br-5-MeO—Ph |
| IV-331 | Me | Me | Me | 2-Br-6-MeO—Ph |
| IV-332 | Me | Et | Me | 2-Br-6-MeO—Ph |
| IV-333 | Me | Me | Me | 2-Br-3-CHF₂O—Ph |
| IV-334 | Me | Et | Me | 2-Br-3-CHF₂O—Ph |
| IV-335 | Me | Me | Me | 2-Br-4-CHF₂O—Ph |
| IV-336 | Me | Et | Me | 2-Br-4-CHF₂O—Ph |
| IV-337 | Me | Me | Me | 2-Br-5-CHF₂O—Ph |
| IV-338 | Me | Et | Me | 2-Br-5-CHF₂O—Ph |
| IV-339 | Me | Me | Me | 2-Br-6-CHF₂O—Ph |
| IV-340 | Me | Et | Me | 2-Br-6-CHF₂O—Ph |
| IV-341 | Me | Me | Me | 2-Br-3-CD₃O—Ph |
| IV-342 | Me | Et | Me | 2-Br-3-CD₃O—Ph |
| IV-343 | Me | Me | Me | 2-Br-4-CD₃O—Ph |
| IV-344 | Me | Et | Me | 2-Br-4-CD₃O—Ph |
| IV-345 | Me | Me | Me | 2-Br-5-CD₃O—Ph |
| IV-346 | Me | Et | Me | 2-Br-5-CD₃O—Ph |
| IV-347 | Me | Me | Me | 2-Br-6-CD₃O—Ph |
| IV-348 | Me | Et | Me | 2-Br-6-CD₃O—Ph |
| IV-349 | Me | Me | Me | 2-Br-3-NC—Ph |
| IV-350 | Me | Et | Me | 2-Br-3-NC—Ph |
| IV-351 | Me | Me | Me | 2-Br-4-NC—Ph |
| IV-352 | Me | Et | Me | 2-Br-4-NC—Ph |
| IV-353 | Me | Me | Me | 2-Br-5-NC—Ph |
| IV-354 | Me | Et | Me | 2-Br-5-NC—Ph |
| IV-355 | Me | Me | Me | 2-Br-6-NC—Ph |
| IV-356 | Me | Et | Me | 2-Br-6-NC—Ph |
| IV-357 | Me | Me | Me | 2-Me-3-F—Ph |
| IV-358 | Me | Et | Me | 2-Me-3-F—Ph |
| IV-359 | Me | Me | Me | 2-Me-4-F—Ph |
| IV-360 | Me | Et | Me | 2-Me-4-F—Ph |
| IV-361 | Me | Me | Me | 2-Me-5-F—Ph |
| IV-362 | Me | Et | Me | 2-Me-5-F—Ph |
| IV-363 | Me | Me | Me | 2-Me-3-Cl—Ph |
| IV-364 | Me | Et | Me | 2-Me-3-Cl—Ph |
| IV-365 | Me | Me | Me | 2-Me-4-Cl—Ph |
| IV-366 | Me | Et | Me | 2-Me-4-Cl—Ph |
| IV-367 | Me | Me | Me | 2-Me-5-Cl—Ph |
| IV-368 | Me | Et | Me | 2-Me-5-Cl—Ph |
| IV-369 | Me | Me | Me | 2-Me-3-Br—Ph |
| IV-370 | Me | Et | Me | 2-Me-3-Br—Ph |
| IV-371 | Me | Me | Me | 2-Me-4-Br—Ph |
| IV-372 | Me | Et | Me | 2-Me-4-Br—Ph |
| IV-373 | Me | Me | Me | 2-Me-5-Br—Ph |
| IV-374 | Me | Et | Me | 2-Me-5-Br—Ph |
| IV-375 | Me | Me | Me | 2,3-diMe—Ph |
| IV-376 | Me | Et | Me | 2,3-diMe—Ph |
| IV-377 | Me | Me | Me | 2,4-diMe—Ph |
| IV-378 | Me | Et | Me | 2,4-diMe—Ph |
| IV-379 | Me | Me | Me | 2,5-diMe—Ph |
| IV-380 | Me | Et | Me | 2,5-diMe—Ph |
| IV-381 | Me | Me | Me | 2,6-diMe—Ph |
| IV-382 | Me | Et | Me | 2,6-diMe—Ph |
| IV-383 | Me | Me | Me | 2-Me-3-Et—Ph |
| IV-384 | Me | Et | Me | 2-Me-3-Et—Ph |
| IV-385 | Me | Me | Me | 2-Me-4-Et—Ph |
| IV-386 | Me | Et | Me | 2-Me-4-Et—Ph |
| IV-387 | Me | Me | Me | 2-Me-5-Et—Ph |
| IV-388 | Me | Et | Me | 2-Me-5-Et—Ph |
| IV-389 | Me | Me | Me | 2-Me-6-Et—Ph |
| IV-390 | Me | Et | Me | 2-Me-6-Et—Ph |
| IV-391 | Me | Me | Me | 2-Me-3-cPr—Ph |
| IV-392 | Me | Et | Me | 2-Me-3-cPr—Ph |
| IV-393 | Me | Me | Me | 2-Me-4-cPr—Ph |
| IV-394 | Me | Et | Me | 2-Me-4-cPr—Ph |
| IV-395 | Me | Me | Me | 2-Me-5-cPr—Ph |
| IV-396 | Me | Et | Me | 2-Me-5-cPr—Ph |
| IV-397 | Me | Me | Me | 2-Me-6-cPr—Ph |
| IV-398 | Me | Et | Me | 2-Me-6-cPr—Ph |
| IV-399 | Me | Me | Me | 2-Me-3-CF₃—Ph |
| IV-400 | Me | Et | Me | 2-Me-3-CF₃—Ph |

TABLE 42

(IV)

| Comp. No. | R¹ | R² | R³ | A |
|---|---|---|---|---|
| IV-401 | Me | Me | Me | 2-Me-4-CF₃—Ph |
| IV-402 | Me | Et | Me | 2-Me-4-CF₃—Ph |
| IV-403 | Me | Me | Me | 2-Me-5-CF₃—Ph |
| IV-404 | Me | Et | Me | 2-Me-5-CF₃—Ph |
| IV-405 | Me | Me | Me | 2-Me-6-CF₃—Ph |

TABLE 42-continued

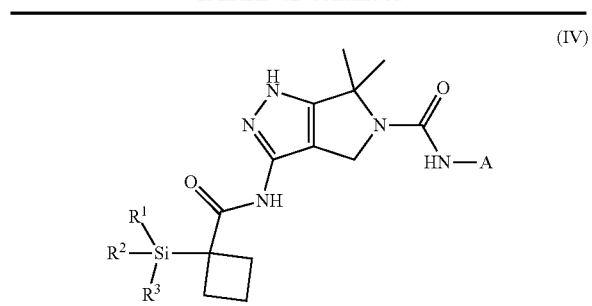

(IV)

| Comp. No. | R¹ | R² | R³ | A |
|---|---|---|---|---|
| IV-406 | Me | Et | Me | 2-Me-6-CF₃—Ph |
| IV-407 | Me | Me | Me | 2-Me-3-MeO—Ph |
| IV-408 | Me | Et | Me | 2-Me-3-MeO—Ph |
| IV-409 | Me | Me | Me | 2-Me-4-MeO—Ph |
| IV-410 | Me | Et | Me | 2-Me-4-MeO—Ph |
| IV-411 | Me | Me | Me | 2-Me-5-MeO—Ph |
| IV-412 | Me | Et | Me | 2-Me-5-MeO—Ph |
| IV-413 | Me | Me | Me | 2-Me-6-MeO—Ph |
| IV-414 | Me | Et | Me | 2-Me-6-MeO—Ph |
| IV-415 | Me | Me | Me | 2-Me-3-CHF₂O—Ph |
| IV-416 | Me | Et | Me | 2-Me-3-CHF₂O—Ph |
| IV-417 | Me | Me | Me | 2-Me-4-CHF₂O—Ph |
| IV-418 | Me | Et | Me | 2-Me-4-CHF₂O—Ph |
| IV-419 | Me | Me | Me | 2-Me-5-CHF₂O—Ph |
| IV-420 | Me | Et | Me | 2-Me-5-CHF₂O—Ph |
| IV-421 | Me | Me | Me | 2-Me-6-CHF₂O—Ph |
| IV-422 | Me | Et | Me | 2-Me-6-CHF₂O—Ph |
| IV-423 | Me | Me | Me | 2-Me-3-CD₃O—Ph |
| IV-424 | Me | Et | Me | 2-Me-3-CD₃O—Ph |
| IV-425 | Me | Me | Me | 2-Me-4-CD₃O—Ph |
| IV-426 | Me | Et | Me | 2-Me-4-CD₃O—Ph |
| IV-427 | Me | Me | Me | 2-Me-5-CD₃O—Ph |
| IV-428 | Me | Et | Me | 2-Me-5-CD₃O—Ph |
| IV-429 | Me | Me | Me | 2-Me-6-CD₃O—Ph |
| IV-430 | Me | Et | Me | 2-Me-6-CD₃O—Ph |
| IV-431 | Me | Me | Me | 2-Me-3-NC—Ph |
| IV-432 | Me | Et | Me | 2-Me-3-NC—Ph |
| IV-433 | Me | Me | Me | 2-Me-4-NC—Ph |
| IV-434 | Me | Et | Me | 2-Me-4-NC—Ph |
| IV-435 | Me | Me | Me | 2-Me-5-NC—Ph |
| IV-436 | Me | Et | Me | 2-Me-5-NC—Ph |
| IV-437 | Me | Me | Me | 2-Me-6-NC—Ph |
| IV-438 | Me | Et | Me | 2-Me-6-NC—Ph |
| IV-439 | Me | Me | Me | 2-Et-3-F—Ph |
| IV-440 | Me | Et | Me | 2-Et-3-F—Ph |
| IV-441 | Me | Me | Me | 2-Et-4-F—Ph |
| IV-442 | Me | Et | Me | 2-Et-4-F—Ph |
| IV-443 | Me | Me | Me | 2-Et-5-F—Ph |
| IV-444 | Me | Et | Me | 2-Et-5-F—Ph |
| IV-445 | Me | Me | Me | 2-Et-3-Cl—Ph |
| IV-446 | Me | Et | Me | 2-Et-3-Cl—Ph |
| IV-447 | Me | Me | Me | 2-Et-4-Cl—Ph |
| IV-448 | Me | Et | Me | 2-Et-4-Cl—Ph |
| IV-449 | Me | Me | Me | 2-Et-5-Cl—Ph |
| IV-450 | Me | Et | Me | 2-Et-5-Cl—Ph |
| IV-451 | Me | Me | Me | 2-Et-3-Br—Ph |
| IV-452 | Me | Et | Me | 2-Et-3-Br—Ph |
| IV-453 | Me | Me | Me | 2-Et-4-Br—Ph |
| IV-454 | Me | Et | Me | 2-Et-4-Br—Ph |
| IV-455 | Me | Me | Me | 2-Et-5-Br—Ph |
| IV-456 | Me | Et | Me | 2-Et-5-Br—Ph |
| IV-457 | Me | Me | Me | 2-Et-3-Me—Ph |
| IV-458 | Me | Et | Me | 2-Et-3-Me—Ph |
| IV-459 | Me | Me | Me | 2-Et-4-Me—Ph |
| IV-460 | Me | Et | Me | 2-Et-4-Me—Ph |
| IV-461 | Me | Me | Me | 2-Et-5-Me—Ph |
| IV-462 | Me | Et | Me | 2-Et-5-Me—Ph |
| IV-463 | Me | Me | Me | 2,3-diEt—Ph |
| IV-464 | Me | Et | Me | 2,3-diEt—Ph |
| IV-465 | Me | Me | Me | 2,4-diEt—Ph |
| IV-466 | Me | Et | Me | 2,4-diEt—Ph |
| IV-467 | Me | Me | Me | 2,5-diEt—Ph |
| IV-468 | Me | Et | Me | 2,5-diEt—Ph |

TABLE 42-continued

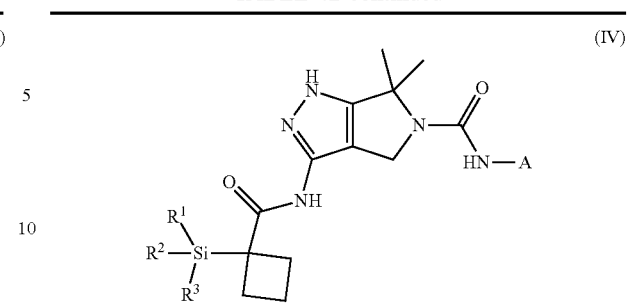

(IV)

| Comp. No. | R¹ | R² | R³ | A |
|---|---|---|---|---|
| IV-469 | Me | Me | Me | 2,6-diEt—Ph |
| IV-470 | Me | Et | Me | 2,6-diEt—Ph |
| IV-471 | Me | Me | Me | 2-Et-3-cPr—Ph |
| IV-472 | Me | Et | Me | 2-Et-3-cPr—Ph |
| IV-473 | Me | Me | Me | 2-Et-4-cPr—Ph |
| IV-474 | Me | Et | Me | 2-Et-4-cPr—Ph |
| IV-475 | Me | Me | Me | 2-Et-5-cPr—Ph |
| IV-476 | Me | Et | Me | 2-Et-5-cPr—Ph |
| IV-477 | Me | Me | Me | 2-Et-6-cPr—Ph |
| IV-478 | Me | Et | Me | 2-Et-6-cPr—Ph |
| IV-479 | Me | Me | Me | 2-Et-3-CF₃—Ph |
| IV-480 | Me | Et | Me | 2-Et-3-CF₃—Ph |
| IV-481 | Me | Me | Me | 2-Et-4-CF₃—Ph |
| IV-482 | Me | Et | Me | 2-Et-4-CF₃—Ph |
| IV-483 | Me | Me | Me | 2-Et-5-CF₃—Ph |
| IV-484 | Me | Et | Me | 2-Et-5-CF₃—Ph |
| IV-485 | Me | Me | Me | 2-Et-6-CF₃—Ph |
| IV-486 | Me | Et | Me | 2-Et-6-CF₃—Ph |
| IV-487 | Me | Me | Me | 2-Et-3-MeO—Ph |
| IV-488 | Me | Et | Me | 2-Et-3-MeO—Ph |
| IV-489 | Me | Me | Me | 2-Et-4-MeO—Ph |
| IV-490 | Me | Et | Me | 2-Et-4-MeO—Ph |
| IV-491 | Me | Me | Me | 2-Et-5-MeO—Ph |
| IV-492 | Me | Et | Me | 2-Et-5-MeO—Ph |
| IV-493 | Me | Me | Me | 2-Et-6-MeO—Ph |
| IV-494 | Me | Et | Me | 2-Et-6-MeO—Ph |
| IV-495 | Me | Me | Me | 2-Et-3-CHF₂O—Ph |
| IV-496 | Me | Et | Me | 2-Et-3-CHF₂O—Ph |
| IV-497 | Me | Me | Me | 2-Et-4-CHF₂O—Ph |
| IV-498 | Me | Et | Me | 2-Et-4-CHF₂O—Ph |
| IV-499 | Me | Me | Me | 2-Et-5-CHF₂O—Ph |
| IV-500 | Me | Et | Me | 2-Et-5-CHF₂O—Ph |

TABLE 43

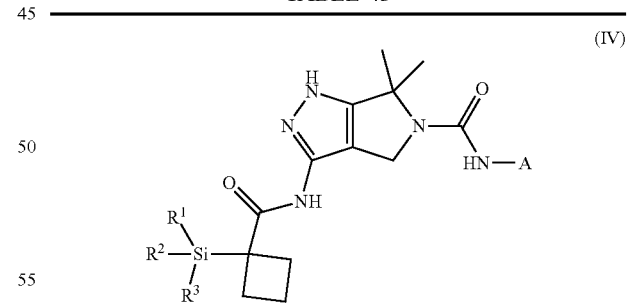

(IV)

| Comp. No. | R¹ | R² | R³ | A |
|---|---|---|---|---|
| IV-501 | Me | Me | Me | 2-Et-6-CHF₂O—Ph |
| IV-502 | Me | Et | Me | 2-Et-6-CHF₂O—Ph |
| IV-503 | Me | Me | Me | 2-Et-3-CD₃O—Ph |
| IV-504 | Me | Et | Me | 2-Et-3-CD₃O—Ph |
| IV-505 | Me | Me | Me | 2-Et-4-CD₃O—Ph |
| IV-506 | Me | Et | Me | 2-Et-4-CD₃O—Ph |
| IV-507 | Me | Me | Me | 2-Et-5-CD₃O—Ph |
| IV-508 | Me | Et | Me | 2-Et-5-CD₃O—Ph |
| IV-509 | Me | Me | Me | 2-Et-6-CD₃O—Ph |
| IV-510 | Me | Et | Me | 2-Et-6-CD₃O—Ph |

TABLE 43-continued

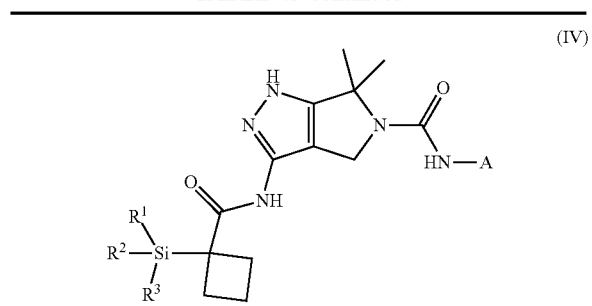

(IV)

| Comp. No. | R¹ | R² | R³ | A |
|---|---|---|---|---|
| IV-511 | Me | Me | Me | 2-Et-3-NC—Ph |
| IV-512 | Me | Et | Me | 2-Et-3-NC—Ph |
| IV-513 | Me | Me | Me | 2-Et-4-NC—Ph |
| IV-514 | Me | Et | Me | 2-Et-4-NC—Ph |
| IV-515 | Me | Me | Me | 2-Et-5-NC—Ph |
| IV-516 | Me | Et | Me | 2-Et-5-NC—Ph |
| IV-517 | Me | Me | Me | 2-Et-6-NC—Ph |
| IV-518 | Me | Et | Me | 2-Et-6-NC—Ph |
| IV-519 | Me | Me | Me | 2-MeO-3-F—Ph |
| IV-520 | Me | Et | Me | 2-MeO-3-F—Ph |
| IV-521 | Me | Me | Me | 2-MeO-4-F—Ph |
| IV-522 | Me | Et | Me | 2-MeO-4-F—Ph |
| IV-523 | Me | Me | Me | 2-MeO-5-F—Ph |
| IV-524 | Me | Et | Me | 2-MeO-5-F—Ph |
| IV-525 | Me | Me | Me | 2-MeO-3-Cl—Ph |
| IV-526 | Me | Et | Me | 2-MeO-3-Cl—Ph |
| IV-527 | Me | Me | Me | 2-MeO-4-Cl—Ph |
| IV-528 | Me | Et | Me | 2-MeO-4-Cl—Ph |
| IV-529 | Me | Me | Me | 2-MeO-5-Cl—Ph |
| IV-530 | Me | Et | Me | 2-MeO-5-Cl—Ph |
| IV-531 | Me | Me | Me | 2-MeO-3-Br—Ph |
| IV-532 | Me | Et | Me | 2-MeO-3-Br—Ph |
| IV-533 | Me | Me | Me | 2-MeO-4-Br—Ph |
| IV-534 | Me | Et | Me | 2-MeO-4-Br—Ph |
| IV-535 | Me | Me | Me | 2-MeO-5-Br—Ph |
| IV-536 | Me | Et | Me | 2-MeO-5-Br—Ph |
| IV-537 | Me | Me | Me | 2-MeO-3-Me—Ph |
| IV-538 | Me | Et | Me | 2-MeO-3-Me—Ph |
| IV-539 | Me | Me | Me | 2-MeO-4-Me—Ph |
| IV-540 | Me | Et | Me | 2-MeO-4-Me—Ph |
| IV-541 | Me | Me | Me | 2-MeO-5-Me—Ph |
| IV-542 | Me | Et | Me | 2-MeO-5-Me—Ph |
| IV-543 | Me | Me | Me | 2-MeO-3-Et—Ph |
| IV-544 | Me | Et | Me | 2-MeO-3-Et—Ph |
| IV-545 | Me | Me | Me | 2-MeO-4-Et—Ph |
| IV-546 | Me | Et | Me | 2-MeO-4-Et—Ph |
| IV-547 | Me | Me | Me | 2-MeO-5-Et—Ph |
| IV-548 | Me | Et | Me | 2-MeO-5-Et—Ph |
| IV-549 | Me | Me | Me | 2-MeO-3-cPr—Ph |
| IV-550 | Me | Et | Me | 2-MeO-3-cPr—Ph |
| IV-551 | Me | Me | Me | 2-MeO-4-cPr—Ph |
| IV-552 | Me | Et | Me | 2-MeO-4-cPr—Ph |
| IV-553 | Me | Me | Me | 2-MeO-5-cPr—Ph |
| IV-554 | Me | Et | Me | 2-MeO-5-cPr—Ph |
| IV-555 | Me | Me | Me | 2-MeO-6-cPr—Ph |
| IV-556 | Me | Et | Me | 2-MeO-6-cPr—Ph |
| IV-557 | Me | Me | Me | 2-MeO-3-CF₃—Ph |
| IV-558 | Me | Et | Me | 2-MeO-3-CF₃—Ph |
| IV-559 | Me | Me | Me | 2-MeO-4-CF₃—Ph |
| IV-560 | Me | Et | Me | 2-MeO-4-CF₃—Ph |
| IV-561 | Me | Me | Me | 2-MeO-5-CF₃—Ph |
| IV-562 | Me | Et | Me | 2-MeO-5-CF₃—Ph |
| IV-563 | Me | Me | Me | 2-MeO-6-CF₃—Ph |
| IV-564 | Me | Et | Me | 2-MeO-6-CF₃—Ph |
| IV-565 | Me | Me | Me | 2,3-diMeO—Ph |
| IV-566 | Me | Et | Me | 2,3-diMeO—Ph |
| IV-567 | Me | Me | Me | 2,4-diMeO—Ph |
| IV-568 | Me | Et | Me | 2,4-diMeO—Ph |
| IV-569 | Me | Me | Me | 2,5-diMeO—Ph |
| IV-570 | Me | Et | Me | 2,5-diMeO—Ph |
| IV-571 | Me | Me | Me | 2,6-diMeO—Ph |
| IV-572 | Me | Et | Me | 2,6-diMeO—Ph |
| IV-573 | Me | Me | Me | 2-MeO-3-CHF₂O—Ph |

TABLE 43-continued

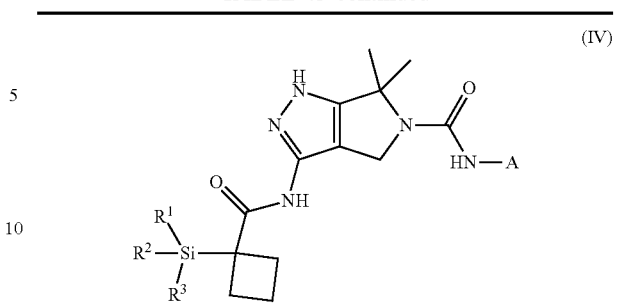

(IV)

| Comp. No. | R¹ | R² | R³ | A |
|---|---|---|---|---|
| IV-574 | Me | Et | Me | 2-MeO-3-CHF₂O—Ph |
| IV-575 | Me | Me | Me | 2-MeO-4-CHF₂O—Ph |
| IV-576 | Me | Et | Me | 2-MeO-4-CHF₂O—Ph |
| IV-577 | Me | Me | Me | 2-MeO-5-CHF₂O—Ph |
| IV-578 | Me | Et | Me | 2-MeO-5-CHF₂O—Ph |
| IV-579 | Me | Me | Me | 2-MeO-6-CHF₂O—Ph |
| IV-580 | Me | Et | Me | 2-MeO-6-CHF₂O—Ph |
| IV-581 | Me | Me | Me | 2-MeO-3-CD₃O—Ph |
| IV-582 | Me | Et | Me | 2-MeO-3-CD₃O—Ph |
| IV-583 | Me | Me | Me | 2-MeO-4-CD₃O—Ph |
| IV-584 | Me | Et | Me | 2-MeO-4-CD₃O—Ph |
| IV-585 | Me | Me | Me | 2-MeO-5-CD₃O—Ph |
| IV-586 | Me | Et | Me | 2-MeO-5-CD₃O—Ph |
| IV-587 | Me | Me | Me | 2-MeO-6-CD₃O—Ph |
| IV-588 | Me | Et | Me | 2-MeO-6-CD₃O—Ph |
| IV-589 | Me | Me | Me | 2-MeO-3-NC—Ph |
| IV-590 | Me | Et | Me | 2-MeO-3-NC—Ph |
| IV-591 | Me | Me | Me | 2-MeO-4-NC—Ph |
| IV-592 | Me | Et | Me | 2-MeO-4-NC—Ph |
| IV-593 | Me | Me | Me | 2-MeO-5-NC—Ph |
| IV-594 | Me | Et | Me | 2-MeO-5-NC—Ph |
| IV-595 | Me | Me | Me | 2-MeO-6-NC—Ph |
| IV-596 | Me | Et | Me | 2-MeO-6-NC—Ph |
| IV-597 | Me | Me | Me | 2,3,6-triF—Ph |
| IV-598 | Me | Et | Me | 2,3,6-triF—Ph |
| IV-599 | Me | Me | Me | 2,4,6-triF—Ph |
| IV-600 | Me | Et | Me | 2,4,6-triF—Ph |

TABLE 44

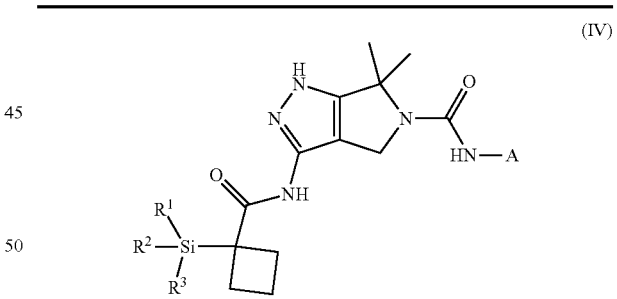

(IV)

| Comp. No. | R¹ | R² | R³ | A |
|---|---|---|---|---|
| IV-601 | Me | Me | Me | 2,6-diF-3-Cl—Ph |
| IV-602 | Me | Et | Me | 2,6-diF-3-Cl—Ph |
| IV-603 | Me | Me | Me | 2,6-diF-4-Cl—Ph |
| IV-604 | Me | Et | Me | 2,6-diF-4-Cl—Ph |
| IV-605 | Me | Me | Me | 2,6-diF-3-Br—Ph |
| IV-606 | Me | Et | Me | 2,6-diF-3-Br—Ph |
| IV-607 | Me | Me | Me | 2,6-diF-4-Br—Ph |
| IV-608 | Me | Et | Me | 2,6-diF-4-Br—Ph |
| IV-609 | Me | Me | Me | 2,6-diF-3-Me—Ph |
| IV-610 | Me | Et | Me | 2,6-diF-3-Me—Ph |
| IV-611 | Me | Me | Me | 2,6-diF-4-Me—Ph |
| IV-612 | Me | Et | Me | 2,6-diF-4-Me—Ph |
| IV-613 | Me | Me | Me | 2,6-diF-3-MeO—Ph |
| IV-614 | Me | Et | Me | 2,6-diF-3-MeO—Ph |
| IV-615 | Me | Me | Me | 2,6-diF-4-MeO—Ph |

TABLE 44-continued (IV)

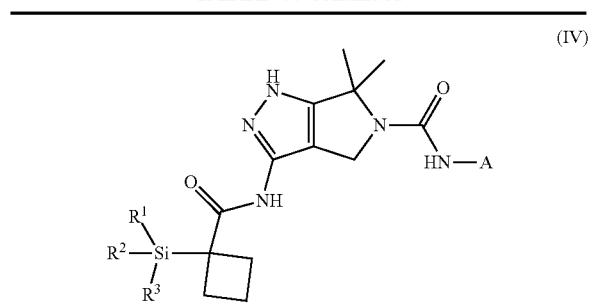

| Comp. No. | R¹ | R² | R³ | A |
|---|---|---|---|---|
| IV-616 | Me | Et | Me | 2,6-diF-4-MeO—Ph |
| IV-617 | Me | Me | Me | 2,3-diF-6-Cl—Ph |
| IV-618 | Me | Et | Me | 2,3-diF-6-Cl—Ph |
| IV-619 | Me | Me | Me | 2,4-diF-6-Cl—Ph |
| IV-620 | Me | Et | Me | 2,4-diF-6-Cl—Ph |
| IV-621 | Me | Me | Me | 2-F-3,6-diCl—Ph |
| IV-622 | Me | Et | Me | 2-F-3,6-diCl—Ph |
| IV-623 | Me | Me | Me | 2-F-4,6-diCl—Ph |
| IV-624 | Me | Et | Me | 2-F-4,6-diCl—Ph |
| IV-625 | Me | Me | Me | 2-F-3-Br-6-Cl—Ph |
| IV-626 | Me | Et | Me | 2-F-3-Br-6-Cl—Ph |
| IV-627 | Me | Me | Me | 2-F-4-Br-6-Cl—Ph |
| IV-628 | Me | Et | Me | 2-F-4-Br-6-Cl—Ph |
| IV-629 | Me | Me | Me | 2-F-3-Me-6-Cl—Ph |
| IV-630 | Me | Et | Me | 2-F-3-Me-6-Cl—Ph |
| IV-631 | Me | Me | Me | 2-F-4-Me-6-Cl—Ph |
| IV-632 | Me | Et | Me | 2-F-4-Me-6-Cl—Ph |
| IV-633 | Me | Me | Me | 2-F-3-MeO-6-Cl—Ph |
| IV-634 | Me | Et | Me | 2-F-3-MeO-6-Cl—Ph |
| IV-635 | Me | Me | Me | 2-F-4-MeO-6-Cl—Ph |
| IV-636 | Me | Et | Me | 2-F-4-MeO-6-Cl—Ph |
| IV-637 | Me | Me | Me | 2,3-diF-6-Br—Ph |
| IV-638 | Me | Et | Me | 2,3-diF-6-Br—Ph |
| IV-639 | Me | Me | Me | 2,4-diF-6-Br—Ph |
| IV-640 | Me | Et | Me | 2,4-diF-6-Br—Ph |
| IV-641 | Me | Me | Me | 2-F-3-C-6-Br—Ph |
| IV-642 | Me | Et | Me | 2-F-3-Cl-6-Br—Ph |
| IV-643 | Me | Me | Me | 2-F-4-Cl-6-Br—Ph |
| IV-644 | Me | Et | Me | 2-F-4-Cl-6-Br—Ph |
| IV-645 | Me | Me | Me | 2-F-3,6-diBr—Ph |
| IV-646 | Me | Et | Me | 2-F-3,6-diBr—Ph |
| IV-647 | Me | Me | Me | 2-F-4,6-diBr—Ph |
| IV-648 | Me | Et | Me | 2-F-4,6-diBr—Ph |
| IV-649 | Me | Me | Me | 2-F-3-Me-6-Br—Ph |
| IV-650 | Me | Et | Me | 2-F-3-Me-6-Br—Ph |
| IV-651 | Me | Me | Me | 2-F-4-Me-6-Br—Ph |
| IV-652 | Me | Et | Me | 2-F-4-Me-6-Br—Ph |
| IV-653 | Me | Me | Me | 2-F-3-MeO-6-Br—Ph |
| IV-654 | Me | Et | Me | 2-F-3-MeO-6-Br—Ph |
| IV-655 | Me | Me | Me | 2-F-4-MeO-6-Br—Ph |
| IV-656 | Me | Et | Me | 2-F-4-MeO-6-Br—Ph |
| IV-657 | Me | Me | Me | 2,3-diF-6-Me—Ph |
| IV-658 | Me | Et | Me | 2,3-diF-6-Me—Ph |
| IV-659 | Me | Me | Me | 2,4-diF-6-Me—Ph |
| IV-660 | Me | Et | Me | 2,4-diF-6-Me—Ph |
| IV-661 | Me | Me | Me | 2-F-3-Cl-6-Me—Ph |
| IV-662 | Me | Et | Me | 2-F-3-Cl-6-Me—Ph |
| IV-663 | Me | Me | Me | 2-F-4-Cl-6-Me—Ph |
| IV-664 | Me | Et | Me | 2-F-4-Cl-6-Me—Ph |
| IV-665 | Me | Me | Me | 2-F-3-Br-6-Me—Ph |
| IV-666 | Me | Et | Me | 2-F-3-Br-6-Me—Ph |
| IV-667 | Me | Me | Me | 2-F-4-Br-6-Me—Ph |
| IV-668 | Me | Et | Me | 2-F-4-Br-6-Me—Ph |
| IV-669 | Me | Me | Me | 2-F-3,6-diMe—Ph |
| IV-670 | Me | Et | Me | 2-F-3,6-diMe—Ph |
| IV-671 | Me | Me | Me | 2-F-4,6-diMe—Ph |
| IV-672 | Me | Et | Me | 2-F-4,6-diMe—Ph |
| IV-673 | Me | Me | Me | 2-F-3-MeO-6-Me—Ph |
| IV-674 | Me | Et | Me | 2-F-3-MeO-6-Me—Ph |
| IV-675 | Me | Me | Me | 2-F-4-MeO-6-Me—Ph |
| IV-676 | Me | Et | Me | 2-F-4-MeO-6-Me—Ph |
| IV-677 | Me | Me | Me | 2,3-diF-6-MeO—Ph |
| IV-678 | Me | Et | Me | 2,3-diF-6-MeO—Ph |

TABLE 44-continued (IV)

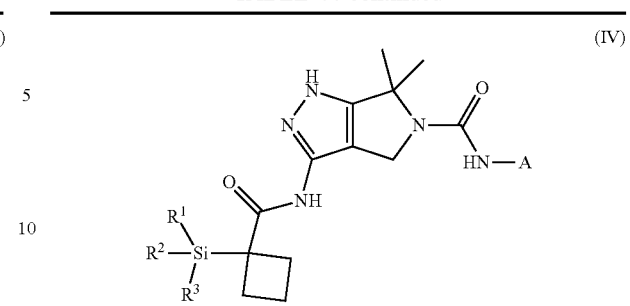

| Comp. No. | R¹ | R² | R³ | A |
|---|---|---|---|---|
| IV-679 | Me | Me | Me | 2,4-diF-6-MeO—Ph |
| IV-680 | Me | Et | Me | 2,4-diF-6-MeO—Ph |
| IV-681 | Me | Me | Me | 2-F-3-Cl-6-MeO—Ph |
| IV-682 | Me | Et | Me | 2-F-3-Cl-6-MeO—Ph |
| IV-683 | Me | Me | Me | 2-F-4-Cl-6-MeO—Ph |
| IV-684 | Me | Et | Me | 2-F-4-Cl-6-MeO—Ph |
| IV-685 | Me | Me | Me | 2-F-3-Br-6-MeO—Ph |
| IV-686 | Me | Et | Me | 2-F-3-Br-6-MeO—Ph |
| IV-687 | Me | Me | Me | 2-F-4-Br-6-MeO—Ph |
| IV-688 | Me | Et | Me | 2-F-4-Br-6-MeO—Ph |
| IV-689 | Me | Me | Me | 2-F-3-Me-6-MeO—Ph |
| IV-690 | Me | Et | Me | 2-F-3-Me-6-MeO—Ph |
| IV-691 | Me | Me | Me | 2-F-4-Me-6-MeO—Ph |
| IV-692 | Me | Et | Me | 2-F-4-Me-6-MeO—Ph |
| IV-693 | Me | Me | Me | 2-F-3,6-diMeO—Ph |
| IV-694 | Me | Et | Me | 2-F-3,6-diMeO—Ph |
| IV-695 | Me | Me | Me | 2-F-4,6-diMeO—Ph |
| IV-696 | Me | Et | Me | 2-F-4,6-diMeO—Ph |
| IV-697 | Me | Me | Me | 2-Cl-3,6-diF—Ph |
| IV-698 | Me | Et | Me | 2-Cl-3,6-diF—Ph |
| IV-699 | Me | Me | Me | 2,3-diCl-6-F—Ph |
| IV-700 | Me | Et | Me | 2,3-diCl-6-F—Ph |

TABLE 45

(IV)

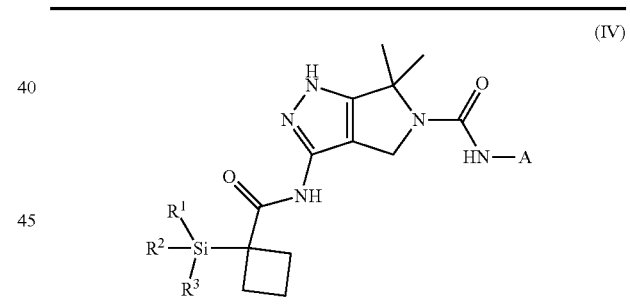

| Comp. No. | R¹ | R² | R³ | A |
|---|---|---|---|---|
| IV-701 | Me | Me | Me | 2-Cl-3-Br-6-F—Ph |
| IV-702 | Me | Et | Me | 2-Cl-3-Br-6-F—Ph |
| IV-703 | Me | Me | Me | 2-Cl-3-Me-6-F—Ph |
| IV-704 | Me | Et | Me | 2-Cl-3-Me-6-F—Ph |
| IV-705 | Me | Me | Me | 2-Cl-3-MeO-6-F—Ph |
| IV-706 | Me | Et | Me | 2-Cl-3-MeO-6-F—Ph |
| IV-707 | Me | Me | Me | 2,6-diCl-3-F—Ph |
| IV-708 | Me | Et | Me | 2,6-diCl-3-F—Ph |
| IV-709 | Me | Me | Me | 2,6-diCl-4-F—Ph |
| IV-710 | Me | Et | Me | 2,6-diCl-4-F—Ph |
| IV-711 | Me | Me | Me | 2,3,6-triCl—Ph |
| IV-712 | Me | Et | Me | 2,3,6-triCl—Ph |
| IV-713 | Me | Me | Me | 2,4,6-triCl—Ph |
| IV-714 | Me | Et | Me | 2,4,6-triCl—Ph |
| IV-715 | Me | Me | Me | 2,6-diCl-3-Br—Ph |
| IV-716 | Me | Et | Me | 2,6-diCl-3-Br—Ph |
| IV-717 | Me | Me | Me | 2,6-diCl-4-Br—Ph |
| IV-718 | Me | Et | Me | 2,6-diCl-4-Br—Ph |
| IV-719 | Me | Me | Me | 2,6-diCl-3-Me—Ph |
| IV-720 | Me | Et | Me | 2,6-diCl-3-Me—Ph |

TABLE 45-continued

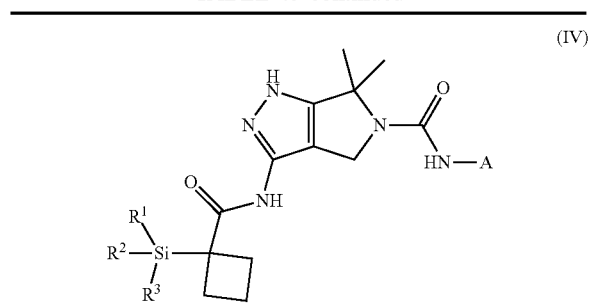

(IV)

| Comp. No. | R¹ | R² | R³ | A |
|---|---|---|---|---|
| IV-721 | Me | Me | Me | 2,6-diCl-4-Me—Ph |
| IV-722 | Me | Et | Me | 2,6-diCl-4-Me—Ph |
| IV-723 | Me | Me | Me | 2,6-diCl-3-MeO—Ph |
| IV-724 | Me | Et | Me | 2,6-diCl-3-MeO—Ph |
| IV-725 | Me | Me | Me | 2,6-diCl-4-MeO—Ph |
| IV-726 | Me | Et | Me | 2,6-diCl-4-MeO—Ph |
| IV-727 | Me | Me | Me | 2-Cl-3-F-6-Br—Ph |
| IV-728 | Me | Et | Me | 2-Cl-3-F-6-Br—Ph |
| IV-729 | Me | Me | Me | 2-Cl-4-F-6-Br—Ph |
| IV-730 | Me | Et | Me | 2-Cl-4-F-6-Br—Ph |
| IV-731 | Me | Me | Me | 2,3-diCl-6-Br—Ph |
| IV-732 | Me | Et | Me | 2,3-diCl-6-Br—Ph |
| IV-733 | Me | Me | Me | 2,4-diCl-6-Br—Ph |
| IV-734 | Me | Et | Me | 2,4-diCl-6-Br—Ph |
| IV-735 | Me | Me | Me | 2-Cl-3,6-diBr—Ph |
| IV-736 | Me | Et | Me | 2-Cl-3,6-diBr—Ph |
| IV-737 | Me | Me | Me | 2-Cl-4,6-diBr—Ph |
| IV-738 | Me | Et | Me | 2-Cl-4,6-diBr—Ph |
| IV-739 | Me | Me | Me | 2-Cl-3-Me-6-Br—Ph |
| IV-740 | Me | Et | Me | 2-Cl-3-Me-6-Br—Ph |
| IV-741 | Me | Me | Me | 2-Cl-4-Me-6-Br—Ph |
| IV-742 | Me | Et | Me | 2-Cl-4-Me-6-Br—Ph |
| IV-743 | Me | Me | Me | 2-Cl-3-MeO-6-Br—Ph |
| IV-744 | Me | Et | Me | 2-Cl-3-MeO-6-Br—Ph |
| IV-745 | Me | Me | Me | 2-Cl-4-MeO-6-Br—Ph |
| IV-746 | Me | Et | Me | 2-Cl-4-MeO-6-Br—Ph |
| IV-747 | Me | Me | Me | 2-Cl-3-F-6-Me—Ph |
| IV-748 | Me | Et | Me | 2-Cl-3-F-6-Me—Ph |
| IV-749 | Me | Me | Me | 2-Cl-4-F-6-Me—Ph |
| IV-750 | Me | Et | Me | 2-Cl-4-F-6-Me—Ph |
| IV-751 | Me | Me | Me | 2,3-diCl-6-Me—Ph |
| IV-752 | Me | Et | Me | 2,3-diCl-6-Me—Ph |
| IV-753 | Me | Me | Me | 2,4-diCl-6-Me—Ph |
| IV-754 | Me | Et | Me | 2,4-diCl-6-Me—Ph |
| IV-755 | Me | Me | Me | 2-Cl-3-Br-6-Me—Ph |
| IV-756 | Me | Et | Me | 2-Cl-3-Br-6-Me—Ph |
| IV-757 | Me | Me | Me | 2-Cl-4-Br-6-Me—Ph |
| IV-758 | Me | Et | Me | 2-Cl-4-Br-6-Me—Ph |
| IV-759 | Me | Me | Me | 2-Cl-3,6-diMe—Ph |
| IV-760 | Me | Et | Me | 2-Cl-3,6-diMe—Ph |
| IV-761 | Me | Me | Me | 2-Cl-4,6-diMe—Ph |
| IV-762 | Me | Et | Me | 2-Cl-4,6-diMe—Ph |
| IV-763 | Me | Me | Me | 2-Cl-3-MeO-6-Me—Ph |
| IV-764 | Me | Et | Me | 2-Cl-3-MeO-6-Me—Ph |
| IV-765 | Me | Me | Me | 2-Cl-4-MeO-6-Me—Ph |
| IV-766 | Me | Et | Me | 2-Cl-4-MeO-6-Me—Ph |
| IV-767 | Me | Me | Me | 2-Cl-3-F-6-MeO—Ph |
| IV-768 | Me | Et | Me | 2-Cl-3-F-6-MeO—Ph |
| IV-769 | Me | Me | Me | 2-Cl-4-F-6-MeO—Ph |
| IV-770 | Me | Et | Me | 2-Cl-4-F-6-MeO—Ph |
| IV-771 | Me | Me | Me | 2,3-diCl-6-MeO—Ph |
| IV-772 | Me | Et | Me | 2,3-diCl-6-MeO—Ph |
| IV-773 | Me | Me | Me | 2,4-diCl-6-MeO—Ph |
| IV-774 | Me | Et | Me | 2,4-diCl-6-MeO—Ph |
| IV-775 | Me | Me | Me | 2-Cl-3-Br-6-MeO—Ph |
| IV-776 | Me | Et | Me | 2-Cl-3-Br-6-MeO—Ph |
| IV-777 | Me | Me | Me | 2-Cl-4-Br-6-MeO—Ph |
| IV-778 | Me | Et | Me | 2-Cl-4-Br-6-MeO—Ph |
| IV-779 | Me | Me | Me | 2-Cl-3-Me-6-MeO—Ph |
| IV-780 | Me | Et | Me | 2-Cl-3-Me-6-MeO—Ph |
| IV-781 | Me | Me | Me | 2-Cl-4-Me-6-MeO—Ph |
| IV-782 | Me | Et | Me | 2-Cl-4-Me-6-MeO—Ph |
| IV-783 | Me | Me | Me | 2-Cl-3,6-diMeO—Ph |

TABLE 45-continued

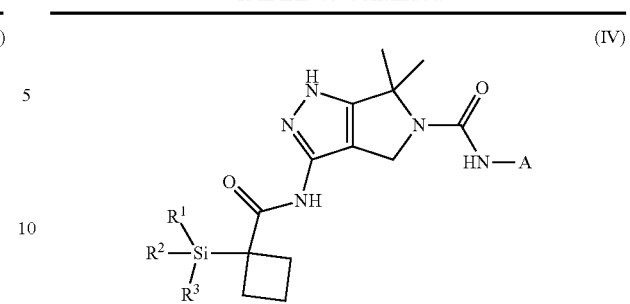

(IV)

| Comp. No. | R¹ | R² | R³ | A |
|---|---|---|---|---|
| IV-784 | Me | Et | Me | 2-Cl-3,6-diMeO—Ph |
| IV-785 | Me | Me | Me | 2-Cl-4,6-diMeO—Ph |
| IV-786 | Me | Et | Me | 2-Cl-4,6-diMeO—Ph |
| IV-787 | Me | Me | Me | 2-Br-3,6-diF—Ph |
| IV-788 | Me | Et | Me | 2-Br-3,6-diF—Ph |
| IV-789 | Me | Me | Me | 2-Br-3-Cl-6-F—Ph |
| IV-790 | Me | Et | Me | 2-Br-3-Cl-6-F—Ph |
| IV-791 | Me | Me | Me | 2,3-diBr-6-F—Ph |
| IV-792 | Me | Et | Me | 2,3-diBr-6-F—Ph |
| IV-793 | Me | Me | Me | 2-Br-3-Me-6-F—Ph |
| IV-794 | Me | Et | Me | 2-Br-3-Me-6-F—Ph |
| IV-795 | Me | Me | Me | 2-Br-3-MeO-6-F—Ph |
| IV-796 | Me | Et | Me | 2-Br-3-MeO-6-F—Ph |
| IV-797 | Me | Me | Me | 2-Br-3-F-6-Cl—Ph |
| IV-798 | Me | Et | Me | 2-Br-3-F-6-Cl—Ph |
| IV-799 | Me | Me | Me | 2-Br-3,6-diCl—Ph |
| IV-800 | Me | Et | Me | 2-Br-3,6-diCl—Ph |

TABLE 46

(IV)

| Comp. No. | R¹ | R² | R³ | A |
|---|---|---|---|---|
| IV-801 | Me | Me | Me | 2,3-diBr-6-Cl—Ph |
| IV-802 | Me | Et | Me | 2,3-diBr-6-Cl—Ph |
| IV-803 | Me | Me | Me | 2-Br-3-Me-6-Cl—Ph |
| IV-804 | Me | Et | Me | 2-Br-3-Me-6-Cl—Ph |
| IV-805 | Me | Me | Me | 2-Br-3-MeO-6-Cl—Ph |
| IV-806 | Me | Et | Me | 2-Br-3-MeO-6-Cl—Ph |
| IV-807 | Me | Me | Me | 2,6-diBr-3-F—Ph |
| IV-808 | Me | Et | Me | 2,6-diBr-3-F—Ph |
| IV-809 | Me | Me | Me | 2,6-diBr-4-F—Ph |
| IV-810 | Me | Et | Me | 2,6-diBr-4-F—Ph |
| IV-811 | Me | Me | Me | 2,6-diBr-3-Cl—Ph |
| IV-812 | Me | Et | Me | 2,6-diBr-3-Cl—Ph |
| IV-813 | Me | Me | Me | 2,6-diBr-4-Cl—Ph |
| IV-814 | Me | Et | Me | 2,6-diBr-4-Cl—Ph |
| IV-815 | Me | Me | Me | 2,3,6-triBr—Ph |
| IV-816 | Me | Et | Me | 2,3,6-triBr—Ph |
| IV-817 | Me | Me | Me | 2,4,6-triBr—Ph |
| IV-818 | Me | Et | Me | 2,4,6-triBr—Ph |
| IV-819 | Me | Me | Me | 2,6-diBr-3-Me—Ph |
| IV-820 | Me | Et | Me | 2,6-diBr-3-Me—Ph |
| IV-821 | Me | Me | Me | 2,6-diBr-4-Me—Ph |
| IV-822 | Me | Et | Me | 2,6-diBr-4-Me—Ph |
| IV-823 | Me | Me | Me | 2,6-diBr-3-MeO—Ph |
| IV-824 | Me | Et | Me | 2,6-diBr-3-MeO—Ph |
| IV-825 | Me | Me | Me | 2,6-diBr-4-MeO—Ph |

TABLE 46-continued

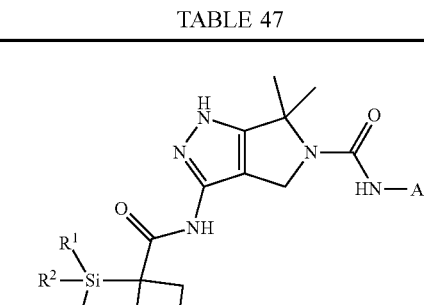

(IV)

| Comp. No. | R¹ | R² | R³ | A |
|---|---|---|---|---|
| IV-826 | Me | Et | Me | 2,6-diBr-4-MeO—Ph |
| IV-827 | Me | Me | Me | 2-Br-3-F-6-Me—Ph |
| IV-828 | Me | Et | Me | 2-Br-3-F-6-Me—Ph |
| IV-829 | Me | Me | Me | 2-Br-4-F-6-Me—Ph |
| IV-830 | Me | Et | Me | 2-Br-4-F-6-Me—Ph |
| IV-831 | Me | Me | Me | 2-Br-3-Cl-6-Me—Ph |
| IV-832 | Me | Et | Me | 2-Br-3-Cl-6-Me—Ph |
| IV-833 | Me | Me | Me | 2-Br-4-Cl-6-Me—Ph |
| IV-834 | Me | Et | Me | 2-Br-4-Cl-6-Me—Ph |
| IV-835 | Me | Me | Me | 2,3-diBr-6-Me—Ph |
| IV-836 | Me | Et | Me | 2,3-diBr-6-Me—Ph |
| IV-837 | Me | Me | Me | 2,4-diBr-6-Me—Ph |
| IV-838 | Me | Et | Me | 2,4-diBr-6-Me—Ph |
| IV-839 | Me | Me | Me | 2-Br-3,6-diMe—Ph |
| IV-840 | Me | Et | Me | 2-Br-3,6-diMe—Ph |
| IV-841 | Me | Me | Me | 2-Br-4,6-diMe—Ph |
| IV-842 | Me | Et | Me | 2-Br-4,6-diMe—Ph |
| IV-843 | Me | Me | Me | 2-Br-3-MeO-6-Me—Ph |
| IV-844 | Me | Et | Me | 2-Br-3-MeO-6-Me—Ph |
| IV-845 | Me | Me | Me | 2-Br-4-MeO-6-Me—Ph |
| IV-846 | Me | Et | Me | 2-Br-4-MeO-6-Me—Ph |
| IV-847 | Me | Me | Me | 2-Br-3-F-6-MeO—Ph |
| IV-848 | Me | Et | Me | 2-Br-3-F-6-MeO—Ph |
| IV-849 | Me | Me | Me | 2-Br-4-F-6-MeO—Ph |
| IV-850 | Me | Et | Me | 2-Br-4-F-6-MeO—Ph |
| IV-851 | Me | Me | Me | 2-Br-3-Cl-6-MeO—Ph |
| IV-852 | Me | Et | Me | 2-Br-3-Cl-6-MeO—Ph |
| IV-853 | Me | Me | Me | 2-Br-4-Cl-6-MeO—Ph |
| IV-854 | Me | Et | Me | 2-Br-4-Cl-6-MeO—Ph |
| IV-855 | Me | Me | Me | 2,3-diBr-6-MeO—Ph |
| IV-856 | Me | Et | Me | 2,3-diBr-6-MeO—Ph |
| IV-857 | Me | Me | Me | 2,4-diBr-6-MeO—Ph |
| IV-858 | Me | Et | Me | 2,4-diBr-6-MeO—Ph |
| IV-859 | Me | Me | Me | 2-Br-3-Me-6-MeO—Ph |
| IV-860 | Me | Et | Me | 2-Br-3-Me-6-MeO—Ph |
| IV-861 | Me | Me | Me | 2-Br-4-Me-6-MeO—Ph |
| IV-862 | Me | Et | Me | 2-Br-4-Me-6-MeO—Ph |
| IV-863 | Me | Me | Me | 2-Br-3,6-diMeO—Ph |
| IV-864 | Me | Et | Me | 2-Br-3,6-diMeO—Ph |
| IV-865 | Me | Me | Me | 2-Br-4,6-diMeO—Ph |
| IV-866 | Me | Et | Me | 2-Br-4,6-diMeO—Ph |
| IV-867 | Me | Me | Me | 2-Me-3,6-diF—Ph |
| IV-868 | Me | Et | Me | 2-Me-3,6-diF—Ph |
| IV-869 | Me | Me | Me | 2-Me-3-Cl-6-F—Ph |
| IV-870 | Me | Et | Me | 2-Me-3-Cl-6-F—Ph |
| IV-871 | Me | Me | Me | 2-Me-3-Br-6-F—Ph |
| IV-872 | Me | Et | Me | 2-Me-3-Br-6-F—Ph |
| IV-873 | Me | Me | Me | 2,3-diMe-6-F—Ph |
| IV-874 | Me | Et | Me | 2,3-diMe-6-F—Ph |
| IV-875 | Me | Me | Me | 2,4-diMe-6-F—Ph |
| IV-876 | Me | Et | Me | 2,4-diMe-6-F—Ph |
| IV-877 | Me | Me | Me | 2-Me-3-MeO-6-F—Ph |
| IV-878 | Me | Et | Me | 2-Me-3-MeO-6-F—Ph |
| IV-879 | Me | Me | Me | 2-Me-4-MeO-6-F—Ph |
| IV-880 | Me | Et | Me | 2-Me-4-MeO-6-F—Ph |
| IV-881 | Me | Me | Me | 2-Me-3-F-6-Cl—Ph |
| IV-882 | Me | Et | Me | 2-Me-3-F-6-Cl—Ph |
| IV-883 | Me | Me | Me | 2-Me-3,6-diCl—Ph |
| IV-884 | Me | Et | Me | 2-Me-3,6-diCl—Ph |
| IV-885 | Me | Me | Me | 2-Me-3-Br-6-Cl—Ph |
| IV-886 | Me | Et | Me | 2-Me-3-Br-6-Cl—Ph |
| IV-887 | Me | Me | Me | 2,3-diMe-6-Cl—Ph |
| IV-888 | Me | Et | Me | 2,3-diMe-6-Cl—Ph |

TABLE 46-continued

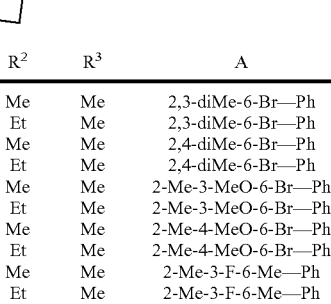

(IV)

| Comp. No. | R¹ | R² | R³ | A |
|---|---|---|---|---|
| IV-889 | Me | Me | Me | 2,4-diMe-6-Cl—Ph |
| IV-890 | Me | Et | Me | 2,4-diMe-6-Cl—Ph |
| IV-891 | Me | Me | Me | 2-Me-3-MeO-6-Cl—Ph |
| IV-892 | Me | Et | Me | 2-Me-3-MeO-6-Cl—Ph |
| IV-893 | Me | Me | Me | 2-Me-4-MeO-6-Cl—Ph |
| IV-894 | Me | Et | Me | 2-Me-4-MeO-6-Cl—Ph |
| IV-895 | Me | Me | Me | 2-Me-3-F-6-Br—Ph |
| IV-896 | Me | Et | Me | 2-Me-3-F-6-Br—Ph |
| IV-897 | Me | Me | Me | 2-Me-3-Cl-6-Br—Ph |
| IV-898 | Me | Et | Me | 2-Me-3-Cl-6-Br—Ph |
| IV-899 | Me | Me | Me | 2-Me-3,6-diBr—Ph |
| IV-900 | Me | Et | Me | 2-Me-3,6-diBr—Ph |

TABLE 47

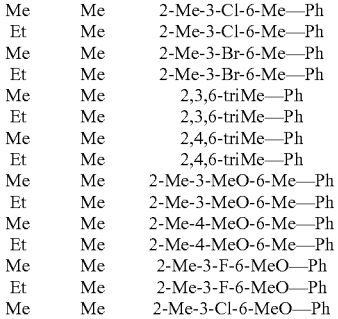

(IV)

| Comp. No. | R¹ | R² | R³ | A |
|---|---|---|---|---|
| IV-901 | Me | Me | Me | 2,3-diMe-6-Br—Ph |
| IV-902 | Me | Et | Me | 2,3-diMe-6-Br—Ph |
| IV-903 | Me | Me | Me | 2,4-diMe-6-Br—Ph |
| IV-904 | Me | Et | Me | 2,4-diMe-6-Br—Ph |
| IV-905 | Me | Me | Me | 2-Me-3-MeO-6-Br—Ph |
| IV-906 | Me | Et | Me | 2-Me-3-MeO-6-Br—Ph |
| IV-907 | Me | Me | Me | 2-Me-4-MeO-6-Br—Ph |
| IV-908 | Me | Et | Me | 2-Me-4-MeO-6-Br—Ph |
| IV-909 | Me | Me | Me | 2-Me-3-F-6-Me—Ph |
| IV-910 | Me | Et | Me | 2-Me-3-F-6-Me—Ph |
| IV-911 | Me | Me | Me | 2-Me-3-Cl-6-Me—Ph |
| IV-912 | Me | Et | Me | 2-Me-3-Cl-6-Me—Ph |
| IV-913 | Me | Me | Me | 2-Me-3-Br-6-Me—Ph |
| IV-914 | Me | Et | Me | 2-Me-3-Br-6-Me—Ph |
| IV-915 | Me | Me | Me | 2,3,6-triMe—Ph |
| IV-916 | Me | Et | Me | 2,3,6-triMe—Ph |
| IV-917 | Me | Me | Me | 2,4,6-triMe—Ph |
| IV-918 | Me | Et | Me | 2,4,6-triMe—Ph |
| IV-919 | Me | Me | Me | 2-Me-3-MeO-6-Me—Ph |
| IV-920 | Me | Et | Me | 2-Me-3-MeO-6-Me—Ph |
| IV-921 | Me | Me | Me | 2-Me-4-MeO-6-Me—Ph |
| IV-922 | Me | Et | Me | 2-Me-4-MeO-6-Me—Ph |
| IV-923 | Me | Me | Me | 2-Me-3-F-6-MeO—Ph |
| IV-924 | Me | Et | Me | 2-Me-3-F-6-MeO—Ph |
| IV-925 | Me | Me | Me | 2-Me-3-Cl-6-MeO—Ph |
| IV-926 | Me | Et | Me | 2-Me-3-Cl--6-MeO—Ph |
| IV-927 | Me | Me | Me | 2-Me-3-Br-6-MeO—Ph |
| IV-928 | Me | Et | Me | 2-Me-3-Br-6-MeO—Ph |
| IV-929 | Me | Me | Me | 2,3-diMe-6-MeO—Ph |
| IV-930 | Me | Et | Me | 2,3-diMe-6-MeO—Ph |

TABLE 47-continued (IV)

| Comp. No. | R¹ | R² | R³ | A |
|---|---|---|---|---|
| IV-931 | Me | Me | Me | 2,4-diMe-6-MeO—Ph |
| IV-932 | Me | Et | Me | 2,4-diMe-6-MeO—Ph |
| IV-933 | Me | Me | Me | 2-Me-3,6-diMeO—Ph |
| IV-934 | Me | Et | Me | 2-Me-3,6-diMeO—Ph |
| IV-935 | Me | Me | Me | 2-Me-4,6-diMeO—Ph |
| IV-936 | Me | Et | Me | 2-Me-4,6-diMeO—Ph |
| IV-937 | Me | Me | Me | 2-MeO-3,6-diF—Ph |
| IV-938 | Me | Et | Me | 2-MeO-3,6-diF—Ph |
| IV-939 | Me | Me | Me | 2-MeO-3-Cl-6-F—Ph |
| IV-940 | Me | Et | Me | 2-MeO-3-Cl-6-F—Ph |
| IV-941 | Me | Me | Me | 2-MeO-3-Br-6-F—Ph |
| IV-942 | Me | Et | Me | 2-MeO-3-Br-6-F—Ph |
| IV-943 | Me | Me | Me | 2-MeO-3-Me-6-F—Ph |
| IV-944 | Me | Et | Me | 2-MeO-3-Me-6-F—Ph |
| IV-945 | Me | Me | Me | 2,3-diMeO-6-F—Ph |
| IV-946 | Me | Et | Me | 2,3-diMeO-6-F—Ph |
| IV-947 | Me | Me | Me | 2,4-diMeO-6-F—Ph |
| IV-948 | Me | Et | Me | 2,4-diMeO-6-F—Ph |
| IV-949 | Me | Me | Me | 2-MeO-3-F-6-Cl—Ph |
| IV-950 | Me | Et | Me | 2-MeO-3-F-6-Cl—Ph |
| IV-951 | Me | Me | Me | 2-MeO-3,6-Cl—Ph |
| IV-952 | Me | Et | Me | 2-MeO-3,6-Cl—Ph |
| IV-953 | Me | Me | Me | 2-MeO-3-Br-6-Cl—Ph |
| IV-954 | Me | Et | Me | 2-MeO-3-Br-6-Cl—Ph |
| IV-955 | Me | Me | Me | 2-MeO-3-Me-6-Cl—Ph |
| IV-956 | Me | Et | Me | 2-MeO-3-Me-6-Cl—Ph |
| IV-957 | Me | Me | Me | 2,3-diMeO-6-Cl—Ph |
| IV-958 | Me | Et | Me | 2,3-diMeO-6-Cl—Ph |
| IV-959 | Me | Me | Me | 2,4-diMeO-6-Cl—Ph |
| IV-960 | Me | Et | Me | 2,4-diMeO-6-Cl—Ph |
| IV-961 | Me | Me | Me | 2-MeO-3-F-6-Br—Ph |
| IV-962 | Me | Et | Me | 2-MeO-3-F-6-Br—Ph |
| IV-963 | Me | Me | Me | 2-MeO-3-Cl-6-Br—Ph |
| IV-964 | Me | Et | Me | 2-MeO-3-Cl-6-Br—Ph |
| IV-965 | Me | Me | Me | 2-MeO-3,6-diBr—Ph |
| IV-966 | Me | Et | Me | 2-MeO-3,6-diBr—Ph |
| IV-967 | Me | Me | Me | 2-MeO-3-Me-6-Br—Ph |
| IV-968 | Me | Et | Me | 2-MeO-3-Me-6-Br—Ph |
| IV-969 | Me | Me | Me | 2,3-diMeO-6-Br—Ph |
| IV-970 | Me | Et | Me | 2,3-diMeO-6-Br—Ph |
| IV-971 | Me | Me | Me | 2,4-diMeO-6-Br—Ph |
| IV-972 | Me | Et | Me | 2,4-diMeO-6-Br—Ph |
| IV-973 | Me | Me | Me | 2-MeO-3-F-6-Me—Ph |
| IV-974 | Me | Et | Me | 2-MeO-3-F-6-Me—Ph |
| IV-975 | Me | Me | Me | 2-MeO-3-Cl-6-Me—Ph |
| IV-976 | Me | Et | Me | 2-MeO-3-Cl-6-Me—Ph |
| IV-977 | Me | Me | Me | 2-MeO-3-Br-6-Me—Ph |
| IV-978 | Me | Et | Me | 2-MeO-3-Br-6-Me—Ph |
| IV-979 | Me | Me | Me | 2-MeO-3,6-diMe—Ph |
| IV-980 | Me | Et | Me | 2-MeO-3,6-diMe—Ph |
| IV-981 | Me | Me | Me | 2,3-diMeO-6-Me—Ph |
| IV-982 | Me | Et | Me | 2,3-diMeO-6-Me—Ph |
| IV-983 | Me | Me | Me | 2,4-diMeO-6-Me—Ph |
| IV-984 | Me | Et | Me | 2,4-diMeO-6-Me—Ph |
| IV-985 | Me | Me | Me | 2,6-di-MeO-3-F—Ph |
| IV-986 | Me | Et | Me | 2,6-di-MeO-3-F—Ph |
| IV-987 | Me | Me | Me | 2,6-di-MeO-3-Cl—Ph |
| IV-988 | Me | Et | Me | 2,6-di-MeO-3-Cl—Ph |
| IV-989 | Me | Me | Me | 2,6-di-MeO-3-Br—Ph |
| IV-990 | Me | Et | Me | 2,6-di-MeO-3-Br—Ph |
| IV-991 | Me | Me | Me | 2,6-di-MeO-3-Me—Ph |
| IV-992 | Me | Et | Me | 2,6-di-MeO-3-Me—Ph |
| IV-993 | Me | Me | Me | 2,3,6-triMeO—Ph |
| IV-994 | Me | Et | Me | 2,3,6-triMeO—Ph |
| IV-995 | Me | Me | Me | 2,4,6-triMeO—Ph |
| IV-996 | Me | Et | Me | 2,4,6-triMeO—Ph |

TABLE 48

(IV)

| Comp. No. | R¹ | R² | R³ | A |
|---|---|---|---|---|
| IV-997 | Me | Me | Me | 6-F-2,3-dihydrobenzofuran-7-yl |
| IV-998 | Me | Et | Me | 6-F-2,3-dihydrobenzofuran-7-yl |
| IV-999 | Me | Me | Me | 6-Cl-2,3-dihydrobenzofuran-7-yl |
| IV-1000 | Me | Et | Me | 6-Cl-2,3-dihydrobenzofuran-7-yl |
| IV-1001 | Me | Me | Me | 6-Br-2,3-dihydrobenzofuran-7-yl |
| IV-1002 | Me | Et | Me | 6-Br-2,3-dihydrobenzofuran-7-yl |
| IV-1003 | Me | Me | Me | 6-Me-2,3-dihydrobenzofuran-7-yl |
| IV-1004 | Me | Et | Me | 6-Me-2,3-dihydrobenzofuran-7-yl |
| IV-1005 | Me | Me | Me | 6-MeO-2,3-dihydrobenzofuran-7-yl |
| IV-1006 | Me | Et | Me | 6-MeO-2,3-dihydrobenzofuran-7-yl |
| IV-1007 | Me | Me | Me | pyridin-2-yl |
| IV-1008 | Me | Et | Me | pyridin-2-yl |
| IV-1009 | Me | Me | Me | 3-F-pyridin-2-yl |
| IV-1010 | Me | Et | Me | 3-F-pyridin-2-yl |
| IV-1011 | Me | Me | Me | 3-Cl-pyridin-2-yl |
| IV-1012 | Me | Et | Me | 3-Cl-pyridin-2-yl |
| IV-1013 | Me | Me | Me | 3-Br-pyridin-2-yl |
| IV-1014 | Me | Et | Me | 3-Br-pyridin-2-yl |
| IV-1015 | Me | Me | Me | 3-Me-pyridin-2-yl |
| IV-1016 | Me | Et | Me | 3-Me-pyridin-2-yl |
| IV-1017 | Me | Me | Me | 3-MeO-pyridin-2-yl |
| IV-1018 | Me | Et | Me | 3-MeO-pyridin-2-yl |
| IV-1019 | Me | Me | Me | pyridin-3-yl |
| IV-1020 | Me | Et | Me | pyridin-3-yl |
| IV-1021 | Me | Me | Me | 2-F-pyridin-3-yl |
| IV-1022 | Me | Et | Me | 2-F-pyridin-3-yl |
| IV-1023 | Me | Me | Me | 2-Cl-pyridin-3-yl |
| IV-1024 | Me | Et | Me | 2-Cl-pyridin-3-yl |
| IV-1025 | Me | Me | Me | 2-Br-pyridin-3-yl |
| IV-1026 | Me | Et | Me | 2-Br-pyridin-3-yl |
| IV-1027 | Me | Me | Me | 2-MeO-pyridin-3-yl |
| IV-1028 | Me | Et | Me | 2-MeO-pyridin-3-yl |
| IV-1029 | Me | Me | Me | pyridin-4-yl |
| IV-1030 | Me | Et | Me | pyridin-4-yl |
| IV-1031 | Me | Me | Me | 3-F-isothiazol-4-yl |
| IV-1032 | Me | Et | Me | 3-F-isothiazol-4-yl |
| IV-1033 | Me | Me | Me | 3-Cl-isothiazol-4-yl |
| IV-1034 | Me | Et | Me | 3-Cl-isothiazol-4-yl |
| IV-1035 | Me | Me | Me | 3-Me-isothiazol-4-yl |

TABLE 48-continued (IV)

| Comp. No. | R¹ | R² | R³ | A |
|---|---|---|---|---|
| IV-1036 | Me | Et | Me | 3-Me-isothiazol-4-yl |
| IV-1037 | Me | Me | Me | 3-F-isoxazol-4-yl |
| IV-1038 | Me | Et | Me | 3-F-isoxazol-4-yl |
| IV-1039 | Me | Me | Me | 3-Cl-isoxazol-4-yl |
| IV-1040 | Me | Et | Me | 3-Cl-isoxazol-4-yl |
| IV-1041 | Me | Me | Me | 3-Me-isoxazol-4-yl |
| IV-1042 | Me | Et | Me | 3-Me-isoxazol-4-yl |
| IV-1043 | Me | Me | Me | thiophen-2-yl |
| IV-1044 | Me | Et | Me | thiophen-2-yl |
| IV-1045 | Me | Me | Me | thiophen-3-yl |
| IV-1046 | Me | Et | Me | thiophen-3-yl |

TABLE 49

(IV)

| Comp. No. | R¹ | R² | R³ | A |
|---|---|---|---|---|
| IV-1047 | Me | Me | Me | benzofuran-7-yl |
| IV-1048 | Me | Et | Me | benzofuran-7-yl |
| IV-1049 | Me | Me | Me | 6-F-benzofuran-7-yl |
| IV-1050 | Me | Et | Me | 6-F-benzofuran-7-yl |
| IV-1051 | Me | Me | Me | 6-Cl-benzofuran-7-yl |
| IV-1052 | Me | Et | Me | 6-Cl-benzofuran-7-yl |
| IV-1053 | Me | Me | Me | 6-Br-benzofuran-7-yl |
| IV-1054 | Me | Et | Me | 6-Br-benzofuran-7-yl |
| IV-1055 | Me | Me | Me | 6-Me-benzofuran-7-yl |
| IV-1056 | Me | Et | Me | 6-Me-benzofuran-7-yl |
| IV-1057 | Me | Me | Me | 6-MeO-benzofuran-7-yl |
| IV-1058 | Me | Et | Me | 6-MeO-benzofuran-7-yl |
| IV-1059 | Me | Me | Me | 2-Me-6-F-benzofuran-7-yl |
| IV-1060 | Me | Et | Me | 2-Me-6-F-benzofuran-7-yl |
| IV-1061 | Me | Me | Me | 3-Me-6-F-benzofuran-7-yl |
| IV-1062 | Me | Et | Me | 3-Me-6-F-benzofuran-7-yl |
| IV-1063 | Me | Me | Me | 2-Cl-6-F-benzofuran-7-yl |
| IV-1064 | Me | Et | Me | 2-Cl-6-F-benzofuran-7-yl |
| IV-1065 | Me | Me | Me | 3-Cl-6-F-benzofuran-7-yl |
| IV-1066 | Me | Et | Me | 3-Cl-6-F-benzofuran-7-yl |
| IV-1067 | Me | Me | Me | 2-Me-6-Cl-benzofuran-7-yl |
| IV-1068 | Me | Et | Me | 2-Me-6-Cl-benzofuran-7-yl |
| IV-1069 | Me | Me | Me | 3-Me-6-Cl-benzofuran-7-yl |
| IV-1070 | Me | Et | Me | 3-Me-6-Cl-benzofuran-7-yl |
| IV-1071 | Me | Me | Me | 2-Cl-6-Cl-benzofuran-7-yl |
| IV-1072 | Me | Et | Me | 2-Cl-6-Cl-benzofuran-7-yl |
| IV-1073 | Me | Me | Me | 3-Cl-6-Cl-benzofuran-7-yl |
| IV-1074 | Me | Et | Me | 3-Cl-6-Cl-benzofuran-7-yl |

Advantageous Effects of Invention

A substituted dihydropyrrolopyrazole compound represented by the general formula (Ia) or a pharmacologically acceptable salt thereof has excellent CDK7 inhibitory activity, high selectivity for a kinase inhibitory effect, excellent safety, and excellent pharmacokinetic properties. Thus, the compound represented by the general formula (Ia) or the pharmacologically acceptable salt thereof is useful as a medicament, particularly, a therapeutic drug and/or a prophylactic drug for a cancer, an inflammatory disease, an allergic disease or a chronic respiratory disease.

DESCRIPTION OF EMBODIMENTS

One embodiment of the present invention will be described below. In the present specification, each "compound represented by the general formula (Ia)", etc. is also referred to as "compound (Ia)", etc. for the sake of convenience. Various substituents defined or illustrated below can be arbitrarily selected and combined. In the present specification, the "substituted dihydropyrrolopyrazole compound" is also referred to as a "substituted dihydropyrrolopyrazole derivative".

On embodiment of the present invention is a compound represented by the general formula (Ia) or a pharmaceutically acceptable salt thereof.

[Chemical Formula 9]

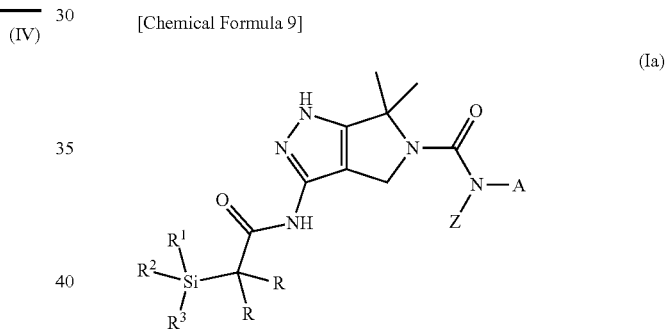

(Ia)

In the general formula (Ia), two R moieties each independently represent a $C_{1-3}$ alkyl group or represent groups bonded to each other to form a $C_{2-5}$ alkylene group;

A represents an optionally substituted $C_{6-10}$ aryl group or an optionally substituted heteroaryl group, and Z represents a hydrogen atom or an optionally substituted $C_{1-6}$ alkyl group, or a group represented by Z—N-A forms an optionally substituted bicyclic condensed heterocyclic group through the bonding between A and Z; and $R^1$, $R^2$ and $R^3$ each independently represent an optionally substituted linear or branched $C_{1-4}$ alkyl group.

In the present specification, the term "optionally substituted" means that the group may be unsubstituted or may be further substituted by a substituent.

The substituent means a monovalent group, and examples thereof include linear or branched $C_{1-6}$ alkyl groups, $C_{3-6}$ cycloalkyl groups, linear or branched $C_{2-6}$ alkenyl groups, $C_{3-6}$ cycloalkenyl groups, linear or branched $C_{2-6}$ alkynyl groups, $C_{1-6}$ alkoxy groups, halogen atoms, a hydroxy group, a cyano group, an oxo group (=O), an amino group, $C_{1-6}$ alkylamino groups, a nitro group, a carboxy group (—COOH), a carbamoyl group (—CONH$_2$), N-mono-$C_{1-6}$ alkylcarbamoyl groups, N,N-di-$C_{1-6}$ alkylcarbamoyl groups (two alkyl groups may be different), $C_{1-6}$ alkanoyloxy groups (—OCOR$^4$; R$^4$ is a $C_{1-3}$ alkyl group), $C_{6-10}$ aryl groups, and heterocyclic groups. The substituent may be further substituted by a halogen atom, a hydroxy group, an amino group, a cyano group, an oxo group (=O), a linear or branched $C_{1-6}$ alkyl group, a $C_{1-6}$ alkoxy group, a $C_{6-10}$ aryl group, a heterocyclic group, or the like. In the case where the substituent is an amino group or a carboxy group, the form may be a salt thereof.

In the case where the group concerned has two or more substituents, two substituents may be bonded to each other to form a cyclic structure. Examples of the case where two substituents are bonded to each other to form a cyclic structure include a cyclopropyl group, a methylenedioxy group, and an oxyethylene group. Specifically, in the case where a methylenedioxy group is bonded to a benzene ring, the substituent becomes a 1,3-benzodioxole group; in the case where an oxyethylene group is bonded to a benzene ring, the substituent becomes a 2,3-dihydrobenzofuranyl group.

The linear or branched $C_{1-6}$ alkyl group described in the present specification means a linear or branched alkyl group having 1 to 6 carbon atoms. Examples of the linear or branched $C_{1-6}$ alkyl group include $C_{1-6}$ alkyl groups such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-ethylpropyl group, a 1-methylbutyl group, a 2-methylbutyl group, a 1,2-dimethylpropyl group, a hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1,2-dimethylbutyl group, a 1,3-dimethylbutyl group, and a 2,3-dimethylbutyl group. The substituent is preferably a methyl group, an ethyl group, a propyl group, an isopropyl group, a butyl group, an isobutyl group, a sec-butyl group, or a tert-butyl group.

Examples of a $C_{1-6}$ alkyl group substituted by a halogen atom include a chloromethyl group, a bromomethyl group, an iodomethyl group, a difluoromethyl group, a dichloromethyl group, a dibromomethyl group, a diiodomethyl group, a trifluoromethyl group, a trichloromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a pentafluoroethyl group, a 2,2-dichloroethyl group, a 2,2,2-trichloroethyl group, a 1-fluoropropyl group, a 2-fluoropropyl group, a 3-fluoropropyl group, a 3,3,3-trifluoropropyl group, a perfluoropropyl group, a 1-fluoromethylethyl group, a 1-difluoromethylethyl group, a 1-trifluoromethylethyl group, a 1-fluoro-1-methylethyl group, a 4-fluorobutyl group, a perfluorobutyl group, a 5-fluoropentyl group, a perfluoropentyl group, a 6-fluorohexyl group, and a perfluorohexyl group.

A $C_{1-6}$ alkyl group substituted by an aryl group may be, for example, a $C_{7-11}$ aralkyl group. The $C_{7-11}$ aralkyl group means an alkyl group having an aryl group and having a total of 7 to 11 carbon atoms, and examples thereof include a benzyl group, a phenylethyl group, and a naphthylmethyl group.

The $C_{3-6}$ cycloalkyl group described in the present specification means a cyclic alkyl group having 3 to 6 carbon atoms. Examples of the $C_{3-6}$ cycloalkyl group include: monocyclic rings such as a cyclopropyl group, a cyclobutyl group, a cyclopentyl group, and a cyclohexyl group; condensed rings such as a bicyclo[3.1.0]hexyl group; and spiro rings such as a spiro[2.3]hexyl group. The substituent is preferably a cyclopropyl group or a cyclobutyl group.

The linear or branched $C_{2-6}$ alkenyl group described in the present specification means a linear or branched alkenyl group having 2 to 6 carbon atoms. Examples of the linear or branched $C_{2-6}$ alkenyl group include alkenyl groups such as a vinyl group, a propen-1-yl group, a propen-2-yl group, a 1-butenyl group, a 2-butenyl group, a 3-butenyl group, a 1-methyl-1-propenyl group, a 2-methyl-1-propenyl group, a 1-pentenyl group, a 2-pentenyl group, a 3-pentenyl group, a 4-pentenyl group, a 5-pentenyl group, a 1-methyl-1-butenyl group, a 2-methyl-1-butenyl group, a 3-methyl-1-butenyl group, a 4-methyl-1-butenyl group, a 1-methyl-2-butenyl group, a 2-methyl-2-butenyl group, a 3-methyl-2-butenyl group, a 4-methyl-2-butenyl group, a 1-methyl-3-butenyl group, a 2-methyl-3-butenyl group, a 3-methyl-3-butenyl group, a 4-methyl-3-butenyl group, a 1,2-dimethyl-1-propenyl group, a 1-hexenyl group, a 2-hexenyl group, a 3-hexenyl group, a 4-hexenyl group, a 5-hexenyl group, a 6-hexenyl group, and structural isomers thereof.

The $C_{3-6}$ cycloalkenyl group described in the present specification means a cycloalkenyl group having 3 to 6 carbon atoms. Examples of the $C_{3-6}$ cycloalkenyl group include a cyclopropenyl group, a cyclobutenyl group, a cyclopentenyl group, and a cyclohexenyl group.

The $C_{2-6}$ alkynyl group described in the present specification means an alkynyl group having 2 to 6 carbon atoms. Examples of the $C_{2-6}$ alkynyl group include an ethynyl group, a propargyl group, a butynyl group, a pentynyl group, and a hexynyl group.

The $C_{1-6}$ alkoxy group described in the present specification means a group consisting of an oxy group (—O—) and a linear or branched $C_{1-6}$ alkyl group or a $C_{3-6}$ cycloalkyl group bonded to the oxy group. Examples of the $C_{1-6}$ alkoxy group include a methoxy group, an ethoxy group, a propyloxy group, an isopropyloxy group, a cyclopropyloxy group, a butoxy group, a cyclobutyloxy group, a pentyloxy group, a cyclopentyloxy group, a hexyloxy group, and a cyclohexyloxy group.

The $C_{1-6}$ alkylamino group described in the present specification means an amino group substituted by one or two independently selected aforementioned linear or branched $C_{1-6}$ alkyl groups or $C_{3-6}$ cycloalkyl groups. Examples of the $C_{1-6}$ alkylamino group include a methylamino group, an ethylamino group, a propylamino group, an isopropylamino group, a cyclopropylamino group, a butylamino group, a cyclobutylamino group, a pentylamino group, a cyclopentylamino group, a hexylamino group, a cyclohexylamino group, a dimethylamino group, a diethylamino group, an ethyl(methyl)amino group, an isopropyl(methyl)amino group, and a cyclopropyl(methyl)amino group.

The halogen atom described in the present specification means a fluorine atom, a chlorine atom, a bromine atom, or an iodine atom.

The $C_{6-10}$ aryl group described in the present specification means an aryl group having 6 to 10 carbon atoms. Examples of the $C_{6-10}$ aryl group include a phenyl group and a naphthyl group.

The heterocyclic group described in the present specification means a cyclic group having at least one nitrogen atom, oxygen atom, or sulfur atom and may be an aromatic heterocyclic group or may be a nonaromatic heterocyclic group. Examples of the aromatic heterocyclic group include a pyridine group, a pyrimidine group, a pyridazine group, a pyrazine group, a triazine group, a pyrrole group, an imidazole group, a pyrazole group, an indole group, an indazole group, a furan group, a benzofuran group, a thiophene group, a benzothiophene group, a thiazole group, an isothiazole group, an oxazole group, an isoxazole group, and an oxadiazole group. Examples of the nonaromatic heterocyclic group include a pyrrolidinyl group, a piperidinyl group, a piperazinyl group, a morpholinyl group, and a thiomorpholinyl group.

The $C_{2-5}$ alkylene group formed by two R moieties bonded to each other means a divalent group obtained by further removing one hydrogen atom from a $C_{2-5}$ alkyl group which corresponds to one having 2 to 5 carbon atoms among the $C_{1-6}$ alkyl groups described above. Examples of the $C_{2-5}$ alkylene group include a 1,2-ethylene group, a 1,2-propylene group, a 1,3-propylene group, a 1,2-butylene group, a 1,3-butylene group, a 1,4-butylene group, a 2,3-butylene group, a 1,2-pentylene group, a 1,3-pentylene group, a 1,4-pentylene group, a 1,5-pentylene group, a 2,3-pentylene group, and a 2,4-pentylene group.

The linear or branched $C_{1-4}$ alkyl group as $R^1$, $R^2$ or $R^3$ is a linear or branched alkyl group having 1 to 4 carbon atoms and corresponds to one having 1 to 4 carbon atoms among the $C_{1-6}$ alkyl groups described above.

The $C_{1-3}$ alkyl group as $R^4$ is an alkyl group having 1 to 3 carbon atoms and corresponds to one having 1 to 3 carbon atoms among the $C_{1-6}$ alkyl groups described above. Examples of the $C_{1-3}$ alkyl group include a methyl group, an ethyl group, a propyl group, and an isopropyl group.

The heteroaryl group as A corresponds to an aromatic heterocyclic group among the heterocyclic groups described above.

The compound according to the present embodiment may be a compound represented by any chemical formula of the general formula (I), the general formula (IIa), the general formula (IIIa), or the general formula (IVa) or may be a compound represented by any chemical formula of the general formula (II), the general formula (III), or the general formula (IV).

[Chemical Formula 10]

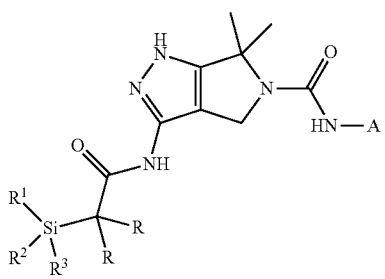

(I)

[Chemical Formula 11]

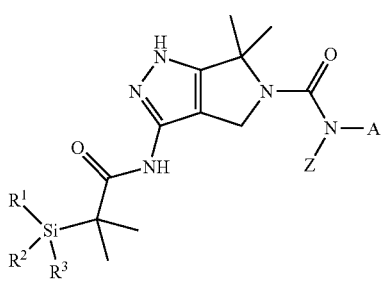

(IIa)

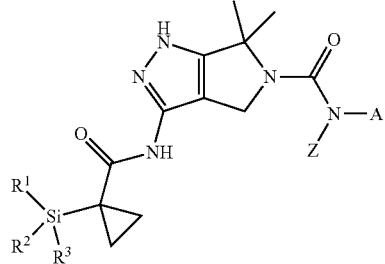

(IIIa)

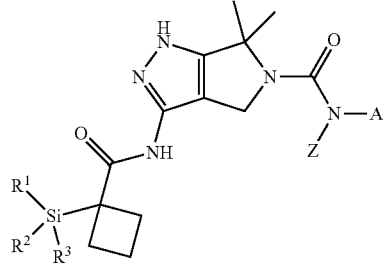

(IVa)

[Chemical Formula 12]

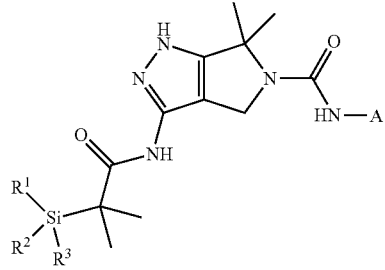

(II)

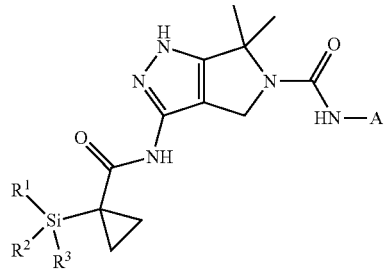

(III)

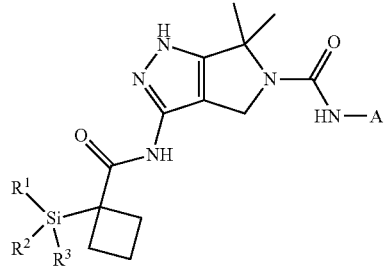

(IV)

In the general formula (I), the general formula (IIa), the general formula (IIIa), the general formula (IVa), the general formula (II), the general formula (III), and the general formula (IV), $R^1$, $R^2$, $R^3$, A, and Z are as defined in the general formula (Ia).

In the general formula (Ia) and the general formula (I), two R moieties may each independently be a $C_{1-3}$ alkyl group or may be groups bonded to each other to form a $C_{2-5}$ alkylene group.

In the general formula (I), the general formula (IIa), the general formula (IIIa), the general formula (IVa), the general formula (II), the general formula (III), and the general formula (IV), $R^1$, $R^2$ and $R^3$ may each independently be an optionally substituted linear or branched $C_{1-4}$ alkyl group.

In the general formula (I), the general formula (IIa), the general formula (IIIa), the general formula (IVa), the general formula (II), the general formula (III), and the general formula (IV), A may be an optionally substituted $C_{6-10}$ aryl group or an optionally substituted heteroaryl group.

Compound (Ia) is preferably a compound selected from the following compound group:

6,6-dimethyl-N-phenyl-3-[1-(trimethylsilyl)cyclobutanecarboxamido]-4,6-dihydropyrrolo[3,4-c]pyrazole-5(1H)-carboxamide (Compound No. IV-1)

6,6-dimethyl-N-(p-tolyl)-3-[1-(trimethylsilyl)cyclobutanecarboxamido]-4,6-dihydro pyrrolo[3,4-c]pyrazole-5 (1H)-carboxamide (Compound No. IV-25)

N-(4-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-79)

N-(4-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-7)

6,6-dimethyl-N-(pyridin-3-yl)-3-[1-(trimethylsilyl)cyclobutanecarboxamido]-4,6-di hydropyrrolo[3,4-c]pyrazole-5 (1H)-carboxamide (Compound No. IV-1019)

N-(2-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-3)

6,6-dimethyl-N-(o-tolyl)-3-[1-(trimethylsilyl)cyclobutanecarboxamido]-4,6-dihydro pyrrolo[3,4-c]pyrazole-5 (1H)-carboxamide (Compound No. IV-21)

6,6-dimethyl-N-(m-tolyl)-3-[1-(trimethylsilyl)cyclobutanecarboxamido]-4,6-dihydro pyrrolo[3,4-c]pyrazole-5 (1H)-carboxamide (Compound No. IV-23)

N-([1,1'-biphenyl]-3-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-71)

N-(3-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-5)

N-(3-chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-11)

N-(2-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-75)

N-(2-chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-9)

N-([1,1'-biphenyl]-2-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-69)

6,6-dimethyl-N-(pyridin-2-yl)-3-[1-(trimethylsilyl)cyclobutanecarboxamido]-4,6-di hydropyrrolo[3,4-c]pyrazole-5 (1H)-carboxamide (Compound No. IV-1007)

N-(2-ethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-27)

N-(2,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-381)

N-(2,3-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-99)

N-(2,3-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-375)

N-(2-fluoro-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-129)

N-[2-(difluoromethoxy)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-87)

N-(2-ethoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-81)

6,6-dimethyl-N-(2-(trifluoromethoxy)phenyl)-3-[1-(trimethylsilyl)cyclobutanecarboxamido]-4,6-dihydropyrrolo[3,4-c]pyrazole-5(1H)-carboxamide (Compound No. IV-93)

N-(2-fluoro-4-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-125)

N-(2,6-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-105)

N-[2-(tert-butyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-57)

6,6-dimethyl-N-(2-(trifluoromethyl)phenyl)-3-[1-(trimethylsilyl)cyclobutanecarboxamido]-4,6-dihydropyrrolo[3,4-c]pyrazole-5 (1H)-carboxamide (Compound No. IV-51)

N-(3-fluoro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-357)

N-(2-cyanophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-63)

N-(4-fluoro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-359)

N-(2-chloro-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-215)

N-(2-fluoro-3-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-123)

N-(2-fluoro-5-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-127)

N-(5-fluoro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-361)

N-(2,4-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-101)

N-(2,5-difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-103)

N-(2,5-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-379)

N-(2-chloro-6-fluorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-113)

N-(2,4-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-377)

3-[1-(ethyldimethylsilyl)cyclobutanecarboxamido]-N-(2-fluorophenyl)-6,6-dimethyl-4,6-dihydropyrrolo[3,4-c]pyrazole-5(1H)-carboxamide (Compound No. IV-4)

6,6-dimethyl-N-(3-methylisothiazol-4-yl)-3-[1-(trimethylsilyl)cyclobutanecarboxamido]-4,6-dihydropyrrolo[3,4-c]pyrazole-5(1H)-carboxamide (Compound No. IV-1035)

6,6-dimethyl-N-(thiophen-2-yl)-3-[1-(trimethylsilyl)cyclobutanecarboxamido]-2,6-dihydropyrrolo[3,4-c]pyrazole-5(1H)-carboxamide (Compound No. IV-1043)

6,6-dimethyl-N-(thiophen-3-yl)-3-[1-(trimethylsilyl)cyclobutanecarboxamido]-2,6-dihydropyrrolo[3,4-c]pyrazole-5(1H)-carboxamide (Compound No. IV-1045)

N-(2,6-difluoro-4-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-615)

N-(2-fluoro-6-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-161)

N-[2-fluoro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-153)

N-(5-chloro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-367)

N-(2,5-dichlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-197)

N-(2-cyclopropylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-39)

N-(2,6-dichlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-199)

6,6-dimethyl-N-(2,4,6-trifluorophenyl)-3-[1-(trimethylsilyl)cyclobutanecarboxamido]-4,6-dihydropyrrolo[3,4-c]pyrazole-5(1H)-carboxamide (Compound No. IV-599)

N-(2-ethyl-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-389)

N-(2-bromophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-15)

N-(2-chloro-5-fluorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-191)

N-(5-chloro-2-fluorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-111)

6,6-dimethyl-N-(2,3,6-trifluorophenyl)-3-[1-(trimethylsilyl)cyclobutanecarboxamido]-4,6-dihydropyrrolo[3,4-c]pyrazole-5(1H)-carboxamide (Compound No. IV-597)

N-(2-chloro-6-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-247)

N-[2-(1,1-difluoroethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-45)

N-(6-chloro-2-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-629)

N-[2-fluoro-6-(methoxy-d3)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-177)

N-[2-chloro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-239)

N-(2-fluoro-6-methoxy-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-689)

N-(2,6-difluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-609)

N-[2-(difluoromethoxy)-6-fluorophenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-169)

N-(2-bromo-6-chlorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-207)

N-(2-chloro-6-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-703)

N-(2-ethyl-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-137)

N-(2-bromo-6-fluorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-121)

N-(2-bromo-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-299)

N-(2-chloro-5-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-213)

N-(6-fluoro-2,3-dihydrobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-997)

N-(2-cyano-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-185)

N-(2-chloro-6-cyclopropylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-231)

N-(2-fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-669)

N-(6-fluorobenzofuran-7-yl)-6,6-dimethyl-3-[1-(trimethylsilyl)cyclobutanecarboxamido]-4,6-dihydropyrrolo[3,4-c]pyrazole-5 (1H)-carboxamide (Compound No. IV-1049)

N-(2-chloro-3-fluoro-6-methylphenyl)-6,6-dimethyl-3-[1-(trimethyl silyl)cyclobutanecarboxamido]-4,6-dihydropyrrolo[3,4-c]pyrazole-5(1H)-carboxamide (Compound No. IV-747)

N-[2-(difluoromethoxy)-6-fluorophenyl]-6,6-dimethyl-3-[1-(trimethylsilyl)cyclopropanecarboxamido]-4,6-dihydropyrrolo[3,4-c]pyrazole-5(1H)-carboxamide (Compound No. III-169)

N-(2,6-dichlorophenyl)-6,6-dimethyl-3-[1-(trimethylsilyl)cyclopropanecarboxamido]-4,6-dihydropyrrolo[3,4-c]pyrazole-5(1H)-carboxamide (Compound No. III-199)

N-(2,6-dichlorophenyl)-6,6-dimethyl-3-[2-methyl-2-(trimethylsilyl)propaneamido]-4,6-dihydropyrrolo[3,4-c]pyrazole-5(1H)-carboxamide (Compound No. II-199)

N-[2-(difluoromethoxy)-6-fluorophenyl]-6,6-dimethyl-3-[2-methyl-2-(trimethylsilyl)propaneamido]-4,6-dihydropyrrolo[3,4-c]pyrazole-5(1H)-carboxamide (Compound No. II-164)

N-(2,6-dichloro-4-fluorophenyl)-6,6-dimethyl-3-[1-(trimethyl silyl)cyclobutanecarboxamido]-4,6-dihydropyrrolo[3,4-c]pyrazole-5(1H)-carboxamide (Compound No. IV-709)

N-(2-ethyl-6-fluorophenyl)-6,6-dimethyl-3-[1-(trimethylsilyl)cyclopropanecarboxamido]-4,6-dihydropyrrolo[3,4-c]pyrazole-5 (1H)-carboxamide (Compound No. III-137)

N-(2-bromo-6-methylphenyl)-6,6-dimethyl-3-[1-(trimethylsilyl)cyclopropanecarboxamido]-4,6-dihydropyrrolo[3,4-c]pyrazole-5(1H)-carboxamide (Compound No. III-299)

N-(2-chloro-5-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-245)

N-(2-ethyl-6-fluorophenyl)-6,6-dimethyl-3-[2-methyl-2-(trimethyl silyl)propaneamido]-4,6-dihydropyrrolo[3,4-c]pyrazole-5(1H)-carboxamide (Compound No. II-137)

N-(2-bromo-6-methylphenyl)-6,6-dimethyl-3-[2-methyl-2-(trimethylsilyl)propaneamido]-4,6-dihydropyrrolo[3,4-c]pyrazole-5 (1H)-carboxamide (Compound No. II-290)

N-(6-fluorobenzofuran-7-yl)-6,6-dimethyl-3-[2-methyl-2-(trimethylsilyl)propaneamido]-4,6-dihydropyrrolo[3,4-c]pyrazole-5(1H)-carboxamide (Compound No. II-1049)

N-(6-fluorobenzofuran-7-yl)-6,6-dimethyl-3-[1-(trimethylsilyl)cyclopropanecarboxamido]-4,6-dihydropyrrolo[3,4-c]pyrazole-5 (1H)-carboxamide (Compound No. III-1049)

N,6,6-trimethyl-N-phenyl-3-[1-(trimethylsilyl)cyclobutanecarboxamido]-4,6-dihydropyrrolo[3,4-c]pyrazole-5 (1H)-carboxamide (Compound No. I-965)

N-(6-fluoro-3-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-1061)

N-(2-chloro-6-fluorobenzofuran-7-yl)-6,6-dimethyl-3-[1-(trimethylsilyl)cyclobutane carboxamido]-4,6-dihydropyrrolo[3,4-c]pyrazole-5(1H)-carboxamide (Compound No. IV-1063)

N-[5-(indoline-1-carbonyl)-6,6-dimethyl-1,4,5,6-tetrahydropyrrolo[3,4-c]pyrazol-3-yl]-1-(trimethyl silyl)cyclobutanecarboxamide (Compound No. I-1000)

N-[5-(3,4-dihydro-2H-benzo[b][1,4]oxazine-4-carbonyl)-6,6-dimethyl-1,4,5,6-tetrahydropyrrolo[3,4-c]pyrazol-3-yl]-1-(trimethylsilyl)cyclobutanecarboxamide (Compound No. I-1036)

N-(6-fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-1059)

N-[5-(1H-indole-1-carbonyl)-6,6-dimethyl-1,4,5,6-tetrahydropyrrolo[3,4-c]pyrazol-3-yl]-1-(trimethylsilyl)cyclobutanecarboxamide (Compound No. I-997)

The compound (Ia) or the pharmacologically acceptable salt thereof may be a single optical isomer or may be a mixture of a plurality of optical isomers.

In the case where geometric isomers or rotational isomers are present in the compound (Ia), these isomers are also encompassed in the present invention. In the case where tautomers are present in the compound according to the present embodiment, these tautomers are also encompassed in the present invention.

The "pharmacologically acceptable salt" according to the present embodiment is not particularly limited as long as being a salt acceptable as a drug, and examples thereof include: salts with inorganic acids such as hydrochloric acid, hydrobromic acid, hydroiodic acid, nitric acid, sulfuric acid, and phosphoric acid; salts with organic carboxylic acids such as acetic acid, fumaric acid, maleic acid, succinic acid, citric acid, tartaric acid, adipic acid, lactic acid, and trifluoroacetic acid; salts with organic sulfonic acids such as methanesulfonic acid, trifluoromethanesulfonic acid, benzenesulfonic acid, p-toluenesulfonic acid, and naphthalenesulfonic acid; salts with alkali metals such as lithium, sodium, and potassium; salts with alkaline earth metals such as calcium and magnesium; and quaternary ammonium salts such as ammonia, morpholine, glucosamine, ethylenediamine, guanidine, diethylamine, triethylamine, dicyclohexylamine, diethanolamine, and piperazine.

The compound (Ia) or the pharmacologically acceptable salt thereof can form a hydrate or a solvate, and each one or a mixture thereof is encompassed in the present invention.

The compound (Ia) may contain a non-natural ratio of an atomic isotope for one or more of the constituting atoms. Examples of the atomic isotope include deuterium ($^2$H), tritium ($^3$H), carbon-11 ($^{11}$C), carbon-14 ($^{14}$C), fluorine-18 ($^{18}$F), sulfur-35 ($^{35}$S), and iodine-125 ($^{125}$I). These compounds are useful as therapeutic or prophylactic agents, research reagents, for example, assay reagents, and diagnostic agents, for example, in vivo diagnostic imaging agents. All isotopic variants of the compound (Ia) are encompassed in the present invention, regardless of whether to be radioactive.

The compound (Ia) or the pharmacologically acceptable salt thereof can be used as a pharmaceutical composition, if necessary, by adding a pharmacologically acceptable carrier such as an excipient, a lubricant, a binder, a disintegrant, a coating agent, a stabilizer, a tonicity agent, a buffer, a pH adjuster, a solubilizer, a thickener, a preservative, an antioxidant, a sweetener, a colorant, and/or a flavor. The pharmaceutical composition can be appropriately prepared according to a purpose by a method well known to those skilled in the art.

In the pharmaceutical composition, the content of the compound (Ia) or the pharmacologically acceptable salt thereof can be appropriately adjusted.

The pharmaceutical composition can be in a dosage form described in General Rules for Preparations, Japanese Pharmacopoeia 16th edition, for example, a preparation for oral administration such as tablets, capsules, granules, or powders, or a preparation for parenteral administration such as injections (e.g., intravenous administration, subcutaneous administration, intramuscular administration, and intraperitoneal administration), eye drops, nasal drops, suppositories, ointments, lotions, creams, gels, sprays, patches, inhalants, or percutaneous absorption preparations.

Examples of the excipient include lactose, mannitol, starch, crystalline cellulose, light anhydrous silicic acid, calcium carbonate, and calcium hydrogen phosphate, and examples of the lubricant include stearic acid, magnesium stearate, and talc. Examples of the binder include starch, hydroxypropylcellulose, hydroxypropylmethylcellulose, and polyvinylpyrrolidone, and examples of the disintegrant include carboxymethylcellulose, low-substituted hydroxypropylmethylcellulose, and calcium citrate. Examples of the coating agent include hydroxypropylmethylcellulose, macrogol, and silicone resins, and examples of the stabilizer include ethyl p-hydroxybenzoate and benzyl alcohol.

Examples of the tonicity agent include glycerin, propylene glycol, sodium chloride, potassium chloride, sorbitol, and mannitol, examples of the buffer include boric acid, boric acid salts, phosphoric acid, phosphoric acid salts, citric acid, citric acid salts, acetic acid, acetic acid salts, ε-aminocaproic acid, and trometamol, and examples of the pH adjuster include hydrochloric acid, citric acid, phosphoric acid, glacial acetic acid, sodium hydroxide, potassium hydroxide, sodium carbonate, and sodium bicarbonate. Examples of the solubilizer include polysorbate 80, polyoxyethylene hydrogenated castor oil 60, macrogol 4000, purified soybean lecithin, and polyoxyethylene (160) polyoxypropylene (30) glycol, and examples of the thickener include cellulose polymers such as hydroxypropylmethylcellulose and hydroxypropylcellulose, polyvinyl alcohol, and polyvinylpyrrolidone. Examples of the stabilizer include edetic acid and sodium edetate, and examples of the preservative include sorbic acid, potassium sorbate, benzalkonium chloride, benzethonium chloride, methyl p-hydroxybenzoate, propyl p-hydroxybenzoate, and chlorobutanol.

Examples of ingredients that may be contained in pharmaceutical compositions for percutaneous administration such as ointments, lotions, creams, gels, and sprays include: absorption promoters such as lauryl alcohol, myristyl alcohol, salicylic acid ethylene glycol, and pyrrothiodecane; fatty acid esters such as diisopropyl adipate, isopropyl myristate, cetyl lactate, myristyl lactate, isopropyl palmitate, diethyl sebacate, hexyl laurate, and cetyl isooctanoate; aliphatic alcohols such as cetyl alcohol, stearyl alcohol, oleyl alcohol, hexadecyl alcohol, and behenyl alcohol; glycols such as propylene glycol, propylenediol, polyethylene glycol, and dipropylene glycol; and surfactants such as sorbitan fatty acid ester, glycerin fatty acid ester, polyoxyethylene sorbitan fatty acid ester, polyoxyethylene glycerin fatty acid ester, polyethylene glycol fatty acid ester, polyoxyethylene alkyl ether, polyoxyethylene castor oil, and polyoxyethylene hydrogenated castor oil.

The dose of the compound (Ia) or the pharmacologically acceptable salt thereof can be appropriately varied according to symptoms, age, a dosage form, etc. In the case of, for example, oral administration, it can usually be administered in one portion or several divided portions of 0.01 to 2000 mg, preferably 1 to 500 mg per day.

As for ointments, lotions, creams, or gels, one having a concentration of 0.0001% (w/v) to 10% (w/v), preferably 0.01% (w/v) to 5% (w/v) can usually be administered in one portion or several divided portions.

Next, a method for producing the compound (Ia) or the pharmaceutically acceptable salt thereof will be described. The compound or the pharmacologically acceptable salt thereof according to the present invention is not limited to compounds or pharmacologically acceptable salts thereof produced by production methods described below.

In the production methods given below, in the case where partial structures that inhibit the desired reactions or produce side reactions (e.g., a hydroxy group, an amino group, a carbonyl group, a carboxyl group, an amide group, a thiol group and the like) are present in compounds, the compounds of interest can be obtained by introducing protective groups to these partial structures, performing the desired reactions, and then removing the protective groups.

The introduction reaction and removal reaction of a protective group can be carried out according to a method routinely used in organic synthetic chemistry (e.g., a method described in, for example, Protective Groups in Organic Synthesis, 4th ed., T. W. Greene, P. GM. Wuts, John Wiley & Sons Inc. (2006)).

Hereinafter, a method for producing the compound (Ia) or the compound (I) by using compound (1) as a starting material will be described as a method for producing the compound (Ia) or the compound (I). A method for producing the compound (1) will be described later.

<Production Method for Compound (Ia)>

This method is a method for producing the compound (Ia) through the reaction of compound (2) obtained by reacting compound (1) with an acylating agent, with amine compound (3a). In this method, R, $R^1$, $R^2$, $R^3$, A, and Z are as defined in the general formula (Ia). $P^1$ group is a protective group for the amino group, and X is a leaving group. Although this method is described by showing the chemical structure of the compound (1) in which the 4,6-dihydropyrrolo[3,4-c]pyrazole skeleton is substituted at position 1 by the $P^1$ group for the sake of convenience, the compound (1) may be a compound having a chemical structure corresponding to a tautomer in which the 4,6-dihydropyrrolo[3,4-c]pyrazole skeleton is substituted at position 2 by the $P^1$ group.

[Chemical Formula 13]

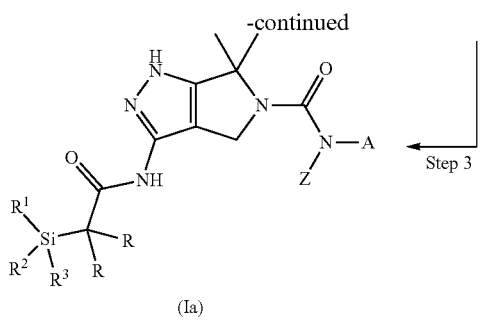

(Ia)

The P¹ group is not particularly limited as long as being a substituent known as a protective group for the amino group to those skilled in the art. Examples of the P¹ group include: optionally substituted $C_{7-11}$ aralkyl groups such as a benzyl group, a p-methoxyphenylmethyl group, and a o-nitrophenylmethyl group; optionally substituted $C_{1-6}$ alkylcarbonyl groups such as an acetyl group and a trifluoroacetyl group; optionally substituted $C_{6-10}$ arylcarbonyl groups such as a benzoyl group; optionally substituted $C_{1-6}$ alkoxycarbonyl groups such as a methoxycarbonyl group, an ethoxycarbonyl group, a Boc group (tert-butoxycarbonyl group), a Cbz group (benzyloxycarbonyl group), a Fmoc group (fluorenylmethyloxycarbonyl group), and a Teoc group (trimethylsilylethyloxycarbonyl group); alkenyloxycarbonyl groups such as an Alloc group (allyloxycarbonyl group); alkylsulfonyl groups such as a methanesulfonyl group; and optionally substituted $C_{6-10}$ arylsulfonyl groups such as a p-toluenesulfonyl group.

The X group is not particularly limited as long as being a substituent known as a leaving group to those skilled in the art. Examples of X include: halogen atoms such as a fluorine atom, a chlorine atom, a bromine atom, and an iodine atom; an imidazolyl group; aminooxy groups such as a succinyl-N-oxy group and a benzotriazolyl-N-oxy group; optionally substituted $C_{1-6}$ alkylcarbonyloxy groups such as a pivaloyloxy group; and optionally substituted $C_{6-10}$ aryl carbonyloxy groups such as a benzoyloxy group. Alternatively, X may be a hydroxy group.

(Step 1)

Step 1 is the step of reacting compound (1) with an acylating agent to obtain compound (2).

As the acylating agent, for example, phosgene, diphosgene, triphosgene, carbonyldiimidazole (CDI), N,N'-disuccinimidyl carbonate, or carbonic acid ester can be used.

The amount of the acylating agent used is preferably 0.4 to 3.0 mol, more preferably 0.7 to 1.5 mol, with respect to 1 mol of the compound (1).

The reaction of step 1 may be performed in a solvent or may be performed without a solvent. The solvent is not limited as long as the solvent does not have influence on the reaction, and an organic solvent is preferred. Examples of the organic solvent include dichloromethane, 1,2-dichloroethane, diethyl ether, 1,2-dimethoxyethane, tetrahydrofuran (THF), N,N-dimethylformamide (DMF), and dimethyl sulfoxide (DMSO).

In step 1, a base can be further added in order to accelerate the reaction. Examples of the base include organic amines such as triethylamine (TEA), diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 10 mol, more preferably 3 to 6 mol, with respect to 1 mol of the compound (1).

The reaction temperature of step 1 can be appropriately set by those skilled in the art. The reaction temperature is usually −100 to 0° C., preferably −80 to −60° C.

(Step 2)

Step 2 is the step of reacting compound (2) with the amine compound (3a) to obtain compound (4a).

The amount of the compound (3a) used is preferably 1 to 20 mol, more preferably 2 to 5 mol, with respect to 1 mol of the compound (2). The compound (3a) and the compound (2) may be dissolved in an organic solvent and added to the reaction solution.

The reaction of step 2 may be performed in a solvent or may be performed without a solvent. The solvent is not limited as long as the solvent does not have influence on the reaction, and an organic solvent is preferred. Examples of the organic solvent include dichloromethane, 1,2-dichloroethane, 1,2-dimethoxyethane, tetrahydrofuran (THF), 1,4-dioxane, N,N-dimethylformamide (DMF), and dimethyl sulfoxide (DMSO).

In step 2, a base can be further added in order to accelerate the reaction. Examples of the base include: organic amines such as triethylamine (TEA), diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP); and inorganic bases such as potassium carbonate and sodium carbonate.

The amount of the base added is preferably 1 to 20 mol, more preferably 2 to 5 mol, with respect to 1 mol of the compound (1).

The reaction temperature of step 2 can be appropriately set by those skilled in the art. The reaction temperature is usually 0 to 160° C., preferably 25 to 120° C.

(Step 3)

Step 3 is the step of removing the P¹ group of compound (4a) to produce compound (Ia).

The reaction conditions of step 3 can be appropriately selected by those skilled in the art according to the type of the P¹ group used. In the case where the P¹ group is, for example, an optionally substituted $C_{7-11}$ aralkyl group, the P¹ group may be removed by hydrogenolysis or may be removed by using protonic acid or Lewis acid. In the case where the P¹ group is an optionally substituted $C_{1-6}$ alkylcarbonyl group, an optionally substituted $C_{6-10}$ arylcarbonyl group or an optionally substituted $C_{6-10}$ arylsulfonyl group, the P¹ group may be removed by using protonic acid or Lewis acid. In the case where the P¹ group is a Boc group, it can be performed by treatment with protonic acid or Lewis acid; in the case where the P¹ group is a Cbz group, it can be performed by hydrogenolysis or treatment with a base; and in the case where the P¹ group is a Teoc group, a reagent that forms a fluoride ion such as tetrabutylammonium fluoride can be used. In the case where the P¹ group is an optionally substituted $C_{1-6}$ alkoxycarbonyl group such as a methoxycarbonyl group or an ethoxycarbonyl group, the P¹ group may be removed by heating in the presence of an organic amine such as triethylamine (TEA), diisopropylethylamine (DIPEA), 2-aminoethanol, or N,N-dimethylethane-1,2-diamine, or an inorganic base such as potassium carbonate or sodium carbonate.

The compound (Ia) obtained by step 3 can be converted to a pharmacologically acceptable salt thereof by a method well known to those skilled in the art.

<Production Method for Compound (4) 1>

This method is a method for reacting compound (1) with isocyanate compound (5) to obtain compound (4), and then producing compound (I) according to step 3 described above. The compound (4) corresponds to the general formula (4a) wherein the Z group is a hydrogen atom. Step 3 is as mentioned above. This method is a suitable method in the case of using isocyanate compound (5). In this method, R, $R^1$, $R^2$, $R^3$, $P^1$ and A are as defined in the aforementioned method for producing the compound (Ia).

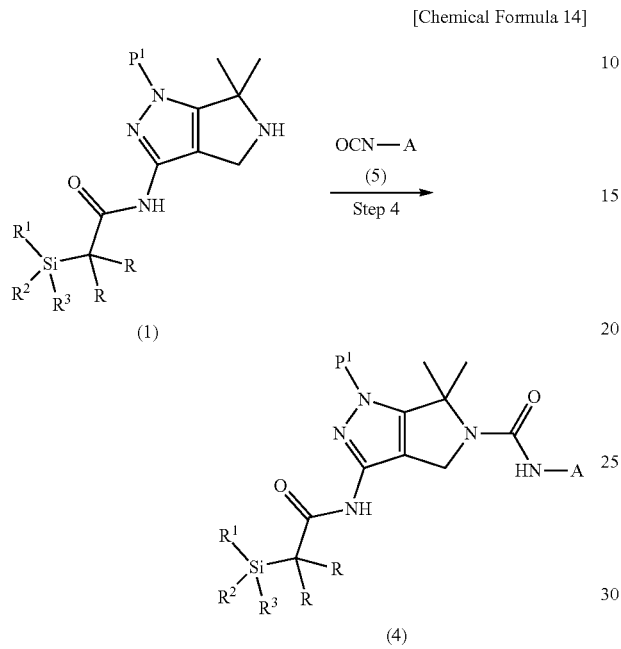

(Step 4)

Step 4 is the step of reacting compound (1) with isocyanate compound (5) to obtain compound (4).

The amount of the compound (5) used is preferably 1 to 10 mol, more preferably 1 to 3 mol, with respect to 1 mol of the compound (1). The compound (5) may be dissolved in an organic solvent and added to the reaction solution.

The reaction of step 4 may be performed in a solvent or may be performed without a solvent. The solvent is not limited as long as the solvent does not have influence on the reaction, and an organic solvent is preferred. Examples of the organic solvent include dichloromethane, 1,2-dichloroethane, 1,2-dimethoxyethane, tetrahydrofuran (THF), 1,4-dioxane, N,N-dimethylformamide (DMF), and dimethyl sulfoxide (DMSO).

The reaction temperature of step 4 can be appropriately set by those skilled in the art. The reaction temperature is usually −20 to 100° C., preferably 0 to 30° C.

<Production Method for Compound (4) 2>

This method is a method for obtaining compound (4) through the reaction of isocyanate compound (6) obtained by conversion from carboxylic acid compound (5) with compound (1), and then producing compound (I) according to step 3 described above. In this method, step 5 and step 6 may be continuously carried out without isolating the compound (6). In this method, R, $R^1$, $R^2$, $R^3$, $P^1$ and A are as defined in the aforementioned method for producing the compound (Ia).

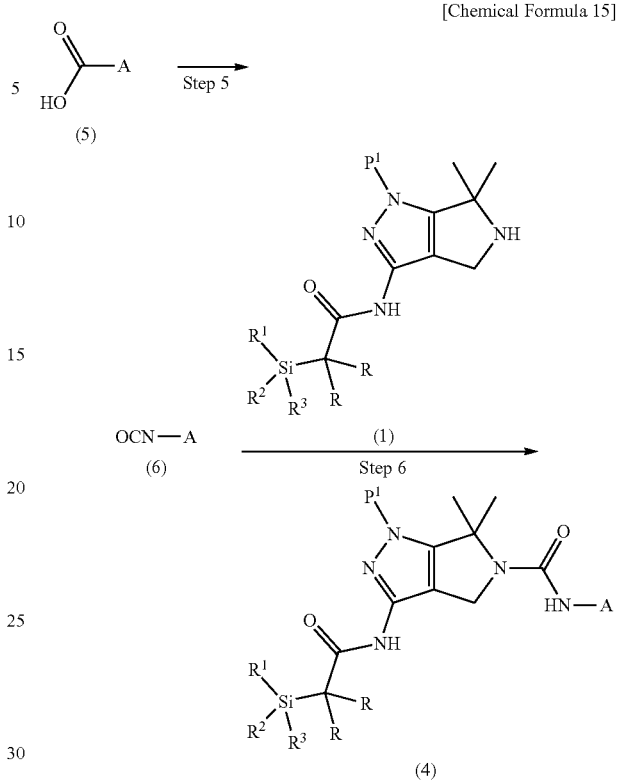

(Step 5)

Step 5 is the step of reacting compound (5) with diphenylphosphorylazide and a base according to a method described in, for example, Journal of the American Chemical Society, 94 (1972), p. 6203-6205 (Curtius rearrangement) to obtain isocyanate compound (6).

The reaction of step 5 may be performed in a solvent or may be performed without a solvent. The solvent is not limited as long as the solvent does not have influence on the reaction, and examples thereof include: aromatic hydrocarbons such as toluene and xylene; and amides such as N,N-dimethylformamide (DMF), N,N-dimethylacetamide, and 1-methyl-2-pyrrolidone. Toluene is preferred.

Examples of the base include organic amines such as triethylamine (TEA) and diisopropylethylamine (DIPEA).

<Production Method for Compound (4) 3>

This method is a method for obtaining compound (4) through the reaction of isocyanate compound (6) obtained by conversion from amide compound (7) with compound (1), and then producing compound (I) according to step 3 described above. In this method, step 7 and step 8 may be continuously carried out without isolating the compound (6). This method is a suitable method in the case of using amide compound (7). In this method, R, $R^1$, $R^2$, $R^3$, $P^1$ and A are as defined in the aforementioned method for producing the compound (Ia).

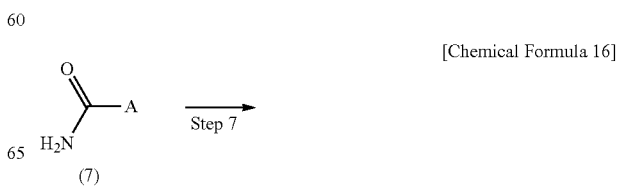

[Chemical Formula 17]

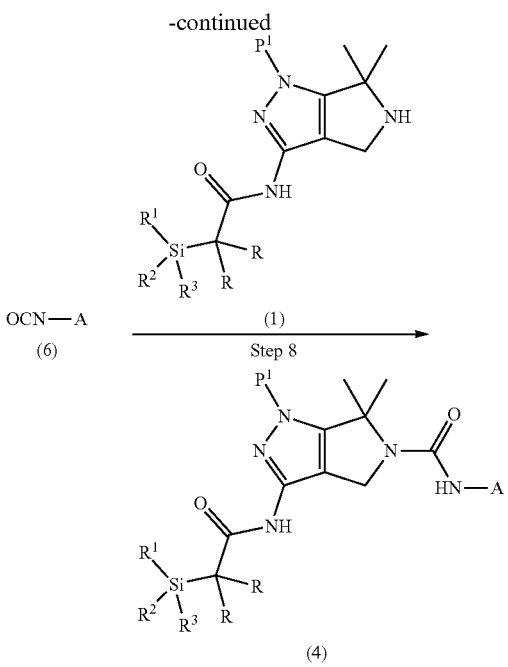

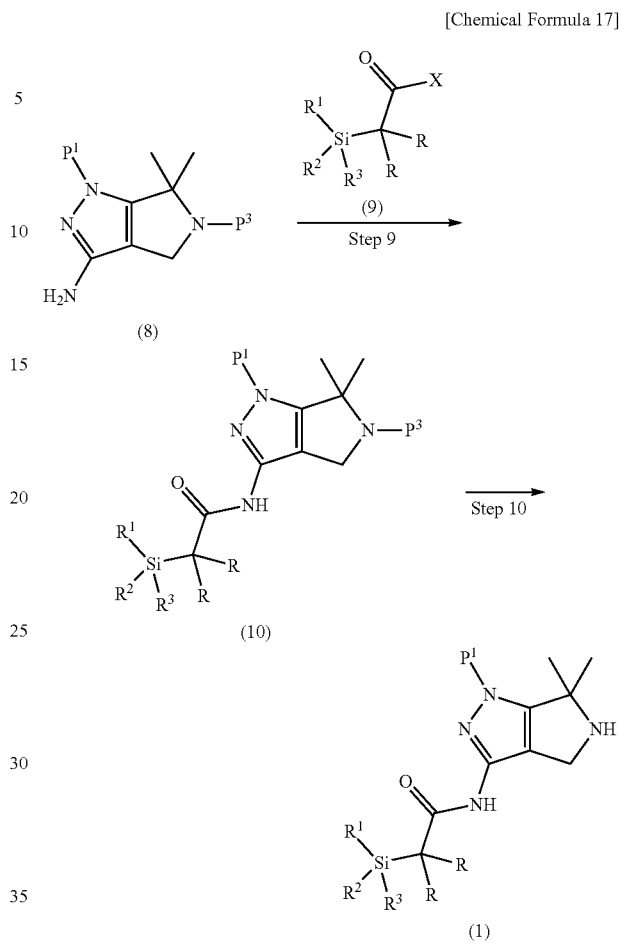

(Step 7)

Step 7 is the step of reacting compound (7) with an oxidizing agent according to a method described in, for example, Organic Synthesis, 66 (1988), p. 132-137 (Hofmann rearrangement) to obtain isocyanate compound (6).

The reaction of step 7 may be performed in a solvent or may be performed without a solvent. The solvent is not limited as long as the solvent does not have influence on the reaction, and examples thereof include: aromatic hydrocarbons such as toluene and xylene; amides such as N,N-dimethylformamide (DMF), N,N-dimethylacetamide, and 1-methyl-2-pyrrolidone; halogenated aliphatic hydrocarbons such as dichloromethane and 1,2-dichloroethane; halogenated aromatic hydrocarbons such as chlorobenzene and 1,2-dichlorobenzene; and nitriles such as acetonitrile and propionitrile. Toluene is preferred.

In step 7, a base may be added for the reaction. Examples of the base include: organic amines such as triethylamine (TEA) and diisopropylethylamine (DIPEA); and pyridines such as pyridine, 2,6-lutidine, and 4-picoline. Pyridine is preferred.

Examples of the oxidizing agent include high-valent iodine compounds such as [bis(acetoxy)iodo]benzene, [bis(trifluoroacetoxy)iodo]benzene, and iodosylbenzene, and [bis(trifluoroacetoxy)iodo]benzene is preferred.

In production methods 1 to 3 for the compound (4) described above, the compound (4) may be converted to compound (4a) (wherein the Z group is not a hydrogen atom) by reaction well known to those skilled in the art, and the compound (I) may be converted to compound (Ia) (wherein the Z group is not a hydrogen atom). For example, in step 4, 6 or 8, the mixture after reaction may be reacted with an alkylating agent Z—X (wherein Z is as defined in the general formula (Ia), and X is a leaving group).

<Production Method for Compound (1)>

The compound (1) can be produced, for example, by the method given below from compound (8) as a starting material. The compound (8) can be produced, for example, with reference to WO2007/72153 or through the following steps 11 to 15.

The compound (8) is 3-amino-6,6-dimethyl-4,6-dihydropyrrolo[3,4-c]pyrazole in which the nitrogen atom on the pyrazole skeleton may be substituted by $P^1$ group, and the nitrogen atom at position 5 may be substituted by $P^3$ group. The $P^1$ group can substitute an acidic proton of pyrazole in the 4,6-dihydropyrrolo[3,4-c]pyrazole skeleton. Thus, the $P^1$ group may be added to position 1 of the 4,6-dihydropyrrolo[3,4-c]pyrazole skeleton or may be added to position 2. Compound (8) and compound (10) will be described by using a chemical formula wherein it is added to position 1 of the 4,6-dihydropyrrolo[3,4-c]pyrazole skeleton, for the sake of convenience.

In the compound (8), $P^1$ has the same meaning as defined in the production method for compound (Ia). The $P^3$ group is not particularly limited as long as being a substituent known as a protective group for the amino group to those skilled in the art. Examples of the $P^3$ group include: optionally substituted $C_{7-11}$ aralkyl groups such as a benzyl group, a p-methoxyphenylmethyl group, and a o-nitrophenylmethyl group; optionally substituted $C_{1-6}$ alkylcarbonyl groups such as an acetyl group and a trifluoroacetyl group; optionally substituted $C_{6-10}$ arylcarbonyl groups such as a benzoyl group; optionally substituted $C_{1-6}$ alkoxycarbonyl groups such as a methoxycarbonyl group, an ethoxycarbonyl group, a Boc group (tert-butoxycarbonyl group), a Cbz group (benzyloxycarbonyl group), a Fmoc group (fluorenylmethyloxycarbonyl group), and a Teoc group (trimethylsilylethyloxycarbonyl group); alkenyloxycarbonyl groups such as an Alloc group (allyloxycarbonyl group); alkylsulfonyl groups such as a methanesulfonyl group; and optionally substituted $C_{6-10}$ arylsulfonyl groups such as a p-toluenesulfonyl group.

In the formulas (9) and (10), R, $R^1$, $R^2$, and $R^3$ have the same meanings as defined in compound (Ia). The group X is not particularly limited as long as being a substituent known as a leaving group to those skilled in the art. Examples of X include: halogen atoms; an imidazolyl group; aminooxy groups such as a succinyl-N-oxy group and a benzotriazolyl-N-oxy group; and acyloxy groups such as a pivaloyloxy group and a benzoyloxy group. Alternatively, X may be a hydroxy group.

In the case where the compound (9) is a carboxylic acid (i.e., X is a hydroxy group), it may be converted to an acid The reaction temperature of step 9 can be appropriately set by those skilled in the art. The reaction temperature is usually −40 to 100° C., preferably −20 to 20° C.

(Step 10)

Step 10 is the step of performing the deprotection reaction of compound (10) to obtain compound (1). The removal reaction of the $P^3$ group can also be performed by a method well known to those skilled in the art (e.g., a method described in, for example, Protective Groups in Organic Synthesis, 4th ed., T. W. Greene, P. GM. Wuts, John Wiley & Sons Inc. (2006)).

<Production Method for Compound (8)>

The compound (8) can be produced, for example, by the method given below from compound (11) as a starting material. In the general formulas (13), (14) and (15), $P^3$ is as defined in the compound (8).

[Chemical Formula 18]

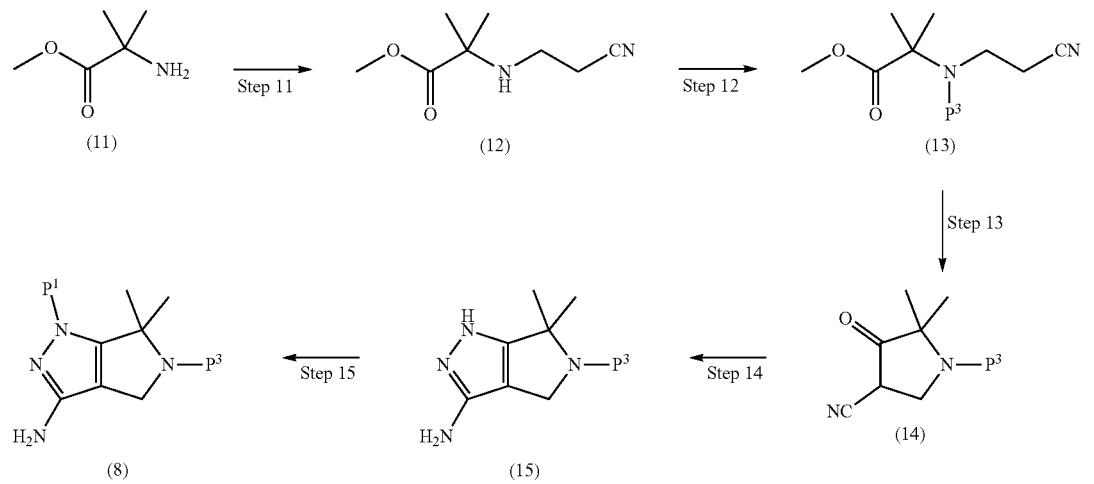

anhydride by a method well known to those skilled in the art and then reacted with the compound (8), or may be reacted with the compound (8) by using a reagent known as a condensing agent used in amide bond formation reaction to those skilled in the art.

(Step 9)

Step 9 is the step of reacting compound (8) with compound (9) to obtain compound (10).

The amount of the compound (9) used is preferably 1 to 10 mol, more preferably 1 to 3 mol, with respect to 1 mol of the compound (8).

The reaction of step 9 may be performed in a solvent or may be performed without a solvent. The solvent is not limited as long as the solvent does not have influence on the reaction, and an organic solvent is preferred. Examples of the organic solvent include dichloromethane, diethyl ether, tetrahydrofuran (THF), N,N-dimethylformamide (DMF), and dimethyl sulfoxide (DMSO).

In step 9, a base can be further added in order to accelerate the reaction. Examples of the base include organic amines such as triethylamine, diisopropylethylamine (DIPEA), 1,5-diazabicyclo[4.3.0]nonene (DBN), 1,8-diazabicyclo[5.4.0]undecene (DBU), pyridine, and 4-dimethylaminopyridine (DMAP).

The amount of the base added is preferably 1 to 20 mol, more preferably 1 to 5 mol, with respect to 1 mol of the compound (8).

(Step 11)

Step 11 is the step of reacting compound (11) with acrylonitrile to obtain compound (12).

The amount of the acrylonitrile used is preferably 1 to 10 mol, more preferably 1 to 3 mol, with respect to 1 mol of the compound (11).

The reaction of step 11 may be performed in a solvent or may be performed without a solvent. The solvent is not limited as long as the solvent does not have influence on the reaction, and a water solvent is preferred.

In step 11, a base can be further added in order to accelerate the reaction. Examples of the base include inorganic bases such as potassium hydroxide. The amount of the base added is preferably 0.8 to 2 mol, with respect to 1 mol of the compound (11).

The reaction temperature of step 11 can be appropriately set by those skilled in the art. The reaction temperature is usually 0 to 100° C., preferably 50 to 90° C.

(Step 12)

Step 12 is the step of protecting the amino group of compound (12) with $P^3$ group to obtain compound (13). The protection reaction of the amino group with the $P^3$ group can be performed according to a method well known to those skilled in the art, for example, a method described in Protective Groups in Organic Synthesis, 4th ed., T. W. Greene, P. GM. Wuts, John Wiley & Sons Inc. (2006).

(Step 13)

Step 13 is the step of performing the cyclization reaction of compound (13) to obtain compound (14).

The reaction of step 13 may be performed in a solvent or may be performed without a solvent. The solvent is not limited as long as the solvent does not have influence on the reaction, and an organic solvent is preferred. Examples of the organic solvent include diethyl ether, tetrahydrofuran (THF), 1,4-dioxane, N,N-dimethylformamide (DMF) toluene.

In step 13, a base can be further added in order to accelerate the reaction. Examples of the base include sodium hydride, potassium hydride, sodium methoxide, sodium ethoxide, n-butyllithium, and tert-butoxy potassium. The amount of the base added is preferably 1 to 3 mol with respect to 1 mol of the compound (13).

The reaction temperature of step 13 can be appropriately set by those skilled in the art. The reaction temperature is usually 20 to 150° C., preferably 50 to 100° C.

(Step 14)

Step 14 is the step of reacting compound (14) with hydrazine to obtain compound (15).

The reaction of step 14 may be performed in a solvent or may be performed without a solvent. The solvent is not limited as long as the solvent does not have influence on the reaction, and an organic solvent is preferred. Examples of the organic solvent include ethanol, n-propanol, and n-butanol.

In step 14, an acid can be further added in order to accelerate the reaction. Examples of the acid include acetic acid, hydrochloric acid, and sulfuric acid. The amount of the acid added is preferably 1 to 10 mol with respect to 1 mol of the compound (14).

The reaction temperature of step 14 can be appropriately set by those skilled in the art. The reaction temperature is usually 20 to 150° C., preferably 50 to 120° C.

(Step 15)

Step 15 is the step of protecting the amino group of compound (15) with $P^1$ group to obtain compound (8). The protection reaction of the amino group with the $P^1$ group can be performed according to a method well known to those skilled in the art, for example, a method described in Protective Groups in Organic Synthesis, 4th ed., T. W. Greene, P. GM. Wuts, John Wiley & Sons Inc. (2006).

An alternative embodiment of the present invention is a method for treating or preventing a cancer, an inflammatory disease, an allergic disease or a chronic respiratory disease, comprising administering the compound represented by the general formula (Ia) or the pharmacologically acceptable salt thereof to a subject in need thereof. In this context, the subject in need of the compound represented by the general formula (Ia) or the pharmacologically acceptable salt thereof is, for example, a patient having a cancer, an inflammatory disease, an allergic disease or a chronic respiratory disease.

Examples of the cancer include: blood cancers such as multiple myeloma, chronic myeloid leukemia, blood tumor, hematological malignancy, childhood leukemia, childhood lymphoma, Hodgkin's disease, lymphocytic lymphoma, cutaneous lymphoma, acute leukemia, chronic leukemia, acute lymphoblastic leukemia, acute myelogenous leukemia, chronic myelogenous leukemia, plasma cell neoplasm, lymphoid neoplasm, and AIDS-related cancer; and solid cancers such as bladder cancer, breast cancer, colon cancer, kidney cancer, liver cancer, lung cancer, small-cell lung cancer, non-small cell lung cancer, head and neck cancer, esophageal cancer, gallbladder cancer, ovary cancer, pancreatic cancer, stomach cancer, uterine cervical cancer, thyroid gland cancer, prostate cancer, skin cancer including squamous cell cancer, fibrosarcoma, rhabdomyosarcoma, astrocytoma, neuroblastoma, glioma and neurilemmoma, melanoma, seminoma, teratocarcinoma, osteosarcoma, xeroderma pigmentosum, keratoacanthoma, follicular thyroid cancer, and Kaposi's sarcoma.

Examples of the inflammatory disease include autoimmune diseases and more specifically include rheumatoid arthritis, psoriasis, multiple sclerosis, and inflammatory bowel disease.

Examples of the chronic respiratory disease include chronic obstructive pulmonary disease (COPD).

Examples of the allergic disease include atopic dermatitis.

When the compound represented by the general formula (Ia) or the pharmacologically acceptable salt thereof is administered, it may be administered in combination with an additional drug. More specifically, a pharmaceutical composition containing the compound represented by the general formula (Ia) or the pharmacologically acceptable salt thereof and another composition containing the additional drug can be separately prepared and administered at the same time or at different times. Alternatively, the pharmaceutical composition containing the compound represented by the general formula (Ia) or the pharmacologically acceptable salt thereof may further contain the additional drug.

The additional drug means a drug necessary for the subject, and examples thereof include anticancer agents, antirheumatic agents, drugs for the treatment of psoriasis, drugs for the treatment of multiple sclerosis, drugs for the treatment of inflammatory bowel disease, drugs for the treatment of chronic obstructive pulmonary disease, and drugs for the treatment of atopic dermatitis.

Examples of the additional drug include tyrosine kinase inhibitors, immune checkpoint inhibitors, DNA alkylating agents, DNA synthesis inhibitors, platinum-containing drugs, antimetabolites, topoisomerase I inhibitors, topoisomerase II inhibitors, tubulin activator, hormone antagonists, aromatase inhibitors, differentiation inducers, proteosome inhibitors, phospholipid kinase inhibitors, adenosine deaminase inhibitors, anti-angiogenic agents, histone deacetylase (HDAC) inhibitors, BET bromodomain inhibitors, histone demethylase inhibitors, histone methyltransferase inhibitors, matrix metalloprotease inhibitors, farnesyltransferase inhibitors, bisphosphonate preparations, Hsp90 inhibitors, kinesin Eg5 inhibitors, serine threonine kinase inhibitors, anti-cytokine agents, immunosuppressants, immunomodulators, active form of vitamin D3 external agent, S1P1 receptor antagonists, interferon preparations, anti-cholinergic drugs, leukotriene antagonists, PDE4 inhibitors, PGD2 receptor antagonists, neutrophil elastase inhibitors, anti-histamine agents, classical non-steroidal anti-inflammatory drugs (e.g., indomethacin and ibuprofen), cyclooxygenase inhibitors (also including COX-1 selective inhibitors and COX-2 selective inhibitors), nitric oxide-releasing non-steroidal anti-inflammatory drugs, gold drugs, penicillamine, aminosalicylic acid preparations, antimalarial drugs, pyrimidine synthesis inhibitors, TNF inhibitors, interleukin inhibitors, interleukin receptor antagonists, interleukin drugs, B-cell activation inhibitors, costimulatory molecule-related protein preparations, MAPK inhibitors, gene regulation drugs, cytokine production inhibitors, TNF-α-converting enzyme inhibitors, interleukin-1β-converting enzyme inhibitors, chemokine antagonists, therapeutic vaccine, gene therapy, antisense compounds, proteasome inhibitors, JAK inhibitors, T cell inhibitors, inosine monophosphate dehydrogenase (IMPDH) inhibitors, adhesion molecule inhibitors, thalidomide, cathepsin inhibitors, glucose-6-phosphate dehydrogenase inhibitors, dihydroorotate dehydrogenase (DHODH) inhibitors, phospholipase A2 inhibitors, iNOS inhibitors, microtubule stimulants, microtubule anti-microtubule agents, MHC class II antagonists, CD4 antagonists, CD23 antagonists, leukotriene B4 receptor antagonists, 5-lipoxygenase inhibitors, cathepsin B inhibitors, osteogenesis stimulators, dipeptidyl peptidase inhibitors, collagen agonists, capsaicin creams, sulfa drugs, hyaluronic acid derivatives, glucosamine sulfate, amiprilose, CD20 inhibitors, CD52 inhibitors, anti-asthmatic drugs, drugs for the treatment of atopic dermatitis, drugs for the treatment of allergic rhinitis, opioid receptor agonists, immunoglobulins, glatiramer acetate, T cell receptor vaccines, adhesion molecule inhibitors, muscle relaxants, local anesthetics, ketamine, short-acting and long-acting muscarine receptor (including M1 receptor, M2 receptor, and M3 receptor) antagonists, short-acting and long-acting β receptor (including β1 receptor, β2 receptor, β3 receptor, and β4 receptor) agonists, inhaled steroids, oral steroids, combination drugs of 0 receptor agonists and inhaled steroids, vitamin derivatives, and adrenocortical steroids.

The additional drug may be, for example, cisplatin, doxorubicin, Taxotere, Taxol, etoposide, irinotecan, topotecan, paclitaxel, docetaxel, epothilone, tamoxifen, 5-fluorouracil, fingolimod, methotrexate, temozolomide, cyclophosphamide, SCH 66336, R115777, L778,123, BMS 214662, gefitinib, erlotinib, panitumumab, afatinib, dasatinib, bosutinib, vandetanib, sunitinib, axitinib, pazopanib, lenvatinib, lapatinib, nintedanib, nilotinib, crizotinib, ceritinib, alectinib, ibrutinib, imatinib, sorafenib, vemurafenib, dabrafenib, trametinib, palbociclib, interferon alpha-2b, cytarabine (also called ara-C), adriamycin, Cytoxan, gemcitabine, uracil mustard, chlormethine, ifosfamide, melphalan, chlorambucil, pipobroman, triethylenemelamine, triethylenethiophosphoramine, ofatumumab, busulfan, carmustine, lomustine, streptozocin, dacarbazine, floxuridine, 6-mercaptopurine, 6-thioguanine, regorafenib, ramucirumab, fludarabine phosphate, oxaliplatin, folinate, pentostatin, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, drostanolone propionate, testolactone, megestrol acetate, methylprednisolone, methyltestosterone, prednisolone, chlorotrianisene, hydroxyprogesterone, aminoglutethimide, estramustine, medroxyprogesterone acetate, leuprolide acetate, flutamide, toremifene, goserelin, carboplatin, hydroxyurea, amsacrine, procarbazine, mitotane, mitoxantrone, levamisole, Navelbine, anastrozole, letrozole, capecitabine, reloxafine, droloxifene, hexamethylmelamine, bevacizumab, omalizumab, mepolizumab, gemtuzumab ozogamicin, mogamulizumab, pertuzumab, ocrelizumab, alemtuzumab, inotuzumab, tositumomab, bortezomib, ibritumomab tiuxetan, diarsenic trioxide, vinorelbine, porfimer sodium, thiotepa, altretamine, trastuzumab, letrozole, fulvestrant, exemestane, rituximab, cetuximab, basiliximab, nivolumab, ipilimumab, pembrolizumab, durvalumab, atezolizumab, avelumab, alcofenac, aceclofenac, sulindac, tolmetin, etodolac, fenoprofen, tiaprofenic acid, meclofenamic acid, meloxicam, tenoxicam, lornoxicam, nabumetone, acetaminophen, phenacetin, ethenzamide, sulpyrine, antipyrine, migrenin, aspirin, mefenamic acid, flufenamic acid, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesilate, camostat mesilate, ulinastatin, colchicine, probenecid, sulfinpyrazone, benzbromarone, allopurinol, brentuximab vedotin, gold sodium thiomalate, sodium hyaluronate, atropine, scopolamine, morphine or salts thereof (e.g., morphine hydrochloride), pethidine, levorphanol, oxymorphone, salicylic acid derivatives (e.g., salicylic acid, sodium salicylate, and methyl salicylate), celecoxib, etoricoxib, valdecoxib, loxoprofen, auranofin, D-penicillamine, sulfasalazine, mesalazine, olsalazine, balsalazide, chloroquine, leflunomide, tacrolimus, infliximab, etanercept, adalimumab, certolizumab pegol, golimumab, PASSTNF-α, soluble TNF-α receptor, TNF-α-binding protein, anti-TNF-α antibodies, denosumab, anakinra, antibodies against soluble interleukin-1 receptor (e.g., rilonacept and canakinumab), tocilizumab, anti-interleukin-6 antibodies (e.g., tocilizumab), interleukin-10, ustekinumab, briakinumab, secukinumab (AIN-457), ixekizumab (LY-2439821), AMG827, Rituxan, belimumab, abatacept, BMS-582949, inhibitors of molecules (e.g., NF-κ, NF-κB, IKK-1, IKK-2, and AP-1) involved in signal transduction (e.g., dimethyl fumarate, dehydroxymethylepoxyquinomicin, DTCM-glutarimide, sesquiterpene lactone, resveratrol, curcumin, diindolylmethane noscapine, parthenolide, ixazomib, carfilzomib, delanzomib, marizomib, MLN-4924, IMD-2560, IMD-0354, IMD-1041, BAY-11-7082, BAY-11-7085, MLN120B, BMS-345541, SC-514, PS-1145 denosumab, vorinostat, romidepsin, SN-50, and T-5224), MAPK inhibitors (e.g., SCI0469, BIRB796, SB203580, VX-702, pamapimod, PH797804, vemurafenib, dabrafenib, trametinib, cobimetinib, CC-359, CC-930, bentamapimod, and XG-104), salicylic acid ointments, urea ointments, iguratimod, tetomilast, belnacasan, HMPL-004, IL-8 antagonists, CXCR1-CXCR2 dual antagonists (e.g., reparixin), CCR9 antagonists (e.g., vercirnon sodium), denileukin diftitox, CCX025, N-{4-chloro-2-[(1-oxidopyridin-4-yl)carbonyl]phenyl}-4-(propan-2-yloxy)benzenesulfonamide, MCP-1 antagonists, irbesartan, TNF-α vaccines, ISIS-104838, natalizumab, vedolizumab, AJM300, TRK-170, E6007, MX-68, BMS-188667, CKD-461, rimexolone, cyclosporine A, mizoribine, gusperimus, sirolimus, temsirolimus, everolimus, antilymphocyte serum, freeze-dried sulfonated normal immunoglobulin, erythropoietin, colony-stimulating factors, atiprimod dihydrochloride, azathioprine, interferon α, interferon β-1b, interferon β-1a, tofacitinib, baricitinib, carfilzomib, ruxolitinib, dexamethasone, hexestrol, methimazole, betamethasone, triamcinolone acetonide, fluocinonide, fluocinolone acetonide, cortisone acetate, hydrocortisone, fluorometholone, beclomethasone propionate, estriol, mycophenolate mofetil, alicaforsen sodium, selectin inhibitors, ELAM-1 inhibitors, VCAM-1 inhibitors, ICAM-1 inhibitors, V-85546, roflumilast, apremilast, VAS203, reumacon, zanolimumab, DW-1350, zileuton, Tyk2 inhibitors (e.g., compounds or salts thereof described in WO2010/142752), Synvisc (hylan G-F 20), Orthovisc, atacicept, blisibimod, tizanidine, eperisone, afloqualone, baclofen, diazepam, dantrolene sodium, vitamin D3 derivatives (e.g., 5,6-trans-cholecalciferol, 2,5-hydroxycholecalciferol, 1-α-hydroxycholecalciferol, and calcipotriol), vitamin D2 derivatives (e.g., 5,6-trans-ergocalciferol), isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, ozagrel hydrochloride, pranlukast hydrate, seratrodast, ciclesonide, chlorpheniramine maleate, alimemazine tartrate, clemastine fumarate, homochlorcyclizine hydrochloride, fexofenadine, ketotifen fumarate, cetirizine hydrochloride, oxatomide, ebastine, epinastine hydrochloride, loratadine, tramadol, promethazine, hydroxyzine, homochlorcyclizine, cyproheptadine, mequitazine, emedastine fumarate, pseudoephedrine, bepotastine besilate, levocetirizine, olopatadine hydrochloride, mycophenolate mofetil, daclizumab, galiximab, metformin hydrochloride, visilizumab, aminopterin, pazopanib hydrochloride, fezakinumab, ruxolitinib phosphate, ixekizumab, guselkumab, SLx-2119, PRX-167700, lidocaine, tiotropium bromide, salmeterol xinafoate, formoterol fumarate, fluticasone propionate, beclometasone propionate, budesonide, or a combination drug of salmeterol xinafoate and fluticasone propionate.

The additional drug is preferably 5-fluorouracil, oxaliplatin or irinotecan.

EXAMPLES

Although the present invention will be further specifically described below about the compound according to the present embodiment or the pharmaceutically acceptable salt thereof with reference to Examples (Examples 1 to 95), Reference Examples (Reference Examples 1 to 43), and Test Examples (Test Examples 1 to 20), these examples are given for better understanding of the present invention and are not intended to limit the scope of the present invention.

In purification by preparative column chromatography, the following apparatuses were used:
Apparatus 1: EPCLC-W-Prep 2XY A-Type (manufactured by Yamazen Corp., trade name)
Apparatus 2: Purif (trademark)-compact (manufactured by Moritex Corp., trade name)
Apparatus 3: Prominence preparative system (manufactured by Shimadzu Corp., trade name)

The stationary phases used in purification by preparative column chromatography are as follows:
DIOL silica gel: CHROMATOREX (trade name) DIOL MB 100-40/75 (manufactured by Fuji Silysia Chemical Ltd.)
DNH silica gel: CHROMATOREX (trade name) DNH MB 100-40/75 (manufactured by Fuji Silysia Chemical Ltd.)
ODS silica gel: XBridge C18 Prep (trade name), particle size: 5 μm, OBD, size: 19×150 mm (manufactured by Waters Corp.)
CSH ODS silica gel: XSelect CSH C18 Prep (trade name), particle size: 5 μm, OBD, size: 19×150 mm (manufactured by Waters Corp.)
Fluoro-phenyl silica gel: XSelect CSH Prep Fluoro-phenyl (trade name), particle size: 5 μm, OBD, size: 19×150 mm (manufactured by Waters Corp.)

In the case where a plurality of values of mass spectra are observed due to the presence of isotopes, only one having minimum m/z was described. DUIS in an ionization mode of a mass spectrum is a mixed mode of ESI and APCI.

$^1$H-NMR is indicated by chemical shift (δ) with tetramethylsilane as an internal standard (0 ppm), and a coupling constant (J value) is indicated by Hz unit, unless otherwise specified. An abbreviation for the split pattern of each peak has the following meaning: s: singlet, d: doublet, t: triplet, q: quartet, br s: broad singlet, and m: multiplet.

Abbreviations described in Examples and Reference Examples are usually used as meanings generally used in the fields of organic chemistry and pharmacy. Each abbreviation is specifically understood by those skilled in the art as follows.

ATP: Adenosine triphosphate
Boc: tert-Butyloxycarbonyl
Cbz: Benzyloxycarbonyl
CI: Chemical ionization
DIPEA: N,N-Diisopropylethylamine
DMF: N,N-Dimethylformamide
DMSO: Dimethyl sulfoxide
DPPA: Diphenylphosphonyl azide
DTT: dithiothreitol
DUIS: Dual ion source
Et: Ethyl
FBS: Fetal bovine serum
HEPES: N-2-Hydroxyethylpiperazine-N'-2-ethanesulfonic acid
MBP: Myelin basic protein
NADPH: Nicotinamide adenine dinucleotide phosphate
PBMC: Periphery blood mononuclear cell
PBS: Phosphate-buffered aqueous sodium chloride solution
TBS: tert-Butyldimethylsilyl
TEA: Triethylamine
THF: Tetrahydrofuran
Tris: Trishydroxymethylaminomethane (Example 1)

6,6-Dimethyl-N-phenyl-3-[1-(trimethylsilyl)cyclobutanecarboxamido]-4,6-dihydropyrrolo[3,4-c]pyrazole-5(1H)-carboxamide (Compound No. IV-1)

[Chemical Formula 19]

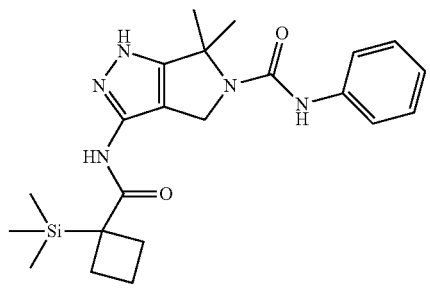

To a solution of 101 mg (0.229 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.116 ml (0.679 mmol) of DIPEA and 0.062 ml (0.68 mmol) of aniline were added at room temperature in an argon atmosphere and reacted at 100° C. for 1 hour with stirring. Subsequently, the reaction solution was concentrated under reduced pressure, and 2 ml of methanol and 0.068 ml (1.1 mmol) of 2-aminoethanol were added to the obtained concentration residue and then reacted at room temperature for 1 hour with stirring.

After completion of the reaction, the reaction solution was concentrated under reduced pressure, and 5 ml of ethyl acetate was added to the obtained concentration residue, followed by washing twice with 5 ml of a 5% aqueous potassium dihydrogen phosphate solution. The whole organic layer thus obtained was washed with 5 ml of a saturated aqueous solution of sodium bicarbonate and saturated saline, then dried over anhydrous magnesium sulfate, and concentrated under reduced pressure.

The obtained concentration residue was subjected to preparative column chromatography (apparatus 1, silica gel, elution solvent:ethyl acetate:methanol=100:0→88:12

(V/V)), and a fraction containing the compound of interest was concentrated under reduced pressure. The obtained concentration residue was dissolved by the addition of dichloromethane, and then, the solid was deposited by the addition of n-hexane. The obtained solid was collected by filtration and dried under reduced pressure to obtain 77.2 mg of the title compound (yield: 79%) as a white solid.

Mass spectrum (CI, m/z): 426 [M+1]$^+$.

$^1$H-NMR spectrum (400 MHz, DMSO-d$_6$) δ: 12.27 & 11.86 (br s, total 1H), 9.83-9.42 (m, 1H), 8.22-7.91 (m, 1H), 7.56-7.47 (m, 2H), 7.26-7.16 (m, 2H), 6.96-6.88 (m, 1H), 4.64 (br s, 2H), 2.55-2.40 (m, 2H), 2.28-2.13 (m, 2H), 1.94-1.74 (m, 2H), 1.67 (br s, 6H), 0.09 (s, 9H).

Example 2

6,6-Dimethyl-N-(p-tolyl)-3-[1-(trimethylsilyl)cyclobutanecarboxamido]-4,6-dihydropyrrolo[3,4-c]pyrazole-5(1H)-carboxamide (Compound No. IV-25)

[Chemical Formula 20]

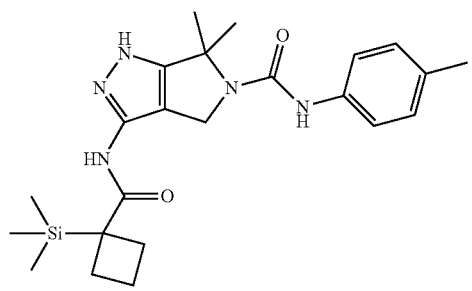

To a solution of 121 mg (0.274 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.15 ml (0.86 mmol) of DIPEA and 92.6 mg (0.864 mmol) of p-toluidine were added at room temperature in a nitrogen atmosphere and reacted at 90° C. for 1.5 hours with stirring. Subsequently, the reaction solution was cooled to room temperature, and 0.15 ml (1.4 mmol) of N,N-dimethylethane-1,2-diamine was added thereto at room temperature and then reacted at room temperature for 4 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70:30→50:50→40:60 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 93.6 mg of the title compound (yield: 78%) as a white solid.

Mass spectrum (CI, m/z): 440 [M+1]$^+$.

$^1$H-NMR spectrum (400 MHz, DMSO-d$_6$) δ: 12.25 & 11.76 (br s, total 1H), 9.75-9.45 (m, 1H), 8.13-7.84 (m, 1H), 7.42-7.36 (m, 2H), 7.05-6.99 (m, 2H), 4.62 (br s, 2H), 2.54-2.41 (m, 2H), 2.28-2.12 (m, 5H), 1.92-1.74 (m, 2H), 1.66 (br s, 6H), 0.09 (s, 9H).

Example 3

N-(4-Methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-79)

[Chemical Formula 21]

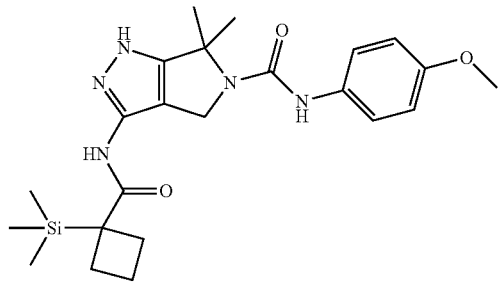

To a solution of 126 mg (0.286 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.18 ml (1.0 mmol) of DIPEA and 121 mg (0.984 mmol) of 4-methoxyaniline were added at room temperature in a nitrogen atmosphere and reacted at 90° C. for 1.5 hours with stirring. Subsequently, the reaction solution was cooled to room temperature, and 0.16 ml (1.5 mmol) of N,N-dimethylethane-1,2-diamine was added thereto at room temperature and then reacted at room temperature for 14.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70:30→50:50→40:60 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 106 mg of the title compound (yield: 81%) as a white solid.

Mass spectrum (CI, m/z): 456 [M+1]$^+$.

$^1$H-NMR spectrum (400 MHz, DMSO-d$_6$) δ: 12.47-11.54 (m, 1H), 9.58 (br s, 1H), 7.94 (br s, 1H), 7.43-7.34 (m, 2H), 6.85-6.76 (m, 2H), 4.59 (s, 2H), 3.70 (s, 3H), 2.54-2.41 (m, 2H), 2.27-2.13 (m, 2H), 1.90-1.74 (m, 2H), 1.66 (s, 6H), 0.09 (s, 9H).

Example 4

N-(4-Fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-7)

[Chemical Formula 22]

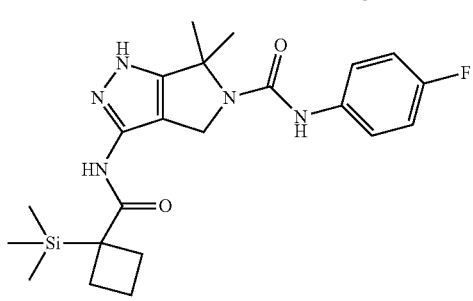

To a solution of 119 mg (0.270 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.15 ml (0.86 mmol) of DIPEA and 0.080 ml (0.83 mmol) of 4-fluoroaniline were added at room temperature in a nitrogen atmosphere and reacted at 90° C. for 2 hours with stirring. Subsequently, the reaction solution was cooled to room temperature, and 0.15 ml (1.4 mmol) of N,N-dimethylethane-1,2-diamine was added thereto at room temperature and then reacted at room temperature for 2 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70:30→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 95.9 mg of the title compound (yield: 80%) as a white solid.

Mass spectrum (CI, m/z): 444 [M+1]$^+$.

$^1$H-NMR spectrum (400 MHz, DMSO-$d_6$) δ: 12.27 & 11.76 (br s, total 1H), 9.71-9.52 (m, 1H), 8.24-8.05 (m, 1H), 7.57-7.45 (m, 2H), 7.11-7.00 (m, 2H), 4.71-4.52 (m, 2H), 2.55-2.40 (m, 2H), 2.28-2.12 (m, 2H), 1.92-1.74 (m, 2H), 1.73-1.57 (m, 6H), 0.09 (s, 9H).

Example 5

6,6-Dimethyl-N-(pyridin-3-yl)-3-[1-(trimethylsilyl)cyclobutanecarboxamido]-4,6-dihydropyrrolo[3,4-c]pyrazole-5(1H)-carboxamide (Compound No. IV-1019)

[Chemical Formula 23]

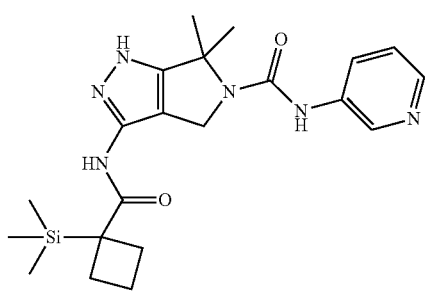

To a solution of 123 mg (0.278 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.15 ml (0.86 mmol) of DIPEA and 79.7 mg (0.847 mmol) of pyridin-3-amine were added at room temperature in a nitrogen atmosphere and reacted at 90° C. for 5 hours with stirring. Subsequently, the reaction solution was cooled to room temperature, and 0.15 ml (1.4 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, silica gel, elution solvent:dichloromethane:methanol=99:1→98:2→97:3→95:5 (V/V)), and a fraction containing the compound of interest was concentrated under reduced pressure. The obtained concentration residue was subjected to preparative column chromatography (apparatus 2, DIOL silica gel, elution solvent:n-hexane:ethyl acetate=50:50→30:70 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=40:60 (V/V)), and a fraction containing the compound of interest was concentrated under reduced pressure, followed by the distilling off of acetonitrile. The obtained concentration residue was subjected to extraction three times with ethyl acetate, and subsequently, the whole organic layer was washed with saturated saline, then dried over anhydrous magnesium sulfate, filtered, and concentrated under reduced pressure. The obtained concentration residue was dissolved in ethyl acetate, then n-hexane was added thereto, and the deposited solid was collected by filtration, washed with n-hexane, and then dried under reduced pressure to obtain 34.5 mg of the title compound (yield: 29%) as a white solid.

Mass spectrum (CI, m/z): 427 [M+1]$^+$.

$^1$H-NMR spectrum (400 MHz, DMSO-d$_6$) δ: 12.29 & 11.66 (br s, total 1H), 9.60 (s, 1H), 8.77-8.64 (m, 1H), 8.44-8.25 (m, 1H), 8.18-8.11 (m, 1H), 7.98-7.91 (m, 1H), 7.26 (dd, J=4.6, 8.3 Hz, 1H), 4.74-4.57 (m, 2H), 2.57-2.41 (m, 2H), 2.28-2.13 (m, 2H), 1.92-1.75 (m, 2H), 1.74-1.59 (m, 6H), 0.09 (s, 9H).

Example 6

N-(2-Fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-3)

[Chemical Formula 24]

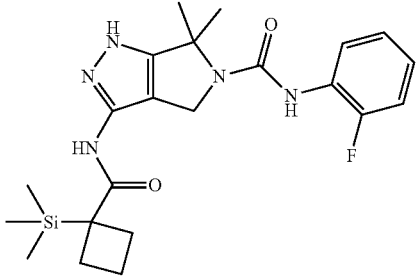

To a solution of 118 mg (0.267 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.15 ml (0.86 mmol) of DIPEA and 0.080 ml (0.83 mmol) of 2-fluoroaniline were added at room temperature in a nitrogen atmosphere and reacted at 90° C. for 9 hours with stirring. Subsequently, the reaction solution was cooled to room temperature, and 0.15 ml (1.4 mmol) of N,N-dimethylethane-1,2-diamine was added thereto at room temperature and then reacted at room temperature for 2.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70:30→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 62.2 mg of the title compound (yield: 53%) as a white solid.

Mass spectrum (CI, m/z): 444 [M+1]$^+$.

$^1$H-NMR spectrum (400 MHz, DMSO-d$_6$) δ: 12.27 & 11.85 (br s, total 1H), 9.80-9.50 (m, 1H), 7.91-7.69 (m, 1H), 7.68-7.47 (m, 1H), 7.24-7.03 (m, 3H), 4.74-4.51 (m, 2H), 2.56-2.39 (m, 2H), 2.28-2.13 (m, 2H), 1.93-1.74 (m, 2H), 1.72-1.57 (m, 6H), 0.09 (s, 9H).

Example 7

6,6-Dimethyl-N-(o-tolyl)-3-[1-(trimethylsilyl)cyclobutanecarboxamido]-4,6-dihydropyrrolo[3,4-c]pyrazole-5(1H)-carboxamide (Compound No. IV-21)

[Chemical Formula 25]

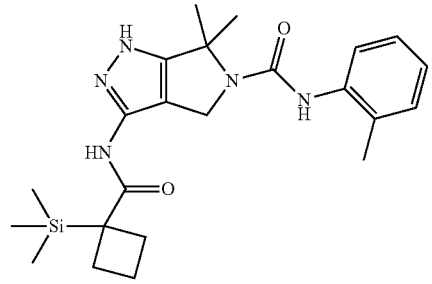

To a solution of 117 mg (0.265 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.15 ml (0.86 mmol) of DIPEA and 0.090 ml (0.84 mmol) of o-toluidine were added at room temperature in a nitrogen atmosphere and reacted at 90° C. for 5 hours with stirring. Subsequently, the reaction solution was cooled to room temperature, and 0.15 ml (1.4 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70:30→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 97.7 mg of the title compound (yield: 84%) as a white solid.

Mass spectrum (CI, m/z): 440 [M+1]$^+$.

$^1$H-NMR spectrum (400 MHz, DMSO-d$_6$) δ: 12.26 & 11.83 (br s, total 1H), 9.73-9.49 (m, 1H), 7.76-7.54 (m, 1H), 7.34-7.21 (m, 1H), 7.19-7.07 (m, 2H), 7.02 (dt, J=1.2, 7.4 Hz, 1H), 4.71-4.52 (m, 2H), 2.54-2.40 (m, 2H), 2.27-2.12 (m, 5H), 1.93-1.73 (m, 2H), 1.72-1.54 (m, 6H), 0.09 (s, 9H).

Example 8

6,6-Dimethyl-N-(m-tolyl)-3-[1-(trimethylsilyl)cyclobutanecarboxamido]-4,6-dihydropyrrolo[3,4-c]pyrazole-5(1H)-carboxamide (Compound No. IV-23)

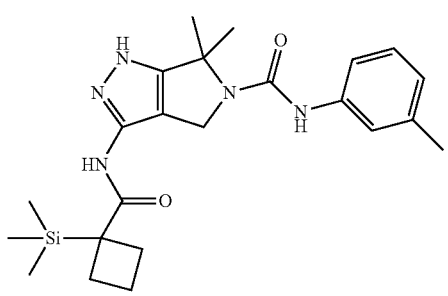

[Chemical Formula 26]

Example 9

N-([1,1'-Biphenyl]-3-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-71)

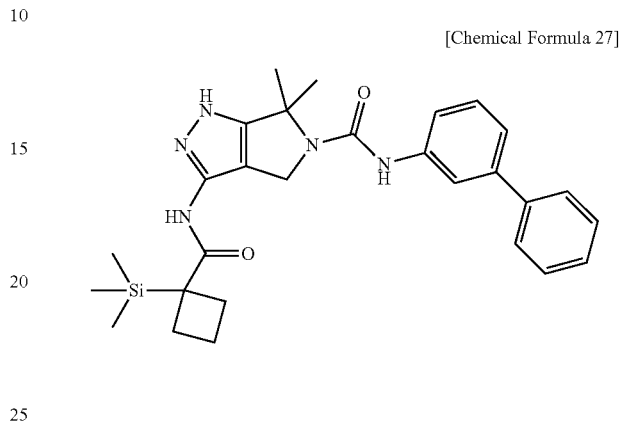

[Chemical Formula 27]

To a solution of 105 mg (0.238 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.13 ml (0.75 mmol) of DIPEA and 0.080 ml (0.74 mmol) of m-toluidine were added at room temperature in a nitrogen atmosphere and reacted at 90° C. for 2 hours with stirring. Subsequently, the reaction solution was cooled to room temperature, and 0.13 ml (1.2 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70:30→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 90.1 mg of the title compound (yield: 86%) as a white solid.

Mass spectrum (CI, m/z): 440 [M+1]$^+$.

$^1$H-NMR spectrum (400 MHz, DMSO-d$_6$) δ: 12.26 & 11.71 (br s, total 1H), 9.64-9.51 (m, 1H), 8.09-7.91 (m, 1H), 7.39-7.35 (m, 1H), 7.34-7.26 (m, 1H), 7.09 (t, J=7.8 Hz, 1H), 6.77-6.71 (m, 1H), 4.70-4.52 (m, 2H), 2.54-2.42 (m, 2H), 2.29-2.13 (m, 5H), 1.92-1.73 (m, 2H), 1.73-1.58 (m, 6H), 0.14-0.05 (m, 9H).

To a solution of 101 mg (0.230 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.13 ml (0.75 mmol) of DIPEA and 119 mg (0.700 mmol) of [1,1'-biphenyl]-3-amine were added at room temperature in a nitrogen atmosphere and reacted at 90° C. for 4 hours with stirring. Subsequently, the reaction solution was cooled to room temperature, and 0.13 ml (1.2 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was suspended in an ethyl acetate/n-hexane mixed solvent and stirred at room temperature, and then, the solid remaining without being dissolved was collected by filtration, washed with n-hexane, and then dried under reduced pressure to obtain 92.4 mg of the title compound (yield: 80%) as a white solid.

Mass spectrum (CI, m/z): 502 [M+1]$^+$.

$^1$H-NMR spectrum (400 MHz, DMSO-d$_6$) δ: 12.28 & 11.71 (br s, total 1H), 9.60 (s, 1H), 8.20 (br s, 1H), 7.84 (t, J=1.8 Hz, 1H), 7.66-7.54 (m, 3H), 7.51-7.43 (m, 2H), 7.39-7.28 (m, 2H), 7.25-7.19 (m, 1H), 4.67 (br s, 2H), 2.56-2.40 (m, 2H), 2.29-2.13 (m, 2H), 1.93-1.75 (m, 2H), 1.69 (br s, 6H), 0.10 (s, 9H).

Example 10

N-(3-Fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-5)

[Chemical Formula 28]

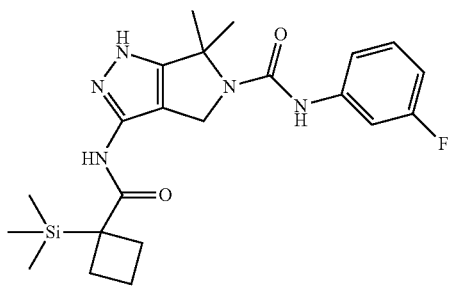

To a solution of 102 mg (0.231 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.13 ml (0.75 mmol) of DIPEA and 0.070 ml (0.72 mmol) of 3-fluoroaniline were added at room temperature in a nitrogen atmosphere and reacted at 90° C. for 3.5 hours with stirring. Subsequently, the reaction solution was cooled to room temperature, and 0.13 ml (1.2 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=75:25→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 70.6 mg of the title compound (yield: 69%) as a white solid.

Mass spectrum (CI, m/z): 444 [M+1]$^+$.

$^1$H-NMR spectrum (400 MHz, DMSO-d$_6$) δ: 12.28 & 11.68 (s, total 1H), 9.59 (s, 1H), 8.39-8.24 (m, 1H), 7.49 (td, J=2.2, 12.4 Hz, 1H), 7.38-7.31 (m, 1H), 7.28-7.19 (m, 1H), 6.76-6.68 (m, 1H), 4.70-4.56 (m, 2H), 2.54-2.41 (m, 2H), 2.28-2.14 (m, 2H), 1.92-1.74 (m, 2H), 1.72-1.60 (m, 6H), 0.15-0.05 (m, 9H).

Example 11

N-(3-Chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-11)

[Chemical Formula 29]

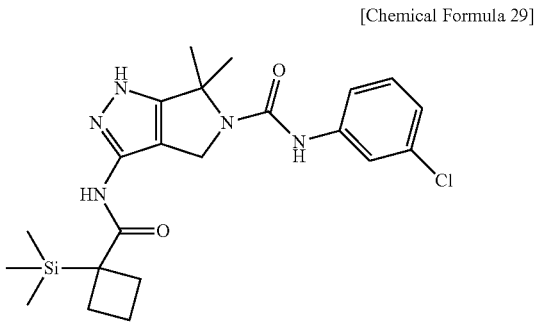 [SMILES: CC1(C)c2[nH]nc(NC(=O)C3([Si](C)(C)C)CCC3)c2CN1C(=O)Nc1cccc(Cl)c1]

To a solution of 108 mg (0.245 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.13 ml (0.75 mmol) of DIPEA and 0.080 ml (0.76 mmol) of 3-chloroaniline were added at room temperature in a nitrogen atmosphere and reacted at 90° C. for 4 hours with stirring. Subsequently, the reaction solution was cooled to room temperature, and 0.14 ml (1.3 mmol) of N,N-dimethylethane-1,2-diamine was added thereto at room temperature and then reacted at room temperature for 13.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=75:25→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 93.0 mg of the title compound (yield: 82%) as a white solid.

Mass spectrum (CI, m/z): 460 [M+1]$^+$.

$^1$H-NMR spectrum (400 MHz, DMSO-d$_6$) δ: 12.28 & 11.67 (s, total 1H), 9.64-9.55 (m, 1H), 8.38-8.24 (m, 1H), 7.72 (t, J=2.1 Hz, 1H), 7.53-7.44 (m, 1H), 7.24 (t, J=8.0, 1H), 6.96 (ddd, J=0.8, 2.1, 8.0 Hz, 1H), 4.70-4.56 (m, 2H), 2.56-2.40 (m, 2H), 2.28-2.14 (m, 2H), 1.92-1.74 (m, 2H), 1.72-1.59 (m, 6H), 0.15-0.03 (m, 9H).

Example 12

N-(2-Methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-75)

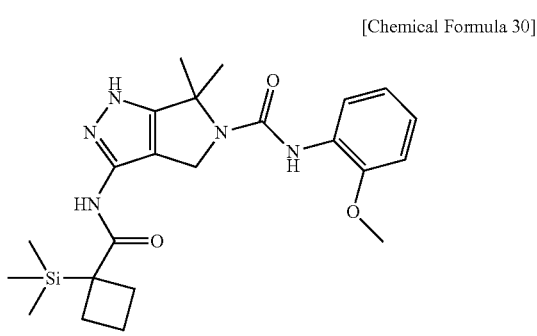 [SMILES: COc1ccccc1NC(=O)N1Cc2c(NC(=O)C3([Si](C)(C)C)CCC3)n[nH]c2C1(C)C]

[Chemical Formula 30]

To a solution of 105 mg (0.238 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.13 ml (0.75 mmol) of DIPEA and 0.13 ml (1.2 mmol) of 2-methoxyaniline were added at room temperature in a nitrogen atmosphere and reacted at 90° C. for 3.5 hours with stirring. Subsequently, the reaction solution was cooled to room temperature, and 0.13 ml (1.2 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=75:25→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 94.1 mg of the title compound (yield: 87%) as a white solid.

Mass spectrum (CI, m/z): 456 [M+1]$^+$.

$^1$H-NMR spectrum (400 MHz, DMSO-d$_6$) δ: 12.30 & 11.93 (br s, total 1H), 9.85-9.52 (m, 1H), 8.05-7.85 (m, 1H), 7.11 (s, 1H), 7.01 (dd, J=1.4, 8.0 Hz, 1H), 6.99-6.92 (m, 1H), 6.88 (dt, J=1.4, 7.6 Hz, 1H), 4.53 (br s, 2H), 3.84 (s, 3H), 2.57-2.40 (m, 2H), 2.28-2.13 (m, 2H), 1.93-1.75 (m, 2H), 1.68 (br s, 6H), 0.10 (s, 9H).

Example 13

N-(2-Chlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-9)

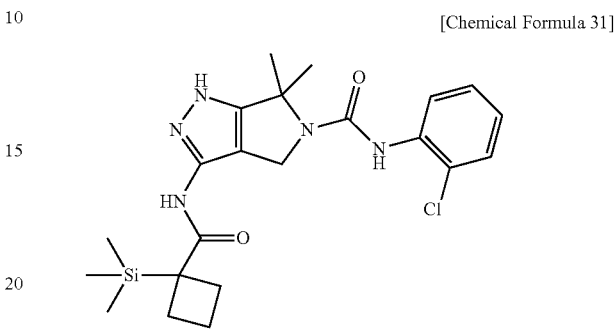

[Chemical Formula 31]

To a solution of 106 mg (0.239 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.13 ml (0.75 mmol) of DIPEA and 0.13 ml (1.2 mmol) of 2-chloroaniline were added at room temperature in a nitrogen atmosphere and reacted at 90° C. for 15 hours with stirring. Subsequently, the reaction solution was cooled to room temperature, and 0.13 ml (1.2 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=75:25→50:50 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain a pale yellow solid.

The obtained solid was subjected to preparative column chromatography (apparatus 3, ODS silica gel, elution solvent:acetonitrile:1 mM aqueous dipotassium biphosphate solution=50:50 (V/V)), and a fraction containing the compound of interest was concentrated under reduced pressure, followed by the distilling off of acetonitrile. The obtained concentration residue was subjected to extraction three times with ethyl acetate, and subsequently, the whole organic layer was washed with saturated saline, then dried over anhydrous magnesium sulfate, filtered, and concentrated under reduced pressure. The obtained concentration residue was dissolved in ethyl acetate, then n-hexane was added thereto, and the deposited solid was collected by filtration, washed with n-hexane, and then dried under reduced pressure to obtain 36.5 mg of the title compound (yield: 33%) as a white solid.

Mass spectrum (CI, m/z): 460 [M+1]$^+$.

$^1$H-NMR spectrum (400 MHz, DMSO-d$_6$) δ: 12.29 & 11.86 (br s, total 1H), 9.62 (br s, 1H), 7.85-7.52 (m, 2H), 7.45 (dd, J=1.4, 8.0 Hz, 1H), 7.32-7.23 (m, 1H), 7.15-7.05 (m, 1H), 4.62 (br s, 2H), 2.58-2.39 (m, 2H), 2.26-2.14 (m, 2H), 1.89-1.74 (m, 2H), 1.67 (s, 6H), 0.09 (s, 9H).

Example 14

N-([1,1'-Biphenyl]-2-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-69)

[Chemical Formula 32]

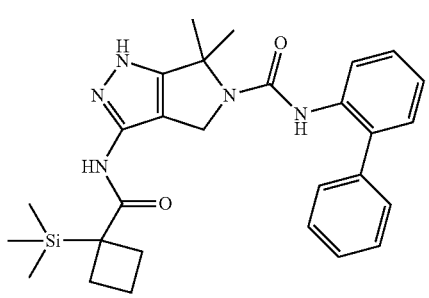

To a solution of 150 mg (0.340 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of DMF, 0.304 ml (1.70 mmol) of DIPEA and 173 mg (1.02 mmol) of [1,1'-biphenyl]-2-amine were added at room temperature in an argon atmosphere and reacted at 80° C. for 2 hours and at room temperature for 18 hours with stirring. Subsequently, 0.162 ml (1.70 mmol) of N,N-dimethylethane-1,2-diamine was added thereto at room temperature and then reacted at room temperature for 2 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=75:25→50:50 (V/V)), and a fraction containing the compound of interest was concentrated under reduced pressure. The obtained concentration residue was dissolved in ethyl acetate, then n-hexane was added thereto, and the deposited solid was collected by filtration and dried under reduced pressure to obtain 53 mg of the title compound (yield: 31%) as a white solid.

Mass spectrum (CI, m/z): 502 [M+1]$^+$.

$^1$H-NMR spectrum (400 MHz, DMSO-d$_6$) δ: 12.20 & 11.70 (br s, total 1H), 9.54 (s, 1H), 7.67-7.37 (m, 6H), 7.35-7.15 (m, 4H), 4.43-4.20 (m, 2H), 2.57-2.39 (m, 2H), 2.26-2.11 (m, 2H), 1.92-1.72 (m, 2H), 1.49 (s, 6H), 0.08 (s, 9H).

Example 15

6,6-Dimethyl-N-(pyridin-2-yl)-3-[1-(trimethylsilyl)cyclobutanecarboxamido]-4,6-dihydropyrrolo[3,4-c]pyrazole-5(1H)-carboxamide (Compound No. IV-1007)

[Chemical Formula 33]

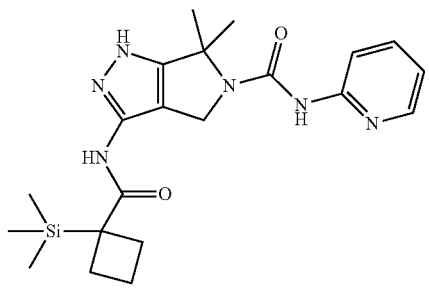

To a solution of 129 mg (0.293 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.16 ml (0.92 mmol) of DIPEA and 90.7 mg (0.964 mmol) of pyridin-2-amine were added at room temperature in a nitrogen atmosphere and reacted at 90° C. for 10.5 hours with stirring. Subsequently, the reaction solution was cooled to room temperature, and 0.16 ml (1.5 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. An ethyl acetate/n-hexane mixed solvent was added to the obtained concentration residue, and after ultrasonication, insoluble matter was collected by filtration. The solid thus collected by filtration was washed with n-hexane and then dried under reduced pressure to obtain a pale yellow solid.

The obtained solid was subjected to preparative column chromatography (apparatus 3, ODS silica gel, elution solvent:acetonitrile:1 mM aqueous dipotassium biphosphate solution=40:60→80:20 (V/V)), and a fraction containing the compound of interest was concentrated under reduced pressure, followed by the distilling off of acetonitrile. The obtained concentration residue was subjected to extraction three times with ethyl acetate, and subsequently, the whole organic layer was washed with saturated saline, then dried over anhydrous magnesium sulfate, filtered, and concentrated under reduced pressure. The obtained concentration residue was suspended in an ethyl acetate/n-hexane mixed solvent and stirred at room temperature, and then, the solid remaining without being dissolved was collected by filtration. The solid thus collected by filtration was washed with n-hexane and then dried under reduced pressure to obtain 49.9 mg of the title compound (yield: 40%) as a white solid.

Mass spectrum (CI, m/z): 427 [M+1]$^+$.

$^1$H-NMR spectrum (400 MHz, DMSO-d$_6$) δ: 12.27 & 11.79 (br s, total 1H), 9.60 (br s, 1H), 8.31 (br s, 1H), 8.22 (ddd, J=0.9, 1.9, 4.9, 1H), 7.89-7.84 (m, 1H), 7.72-7.64 (m, 1H), 6.97 (ddd, J=0.9, 4.9, 7.2 Hz, 1H), 4.78-4.59 (m, 2H), 2.57-2.40 (m, 2H), 2.28-2.13 (m, 2H), 1.92-1.75 (m, 2H), 1.69 (br s, 6H), 0.09 (s, 9H).

Example 16

N-(2-Ethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-27)

[Chemical Formula 34]

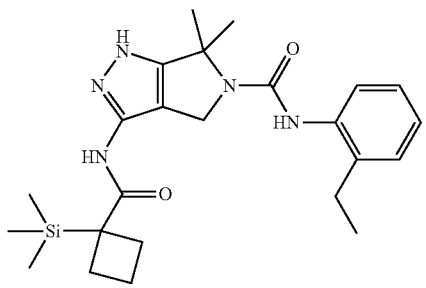

To a solution of 105 mg (0.238 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 and 0.20 ml (1.2 mmol) of DIPEA in 3 ml of 1,4-dioxane, 0.085 ml (0.69 mmol) of 2-ethylaniline was added at room temperature in an argon atmosphere and reacted at 100° C. for 2 hours with stirring. Subsequently, the reaction solution was cooled to room temperature, and 0.13 ml (1.2 mmol) of N,N-dimethylethane-1,2-diamine was added thereto at room temperature and then reacted at room temperature for 1 hour with stirring.

After completion of the reaction, a 5% aqueous potassium bisulfate solution was added to the reaction solution, followed by extraction with ethyl acetate. The whole organic layer thus obtained was washed with water and saturated saline in this order, then dried over anhydrous magnesium sulfate, filtered, and concentrated under reduced pressure. The obtained concentration residue was subjected to preparative column chromatography (apparatus 2, DIOL silica gel, elution solvent:n-hexane:ethyl acetate=80:20→30:70 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=35:65→55:45 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 17.6 mg of the title compound (yield: 16%) as a white solid.

Mass spectrum (CI, m/z): 454 [M+1]$^+$.
$^1$H-NMR spectrum (400 MHz, DMSO-d$_6$) δ: 12.26 & 11.76 (br s, total 1H), 9.62-9.53 (m, 1H), 7.71-7.53 (m, 1H), 7.29-7.16 (m, 2H), 7.15-7.06 (m, 2H), 4.66-4.52 (m, 2H), 2.59 (q, J=7.6 Hz, 2H), 2.54-2.40 (m, 2H), 2.27-2.13 (m, 2H), 1.92-1.74 (m, 2H), 1.71-1.57 (m, 6H), 1.13 (t, J=7.6 Hz, 3H), 0.09 (s, 9H).

Example 17

N-(2,6-Dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-381)

[Chemical Formula 35]

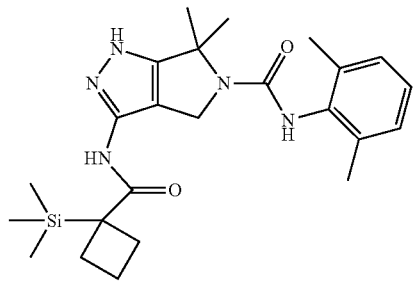

To a solution of 100 mg (0.227 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.101 ml (0.566 mmol) of DIPEA and 0.042 ml (0.34 mmol) of 2,6-dimethylaniline were added at room temperature in an argon atmosphere and reacted at 100° C. for 7 hours. Subsequently, the reaction solution was cooled to room temperature and reacted for 20 hours. The resultant was further reacted at 150° C. for 1 hour in a microwave reaction apparatus. Then, the reaction solution was cooled to room temperature, and 0.053 ml (0.56 mmol) of N,N-dimethylethane-1,2-diamine was added thereto at room temperature and then reacted at room temperature for 1 hour with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=75:25→49:51 (V/V)), and a fraction containing the compound of interest was concentrated under reduced pressure. The obtained concentration residue was subjected to preparative column chromatography (apparatus 1, silica gel, elution solvent: 1,2-dichloroethane:methanol=98:2→90:10 (V/V)), and a fraction containing the compound of interest was concentrated under reduced pressure. The obtained concentration residue was dissolved by the addition of ethyl acetate, then n-hexane was added thereto, and the deposited solid was collected by filtration and dried under reduced pressure to obtain 14.7 mg of the title compound (yield: 14%) as a white solid.

Mass spectrum (CI, m/z): 454 [M+1]$^+$.

$^1$H-NMR spectrum (400 MHz, DMSO-d$_6$) δ: 12.25 & 11.74 (br s, total 1H), 9.55 (br s, 1H), 7.62-7.40 (m, 1H), 7.08-6.97 (m, 3H), 4.68-4.48 (m, 2H), 2.58-2.39 (m, 2H), 2.27-2.08 (m, 8H), 1.93-1.73 (m, 2H), 1.71-1.54 (m, 6H), 0.09 (s, 9H).

Example 18

N-(2,3-Difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-99)

[Chemical Formula 36]

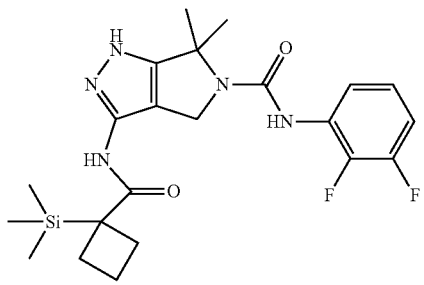

To a solution of 100 mg (0.227 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.120 ml (0.689 mmol) of DIPEA and 100 mg (0.775 mmol) of 2,3-difluoroaniline were added at room temperature in an argon atmosphere, reacted at 90° C. for 3 hours with stirring, and then reacted at 150° C. for 2 hours in a microwave reaction apparatus. Subsequently, 0.120 ml (1.10 mmol) of N,N-dimethylethane-1,2-diamine was added at room temperature and then reacted at room temperature for 2 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=60:40→20:80 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=50:50 (V/V)), and a fraction containing the compound of interest was subjected to extraction with ethyl acetate. The whole organic layer thus obtained was washed with water, dried over anhydrous sodium sulfate, then filtered, and concentrated under reduced pressure. The obtained concentration residue was dissolved by the addition of methanol, then water was added thereto, and the deposited solid was collected by filtration and dried under reduced pressure to obtain 13.0 mg of the title compound (yield: 12%) as a white solid.

Mass spectrum (CI, m/z): 462 [M+1]+.

$^1$H-NMR spectrum (400 MHz, DMSO-d$_6$) δ: 12.27 & 11.74 (br s, total 1H), 9.63 (s, 1H), 8.29-7.91 (m, 1H), 7.42-7.24 (m, 1H), 7.17-7.05 (m, 2H), 4.64 (br s, 2H), 2.59-2.39 (m, 2H), 2.27-2.12 (m, 2H), 1.92-1.73 (m, 2H), 1.65 (s, 6H), 0.09 (s, 9H).

Example 19

N-(2,3-Dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-375)

[Chemical Formula 37]

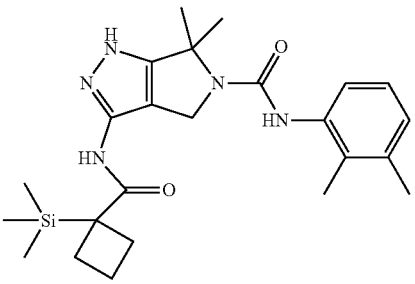

To a solution of 100 mg (0.227 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.120 ml (0.689 mmol) of DIPEA and 82.0 mg (0.677 mmol) of 2,3-dimethylaniline were added at room temperature and reacted at 170° C. for 1 hour in a microwave reaction apparatus. Subsequently, 0.120 ml (1.10 mmol) of N,N-dimethylethane-1,2-diamine was added at room temperature and then reacted at room temperature for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=60:40→20:80 (V/V)), and a fraction containing the compound of interest was concentrated under reduced pressure. The obtained concentration residue was subjected to preparative column chromatography (apparatus 3, Fluoro-phenyl silica gel, elution solvent:acetonitrile:1 mM aqueous potassium dihydrogen phosphate solution=40:60 (V/V)), and a fraction containing the compound of interest was subjected to extraction with ethyl acetate. The whole organic layer thus obtained was washed with water, dried over anhydrous sodium sulfate, then filtered, and concentrated under reduced pressure. The obtained concentration residue was dissolved by the addition of methanol, then water was added thereto, and the deposited solid was collected by filtration and dried under reduced pressure to obtain 12.3 mg of the title compound (yield: 12%) as a white solid.

Mass spectrum (CI, m/z): 454 [M+1]$^+$.

$^1$H-NMR spectrum (400 MHz, DMSO-d$_6$) δ: 12.25 & 11.74 (br s, total 1H), 9.64-9.51 (m, 1H), 7.80-7.62 (m, 1H), 7.10-6.92 (m, 3H), 4.68-4.54 (m, 2H), 2.56-2.40 (m, 2H), 2.29-2.13 (m, 5H), 2.05 (s, 3H), 1.91-1.73 (m, 2H), 1.71-1.56 (m, 6H), 0.09 (s, 9H).

Example 20

N-(2-Fluoro-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-129)

[Chemical Formula 38]

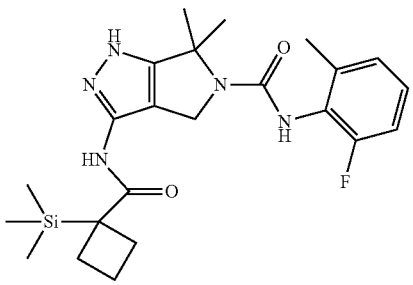

To a solution of 133 mg (0.301 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.21 ml (1.2 mmol) of DIPEA and 151 mg (1.21 mmol) of 2-fluoro-6-methylaniline were added at room temperature, reacted at 90° C. for 4 hours with stirring, and then reacted at 160° C. for 1 hour in a microwave reaction apparatus. Subsequently, the reaction solution was cooled to room temperature, and 0.17 ml (1.6 mmol) of N,N-dimethylethane-1,2-diamine was added thereto at room temperature and then reacted at room temperature for 17.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure.

The obtained concentration residue was suspended in an ethyl acetate/n-hexane mixed solvent and stirred at room temperature, and then, the solid remaining without being dissolved was collected by filtration, washed with n-hexane, and then dried under reduced pressure to obtain a pale yellow solid (approximately 110 mg). The obtained solid was subjected to preparative column chromatography (apparatus 3, ODS silica gel, elution solvent:acetonitrile:1 mM aqueous dipotassium biphosphate solution=50:50→80:20 (V/V)), and a fraction containing the compound of interest was concentrated under reduced pressure, followed by the distilling off of acetonitrile. The obtained concentration residue was subjected to extraction three times with ethyl acetate, and subsequently, the whole organic layer was washed with saturated saline, then dried over anhydrous magnesium sulfate, filtered, and concentrated under reduced pressure. The obtained concentration residue was dissolved in ethyl acetate, then n-hexane was added thereto, and the deposited solid was collected by filtration, washed with n-hexane, and then dried under reduced pressure to obtain 33.4 mg of the title compound (yield: 24% [calculation value with the purity of the starting material defined as 100%]) as a white solid.

Mass spectrum (CI, m/z): 458 [M+1]$^+$.

$^1$H-NMR spectrum (400 MHz, DMSO-d$_6$) δ: 12.26 & 11.69 (s, total 1H), 9.62-9.52 (m, 1H), 7.79-7.63 (m, 1H), 7.18-7.09 (m, 1H), 7.06-6.97 (m, 2H), 4.68-4.50 (m, 2H), 2.57-2.40 (m, 2H), 2.28-2.13 (m, 5H), 1.93-1.72 (m, 2H), 1.71-1.54 (m, 6H), 0.17-0.03 (m, 9H).

Example 21

N-[2-(Difluoromethoxy)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-87)

[Chemical Formula 39]

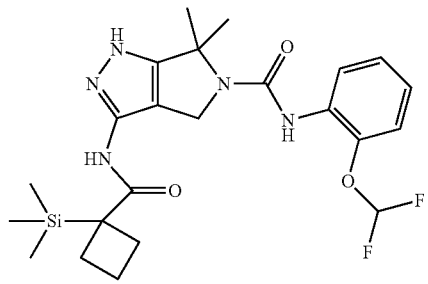

To a solution of 111 mg (0.251 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.14 ml (0.80 mmol) of DIPEA and 0.10 ml (0.80 mmol) of 2-(difluoromethoxy)aniline were added at room temperature in a nitrogen atmosphere and reacted at 100° C. for 9.5 hours with stirring. Subsequently, the reaction solution was cooled to room temperature, and 0.14 ml (1.3 mmol) of N,N-dimethylethane-1,2-diamine was added thereto at room temperature and then reacted at room temperature for 2 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=80:20→65:35→50:50 (V/V)), and a fraction containing the compound of interest was concentrated under reduced pressure. The obtained concentration residue was subjected to preparative column chromatography (apparatus 2, silica gel, elution solvent:dichloromethane:methanol=100:0→4 99:1→4 98:2→4 97:3 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 62.9 mg of the title compound (yield: 51% [calculation value with the purity of the starting material defined as 100%]) as a white solid.

Mass spectrum (CI, m/z): 492 [M+1]$^+$.

$^1$H-NMR spectrum (400 MHz, DMSO-$d_6$) δ: 12.28 & 11.82 (br s, total 1H), 9.62 (br s, 1H), 7.83-7.43 (m, 2H), 7.26-6.80 (m, 4H), 4.59 (br s, 2H), 2.57-2.40 (m, 2H), 2.26-2.13 (m, 2H), 1.91-1.74 (m, 2H), 1.66 (s, 6H), 0.09 (s, 9H).

Example 22

N-(2-Ethoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-81)

[Chemical Formula 40]

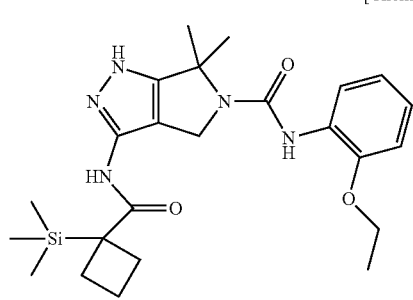

To a solution of 108 mg (0.245 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.215 ml (1.23 mmol) of DIPEA and 0.100 ml (0.765 mmol) of 2-ethoxyaniline were added at room temperature in an argon atmosphere and reacted at 100° C. for 3 hours with stirring. Subsequently, the reaction solution was cooled to room temperature, and 0.135 ml (1.24 mmol) of N,N-dimethylethane-1,2-diamine was added thereto at room temperature and then reacted at room temperature for 1 hour with stirring.

After completion of the reaction, a 5% aqueous potassium bisulfate solution was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=60:40→80:20 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 52.3 mg of the title compound (yield: 45%) as a white solid.

Mass spectrum (CI, m/z): 470 [M+1]$^+$.

$^1$H-NMR spectrum (400 MHz, DMSO-$d_6$) δ: 12.31 & 11.84 (br s, total 1H), 9.65 (br s, 1H), 8.05-7.96 (m, 1H), 7.20 (s, 1H), 7.02-6.97 (m, 1H), 6.96-6.84 (m, 2H), 4.63-4.45 (m, 2H), 4.14-4.02 (m, 2H), 2.55-2.40 (m, 2H), 2.29-2.11 (m, 2H), 1.94-1.59 (m, 8H), 1.38 (t, J=7.0 Hz, 3H), 0.08 (s, 9H).

Example 23

6,6-Dimethyl-N-[2-(trifluoromethoxy)phenyl]-3-[1-(trimethylsilyl)cyclobutanecarboxamido]-4,6-dihydropyrrolo[3,4-c]pyrazole-5(1H)-carboxamide (Compound No. IV-93)

[Chemical Formula 41]

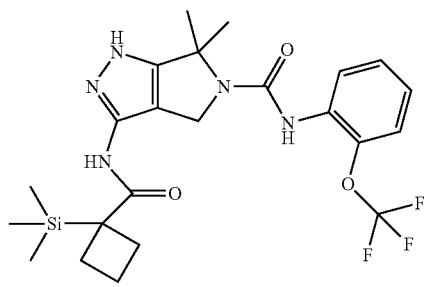

To a solution of 114 mg (0.259 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.23 ml (1.3 mmol) of DIPEA and 0.17 ml (1.3 mmol) of 2-(trifluoromethoxy)aniline were added at room temperature in a nitrogen atmosphere and reacted at 100° C. for 18 hours with stirring. Subsequently, the reaction solution was cooled to room temperature, and 0.14 ml (1.3 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=80:20→65:35→50:50 (V/V)), and a fraction containing the compound of interest was concentrated under reduced pressure. The obtained concentration residue was subjected to preparative column chromatography (apparatus 2, silica gel, elution solvent:dichloromethane:methanol=99:1→98:2 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 30.2 mg of the title compound (yield: 23% [calculation value with the purity of the starting material defined as 100%]) as a white solid.

Mass spectrum (CI, m/z): 510 [M+1]⁺.

¹H-NMR spectrum (400 MHz, DMSO-d₆) δ: 12.28 & 11.74 (br s, total 1H), 9.61 (s, 1H), 7.89 (br s, 1H), 7.68-7.55 (m, 1H), 7.36-7.28 (m, 2H), 7.18 (dt, J=1.6, 7.8 Hz, 1H), 4.60 (br s, 2H), 2.58-2.39 (m, 2H), 2.26-2.13 (m, 2H), 1.90-1.71 (m, 2H), 1.65 (s, 6H), 0.08 (s, 9H).

Example 24

N-(2-Fluoro-4-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-125)

[Chemical Formula 42]

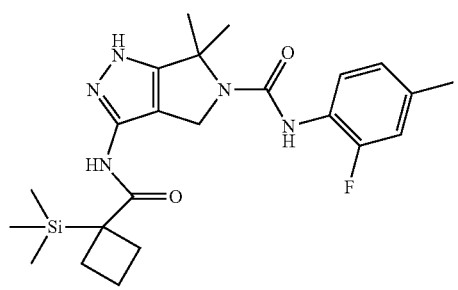

To a solution of 117 mg (0.266 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.23 ml (1.3 mmol) of DIPEA and 0.15 ml (1.3 mmol) of 2-fluoro-4-methylaniline were added at room temperature in a nitrogen atmosphere and reacted at 100° C. for 6.5 hours with stirring. Subsequently, the reaction solution was cooled to room temperature, and 0.15 ml (1.4 mmol) of N,N-dimethylethane-1,2-diamine was added at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=80:20→65:35→50:50 (V/V)), and a fraction containing the compound of interest was concentrated under reduced pressure. The obtained concentration residue was subjected to preparative column chromatography (apparatus 2, silica gel, elution solvent:dichloromethane:methanol=100:0→99:1→98:2 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 92.8 mg of the title compound (yield: 76%) as a white solid.

Mass spectrum (CI, m/z): 458 [M+1]⁺.

¹H-NMR spectrum (400 MHz, DMSO-d₆) δ: 12.26 & 11.75 (br s, total 1H), 9.60 (br s, 1H), 7.83-7.57 (m, 1H), 7.38 (br s, 1H), 7.03-6.96 (m, 1H), 6.94-6.88 (m, 1H), 4.60 (br s, 2H), 2.56-2.40 (m, 2H), 2.27 (s, 3H), 2.25-2.13 (m, 2H), 1.92-1.72 (m, 2H), 1.64 (br s, 6H), 0.09 (s, 9H).

Example 25

N-(2,6-Difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-105)

[Chemical Formula 43]

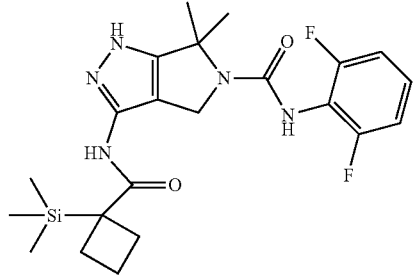

To a solution of 100 mg (0.227 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.20 ml (1.1 mmol) of DIPEA and 0.073 ml (0.68 mmol) of 2,6-difluoroaniline were added at room temperature in an argon atmosphere and reacted at 120° C. for 0.5 hours and at 150° C. for 2 hours in a microwave reaction apparatus. Subsequently, the reaction solution was cooled to room temperature, and 0.11 ml (1.1 mmol) of N,N-dimethylethane-1,2-diamine was added thereto at room temperature and then reacted at room temperature for 1 hour with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, silica gel, elution solvent: 1,2-dichloroethane:methanol=99:1→92:8 (V/V)), and a fraction containing the compound of interest was concentrated under reduced pressure. The obtained concentration residue was dissolved by the addition of ethyl acetate, then n-hexane was added thereto, and the deposited solid was collected by filtration and dried under reduced pressure to obtain 8.2 mg of the title compound (yield: 8% [calculation value with the purity of the starting material defined as 100%]) as a white solid.

Mass spectrum (CI, m/z): 462 [M+1]⁺.

$^1$H-NMR spectrum (400 MHz, DMSO-$d_6$) δ: 12.26 & 11.77 (br s, total 1H), 9.60 (br s, 1H), 7.94 (br s, 1H), 7.27 (tt, J=6.3, 8.5 Hz, 1H), 7.13-7.04 (m, 2H), 4.60 (br s, 2H), 2.53-2.41 (m, 2H), 2.25-2.14 (m, 2H), 1.89-1.74 (m, 2H), 1.63 (s, 6H), 0.09 (s, 9H).

Example 26

N-[2-(tert-Butyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-57)

[Chemical Formula 44]

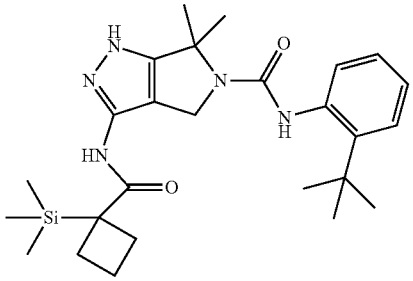

To a solution of 154 mg (0.349 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.300 ml (1.72 mmol) of DIPEA and 0.160 ml (1.03 mmol) of 2-(tert-butyl)aniline were added at room temperature in an argon atmosphere, reacted at 100° C. for 12 hours with stirring, and then reacted at 150° C. for 2 hours in a microwave reaction apparatus. Subsequently, 0.185 ml (1.70 mmol) of N,N-dimethylethane-1,2-diamine was added to the reaction solution at room temperature and then reacted at room temperature for 2 hours with stirring.

After completion of the reaction, a 5% aqueous potassium bisulfate solution was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=60:40→80:20 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 31.4 mg of the title compound (yield: 19%) as a white solid.

Mass spectrum (CI, m/z): 482 [M+1]$^+$.

$^1$H-NMR spectrum (400 MHz, DMSO-$d_6$) δ: 12.26 & 11.83 (br s, total 1H), 9.66-9.49 (m, 1H), 7.53-7.40 (m, 1H), 7.38-7.33 (m, 1H), 7.20-7.12 (m, 2H), 7.11-7.04 (m, 1H), 4.67-4.52 (m, 2H), 2.57-2.39 (m, 2H), 2.27-2.12 (m, 2H), 1.93-1.72 (m, 2H), 1.71-1.53 (m, 6H), 1.35 (s, 9H), 0.08 (s, 9H).

Example 27

6,6-Dimethyl-N-[2-(trifluoromethyl)phenyl]-3-[1-(trimethylsilyl)cyclobutanecarboxamido]-4,6-dihydropyrrolo[3,4-c]pyrazole-5 (1H)-carboxamide (Compound No. IV-51)

[Chemical Formula 45]

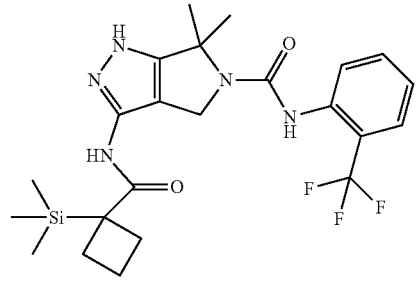

To a solution of 108 mg (0.284 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of 1,4-dioxane, 0.076 ml (0.55 mmol) of 1-isocyanato-2-(trifluoromethyl)benzene was added at room temperature in an argon atmosphere and reacted at room temperature for 1 hour with stirring. Subsequently, 0.150 ml (1.38 mmol) of N,N-dimethylethane-1,2-diamine was added to the reaction solution at room temperature and reacted at room temperature for 1 hour with stirring.

After completion of the reaction, a 5% aqueous potassium bisulfate solution was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=60:40→80:20 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 71.9 mg of the title compound (yield: 51%) as a white solid.

Mass spectrum (CI, m/z): 494 [M+1]$^+$.

$^1$H-NMR spectrum (400 MHz, DMSO-d$_6$) δ: 12.28 & 11.80 (s, total 1H), 9.69-9.55 (m, 1H), 7.88-7.51 (m, 4H), 7.40-7.33 (m, 1H), 4.66-4.49 (m, 2H), 2.56-2.40 (m, 2H), 2.27-2.13 (m, 2H), 1.91-1.73 (m, 2H), 1.71-1.55 (m, 6H), 0.09 (s, 9H).

Example 28

N-(3-Fluoro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-357)

[Chemical Formula 46]

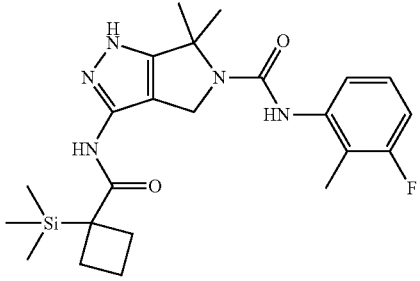

To a solution of 120 mg (0.272 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.15 ml (0.86 mmol) of DIPEA and 100 mg (0.799 mmol) of 3-fluoro-2-methylaniline were added at room temperature and reacted at 170° C. for 1 hour in a microwave reaction apparatus. Subsequently, 0.15 ml (1.4 mmol) of N,N-dimethylethane-1,2-diamine was added thereto at room temperature and then reacted at room temperature for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=60:40→20:80 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=40:60 (V/V)), and a fraction containing the compound of interest was subjected to extraction by the addition of ethyl acetate. The obtained organic layer was washed with water, dried over anhydrous magnesium sulfate, then filtered, and concentrated under reduced pressure. The obtained concentration residue was dissolved by the addition of methanol, then water was added thereto, and the deposited solid was collected by filtration and dried under reduced pressure to obtain 12.4 mg of the title compound (yield: 10% [calculation value with the purity of the starting material defined as 100%]) as a white solid.

Mass spectrum (CI, m/z): 458 [M+1]$^+$.

$^1$H-NMR spectrum (400 MHz, DMSO-d$_6$) δ: 12.27 & 11.76 (br s, total 1H), 9.66-9.54 (m, 1H), 8.02-7.81 (m, 1H), 7.18-7.04 (m, 2H), 6.97-6.89 (m, 1H), 4.71-4.55 (m, 2H), 2.56-2.40 (m, 2H), 2.27-2.13 (m, 2H), 2.06 (d, J=1.4 Hz, 3H), 1.91-1.73 (m, 2H), 1.71-1.55 (m, 6H), 0.09 (s, 9H).

Example 29

N-(2-Cyanophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-63)

[Chemical Formula 47]

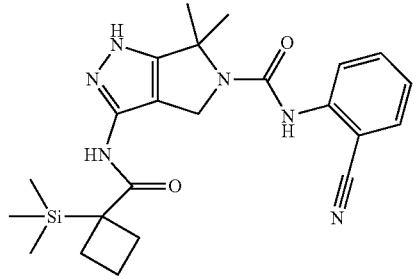

To a solution of 160 mg (0.363 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.30 ml (1.7 mmol) of DIPEA and 132 mg (1.12 mmol) of 2-aminobenzonitrile were added at room temperature in an argon atmosphere and reacted at 150° C. for 6 hours in a microwave reaction apparatus. Subsequently, 0.200 ml (1.84 mmol) of N,N-dimethylethane-1,2-diamine was added thereto at room temperature and then reacted at room temperature for 2 hours with stirring.

After completion of the reaction, a 5% aqueous potassium bisulfate solution was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=60:40→80:20 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 24.5 mg of the title compound (yield: 15%) as a white solid.

Mass spectrum (CI, m/z): 451 [M+1]$^+$.

$^1$H-NMR spectrum (400 MHz, DMSO-d$_6$) δ: 12.29 & 11.72 (br s, total 1H), 9.63 (s, 1H), 8.62-8.42 (m, 1H), 7.72 (dd, J=1.3, 7.7 Hz, 1H), 7.64-7.58 (m, 1H), 7.55-7.44 (m, 1H), 7.28-7.20 (m, 1H), 4.72-4.59 (m, 2H), 2.56-2.41 (m, 2H), 2.26-2.14 (m, 2H), 1.90-1.74 (m, 2H), 1.73-1.59 (m, 6H), 0.09 (s, 9H).

Example 30

N-(4-Fluoro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-359)

[Chemical Formula 48]

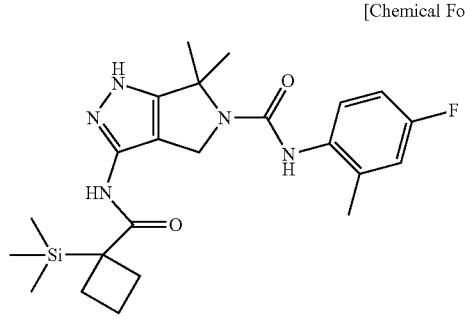

To a solution of 154 mg (0.349 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.30 ml (1.7 mmol) of DIPEA and 0.115 ml (1.03 mmol) of 4-fluoro-2-methylaniline were added at room temperature in an argon atmosphere and reacted at 100° C. for 5 hours with stirring. Subsequently, the reaction solution was cooled to room temperature, and 0.18 ml (1.7 mmol) of N,N-dimethylethane-1,2-diamine was added thereto at room temperature and then reacted at room temperature for 0.5 hours with stirring.

After completion of the reaction, a 5% aqueous potassium bisulfate solution was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=50:50 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 76.4 mg of the title compound (yield: 48%) as a white solid.

Mass spectrum (CI, m/z): 458 [M+1]$^+$.

$^1$H-NMR spectrum (400 MHz, DMSO-d$_6$) δ: 12.25 & 11.72 (br s, total 1H), 9.61-9.54 (m, 1H), 7.79-7.62 (m, 1H), 7.29-7.15 (m, 1H), 7.02 (dd, J=2.9, 9.7 Hz, 1H), 6.93 (dt, J=2.9, 8.6 Hz, 1H), 4.68-4.50 (m, 2H), 2.56-2.40 (m, 2H), 2.28-2.11 (m, 5H), 1.92-1.73 (m, 2H), 1.71-1.56 (m, 6H), 0.16-0.03 (m, 9H).

Example 31

N-(2-Chloro-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-215)

[Chemical Formula 49]

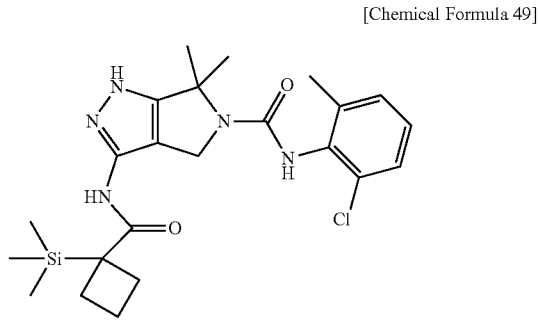 [SMILES: Cc1cccc(Cl)c1NC(=O)N1Cc2c(NC(=O)C3([Si](C)(C)C)CCC3)n[nH]c2C1(C)C]

To a solution of 200 mg (0.454 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 3 ml of 1,4-dioxane, 0.39 ml (2.3 mmol) of DIPEA and 0.16 ml (1.4 mmol) of 2-chloro-6-methylaniline were added at room temperature in an argon atmosphere, reacted at 120° C. for 0.5 hours in a microwave reaction apparatus, and then reacted at 150° C. for 2 hours. Subsequently, 0.21 ml (2.3 mmol) of N,N-dimethylethane-1,2-diamine was added thereto at room temperature and then reacted at room temperature for 2 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=70:30→50:50 (V/V)), and a fraction containing the compound of interest was concentrated under reduced pressure. The obtained concentration residue was subjected to preparative column chromatography (apparatus 1, silica gel, elution solvent: 1,2-dichloroethane:methanol=99:1→92:8 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=50:50 (V/V)), and a fraction containing the compound of interest was concentrated under reduced pressure, followed by the distilling off of acetonitrile. The obtained concentrate was subjected to extraction with ethyl acetate, and subsequently, the whole organic layer was washed with saturated saline, then dried over anhydrous magnesium sulfate, filtered, and concentrated under reduced pressure. The obtained concentration residue was dissolved by the addition of ethyl acetate, then n-hexane was added thereto, and the deposited solid was collected by filtration and dried under reduced pressure to obtain 23.6 mg of the title compound (yield: 11% [calculation value with the purity of the starting material defined as 100%]) as a white solid.

Mass spectrum (CI, m/z): 474 [M+1]$^+$.

$^1$H-NMR spectrum (400 MHz, DMSO-d$_6$) δ: 12.26 & 11.73 (br s, total 1H), 9.58 (s, 1H), 7.81 (br s, 1H), 7.30 (dd, J=1.3, 7.8 Hz, 1H), 7.23-7.11 (m, 2H), 4.61 (br s, 2H), 2.56-2.41 (m, 2H), 2.27-2.12 (m, 5H), 1.90-1.73 (m, 2H), 1.64 (s, 6H), 0.09 (s, 9H).

Example 32

N-(2-Fluoro-3-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-123)

[Chemical Formula 50]

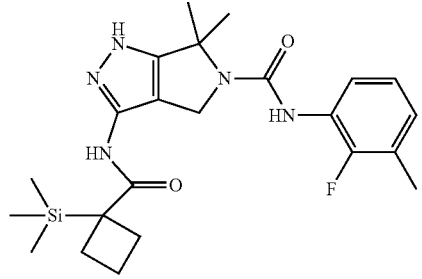

To a solution of 120 mg (0.272 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.150 ml (0.861 mmol) of DIPEA and 100 mg (0.799 mmol) of 2-fluoro-3-methylaniline were added at room temperature in an argon atmosphere and reacted at 90° C. for 11 hours with stirring. Subsequently, the reaction solution was cooled to room temperature, and 0.150 ml (1.38 mmol) of N,N-dimethylethane-1,2-diamine was added thereto at room temperature and then reacted at room temperature for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=60: 40→20:80 (V/V)), and a fraction containing the compound of interest was concentrated under reduced pressure. The obtained concentration residue was dissolved by the addition of methanol, then water was added thereto, and the deposited solid was collected by filtration and dried under reduced pressure to obtain 42.0 mg of the title compound (yield: 34% [calculation value with the purity of the starting material defined as 100%]) as a white solid.

Mass spectrum (CI, m/z): 458 [M+1]$^+$.

$^1$H-NMR spectrum (400 MHz, DMSO-d$_6$) δ: 12.27 & 11.76 (br s, total 1H), 9.61 (br s, 1H), 7.88-7.57 (m, 1H), 7.52-7.29 (m, 1H), 7.02-6.92 (m, 2H), 4.62 (br s, 2H), 2.56-2.41 (m, 2H), 2.29-2.13 (m, 5H), 1.93-1.72 (m, 2H), 1.65 (s, 6H), 0.09 (s, 9H).

Example 33

N-(2-Fluoro-5-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-127)

[Chemical Formula 51]

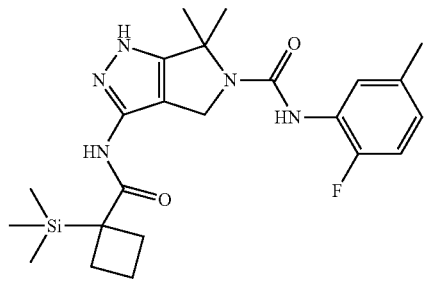

To a solution of 103 mg (0.273 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of 1,4-dioxane, 0.085 ml (0.65 mmol) of 2-fluoro-5-methylphenyl isocyanate was added at room temperature in an argon atmosphere and reacted at room temperature for 0.5 hours with stirring. Subsequently, 0.140 ml (1.29 mmol) of N,N-dimethylethane-1,2-diamine was added to the reaction solution at room temperature and then reacted at room temperature for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=100: 0→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=40:60 (V/V)), and a fraction containing the compound of interest was subjected to extraction by the addition of ethyl acetate. The obtained organic layer was washed with water, dried over anhydrous sodium sulfate, then filtered, and concentrated under reduced pressure.

The obtained concentration residue was dissolved by the addition of methanol, then water was added thereto, and the deposited solid was collected by filtration and dried under reduced pressure to obtain 63.6 mg of the title compound (yield: 51%) as a white solid.

Mass spectrum (CI, m/z): 458 [M+1]$^+$.

$^1$H-NMR spectrum (400 MHz, DMSO-d$_6$) δ: 12.27 & 11.79 (br s, total 1H), 9.62 (br s, 1H), 7.74 (br s, 1H), 7.41 (br s, 1H), 7.04 (dd, J=8.4, 10.8 Hz, 1H), 6.91-6.84 (m, 1H), 4.61 (br s, 2H), 2.56-2.40 (m, 2H), 2.30-2.14 (m, 5H), 1.93-1.72 (m, 2H), 1.65 (s, 6H), 0.09 (s, 9H).

Example 34

N-(5-Fluoro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-361)

[Chemical Formula 52]

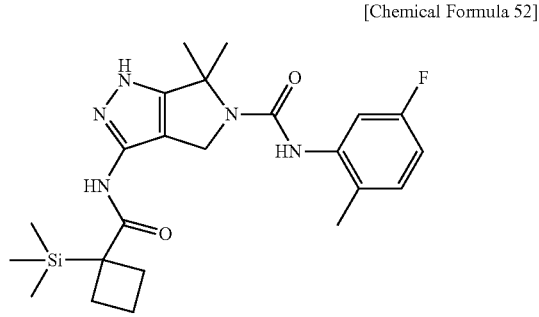 [SMILES: Cc1ccc(F)cc1NC(=O)N1Cc2c(NC(=O)C3([Si](C)(C)C)CCC3)n[nH]c2C1(C)C]

To a solution of 103 mg (0.273 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of 1,4-dioxane, 0.085 ml (0.66 mmol) of 5-fluoro-2-methylphenyl isocyanate was added at room temperature in an argon atmosphere and reacted at room temperature for 1 hour with stirring. Subsequently, the reaction solution was cooled in ice, and 0.140 ml (1.29 mmol) of N,N-dimethylethane-1,2-diamine was added thereto and then reacted at 0° C. for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The organic layer was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=100:0→50:50 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous potassium dihydrogen phosphate solution=40:60 (V/V)), and a fraction containing the compound of interest was subjected to extraction by the addition of ethyl acetate. The obtained organic layer was washed with water, dried over anhydrous sodium sulfate, then filtered, and concentrated under reduced pressure. The obtained concentration residue was dissolved by the addition of methanol, then water was added thereto, and the deposited solid was collected by filtration and dried under reduced pressure to obtain 42.7 mg of the title compound (yield: 34%) as a white solid.

Mass spectrum (CI, m/z): 458 [M+1]$^+$.

$^1$H-NMR spectrum (400 MHz, DMSO-d$_6$) δ: 12.28 & 11.78 (br s, total 1H), 9.60 (br s, 1H), 7.79-7.50 (m, 1H), 7.38-7.11 (m, 2H), 6.83 (dt, J=2.8, 8.4 Hz, 1H), 4.63 (br s, 2H), 2.58-2.39 (m, 2H), 2.27-2.12 (m, 5H), 1.92-1.73 (m, 2H), 1.66 (s, 6H), 0.09 (s, 9H).

Example 35

N-(2,4-Difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-101)

[Chemical Formula 53]

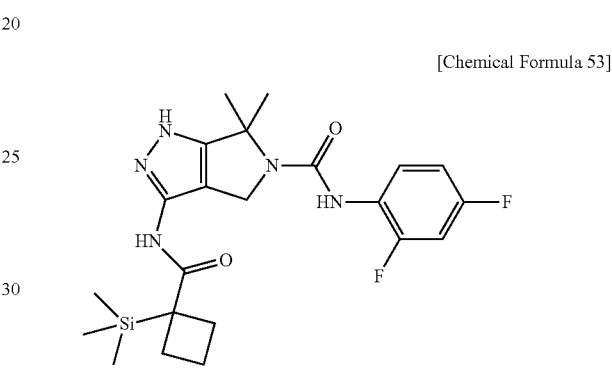

To a solution of 103 mg (0.273 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of 1,4-dioxane, 0.050 ml (0.42 mmol) of 2,4-difluoro-1-isocyanatobenzene was added at room temperature in an argon atmosphere and reacted at room temperature for 0.5 hours with stirring. Subsequently, 0.150 ml (1.38 mmol) of N,N-dimethylethane-1,2-diamine was added to the reaction solution at room temperature and then reacted at room temperature for 1 hour with stirring.

After completion of the reaction, a 5% aqueous potassium bisulfate solution was added to the reaction solution, followed by extraction with ethyl acetate. The whole organic layer thus obtained was washed with a saturated aqueous solution of sodium bicarbonate and saturated saline in this order, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous dipotassium biphosphate solution=65:35 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 50.2 mg of the title compound (yield: 40%) as a white solid.

Mass spectrum (CI, m/z): 462 [M+1]$^+$.

$^1$H-NMR spectrum (400 MHz, DMSO-d$_6$) δ: 12.27 & 11.77 (br s, total 1H), 9.62 (br s, 1H), 7.92 (br s, 1H), 7.59-7.39 (m, 1H), 7.22 (ddd, J=2.9, 9.1, 10.7 Hz, 1H), 7.03-6.96 (m, 1H), 4.61 (br s, 2H), 2.56-2.40 (m, 2H), 2.26-2.14 (m, 2H), 1.91-1.72 (m, 2H), 1.64 (s, 6H), 0.09 (s, 9H).

Example 36

N-(2,5-Difluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-103)

[Chemical Formula 54]

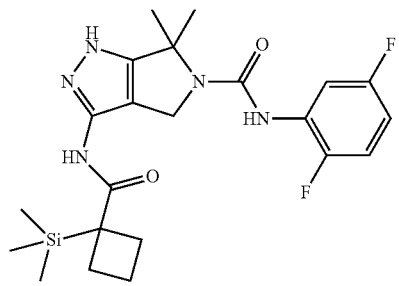

To a solution of 105 mg (0.277 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of 1,4-dioxane, 0.048 ml (0.41 mmol) of 2,5-difluorophenyl isocyanate was added at room temperature in an argon atmosphere and reacted at room temperature for 0.5 hours with stirring. Subsequently, 0.150 ml (1.38 mmol) of N,N-dimethylethane-1,2-diamine was added to the reaction solution at room temperature and then reacted at room temperature for 0.5 hours with stirring.

A 5% aqueous potassium bisulfate solution was added to the reaction solution, followed by extraction with ethyl acetate. The organic layer thus obtained was washed with saturated saline, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous dipotassium biphosphate solution=65:35 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 55.2 mg of the title compound (yield: 43%) as a white solid.

Mass spectrum (CI, m/z): 462 [M+1]$^+$.

$^1$H-NMR spectrum (400 MHz, DMSO-d$_6$) δ: 12.29 & 11.80 (br s, total 1H), 9.74-9.58 (m, 1H), 8.00-7.75 (m, 1H), 7.68-7.47 (m, 1H), 7.24 (ddd, J=5.2, 9.2, 10.3 Hz, 1H), 6.94-6.84 (m, 1H), 4.71-4.58 (m, 2H), 2.57-2.41 (m, 2H), 2.27-2.14 (m, 2H), 1.92-1.73 (m, 2H), 1.66 (br s, 6H), 0.09 (s, 9H).

Example 37

N-(2,5-Dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-379)

[Chemical Formula 55]

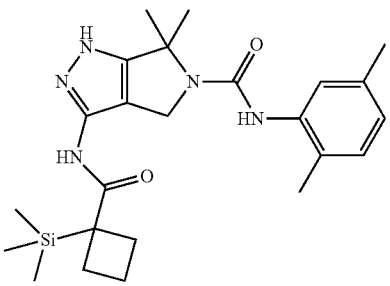

To a solution of 103 mg (0.273 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of 1,4-dioxane, 0.060 ml (0.43 mmol) of 2,5-dimethylphenyl isocyanate was added at room temperature in an argon atmosphere and reacted at room temperature for 0.5 hours with stirring. Subsequently, 0.150 ml (1.38 mmol) of N,N-dimethylethane-1,2-diamine was added to the reaction solution at room temperature and then reacted at room temperature for 1 hour with stirring.

After completion of the reaction, a 5% aqueous potassium bisulfate solution was added to the reaction solution, followed by extraction with ethyl acetate. The whole organic layer thus obtained was washed with a saturated aqueous solution of sodium bicarbonate and saturated saline in this order, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→60:40 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous dipotassium biphosphate solution=65:35 (V/V)), and a saturated aqueous solution of sodium bicarbonate was added to a fraction containing the compound of interest, followed by extraction with ethyl acetate. The whole organic layer thus obtained was washed with water and saturated saline in this order, dried over anhydrous magnesium sulfate, filtered, and concentrated under reduced pressure. The obtained concentration residue was dissolved by the addition of dichloromethane, then n-hexane was added thereto, and the deposited solid was collected by filtration and dried under reduced pressure to obtain 60.2 mg of the title compound (yield: 49%) as a white solid.

Mass spectrum (CI, m/z): 454 [M+1]$^+$.

$^1$H-NMR spectrum (400 MHz, DMSO-d$_6$) δ: 12.25 & 11.78 (br s, total 1H), 9.67-9.49 (m, 1H), 7.67-7.45 (m, 1H), 7.19-7.06 (m, 1H), 7.03 (d, J=7.6 Hz, 1H), 6.83 (dd, J=1.3, 7.6 Hz, 1H), 4.67-4.50 (m, 2H), 2.57-2.38 (m, 2H), 2.27-2.09 (m, 8H), 1.91-1.72 (m, 2H), 1.65 (br s, 6H), 0.09 (s, 9H).

Example 38

N-(2-Chloro-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-113) [Chemical Formula 56]

[Chemical Formula 56]

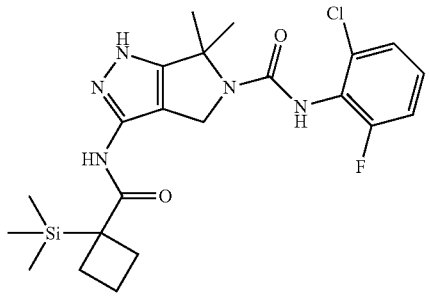

To a solution of 392 mg (0.890 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2.5 ml of 1,4-dioxane, 0.60 ml (3.4 mmol) of DIPEA and 807 mg (5.54 mmol) of 2-chloro-6-fluoroaniline were added at room temperature in a nitrogen atmosphere, reacted at 100° C. for 1 hour with stirring, and then reacted at 130° C. for 0.5 hours and further at 150° C. for 2 hours in a microwave reaction apparatus. Subsequently, 0.50 ml (4.6 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=80:20→65:35→50:50 (V/V)), and a fraction containing the compound of interest was concentrated under reduced pressure. The obtained concentration residue was subjected to preparative column chromatography (apparatus 2, silica gel, elution solvent:dichloromethane:methanol=100:0→99:1→98:2→97:3 (V/V)), and a fraction containing the compound of interest was concentrated under reduced pressure to obtain a white solid (approximately 70 mg). The obtained solid was subjected to preparative column chromatography (apparatus 3, ODS silica gel, elution solvent:acetonitrile:1 mM aqueous dipotassium biphosphate solution=50:50→80:20 (V/V)), and a fraction containing the compound of interest was concentrated under reduced pressure, followed by the distilling off of acetonitrile. The obtained concentration residue was subjected to extraction three times with ethyl acetate, and subsequently, the whole organic layer was washed with saturated saline, then dried over anhydrous magnesium sulfate, filtered, and concentrated under reduced pressure. The obtained concentration residue was dissolved in ethyl acetate, then n-hexane was added thereto, and the deposited solid was collected by filtration, washed with n-hexane, and then dried under reduced pressure to obtain 57.1 mg of the title compound (yield: 13% [calculation value with the purity of the starting material defined as 100%]) as a white solid.

Mass spectrum (CI, m/z): 478 [M+1]$^+$.

$^1$H-NMR spectrum (400 MHz, DMSO-d$_6$) δ:12.27 & 11.69 (br s, total 1H), 9.64-9.54 (m, 1H), 8.09-7.89 (m, 1H), 7.38-7.19 (m, 3H), 4.69-4.52 (m, 2H), 2.56-2.39 (m, 2H), 2.28-2.13 (m, 2H), 1.93-1.73 (m, 2H), 1.70-1.54 (m, 6H), 0.15-0.04 (m, 9H).

Example 39

N-(2,4-Dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-377)

[Chemical Formula 57]

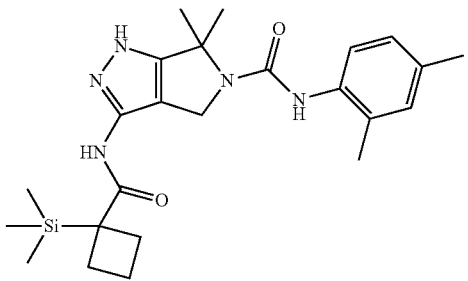

To a solution of 121 mg (0.273 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.23 ml (1.3 mmol) of DIPEA and 0.17 ml (1.4 mmol) of 2,4-dimethylaniline were added at room temperature in a nitrogen atmosphere and reacted at 100° C. for 4 hours with stirring. Subsequently, the reaction solution was cooled to room temperature, and 0.15 ml (1.4 mmol) of N,N-dimethylethane-1,2-diamine was added thereto at room temperature and then reacted at room temperature for 2 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=80:20→65:35→50:50→40:60 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 99.6 mg of the title compound (yield: 80%) as a white solid.

Mass spectrum (CI, m/z): 454 [M+1]$^+$.

$^1$H-NMR spectrum (400 MHz, DMSO-d$_6$) δ: 12.25 & 11.72 (br s, total 1H), 9.56 (s, 1H), 7.67-7.45 (m, 1H), 7.19-7.05 (m, 1H), 7.00-6.95 (m, 1H), 6.94-6.87 (m, 1H), 4.67-4.50 (m, 2H), 2.56-2.39 (m, 2H), 2.28-2.10 (m, 8H), 1.93-1.72 (m, 2H), 1.71-1.55 (m, 6H), 0.09 (s, 9H).

Example 40

3-[1-(Ethyldimethylsilyl)cyclobutanecarboxamido]-N-(2-fluorophenyl)-6,6-dimethyl-4,6-dihydropyrrolo[3,4-c]pyrazole-5(1H)-carboxamide (Compound No. IV-4)

[Chemical Formula 58]

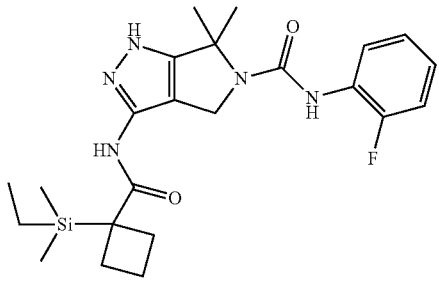

To a solution of 118 mg (0.301 mmol) of ethyl 3-[1-(ethyldimethylsilyl)cyclobutanecarboxamido]-6,6-dimethyl-5,6-dihydropyrrolo [3,4-c]pyrazole-2(4H)-carboxylate synthesized in the same way as in Reference Example 7 in 2 ml of 1,4-dioxane, 0.050 ml (0.44 mmol) of 1-fluoro-2-isocyanatobenzene was added at room temperature in a nitrogen atmosphere and reacted at room temperature for 50 minutes with stirring. Subsequently, 0.17 ml (1.6 mmol) of N,N-dimethylethane-1,2-diamine was added to the reaction solution at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=80:20→65:35→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=50:50 (V/V)), and a fraction containing the compound of interest was concentrated under reduced pressure, followed by the distilling off of acetonitrile. The obtained concentrate was subjected to extraction three times with ethyl acetate, and subsequently, the whole organic layer was washed with saturated saline, then dried over anhydrous magnesium sulfate, filtered, and concentrated under reduced pressure. The obtained concentration residue was dissolved in ethyl acetate, then n-hexane was added thereto, and the deposited solid was collected by filtration, washed with n-hexane, and then dried under reduced pressure to obtain 65.1 mg of the title compound (yield: 47%) as a white solid.

Mass spectrum (CI, m/z): 458 [M+1]$^+$.

$^1$H-NMR spectrum (400 MHz, DMSO-d$_6$) δ: 12.28 & 11.76 (br s, total 1H), 9.61 (br s, 1H), 7.92-7.48 (m, 2H), 7.21-7.13 (m, 1H), 7.13-7.05 (m, 2H), 4.63 (br s, 2H), 2.56-2.42 (m, 2H), 2.29-2.14 (m, 2H), 1.93-1.73 (m, 2H), 1.65 (s, 6H), 0.92 (t, J=7.9 Hz, 3H), 0.59 (q, J=7.9 Hz, 2H), 0.08 (s, 6H).

Example 41

6,6-Dimethyl-N-(3-methylisothiazol-4-yl)-3-[1-(trimethylsilyl)cyclobutanecarboxamido]-4,6-dihydropyrrolo[3,4-c]pyrazole-5 (1H)-carboxamide (Compound No. IV-1035)

[Chemical Formula 59]

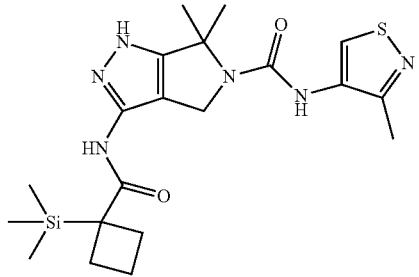

To a solution of 142 mg (0.323 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.28 ml (1.6 mmol) of DIPEA and 197 mg (1.72 mmol) of 3-methylisothiazol-4-amine were added at room temperature in a nitrogen atmosphere and reacted at 100° C. for 2 hours with stirring. Subsequently, the reaction solution was cooled to room temperature, and 0.18 ml (1.7 mmol) of N,N-dimethylethane-1,2-diamine was added thereto at room temperature and then reacted at room temperature for 1.5 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=70: 30→60:40→50:50→40:60 (V/V)), and a fraction containing the compound of interest was concentrated under reduced pressure. The obtained concentration residue was subjected to preparative column chromatography (apparatus 2, silica gel, elution solvent:dichloromethane:methanol=99:1→98: 2→97:3→95:5 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 102 mg of the title compound (yield: 71%) as a white solid.

Mass spectrum (CI, m/z): 447 [M+1]$^+$.

$^1$H-NMR spectrum (400 MHz, DMSO-d$_6$) δ: 12.28 & 11.79 (br s, total 1H), 9.73-9.54 (m, 1H), 8.70-8.54 (m, 1H), 8.00-7.74 (m, 1H), 4.71-4.53 (m, 2H), 2.59-2.40 (m, 2H), 2.33 (s, 3H), 2.27-2.14 (m, 2H), 1.91-1.73 (m, 2H), 1.72-1.57 (m, 6H), 0.09 (s, 9H).

Example 42

6,6-Dimethyl-N-(thiophen-2-yl)-3-[1-(trimethylsilyl) cyclobutanecarboxamido]-4,6-dihydropyrrolo[3,4-c] pyrazole-5(1H)-carboxamide (Compound No. IV-1043)

[Chemical Formula 60]

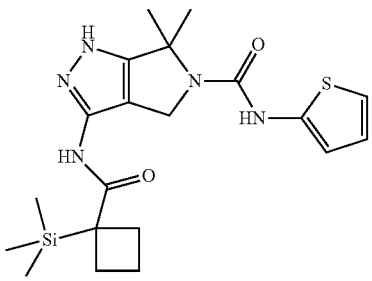

To a solution of 129 mg (0.341 mmol) of ethyl 6,6-dimethyl-3-[1-(trimethylsilyl)cyclobutanecarboxamido]-5, 6-dihydropyrrolo[3,4-c]pyrazole-2(4H)-carboxylate synthesized in the same way as in Reference Example 3 in 2 ml of 1,4-dioxane, 0.060 ml (0.59 mmol) of 2-isocyanatothiophene was added at room temperature in an argon atmosphere and reacted at room temperature for 1 hour with stirring. Subsequently, 0.185 ml (1.98 mmol) of N,N-dimethylethane-1,2-diamine was added to the reaction solution at room temperature and then reacted at room temperature for 1 hour with stirring.

After completion of the reaction, an aqueous potassium bisulfate solution was added to the reaction solution, followed by extraction with ethyl acetate. The organic layer was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=56: 44→35:65 (V/V)), and a fraction containing the compound of interest was concentrated under reduced pressure. The obtained concentration residue was subjected to preparative column chromatography (apparatus 1, DIOL silica gel, elution solvent:n-hexane:ethyl acetate=79:21→50:50 (V/V)), and a fraction containing the compound of interest was concentrated under reduced pressure. The obtained concentration residue was dissolved by the addition of ethyl acetate, then n-hexane was added thereto, and the deposited solid was collected by filtration and dried under reduced pressure to obtain 68.7 mg of the title compound (yield: 47%) as a white solid.

Mass spectrum (CI, m/z): 432 [M+1]$^+$.

$^1$H-NMR spectrum (400 MHz, DMSO-d$_6$) δ: 12.28 & 11.63 (br s, total 1H), 9.60 (br s, 1H), 9.48-9.28 (m, 1H), 6.84-6.64 (m, 3H), 4.61 (br s, 2H), 2.58-2.42 (m, 2H), 2.28-2.14 (m, 2H), 1.93-1.74 (m, 2H), 1.67 (s, 6H), 0.10 (s, 9H).

Example 43

6,6-Dimethyl-N-(thiophen-3-yl)-3-[1-(trimethylsilyl) cyclobutanecarboxamido]-4,6-dihydropyrrolo[3,4-c] pyrazole-5(1H)-carboxamide (Compound No. IV-1045)

[Chemical Formula 61]

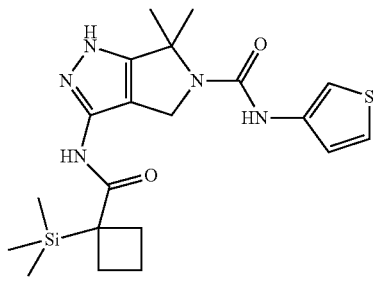

To a solution of 129 mg (0.341 mmol) of ethyl 6,6-dimethyl-3-[1-(trimethylsilyl)cyclobutanecarboxamido]-5, 6-dihydropyrrolo[3,4-c]pyrazole-2(4H)-carboxylate synthesized in the same way as in Reference Example 3 in 2 ml of 1,4-dioxane, 0.060 ml (0.59 mmol) of 3-isocyanatothiophene was added at room temperature in an argon atmosphere and reacted at room temperature for 2 hours with stirring. Subsequently, 0.19 ml (2.0 mmol) of N,N-dimethylethane-1,2-diamine was added to the reaction solution at room temperature and then reacted at room temperature for 1 hour with stirring.

After completion of the reaction, an aqueous potassium bisulfate solution was added to the reaction solution, followed by extraction with ethyl acetate. The organic layer was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=47: 53→35:65 (V/V)), and a fraction containing the compound of interest was concentrated under reduced pressure. The obtained concentration residue was subjected to preparative column chromatography (apparatus 1, DIOL silica gel, elution solvent:n-hexane:ethyl acetate=80:20→59:41 (V/V)), and a fraction containing the compound of interest was concentrated under reduced pressure. The obtained concentration residue was dissolved by the addition of ethyl acetate, then n-hexane was added thereto, and the deposited solid was collected by filtration and dried under reduced pressure to obtain 48.4 mg of the title compound (yield: 33%) as a white solid.

Mass spectrum (CI, m/z): 432 [M+1]$^+$.

$^1$H-NMR spectrum (400 MHz, DMSO-d$_6$) δ: 12.26 & 11.68 (s, total 1H), 9.58 (s, 1H), 8.62-8.46 (m, 1H), 7.38-7.29 (m, 2H), 7.28-7.18 (m, 1H), 4.66-4.49 (m, 2H), 2.59-2.38 (m, 2H), 2.28-2.13 (m, 2H), 1.93-1.73 (m, 2H), 1.72-1.57 (m, 6H), 0.09 (s, 9H).

Example 44

N-(2,6-Difluoro-4-methoxyphenyl)-6,6-dimethyl-3-[1-(trimethyl silyl)cyclobutanecarboxamido]-4,6-dihydropyrrolo[3,4-c]pyrazole-5(1H)-carboxamide (Compound No. IV-615)

[Chemical Formula 62]

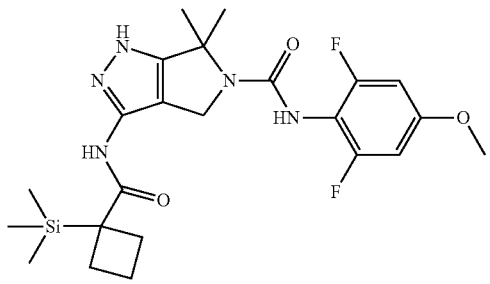

To a solution of 164 mg (0.372 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 1.5 ml of 1,4-dioxane, 0.33 ml (1.9 mmol) of DIPEA and 516 mg (3.24 mmol) of 2,6-difluoro-4-methoxyaniline were added at room temperature in a nitrogen atmosphere and reacted at 100° C. for 9.5 hours with stirring. Subsequently, the reaction solution was cooled to room temperature, and 0.20 ml (1.8 mmol) of N,N-dimethylethane-1,2-diamine was added thereto at room temperature and then reacted at room temperature for 4 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=75:25→60:40→45:55 (V/V)), and a fraction containing the compound of interest was concentrated under reduced pressure. The obtained concentration residue was subjected to preparative column chromatography (apparatus 1, silica gel, elution solvent: 1,2-dichloroethane:methanol=99:1→98:2→95:5 (V/V)), and a fraction containing the compound of interest was concentrated under reduced pressure. The obtained concentration residue was dissolved in ethyl acetate, then n-hexane was added thereto, and the deposited solid was collected by filtration, washed with n-hexane, and then dried under reduced pressure to obtain 105 mg of the title compound (yield: 57% [calculation value with the purity of the starting material defined as 100%]) as a white solid.

Mass spectrum (CI, m/z): 492 [M+1]$^+$.

$^1$H-NMR spectrum (400 MHz, DMSO-d$_6$) δ: 12.26 & 11.72 (br s, total 1H), 9.59 (s, 1H), 7.80-7.59 (m, 1H), 6.79-6.69 (m, 2H), 4.64-4.47 (m, 2H), 3.77 (s, 3H), 2.56-2.40 (m, 2H), 2.28-2.11 (m, 2H), 1.92-1.71 (m, 2H), 1.69-1.53 (m, 6H), 0.13-0.05 (m, 9H).

Example 45

N-(2-Fluoro-6-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-161)

[Chemical Formula 63]

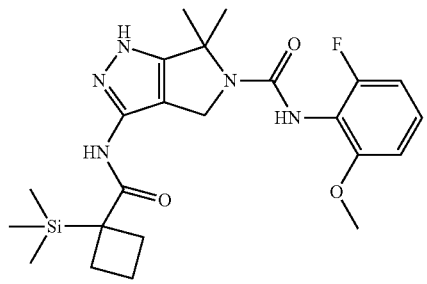

To a solution of 58.5 mg (0.344 mmol) of 2-fluoro-6-methoxybenzoic acid and 0.065 ml (0.37 mmol) of DIPEA in 2 ml of 1,4-dioxane, 0.075 ml (0.35 mmol) of DPPA was added at room temperature in an argon atmosphere and reacted at room temperature for 0.5 hours and subsequently at 100° C. for 1 hour with stirring. The reaction solution was cooled to room temperature, and then, a solution of 90 mg (0.24 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of 1,4-dioxane was added to the reaction solution at room temperature and reacted at room temperature for 1 hour with stirring. Subsequently, 0.125 ml (1.15 mmol) of N,N-dimethylethane-1,2-diamine was added to the reaction solution at room temperature and then reacted at room temperature for 0.5 hours with stirring.

After completion of the reaction, a 5% aqueous potassium bisulfate solution was added to the reaction solution, followed by extraction with ethyl acetate. The organic layer was washed with a saturated aqueous solution of sodium bicarbonate and saturated saline in this order, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 2, silica gel, elution solvent:n-hexane:ethyl acetate=80:20→0:100 (V/V)), and a fraction containing the compound of interest was concentrated under reduced pressure. The obtained concentration residue was dissolved by the addition of ethyl acetate, then n-hexane was added thereto, and the deposited solid was collected by filtration and dried under reduced pressure to obtain 42.8 mg of the title compound (yield: 38%) as a white solid.

Mass spectrum (CI, m/z): 474 [M+1]$^+$.

$^1$H-NMR spectrum (400 MHz, DMSO-d$_6$) δ: 12.25 & 11.76 (br s, total 1H), 9.57 (br s, 1H), 7.46-7.27 (m, 1H), 7.19 (dt, J=6.5, 8.4 Hz, 1H), 6.88-6.83 (m, 1H), 6.82-6.75 (m, 1H), 4.61-4.49 (m, 2H), 3.79 (s, 3H), 2.57-2.41 (m, 2H), 2.26-2.13 (m, 2H), 1.90-1.71 (m, 2H), 1.69-1.54 (m, 6H), 0.09 (s, 9H).

Example 46

N-[2-Fluoro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-153)

[Chemical Formula 64]

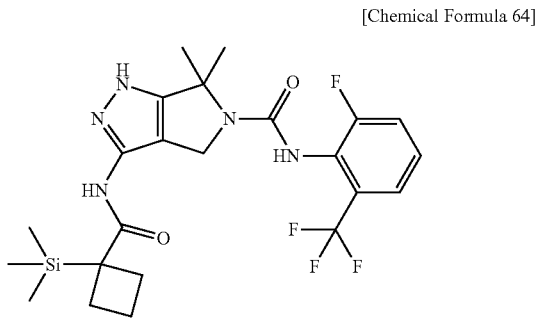 [SMILES: CC1(C)c2[nH]nc(NC(=O)C3([Si](C)(C)C)CCC3)c2CN1C(=O)Nc1c(F)cccc1C(F)(F)F]

To a solution of 84.2 mg (0.405 mmol) of 2-fluoro-6-(trifluoromethyl)benzoic acid and 0.075 ml (0.43 mmol) of DIPEA in 2 ml of 1,4-dioxane, 0.085 ml (0.40 mmol) of DPPA was added at room temperature in an argon atmosphere and reacted at room temperature for 0.5 hours and subsequently at 100° C. for 1 hour with stirring. The reaction solution was cooled to room temperature, and then, a solution of 96 mg (0.25 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of 1,4-dioxane was added to the reaction solution at room temperature and reacted at room temperature for 16 hours with stirring. Subsequently, 0.145 ml (1.33 mmol) of N,N-dimethylethane-1,2-diamine was added to the reaction solution at room temperature and then reacted at room temperature for 1 hour with stirring.

After completion of the reaction, a 5% aqueous potassium bisulfate solution was added to the reaction solution, followed by extraction with ethyl acetate. The organic layer was washed with a saturated aqueous solution of sodium bicarbonate and saturated saline in this order, dried over anhydrous magnesium sulfate, then filtered, and concentrated under reduced pressure. The obtained concentration residue was subjected to preparative column chromatography (apparatus 2, DIOL silica gel, elution solvent:n-hexane:ethyl acetate=90:10→50:50 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=60:40-80:20 (V/V)), and the operation of separating a fraction containing the compound of interest into an organic layer and an aqueous layer was performed by the addition of ethyl acetate and a saturated aqueous solution of sodium bicarbonate. The obtained organic layer was washed with saturated saline, then dried over anhydrous magnesium sulfate, filtered, and concentrated under reduced pressure. The obtained concentration residue was dissolved by the addition of ethyl acetate, then n-hexane was added thereto, and the deposited solid was collected by filtration and dried under reduced pressure to obtain 33.9 mg of the title compound (yield: 26%) as a white solid.

Mass spectrum (CI, m/z): 512 [M+1]$^+$.

$^1$H-NMR spectrum (400 MHz, DMSO-d$_6$) δ: 12.27 & 11.78 (br s, total 1H), 9.68-9.57 (m, 1H), 8.00-7.82 (m, 1H), 7.62-7.49 (m, 3H), 4.66-4.50 (m, 2H), 2.56-2.41 (m, 2H), 2.27-2.14 (m, 2H), 1.92-1.72 (m, 2H), 1.67-1.51 (m, 6H), 0.09 (s, 9H).

Example 47

N-(5-Chloro-2-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-367)

[Chemical Formula 65]

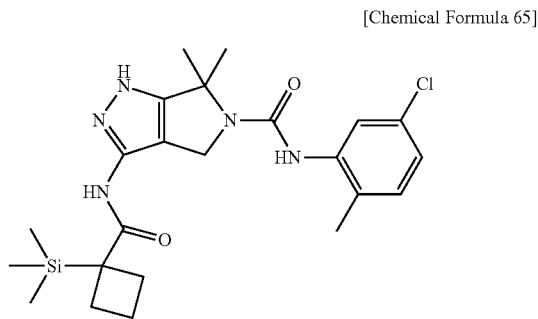 [SMILES: Cc1ccc(Cl)cc1NC(=O)N1Cc2c(NC(=O)C3([Si](C)(C)C)CCC3)n[nH]c2C1(C)C]

To a solution of 150 mg (0.340 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.474 ml (2.72 mmol) of DIPEA and 0.204 ml (1.70 mmol) of 5-chloro-2-methylaniline were added at room temperature in an argon atmosphere, reacted at 100° C. for 6 hours with stirring, and subsequently reacted at room temperature for 60 hours. Subsequently, 0.318 ml (3.40 mmol) of N,N-dimethylethane-1,2-diamine was added to the reaction solution at room temperature and then reacted at room temperature for 1 hour with stirring.

After completion of the reaction, a saturated aqueous solution of ammonium chloride was added to the reaction solution, followed by extraction with ethyl acetate. The organic layer was washed with saturated saline, dried over anhydrous magnesium sulfate, then filtered, and concentrated under reduced pressure. The obtained concentration residue was subjected to preparative column chromatography (apparatus 1, silica gel, elution solvent: 1,2-dichloroethane:methanol=95:5 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=50:50 (V/V)), and a fraction containing the compound of interest was concentrated under reduced pressure, followed by the distilling off of acetonitrile. The obtained concentrate was subjected to extraction with ethyl acetate, and the whole organic layer thus obtained was washed with saturated saline, dried over anhydrous magnesium sulfate, then filtered, and concentrated under reduced pressure. The obtained concentration residue was dissolved by the addition of ethyl acetate, then n-hexane was added thereto, and the deposited solid was collected by filtration and dried under reduced pressure to obtain 50 mg of the title compound (yield: 31% [calculation value with the purity of the starting material defined as 100%]) as a white solid.

Mass spectrum (CI, m/z): 474 $[M+1]^+$.

$^1$H-NMR spectrum (400 MHz, DMSO-$d_6$) δ: 12.28 & 11.79 (br s, total 1H), 9.70-9.55 (m, 1H), 7.84-7.58 (m, 1H), 7.53-7.35 (m, 1H), 7.19 (d, J=8.2 Hz, 1H), 7.06 (dd, J=2.3, 8.2 Hz, 1H), 4.73-4.52 (m, 2H), 2.58-2.39 (m, 2H), 2.29-2.11 (m, 5H), 1.93-1.73 (m, 2H), 1.72-1.56 (m, 6H), 0.09 (s, 9H).

Example 48

N-(2,5-Dichlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-197)

[Chemical Formula 66]

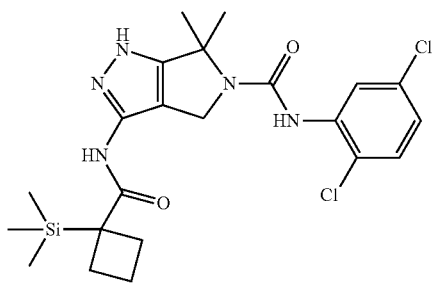

To a solution of 344 mg (0.909 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 6 ml of 1,4-dioxane, 209 mg (1.11 mmol) of 1,4-dichloro-2-isocyanatobenzene was added at room temperature in an argon atmosphere and reacted at room temperature for 2 hours with stirring.

After completion of the reaction, a saturated aqueous solution of ammonium chloride was added to the reaction solution, followed by extraction with ethyl acetate. The organic layer was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=93:7→72:28 (V/V)), and a fraction containing ethyl 5-[(2,5-dichlorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 3 ml of 1,4-dioxane, 0.49 ml (5.3 mmol) of N,N-dimethylethane-1,2-diamine was added and then reacted at room temperature for 1 hour with stirring.

After completion of the reaction, an aqueous potassium bisulfate solution was added to the reaction solution, followed by extraction with ethyl acetate. The obtained organic layer was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=50:50→30:70 (V/V)), and a fraction containing the compound of interest was concentrated under reduced pressure. The obtained concentration residue was dissolved by the addition of ethyl acetate, then n-hexane was added thereto, and the deposited solid was collected by filtration and dried under reduced pressure to obtain 172 mg of the title compound (yield: 38%) as a white solid.

Mass spectrum (CI, m/z): 494 $[M+1]^+$.

$^1$H-NMR spectrum (400 MHz, DMSO-$d_6$) δ: 12.31 & 11.84 (br s, total 1H), 9.77-9.54 (m, 1H), 8.03-7.81 (m, 1H), 7.81-7.56 (m, 1H), 7.50 (d, J=8.6 Hz, 1H), 7.16 (dd, J=2.5, 8.6 Hz, 1H), 4.65 (br s, 2H), 2.57-2.40 (m, 2H), 2.29-2.13 (m, 2H), 1.92-1.74 (m, 2H), 1.67 (s, 6H), 0.09 (s, 9H).

Example 49

N-(2-Cyclopropylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-39)

[Chemical Formula 67]

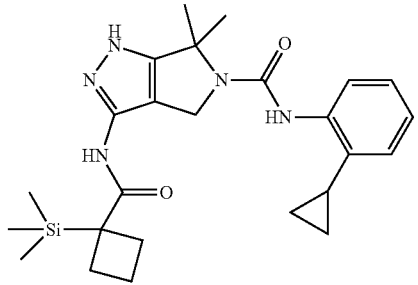

To a solution of 257 mg (1.59 mmol) of 2-cyclopropylbenzoic acid in 8 ml of toluene, 0.313 ml (1.80 mmol) of DIPEA and 0.353 ml (1.64 mmol) of DPPA were added at room temperature in an argon atmosphere and reacted at room temperature for 0.5 hours and subsequently at 100° C. for 1 hour with stirring. The reaction solution was cooled to room temperature, and then, a solution of 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of toluene was added to the reaction solution at 0° C. and reacted at 0° C. for 1 hour with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=80:20→60:40 (V/V)), and a fraction containing ethyl 5-[(2-cyclopropylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.494 ml (5.28 mmol) of N,N-dimethylethane-1,2-diamine was added at room temperature and then reacted at room temperature for 1 hour with stirring.

After completion of the reaction, a saturated aqueous solution of potassium bisulfate was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=60:40→40:60 (V/V)), and a fraction containing the compound of interest was concentrated under reduced pressure. The obtained concentration residue was dissolved in aqueous acetonitrile and freeze-dried to obtain 291 mg of the title compound (yield: 59%) as a white solid.

Mass spectrum (CI, m/z): 466 [M+1]$^+$.

$^1$H-NMR spectrum (400 MHz, DMSO-d$_6$) δ: 12.28 & 11.81 (br s, total 1H), 9.60 (br s, 1H), 7.73-7.62 (m, 1H), 7.55 (br s, 1H), 7.18-7.08 (m, 1H), 7.07-7.01 (m, 1H), 7.00-6.93 (m, 1H), 4.66 (br s, 2H), 2.60-2.39 (m, 2H), 2.28-2.12 (m, 2H), 2.02-1.91 (m, 1H), 1.89-1.75 (m, 2H), 1.68 (s, 6H), 0.97-0.86 (m, 2H), 0.65-0.54 (m, 2H), 0.09 (s, 9H).

Example 50

N-(2,6-Dichlorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-199)

[Chemical Formula 68]

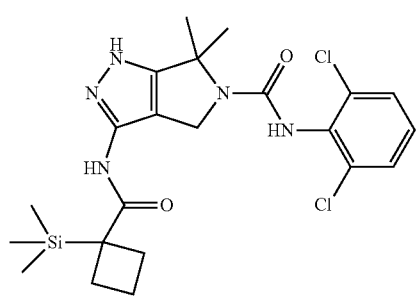

To a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 6 ml of 1,4-dioxane, 260 mg (1.38 mmol) of 1,3-dichloro-2-isocyanatobenzene was added at room temperature in an argon atmosphere and reacted at room temperature for 0.5 hours with stirring. Subsequently, 25.0 mg (0.133 mmol) of 1,3-dichloro-2-isocyanatobenzene was added to the reaction solution and further reacted for 1.5 hours with stirring. Then, the reaction solution was cooled in ice, and 0.580 ml (5.33 mmol) of N,N-dimethylethane-1,2-diamine was added thereto and then reacted at room temperature for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous sodium sulfate, then filtered, and concentrated under reduced pressure. The obtained concentration residue was subjected to preparative column chromatography (apparatus 1, DIOL silica gel, elution solvent:n-hexane:ethyl acetate=100:0→50:50 (V/V)), and a fraction containing the compound of interest was concentrated under reduced pressure. The obtained concentration residue was subjected to preparative column chromatography (apparatus 1, DNH silica gel, elution solvent: 1,2-dichloroethane:methanol=100:0→95:5 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=52:48 (V/V)), and a fraction containing the compound of interest was collected, followed by extraction with ethyl acetate. The whole organic layer thus obtained was washed with water, dried over anhydrous sodium sulfate, then filtered, and concentrated under reduced pressure. The obtained concentration residue was dissolved by the addition of aqueous acetonitrile and then freeze-dried to obtain 136 mg of the title compound (yield: 21%) as a white solid.

Mass spectrum (CI, m/z): 494 [M+1]$^+$.

$^1$H-NMR spectrum (400 MHz, DMSO-d$_6$) δ: 12.28 & 11.75 (br s, total 1H), 9.60 (s, 1H), 8.22-8.01 (m, 1H), 7.49 (d, J=8.1 Hz, 2H), 7.28 (t, J=8.1 Hz, 1H), 4.68-4.54 (m, 2H), 2.56-2.41 (m, 2H), 2.26-2.13 (m, 2H), 1.92-1.72 (m, 2H), 1.70-1.55 (m, 6H), 0.09 (s, 9H).

Example 51

6,6-Dimethyl-N-(2,4,6-trifluorophenyl)-3-[1-(trimethylsilyl)cyclobutanecarboxamido]-4,6-dihydropyrrolo[3,4-c]pyrazole-5(1H)-carboxamide (Compound No. IV-599)

[Chemical Formula 69]

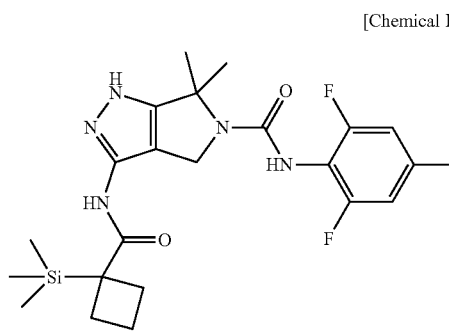

To a solution of 350 mg (1.99 mmol) of 2,4,6-trifluorobenzoic acid and 0.370 ml (2.12 mmol) of DIPEA in 2 ml of toluene, 0.430 ml (2.00 mmol) of DPPA was added at room temperature in an argon atmosphere and reacted at room temperature for 0.5 hours and subsequently at 100° C. for 1 hour with stirring. The reaction solution was cooled to room temperature, and then, a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2 (4H)-carboxylate synthesized in the same way as in Reference Example 3 in 2 ml of toluene was added to the reaction solution at room temperature and reacted at room temperature for 1 hour with stirring. Subsequently, 0.720 ml (6.61 mmol) of N,N-dimethylethane-1,2-diamine was added to the reaction solution at room temperature and then reacted at room temperature for 2 hours with stirring.

After completion of the reaction, a 5% aqueous potassium bisulfate solution was added to the reaction solution, followed by extraction with ethyl acetate. The whole organic layer thus obtained was washed with a saturated aqueous solution of sodium bicarbonate and saturated saline in this order, dried over anhydrous sodium sulfate, then filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=52:48 (V/V)), and a fraction containing the compound of interest was collected, followed by extraction with ethyl acetate. The whole organic layer thus obtained was washed with water, dried over anhydrous sodium sulfate, then filtered, and concentrated under reduced pressure. The obtained concentration residue was dissolved in aqueous acetonitrile and freeze-dried to obtain 236 mg of the title compound (yield: 37%) as a white solid.

Mass spectrum (CI, m/z): 480 [M+1]$^+$.

$^1$H-NMR spectrum (400 MHz, DMSO-d$_6$) δ: 12.27 & 11.73 (br s, total 1H), 9.61 (s, 1H), 8.00-7.81 (m, 1H), 7.26-7.13 (m, 2H), 4.59 (br s, 2H), 2.55-2.41 (m, 2H), 2.26-2.13 (m, 2H), 1.91-1.72 (m, 2H), 1.63 (br s, 6H), 0.09 (s, 9H).

Example 52

N-(2-Ethyl-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-389)

[Chemical Formula 70]

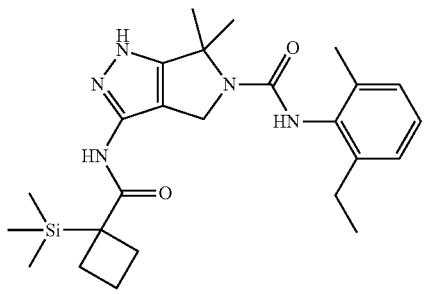

Reaction 1.

To a solution of 79.6 mg (0.210 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1.5 ml of 1,4-dioxane, 0.040 ml (0.26 mmol) of 1-ethyl-2-isocyanato-3-methylbenzene was added at room temperature in a nitrogen atmosphere and reacted at room temperature for 2 hours with stirring. Subsequently, 0.110 ml (1.01 mmol) of N,N-dimethylethane-1,2-diamine was added to the reaction solution at room temperature and then reacted at room temperature for 17 hours with stirring.

Reaction 2.

To a solution of 81.3 mg (0.215 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in a mixed solvent of 1.5 ml of 1,4-dioxane and 1.0 ml of THF, 0.040 ml (0.26 mmol) of 1-ethyl-2-isocyanato-3-methylbenzene was added at 0° C. in a nitrogen atmosphere and reacted at 0° C. for 2 hours with stirring. Subsequently, 0.110 ml (1.01 mmol) of N,N-dimethylethane-1,2-diamine was added to the reaction solution at room temperature and then reacted at room temperature for 17 hours with stirring.

Reaction 3.

To a solution of 79.7 mg (0.211 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1.5 ml of dichloromethane, 0.040 ml (0.26 mmol) of 1-ethyl-2-isocyanato-3-methylbenzene was added at room temperature in a nitrogen atmosphere and reacted at room temperature for 2 hours with stirring. Subsequently, 0.110 ml (1.01 mmol) of N,N-dimethylethane-1,2-diamine was added to the reaction solution at room temperature and then reacted at room temperature for 17 hours with stirring.

Reaction 4.

To a solution of 79.7 mg (0.211 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1.5 ml of dichloromethane, 0.040 ml (0.26 mmol) of 1-ethyl-2-isocyanato-3-methylbenzene was added at 0° C. in a nitrogen atmosphere and reacted at 0° C. for 2 hours with stirring. Subsequently, 0.110 ml (1.01 mmol) of N,N-dimethylethane-1,2-diamine was added to the reaction solution at room temperature and then reacted at room temperature for 17 hours with stirring.

Reaction 5.

To a solution of 80.2 mg (0.212 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1.5 ml of dichloromethane, 0.080 ml (0.46 mmol) of DIPEA and 0.040 ml (0.26 mmol) of 1-ethyl-2-isocyanato-3-methylbenzene were added in this order at 0° C. in a nitrogen atmosphere and reacted at 0° C. for 2 hours with stirring. Subsequently, 0.110 ml (1.01 mmol) of N,N-dimethylethane-1,2-diamine was added to the reaction solution at room temperature and then reacted at room temperature for 17 hours with stirring.

Reaction 6.

To a solution of 79.7 mg (0.211 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1.5 ml of pyridine, 0.040 ml (0.26 mmol) of 1-ethyl-2-isocyanato-3-methylbenzene was added at 0° C. in a nitrogen atmosphere and reacted at 0° C. for 2 hours with stirring. Subsequently, 0.110 ml (1.01 mmol) of N,N-dimethylethane-1,2-diamine was added to the reaction solution at room temperature and then reacted at room temperature for 17 hours with stirring.

After completion of the reaction, ethyl acetate was added to the reaction solution of reaction 3, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, elution solvent: 1,2-dichloroethane:methanol=98:2→97:3→95:5 (V/V)), and a fraction containing the compound of interest was concentrated under reduced pressure to obtain 78.6 mg of a white foam.

Also, the reaction solutions of reactions 1, 2, 4, 5, and 6 were united, and then, the same purification operation as above was performed to obtain 440 mg of a white foam.

These two products thus obtained were combined, dissolved in aqueous acetonitrile, and freeze-dried to obtain 429 mg of the title compound (yield: 72%) as a white solid.

Mass spectrum (CI, m/z): 468 [M+1]$^+$.

$^1$H-NMR spectrum (400 MHz, DMSO-d$_6$) δ: 12.25 & 11.74 (br s, total 1H), 9.56 (s, 1H), 7.51 (br s, 1H), 7.11-7.00 (m, 3H), 4.59 (br s, 2H), 2.57 (q, J=7.5 Hz, 2H), 2.53-2.41 (m, 2H), 2.26-2.12 (m, 5H), 1.88-1.73 (m, 2H), 1.63 (s, 6H), 1.11 (t, J=7.5 Hz, 3H), 0.09 (s, 9H).

Example 53

N-(2-Bromophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-15)

[Chemical Formula 71]

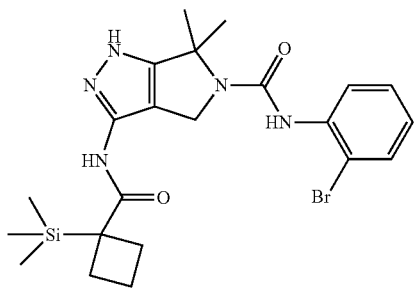

To a solution of 152 mg (0.345 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 and 0.300 ml (1.72 mmol) of DIPEA in 3 ml of 1,4-dioxane, 182 mg (1.06 mmol) of 2-bromoaniline was added at room temperature in an argon atmosphere and reacted at 100° C. for 30 hours with stirring. The reaction solution was cooled to room temperature, and then, 0.185 ml (1.70 mmol) of N,N-dimethylethane-1,2-diamine was added to the reaction solution at room temperature and reacted at room temperature for 0.5 hours with stirring.

After completion of the reaction, a 5% aqueous potassium bisulfate solution was added to the reaction solution, followed by extraction with ethyl acetate. The whole organic layer thus obtained was washed with a saturated aqueous solution of sodium bicarbonate and saturated saline in this order, then dried over anhydrous magnesium sulfate, filtered, and concentrated under reduced pressure. The obtained concentration residue was subjected to preparative column chromatography (apparatus 2, DIOL silica gel, elution solvent:n-hexane:ethyl acetate=90:10→50:50), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=65:35 (V/V)), and the operation of separating a fraction containing the compound of interest into an organic layer and an aqueous layer was performed by the addition of ethyl acetate and a saturated aqueous solution of sodium bicarbonate. The obtained organic layer was washed with saturated saline, dried over anhydrous magnesium sulfate, and concentrated under reduced pressure. The obtained concentration residue was dissolved by the addition of ethyl acetate, then n-hexane was added thereto, and the deposited solid was collected by filtration and dried under reduced pressure. The obtained solid was dissolved in aqueous acetonitrile and freeze-dried. The obtained solid was subjected again to preparative column chromatography (apparatus 2, DIOL silica gel, elution solvent:n-hexane:ethyl acetate=100:0→50:50), and a fraction containing the compound of interest was concentrated under reduced pressure. The obtained concentration residue was dissolved in aqueous acetonitrile and freeze-dried to obtain 20.5 mg of the title compound (yield: 12%) as a white solid.

Mass spectrum (CI, m/z): 504 [M+1]$^+$.

$^1$H-NMR spectrum (400 MHz, DMSO-d$_6$) δ: 12.30 & 11.89 (br s, total 1H), 9.74-9.57 (m, 1H), 7.79-7.54 (m, 3H), 7.36-7.29 (m, 1H), 7.08-7.00 (m, 1H), 4.69-4.55 (m, 2H), 2.58-2.40 (m, 2H), 2.28-2.14 (m, 2H), 1.91-1.74 (m, 2H), 1.73-1.57 (m, 6H), 0.15-0.04 (m, 9H).

Example 54

N-(5-Chloro-2-fluorophenyl)-6,6-dimethyl-3-[1-(trimethyl silyl)cyclobutanecarboxamido]-4,6-dihydropyrrolo[3,4-c]pyrazole-5 (1H)-carboxamide (Compound No. IV-111)

[Chemical Formula 72]

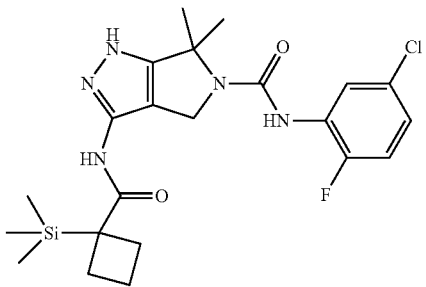

To a solution of 346 mg (1.98 mmol) of 5-chloro-2-fluorobenzoic acid in 10 ml of 1,4-dioxane, 0.391 ml (2.25 mmol) of DIPEA and 0.441 ml (2.05 mmol) of DPPA were added in this order at room temperature in an argon atmosphere and reacted at room temperature for 0.5 hours and subsequently at 100° C. for 1 hour with stirring. The reaction solution was cooled to room temperature, and then, a solution of 500 mg (1.32 mmol) of ethyl 6,6-dimethyl-3-[1-

(trimethylsilyl)cyclobutanecarboxamido]-5,6-dihydropyrrolo[3,4-c]pyrazole-2(4H)-carboxylate synthesized in the same way as in Reference Example 3 in 1 ml of 1,4-dioxane was added to the reaction solution at room temperature and reacted at room temperature for 2 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=95:5→75:25 (V/V)), and a fraction containing ethyl 5-[(5-chloro-2-fluorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.617 ml (6.60 mmol) of N,N-dimethylethane-1,2-diamine was added at room temperature and then reacted at room temperature for 1 hour with stirring.

After completion of the reaction, an aqueous potassium bisulfate solution was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=55:45→45:55 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=50:50 (V/V)), and a fraction containing the compound of interest was concentrated under reduced pressure, followed by the distilling off of acetonitrile. The obtained concentrate was subjected to extraction with ethyl acetate. The obtained organic layer was washed with saturated saline, dried over anhydrous magnesium sulfate, filtered, and dried under reduced pressure. The obtained concentration residue was dissolved in aqueous acetonitrile and freeze-dried to obtain 141 mg of the title compound (yield: 22%) as a white solid.

Mass spectrum (CI, m/z): 478 [M+1]$^+$.

$^1$H-NMR spectrum (400 MHz, DMSO-d$_6$) δ: 12.29 & 11.77 (br s, total 1H), 9.72-9.58 (m, 1H), 8.05-7.84 (m, 1H), 7.84-7.67 (m, 1H), 7.30-7.19 (m, 1H), 7.17-7.08 (m, 1H), 4.71-4.55 (m, 2H), 2.57-2.40 (m, 2H), 2.28-2.13 (m, 2H), 1.92-1.74 (m, 2H), 1.73-1.59 (m, 6H), 0.14-0.04 (m, 9H).

Example 55

N-(2-Chloro-5-fluorophenyl)-6,6-dimethyl-3-[1-(trimethyl silyl)cyclobutanecarboxamido]-4,6-dihydropyrrolo[3,4-c]pyrazole-5 (1H)-carboxamide
(Compound No. IV-191)

[Chemical Formula 73]

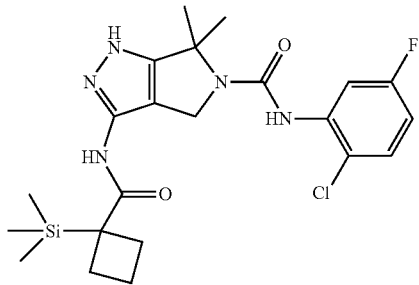

To a solution of 346 mg (1.98 mmol) of 2-chloro-5-fluorobenzoic acid in 5 ml of 1,4-dioxane, 0.391 ml (2.25 mmol) of DIPEA and 0.441 ml (2.05 mmol) of DPPA were added in this order at room temperature in an argon atmosphere and reacted at room temperature for 0.5 hours and subsequently at 100° C. for 1 hour with stirring. The reaction solution was cooled to room temperature, and then, a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2(4H)-carboxylate in 1 ml of 1,4-dioxane synthesized in the same way as in Reference Example 3 was added to the reaction solution at room temperature and reacted at room temperature for 2 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, silica gel, elution solvent: n-hexane:ethyl acetate=95:5→75:25 (V/V)), and a fraction containing ethyl 5-[(2-chloro-5-fluorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.62 ml (6.6 mmol) of N,N-dimethylethane-1,2-diamine was added at room temperature and then reacted at room temperature for 1 hour with stirring.

After completion of the reaction, an aqueous potassium bisulfate solution was added to the reaction solution, followed by extraction with ethyl acetate. The organic layer was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=55:45→45:55 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=50:50 (V/V)), and a fraction containing the compound of interest was concentrated under reduced pressure, followed by the distilling off of acetonitrile. The obtained concentrate was subjected to extraction with ethyl acetate. The whole organic layer thus obtained was washed with saturated saline, dried over anhydrous magnesium sulfate, then filtered, and dried under reduced pressure. The obtained concentration residue was dissolved in aqueous acetonitrile and freeze-dried to obtain 163 mg of the title compound (yield: 26%) as a white solid.

Mass spectrum (CI, m/z): 478 [M+1]$^+$.

$^1$H-NMR spectrum (400 MHz, DMSO-d$_6$) δ: 12.32 & 11.87 (br s, total 1H), 9.75-9.58 (m, 1H), 7.86-7.54 (m, 2H), 7.50 (dd, J=5.9, 8.9 Hz, 1H), 7.00-6.91 (m, 1H), 4.73-4.54 (m, 2H), 2.57-2.39 (m, 2H), 2.29-2.12 (m, 2H), 1.93-1.75 (m, 2H), 1.74-1.57 (m, 6H), 0.15-0.03 (m, 9H).

Example 56

6,6-Dimethyl-N-(2,3,6-trifluorophenyl)-3-[1-(trimethylsilyl)cyclobutanecarboxamido]-4,6-dihydropyrrolo[3,4-c]pyrazole-5(1H)-carboxamide (Compound No. IV-597)

[Chemical Formula 74]

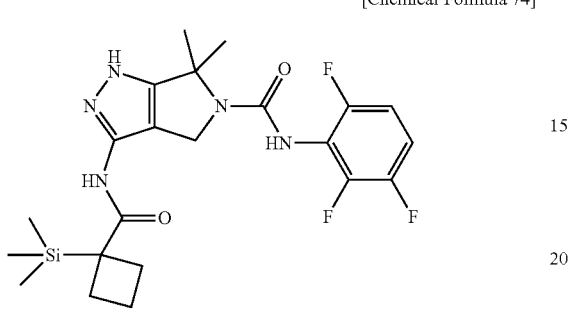

To a suspension of 356 mg (2.02 mmol) of 2,3,6-trifluorobenzoic acid in 4.0 ml of toluene, 0.380 ml (2.73 mmol) of triethylamine and 0.430 ml (2.00 mmol) of DPPA were added in this order at room temperature in an argon atmosphere and reacted at 100° C. for 1 hour with stirring. The reaction solution was cooled to room temperature, then added to a solution of 509 mg (1.35 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 4.0 ml of toluene at 0° C., and reacted at 0° C. for 1.5 hours with stirring. Subsequently, 0.730 ml (6.71 mmol) of N,N-dimethylethane-1,2-diamine was added to the reaction solution at room temperature and then reacted at room temperature for 2 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, n-hexane:ethyl acetate=80:20→70:30→60:40→50:50), and a fraction containing the compound of interest was concentrated under reduced pressure. The obtained concentration residue was subjected to preparative column chromatography (apparatus 1, silica gel, elution solvent: 1,2-dichloroethane:methanol=98:2→97:3 (V/V)), and a fraction containing the compound of interest was concentrated under reduced pressure. The obtained concentration residue was subjected to preparative column chromatography (apparatus 3, ODS silica gel, elution solvent: acetonitrile:1 mM aqueous potassium dihydrogen phosphate solution=50:50 (V/V)), and a fraction containing the compound of interest was concentrated under reduced pressure, followed by the distilling off of acetonitrile. The deposited solid was collected by filtration, washed with water, and then dried under reduced pressure. Subsequently, the obtained solid was dissolved in aqueous acetonitrile and freeze-dried to obtain 44.6 mg of the title compound (yield: 7%) as a white solid.

Mass spectrum (CI, m/z): 480 [M+1]$^+$.

$^1$H-NMR spectrum (400 MHz, DMSO-d$_6$) δ: 12.28 & 11.71 (br s, total 1H), 9.61 (s, 1H), 8.18 (br s, 1H), 7.41-7.29 (m, 1H), 7.18-7.10 (m, 1H), 4.62 (br s, 2H), 2.58-2.40 (m, 2H), 2.28-2.12 (m, 2H), 1.93-1.72 (m, 2H), 1.63 (br s, 6H), 0.09 (s, 9H).

Example 57

N-(2-Chloro-6-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-247)

[Chemical Formula 75]

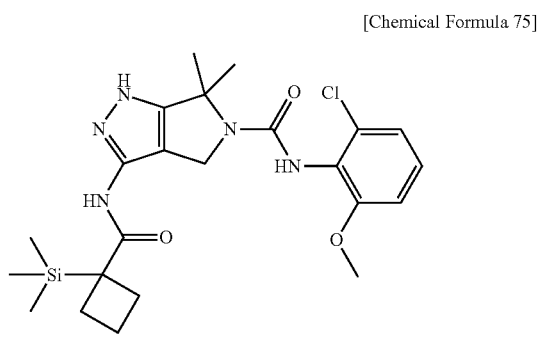 [SMILES: COc1cccc(Cl)c1NC(=O)N1Cc2c(NC(=O)C3([Si](C)(C)C)CCC3)n[nH]c2C1(C)C]

To a solution of 370 mg (1.98 mmol) of 2-chloro-6-methoxybenzoic acid in 10 ml of 1,4-dioxane, 0.391 ml (2.25 mmol) of DIPEA and 0.427 ml (1.98 mmol) of DPPA were added in this order at room temperature in an argon atmosphere and reacted at room temperature for 0.5 hours and subsequently at 100° C. for 1 hour with stirring. The reaction solution was cooled to room temperature, and then, a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1 ml of 1,4-dioxane was added to the reaction solution at room temperature and reacted at room temperature for 2 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=72:28→30:70 (V/V)), and a fraction containing ethyl 5-[(2-chloro-6-methoxyphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 3 ml of 1,4-dioxane, 0.617 ml (6.60 mmol) of N,N-dimethylethane-1,2-diamine was added at room temperature and then reacted at room temperature for 15 hours with stirring.

After completion of the reaction, an aqueous potassium bisulfate solution was added to the reaction solution, followed by extraction with ethyl acetate. The organic layer was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=70:30→30:70 (V/V)), and a fraction containing the compound of interest was concentrated under reduced pressure. The obtained concentration residue was subjected to preparative column chromatography (apparatus 3, ODS silica gel, elution solvent:acetonitrile:1 mM aqueous potassium dihydrogen phosphate solution=50:50 (V/V)), and a fraction containing the compound of interest was concentrated under reduced pressure, followed by the distilling off of acetonitrile. The obtained concentrate was subjected to extraction with ethyl acetate. The obtained organic layer was washed with saturated saline, dried over anhydrous magnesium sulfate, filtered, and dried under reduced pressure. The obtained concentration residue was dissolved in aqueous acetonitrile and freeze-dried to obtain 172 mg of the title compound (yield: 27%) as a white solid.

Mass spectrum (CI, m/z): 490 [M+1]$^+$.

$^1$H-NMR spectrum (400 MHz, DMSO-d$_6$) δ: 12.25 & 11.75 (br s, total 1H), 9.55 (br s, 1H), 7.64-7.43 (m, 1H), 7.20 (t, J=8.3 Hz, 1H), 7.08-6.95 (m, 2H), 4.66-4.47 (m, 2H), 3.78 (s, 3H), 2.56-2.39 (m, 2H), 2.28-2.11 (m, 2H), 1.93-1.72 (m, 2H), 1.71-1.52 (m, 6H), 0.09 (s, 9H).

Example 58

N-[2-(1,1-Difluoroethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-45)

[Chemical Formula 76]

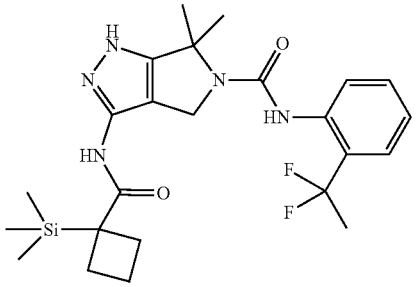

To a suspension of 334 mg (1.79 mmol) of 2-(1,1-difluoroethyl)benzoic acid in 4.0 ml of toluene, 0.410 ml (2.35 mmol) of DIPEA and 0.390 ml (1.81 mmol) of DPPA were added in this order at room temperature in a nitrogen atmosphere and reacted at room temperature for 50 minutes and subsequently at 100° C. for 75 minutes with stirring. The reaction solution was cooled to room temperature and then diluted with 2.0 ml of dichloromethane, and subsequently, this solution was added to a solution of 462 mg (1.22 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 4.0 ml of dichloromethane at 0° C. and reacted at 0° C. for 2 hours with stirring.

After completion of the reaction, a 5% aqueous potassium bisulfate solution was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=80: 20→70:30→50:50→40:60→30:70 (V/V)), and a fraction containing ethyl 5-{[2-(1,1-difluoroethyl)phenyl]carbamoyl}-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of 334 mg (0.594 mmol) of obtained ethyl 5-{[2-(1,1-difluoroethyl)phenyl]carbamoyl}-6,6-dimethyl-3-[1-(trimethylsilyl)cyclobutanecarboxamido]-5,6-dihydropyrrolo[3,4-c]pyrazole-2(4H)-carboxylate in a mixed solvent of 3.0 ml of THF and 0.50 ml of ethanol, 0.330 ml (3.03 mmol) of N,N-dimethylethane-1,2-diamine was added at room temperature in a nitrogen atmosphere and then reacted at room temperature for 1.5 hours with stirring.

After completion of the reaction, a 5% aqueous potassium bisulfate solution was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=80:20→65:35→50:50 (V/V)), and a fraction containing the compound of interest was concentrated under reduced pressure. The obtained concentration residue was dissolved in aqueous acetonitrile and freeze-dried to obtain 246 mg of the title compound (yield: 41%) as a white solid.

Mass spectrum (CI, m/z): 490 [M+1]$^+$.

$^1$H-NMR spectrum (400 MHz, DMSO-d$_6$) δ: 12.29 & 11.86 (br s, total 1H), 9.60 (br s, 1H), 7.77-7.63 (m, 1H), 7.54-7.35 (m, 3H), 7.27-7.17 (m, 1H), 4.54 (br s, 2H), 2.57-2.39 (m, 2H), 2.29-2.12 (m, 2H), 1.99 (t, J=19.4 Hz, 3H), 1.90-1.74 (m, 2H), 1.66 (br s, 6H), 0.09 (s, 9H).

Example 59

N-(6-Chloro-2-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-629)

[Chemical Formula 77]

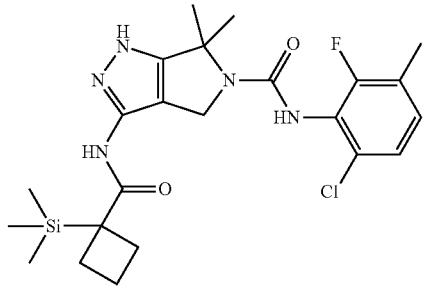

To a suspension of 349 mg (1.85 mmol) of 6-chloro-2-fluoro-3-methylbenzoic acid in 4.0 ml of toluene, 0.430 ml (2.47 mmol) of DIPEA and 0.400 ml (1.86 mmol) of DPPA were added in this order at room temperature in a nitrogen atmosphere and reacted at room temperature for 45 minutes and subsequently at 90° C. for 1.5 hours with stirring. The reaction solution was cooled to room temperature and then diluted with 2.0 ml of dichloromethane, and subsequently, this solution was added dropwise to a solution of 443 mg (1.17 mmol) of ethyl 6,6-dimethyl-3-[1-(trimethylsilyl)cyclobutanecarboxamido]-5,6-dihydropyrrolo[3,4-c]pyrazole- 2(4H)-carboxylate synthesized in the same way as in Reference Example 3 in 4.0 ml of dichloromethane at 0° C. and reacted at 0° C. for 1.5 hours with stirring.

After completion of the reaction, a 5% aqueous potassium bisulfate solution was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=80:20→70:30→60:40→50:50→40:60 (V/V)), and a fraction containing ethyl 5-[(6-chloro-2-fluoro-3-methylphenyl)carbamoyl]-6,6-dimethyl-3-[1-(trimethylsilyl) cyclobutanecarboxamido]-5,6-dihydropyrrolo[3,4-c]pyrazole-2(4H)-carboxylate was concentrated under reduced pressure.

To a solution of 401 mg (0.711 mmol) of obtained ethyl 5-[(6-chloro-2-fluoro-3-methylphenyl)carbamoyl]-6,6-dimethyl-3-[1-(trimethylsilyl) cyclobutanecarboxamido]-5,6-dihydropyrrolo[3,4-c]pyrazole-2(4H)-carboxylate in 3.0 ml of THF, 0.400 ml (3.68 mmol) of N,N-dimethylethane-1,2-diamine was added at room temperature in a nitrogen atmosphere and then reacted at room temperature for 1.5 hours with stirring.

After completion of the reaction, a 5% aqueous potassium bisulfate solution was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=80:20→65:35→50:50→40:60 (V/V)), and a fraction containing the compound of interest was concentrated under reduced pressure. The obtained concentration residue was dissolved in aqueous acetonitrile and freeze-dried to obtain 285 mg of the title compound (yield: 50%) as a white solid.

Mass spectrum (CI, m/z): 492 [M+1]$^+$.

$^1$H-NMR spectrum (400 MHz, DMSO-d$_6$) δ: 12.26 & 11.69 (br s, total 1H), 9.61-9.53 (m, 1H), 8.03-7.83 (m, 1H), 7.26-7.12 (m, 2H), 4.68-4.50 (m, 2H), 2.57-2.39 (m, 2H), 2.28-2.13 (m, 5H), 1.93-1.72 (m, 2H), 1.70-1.54 (m, 6H), 0.17-0.03 (m, 9H).

Example 60

N-[2-Fluoro-6-(methoxy-d3)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-177)

[Chemical Formula 78]

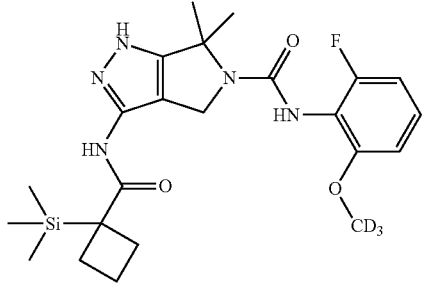

To a solution of 300 mg (0.680 mmol [calculation value with the purity defined as 100%]) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 5 ml of 1,4-dioxane, 0.592 ml (3.40 mmol) of DIPEA and 294 mg (2.04 mmol) of 2-fluoro-6-(methoxy-d3)aniline synthesized in the same way as in Reference Example 9 were added at room temperature in an argon atmosphere and reacted at room temperature for 66 hours and subsequently at 100° C. for 20 hours with stirring.

After completion of the reaction, a saturated aqueous solution of ammonium chloride was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, silica gel, elution solvent:n-hexane:ethyl acetate=95:5→30:70 (V/V)), and a fraction containing ethyl 5-{[2-fluoro-6-(methoxy-d3)phenyl]carbamoyl}-6,6-dimethyl-3-[1-(trimethyl silyl)cyclobutanecarboxamido]-5,6-dihydropyrrolo[3,4-c]pyrazole-2(4H)-carboxylate was concentrated under reduced pressure.

To a solution of the obtained concentration residue in 3 ml of 1,4-dioxane, 0.318 ml (3.40 mmol) of N,N-dimethylethane-1,2-diamine was added at room temperature and then reacted at room temperature for 1 hour with stirring.

After completion of the reaction, a saturated aqueous solution of potassium bisulfate was added to the reaction solution, followed by extraction with ethyl acetate. The whole organic layer thus obtained was washed with saturated saline, dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=65:35→40:60 (V/V)), and a fraction containing the compound of interest was concentrated under reduced pressure. The obtained concentration residue was dissolved in aqueous acetonitrile and freeze-dried to obtain 77.8 mg of the title compound (yield: 24% [calculation value with the purity of the starting material defined as 100%]) as a white solid.

Mass spectrum (CI, m/z): 477 [M+1]$^+$.

$^1$H-NMR spectrum (400 MHz, DMSO-d$_6$) δ: 12.25 & 11.73 (br s, total 1H), 9.56 (s, 1H), 7.46-7.25 (m, 1H), 7.18 (dt, J=6.5, 8.4 Hz, 1H), 6.88-6.82 (m, 1H), 6.82-6.74 (m, 1H), 4.65-4.45 (m, 2H), 2.56-2.39 (m, 2H), 2.28-2.11 (m, 2H), 1.92-1.72 (m, 2H), 1.70-1.53 (m, 6H), 0.09 (s, 9H).

Example 61

N-[2-Chloro-6-(trifluoromethyl)phenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-239)

[Chemical Formula 79]

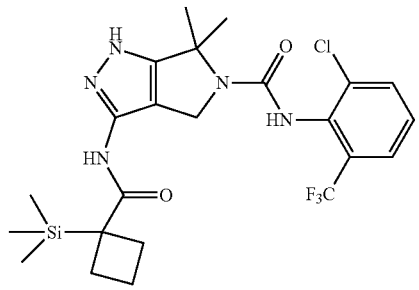

To a solution of 389 mg (1.73 mmol) of 2-chloro-6-(trifluoromethyl)benzoic acid and 0.32 ml (1.8 mmol) of DIPEA in 2 ml of toluene, 0.37 ml (1.7 mmol) of DPPA was added at room temperature in an argon atmosphere and reacted at room temperature for 0.5 hours and subsequently at 100° C. for 1 hour with stirring. The reaction solution was cooled to room temperature, and then, a solution of 450 mg (1.19 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of toluene was added to the reaction solution at room temperature and reacted at room temperature for 12 hours with stirring. Subsequently, 0.82 ml (7.5 mmol) of N,N-dimethylethane-1,2-diamine was added to the reaction solution at room temperature and then reacted at room temperature for 2 hours with stirring.

After completion of the reaction, a 5% aqueous potassium bisulfate solution was added to the reaction solution, followed by extraction with ethyl acetate. The whole organic layer thus obtained was washed with a saturated aqueous solution of sodium bicarbonate and saturated saline in this order, dried over anhydrous magnesium sulfate, then filtered, and concentrated under reduced pressure. The obtained concentration residue was subjected to preparative column chromatography (apparatus 2, DIOL silica gel, n-hexane:ethyl acetate=80:20→30:70), and a fraction containing the compound of interest was concentrated under reduced pressure. The obtained concentration residue was subjected to preparative column chromatography (apparatus 3, ODS silica gel, elution solvent:acetonitrile:1 mM aqueous dipotassium biphosphate solution=55:45 (V/V)), and a fraction containing the compound of interest was separated into an organic layer and an aqueous layer by the addition of ethyl acetate and a saturated aqueous solution of sodium bicarbonate. The obtained organic layer was washed with saturated saline, dried over anhydrous magnesium sulfate, then filtered, and concentrated under reduced pressure. The obtained concentration residue was dissolved in aqueous acetonitrile and freeze-dried to obtain 29.5 mg of the title compound (yield: 5%) as a white solid.

Mass spectrum (DUIS, m/z): 528 [M+1]$^+$.

$^1$H-NMR spectrum (400 MHz, DMSO-d$_6$) δ: 12.27 & 11.72 (br s, total 1H), 9.58 (s, 1H), 8.16-7.98 (m, 1H), 7.84 (d, J=8.0 Hz, 1H), 7.73-7.68 (m, 1H), 7.50 (t, J=8.0 Hz, 1H), 4.78-4.38 (m, 2H), 2.55-2.41 (m, 2H), 2.27-2.12 (m, 2H), 1.91-1.72 (m, 2H), 1.70-1.52 (m, 6H), 0.15-0.03 (m, 9H).

Example 62

N-(2-Fluoro-6-methoxy-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-689)

[Chemical Formula 80]

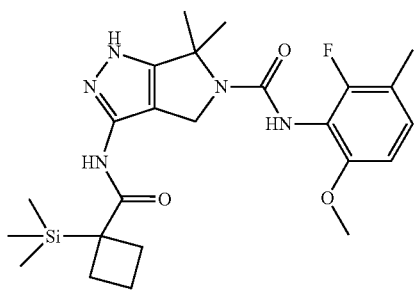

To a solution of 276 mg (1.50 mmol) of 2-fluoro-6-methoxy-3-methylbenzoic acid synthesized in the same way as in Reference Example 11 in 2 ml of dehydrated toluene, 0.350 ml (2.00 mmol) of DIPEA and 0.320 ml (1.49 mmol) of DPPA were added at room temperature in an argon atmosphere and reacted at room temperature for 0.5 hours and subsequently at 100° C. for 1 hour with stirring. The reaction solution was cooled, and then, a solution of 475 mg (1.25 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of dehydrated toluene was added thereto at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, dried over anhydrous sodium sulfate, then filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(2-fluoro-6-methoxy-3-methylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure and dried under reduced pressure.

To a solution of the obtained concentration residue in 2 ml of dehydrated dichloromethane, 0.400 ml (3.67 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing the compound of interest was concentrated under reduced pressure. The obtained concentration residue was dissolved in aqueous acetonitrile and freeze-dried to obtain 466 mg of the title compound (yield: 76%) as a white solid.

Mass spectrum (CI, m/z): 488 [M+1]$^+$.

$^1$H-NMR spectrum (400 MHz, DMSO-d$_6$) δ: 12.23 & 11.75 (br s, total 1H), 9.56 (s, 1H), 7.33 (br s, 1H), 7.08-7.01 (m, 1H), 6.78-6.71 (m, 1H), 4.55 (br s, 2H), 3.75 (s, 3H), 2.55-2.41 (m, 2H), 2.24-2.13 (m, 5H), 1.88-1.75 (m, 2H), 1.62 (s, 6H), 0.09 (s, 9H).

Example 63

N-(2,6-Difluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-609)

[Chemical Formula 81]

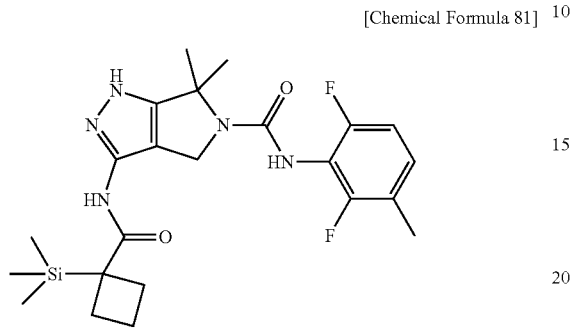

To a solution of 341 mg (1.98 mmol) of 2,6-difluoro-3-methylbenzoic acid [purchased from Aurum Pharmatech LLC] in 8 ml of toluene, 0.391 ml (2.24 mmol) of DIPEA and 0.44 ml (2.0 mmol) of DPPA were added at room temperature in an argon atmosphere and reacted at room temperature for 0.5 hours and subsequently at 100° C. for 1 hour with stirring. The reaction solution was cooled, and then, a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of toluene was added thereto at room temperature and reacted at room temperature for 2 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→4 70:30 (v/v)), and a fraction containing ethyl 5-[(2,6-difluoro-3-methylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.617 ml (6.60 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 409 mg of the title compound (yield: 65%) as a white solid.

Mass spectrum (CI, m/z): 476 [M+1]$^+$.

$^1$H-NMR spectrum (400 MHz, DMSO-d$_6$) δ: 12.26 & 11.70 (br s, total 1H), 9.58 (s, 1H), 7.99-7.75 (m, 1H), 7.20-7.07 (m, 1H), 7.03-6.92 (m, 1H), 4.68-4.49 (m, 2H), 2.56-2.40 (m, 2H), 2.27-2.13 (m, 5H), 1.92-1.74 (m, 2H), 1.70-1.55 (m, 6H), 0.09 (s, 9H).

Example 64

N-[2-(Difluoromethoxy)-6-fluorophenyl]-6,6-dimethyl-3-[1-(trimethylsilyl)cyclobutanecarboxamido]-4,6-dihydropyrrolo[3,4-c]pyrazole-5(1H)-carboxamide (Compound No. IV-169)

[Chemical Formula 82]

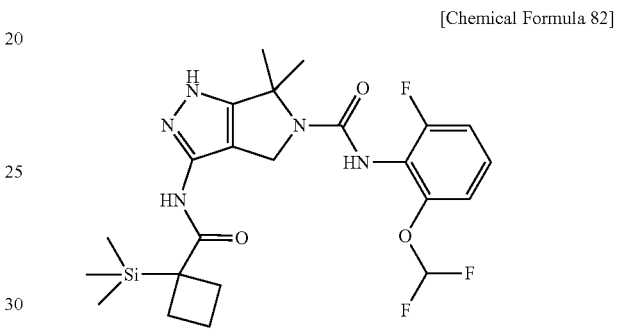

To a solution of 325 mg (1.58 mmol) of 2-(difluoromethoxy)-6-fluorobenzamide synthesized in the same way as in Reference Example 12 in 10 ml of toluene, 1.02 g (3.17 mmol) of iodobenzene diacetate was added at room temperature in an argon atmosphere and reacted at room temperature for 10 minutes and subsequently at 60° C. for 0.5 hours with stirring. The reaction solution was cooled, and then, 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 was added at room temperature and reacted at room temperature for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-{[2-(difluoromethoxy)-6-fluorophenyl]carbamoyl}-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.395 ml (4.23 mmol) of N,N-dimethylethane-1,2-diamine was added at room temperature in an argon atmosphere and reacted at room temperature for 16 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 367 mg of the title compound (yield: 68%) as a white solid.

Mass spectrum (CI, m/z): 510 [M+1]$^+$.

$^1$H-NMR spectrum (400 MHz, DMSO-d$_6$) δ: 12.27 & 11.69 (br s, total 1H), 9.59 (s, 1H), 7.96-7.71 (m, 1H), 7.31 (dt, J=6.2, 8.4 Hz, 1H), 7.23-7.12 (m, 1H), 7.08-7.03 (m, 1H), 7.01 (t, J=74.3 Hz, 1H), 4.68-4.48 (m, 2H), 2.57-2.40 (m, 2H), 2.27-2.12 (m, 2H), 1.94-1.73 (m, 2H), 1.70-1.54 (m, 6H), 0.09 (s, 9H).

Example 65

N-(2-Bromo-6-chlorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-207)

[Chemical Formula 83]

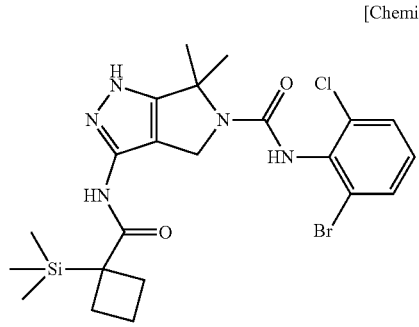

To a suspension of 374 mg (1.59 mmol) of 2-bromo-6-chlorobenzoic acid in 4.0 ml of dehydrated toluene, 0.370 ml (2.12 mmol) of DIPEA and 0.340 ml (1.58 mmol) of DPPA were added at room temperature in a nitrogen atmosphere and reacted at room temperature for 0.5 hours and subsequently at 90° C. for 1 hour with stirring. The reaction solution was cooled, then added to a solution of 398 mg (1.05 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 4.0 ml of dehydrated dichloromethane at 0° C. and reacted at 0° C. for 3 hours with stirring.

After completion of the reaction, a 5% aqueous potassium bisulfate solution was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, n-hexane:ethyl acetate=80:20→75:25→65:35), and a fraction containing ethyl 5-[(2-bromo-6-chlorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 3.0 ml of THF, 0.450 ml (4.13 mmol) of N,N-dimethylethane-1,2-diamine was added at room temperature in a nitrogen atmosphere and then reacted at room temperature for 2 hours with stirring.

After completion of the reaction, a 5% aqueous potassium bisulfate solution was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, n-hexane:ethyl acetate=80:20→65:35→50:50), and a fraction containing the compound of interest was concentrated under reduced pressure and dried under reduced pressure. The obtained concentration residue was dissolved in aqueous acetonitrile and freeze-dried to obtain 339 mg of the title compound (yield: 60%) as a white solid.

Mass spectrum (CI, m/z): 538 [M+1]$^+$.

$^1$H-NMR spectrum (400 MHz, DMSO-d$_6$) δ: 12.26 & 11.71 (br s, total 1H), 9.58 (s, 1H), 8.28-7.99 (m, 1H), 7.68-7.61 (m, 1H), 7.56-7.49 (m, 1H), 7.20 (t, J=8.1 Hz, 1H), 4.71-4.51 (m, 2H), 2.55-2.41 (m, 2H), 2.27-2.13 (m, 2H), 1.92-1.73 (m, 2H), 1.71-1.55 (m, 6H), 0.16-0.04 (m, 9H).

Example 66

N-(2-Chloro-6-fluoro-3-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-703)

[Chemical Formula 84]

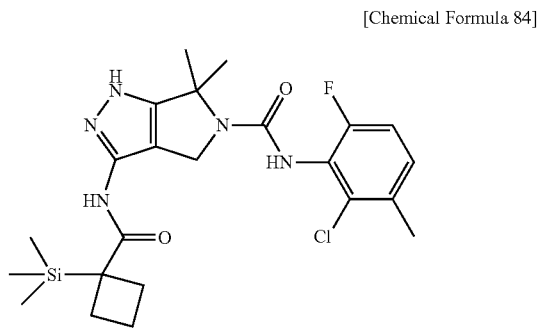

To a solution of 299 mg (1.59 mmol) of 2-chloro-6-fluoro-3-methylbenzoic acid [purchased from AOBChem] in 8 ml of toluene, 0.313 ml (1.80 mmol) of DIPEA and 0.353 ml (1.64 mmol) of DPPA were added at room temperature in an argon atmosphere and reacted at room temperature for 0.5 hours and subsequently at 100° C. for 1 hour with stirring. The reaction solution was cooled, and then, a solution of 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 1 ml of 1,4-dioxane was added thereto at room temperature and reacted at room temperature for 2 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-[(2-chloro-6-fluoro-3-methylphenyl)carbamoyl]-6,6-dimethyl-3-[1-(trimethylsilyl) cyclobutanecarboxamido]-5,6-dihydropyrrolo[3,4-c]pyrazole-2(4H)-carboxylate was concentrated under reduced pressure.

To a solution of the obtained concentration residue in 3 ml of 1,4-dioxane, 0.494 ml (5.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 407 mg of the title compound (yield: 78%) as a white solid.

Mass spectrum (CI, m/z): 492 [M+1]$^+$.

$^1$H-NMR spectrum (400 MHz, DMSO-d$_6$) δ: 12.26 & 11.74 (br s, total 1H), 9.58 (s, 1H), 8.06-7.82 (m, 1H), 7.25 (dd, J=5.7, 8.5 Hz, 1H), 7.17-7.10 (m, 1H), 4.71-4.50 (m, 2H), 2.55-2.40 (m, 2H), 2.32 (s, 3H), 2.26-2.13 (m, 2H), 1.92-1.73 (m, 2H), 1.70-1.54 (m, 6H), 0.09 (s, 9H).

Example 67

N-(2-Ethyl-6-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-137)

[Chemical Formula 85]

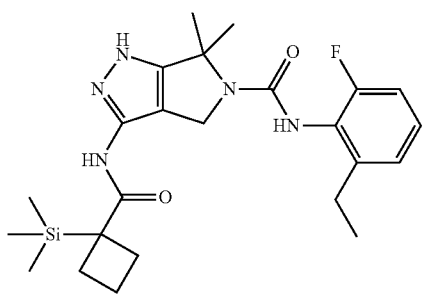

To a solution of 267 mg (1.59 mmol) of 2-ethyl-6-fluorobenzoic acid synthesized in the same way as in Reference Example 14 in 8 ml of toluene, 0.313 ml (1.80 mmol) of DIPEA and 0.353 ml (1.64 mmol) of DPPA were added at room temperature in an argon atmosphere and reacted at room temperature for 0.5 hours and subsequently at 100° C. for 1 hour with stirring. The reaction solution was cooled, and then, a solution of 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of 1,4-dioxane was added thereto at room temperature and reacted at room temperature for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-[(2-ethyl-6-fluorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.494 ml (5.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 325 mg of the title compound (yield: 65%) as a white solid.

Mass spectrum (CI, m/z): 472 [M+1]$^+$.

$^1$H-NMR spectrum (400 MHz, DMSO-d$_6$) δ: 12.26 & 11.74 (br s, total 1H), 9.57 (s, 1H), 7.77-7.55 (m, 1H), 7.19 (dt, J=5.6, 7.9 Hz, 1H), 7.09-6.97 (m, 2H), 4.70-4.48 (m, 2H), 2.60 (q, J=7.5 Hz, 2H), 2.54-2.39 (m, 2H), 2.27-2.13 (m, 2H), 1.92-1.74 (m, 2H), 1.63 (br s, 6H), 1.13 (t, J=7.5 Hz, 3H), 0.09 (s, 9H).

Example 68

N-(2-Bromo-6-fluorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-121)

[Chemical Formula 86]

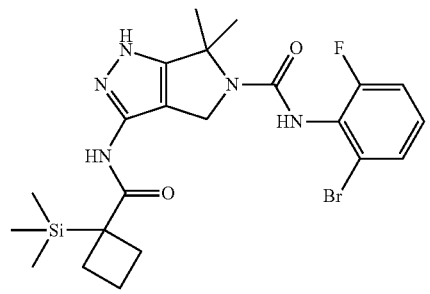

To a suspension of 350 mg (1.60 mmol) of 2-bromo-6-fluorobenzoic acid in 2 ml of dehydrated toluene, 0.300 ml (1.72 mmol) of DIPEA and 0.340 ml (1.58 mmol) of DPPA were added at room temperature in an argon atmosphere and reacted at room temperature for 0.5 hours and subsequently at 100° C. for 1 hour with stirring. The reaction solution was cooled, and then, a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of dehydrated toluene was added thereto at room temperature and reacted at room temperature for 2 hours with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(2-bromo-6-fluorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.340 ml (3.12 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100: 0→60:40 (V/V)), and a fraction containing the compound of interest was concentrated under reduced pressure. The obtained concentration residue was dissolved in aqueous acetonitrile and freeze-dried to obtain 319 mg of the title compound (yield: 46%) as a white solid.

Mass spectrum (CI, m/z): 522 [M+1]$^+$.

$^1$H-NMR spectrum (400 MHz, DMSO-d$_6$) δ: 12.26 & 11.73 (br s, total 1H), 9.59 (s, 1H), 8.01 (br s, 1H), 7.52-7.46 (m, 1H), 7.30-7.19 (m, 2H), 4.61 (br s, 2H), 2.55-2.41 (m, 2H), 2.25-2.14 (m, 2H), 1.88-1.75 (m, 2H), 1.63 (s, 6H), 0.09 (s, 9H).

Example 69

N-(2-Bromo-6-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-299)

[Chemical Formula 87]

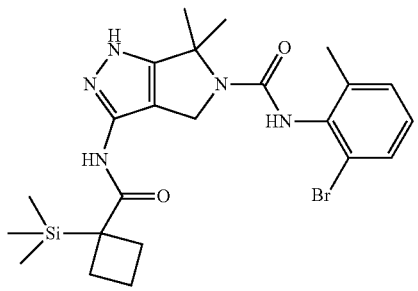

To a solution of 340 mg (1.58 mmol) of 2-bromo-6-methylbenzoic acid in 2 ml of dehydrated toluene, 0.300 ml (1.72 mmol) of DIPEA and 0.340 ml (1.58 mmol) of DPPA were added at room temperature in an argon atmosphere and reacted at room temperature for 0.5 hours and subsequently at 100° C. for 1 hour with stirring. The reaction solution was cooled, and then, a solution of 500 mg (1.32 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of dehydrated toluene was added thereto at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(2-bromo-6-methylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.340 ml (3.12 mmol) of N,N-dimethylethane-1,2-diamine was added at room temperature in an argon atmosphere and reacted at room temperature for 0.5 hours with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100: 0→60:40 (V/V)), and a fraction containing the compound of interest was concentrated under reduced pressure. The obtained concentration residue was dissolved in aqueous acetonitrile and freeze-dried to obtain 507 mg of the title compound (yield: 74%) as a white solid.

Mass spectrum (CI, m/z): 518 [M+1]$^+$.

$^1$H-NMR spectrum (400 MHz, DMSO-d$_6$) δ: 12.25 & 11.75 (br s, total 1H), 9.57 (s, 1H), 7.82 (br s, 1H), 7.49-7.43 (m, 1H), 7.26-7.20 (m, 1H), 7.11-7.03 (m, 1H), 4.61 (br s, 2H), 2.56-2.41 (m, 2H), 2.27-2.13 (m, 5H), 1.89-1.74 (m, 2H), 1.64 (s, 6H), 0.09 (s, 9H).

Example 70

N-(2-Chloro-5-methylphenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-213)

[Chemical Formula 88]

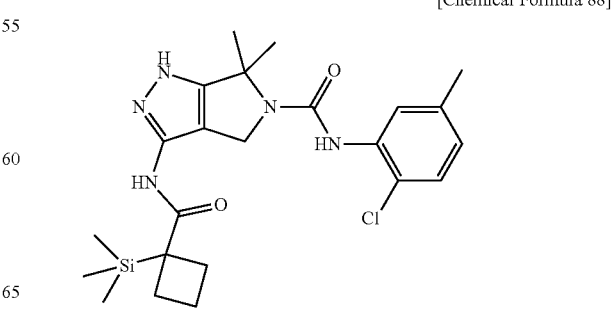

To a suspension of 270 mg (1.58 mmol) of 2-chloro-5-methylbenzoic acid in 4 ml of dehydrated toluene, 0.368 ml (2.11 mmol) of DIPEA and 0.341 ml (1.58 mmol) of DPPA were added at room temperature in an argon atmosphere and reacted at room temperature for 0.5 hours and subsequently at 100° C. for 1 hour with stirring. The reaction solution was cooled, and then, a solution of 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 4 ml of dehydrated dichloromethane was added dropwise thereto at 0° C. and reacted at room temperature for 3 hours with stirring.

After completion of the reaction, a saturated aqueous solution of ammonium chloride was added to the reaction solution, followed by extraction three times with ethyl acetate. The whole organic layer thus obtained was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane: ethyl acetate=91:9→70:30 (V/V)), and a fraction containing ethyl 5-[(2-chloro-5-methylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 3 ml of THF and 3 ml of dichloromethane, 0.575 ml (5.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction three times with ethyl acetate. The whole organic layer thus obtained was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane: ethyl acetate=71:29→50:50 (V/V)), and a fraction containing the compound of interest was concentrated under reduced pressure. The obtained concentration residue was dissolved in aqueous acetonitrile and freeze-dried to obtain 430 mg of the title compound (yield: 86%) as a white solid.

Mass spectrum (CI, m/z): 474 [M+1]⁺.

¹H-NMR spectrum (400 MHz, DMSO-d₆) δ: 12.29 & 11.86 (br s, total 1H), 9.80-9.47 (m, 1H), 7.75-7.39 (m, 2H), 7.31 (d, J=8.2 Hz, 1H), 6.91 (dd, J=1.6, 8.2 Hz, 1H), 4.62 (br s, 2H), 2.55-2.40 (m, 2H), 2.28 (s, 3H), 2.26-2.14 (m, 2H), 1.92-1.72 (m, 2H), 1.67 (br s, 6H), 0.09 (s, 9H).

Example 71

N-(6-Fluoro-2,3-dihydrobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-997)

[Chemical Formula 89]

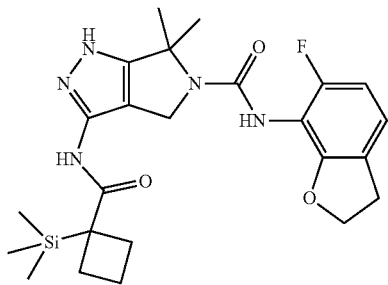

To a suspension of 289 mg (1.59 mmol) of 6-fluoro-2,3-dihydrobenzofuran-7-carboxylic acid synthesized in the same way as in Reference Example 16 in 4 ml of dehydrated toluene, 0.368 ml (2.11 mmol) of DIPEA and 0.341 ml (1.58 mmol) of DPPA were added at room temperature in an argon atmosphere and reacted at room temperature for 0.5 hours and subsequently at 100° C. for 1 hour with stirring. The reaction solution was cooled, and then, a solution of 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 4 ml of dehydrated dichloromethane was added dropwise thereto at 0° C. and reacted at room temperature for 1 hour with stirring.

After completion of the reaction, a saturated aqueous solution of ammonium chloride was added to the reaction solution, followed by extraction three times with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, elution solvent:n-hexane: ethyl acetate=47:53→27:73 (V/V)), and a fraction containing ethyl 5-[(6-fluoro-2,3-dihydrobenzofuran-7-yl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 3 ml of dichloromethane, 0.575 ml (5.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction three times with ethyl acetate. The whole organic layer thus obtained was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane: ethyl acetate=44:56→23:77 (V/V)), and a fraction containing the compound of interest was concentrated under reduced pressure. The obtained concentration residue was dissolved in 30 ml of ethyl acetate and washed three times with 5 ml of a 5% aqueous potassium bisulfate solution. The organic layer was washed with a saturated aqueous solution of sodium chloride, then dried over anhydrous magnesium sulfate, filtered, and concentrated under reduced pressure. The obtained concentration residue was dissolved in aqueous acetonitrile and freeze-dried to obtain 401 mg of the title compound (yield: 78%) as a white solid.

Mass spectrum (CI, m/z): 486 [M+1]⁺.

¹H-NMR spectrum (400 MHz, DMSO-d₆) δ: 12.67-11.22 (m, 1H), 9.54 (s, 1H), 7.59 (br s, 1H), 7.03 (dd, J=5.3, 8.1 Hz, 1H), 6.61 (dd, J=8.1, 10.2 Hz, 1H), 4.65-4.47 (m, 4H), 3.17 (t, J=8.7 Hz, 2H), 2.57-2.40 (m, 2H), 2.26-2.13 (m, 2H), 1.89-1.74 (m, 2H), 1.62 (s, 6H), 0.09 (s, 9H).

Example 72

N-(2-Cyano-6-fluorophenyl)-6,6-dimethyl-3-[1-(trimethylsilyl)cyclobutanecarboxamido]-4,6-dihydropyrrolo[3,4-c]pyrazole-5 (1H)-carboxamide (Compound No. IV-185)

[Chemical Formula 90]

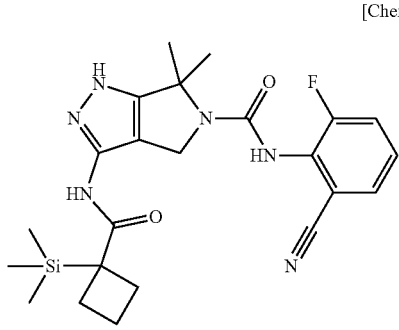

To a solution of 4.60 g (25.7 mmol) of methyl 2-cyano-6-fluorobenzoate [purchased from AstaTech Inc.] in 20 ml of methanol, 28.0 ml of a 1 N aqueous sodium hydroxide solution was added at room temperature and reacted at room temperature for 3 hours with stirring.

After completion of the reaction, the reaction solution was adjusted to pH 3 by the addition of 1 N hydrochloric acid, followed by extraction with dichloromethane. The obtained organic layer was washed with a saturated aqueous solution of sodium chloride, then dried over anhydrous magnesium sulfate, filtered, and concentrated under reduced pressure to obtain 3.42 g of a concentration residue containing 2-cyano-6-fluorobenzoic acid.

To a solution of a 0.654 g aliquot of the obtained concentration residue in 10 ml of dehydrated toluene, 0.750 ml (4.29 mmol) of DIPEA and 0.850 ml (3.95 mmol) of DPPA were added at room temperature in an argon atmosphere and reacted at room temperature for 0.5 hours with stirring. Subsequently, a solution of 1.00 g (2.64 mmol) of ethyl 6,6-dimethyl-3-[1-(trimethylsilyl)cyclobutanecarboxamido]-5,6-dihydropyrrolo[3,4-c]pyrazole-2(4H)-carboxylate in 2 ml of dehydrated toluene synthesized in the same way as in Reference Example 3 was added thereto at room temperature and reacted at 80° C. for 1 hour with stirring.

After completion of the reaction, water was added to the reaction solution cooled to room temperature, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent: n-hexane:ethyl acetate=100:0→80:20 (V/V)), and a fraction containing ethyl 5-[(2-cyano-6-fluorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 6 ml of dehydrated dichloromethane, 1.15 ml (10.6 mmol) of N,N-dimethylethane-1,2-diamine was added at room temperature in an argon atmosphere and reacted at room temperature for 0.5 hours with stirring.

After completion of the reaction, a 5% aqueous potassium bisulfate solution was added to the reaction solution, followed by extraction with ethyl acetate. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing the compound of interest was concentrated under reduced pressure. The obtained concentration residue was subjected again to preparative column chromatography (apparatus 1, silica gel, elution solvent: 1,2-dichloroethane:methanol=100:0→95:5 (V/V)), and a fraction containing the compound of interest was concentrated under reduced pressure. The obtained concentration residue was subjected again to preparative column chromatography (apparatus 3, ODS silica gel, elution solvent:acetonitrile:1 mM aqueous potassium dihydrogen phosphate solution=40:60 (V/V)), and a fraction containing the compound of interest was collected, followed by extraction with ethyl acetate. The obtained organic layer was washed with water, then dried over anhydrous sodium sulfate, filtered, and concentrated under reduced pressure. The obtained concentration residue was dissolved in aqueous acetonitrile and freeze-dried to obtain 236 mg of the title compound (yield: 19%) as a white solid.

Mass spectrum (ES TOF MS, m/z): 469 [M+1]$^+$.

$^1$H-NMR spectrum (400 MHz, DMSO-$d_6$) δ: 12.29 & 11.71 (br s, total 1H), 9.62 (s, 1H), 8.61-8.40 (m, 1H), 7.68-7.58 (m, 2H), 7.45-7.38 (m, 1H), 4.72-4.57 (m, 2H), 2.57-2.41 (m, 2H), 2.26-2.14 (m, 2H), 1.90-1.73 (m, 2H), 1.65 (br s, 6H), 0.09 (s, 9H).

Example 73

N-(2-Chloro-6-cyclopropylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-231)

[Chemical Formula 91]

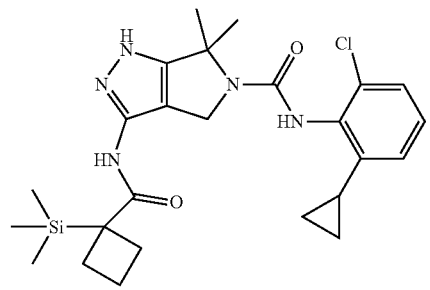

To a solution of 174 mg (0.885 mmol) of 2-chloro-6-cyclopropylbenzoic acid synthesized in the same way as in Reference Example 17 in 2 ml of dehydrated toluene, 0.212 ml (1.21 mmol) of DIPEA and 0.204 ml (0.949 mmol) of DPPA were added at room temperature in an argon atmosphere and reacted at room temperature for 0.5 hours and subsequently at 100° C. for 1 hour with stirring. The reaction solution was cooled, and then, a solution of 287 mg (0.758 mmol) of ethyl 6,6-dimethyl-3-[1-(trimethylsilyl)cyclobutanecarboxamido]-5,6-dihydropyrrolo[3,4-c]pyrazole-2 (4H)-carboxylate synthesized in the same way as in Reference Example 3 in 2 ml of dehydrated toluene was added at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(2-chloro-6-cyclopropylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.248 ml (2.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing the compound of interest was concentrated under reduced pressure. A 5% aqueous potassium bisulfate solution was added to the obtained concentration residue, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was dissolved in aqueous acetonitrile and freeze-dried to obtain 219 mg of the title compound (yield: 58%) as a white solid.

Mass spectrum (CI, m/z): 500 [M+1]$^+$.

$^1$H-NMR spectrum (400 MHz, DMSO-d$_6$) δ: 12.25 & 11.71 (br s, total 1H), 9.55 (s, 1H), 7.93-7.74 (m, 1H), 7.30-7.24 (m, 1H), 7.18-7.11 (m, 1H), 6.90-6.84 (m, 1H), 4.71-4.53 (m, 2H), 2.56-2.40 (m, 2H), 2.26-2.14 (m, 2H), 2.14-2.05 (m, 1H), 1.91-1.73 (m, 2H), 1.69-1.56 (m, 6H), 0.92-0.84 (m, 2H), 0.64-0.57 (m, 2H), 0.09 (s, 9H).

Example 74

N-(2-Fluoro-3,6-dimethylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-669)

[Chemical Formula 92]

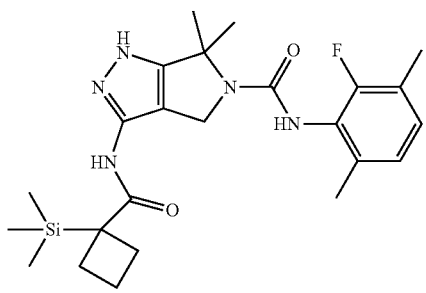

To a solution of 267 mg (1.59 mmol) of 2-fluoro-3,6-dimethylbenzoic acid synthesized in the same way as in Reference Example 20 in 8 ml of toluene, 0.313 ml (1.80 mmol) of DIPEA and 0.353 ml (1.64 mmol) of DPPA were added at room temperature in an argon atmosphere and reacted at room temperature for 0.5 hours and subsequently at 100° C. for 1 hour with stirring. The reaction solution was cooled, and then, a solution of 400 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of toluene was added thereto at 0° C. and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-[(2-fluoro-3,6-dimethylphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.494 ml (5.28 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 283 mg of the title compound (yield: 57%) as a white solid.

Mass spectrum (CI, m/z): 472 [M+1]$^+$.

$^1$H-NMR spectrum (400 MHz, DMSO-d$_6$) δ: 12.25 & 11.73 (br s, total 1H), 9.56 (s, 1H), 7.75-7.55 (m, 1H), 7.04-6.96 (m, 1H), 6.91 (d, J=7.8 Hz, 1H), 4.68-4.49 (m, 2H), 2.55-2.40 (m, 2H), 2.26-2.12 (m, 8H), 1.91-1.74 (m, 2H), 1.69-1.55 (m, 6H), 0.09 (s, 9H).

Example 75

N-(6-Fluorobenzofuran-7-yl)-6,6-dimethyl-3-[1-(trimethylsilyl)cyclobutanecarboxamido]-4,6-dihydropyrrolo[3,4-c]pyrazole-5 (1H)-carboxamide (Compound No. IV-1049)

[Chemical Formula 93]

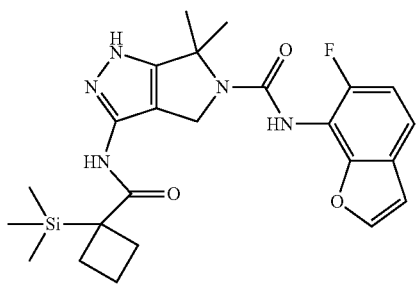

To a suspension of 287 mg (1.59 mmol) of 6-fluorobenzofuran-7-carboxylic acid synthesized in the same way as in Reference Example 15 in 4 ml of dehydrated toluene, 0.360 ml (2.11 mmol) of DIPEA, 0.340 ml (1.58 mmol) of DPPA, and 1 ml of dehydrated dichloromethane were added at room temperature in an argon atmosphere and reacted at room temperature for 1 hour and subsequently at 90° C. for 1 hour with stirring. The reaction solution was cooled, and then, 2 ml of dehydrated dichloromethane was added thereto, and the solution was added dropwise to a solution of 403 mg (1.06 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 4 ml of dichloromethane at 0° C. and reacted at 0° C. for 1 hour with stirring.

After completion of the reaction, a 5% aqueous potassium bisulfate solution was added to the reaction solution, followed by extraction twice with ethyl acetate. The whole organic layer thus obtained was washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=59:41→39:61 (V/V)), and a fraction containing ethyl 5-[(6-fluorobenzofuran-7-yl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 3 ml of dehydrated tetrahydrofuran, 0.540 ml (4.96 mmol) of N,N-dimethylethane-1,2-diamine was added at room temperature in an argon atmosphere and reacted at room temperature for 45 minutes with stirring.

After completion of the reaction, a 5% aqueous potassium bisulfate solution was added to the reaction solution, followed by extraction twice with ethyl acetate. The whole organic layer thus obtained was washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=49:51→28:72 (V/V)), and a fraction containing the compound of interest was concentrated under reduced pressure. The obtained concentration residue was dissolved in aqueous acetonitrile and freeze-dried to obtain 396 mg of the title compound (yield: 77%) as a white solid.

Mass spectrum (CI, m/z): 484 [M+1]$^+$.

$^1$H-NMR spectrum (400 MHz, DMSO-d$_6$) δ: 12.27 & 11.71 (s, total 1H), 9.58 (s, 1H), 8.23-8.04 (m, 1H), 8.00 (d, J=2.2 Hz, 1H), 7.48 (dd, J=4.8, 8.6 Hz, 1H), 7.14 (dd, J=8.6, 10.4 Hz, 1H), 6.97 (d, J=2.2 Hz, 1H), 4.76-4.55 (m, 2H), 2.55-2.40 (m, 2H), 2.28-2.12 (m, 2H), 1.94-1.74 (m, 2H), 1.72-1.55 (m, 6H), 0.09 (s, 9H).

Example 76

N-(2-Chloro-3-fluoro-6-methylphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-747)

[Chemical Formula 94]

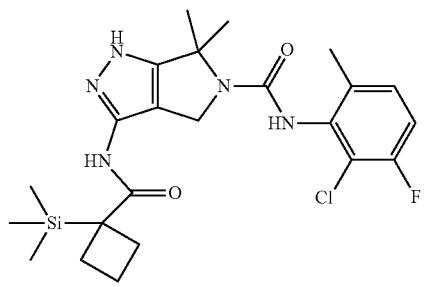

To a solution of 180 mg (0.954 mmol) of 2-chloro-3-fluoro-6-methylbenzoic acid synthesized in the same way as in Reference Example 21 in 5 ml of toluene, 0.180 ml (1.03 mmol) of DIPEA and 0.225 ml (1.05 mmol) of DPPA were added at room temperature in an argon atmosphere and reacted at room temperature for 0.5 hours and subsequently at 100° C. for 1 hour with stirring. The reaction solution was cooled, and then, a solution of 302 mg (0.798 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 5 ml of toluene was added thereto at room temperature and reacted at room temperature for 0.5 hours with stirring.

After completion of the reaction, water was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 2, silica gel, elution solvent:n-hexane:ethyl acetate=90:10→70:30 (V/V)), and a fraction containing ethyl 5-[(2-chloro-3-fluoro-6-methylphenyl)carbamoyl]-6,6-dimethyl-3-[1-(trimethylsilyl) cyclobutanecarboxamido]-5,6-dihydropyrrolo[3,4-c]pyrazole-2(4H)-carboxylate was concentrated under reduced pressure.

To a solution of the obtained concentration residue in 10 ml of tetrahydrofuran, 0.435 ml (4.00 mmol) of N,N-dimethylethane-1,2-diamine was added at room temperature and reacted at room temperature for 2 hours with stirring.

After completion of the reaction, a 5% aqueous potassium bisulfate solution was added to the reaction solution, followed by extraction with ethyl acetate. The obtained organic layer was washed with water and a saturated aqueous solution of sodium chloride in this order, then dried over anhydrous magnesium sulfate, filtered, and concentrated under reduced pressure. The obtained concentration residue was subjected to preparative column chromatography (apparatus 2, silica gel, elution solvent:n-hexane:ethyl acetate=80:20→30:70 (V/V)), and a fraction containing the compound of interest was concentrated under reduced pressure. The obtained concentration residue was dissolved in aqueous acetonitrile and freeze-dried to obtain 301 mg of the title compound (yield: 77%) as a white solid.

Mass spectrum (CI, m/z): 492 [M+1]$^+$.

$^1$H-NMR spectrum (400 MHz, DMSO-$d_6$) δ: 12.27 & 11.74 (br s, total 1H), 9.59 (br s, 1H), 8.02-7.85 (m, 1H), 7.26-7.15 (m, 2H), 4.69-4.55 (m, 2H), 2.55-2.41 (m, 2H), 2.26-2.14 (m, 5H), 1.91-1.73 (m, 2H), 1.69-1.56 (m, 6H), 0.09 (s, 9H).

Example 77

N-[2-(Difluoromethoxy)-6-fluorophenyl]-6,6-dimethyl-3-[1-(trimethylsilyl)cyclopropanecarboxamido]-4,6-dihydropyrrolo[3,4-c]pyrazole-5(1H)-carboxamide (Compound No. III-169)

[Chemical Formula 95]

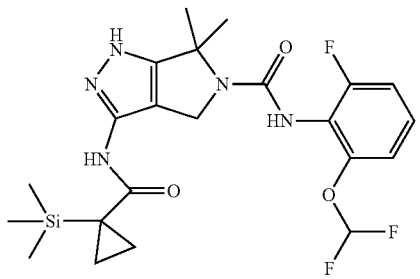

To a solution of 42 mg (0.20 mmol) of 2-(difluoromethoxy)-6-fluorobenzamide synthesized in the same way as in Reference Example 12 in 2 ml of toluene, 133 mg (0.413 mmol) of iodobenzene diacetate was added at room temperature in an argon atmosphere and reacted at room temperature for 10 minutes and subsequently at 60° C. for 1 hour with stirring. The reaction solution was cooled, and then, 50 mg (0.14 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the same way as in Reference Example 22 was added thereto at room temperature and reacted at room temperature for 20 minutes with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=80:20→60:40 (v/v)), and a fraction containing ethyl 5-{[2-(difluoromethoxy)-6-fluorophenyl]carbamoyl}-6,6-dimethyl-3-[1-(trimethylsilyl)cyclopropanecarboxamido]-5,6-dihydropyrrolo[3,4-c]pyrazole-2(4H)-carboxylat e was concentrated under reduced pressure.

To a solution of the obtained concentration residue in 3 ml of 1,4-dioxane, 0.051 ml (0.55 mmol) of N,N-dimethylethane-1,2-diamine was added at room temperature in an argon atmosphere and reacted at room temperature for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 37 mg of the title compound (yield: 54%) as a white solid.

Mass spectrum (CI, m/z): 496 [M+1]$^+$.

$^1$H-NMR spectrum (400 MHz, DMSO-$d_6$) δ: 12.29 & 11.90 (br s, total 1H), 9.78 (br s, 1H), 7.92-7.71 (m, 1H), 7.31 (dt, J=6.3, 8.3 Hz, 1H), 7.21-7.13 (m, 1H), 7.08-7.03 (m, 1H), 7.01 (t, J=74.3 Hz, 1H), 4.54 (br s, 2H), 1.61 (br s, 6H), 1.07-0.94 (m, 2H), 0.80-0.59 (m, 2H), 0.03 (s, 9H).

Example 78

N-(2,6-Dichlorophenyl)-6,6-dimethyl-3-[1-(trimethylsilyl)cyclopropanecarboxamido]-4,6-dihydropyrrolo[3,4-c]pyrazole-5(1H)-carboxamide (Compound No. III-199)

[Chemical Formula 96]

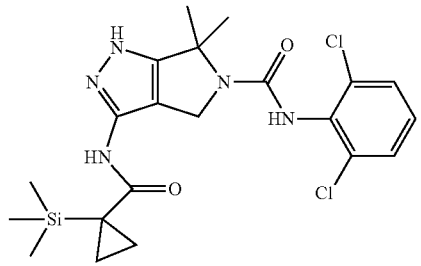

To a solution of 100 mg (0.274 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the same way as in Reference Example 22 in 3 ml of toluene, 61.9 mg (0.329 mmol) of 1,3-dichloro-2-isocyanatobenzene was added at room temperature in an argon atmosphere and reacted at room temperature for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-[(2,6-dichlorophenyl)carbamoyl]-6,6-dimethyl-3-[1-(trimethylsilyl)cyclopropanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.128 ml (1.37 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40-40:60 (v/v)), and a fraction containing the compound of interest was concentrated under reduced pressure and dried under reduced pressure. The obtained concentration residue was dissolved in aqueous acetonitrile and freeze-dried to obtain 89 mg of the title compound (yield: 68%) as a white solid.

Mass spectrum (CI, m/z): 480 [M+1]$^+$.

$^1$H-NMR spectrum (400 MHz, DMSO-d$_6$) δ: 12.49-11.61 (m, 1H), 9.78 (s, 1H), 8.09 (br s, 1H), 7.49 (d, J=8.1 Hz, 2H), 7.28 (t, J=8.1 Hz, 1H), 4.56 (s, 2H), 1.62 (s, 6H), 1.05-0.97 (m, 2H), 0.75-0.63 (m, 2H), 0.04 (s, 9H).

Example 79

N-(2,6-Dichlorophenyl)-6,6-dimethyl-3-[2-methyl-2-(trimethylsilyl)propanamido]-4,6-dihydropyrrolo[3,4-c]pyrazole-5(1H)-carboxamide (Compound No. II-199)

[Chemical Formula 97]

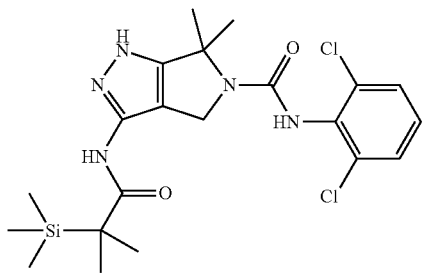

To a solution of 100 mg (0.273 mmol) of ethyl 6,6-dimethyl-3-[2-methyl-2-(trimethylsilyl)propanamido]-5,6-dihydropyrrolo[3,4-c]pyrazole-2(4H)-carboxylate synthesized in the same way as in Reference Example 25 in 3 ml of toluene, 61.6 mg (0.328 mmol) of 1,3-dichloro-2-isocyanatobenzene was added at 0° C. in an argon atmosphere and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-[(2,6-dichlorophenyl)carbamoyl]-6,6-dimethyl-3-[2-methyl-2-(trimethylsilyl)propanamido]-5,6-dihydropyrrolo[3,4-c]pyrazole-2(4H)-carboxylate was concentrated under reduced pressure.

To a solution of the obtained concentration residue in 5 ml of 1,4-dioxane, 0.128 ml (1.37 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 107 mg of the title compound (yield: 81%) as a white solid.

Mass spectrum (CI, m/z): 482 [M+1]+.

$^1$H-NMR spectrum (400 MHz, DMSO-d$_6$) δ: 12.53-11.57 (m, 1H), 9.30 (br s, 1H), 8.11 (br s, 1H), 7.49 (d, J=8.0 Hz, 2H), 7.28 (t, J=8.0 Hz, 1H), 4.58 (s, 2H), 1.63 (s, 6H), 1.24 (s, 6H), 0.04 (s, 9H).

Example 80

N-[2-(Difluoromethoxy)-6-fluorophenyl]-6,6-dimethyl-3-[2-methyl-2-(trimethylsilyl)propanamido]-4,6-dihydropyrrolo[3,4-c]pyrazole-5(1H)-carboxamide (Compound No. II-169)

[Chemical Formula 98]

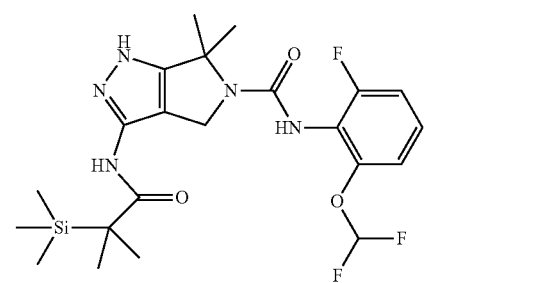

To a solution of 25.2 mg (0.123 mmol) of 2-(difluoromethoxy)-6-fluorobenzamide synthesized in the same way as in Reference Example 12 in 3 ml of toluene, 79 mg (0.25 mmol) of iodobenzene diacetate was added at room temperature in an argon atmosphere and reacted at room temperature for 10 minutes and subsequently at 60° C. for 1 hour with stirring. The reaction solution was cooled, and then, 30 mg (0.082 mmol) of ethyl 6,6-dimethyl-3-[2-methyl-2-(trimethylsilyl)propanamido]-5,6-dihydropyrrolo[3,4-c]pyrazole-2(4H)-carboxylate synthesized in the same way as in Reference Example 25 was added thereto at room temperature and reacted at room temperature for 20 minutes with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=85:15→70:30 (v/v)), and a fraction containing ethyl 5-{[2-(difluoromethoxy)-6-fluorophenyl]carbamoyl}-6,6-dimethyl-3-[2-methyl-2-(trimethylsilyl)propanamido]-5,6-dihydropyrrolo[3,4-c]pyrazole-2(4H)-carboxylate was concentrated under reduced pressure.

To a solution of the obtained concentration residue in 3 ml of 1,4-dioxane, 0.031 ml (0.33 mmol) of N,N-dimethylethane-1,2-diamine was added at room temperature in an argon atmosphere and reacted at room temperature for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 8.5 mg of the title compound (yield: 21%) as a white solid.

Mass spectrum (CI, m/z): 498 [M+1]$^+$.

$^1$H-NMR spectrum (400 MHz, DMSO-d$_6$) δ: 12.43-11.62 (m, 1H), 9.31 (br s, 1H), 7.84 (br s, 1H), 7.31 (dt, J=6.3, 8.3 Hz, 1H), 7.21-7.14 (m, 1H), 7.07-7.02 (m, 1H), 7.01 (t, J=74.3 Hz, 1H), 4.56 (s, 2H), 1.62 (s, 6H), 1.24 (s, 6H), 0.04 (s, 9H).

Example 81

N-(2,6-Dichloro-4-fluorophenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-709)

[Chemical Formula 99]

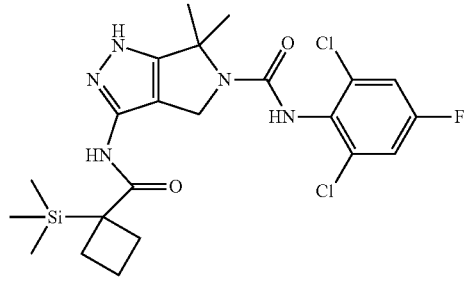

To a solution of 166 mg (0.794 mmol) of 2,6-dichloro-4-fluorobenzoic acid [purchased from Abamachem Ltd.] in 5 ml of toluene, 0.156 ml (0.896 mmol) of DIPEA and 0.176 ml (0.817 mmol) of DPPA were added at room temperature in an argon atmosphere and reacted at room temperature for 0.5 hours and subsequently at 100° C. for 1 hour with stirring. The reaction solution was cooled, and then, a solution of 200 mg (0.528 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of toluene was added dropwise thereto at 0° C. and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=90:10→70:30 (v/v)), and a fraction containing ethyl 5-[(2,6-dichloro-4-fluorophenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.247 ml (2.64 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 149 mg of the title compound (yield: 55%) as a white solid.

Mass spectrum (CI, m/z): 512 [M+1]$^+$.

$^1$H-NMR spectrum (400 MHz, DMSO-d$_6$) δ: 12.47-11.59 (m, 1H), 9.60 (s, 1H), 8.10 (br s, 1H), 7.55 (d, J=8.4 Hz, 2H), 4.60 (s, 2H), 2.57-2.41 (m, 2H), 2.25-2.14 (m, 2H), 1.89-1.73 (m, 2H), 1.63 (s, 6H), 0.09 (s, 9H).

Example 82

N-(2-Ethyl-6-fluorophenyl)-6,6-dimethyl-3-[1-(trimethylsilyl)cyclopropanecarboxamido]-4,6-dihydropyrrolo[3,4-c]pyrazole-5 (1H)-carboxamide (Compound No. III-137)

[Chemical Formula 100]

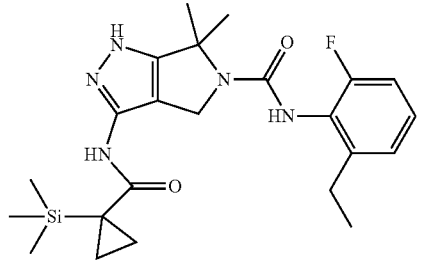

To a solution of 69.2 mg (0.412 mmol) of 2-ethyl-6-fluorobenzoic acid synthesized in the same way as in Reference Example 14 in 5 ml of toluene, 0.081 ml (0.47 mmol) of DIPEA and 0.092 ml (0.43 mmol) of DPPA were added at room temperature in an argon atmosphere and reacted at room temperature for 0.5 hours and subsequently at 100° C. for 1 hour with stirring. The reaction solution was cooled, and then, a solution of 100 mg (0.274 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the same way as in Reference Example 22 in 2 ml of toluene was added dropwise at 0° C. and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=95:5→80:20 (v/v)), and a fraction containing ethyl 5-[(2-ethyl-6-fluorophenyl)carbamoyl]-6,6-dimethyl-3-[1-(trimethylsilyl)cyclopropanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.128 ml (1.37 mmol) of N,N-dimethylethane-1,2-diamine was added at room temperature in an argon atmosphere and reacted at room temperature for 2 hours with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=70:30→50:50 (v/v)), and a fraction containing the compound of interest was concentrated under reduced pressure and dried under reduced pressure. The obtained concentration residue was dissolved in aqueous acetonitrile and freeze-dried to obtain 98 mg of the title compound (yield: 78%) as a white solid.

Mass spectrum (CI, m/z): 458 [M+1]$^+$.

$^1$H-NMR spectrum (400 MHz, DMSO-$d_6$) δ: 12.28 & 11.86 (br s, total 1H), 9.75 (br s, 1H), 7.65 (br s, 1H), 7.19 (dt, J=5.6, 7.9 Hz, 1H), 7.10-6.96 (m, 2H), 4.55 (br s, 2H), 2.60 (q, J=7.5 Hz, 2H), 1.62 (s, 6H), 1.12 (t, J=7.5 Hz, 3H), 1.05-0.96 (m, 2H), 0.81-0.60 (m, 2H), 0.04 (s, 9H).

Example 83

N-(2-Bromo-6-methylphenyl)-6,6-dimethyl-3-[1-(trimethylsilyl)cyclopropanecarboxamido]-4,6-dihydropyrrolo[3,4-c]pyrazole-5(1H)-carboxamide (Compound No. III-299)

[Chemical Formula 101]

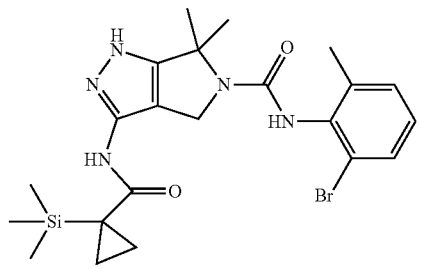

To a solution of 88 mg (0.41 mmol) of 2-bromo-6-methylbenzoic acid in 5 ml of toluene, 0.081 ml (0.47 mmol) of DIPEA and 0.092 ml (0.43 mmol) of DPPA were added at room temperature in an argon atmosphere and reacted at room temperature for 0.5 hours and subsequently at 100° C. for 1 hour with stirring. The reaction solution was cooled, and then, a solution of 100 mg (0.274 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the same way as in Reference Example 22 in 2 ml of toluene was added dropwise thereto at 0° C. and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=85:15→70:30 (v/v)), and a fraction containing ethyl 5-[(2-bromo-6-methylphenyl)carbamoyl]-6,6-dimethyl-3-[1-(trimethylsilyl)cyclopropanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.128 ml (1.37 mmol) of N,N-dimethylethane-1,2-diamine was added at room temperature in an argon atmosphere and reacted at room temperature for 2 hours with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:n-hexane:ethyl acetate=60:40→40:60 (v/v)), and a fraction containing the compound of interest was concentrated under reduced pressure and dried under reduced pressure. The obtained concentration residue was dissolved in aqueous acetonitrile and freeze-dried to obtain 92 mg of the title compound (yield: 66%) as a white solid.

Mass spectrum (CI, m/z): 504 [M+1]$^+$.

$^1$H-NMR spectrum (400 MHz, DMSO-d$_6$) δ: 12.28 & 11.85 (br s, total 1H), 9.75 (br s, 1H), 7.80 (br s, 1H), 7.50-7.43 (m, 1H), 7.26-7.19 (m, 1H), 7.12-7.03 (m, 1H), 4.56 (br s, 2H), 2.23 (s, 3H), 1.63 (s, 6H), 1.05-0.97 (m, 2H), 0.80-0.58 (m, 2H), 0.04 (s, 9H).

Example 84

N-(2-Chloro-5-methoxyphenyl)-6,6-dimethyl-3-[1-(trimethylsilyl)cyclobutanecarboxamido]-4,6-dihydropyrrolo[3,4-c]pyrazole-5(1H)-carboxamide (Compound No. IV-245)

[Chemical Formula 102]

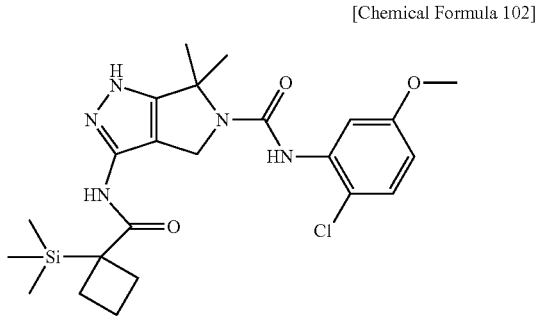

To a solution of 148 mg (0.793 mmol) of 2-chloro-5-methoxybenzoic acid in 5 ml of toluene, 0.156 ml (0.896 mmol) of DIPEA and 0.176 ml (0.817 mmol) of DPPA were added at room temperature in an argon atmosphere and reacted at room temperature for 0.5 hours and subsequently at 100° C. for 1 hour with stirring. The reaction solution was cooled, and then, a solution of 200 mg (0.528 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 2 ml of toluene was added dropwise thereto at 0° C. and reacted at 0° C. for 1 hour with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=85:15→70:30 (v/v)), and a fraction containing ethyl 5-[(2-chloro-5-methoxyphenyl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure.

To a solution of the obtained concentration residue in 5 ml of 1,4-dioxane, 0.247 ml (2.64 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with ethyl acetate. The obtained organic layer was washed with a saturated aqueous solution of sodium chloride, then dried over anhydrous magnesium sulfate, filtered, and concentrated under reduced pressure.

The obtained concentration residue was subjected to preparative column chromatography (apparatus 1, DIOL silica gel, elution solvent:n-hexane:ethyl acetate=50:50→30:70 (v/v)), and a fraction containing the compound of interest was concentrated under reduced pressure and dried under reduced pressure. The obtained concentration residue was dissolved in aqueous acetonitrile and freeze-dried to obtain 111 mg of the title compound (yield: 43%) as a white solid.

Mass spectrum (CI, m/z): 490 [M+1]$^+$.

$^1$H-NMR spectrum (400 MHz, DMSO-d$_6$) δ: 12.42-11.71 (m, 1H), 9.63 (br s, 1H), 7.59-7.39 (m, 2H), 7.34 (d, J=8.9 Hz, 1H), 6.68 (dd, J=3.1, 8.9 Hz, 1H), 4.62 (br s, 2H), 3.75 (s, 3H), 2.56-2.40 (m, 2H), 2.27-2.14 (m, 2H), 1.90-1.74 (m, 2H), 1.67 (s, 6H), 0.09 (s, 9H).

Example 85

N-(2-Ethyl-6-fluorophenyl)-6,6-dimethyl-3-[2-methyl-2-(trimethylsilyl)propanamido]-4,6-dihydropyrrolo[3,4-c]pyrazole-5(1H)-carboxamide (Compound No. II-137)

[Chemical Formula 103]

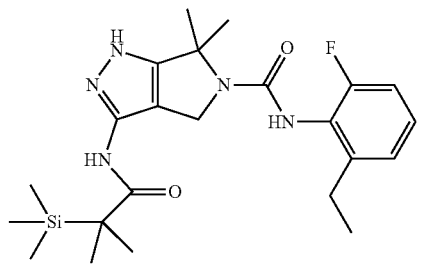

To a solution of 55.1 mg (0.328 mmol) of 2-ethyl-6-fluorobenzoic acid synthesized in the same way as in Reference Example 14 in 2 ml of dehydrated toluene, 0.076 ml (0.44 mmol) of DIPEA and 0.074 ml (0.34 mmol) of DPPA were added at room temperature in an argon atmosphere and reacted at room temperature for 0.5 hours and subsequently at 100° C. for 1 hour with stirring. The reaction solution was cooled, and then, a solution of 100 mg (0.273 mmol) of ethyl 6,6-dimethyl-3-[2-methyl-2-(trimethylsilyl)propanamido]-5,6-dihydropyrrolo[3,4-c]pyrazole-2(4H)-carboxylate synthesized in the same way as in Reference Example 25 in 2 ml of dehydrated toluene was added thereto at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(2-ethyl-6-fluorophenyl)carbamoyl]-6,6-dimethyl-3-[2-methyl-2-(trimethylsilyl)propanamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.089 ml (0.82 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing the compound of interest was concentrated under reduced pressure. The obtained concentration residue was dissolved in ethyl acetate, then n-hexane was added thereto, and the deposited solid was collected by filtration and dried under reduced pressure to obtain 64 mg of the title compound (yield: 51%) as a white solid.

Mass spectrum (CI, m/z): 460 [M+1]$^+$.

$^1$H-NMR spectrum (400 MHz, DMSO-$d_6$) δ: 12.31 & 11.74 (br s, total 1H), 9.40-9.18 (m, 1H), 7.76-7.56 (m, 1H), 7.19 (dt, J=5.7, 7.9, 1H), 7.09-6.98 (m, 2H), 4.63-4.49 (m, 2H), 2.60 (q, J=7.6 Hz, 2H), 1.71-1.53 (m, 6H), 1.24 (s, 6H), 1.13 (t, J=7.6 Hz, 3H), 0.04 (s, 9H).

Example 86

N-(2-Bromo-6-methylphenyl)-6,6-dimethyl-3-[2-methyl-2-(trimethylsilyl)propanamido]-4,6-dihydropyrrolo[3,4-c]pyrazole-5(1H)-carboxamide (Compound No. II-290)

[Chemical Formula 104]

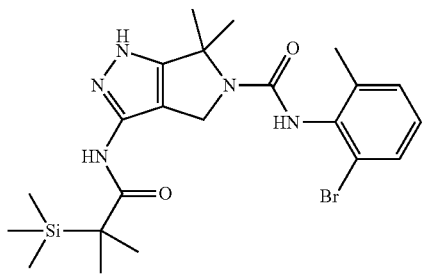

To a solution of 53.0 mg (0.246 mmol) of 2-bromo-6-methylbenzoic acid in 2 ml of dehydrated toluene, 0.057 ml (0.33 mmol) of DIPEA and 0.055 ml (0.26 mmol) of DPPA were added at room temperature in an argon atmosphere and reacted at room temperature for 0.5 hours and subsequently at 100° C. for 1 hour with stirring. The reaction solution was cooled, and then, a solution of 75.0 mg (0.205 mmol) of ethyl 6,6-dimethyl-3-[2-methyl-2-(trimethylsilyl)propanamido]-5,6-dihydropyrrolo[3,4-c]pyrazole-2(4H)-carboxylate synthesized in the same way as in Reference Example 25 in 2 ml of dehydrated toluene was added thereto at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(2-bromo-6-methylphenyl)carbamoyl]-6,6-dimethyl-3-[2-methyl-2-(trimethylsilyl)propanamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.067 ml (0.61 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=80:20→50:50 (V/V)), and a fraction containing the compound of interest was concentrated under reduced pressure. The obtained concentration residue was dissolved in ethyl acetate, then n-hexane was added thereto, and the deposited solid was collected by filtration and dried under reduced pressure to obtain 40 mg of the title compound (yield: 39%) as a white solid.

Mass spectrum (CI, m/z): 506 [M+1]$^+$.

$^1$H-NMR spectrum (400 MHz, DMSO-$d_6$) δ: 12.30 & 11.72 (br s, total 1H), 9.40-9.15 (m, 1H), 7.82 (br s, 1H), 7.49-7.43 (m, 1H), 7.27-7.20 (m, 1H), 7.07 (t, J=7.8, 1H), 4.59 (s, 2H), 2.24 (s, 3H), 1.64 (br s, 6H), 1.24 (s, 6H), 0.04 (s, 9H).

Example 87

N-(6-Fluorobenzofuran-7-yl)-6,6-dimethyl-3-[2-methyl-2-(trimethylsilyl)propanamido]-4,6-dihydropyrrolo[3,4-c]pyrazole-5(1H)-carboxamide (Compound No. II-1049)

[Chemical Formula 105]

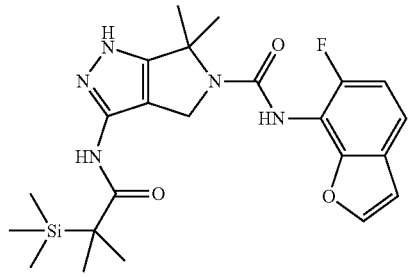

To a solution of 44.2 mg (0.245 mmol) of 6-fluorobenzofuran-7-carboxylic acid synthesized in the same way as in Reference Example 15 in 2 ml of dehydrated toluene, 0.057 ml (0.33 mmol) of DIPEA and 0.055 ml (0.26 mmol) of DPPA were added at room temperature in an argon atmosphere and reacted at room temperature for 0.5 hours and subsequently at 100° C. for 1 hour with stirring. The reaction solution was cooled, and then, a solution of 75.0 mg (0.205 mmol) of ethyl 6,6-dimethyl-3-[2-methyl-2-(trimethylsilyl)propanamido]-5,6-dihydropyrrolo[3,4-c]pyrazole-2(4H)-carboxylate synthesized in the same way as in Reference Example 25 in 2 ml of dehydrated toluene was added thereto at room temperature and reacted at room temperature for 2 hours with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(6-fluorobenzofuran-7-yl)carbamoyl]-6,6-dimethyl-3-[2-methyl-2-(trimethylsilyl) propanamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.067 ml (0.61 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=80:20→50:50 (V/V)), and a fraction containing the compound of interest was concentrated under reduced pressure. The obtained concentration residue was dissolved in ethyl acetate, then n-hexane was added thereto, and the deposited solid was collected by filtration and dried under reduced pressure to obtain 14 mg of the title compound (yield: 14%) as a white solid.

Mass spectrum (CI, m/z): 472 [M+1]$^+$.

$^1$H-NMR spectrum (400 MHz, DMSO-d$_6$) δ: 12.32 & 11.77 (br s, total 1H), 9.43-9.20 (m, 1H), 8.14 (br s, 1H), 8.00 (d, J=2.2 Hz, 1H), 7.48 (dd, J=4.8, 8.5 Hz, 1H), 7.15 (dd, J=8.5, 10.5 Hz, 1H), 6.97 (d, J=2.2 Hz, 1H), 4.63 (s, 2H), 1.65 (br s, 6H), 1.25 (s, 6H), 0.05 (s, 9H).

Example 88

N-(6-Fluorobenzofuran-7-yl)-6,6-dimethyl-3-[1-(trimethylsilyl)cyclopropanecarboxamido]-4,6-dihydropyrrolo[3,4-c]pyrazole-5 (1H)-carboxamide (Compound No. III-1049)

[Chemical Formula 106]

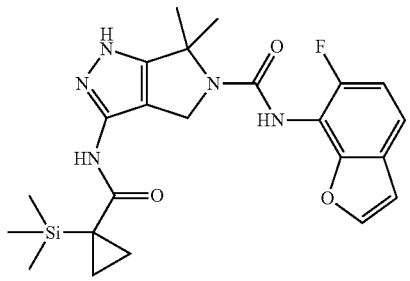

To a solution of 44.5 mg (0.247 mmol) of 6-fluorobenzofuran-7-carboxylic acid synthesized in the same way as in Reference Example 15 in 2 ml of dehydrated toluene, 0.057 ml (0.33 mmol) of DIPEA and 0.055 ml (0.26 mmol) of DPPA were added at room temperature and reacted at room temperature for 0.5 hours and subsequently at 100° C. for 1 hour with stirring. The reaction solution was cooled, and then, a solution of 75.0 mg (0.206 mmol) of ethyl 6,6-dimethyl-3-[1-(trimethylsilyl)cyclopropanecarboxamido]-5,6-dihydropyrrolo[3,4-c]pyrazole-2(4H)-carboxylate synthesized in the same way as in Reference Example 22 in 2 ml of dehydrated toluene was added thereto at room temperature and reacted at room temperature for 1 hour with stirring.

After completion of the reaction, water was added to the reaction solution, followed by extraction with ethyl acetate. The obtained organic layer was washed with a saturated aqueous solution of sodium chloride, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=100:0→60:40 (V/V)), and a fraction containing ethyl 5-[(6-fluorobenzofuran-7-yl)carbamoyl]-6,6-dimethyl-3-[1-(trimethylsilyl)cyclopropanecarboxamido]-5,6-dihydropyrrolo[3,4-c]pyrazole-2(4H)-carboxylate was concentrated under reduced pressure.

To a solution of the obtained concentration residue in 2 ml of dehydrated dichloromethane, 0.067 ml (0.61 mmol) of N,N-dimethylethane-1,2-diamine was added at room temperature in an argon atmosphere and reacted at room temperature for 1 hour with stirring.

After completion of the reaction, a 5% aqueous potassium bisulfate solution was added to the reaction solution, followed by extraction with dichloromethane. The obtained organic layer was washed with a saturated aqueous solution of sodium bicarbonate and a saturated aqueous solution of sodium chloride in this order, then dried over anhydrous sodium sulfate, filtered, and concentrated under reduced pressure. The obtained concentration residue was subjected to preparative column chromatography (apparatus 1, DIOL silica gel, elution solvent:n-hexane:ethyl acetate=80:20→50:50 (V/V)), and a fraction containing the compound of interest was concentrated under reduced pressure. The obtained concentration residue was subjected again to preparative column chromatography (apparatus 3, ODS silica gel, elution solvent:acetonitrile:1 mM aqueous potassium dihydrogen phosphate solution=35:65 (V/V)), and a fraction containing the compound of interest was collected, followed by extraction with ethyl acetate. The obtained organic layer was washed with water, then dried over anhydrous sodium sulfate, filtered, and concentrated under reduced pressure. The obtained concentration residue was dissolved in ethyl acetate, then n-hexane was added thereto, and the deposited solid was collected by filtration and dried under reduced pressure to obtain 11 mg of the title compound (yield: 11%) as a white solid.

Mass spectrum (CI, m/z): 470 [M+1]$^+$.

$^1$H-NMR spectrum (400 MHz, DMSO-d$_6$) δ: 12.29 & 11.85 (br s, total 1H), 9.76 (br s, 1H), 8.19-8.01 (m, 1H), 8.00 (d, J=2.1 Hz, 1H), 7.48 (dd, J=4.9, 8.5 Hz, 1H), 7.14 (dd, J=8.5, 10.5 Hz, 1H), 6.97 (d, J=2.1 Hz, 1H), 4.67-4.53 (m, 2H), 1.64 (br s, 6H), 1.08-0.96 (m, 2H), 0.80-0.60 (m, 2H), 0.04 (s, 9H).

Example 89

N,6,6-Trimethyl-N-phenyl-3-[1-(trimethylsilyl)cyclobutanecarboxamido]-4,6-dihydropyrrolo[3,4-c]pyrazole-5(1H)-carboxamide (Compound No. 1-965)

[Chemical Formula 107]

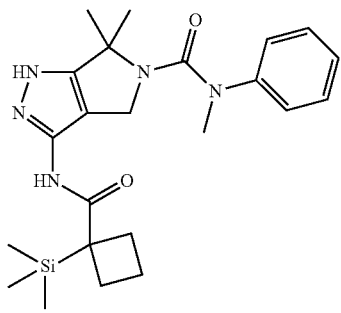

To a solution of 150 mg (including impurities, <0.340 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.180 ml (1.03 mmol) of DIPEA and 0.110 ml (1.02 mmol) of N-methylaniline were added at room temperature in an argon atmosphere and then reacted at 100° C. for 1 hour with stirring. The reaction solution was cooled, and 0.200 ml (1.84 mmol) of N,N-dimethylethane-1,2-diamine was added thereto at room temperature and then reacted at room temperature for 16 hours with stirring.

After completion of the reaction, ethyl acetate was added to the reaction solution, followed by washing with a 5% aqueous potassium bisulfate solution. After separation into an organic layer and an aqueous layer, the aqueous layer was subjected to extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, DIOL silica gel, elution solvent:n-hexane:ethyl acetate=60:40→20:80 (V/V)), and a fraction containing the compound of interest was concentrated under reduced pressure. The obtained concentration residue was dissolved by the addition of methanol, then water was added thereto, and the deposited solid was collected by filtration and dried under reduced pressure to obtain 59.6 mg of the title compound (yield: 40% [*calculation value with the purity of the starting material defined as 100%]) as a white solid.

Mass spectrum (CI, m/z): 440 [M+1]$^+$.

$^1$H-NMR spectrum (400 MHz, DMSO-d$_6$) δ: 12.37-11.66 (m, 1H), 9.41 (br s, 1H), 7.33-7.25 (m, 2H), 7.08-7.00 (m, 3H), 3.90 (s, 2H), 3.01 (s, 3H), 2.38-2.27 (m, 2H), 2.17-2.02 (m, 2H), 1.82-1.62 (m, 8H), −0.07 (s, 9H).

Example 90

N-(6-Fluoro-3-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-1061)

[Chemical Formula 108]

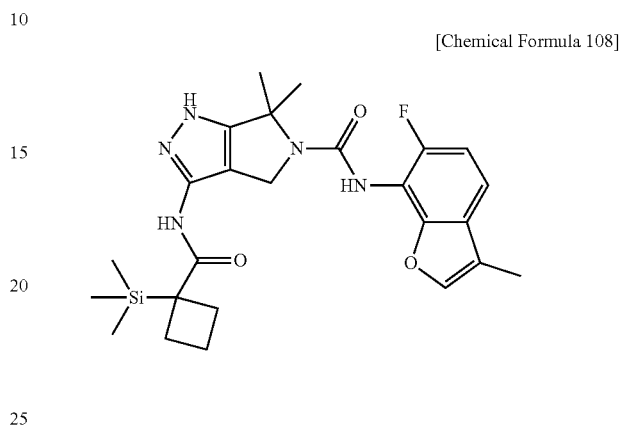

To a solution of 0.296 g (0.520 mmol) of ethyl 5-[(6-fluoro-3-methylbenzofuran-7-yl)carbamoyl]-6,6-dimethyl-3-[1-(trimethylsilyl) cyclobutanecarboxamido]-5,6-dihydropyrrolo[3,4-c]pyrazole-2(4H)-carboxylate synthesized in Reference Example 36 in 5 ml of THF, 0.17 ml (1.6 mmol) of N,N-dimethylethane-1,2-diamine was added at room temperature and then reacted at room temperature for 1 hour with stirring.

After completion of the reaction, ethyl acetate was added to the reaction solution, followed by washing with a 5% aqueous potassium bisulfate solution. After separation into an organic layer and an aqueous layer, the obtained organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=50:50→28:72 (V/V)), and a fraction containing the compound of interest was concentrated under reduced pressure and dried under reduced pressure. The obtained concentration residue was dissolved in aqueous acetonitrile and freeze-dried to obtain 217 mg of the title compound (yield: 84%) as a white solid.

Mass spectrum (CI, m/z): 498 [M+1]$^+$.

$^1$H-NMR spectrum (400 MHz, DMSO-d$_6$) δ: 12.27 & 11.77 (br s, total 1H), 9.59 (br s, 1H), 8.18-8.01 (m, 1H), 7.80-7.74 (m, 1H), 7.41 (dd, J=4.8, 8.6 Hz, 1H), 7.14 (dd, J=8.6, 10.5 Hz, 1H), 4.70-4.57 (m, 2H), 2.55-2.42 (m, 2H), 2.28-2.13 (m, 5H), 1.92-1.73 (m, 2H), 1.65 (br s, 6H), 0.09 (s, 9H).

Example 91

N-(2-Chloro-6-fluorobenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-1063)

[Chemical Formula 109]

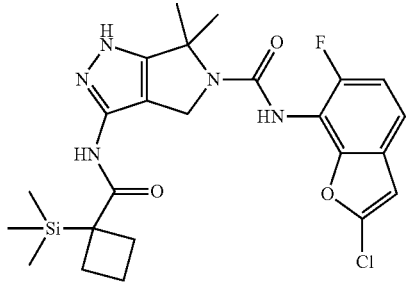

To a solution of 210 mg (0.356 mmol) of ethyl 5-[(2-chloro-6-fluorobenzofuran-7-yl)carbamoyl]-6,6-dimethyl-3-[1-(trimethylsilyl) cyclobutanecarboxamido]-5,6-dihydropyrrolo[3,4-c]pyrazole-2(4H)-carboxylate synthesized in Reference Example 40 in 5 ml of THF, 0.12 ml (1.1 mmol) of N,N-dimethylethane-1,2-diamine was added at room temperature and then reacted at room temperature for 1 hour with stirring.

After completion of the reaction, ethyl acetate was added to the reaction solution, followed by washing with a 5% aqueous potassium bisulfate solution. After separation into an organic layer and an aqueous layer, the obtained organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=50:50→28:72 (V/V)), and a fraction containing the compound of interest was concentrated under reduced pressure. The obtained concentration residue was dissolved in aqueous acetonitrile and freeze-dried to obtain 164 mg of the title compound (yield: 89%) as a white solid.

Mass spectrum (CI, m/z): 518 [M+1]$^+$.

$^1$H-NMR spectrum (400 MHz, DMSO-d$_6$) δ: 12.28 & 11.78 (br s, total 1H), 9.61 (br s, 1H), 8.34-8.10 (m, 1H), 7.44 (dd, J=4.8, 8.6 Hz, 1H), 7.20 (dd, J=8.6, 10.7 Hz, 1H), 7.05 (s, 1H), 4.72-4.57 (m, 2H), 2.58-2.41 (m, 2H), 2.28-2.13 (m, 2H), 1.92-1.73 (m, 2H), 1.66 (br s, 6H), 0.10 (s, 9H).

Example 92

N-[5-(Indoline-1-carbonyl)-6,6-dimethyl-1,4,5,6-tetrahydropyrrolo[3,4-c]pyrazol-3-yl]-1-(trimethylsilyl)cyclobutanecarboxamide (Compound No. I-1000)

[Chemical Formula 110]

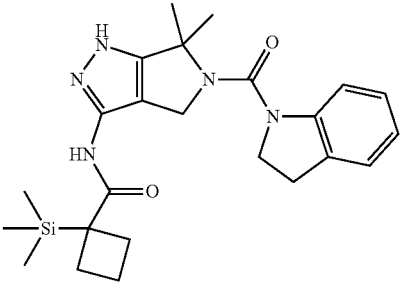

To a solution of 187 mg (0.424 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.24 ml (1.4 mmol) of DIPEA and 0.15 ml (1.3 mmol) of indoline were added at room temperature in an argon atmosphere and then reacted at 100° C. for 110 minutes with stirring. The reaction solution was cooled, and 0.24 ml (2.2 mmol) of N,N-dimethylethane-1,2-diamine was added thereto at room temperature and then reacted at room temperature for 1 hour with stirring.

After completion of the reaction, the reaction solution was separated into an organic layer and an aqueous layer by the addition of ethyl acetate and a 5% aqueous potassium bisulfate solution. The organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=50:50→29:71 (V/V)), and a fraction containing the compound of interest was concentrated under reduced pressure. The obtained concentration residue was dissolved in aqueous acetonitrile and freeze-dried to obtain 163 mg of the title compound (yield: 85%) as a white solid.

Mass spectrum (CI, m/z): 452 [M+1]$^+$.

$^1$H-NMR spectrum (400 MHz, DMSO-d$_6$) δ: 12.31 & 11.93 (br s, total 1H), 9.87-9.47 (m, 1H), 7.23-7.18 (m, 1H), 7.09-7.02 (m, 1H), 6.82 (dt, J=0.8, 7.4 Hz, 1H), 6.70-6.60 (m, 1H), 4.62-4.41 (m, 2H), 3.80-3.66 (m, 2H), 3.03-2.92 (m, 2H), 2.44-2.32 (m, 2H), 2.20-2.07 (m, 2H), 1.83-1.64 (m, 8H), 0.01 (br s, 9H).

Example 93

N-[5-(3,4-Dihydro-2H-benz[b][1,4]oxazine-4-carbonyl)-6,6-dimethyl-1,4,5,6-tetrahydropyrrolo[3,4-c]pyrazol-3-yl]-1-(trimethylsilyl)cyclobutanecarboxamide (Compound No. I-1036)

[Chemical Formula 111]

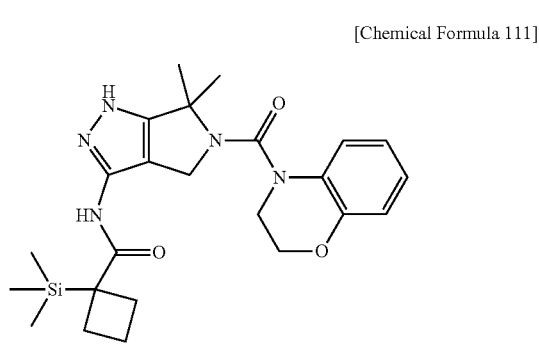 [SMILES: CC1(C)c2[nH]nc(NC(=O)C3([Si](C)(C)C)CCC3)c2CN1C(=O)N1CCOc2ccccc21]

To a solution of 192 mg (0.435 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 in 2 ml of 1,4-dioxane, 0.24 ml (1.4 mmol) of DIPEA and 180 mg (1.33 mmol) of 3,4-dihydro-2H-1,4-benzoxazine [purchased from Combi-Blocks Inc.] were added at room temperature in an argon atmosphere and then reacted at 100° C. for 3 hours with stirring. The reaction solution was cooled, and 0.24 ml (2.2 mmol) of N,N-dimethylethane-1,2-diamine was added thereto at room temperature and then reacted at room temperature for 1.5 hours with stirring.

After completion of the reaction, the reaction solution was separated into an organic layer and an aqueous layer by the addition of ethyl acetate and a 5% aqueous potassium bisulfate solution. The organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=41:59→20:80 (V/V)), and a fraction containing the compound of interest was concentrated under reduced pressure. The obtained concentration residue was dissolved in aqueous acetonitrile and freeze-dried to obtain 150 mg of the title compound (yield: 74%) as a pale yellow solid.

Mass spectrum (CI, m/z): 468 [M+1]$^+$.

$^1$H-NMR spectrum (400 MHz, DMSO-$d_6$) δ: 12.30 & 11.99 (br s, total 1H), 9.90-9.41 (m, 1H), 6.83-6.74 (m, 4H), 4.53-4.42 (m, 2H), 4.34-4.26 (m, 2H), 3.50-3.46 (m, 2H), 2.43-2.33 (m, 2H), 2.19-2.07 (m, 2H), 1.83-1.66 (m, 8H), 0.09--0.09 (m, 9H).

Example 94

N-(6-Fluoro-2-methylbenzofuran-7-yl)-6,6-dimethyl-3-[1-(trimethylsilyl)cyclobutanecarboxamido]-4,6-dihydropyrrolo[3,4-c]pyrazole-5(1H)-carboxamide (Compound No. IV-1059)

[Chemical Formula 112]

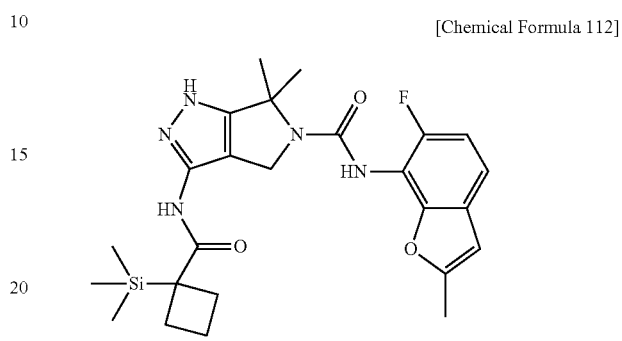

To 144 mg (0.742 mmol) of 6-fluoro-2-methylbenzofuran-7-carboxylic acid synthesized in Reference Example 43, 2 ml of toluene was added, followed by azeotropic dehydration under reduced pressure. To a suspension of the obtained residue in 2 ml of dehydrated toluene, 0.170 ml (1.22 mmol) of triethylamine and 0.200 ml (0.929 mmol) of DPPA were added at room temperature in an argon atmosphere and then reacted at room temperature for 35 minutes and subsequently at 85° C. for 1.5 hours with stirring. The reaction solution was cooled and then added in divided portions to a solution of 232 mg (0.613 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of dehydrated toluene at 0° C. and reacted at 0° C. for 1 hour with stirring.

After completion of the reaction, the reaction solution was separated into an organic layer and an aqueous layer by the addition of water and ethyl acetate, and then, the organic layer was washed with a saturated aqueous solution of sodium bicarbonate, dried over anhydrous magnesium sulfate, filtered, and concentrated under reduced pressure. The obtained concentration residue was subjected to preparative column chromatography (apparatus 1, silica gel, n-hexane:ethyl acetate=63:37→42:58 (V/V)), and a fraction containing ethyl 5-[(6-fluoro-2-methylbenzofuran-7-yl)carbamoyl]-6,6-dimethyl-3-[1-(trimethylsilyl)cyclobutanecarboxamido]-5,6-dihydropyrrolo[3,4-c]pyrazole-2(4H)-carboxylate was concentrated under reduced pressure and dried under reduced pressure.

To a solution of the obtained concentration residue in 5 ml of THF, 0.22 ml (2.0 mmol) of N,N-dimethylethane-1,2-diamine was added at room temperature and then reacted at room temperature for 1 hour with stirring.

After completion of the reaction, ethyl acetate was added to the reaction solution, followed by washing with a 5% aqueous potassium bisulfate solution. After separation into an organic layer and an aqueous layer, the obtained organic layer was washed with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=46:54→25:75 (V/V)), and a fraction containing the compound of interest was concentrated under reduced pressure. The obtained concentration residue was dissolved in aqueous acetonitrile and freeze-dried to obtain 230 mg of the title compound (yield: 75%) as a white solid.

Mass spectrum (CI, m/z): 498 [M+1]$^+$.

$^1$H-NMR spectrum (400 MHz, DMSO-d$_6$) δ: 12.27 & 11.81 (br s, total 1H), 9.69-9.49 (m, 1H), 8.16-7.97 (m, 1H), 7.33 (dd, J=5.0, 8.5 Hz, 1H), 7.06 (dd, J=8.5, 10.6 Hz, 1H), 6.60-6.55 (m, 1H), 4.64 (br s, 2H), 2.55-2.40 (m, 5H), 2.26-2.14 (m, 2H), 1.89-1.75 (m, 2H), 1.65 (br s, 6H), 0.10 (s, 9H).

Example 95

N-[5-(1H-Indole-1-carbonyl)-6,6-dimethyl-1,4,5,6-tetrahydropyrrolo[3,4-c]pyrazol-3-yl]-1-(trimethylsilyl)cyclobutanecarboxamide (Compound No. 1-997)

[Chemical Formula 113]

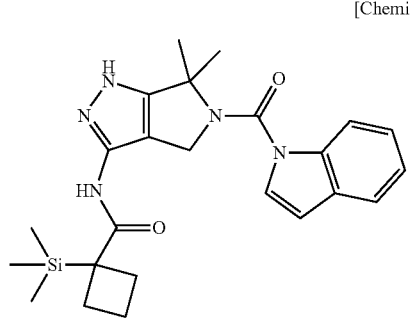

To a solution of 1.00 g (including impurities, <0.916 mmol) of ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 4 and 3.52 g (30.0 mmol) of indole in 10 ml of 1,4-dioxane, 1.74 ml (9.99 mmol) of DIPEA was added at room temperature and then reacted at 150° C. for 0.5 hours and further at 180° C. for 1 hour in a microwave reaction apparatus. Subsequently, 1.00 ml (9.19 mmol) of N,N-dimethylethane-1,2-diamine was added thereto at room temperature and then reacted at room temperature for 16 hours with stirring.

After completion of the reaction, ethyl acetate was added to the reaction solution, and the resultant was washed twice with a 5% aqueous potassium bisulfate solution and once with a saturated aqueous solution of sodium bicarbonate, then dried over anhydrous magnesium sulfate, filtered, and concentrated under reduced pressure. The obtained concentration residue was subjected to preparative column chromatography (apparatus 1, DIOL silica gel, n-hexane:ethyl acetate=69:31→0:100 (V/V)), and a fraction containing the compound of interest was concentrated under reduced pressure. The obtained concentration residue was subjected to preparative column chromatography (apparatus 3, CSH ODS silica gel, elution solvent: 0.1 vol % acetonitrile formate:0.1 vol % aqueous formic acid solution=45:55→99:1 (V/V)), and a fraction containing the compound of interest was separated into an organic layer and an aqueous layer by the addition of ethyl acetate and a saturated aqueous solution of sodium bicarbonate. The aqueous layer was subjected to extraction with ethyl acetate, and the whole organic layer thus obtained was dried over anhydrous magnesium sulfate, filtered, and concentrated under reduced pressure. The obtained concentration residue was purified using VARIAN Bond Elute (water:acetonitrile=100:0→0:100 (V/V)), and water was added to the eluate containing the compound of interest and freeze-dried to obtain 15.8 mg of the title compound (yield: 2% [*calculation value with the purity of the starting material defied as 100%]) as a white solid.

Mass spectrum (CI, m/z): 450 [M+1]$^+$.

$^1$H-NMR spectrum (400 MHz, DMSO-d$_6$) δ: 12.45-11.84 (m, 1H), 11.60-11.40 (m, 1H), 9.87-9.47 (m, 1H), 7.97-7.86 (m, 1H), 7.73 (d, J=2.6 Hz, 1H), 7.47-7.38 (m, 1H), 7.18-7.12 (m, 1H), 7.11-7.04 (m, 1H), 4.86-4.55 (m, 2H), 2.53-2.37 (m, 2H), 2.21-2.10 (m, 2H), 1.87-1.69 (m, 8H), 0.04 (s, 9H).

Reference Example 1

1-(Trimethylsilyl)cyclobutanecarboxylic acid

[Chemical Formula 114]

To 200 ml of THF, 214 ml (428 mmol) of a 2 M solution of lithium diisopropylamide in THF was added in an argon atmosphere, and then, 10.1 ml (107 mmol) of cyclobutanecarboxylic acid was added dropwise thereto with stirring under cooling in ice water and reacted for 4 hours while the temperature was raised to room temperature according to the circumstances. Subsequently, 20 ml (116 mmol) of hexamethylphosphoric triamide was added thereto, 51 ml (490 mmol) of chlorotrimethylsilane was added dropwise thereto with stirring with the internal temperature kept at −60° C. or lower under cooling with a dry ice/acetone refrigerant, and then reacted at −78° C. for 16.5 hours with stirring.

After completion of the reaction, 67 ml of methanol was added to the reaction solution, the temperature was raised to 0° C., and then, 134 ml of cold water was added thereto. The resultant was adjusted to pH 2.1 by the addition of 2 N hydrochloric acid and separated into an organic layer and an aqueous layer by the addition of 268 ml of diethyl ether, and the organic layer was washed with 268 ml of a saturated aqueous solution of sodium chloride. The organic layer was dried over anhydrous magnesium sulfate, filtered, and concentrated under reduced pressure. The obtained concentration residue was separated into an organic layer and an aqueous layer by the addition of 50 ml of a 2 N aqueous sodium hydroxide solution and 267 ml of n-hexane. Subsequently, the aqueous layer was adjusted to pH 2.7 by the addition of 1 N hydrochloric acid, and this solution was separated into an organic layer and an aqueous layer by the addition of 267 ml of ethyl acetate. The obtained organic layer was dried over anhydrous magnesium sulfate, filtered, and concentrated under reduced pressure. n-Hexane was added to the obtained concentration residue and cooled in an ice water bath. The resulting solid was filtered, washed with cooled n-hexane, and then dried under reduced pressure to obtain 6.24 g of the title compound (yield: 34%) as a white solid. The filtrate was further concentrated under reduced pressure, and the obtained residue was subjected to silica gel column chromatography (elution solvent: 1,2-dichloroethane:methanol=100:0→95:5 (V/V)), and a fraction containing the compound of interest was concentrated under reduced pressure and dried under reduced pressure to obtain 4.33 g of the title compound (yield: 23%) as a white solid.

Mass spectrum (CI, m/z): 173 [M+1]$^+$.

$^1$H-NMR spectrum (400 MHz, DMSO-d$_6$) δ: 11.64 br s, 1H), 2.45-2.34 (m, 2H), 2.17-2.06 (m, 2H), 1.91-1.70 (m, 2H), 0.06 (s, 9H).

Reference Example 2

5-tert-Butyl 2-ethyl 6,6-dimethyl-3-[1-(trimethylsilyl)cyclobutanecarboxamido]pyrrolo[3,4-c]pyrazole-2,5(4H,6H)-dicarboxylate

[Chemical Formula 115]

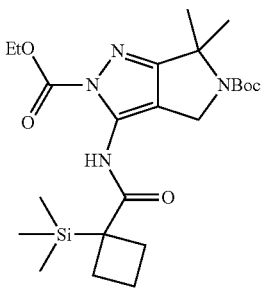

To a solution of 13.9 g (80.4 mmol) of 1-(trimethylsilyl)cyclobutanecarboxylic acid synthesized in the same way as in Reference Example 1 in 105 ml of dichloromethane, 6.96 ml (81.2 mmol) of oxalyl chloride and 0.32 ml (4.14 mmol) of DMF were added dropwise in this order between −25° C. and −10° C. in an argon atmosphere, then the temperature was raised to 0° C., and the resultant was reacted for 2 hours with stirring. This reaction solution was added dropwise into a solution of 8.74 g (26.9 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] and 23.5 ml (135 mmol) of DIPEA in 122 ml of dichloromethane at 0° C. in an argon atmosphere and reacted at 0° C. for 16 hours with stirring.

After completion of the reaction, the reaction solution was separated into an organic layer and an aqueous layer by the addition of 486 ml of a 5% aqueous potassium bisulfate solution, and then, the aqueous layer was subjected to extraction twice with 200 ml of dichloromethane. The whole organic layer thus obtained was dried over anhydrous magnesium sulfate, filtered, and concentrated under reduced pressure. The obtained concentration residue was subjected to silica gel column chromatography (elution solvent:n-hexane:ethyl acetate=86:14→53:47 (V/V)), and a fraction containing the compound of interest was concentrated under reduced pressure and dried under reduced pressure to obtain 8.30 g of the title compound (yield: 64%) as a white foam.

Mass spectrum (CI, m/z): 479 [M+1]$^+$.

$^1$H-NMR spectrum (400 MHz, DMSO-d$_6$) δ: 9.98 & 9.72 & 9.71 (s, total 1H), 4.50-4.37 (m, 4H), 2.53-2.43 (m, 2H), 2.32-2.07 (m, 2H), 2.02-1.72 (m, 2H), 1.65-1.55 (m, 6H), 1.51-1.42 (m, 9H), 1.38-1.31 (m, 3H), 0.10 & 0.06 & 0.01 (s, total 9H).

Reference Example 3

Ethyl 6,6-dimethyl-3-[1-(trimethylsilyl)cyclobutanecarboxamido]-5,6-dihydropyrrolo[3,4-c]pyrazole-2(4H)-carboxylate

[Chemical Formula 116]

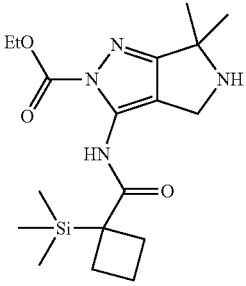

To a solution of 43.2 g (90.0 mmol) of 5-tert-butyl 2-ethyl 6,6-dimethyl-3-[1-(trimethylsilyl)cyclobutanecarboxamido]pyrrolo[3,4-c]pyrazole-2,5(4H,6H)-dicarboxylate synthesized in the same way as in Reference Example 2 in 430 ml of dichloromethane, 30 ml (259 mmol) of 2,6-dimethylpyridine and 46 ml (255 mmol) of trimethylsilyl trifluoromethanesulfonate were added dropwise in this order at 0° C. with stirring in an argon atmosphere and reacted at 0° C. for 1 hour with stirring.

After completion of the reaction, 260 ml of a saturated aqueous solution of sodium bicarbonate and 260 ml of dichloromethane were added to the reaction solution, followed by separation into an organic layer and an aqueous layer. The aqueous layer was subjected to extraction twice with 260 ml of dichloromethane, and then, the whole organic layer thus obtained was washed with 260 ml of a saturated aqueous solution of sodium bicarbonate and 260 ml of saturated saline in this order, subsequently dried over anhydrous magnesium sulfate, filtered, and concentrated under reduced pressure. The operation of adding toluene to the obtained concentration residue and concentrating the resultant under reduced pressure is repeated to obtain 39.7 g of the title compound as a pale yellow solid.

The title compound was also synthesized as follows.

To a solution of 57.1 g (119 mmol) of 5-tert-butyl 2-ethyl 6,6-dimethyl-3-[1-(trimethylsilyl)cyclobutanecarboxamido]pyrrolo[3,4-c]pyrazole-2,5(4H,6H)-dicarboxylate synthesized in the same way as in Reference Example 2 in 500 ml of dichloromethane, 28.0 ml (242 mmol) of 2,6-dimethylpyridine and 43.0 ml (238 mmol) of trimethylsilyl trifluoromethanesulfonate were added dropwise in this order at 0° C. in a nitrogen atmosphere and reacted at 0° C. for 2 hours with stirring.

After completion of the reaction, the reaction solution was poured into 1000 ml of a saturated aqueous solution of sodium bicarbonate, then stirred at room temperature, and subsequently separated into an organic layer and an aqueous layer. The aqueous layer was subjected to extraction twice with 500 ml of ethyl acetate, and then, the whole organic layer thus obtained was washed with saturated saline, dried over anhydrous magnesium sulfate, filtered, and concentrated under reduced pressure. The operation of adding toluene to the obtained concentration residue and concentrating the resultant under reduced pressure was performed three times, then the obtained brown oil was refrigerated overnight, and subsequently, 50 ml of diethyl ether and 100 ml of n-hexane were added and stirred at room temperature for 0.5 hours. The deposited solid was collected by filtration, washed with n-hexane, and then dried under reduced pressure to obtain 17.0 g of the title compound (yield: 38%) as a white solid.

Mass spectrum (DUIS, m/z): 379 [M+1]$^+$.

$^1$H-NMR spectrum (400 MHz, CDCl$_3$) δ: 9.86 (s, 1H), 4.52 (q, J=7.1 Hz, 2H), 4.23 (s, 2H), 2.64-2.52 (m, 2H), 2.38-2.27 (m, 2H), 2.03-1.89 (m, 2H), 1.53-1.42 (m, 9H), 0.14 (s, 9H).

Reference Example 4

Ethyl 5-(chlorocarbonyl)-6,6-dimethyl-3-[1-(trimethylsilyl)cyclobutanecarboxamido]-5,6-dihydropyrrolo[3,4-c]pyrazole-2(4H)-carboxylate

[Chemical Formula 117]

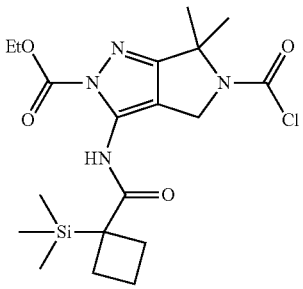

To a solution of 4.90 g (11.1 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 50 ml of dichloromethane, 6.80 ml (39.0 mmol) of DIPEA was added at room temperature in a nitrogen atmosphere, and then, a solution of 2.34 g (7.89 mmol) of bis(trichloromethyl)carbonate in 10 ml of dichloromethane was added dropwise thereto at −78° C. and reacted at −78° C. for 2 hours with stirring.

After completion of the reaction, 80 ml of a saturated aqueous solution of sodium bicarbonate was added to the reaction solution and stirred for 5 minutes. Dichloromethane was added thereto and then stirred while the temperature was raised to room temperature. The reaction solution was separated into an organic layer and an aqueous layer, and then, the aqueous layer was subjected to extraction twice with dichloromethane. The whole organic layer thus obtained was dried over anhydrous magnesium sulfate, filtered, and concentrated under reduced pressure. The obtained concentration residue was subjected to preparative column chromatography (apparatus 2, silica gel, elution solvent:n-hexane:ethyl acetate=90:10→85:15→75:25 (V/V)), and a fraction containing the compound of interest was concentrated under reduced pressure. n-Hexane was added to the obtained concentration residue, and the deposited solid was collected by filtration, washed with n-hexane, and then dried under reduced pressure to obtain 2.00 g of the title compound (yield: 41%) as a white solid. Also, the obtained filtrate was concentrated under reduced pressure and dried under reduced pressure to obtain 2.50 g of the title compound including impurities (yield: 51% [calculation value with the purity defined as 100%]) as a pale yellow foam.

Mass spectrum (DUIS, m/z): 441 [M+1]$^+$.

$^1$H-NMR spectrum (400 MHz, CDCl$_3$) δ: 9.94 (s, 1H), 4.97 (s, 2H), 4.55 (q, J=7.1 Hz, 2H), 2.64-2.53 (m, 2H), 2.39-2.30 (m, 2H), 2.05-1.93 (m, 2H), 1.78 (s, 6H), 1.48 (t, J=7.1 Hz, 3H), 0.16 (s, 9H).

Reference Example 5

1-(Ethyldimethylsilyl)cyclobutanecarboxylic acid

[Chemical Formula 118]

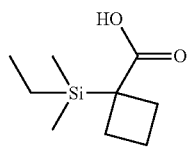

To 200 ml of THF, 214 ml (428 mmol) of a 2 M solution of lithium diisopropylamide in THF was added in an argon atmosphere, and then, 10.7 ml (112 mmol) of cyclobutanecarboxylic acid was added dropwise thereto under cooling in ice water and stirred while the temperature was raised to room temperature according to the circumstances. Subsequently, 20 ml (120 mmol) of hexamethylphosphoric triamide was added thereto. After cooling with a dry ice/ethanol refrigerant, 67.6 ml (485 mmol) of chloro(ethyl)dimethylsilane was added dropwise thereto at −75° C. to −69° C. and stirred overnight at a temperature of −60° C. or lower.

After completion of the reaction, 67 ml of methanol and subsequently 134 ml of cold water were added dropwise to the reaction solution and then brought about to room temperature. 240 ml of 2 N hydrochloric acid was added thereto to attain acidity (pH 2.0), and 200 ml of diethyl ether was added thereto, followed by separation into an organic layer and an aqueous layer. The obtained organic layer was washed with 250 ml of a saturated aqueous solution of sodium chloride, then dried over anhydrous magnesium sulfate, filtered, and concentrated under reduced pressure. 41 ml of a 2 N aqueous sodium hydroxide solution was added to the obtained concentration residue, followed by washing with 250 ml of n-hexane. The aqueous layer was rendered acidic (pH 2.0) again by the addition of 82 ml of 1 N hydrochloric acid. This solution was subjected to extraction with 250 ml of ethyl acetate, and the organic layer was concentrated under reduced pressure. The obtained residue was subjected to silica gel column chromatography (elution solvent: 1,2-dichloroethane:methanol=100:0→95:5 (V/V)), and a fraction containing the compound of interest was concentrated under reduced pressure and dried under reduced pressure to obtain 11.7 g of the title compound (yield: 59%) as a white solid.

$^1$H-NMR spectrum (400 MHz, DMSO-d$_6$) δ: 11.71 (br s, 1H), 2.44-2.33 (m, 2H), 2.19-2.08 (m, 2H), 1.91-1.73 (m, 2H), 0.92 (t, J=7.9 Hz, 3H), 0.55 (q, J=7.9 Hz, 2H), 0.05 (s, 6H).

Reference Example 6

5-tert-Butyl 2-ethyl 3-[1-(ethyldimethylsilyl)cyclobutanecarboxamido]-6,6-dimethylpyrrolo[3,4-c]pyrazole-2,5(4H,6H)-dicarboxylate

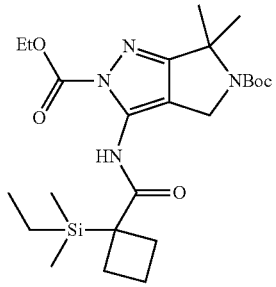

[Chemical Formula 119]

To a solution of 11.7 g (62.8 mmol) of 1-(ethyldimethylsilyl)cyclobutanecarboxylic acid synthesized in the same way as in Reference Example 5 in 81 ml of dichloromethane, 5.3 ml (62 mmol) of oxalyl chloride and 0.24 ml (3.1 mmol) of DMF were added in this order under cooling in ice water in an argon atmosphere and stirred at the same temperature as above for 2 hours.

After completion of the reaction, the reaction solution was concentrated under reduced pressure at room temperature to obtain a concentration residue. A solution of the obtained concentration residue in 5 ml of dehydrated dichloromethane was added dropwise to a solution of 6.73 g (20.7 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] and 18 ml (100 mmol) of DIPEA in 94 ml of dichloromethane under cooling in ice water in a nitrogen atmosphere and stirred at the same temperature as above for 16 hours.

After completion of the reaction, the reaction solution was separated into an organic layer and an aqueous layer by the addition of 350 ml of a 5% aqueous potassium bisulfate solution, and then, the aqueous layer was subjected to extraction twice with 150 ml of dichloromethane. The whole organic layer thus obtained was dried over anhydrous magnesium sulfate and then filtered, and the filtrate was concentrated under reduced pressure. The obtained residue was subjected to silica gel column chromatography (elution solvent:n-hexane:ethyl acetate=86:14→53:47 (V/V)), and a fraction containing the compound of interest was concentrated under reduced pressure to obtain 7.51 g of the title compound (yield: 74%) as a pale yellow oil.

Mass spectrum (DUIS, m/z): 493 [M+1]$^+$.

$^1$H-NMR spectrum (400 MHz, DMSO-d$_6$) δ: 9.82-9.69 (m, 1H), 4.51-4.36 (m, 4H), 2.49-2.42 (m, 2H), 2.32-2.23 (m, 2H), 1.95-1.84 (m, 2H), 1.62-1.55 (m, 6H), 1.49-1.42 (m, 9H), 1.38-1.31 (m, 3H), 0.91 (t, J=7.9 Hz, 3H), 0.57 (q, J=7.9 Hz, 2H), 0.09 (s, 6H).

Reference Example 7

Ethyl 3-[1-(ethyldimethylsilyl)cyclobutanecarboxamido]-6,6-dimethyl-5,6-dihydropyrrolo[3,4-c]pyrazole-2(4H)-carboxylate

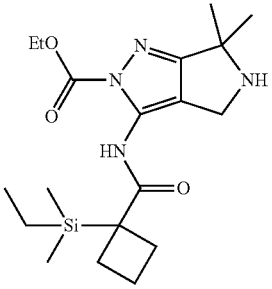

[Chemical Formula 120]

To a solution of 2.87 g (5.79 mmol) of 5-tert-butyl 2-ethyl 3-[1-(ethyldimethylsilyl)cyclobutanecarboxamido]-6,6-dimethylpyrrolo[3,4-c]pyrazole-2,5(4H,6H)-dicarboxylate synthesized in the same way as in Reference Example 6 in 30 ml of dichloromethane, 2.10 ml (18.1 mmol) of 2,6-dimethylpyridine and 3.20 ml (17.8 mmol) of trimethylsilyl trifluoromethanesulfonate were added dropwise in this order at 0° C. in a nitrogen atmosphere and reacted at 0° C. for 2.5 hours with stirring.

After completion of the reaction, dichloromethane was added to the reaction solution, followed by washing with a saturated aqueous solution of sodium bicarbonate. After separation into an organic layer and an aqueous layer, the aqueous layer was subjected to extraction twice with dichloromethane. The whole organic layer thus obtained was washed with saturated saline, then dried over anhydrous magnesium sulfate, filtered, and concentrated under reduced pressure. The operation of adding toluene to the obtained concentration residue and concentrating the resultant under reduced pressure was performed twice. The obtained concentration residue was subjected to preparative column chromatography (apparatus 2, silica gel, elution solvent: dichloromethane:methanol=98:2→95:5→92:8 (V/V)), and a fraction containing the compound of interest was concentrated under reduced pressure, dried under reduced pressure to obtain 2.17 g of the title compound (yield: 92%) as a pale yellow oil.

Mass spectrum (DUIS, m/z): 393 [M+1]$^+$.

$^1$H-NMR spectrum (400 MHz, CDCl$_3$) δ: 9.88 (s, 1H), 4.52 (q, J=7.1 Hz, 2H), 4.21 (s, 2H), 2.63-2.52 (m, 2H), 2.39-2.29 (m, 2H), 2.03-1.90 (m, 2H), 1.52-1.42 (m, 9H), 0.96 (t, J=7.9 Hz, 3H), 0.64 (q, J=7.9 Hz, 2H), 0.13 (s, 6H).

Reference Example 8

1-Fluoro-3-(methoxy-d3)-2-nitrobenzene

[Chemical Formula 121]

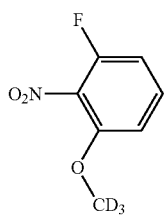

To a solution of 1.0 g (6.4 mmol) of 3-fluoro-2-nitrophenol in 20 ml of DMF, 0.79 ml (13 mmol) of ($^2$H$_3$) methyl iodide and 2.20 g (15.9 mmol) of anhydrous potassium carbonate were added at 0° C. in an argon atmosphere and reacted at 0° C. for 3 hours with stirring.

After completion of the reaction, a saturated aqueous solution of ammonium chloride was added to the reaction solution, followed by extraction with ethyl acetate. The obtained organic layer was washed with saturated saline, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=95:5→75:25 (V/V)), and a fraction containing the compound of interest was concentrated under reduced pressure to obtain 1.04 g of the title compound (yield: 94%) as a colorless oil.

Mass spectrum (CI, m/z): 175 [M+1]$^+$.
$^1$H-NMR spectrum (400 MHz, DMSO-d$_6$) δ: 7.64 (dt, J=6.7, 8.7 Hz, 1H), 7.21 (td, J=1.0, 8.7 Hz, 1H), 7.15 (ddd, J=1.0, 8.7, 9.6 Hz, 1H).

Reference Example 9

2-Fluoro-6-(methoxy-d3)aniline

[Chemical Formula 122]

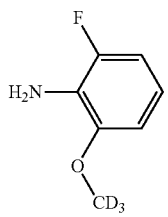

To a solution of 1.04 g (5.97 mmol) of 1-fluoro-3-(methoxy-d3)-2-nitrobenzene synthesized in the same way as in Reference Example 8 in 20 ml of ethanol, 200 mg of 10% Pd—C(containing 54.33% water, PE-type manufactured by N.E. Chemcat Corp.) was added at room temperature in an argon atmosphere and after replacement with a hydrogen atmosphere, reacted at room temperature for 4 hours with stirring.

After completion of the reaction, the reaction solution was diluted with ethyl acetate, subsequently filtered through celite, and concentrated under reduced pressure. The obtained concentration residue was subjected to preparative column chromatography (apparatus 1, silica gel, elution solvent:n-hexane:ethyl acetate=53:47→45:55 (V/V)), and a fraction containing the compound of interest was concentrated under reduced pressure to obtain 721 mg of the title compound (yield: 84%) as a white solid.

Mass spectrum (CI, m/z): 145 [M+1]$^+$.
$^1$H-NMR spectrum (400 MHz, DMSO-d$_6$) δ: 6.71-6.63 (m, 2H), 6.52 (dt, J=6.3, 8.3 Hz, 1H), 4.58 (s, 2H).

Reference Example 10

2-Fluoro-4-methoxy-1-methylbenzene

[Chemical Formula 123]

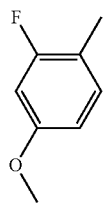

To a solution of 1.00 g (7.93 mmol) of 3-fluoro-4-methylphenol in 20 ml of dehydrated DMF, 3.30 g (23.9 mmol) of potassium carbonate and 0.750 ml (12.0 mmol) of methyl iodide were added at room temperature in an argon atmosphere and reacted at room temperature for 16 hours with stirring.

After completion of the reaction, water was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=100:0→80:20 (V/V)), and a fraction containing the compound of interest was concentrated under reduced pressure to obtain 725 mg of the title compound (yield: 65%) as a colorless oil.

Mass spectrum (CI, m/z): 141 [M+1]$^+$.
$^1$H-NMR spectrum (400 MHz, CDCl$_3$) δ: 7.10-7.01 (m, 1H), 6.62-6.55 (m, 2H), 3.77 (s, 3H), 2.21-2.18 (m, 3H).

Reference Example 11

2-Fluoro-6-methoxy-3-methylbenzoic acid

[Chemical Formula 124]

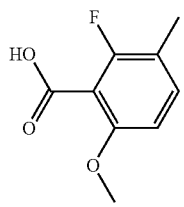

To a solution of 725 mg (5.17 mmol) of 2-fluoro-4-methoxy-1-methylbenzene synthesized in the same way as in Reference Example 10 in 15 ml of THF, 5.70 ml (6.21 mmol) of a 1.09 M solution of lithium diisopropylamide in THF and hexane was added dropwise at −78° C. in an argon atmosphere and reacted at −78° C. for 1 hour with stirring. Subsequently, an excessive amount of dry ice was added thereto at −78° C. and reacted at −78° C. for 2 hours with stirring.

After completion of the reaction, the reaction solution whose temperature was raised to room temperature was adjusted to pH 4 by the addition of 1 N hydrochloric acid, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent: 1,2-dichloroethane:methanol=100: 0→90:10 (V/V)), and a fraction containing the compound of interest was concentrated under reduced pressure to obtain 276 mg of the title compound (yield: 29%) as a white solid.

Mass spectrum (CI, m/z): 185 [M+1]⁺.

¹H-NMR spectrum (400 MHz, CDCl₃) δ: 7.32-7.21 (m, 1H), 6.70 (dd, J=1.0, 8.7 Hz, 1H), 3.94 (s, 3H), 2.28-2.20 (m, 3H).

Reference Example 12

2-(Difluoromethoxy)-6-fluorobenzamide

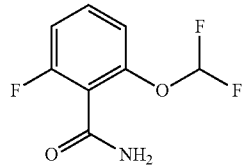

[Chemical Formula 125]

To a solution of 400 mg (2.14 mmol) of 2-(difluoromethoxy)-6-fluorobenzonitrile [purchased from Enamine Ltd.] in 5 ml of ethanol and 5 ml of DMSO, 6.41 ml (6.41 mmol) of a 1 M aqueous sodium hydroxide solution and 1.10 ml (10.7 mmol) of a 30 wt % aqueous hydrogen peroxide solution were added at 0° C. in an argon atmosphere and reacted at room temperature for 2 hours with stirring.

After completion of the reaction, a saturated aqueous solution of sodium thiosulfate was added to the reaction solution and stirred for 0.5 hours, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane: ethyl acetate=80:20→60:40 (v/v)), and a fraction containing the compound of interest was concentrated under reduced pressure to obtain 406 mg of the title compound (yield: 93%) as a white solid.

Mass spectrum (DUIS, m/z): 206 [M+1]⁺.

¹H-NMR spectrum (400 MHz, DMSO-d₆) δ: 8.01 (br s, 1H), 7.75 (br s, 1H), 7.49 (dt, J=6.7, 8.4 Hz, 1H), 7.21 (t, J=73.7 Hz, 1H), 7.20-7.14 (m, 1H), 7.11-7.06 (m, 1H).

Reference Example 13

Methyl 2-ethyl-6-fluorobenzoate

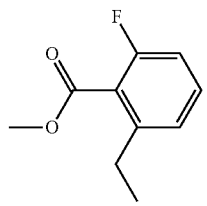

[Chemical Formula 126]

To a solution of 2.01 g (8.63 mmol) of methyl 2-bromo-6-fluorobenzoate in 20 ml of 1,4-dioxane and 4.0 ml of water, 2.80 g (26.4 mmol) of sodium carbonate and 2.90 ml (16.9 mmol) of 4,4,5,5-tetramethyl-2-vinyl-1,3,2-dioxaborolane were added in a nitrogen atmosphere and then stirred at room temperature for 10 minutes while argon gas was bubbled into the reaction solution. Subsequently, 1.02 g (0.883 mmol) of tetrakis(triphenylphosphine)palladium(0) was added thereto at room temperature and reacted at 90° C. for 4 hours with stirring.

After completion of the reaction, the reaction solution was diluted with water, followed by extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, n-hexane:ethyl acetate=99: 1→98:2→97:3), and a fraction containing methyl 2-fluoro-6-vinylbenzoate was concentrated under reduced pressure and dried under reduced pressure.

To a solution of the obtained concentration residue in 16 ml of 1,4-dioxane and 4.0 ml of water, 1.34 g (12.6 mmol) of sodium carbonate and 1.40 ml (8.16 mmol) of 4,4,5,5-tetramethyl-2-vinyl-1,3,2-dioxaborolane were added in a nitrogen atmosphere and then stirred at room temperature for 10 minutes while argon gas was bubbled into the reaction solution. Subsequently, 446 mg (0.386 mmol) of tetrakis (triphenylphosphine)palladium(0) was added thereto at room temperature and reacted at 90° C. for 3 hours with stirring. Subsequently, 1.10 ml (6.41 mmol) of 4,4,5,5-tetramethyl-2-vinyl-1,3,2-dioxaborolane and 133 mg (0.115 mmol) of tetrakis(triphenylphosphine)palladium(0) were added to the reaction solution and reacted at 90° C. for 3 hours with stirring.

After completion of the reaction, the reaction solution was diluted with water, followed by extraction twice with ethyl acetate. The whole organic layer thus obtained was dried over anhydrous magnesium sulfate, then filtered, and concentrated under reduced pressure. The obtained concentration residue was subjected to preparative column chromatography (apparatus 1, silica gel, n-hexane:ethyl acetate=99: 1→98:2→97:3), and a fraction containing methyl 2-fluoro-6-vinylbenzoate was concentrated under reduced pressure and dried under reduced pressure.

To a solution of the obtained concentration residue in 20 ml of ethanol, 0.20 g of 10% Pd—C(containing 54% water, PE-type manufactured by N.E. Chemcat Corp.) was added at room temperature in a nitrogen atmosphere. The inside of the reaction container was replaced with a hydrogen atmosphere, followed by reaction at room temperature for 0.5 hours with stirring. The inside of the reaction container was brought back to a nitrogen atmosphere, and then, 0.36 g of 10% Pd—C (containing 54% water, PE-type manufactured by N.E. Chemcat Corp.) was added thereto at room temperature. The inside of the reaction container was replaced again with a hydrogen atmosphere, followed by reaction at room temperature for 1.5 hours with stirring.

After completion of the reaction, the inside of the reaction container was replaced with a nitrogen atmosphere, and subsequently, the reaction solution was filtered using a celite filter. The removed solid was washed with ethyl acetate, and then, the whole filtrate was concentrated under reduced pressure. The obtained concentration residue was subjected to preparative column chromatography (apparatus 1, silica gel, n-hexane:ethyl acetate=99:1→98:2→97:3→96:4), and a fraction containing the compound of interest was concentrated under reduced pressure and dried under reduced pressure to obtain 664 mg of the title compound (yield: 42% [2 steps]) as a colorless oil.

Mass spectrum (CI, m/z): 183 [M+1]⁺.

¹H-NMR spectrum (400 MHz, CDCl₃) δ: 7.32 (dt, J=5.8, 8.0 Hz, 1H), 7.07-7.01 (m, 1H), 6.98-6.90 (m, 1H), 3.94 (s, 3H), 2.71 (q, J=7.6 Hz, 2H), 1.22 (t, J=7.6 Hz, 3H).

Reference Example 14

2-Ethyl-6-fluorobenzoic acid

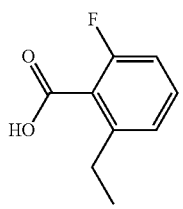

[Chemical Formula 127]

To a solution of 659 mg (3.62 mmol) of methyl 2-ethyl-6-fluorobenzoate synthesized in the same way as in Reference Example 13 in 10 ml of ethanol, 4.0 ml (20 mmol) of a 5 N aqueous sodium hydroxide solution was added at room temperature in a nitrogen atmosphere and reacted at room temperature for 3.5 hours with stirring. Subsequently, 2.0 ml (10 mmol) of a 5 N aqueous sodium hydroxide solution was added to the reaction solution and reacted at room temperature for 3.5 hours and at 60° C. for 1 hour with stirring.

After completion of the reaction, the reaction solution was concentrated under reduced pressure, and ethanol was distilled off. Water was added to the concentration residue, followed by washing twice with toluene. The aqueous layer was adjusted to pH 2 by the addition of 6 N hydrochloric acid, followed by extraction twice with ethyl acetate. The whole organic layer thus obtained was washed with a saturated aqueous solution of sodium chloride, then dried over anhydrous magnesium sulfate, filtered, concentrated under reduced pressure, and dried under reduced pressure to obtain 558 mg of the title compound (yield: 92%) as a yellow solid.

Mass spectrum (CI, m/z): 169 [M+1]⁺.

¹H-NMR spectrum (400 MHz, CDCl₃) δ: 7.38 (dt, J=5.7, 8.1 Hz, 1H), 7.11-7.05 (m, 1H), 7.03-6.95 (m, 1H), 2.84 (q, J=7.6 Hz, 2H), 1.27 (t, J=7.6 Hz, 3H).

Reference Example 15

6-Fluorobenzofuran-7-carboxylic acid

[Chemical Formula 128]

To a solution of 3.76 g (17.5 mmol) of 7-bromo-6-fluorobenzofuran [synthesized according to the method described in EP1204654, page 14-16] in 50 ml of dehydrated THF, 12.3 ml (19.3 mmol) of a 1.57 M solution of n-butyllithium in n-hexane was added dropwise at −78° C. in a nitrogen atmosphere and reacted at −78° C. for 1 hour with stirring. 36.4 g (827 mmol) of dry ice was added in divided portions thereto at −78° C. and reacted at −78° C. for 1 hour with stirring and subsequently for 6.5 hours while the temperature was raised to room temperature according to the circumstances.

After completion of the reaction, water was added to the reaction solution and then concentrated under reduced pressure, and THF was distilled off. A 1 N aqueous sodium hydroxide solution was added to the obtained concentration residue, followed by washing twice with toluene. The obtained aqueous layer was adjusted to pH 2 by the addition of 6 N hydrochloric acid, followed by extraction three times with ethyl acetate. The whole organic layer thus obtained was washed with a saturated aqueous solution of sodium chloride, then dried over anhydrous magnesium sulfate, filtered, and concentrated under reduced pressure and dried under reduced pressure to obtain 2.91 g of the title compound (yield: 92%) as a light orange solid.

Mass spectrum (CI, m/z): 181 [M+1]⁺.

¹H-NMR spectrum (400 MHz, CDCl₃) δ: 7.78 (d, J=2.2 Hz, 1H), 7.75 (dd, J=4.8, 8.6 Hz, 1H), 7.13 (dd, J=8.6, 11.0 Hz, 1H), 6.83 (d, J=2.2 Hz, 1H).

Reference Example 16

6-Fluoro-2,3-dihydrobenzofuran-7-carboxylic acid

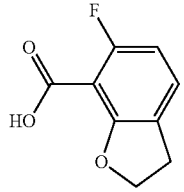

[Chemical Formula 129]

To a solution of 729 mg (4.05 mmol) of 6-fluorobenzofuran-7-carboxylic acid synthesized in the same way as in Reference Example 15 in 15 ml of ethanol, 255 mg of 10% Pd—C(containing 54% water, PE-type manufactured by N.E. Chemcat Corp.) was added at room temperature in a nitrogen atmosphere. The inside of the reaction container was replaced with a hydrogen atmosphere, followed by reaction at room temperature for 1.5 hours with stirring. The inside of the reaction container was brought back to a nitrogen atmosphere, and then, 236 mg of 10% Pd—C (containing 54% water, PE-type manufactured by N.E. Chemcat Corp.) was added thereto at room temperature. The inside of the reaction container was replaced with a hydrogen atmosphere, followed by reaction at room temperature for 6.5 hours with stirring. The inside of the reaction container was brought back to a nitrogen atmosphere, and then, 1.03 g of 10% Pd—C(containing 54% water, PE-type manufactured by N.E. Chemcat Corp.) was added thereto at room temperature. The inside of the reaction container was replaced with a hydrogen atmosphere, followed by reaction at room temperature for 1 hour with stirring.

After completion of the reaction, the inside of the reaction container was replaced with a nitrogen atmosphere, and subsequently, the reaction solution was filtered using a celite filter. The removed solid was washed with ethyl acetate, and then, the whole filtrate was concentrated under reduced pressure. The obtained concentration residue was subjected to preparative column chromatography (apparatus 3, ODS silica gel, elution solvent: 0.1 vol % acetonitrile formate:0.1 vol % aqueous formic acid solution=25:75 (V/V)), and a fraction containing the compound of interest was concentrated under reduced pressure, followed by the distilling off of acetonitrile. The obtained concentration residue was subjected to extraction three times with ethyl acetate, and the whole organic layer thus obtained was washed with a saturated aqueous solution of sodium chloride, then dried over anhydrous magnesium sulfate, filtered, concentrated under reduced pressure, and dried under reduced pressure to obtain 339 mg of the title compound (yield: 46%) as a pale yellow solid.

Mass spectrum (CI, m/z): 183 [M+1]$^+$.

$^1$H-NMR spectrum (400 MHz, CDCl$_3$) δ: 7.31-7.25 (m, 1H), 6.66 (dd, J=8.2, 11.0 Hz, 1H), 4.82 (t, J=8.8 Hz, 2H), 3.28-3.19 (m, 2H).

Reference Example 17

2-Chloro-6-cyclopropylbenzoic acid

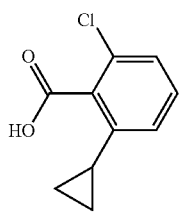

[Chemical Formula 130]

To a solution of 495 mg (3.05 mmol) of 2-cyclopropylbenzoic acid [purchased from WuXi AppTec] in 9.0 ml of DMF, 496 mg (3.71 mmol) of N-chlorosuccinimide and 70.3 mg (0.313 mmol) of palladium(II) acetate were added at room temperature in a nitrogen atmosphere and reacted at 100° C. for 2.5 hours with stirring. Subsequently, 70.3 mg (0.313 mmol) of palladium(II) acetate was added thereto and reacted at 100° C. for 1.5 hours with stirring. Further, 344 mg (2.58 mmol) of N-chlorosuccinimide was added thereto and reacted at 100° C. for 1 hour with stirring.

After completion of the reaction, water was added to the reaction solution, and then, insoluble matter was filtered off using a celite filter. The filtrate was subjected to extraction three times with ethyl acetate, and then, the whole organic layer thus obtained was dried over anhydrous magnesium sulfate, filtered, and concentrated under reduced pressure to obtain 1.38 g of a concentration residue.

To a solution of the obtained concentration residue in 8.0 ml of DMF, 763 mg (5.71 mmol) of N-chlorosuccinimide and 150 mg (0.668 mmol) of palladium(II) acetate were added at room temperature in a nitrogen atmosphere and reacted at 100° C. for 1.5 hours with stirring.

After completion of the reaction, water was added to the reaction solution, and then, insoluble matter was filtered off using a celite filter. The filtrate was subjected to extraction three times with ethyl acetate, and then, the whole organic layer thus obtained was dried over anhydrous magnesium sulfate, filtered, and concentrated under reduced pressure to obtain 1.43 g of a concentration residue.

To a solution of the obtained concentration residue in 10 ml of DMF, 227 mg (1.40 mmol) of 2-cyclopropylbenzoic acid [purchased from WuXi AppTec], 956 mg (7.16 mmol) of N-chlorosuccinimide, and 246 mg (1.10 mmol) of palladium(II) acetate were added at room temperature in a nitrogen atmosphere and reacted at 100° C. for 1 hour with stirring.

After completion of the reaction, water was added to the reaction solution, and then, insoluble matter was filtered off using a celite filter. The filtrate was subjected to extraction three times with ethyl acetate, and then, the whole organic layer thus obtained was dried over anhydrous magnesium sulfate, filtered, and concentrated under reduced pressure. The obtained concentration residue was subjected to preparative column chromatography (apparatus 3, Fluoro-phenyl silica gel, elution solvent: 0.1 vol % acetonitrile formate: 0.1 vol % aqueous formic acid solution=40:60), and a fraction containing the compound of interest was concentrated under reduced pressure to distill off acetonitrile. The obtained concentration residue was subjected to extraction three times with ethyl acetate, and then, the whole organic layer thus obtained was washed with a saturated aqueous solution of sodium chloride, dried over anhydrous magnesium sulfate, filtered, and concentrated under reduced pressure. The obtained concentration residue was subjected again to preparative column chromatography (apparatus 3, ODS silica gel, elution solvent: 0.1 vol % acetonitrile formate:0.1 vol % aqueous formic acid solution=40:60), and a fraction containing the compound of interest was concentrated under reduced pressure to distill off acetonitrile. The obtained concentration residue was subjected to extraction three times with ethyl acetate, and then, the whole organic layer thus obtained was washed with a saturated aqueous solution of sodium chloride, dried over anhydrous magnesium sulfate, filtered, concentrated under reduced pressure, and dried under reduced pressure to obtain 178 mg of the title compound (yield: 20%).

Mass spectrum (CI, m/z): 197 [M+1]$^+$.

$^1$H-NMR spectrum (400 MHz, CD$_2$Cl$_2$) δ: 7.33-7.23 (m, 2H), 6.97-6.91 (m, 1H), 2.03 (tt, J=5.2, 8.5 Hz, 1H), 1.08-0.93 (m, 2H), 0.81-0.68 (m, 2H).

Reference Example 18

Methyl 6-chloro-2-fluoro-3-methylbenzoate

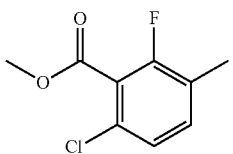

[Chemical Formula 131]

To a solution of 3.00 g (15.9 mmol) of 6-chloro-2-fluoro-3-methylbenzoic acid in 80 ml of DMF, 7.26 g (22.3 mmol) of cesium carbonate and 1.19 ml (19.1 mmol) of methyl iodide were added at room temperature in an argon atmosphere and reacted at room temperature for 2 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=100:0→95:5 (v/v)), and a fraction containing the compound of interest was concentrated under reduced pressure to obtain 2.81 g of the title compound (yield: 87%) as a colorless oil.

Mass spectrum (CI, m/z): 203 [M+1]$^+$.

$^1$H-NMR spectrum (400 MHz, CDCl$_3$) δ: 7.22-7.15 (m, 1H), 7.14-7.07 (m, 1H), 3.97 (s, 3H), 2.30-2.24 (m, 3H).

Reference Example 19

Methyl 2-fluoro-3,6-dimethylbenzoate

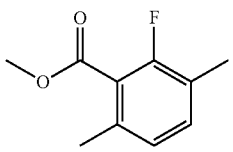

[Chemical Formula 132]

To a solution of 1.00 g (4.94 mmol) of methyl 6-chloro-2-fluoro-3-methylbenzoate synthesized in the same way as in Reference Example 18 in 20 ml of 1,4-dioxane, 2.07 ml (14.8 mmol) of trimethylboroxine, 2.73 g (19.8 mmol) of anhydrous potassium carbonate, and 336 mg (0.493 mmol) of (1,3-diisopropylimidazol-2-ylidene)(3-chloropyridyl)palladium(II) dichloride were added at room temperature in an argon atmosphere and reacted at 100° C. for 2 hours with stirring.

After completion of the reaction, the reaction solution was diluted with ethyl acetate and filtered through a membrane filter. A saturated aqueous solution of ammonium chloride was added to the filtrate, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=100:0→95:5 (v/v)), and a fraction containing the compound of interest was concentrated under reduced pressure to obtain 849 mg of the title compound (yield: 94%) as a colorless oil.

Mass spectrum (CI, m/z): 183 [M+1]$^+$.

$^1$H-NMR spectrum (400 MHz, CDCl$_3$) δ: 7.12 (t, J=7.8 Hz, 1H), 6.89 (d, J=7.8 Hz, 1H), 3.93 (s, 3H), 2.34 (s, 3H), 2.27-2.22 (m, 3H).

Reference Example 20

2-Fluoro-3,6-dimethylbenzoic acid

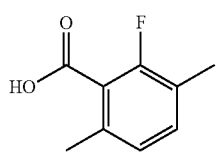

[Chemical Formula 133]

To a solution of 843 mg (4.63 mmol) of methyl 2-fluoro-3,6-dimethylbenzoate synthesized in the same way as in Reference Example 19 in 5 ml of THF and 10 ml of water, 332 mg (13.9 mmol) of lithium hydroxide was added at room temperature in an argon atmosphere and reacted at room temperature for 15 hours and at 80° C. for 8 hours with stirring.

After completion of the reaction, a saturated aqueous solution of ammonium chloride was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=50:50→30:70 (v/v)), and a fraction containing the compound of interest was concentrated under reduced pressure to obtain 565 mg of the title compound (yield: 73%) as a white solid.

Mass spectrum (CI, m/z): 169 [M+1]$^+$.

$^1$H-NMR spectrum (400 MHz, DMSO-d$_6$) δ: 13.42 (br s, 1H), 7.23 (t, J=7.9 Hz, 1H), 6.99 (d, J=7.9 Hz, 1H), 2.28 (s, 3H), 2.22-2.18 (m, 3H).

Reference Example 21

2-Chloro-3-fluoro-6-methylbenzoic acid

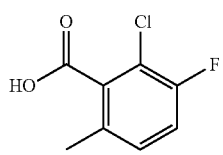

[Chemical Formula 134]

To a solution of 4.00 g (26.0 mmol) of 5-fluoro-2-methylbenzoic acid in 100 ml of DMF, 0.31 g (1.4 mmol) of palladium(II) acetate was added in an argon atmosphere, and then, 4.35 g (32.6 mmol) of N-chlorosuccinimide was added in divided portions thereto at room temperature and reacted at 100° C. for 5 hours with stirring.

After completion of the reaction, the reaction solution was cooled to room temperature, and water was added thereto. The resulting solid was filtered using a celite filter. The filtrate was subjected to extraction with ethyl acetate, and the obtained organic layer was washed with water and a saturated aqueous solution of sodium chloride in this order, then dried over anhydrous magnesium sulfate, filtered, and concentrated under reduced pressure. The obtained concentration residue was subjected to preparative column chromatography (apparatus 2, silica gel, elution solvent:n-hexane:ethyl acetate=70:30→30:70 (V/V)), and a fraction containing the compound of interest was concentrated under reduced pressure. The obtained concentration residue was subjected again to preparative column chromatography (apparatus 2, silica gel, elution solvent:n-hexane:ethyl acetate=70:30→30:70 (V/V)), and a fraction containing the compound of interest was concentrated under reduced pressure to obtain 182 mg of the title compound (yield: 4%) as a white solid.

Mass spectrum (DUIS, m/z): 187 [M−1]$^-$.

$^1$H-NMR spectrum (400 MHz, DMSO-d$_6$) δ: 13.91 (br s, 1H), 7.37 (t, J=8.9 Hz, 1H), 7.32-7.26 (m, 1H), 2.29-2.25 (m, 3H).

Reference Example 22

Ethyl 6,6-dimethyl-3-[1-(trimethylsilyl)cyclopropanecarboxamido]-5,6-dihydropyrrolo[3,4-c]pyrazole-2(4H)-carboxylate

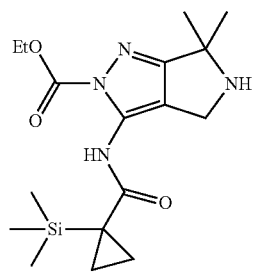

[Chemical Formula 135]

To a solution of 9.70 g (61.3 mmol) of 1-(trimethylsilyl)cyclopropanecarboxylic acid [synthesized according to the method described in J. Org. Chem., 1982 (47) 5, 893-895] in 120 ml of dehydrated dichloromethane, 6.60 ml (76.9 mmol) of oxalyl chloride and 0.25 ml (3.2 mmol) of dehydrated DMF were added in this order at 0° C. in a nitrogen atmosphere and reacted at 0° C. for 2.5 hours with stirring.

After completion of the reaction, the reaction solution was concentrated under reduced pressure and dried under reduced pressure.

A solution of the obtained concentration residue in 30 ml of dehydrated dichloromethane was added to a solution of 19.0 ml (109 mmol) of DIPEA and 9.94 g (30.6 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] in 170 ml of dehydrated dichloromethane at 0° C. in a nitrogen atmosphere and reacted at 0° C. for 24 hours with stirring.

After completion of the reaction, a saturated aqueous solution of sodium bicarbonate was added to the reaction solution and stirred, followed by extraction once with dichloromethane and twice with ethyl acetate. The whole organic layer thus obtained was dried over anhydrous magnesium sulfate, then filtered, and concentrated under reduced pressure. The obtained concentration residue was subjected to preparative column chromatography (apparatus 2, silica gel, elution solvent:n-hexane:ethyl acetate=90:10→70:30 (V/V)), and a fraction containing 5-tert-butyl 2-ethyl 6,6-dimethyl-3-[1-(trimethylsilyl)cyclopropanecarboxamido]pyrrolo[3,4-c]pyrazole-2,5(4H,6H)-dicarboxylate was concentrated under reduced pressure. The concentration residue of the fraction containing impurities was subjected again to preparative column chromatography (apparatus 2, silica gel, elution solvent:n-hexane:ethyl acetate=90:10→75:25 (V/V)), combined with the preliminarily obtained fraction, concentrated under reduced pressure, and dried under reduced pressure.

To a solution of the obtained concentration residue in 100 ml of ethyl acetate, 60.0 ml (240 mmol) of 4 N hydrogen chloride/ethyl acetate was added at room temperature in a nitrogen atmosphere and reacted at room temperature for 5 hours with stirring.

After completion of the reaction, the reaction solution was concentrated under reduced pressure. The obtained concentration residue was suspended in diisopropyl ether, and the suspension was stirred at room temperature. Insoluble matter was collected by filtration and washed with diisopropyl ether. The obtained solid was dissolved in water, and then, a saturated aqueous solution of sodium bicarbonate and dichloromethane were added thereto and stirred at room temperature for 5 minutes. After separation into an organic layer and an aqueous layer, the aqueous layer was subjected to extraction twice with dichloromethane. The whole organic layer thus obtained was washed with a saturated aqueous solution of sodium chloride, then dried over anhydrous magnesium sulfate, filtered, concentrated under reduced pressure, and dried under reduced pressure to obtain 8.15 g of the title compound (yield: 73% [2 steps]) as a light orange solid.

Mass spectrum (DUIS, m/z): 365 [M+1]$^+$.

$^1$H-NMR spectrum (400 MHz, CDCl$_3$) δ: 10.02 (s, 1H), 4.53 (q, J=7.2 Hz, 2H), 4.16 (s, 2H), 1.50-1.43 (m, 9H), 1.14-1.08 (m, 2H), 0.84-0.77 (m, 2H), 0.12 (s, 9H).

Reference Example 23

2-Methyl-2-(trimethylsilyl)propanoic acid

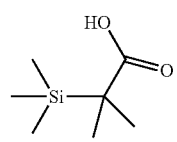

[Chemical Formula 136]

To 100 ml of dehydrated THF, 200 ml (400 mmol) of a 2 M solution of lithium diisopropylamide in THF was added in an argon atmosphere, and subsequently, 4.7 ml (51 mmol) of isobutanoic acid was added dropwise thereto at 0° C. and reacted at room temperature for 4 hours with stirring. 10 ml (57 mmol) of hexamethylphosphoric triamide was added thereto at room temperature, and subsequently, 29 ml (230 mmol) of chlorotrimethylsilane was added dropwise thereto at −78° C. and stirred for 24 hours while the temperature was gradually raised to room temperature.

After completion of the reaction, the solution was rendered acidic by the addition of 25 ml of methanol, 50 ml of water, and 2 N hydrochloric acid in this order to the reaction solution, followed by extraction with diethyl ether. The obtained organic layer was washed with a saturated aqueous solution of sodium chloride, then dried over anhydrous magnesium sulfate, filtered, and concentrated under reduced pressure. The obtained concentration residue was dissolved in a 2 N aqueous sodium hydroxide solution and washed with ethyl acetate. The obtained aqueous layer was rendered acidic by the addition of 1 N hydrochloric acid, followed by extraction with ethyl acetate. The obtained organic layer was dried over anhydrous magnesium sulfate, filtered, and concentrated under reduced pressure. The obtained concentration residue was suspended in n-hexane and ultrasonicated, and then, insoluble matter was collected by filtration. The filtrate was concentrated under reduced pressure, and the obtained concentration residue was subjected to preparative column chromatography (apparatus 1, silica gel, elution solvent: 1,2-dichloroethane:methanol=100:0→99:1 (V/V)), and a fraction containing the compound of interest and the preceding solid collected by filtration were combined, concentrated under reduced pressure, and dried under reduced pressure to obtain 2.66 g of the title compound (yield: 32%) as a white solid.

Mass spectrum (CI, m/z): 161 [M+1]$^+$.

$^1$H-NMR spectrum (400 MHz, CDCl$_3$) δ: 1.22 (s, 6H), 0.08 (s, 9H).

Reference Example 24

5-tert-Butyl 2-ethyl 6,6-dimethyl-3-[2-methyl-2-(trimethylsilyl)propanamido]pyrrolo[3,4-c]pyrazole-2,5 (4H,6H)-dicarboxylate

[Chemical Formula 137]

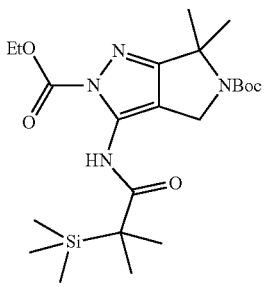

To a solution of 888 mg (5.54 mmol) of 2-methyl-2-(trimethylsilyl)propanoic acid synthesized in the same way as in Reference Example 23 in 15 ml of dichloromethane, 0.594 ml (6.93 mmol) of oxalyl chloride and 0.021 ml (0.27 mmol) of DMF were added at 0° C. in an argon atmosphere and reacted at 0° C. for 1 hour with stirring.

After completion of the reaction, the reaction solution was concentrated under reduced pressure.

A solution of the obtained concentration residue in 2 ml of 1,4-dioxane was added dropwise to a solution of 899 mg (2.77 mmol) of 5-tert-butyl 2-ethyl 3-amino-6,6-dimethylpyrrolo[3,4-c]pyrazole-2,5(4H,6H)-dicarboxylate [synthesized according to the method described in Journal of Medicinal Chemistry 2012, 55 (10), 4728-4739] and 1.93 ml (11.1 mmol) of DIPEA in 5 ml of 1,4-dioxane at 0° C. and reacted at room temperature for 1 hour with stirring.

After completion of the reaction, a saturated aqueous solution of sodium bicarbonate was added to the reaction solution, followed by extraction with ethyl acetate. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=95:5-80:20 (v/v)), and a fraction containing the compound of interest was concentrated under reduced pressure to obtain 903 mg of the title compound (yield: 70%) as a white solid.

Mass spectrum (DUIS, m/z): 467 [M+1]$^+$.

$^1$H-NMR spectrum (400 MHz, DMSO-d$_6$) δ: 10.13-10.03 (m, 1H), 4.49-4.39 (m, 4H), 1.62-1.55 (m, 6H), 1.49-1.42 (m, 9H), 1.35 (t, J=7.1 Hz, 3H), 1.25 (s, 6H), 0.04 (s, 9H).

Reference Example 25

Ethyl 6,6-dimethyl-3-[2-methyl-2-(trimethylsilyl)propanamido]-5,6-dihydropyrrolo[3,4-c]pyrazole-2 (4H)-carboxylate

[Chemical Formula 138]

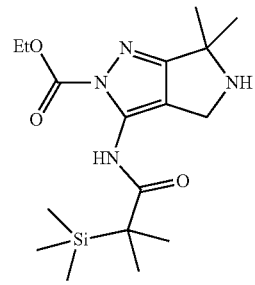

To a solution of 903 mg (1.94 mmol) of 5-tert-butyl 2-ethyl 6,6-dimethyl-3-[2-methyl-2-(trimethylsilyl)propanamido]pyrrolo[3,4-c]pyrazole-2,5 (4H,6H)-dicarboxylate synthesized in the same way as in Reference Example 24 in 15 ml of dichloromethane, 0.67 ml (5.8 mmol) of 2,6-lutidine and 1.05 ml (5.82 mmol) of trimethylsilyl trifluoromethanesulfonate were added at 0° C. in an argon atmosphere and reacted at 0° C. for 1 hour with stirring.

After completion of the reaction, a saturated aqueous solution of sodium bicarbonate was added to the reaction solution, followed by extraction with dichloromethane. The obtained organic layer was washed with a saturated aqueous solution of sodium chloride, then dried over anhydrous magnesium sulfate, filtered, and concentrated under reduced pressure. The obtained concentration residue was subjected to preparative column chromatography (apparatus 1, DIOL silica gel, elution solvent:methanol: 1,2-dichloroethane=0: 100→10:90 (v/v)), and a fraction containing the compound of interest was concentrated under reduced pressure to obtain 566 mg of the title compound (yield: 80%) as a white solid.

Mass spectrum (CI, m/z): 367 [M+1]$^+$.

$^1$H-NMR spectrum (400 MHz, DMSO-d$_6$) δ: 10.01 (s, 1H), 4.41 (q, J=7.2 Hz, 2H), 3.91 (s, 2H), 1.34 (t, J=7.2 Hz, 3H), 1.28 (s, 6H), 1.23 (s, 6H), 0.03 (s, 9H).

Reference Example 26

Methyl 2-{[(benzyloxy)carbonyl](2-cyanoethyl)amino}-2-methylpropanoate

[Chemical Formula 139]

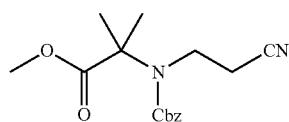

To a solution of 5.00 g (29.4 mmol) of methyl 2-[(2-cyanoethyl)amino]-2-methylpropanoate [synthesized according to the method described in J. Med. Chem., 1968, 11 (3), 616-618] in 23 ml of toluene, 15.5 ml (90.7 mol) of DIPEA and 32.0 ml of a 30 to 35% solution of benzyl chloroformate in toluene [purchased from Tokyo Chemical Industry Co., Ltd.] were added in this order at room temperature in an argon atmosphere and reacted at room temperature for 1.5 hours and subsequently at 50° C. for 1.5 hours with stirring. The reaction solution was cooled, and then, 4.80 ml (44.1 mmol) of N,N-dimethylethane-1,2-diamine was added thereto at room temperature and stirred for 2.5 hours with the temperature unchanged.

After completion of the reaction, the reaction solution was poured into 2 N hydrochloric acid and stirred. An aqueous layer and an organic layer were separated, and the organic layer was washed with a saturated aqueous solution of sodium bicarbonate and a saturated aqueous solution of sodium chloride in this order, then dried over anhydrous magnesium sulfate, filtered, and concentrated under reduced pressure. The obtained concentration residue was subjected to preparative column chromatography (apparatus 1, silica gel, elution solvent:n-hexane:ethyl acetate=84:16→50:50 (V/V)), and a fraction containing the compound of interest was concentrated under reduced pressure to obtain 8.32 g of the title compound (yield: 93%) as a colorless oil.

Mass spectrum (CI, m/z): 305 [M+1]$^+$.

$^1$H-NMR spectrum (400 MHz, DMSO-d$_6$) δ: 7.43-7.28 (m, 5H), 5.07 (s, 2H), 3.64 (t, J=6.7 Hz, 2H), 3.50 (br s, 3H), 2.76 (t, J=6.7 Hz, 2H), 1.45 (s, 6H).

Reference Example 27

Benzyl 4-cyano-3-hydroxy-2,2-dimethyl-2,5-dihydro-1H-pyrrole-1-carboxylate

[Chemical Formula 140]

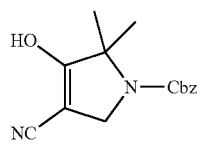

To 52 ml (52 mmol) of a 1 mol/L solution of potassium tert-butoxide in THF heated to 60° C., a solution of 12.1 g (39.7 mmol) of methyl 2-{[(benzyloxy)carbonyl](2-cyanoethyl)amino}-2-methylpropanoate synthesized in the same way as in Reference Example 26 in 30 ml of dehydrated THF was added dropwise under argon stream and stirred for 1 hour while heated to reflux.

After completion of the reaction, the reaction solution allowed to cool to room temperature was adjusted to pH <2 by the addition of 90 ml of water and 2 N hydrochloric acid, followed by extraction twice with 100 ml of ethyl acetate. The whole organic layer thus obtained was washed with 100 ml of water and 100 ml of a saturated aqueous solution of sodium chloride in this order, then dried over magnesium sulfate, filtered, and concentrated under reduced pressure to distill off half the amount of the solvent. 12 g of active carbon was added to the obtained solution, stirred at room temperature for 30 minutes, filtered, and concentrated under reduced pressure. The obtained concentration residue was diluted with 10 ml of diisopropyl ether, 50 ml of n-hexane was added thereto, and the deposited solid was crushed and then stirred at room temperature for 30 minutes. The solid component was collected by filtration and dried under reduced pressure at 50° C. to obtain 8.27 g of the title compound (yield: 76%) as a pale yellow solid.

Mass spectrum (DUIS, m/z): 273 [M+1]$^+$.

$^1$H-NMR spectrum (400 MHz, DMSO-d$_6$) δ: 12.32 (br s, 1H), 7.46-7.25 (m, 5H), 5.18-5.02 (m, 2H), 4.24-4.02 (m, 2H), 1.51-1.35 (m, 6H).

Reference Example 28

Benzyl 3-amino-6,6-dimethyl-4,6-dihydropyrrolo[3,4-c]pyrazole-5(1H)-carboxylate

[Chemical Formula 141]

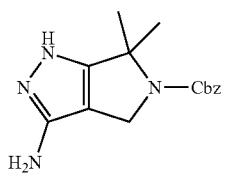

To a solution of 200 mg (0.734 mmol) of benzyl 4-cyano-3-hydroxy-2,2-dimethyl-2,5-dihydro-1H-pyrrole-1-carboxylate synthesized in the same way as in Reference Example 27 in 5 ml of ethanol, 0.336 ml (5.87 mmol) of acetic acid was added at room temperature with stirring under argon stream and stirred at room temperature for 5 minutes. Subsequently, 0.178 ml (3.66 mmol) of hydrazine monohydrate was added dropwise thereto at room temperature with stirring and stirred for 12 hours under heating to reflux.

After completion of the reaction, the reaction solution allowed to cool to room temperature was adjusted to pH 8 by the addition of 15 ml of water and then an aqueous sodium bicarbonate solution, followed by extraction three times with ethyl acetate. The whole organic layer thus obtained was washed with a saturated aqueous solution of sodium chloride, then dried over anhydrous magnesium sulfate, filtered, and concentrated under reduced pressure. The obtained residue was subjected to preparative column chromatography (apparatus 1, silica gel, elution solvent:n-hexane:ethyl acetate=50:50→0:100 (V/V)→1,2-dichloroethane:methanol=80:20 (V/V)), and a fraction containing the compound of interest was concentrated under reduced pressure to obtain 141 mg of the title compound (yield: 67%) as a pale yellow foam.

Mass spectrum (CI, m/z): 287 [M+1]$^+$.

¹H-NMR spectrum (400 MHz, DMSO-d₆) δ: 11.20 (br s, 1H), 7.45-7.28 (m, 5H), 5.18-5.05 (m, 2H), 5.05-4.77 (m, 2H), 4.28-4.14 (m, 2H), 1.58-1.46 (m, 6H).

Reference Example 29

5-Benzyl 2-ethyl 3-amino-6,6-dimethlpyrrolo[3,4-c]pyrazole-2,5(4H,6H)-dicarboxylate

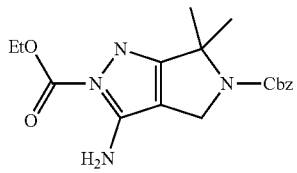

[Chemical Formula 142]

To a solution of 400 mg (1.40 mmol) of benzyl 3-amino-6,6-dimethyl-4,6-dihydropyrrolo[3,4-c]pyrazole-5(1H)-carboxylate synthesized in the same way as in Reference Example 28 in 4 ml of dehydrated THF, 0.594 ml (3.49 mmol) of DIPEA was added at room temperature under argon stream and reacted at room temperature for 3 minutes with stirring. Subsequently, 0.133 ml (1.40 mmol) of ethyl chloroformate was added dropwise thereto at 0° C. and reacted at 0° C. for 30 minutes with stirring.

After completion of the reaction, water was added to the reaction solution, and the mixed solution was subjected to extraction twice with ethyl acetate. The whole organic layer thus obtained was washed with a saturated aqueous solution of sodium chloride, then dried over anhydrous magnesium sulfate, filtered, and concentrated under reduced pressure. The obtained residue was subjected to preparative column chromatography (apparatus 1, silica gel, elution solvent:n-hexane:ethyl acetate=71:29→30:70 (V/V)), and a fraction containing the compound of interest was concentrated under reduced pressure to obtain 200 mg of the title compound (yield: 40%) as a white foam and 190 mg of an isomer of the title compound (5-benzyl 1-ethyl 3-amino-6,6-dimethylpyrrolo[3,4-c]pyrazole-1,5 (4H,6H)-dicarboxylate) (yield: 38%) as a white foam. Title compound (5-benzyl 2-ethyl 3-amino-6,6-dimethylpyrrolo[3,4-c]pyrazole-2,5 (4H,6H)-dicarboxylate)

Mass spectrum (CI, m/z): 359 [M+1]⁺.

¹H-NMR spectrum (400 MHz, DMSO-d₆) δ: 7.45-7.29 (m, 5H), 6.63-6.49 (m, 2H), 5.19-5.04 (m, 2H), 4.41-4.30 (m, 2H), 4.28-4.15 (m, 2H), 1.62-1.49 (m, 6H), 1.36-1.28 (m, 3H).

Isomer of title compound (5-benzyl 1-ethyl 3-amino-6,6-dimethylpyrrolo[3,4-c]pyrazole-1,5 (4H,6H)-dicarboxylate)

Mass spectrum (CI, m/z): 359 [M+1]⁺.

¹H-NMR spectrum (400 MHz, DMSO-d₆) δ: 7.45-7.29 (m, 5H), 5.78-5.65 (m, 2H), 5.19-5.05 (m, 2H), 4.36-4.17 (m, 4H), 1.79-1.66 (m, 6H), 1.33-1.25 (m, 3H).

Reference Example 30

5-Benzyl 2-ethyl 6,6-dimethyl-3-[1-(trimethylsilyl)cyclobutanecarboxamido]pyrrolo[3,4-c]pyrazole-2,5 (4H,6H)-dicarboxylate

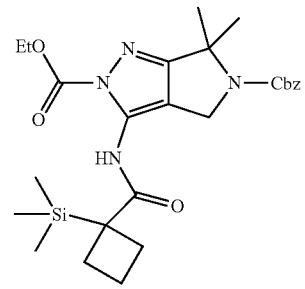

[Chemical Formula 143]

To a solution of 885 mg (5.14 mmol) of 1-(trimethylsilyl) cyclobutanecarboxylic acid synthesized in the same way as in Reference Example 1 in 20 ml of dehydrated dichloromethane, 0.530 ml (6.17 mmol) of oxalyl chloride and 0.020 mL (0.26 mmol) of DMF were added in this order at 0° C. in an argon atmosphere and reacted at 0° C. for 1 hour with stirring.

After completion of the reaction, the reaction solution was concentrated under reduced pressure.

A solution of the obtained concentration residue in 10 ml of dehydrated dichloromethane was added dropwise to a solution of 2.25 ml (12.9 mmol) of DIPEA and 920 mg (2.57 mmol) of 5-benzyl 2-ethyl 3-amino-6,6-dimethylpyrrolo[3,4-c]pyrazole-2,5(4H,6H)-dicarboxylate synthesized in the same way as in Reference Example 29 in 10 ml of dehydrated dichloromethane at 0° C. in an argon atmosphere and reacted at room temperature for 24 hours with stirring.

After completion of the reaction, a saturated aqueous solution of sodium bicarbonate was added to the reaction solution, followed by extraction twice with dichloromethane. The whole organic layer thus obtained was washed with a 5% aqueous potassium bisulfate solution and a saturated aqueous solution of sodium chloride in this order, then dried over anhydrous magnesium sulfate, filtered, and concentrated under reduced pressure. The obtained residue was subjected to preparative column chromatography (apparatus 2, silica gel, elution solvent:n-hexane:ethyl acetate=100:0→70:30 (V/V)), and a fraction containing the compound of interest was concentrated under reduced pressure to obtain 991 mg of the title compound (yield: 75%) as a pale yellow foam.

Mass spectrum (DUIS, m/z): 513 [M+1]⁺.

¹H-NMR spectrum (400 MHz, DMSO-d₆) δ: 9.78-9.70 (m, 1H), 7.45-7.29 (m, 5H), 5.20-5.08 (m, 2H), 4.63-4.50 (m, 2H), 4.47-4.37 (m, 2H), 2.58-2.41 (m, 2H), 2.31-2.18 (m, 2H), 1.95-1.80 (m, 2H), 1.67-1.51 (m, 6H), 1.39-1.29 (m, 3H), 0.12-0.06 (m, 9H).

Reference Example 31

Ethyl 6,6-dimethyl-3-[1-(trimethylsilyl)cyclobutan-ecarboxamido]-5,6-dihydropyrrolo[3,4-c]pyrazole-2(4H)-carboxylate

[Chemical Formula 144]

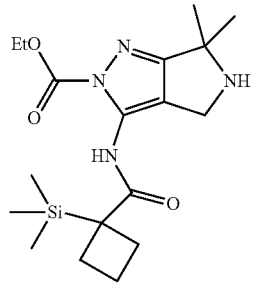

To a solution of 150 mg (0.293 mmol) of 5-benzyl 2-ethyl 6,6-dimethyl-3-[1-(trimethylsilyl)cyclobutanecarboxamido] pyrrolo[3,4-c]pyrazole-2,5(4H,6H)-dicarboxylate synthesized in the same way as in Reference Example 30 in 4 ml of 2-propanol, 75 mg of 10% Pd—C(containing 50% water, PE-type manufactured by N.E. Chemcat Corp.) and 1 ml of acetic acid were added in this order at room temperature. The inside of the reaction container was replaced with a hydrogen atmosphere, followed by reaction at room temperature for 1 hour with stirring.

After completion of the reaction, the inside of the reaction container was replaced with a nitrogen atmosphere, and subsequently, ethyl acetate was added to the reaction solution and filtered by the addition of celite. An aqueous sodium bicarbonate solution was added to the filtrate and stirred, followed by extraction twice with ethyl acetate. The whole organic layer thus obtained was washed with a saturated aqueous solution of sodium bicarbonate, then dried over anhydrous magnesium sulfate, filtered, and concentrated under reduced pressure. The obtained residue was subjected to preparative column chromatography (apparatus 1, silica gel, elution solvent: 1,2-dichloroethane:methanol=100:0→86:14 (V/V)), and a fraction containing the compound of interest was concentrated under reduced pressure to obtain 101 mg of the title compound (yield: 91%) as a white foam.

Mass spectrum (DUIS, m/z): 379 [M+1]$^+$.

$^1$H-NMR spectrum (400 MHz, CDCl$_3$) δ: 9.86 (s, 1H), 4.52 (q, J=7.1 Hz, 2H), 4.22 (s, 2H), 2.65-2.52 (m, 2H), 2.38-2.26 (m, 2H), 2.03-1.88 (m, 2H), 1.50-1.43 (m, 9H), 0.15 (s, 9H).

Reference Example 32 tert-Butyl 2-(2-acetyl-5-fluorophenoxy)acetate

[Chemical Formula 145]

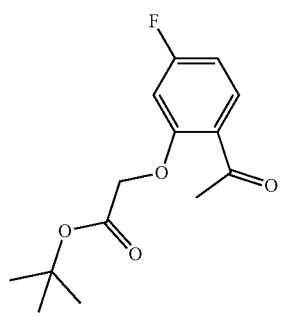

To a solution of 1.00 g (6.49 mmol) of 4'-fluoro-2'-hydroxyacetophenone in 15 ml of acetonitrile, 1.20 ml (8.18 mmol) of tert-butyl bromoacetate and 1.40 g (10.1 mmol) of potassium carbonate were added with stirring in an argon atmosphere and then reacted at 80° C. for 2 hours.

After completion of the reaction, the cooled reaction solution was poured into water, followed by extraction with ethyl acetate. The organic layer was washed twice with water, then dried over anhydrous magnesium sulfate, filtered, and concentrated under reduced pressure. n-Hexane was added to the obtained concentration residue and concentrated under reduced pressure again. n-Hexane was added to the obtained concentration residue and then ultrasonicated, and the deposited solid was collected by filtration. The obtained solid was washed with n-hexane and dried under reduced pressure at room temperature to obtain 1.45 g of the title compound (yield: 83%) as a white solid.

Mass spectrum (CI, m/z): 269 [M+1]$^+$.

$^1$H-NMR spectrum (400 MHz, CDCl$_3$) δ: 7.84 (dd, J=7.0, 8.8 Hz, 1H), 6.74 (ddd, J=2.3, 7.7, 8.8 Hz, 1H), 6.53 (dd, J=2.3, 10.5 Hz, 1H), 4.60 (s, 2H), 2.70 (s, 3H), 1.50 (s, 9H).

Reference Example 33

6-Fluoro-3-methylbenzofuran-2-carboxylic acid

[Chemical Formula 146]

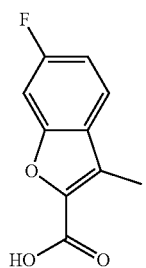

To a solution of 0.30 g (1.1 mmol) of tert-butyl 2-(2-acetyl-5-fluorophenoxy)acetate synthesized in Reference Example 32 in 6 ml of dehydrated ethanol, 0.350 ml (1.75 mmol) of a 28% solution of sodium methoxide in methanol was added with stirring in an argon atmosphere and reacted at 80° C. for 20.5 hours.

After completion of the reaction, the reaction solution was concentrated under reduced pressure, the obtained residue was dissolved by the addition of water, and then, the pH was adjusted to approximately 2 with 2 N hydrochloric acid. The deposited solid was collected by filtration, washed with water, and then dried under reduced pressure at 40° C. to obtain 106 mg of the title compound (yield: 49%) as an ocher solid.

Mass spectrum (CI, m/z): 195 [M+1]$^+$.

$^1$H-NMR spectrum (400 MHz, DMSO-d$_6$) δ: 14.27-12.66 (m, 1H), 7.82 (dd, J=5.5, 8.8 Hz, 1H), 7.61 (dd, J=2.3, 9.4 Hz, 1H), 7.25 (ddd, J=2.3, 8.8, 9.8 Hz, 1H), 2.52 (s, 3H).

Reference Example 34

6-Fluoro-3-methylbenzofuran

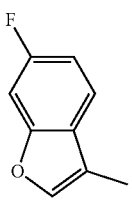

[Chemical Formula 147]

To a solution of 99.0 mg (0.510 mmol) of 6-fluoro-3-methylbenzofuran-2-carboxylic acid synthesized in Reference Example 33 in 1 ml of DMSO, 15.2 mg (0.055 mmol) of silver(I) carbonate and 3 μl (0.05 mmol) of acetic acid were added and then reacted at 120° C. for 18 hours with stirring.

After completion of the reaction, 2 ml of 2 N hydrochloric acid was added to the cooled reaction solution and stirred, followed by extraction with ethyl acetate. The organic layer was washed twice with a saturated aqueous solution of sodium chloride, then dried over anhydrous magnesium sulfate, filtered, and concentrated under reduced pressure. The obtained concentration residue was subjected to preparative column chromatography (apparatus 1, silica gel, n-hexane:ethyl acetate=99:1→97:3 (V/V)), and a fraction containing the compound of interest was concentrated under reduced pressure to obtain 28.4 mg of the title compound (yield: 37%) as a pale yellow oil.

Mass spectrum (CI, m/z): 151 [M+1]$^+$.

$^1$H-NMR spectrum (400 MHz, CDCl$_3$) δ: 7.42 (dd, J=5.5, 8.5 Hz, 1H), 7.39 (q, J=1.4 Hz, 1H), 7.16 (dd, J=2.3, 9.0 Hz, 1H), 7.00 (ddd, J=2.3, 8.5, 9.5 Hz, 1H), 2.23 (d, J=1.4 Hz, 3H).

Reference Example 35

6-Fluoro-3-methylbenzofuran-7-carboxylic acid

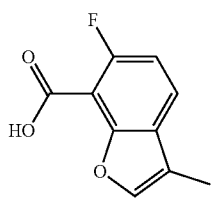

[Chemical Formula 148]

To 150 mg (1.00 mmol) of 6-fluoro-3-methylbenzofuran synthesized in the same way as in Reference Example 34 in 5 ml of dehydrated THF, 1.0 ml (1.6 mmol) of a 1.6 M solution of n-butyllithium in n-hexane was added dropwise at −78° C. with stirring in an argon atmosphere and then stirred at the same temperature as above for 0.5 hours. Subsequently, 2.00 g (45 mmol) of dry ice was added thereto and then reacted at −78° C. for 10 minutes and subsequently for 1 hour while the temperature was raised to room temperature according to the circumstances.

After completion of the reaction, water was added to the reaction solution and then concentrated under reduced pressure, and THF was distilled off. A 2 N aqueous sodium hydroxide solution was added to the obtained concentration residue, followed by extraction with toluene. The pH of the obtained aqueous layer was adjusted to approximately 2 by the addition of 2 N hydrochloric acid, followed by extraction twice with ethyl acetate. The whole organic layer was washed with a saturated aqueous solution of sodium chloride, then dried over anhydrous magnesium sulfate, filtered, and concentrated under reduced pressure. The obtained concentration residue was subjected to preparative column chromatography (apparatus 3, ODS silica gel, elution solvent: 0.1 vol % acetonitrile formate:0.1 vol % aqueous formic acid solution=20:80-95:5 (V/V)), and a fraction containing the compound of interest was concentrated under reduced pressure and dried under reduced pressure to obtain 14.6 mg of the title compound (yield: 8%) as a white solid.

Mass spectrum (CI, m/z): 195 [M+1]$^+$.

$^1$H-NMR spectrum (400 MHz, DMSO-d$_6$) δ: 13.56 (br s, 1H), 7.90-7.85 (m, 1H), 7.77 (dd, J=5.1, 8.6 Hz, 1H), 7.23 (dd, J=8.6, 11.0 Hz, 1H), 2.22 (d, J=1.4 Hz, 3H).

Reference Example 36

Ethyl 5-[(6-fluoro-3-methylbenzofuran-7-yl)carbamoyl]-6,6-dimethyl-3-[1-(trimethylsilyl) cyclobutanecarboxamido]-5,6-dihydropyrrolo[3,4-c]pyrazole-2(4H)-carboxylate

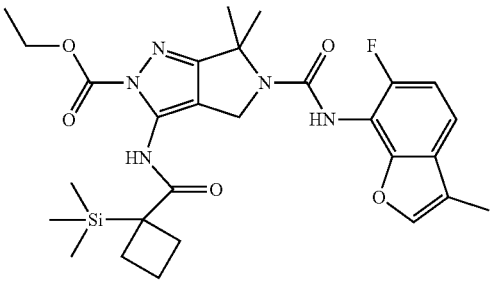

[Chemical Formula 149]

To 123 mg (0.634 mmol) of 6-fluoro-3-methylbenzofuran-7-carboxylic acid synthesized in the same way as in Reference Example 35, 2 ml of toluene was added, followed by azeotropic dehydration under reduced pressure. To a suspension of the obtained residue in 2 ml of dehydrated toluene, 0.150 ml (1.08 mmol) of triethylamine, 0.171 ml (0.794 mmol) of DPPA, and further 0.5 ml of dichloromethane were added at room temperature in an argon atmosphere and then reacted at room temperature for 40 minutes and subsequently at 85° C. for 80 minutes with stirring. The reaction solution was cooled, then added in divided portions to a solution of 203 mg (0.536 mmol) of ethyl 6,6-dimethyl-3-[1-(trimethylsilyl)cyclobutanecarboxamido]-5,6-dihydropyrrolo[3,4-c]pyrazole-2(4H)-carboxylate synthesized in the same way as in Reference Example 3 in 3 ml of dehydrated toluene at 0° C., and reacted at 0° C. for 1 hour with stirring.

After completion of the reaction, the reaction solution was separated into an organic layer and an aqueous layer by the addition of water and ethyl acetate, and then, the organic layer was washed with a saturated aqueous solution of sodium bicarbonate, dried over anhydrous magnesium sulfate, filtered, and concentrated under reduced pressure. The obtained concentration residue was subjected to preparative column chromatography (apparatus 1, silica gel, n-hexane:ethyl acetate=70:30→44:56 (V/V)), and a fraction containing the compound of interest was concentrated under reduced pressure and dried under reduced pressure to obtain 298 mg of the title compound (yield: 98%) as a white foam.

Mass spectrum (CI, m/z): 570 [M+1]+.

$^1$H-NMR spectrum (400 MHz, DMSO-d$_6$) δ: 9.79 (s, 1H), 8.29 (s, 1H), 7.79-7.76 (m, 1H), 7.43 (dd, J=4.8, 8.5 Hz, 1H), 7.15 (dd, J=8.5, 10.5 Hz, 1H), 4.79 (s, 2H), 4.44 (q, J=7.1 Hz, 2H), 2.56-2.45 (m, 2H), 2.32-2.23 (m, 2H), 2.21 (d, J=1.3 Hz, 3H), 1.96-1.86 (m, 2H), 1.66 (s, 6H), 1.36 (t, J=7.1 Hz, 3H), 0.13 (s, 9H).

Reference Example 37 tert-Butyl 6-fluorobenzofuran-7-carboxylate

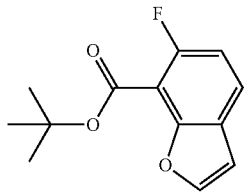

[Chemical Formula 150]

To a solution of 500 mg (2.78 mmol) of 6-fluorobenzofuran-7-carboxylic acid synthesized in Reference Example 15 in 5 ml of pyridine, 1167 mg (6.12 mmol) of p-toluenesulfonyl chloride was added in divided portions at 0° C. in an argon atmosphere and then stirred at 0° C. for 15 minutes with stirring. Subsequently, 0.260 ml (2.74 mmol) of tert-butanol was added thereto at 0° C., then the temperature was raised to room temperature, and the resultant was stirred for 1.5 hours. Further, 0.270 ml (2.84 mmol) of tert-butanol was added thereto and then reacted at room temperature for 16 hours.

After completion of the reaction, the reaction solution was concentrated under reduced pressure, 20 ml of water was added to the obtained concentration residue, and then, the pH was adjusted to 8 with a 2 N aqueous sodium hydroxide solution. After separation into an organic layer and an aqueous layer by the addition of 40 ml of ethyl acetate, the organic layer was washed three times with 10 ml of a 5% aqueous potassium bisulfate solution and once with 10 ml of a saturated aqueous solution of sodium chloride, then dried over anhydrous magnesium sulfate, and filtered, and the filtrate was concentrated under reduced pressure and dried under reduced pressure to obtain 632 mg of the title compound (yield: 96%) as a brown oil.

Mass spectrum (EI, m/z): 236 [M]+.

$^1$H-NMR spectrum (400 MHz, CDCl$_3$) δ: 7.71 (d, J=2.3 Hz, 1H), 7.61 (dd, J=4.9, 8.5 Hz, 1H), 7.05 (dd, J=8.5, 10.8 Hz, 1H), 6.77 (d, J=2.3 Hz, 1H), 1.65 (s, 9H).

Reference Example 38 tert-Butyl 2-chloro-6-fluorobenzofuran-7-carboxylate

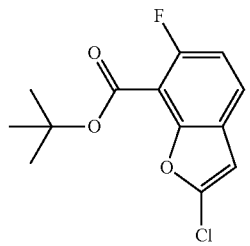

[Chemical Formula 151]

To a solution of 632 mg (2.67 mmol) of tert-butyl 6-fluorobenzofuran-7-carboxylate synthesized in Reference Example 37 in 5 ml of dehydrated DMF, 505 mg (3.78 mmol) of N-chlorosuccinimide was added at room temperature with stirring in an argon atmosphere and then reacted at room temperature for 1 hour, at 50° C. for 6 hours, and further at room temperature for 15.5 hours with stirring.

After completion of the reaction, the reaction solution was separated into an organic layer and an aqueous layer by the addition of toluene and water, and then, the aqueous layer was subjected to extraction once with toluene. The whole organic layer thus obtained was washed with a saturated aqueous solution of sodium bicarbonate, a 5% aqueous sodium thiosulfate solution, a saturated aqueous solution of sodium bicarbonate, and a saturated aqueous solution of sodium chloride in this order, then dried over anhydrous magnesium sulfate, filtered, and concentrated under reduced pressure. The obtained concentration residue was subjected to preparative column chromatography (apparatus 1, silica gel, n-hexane:ethyl acetate=99:1→97:3 (V/V)), and a fraction containing the compound of interest was concentrated under reduced pressure and dried under reduced pressure to obtain 0.20 g of the title compound (yield: 28%) as a colorless oil.

Mass spectrum (EI, m/z): 270 [M]+.

$^1$H-NMR spectrum (400 MHz, CDCl$_3$) δ: 7.51 (dd, J=4.8, 8.6 Hz, 1H), 7.05 (dd, J=8.6, 10.9 Hz, 1H), 6.58 (s, 1H), 1.65 (s, 9H).

Reference Example 39

2-Chloro-6-fluorobenzofuran-7-carboxylic acid

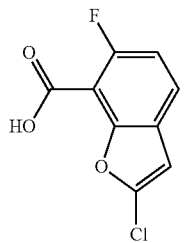

[Chemical Formula 152]

To a solution of 200 mg (0.739 mmol) of tert-butyl 2-chloro-6-fluorobenzofuran-7-carboxylate synthesized in Reference Example 38 in 1.5 ml of dichloromethane, 0.141 ml (1.84 mmol) of trifluoroacetic acid was added at room temperature in an argon atmosphere and then reacted at room temperature for 20 hours with stirring.

After completion of the reaction, the reaction solution was purged with nitrogen gas to distill off the solvent. Diisopropyl ether/n-hexane=1/1 (V/V) was added to the obtained concentration residue and then ultrasonicated, and the obtained solid was collected by filtration. The obtained solid was washed with n-hexane and then dried under reduced pressure at 30° C. to obtain 120 mg of the title compound (yield: 76%) as a white solid.

Mass spectrum (CI, m/z): 215 [M+1]$^+$.
$^1$H-NMR spectrum (400 MHz, CDCl$_3$) δ: 7.63 (dd, J=4.8, 8.7 Hz, 1H), 7.13 (dd, J=8.7, 11.0 Hz, 1H), 6.64 (s, 1H).

Reference Example 40

Ethyl 5-[(2-chloro-6-fluorobenzofuran-7-yl)carbamoyl]-6,6-dimethyl-3-[1-(trimethylsilyl) cyclobutanecarboxamido]-5,6-dihydropyrrolo[3,4-c]pyrazole-2 (4H)-carboxylate

[Chemical Formula 153]

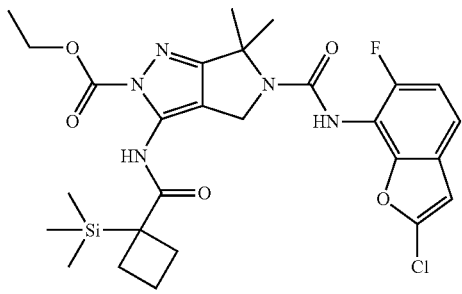

To 116 mg (0.541 mmol) of 2-chloro-6-fluorobenzofuran-7-carboxylic acid synthesized in Reference Example 39, 2 ml of toluene was added, followed by azeotropic dehydration under reduced pressure. To a suspension of the obtained residue in 2 ml of dehydrated toluene, 0.140 ml (1.00 mmol) of triethylamine, 0.155 ml (0.720 mmol) of DPPA, and further 0.5 ml of dichloromethane were added at room temperature in an argon atmosphere and then reacted at room temperature for 40 minutes and subsequently at 85° C. for 1.5 hours with stirring. The reaction solution was cooled, then added in divided portions to a solution of 182 mg (0.481 mmol) of ethyl 6,6-dimethyl-3-[1-(trimethylsilyl)cyclobutanecarboxamido]-5,6-dihydropyrrolo[3,4-c]pyrazole-2 (4H)-carboxylate synthesized in the same way as in Reference Example 3 in 3 ml of dehydrated toluene at 0° C., and reacted at 0° C. for 1 hour with stirring.

After completion of the reaction, the reaction solution was separated into an organic layer and an aqueous layer by the addition of water and ethyl acetate, and then, the organic layer was washed with a saturated aqueous solution of sodium bicarbonate, dried over anhydrous magnesium sulfate, filtered, and concentrated under reduced pressure. The obtained concentration residue was subjected to preparative column chromatography (apparatus 1, silica gel, n-hexane:ethyl acetate=70:30→45:55 (V/V)), and a fraction containing the compound of interest was concentrated under reduced pressure and dried under reduced pressure to obtain 210 mg of the title compound (yield: 74%) as a white foam.

Mass spectrum (CI, m/z): 590 [M+1]$^+$.
$^1$H-NMR spectrum (400 MHz, DMSO-d$_6$) δ: 9.78 (s, 1H), 8.39 (s, 1H), 7.44 (dd, J=4.8, 8.6 Hz, 1H), 7.20 (dd, J=8.6, 10.7 Hz, 1H), 7.05 (s, 1H), 4.78 (s, 2H), 4.43 (q, J=7.1 Hz, 2H), 2.57-2.42 (m, 2H), 2.31-2.20 (m, 2H), 1.95-1.84 (m, 2H), 1.66 (s, 6H), 1.35 (t, J=7.1 Hz, 3H), 0.12 (s, 9H).

Reference Example 41 tert-Butyl 2-bromo-6-fluorobenzofuran-7-carboxylate

[Chemical Formula 154]

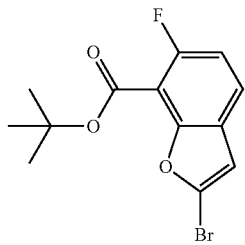

To a solution of 2.26 g (9.57 mmol) of tert-butyl 6-fluorobenzofuran-7-carboxylate synthesized in the same way as in Reference Example 37 in 30 ml of acetonitrile and 10 ml of dehydrated DMF, 1.87 g (10.5 mmol) of N-bromosuccinimide was added at 50° C. in an argon atmosphere and then reacted at 50° C. for 1 hour with stirring. Subsequently, 1.81 g (10.2 mmol) of N-bromosuccinimide was further added thereto and then reacted at 50° C. for 0.5 hours.

After completion of the reaction, the reaction solution was separated into an organic layer and an aqueous layer by the addition of ethyl acetate and water. The obtained organic layer was washed once with a 5% aqueous sodium thiosulfate solution and twice with a saturated aqueous solution of sodium bicarbonate, then dried over anhydrous magnesium sulfate, filtered, and concentrated under reduced pressure. The obtained concentration residue was subjected to preparative column chromatography (apparatus 1, silica gel, n-hexane:ethyl acetate=99:1→97:3 (V/V)), and a fraction containing the compound of interest was concentrated under reduced pressure. The obtained concentration residue was subjected again to preparative column chromatography (apparatus 1, silica gel, n-hexane:ethyl acetate=99:1→98:2 (V/V)), and a fraction containing the compound of interest was concentrated under reduced pressure and dried under reduced pressure to obtain 861 mg of the title compound (yield: 29%) as a pale yellow oil.

Mass spectrum (EI, m/z): 314 [M]$^+$.
$^1$H-NMR spectrum (400 MHz, CDCl$_3$) δ: 7.52 (dd, J=4.8, 8.7 Hz, 1H), 7.05 (dd, J=8.7, 10.8 Hz, 1H), 6.73 (s, 1H), 1.65 (s, 9H).

Reference Example 42 tert-Butyl 6-fluoro-2-methylbenzofuran-7-carboxylate

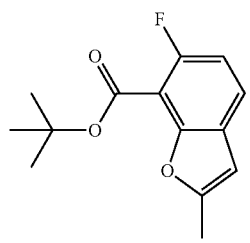

[Chemical Formula 155]

To a heterogeneous solution of 500 mg (1.59 mmol) of tert-butyl 2-bromo-6-fluorobenzofuran-7-carboxylate synthesized in the same way as in Reference Example 41 in 22 ml of toluene and 1.32 ml of water, 1.50 g (7.07 mmol) of anhydrous potassium phosphate and 290 mg (4.84 mmol) of methylboronic acid were added, and then, replacement with an argon atmosphere was performed under reduced pressure under cooling in a dry ice/acetone bath. Subsequently, 10.7 mg (0.048 mmol) of palladium(II) acetate and 35.0 mg (0.098 mmol) of butyl di-1-adamantylphosphine were added thereto and then reacted at 100° C. for 2 hours with stirring.

After completion of the reaction, 5 g of celite was added to the cooled reaction solution, stirred for 10 minutes, and then filtered, and the solid residue was washed with ethyl acetate. The obtained filtrate was separated into an organic layer and an aqueous layer by the addition of water, and then, the organic layer was dried over anhydrous magnesium sulfate, filtered, and concentrated under reduced pressure. The obtained concentration residue was subjected to preparative column chromatography (apparatus 1, silica gel, n-hexane:ethyl acetate=99:1→96:4 (V/V)), and a fraction containing the compound of interest was concentrated under reduced pressure and dried under reduced pressure to obtain 240 mg of the title compound (yield: 60%) as a pale yellow oil.

Mass spectrum (EI, m/z): 250 [M]$^+$.

$^1$H-NMR spectrum (400 MHz, CDCl$_3$) δ: 7.46 (dd, J=4.9, 8.5 Hz, 1H), 6.96 (dd, J=8.5, 10.9 Hz, 1H), 6.35 (q, J=1.0 Hz, 1H), 2.49-2.47 (m, 3H), 1.65 (s, 9H).

Reference Example 43

6-Fluoro-2-methylbenzofuran-7-carboxylic acid

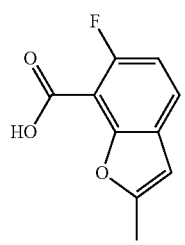

[Chemical Formula 156]

To a solution of 237 mg (0.947 mmol) of tert-butyl 6-fluoro-2-methylbenzofuran-7-carboxylate synthesized in Reference Example 42 in 1.5 ml of dehydrated dichloromethane, 0.181 ml (2.37 mmol) of trifluoroacetic acid was added at room temperature in an argon atmosphere and then reacted at room temperature for 4 hours with stirring. Subsequently, 1.0 ml of dehydrated dichloromethane and 0.181 ml (2.37 mmol) of trifluoroacetic acid were further added thereto and then further reacted for 13.5 hours.

After completion of the reaction, the reaction solution was concentrated under reduced pressure. Diisopropyl ether/n-hexane=1/1 (V/V) was added to the obtained concentration residue and then ultrasonicated, and the obtained solid was collected by filtration, washed with n-hexane, and then dried under reduced pressure at 40° C. to obtain 147 mg of the title compound (yield: 80%) as a white solid.

Mass spectrum (CI, m/z): 195 [M+1]$^+$.

$^1$H-NMR spectrum (400 MHz, DMSO-d$_6$) δ: 7.68 (dd, J=5.2, 8.6 Hz, 1H), 7.15 (dd, J=8.6, 11.1 Hz, 1H), 6.67-6.62 (m, 1H), 2.46-2.45 (m, 3H).

Test Example 1

CDK7 Enzyme Inhibition Test

The preparation of a buffer solution was performed by mixing a N-2-hydroxyethylpiperazine-N'-2-ethanesulfonic acid buffer solution (HEPES buffer solution) (pH 7.4), dithiothreitol (DTT), Triton X-100, and magnesium chloride (MgCl$_2$). A 500 μM [γ-$^{33}$P]ATP solution was used by diluting a 10 mM ATP solution and a commercially available [γ-$^{33}$P]ATP solution (manufactured by PerkinElmer, Inc., Code No. NEG-302H) with the buffer solution. A CDK7 solution was used by diluting commercially available CDK7 (manufactured by Carna Biosciences, Inc., Catalog No. 04-108) with the buffer solution. A substrate solution was used by diluting myelin basic protein (MBP) with the buffer solution. As for the preparation of a reaction solution, the buffer solution, the CDK7 solution, and the substrate solution were mixed at 4° C. to obtain a reaction solution.

CDK7 enzyme reaction was performed by adding 5 μL of a test compound solution prepared with 10% DMSO/90% injectable distilled water, and 40 μL of the reaction solution to a 1.5 mL microtube at 4° C. and preincubating the microtube at 25° C. for 60 minutes in a water bath incubator. Subsequently, reaction was performed at 30° C. for 20 minutes by adding 5 μL of the 500 μM [γ-$^{33}$P]ATP solution. After the reaction, a 10% aqueous trichloroacetic acid (TCA) solution was added to each microtube while cooled to 4° C., and mixed in a vortex mixer to terminate the reaction. The resultant was left standing at 4° C. for 10 minutes and then centrifuged, and the supernatant was discarded. Next, a 2% aqueous trichloroacetic acid (TCA) solution was added thereto, mixed in a vortex mixer, and then centrifuged, and the supernatant was discarded. This washing operation was performed twice. After the washing, precipitates were dissolved in a 1 N aqueous sodium hydroxide (NaOH) solution, and the energy quantity (radioactivity) of the reaction product was measured with a liquid scintillation counter.

The calculation of the inhibitory activity of the test compound against CDK7 was performed as a test compound concentration inhibiting 50% of the amount of $^{33}$P bound to MBP (IC$_{50}$ value) by using EXSUS (version 8.1.0, manufactured by CAC Exicare Corp.).

The calculation of a Ki value was performed according to the following calculation expression wherein S represents the concentration of ATP contained in the reaction solution, and Km represents a Michaelis-Menten constant:

$Ki=IC_{50}/(1+S/Km)$

In this test, the compounds of the present invention exhibited excellent CDK7 inhibitory activity. For example, the Ki values of compounds represented by compound Nos. I-965, II-137, II-169, II-199, II-290, II-1049, III-137, III-169, III-199, III-299, III-1049, IV-1, IV-3, IV-9, IV-7, IV-15, IV-21, IV-23, IV-27, IV-39, IV-45, IV-51, IV-63, IV-75, IV-79, IV-87, IV-93, IV-99, IV-101, IV-103, IV-105, IV-111, IV-113, IV-121, IV-125, IV-127, IV-129, IV-137, IV-153, IV-161, IV-169, IV-177, IV-185, IV-199, IV-207, IV-215, IV-299, IV-231, IV-239, IV-247, IV-357, IV-359, IV-361, IV-367, IV-375, IV-377, IV-379, IV-381, IV-389, IV-597, IV-599, IV-609, IV-615, IV-629, IV-689, IV-669, IV-703, IV-709, IV-747, IV-997, IV-1019, IV-1035, IV-1043, IV-1045, IV-1049, IV-1059, IV-1061, and IV-1063 were 50 nM or lower.

Test Example 2

CDK2 Enzyme Inhibition Test

The preparation of a buffer solution was performed by mixing a N-2-hydroxyethylpiperazine-N'-2-ethanesulfonic acid buffer solution (HEPES buffer solution) (pH 7.4), dithiothreitol (DTT), Triton X-100, and magnesium chloride ($MgCl_2$). A 500 µM [$\gamma$-$^{33}$P]ATP solution was used by diluting a 10 mM ATP solution and a commercially available [$\gamma$-$^{33}$P]ATP solution (manufactured by Perkin Elmer, Inc., Code No. NEG-302H) with the buffer solution. A CDK2 solution was used by diluting commercially available CDK2 (manufactured by Invitrogen Corp., Catalog No. PV3267) with the buffer solution. A substrate solution was used by diluting myelin basic protein (MBP) with the buffer solution. As for the preparation of a reaction solution, the buffer solution, the 500 µM [$\gamma$-$^{33}$P]ATP solution, the CDK2 solution, and the substrate solution were mixed at 4° C. to obtain a reaction solution.

CDK2 enzyme reaction was performed by adding 5 µL of a test compound solution prepared with 10% DMSO/90% injectable distilled water, and 45 µL of the reaction solution in a 1.5 mL microtube at 4° C. and reacting in the microtube at 30° C. for 20 minutes in a water bath incubator. After the reaction, a 10% aqueous trichloroacetic acid (TCA) solution was added to each microtube while cooled to 4° C., and mixed in a vortex mixer to terminate the reaction. The resultant was left standing at 4° C. for 10 minutes and then centrifuged, and the supernatant was discarded. Next, a 2% aqueous trichloroacetic acid (TCA) solution was added thereto, mixed in vortex mixer, and then centrifuged, and the supernatant was discarded. This washing operation was performed twice. After the washing, precipitates were dissolved in a 1 N aqueous sodium hydroxide (NaOH) solution, and the energy quantity (radioactivity) of the reaction product was measured with a liquid scintillation counter.

The calculation of the inhibitory activity of the test compound against CDK2 was performed as a test compound concentration inhibiting 50% of the amount of $^{33}$P bound to MBP ($IC_{50}$ value) by using EXSUS (version 8.1.0, manufactured by CAC Exicare Corp.).

The calculation of a Ki value was performed according to the following calculation expression wherein S represents the concentration of ATP contained in the reaction solution, and Km represents a Michaelis-Menten constant:

$$Ki=IC_{50}/(1+S/Km)$$

In this test, the compounds of the present invention had low CDK2 inhibitory activity. For example, the Ki values of CDK2 inhibitory activity of compounds represented by compound Nos. I-1000, I-1036, II-137, II-169, II-199, II-1049, III-137, III-169, III-199, III-1049, IV-1, IV-3, IV-9, IV-15, IV-21, IV-27, IV-39, IV-45, IV-75, IV-87, IV-105, IV-113, IV-127, IV-129, IV-137, IV-161, IV-169, IV-177, IV-185, IV-199, IV-207, IV-215, IV-231, IV-239, IV-247, IV-299, IV-357, IV-359, IV-361, IV-367, IV-377, IV-379, IV-381, IV-389, IV-597, IV-609, IV-615, IV-629, IV-689, IV-669, IV-703, IV-709, IV-747, IV-997, IV-1043, IV-1045, IV-1049, IV-1059, IV-1061, and IV-1063 were 1000 nM or higher. In short, the compounds of the present invention highly selectively inhibited CDK7 with respect to CDK2.

Test Example 3

PLK1 Enzyme (Polo-Like Kinase) Inhibition Test

The preparation of a buffer solution was performed by mixing a 3-morpholinopropanesulfonic acid buffer solution (MOPS buffer solution) (pH 7.0), dithiothreitol (DTT), and magnesium acetate ($Mg(CH_3COO)_2$). A 1 mM [$\gamma$-$^{33}$P]ATP solution was used by diluting a 10 mM ATP solution and a commercially available [$\gamma$-$^{33}$P]ATP solution (manufactured by Perkin Elmer, Inc., Code No. NEG-302H) with the buffer solution. A PLK1 solution was used by diluting commercially available PLK1 (manufactured by Carna Biosciences, Inc., Catalog No. 05-157) with the buffer solution. A substrate solution was used by diluting casein with the buffer solution. As for the preparation of a reaction solution, the buffer solution, the 500 µM [$\gamma$-$^{33}$P]ATP solution, the PLK1 solution, and the substrate solution were mixed at 4° C. to obtain a reaction solution.

PLK1 enzyme reaction was performed by adding 5 µL of a test compound solution prepared with 10% DMSO/90% injectable distilled water, and 45 µL of the reaction solution in a 1.5 mL microtube at 4° C. and reacting in the microtube at 30° C. for 20 minutes in a water bath incubator. After the reaction, a 10% aqueous trichloroacetic acid (TCA) solution was added to each microtube while cooled to 4° C., and mixed in a vortex mixer to terminate the reaction. The resultant was left standing at 4° C. for 10 minutes and then centrifuged, and the supernatant was discarded. Next, a 2% aqueous trichloroacetic acid (TCA) solution was added thereto, mixed in a vortex mixer, and then centrifuged, and the supernatant was discarded. This washing operation was performed twice. After the washing, precipitates were dissolved in a 1 N aqueous sodium hydroxide (NaOH) solution, and the energy quantity (radioactivity) of the reaction product was measured with a liquid scintillation counter.

The calculation of the inhibitory activity of the test compound against PLK1 was performed as a test compound concentration inhibiting 50% of the amount of $^{33}$P bound to casein ($IC_{50}$ value) by using EXSUS (version 8.1.0, manufactured by CAC Exicare Corp.).

The calculation of a Ki value was performed according to the following calculation expression wherein S represents the concentration of ATP contained in the reaction solution, and Km represents a Michaelis-Menten constant:

$$Ki=IC_{50}/(1+S/Km)$$

In this test, the compounds of the present invention had low PLK1 inhibitory activity. For example, the Ki values of PLK1 inhibitory activity of compounds represented by compound Nos. I-1000, I-1036, II-137, II-169, II-199, II-1049, III-137, III-169, III-199, III-1049, IV-3, IV-15, IV-21, IV-27, IV-39, IV-45, IV-87, IV-105, IV-113, IV-121, IV-127, IV-129, IV-137, IV-153, IV-161, IV-169, IV-177, IV-185, IV-199, IV-207, IV-215, IV-231, IV-239, IV-247, IV-299, IV-357, IV-359, IV-361, IV-367, IV-377, IV-379, IV-381, IV-389, IV-597, IV-609, IV-615, IV-629, IV-669, IV-689, IV-703, IV-709, IV-747, IV-997, IV-1043, IV-1045, IV-1049, IV-1059, IV-1061, and IV-1063 were 5000 nM or higher. In short, the compounds of the present invention highly selectively inhibited CDK7 with respect to PLK1.

Test Example 4

Human Large Intestine Cancer (HCT-116) Cell Growth Inhibition Test

The measurement of a human large intestine cancer cell growth inhibitory effect was carried out by modifying the method of Simak et al. (Cancer Research, 69, 6208 (2009)).

A human large intestine cancer cell line (HCT-116, obtained from DS Pharma Biomedical Co., Ltd.) was cultured in a McCoy's 5A medium (manufactured by Thermo Fisher Scientific, Inc.) containing 10% fetal bovine serum (FBS) (manufactured by Thermo Fisher Scientific, Inc.) and 1% penicillin/streptomycin/amphotericin B (manufactured by Thermo Fisher Scientific, Inc.) and inoculated at 0.5 to $2.0 \times 10^3$ cells/well in a 96-well plate. After overnight culture in a carbon dioxide incubator, the medium was replaced with a fresh medium on the next day, and a test compound dissolved in DMSO (final DMSO concentration: 0.1%) was added thereto and left standing in a carbon dioxide incubator. After culture for 3 days, the absorbance thereof was measured by using In Vitro Toxicology Assay Kit Sulforhodamine B based (manufactured by Sigma-Aldrich Co. LLC.).

The rate of inhibition of cell growth at each concentration was calculated from the test compound concentration and the absorbance of sulforhodamine B, and the concentration of the test compound necessary for inhibiting 50% of cell growth ($GI_{50}$ value) was calculated by using EXSUS (version 8.1.0, manufactured by CAC Exicare Corp.).

In this test, the compounds of the present invention exhibited excellent HCT-116 cell growth inhibitory activity. For example, the $GI_{50}$ values of compounds represented by compound Nos. II-137, II-169, II-199, II-1049, III-137, III-169, III-199, III-299, III-1049, IV-1, IV-3, IV-4, IV-5, IV-9, IV-7, IV-11, IV-15, IV-21, IV-23, IV-25, IV-27, IV-39, IV-45, IV-51, IV-63, IV-75, IV-79, IV-81, IV-87, IV-93, IV-99, IV-101, IV-103, IV-105, IV-111, IV-113, IV-121, IV-123, IV-125, IV-127, IV-129, IV-137, IV-153, IV-161, IV-169, IV-177, IV-185, IV-191, IV-197, IV-199, IV-207, IV-213, IV-215, IV-231, IV-239, IV-245, IV-247, IV-299, IV-357, IV-359, IV-361, IV-367, IV-375, IV-377, IV-379, IV-381, IV-389, IV-597, IV-599, IV-609, IV-615, IV-629, IV-669, IV-689, IV-703, IV-709, IV-747, IV-997, IV-1035, IV-1043, IV-1045, IV-1049, IV-1059, IV-1061, and IV-1063 were 100 nM or lower.

Test Example 5

Tumor Growth Inhibition Test in Human Large Intestine Cancer Cell (HCT 116)-Subcutaneously Transplanted Nude Mouse A human large intestine cancer cell line (HCT-116) was cultured in a McCoy's 5A medium containing 10% FBS and 1% penicillin/streptomycin/amphotericin B and adjusted to $1.0 \times 10^8$ cells/mL with PBS or Hanks solution (HBSS(−)). The prepared cell suspension was subcutaneously injected at 0.1 mL/mouse to the right abdomens of female BALB nude mice (supplied by Charles River Laboratories Japan, Inc.). After rearing for a certain period, the long diameter (mm) and short diameter (mm) of tumor were measured with electronic calipers, and the tumor volume was calculated according to the following expression:

Tumor volume (mm$^3$)=(Long diameter)×(Short diameter)×(Short diameter)×0.5

Individuals whose tumor volume was within the range of 50 to 200 mm$^3$ were selected and grouped such that the tumor volume was almost equivalent, then a test compound or only a solvent was orally administered in a repeated manner, and the body weights and tumor volume were measured. A test compound was suspended in a 0.5 w/v % aqueous methylcellulose solution (0.5% MC) (manufactured by Wako Pure Chemical Industries, Ltd.) and orally administered at 10 mL/kg in a repeated manner. When the tumor volume of the control group was defined as 100%, the rate of suppression of tumor volume (%) at each dose of the test compound was calculated.

In this test, the compounds of the present invention exhibited excellent tumor growth inhibitory activity. For example, compounds represented by compound Nos. IV-1, IV-3, IV-15, IV-21, IV-113, IV-121, IV-127, IV-199, IV-215, IV-299, IV-359, IV-361, IV-379, IV-389, IV-597, IV-669, IV-1049, and IV-1063 exhibited 50% or more rate of suppression of tumor volume at a dose of 100 mg/kg.

Test Example 6

Human PBMC CD3/CD28-Induced IL-2 Production Inhibition Test

PBMC (peripheral blood mononuclear cell) was separated and collected by using Ficoll-Paque (manufactured by GE Healthcare Japan Corp.) from blood collected from a healthy human adult in the presence of heparin. A RPMI1640 medium containing 10% FBS, 1% penicillin/streptomycin/amphotericin B, essential amino acids, and pyruvic acid and containing a test compound dissolved in DMSO and 2 µg/mL CD28 was added at 100 µL/well to T cell Activation Plate Anti-Human CD3 96-well plate (manufactured by Becton, Dickinson and Company), and subsequently, a PBMC suspension prepared such that the number of cells was $2 \times 10^6$ cells/mL was added thereto at 100 µL/well (final DMSO concentration: 0.1%). A RPMI1640 medium containing 10% FBS and containing 0.1% DMSO and 2 µg/mL CD28 was similarly added to wells not supplemented with the test compound. After culture for 2 days in a carbon dioxide incubator, the culture supernatant was collected. The collected culture supernatant was stored at −20° C. until IL-2 content measurement.

In the measurement of an L-2 content in the culture supernatant, a sandwich ELISA kit (Quantikine Human IL-2, manufactured by R&D Systems, Inc.) was used. The L-2 content of each sample was calculated from the calibration curve of Standard IL-2 included in the kit. When the amount of IL-2 produced by CD3/CD28 stimulation in the case of the addition of only DMSO was defined as 100%, the rate of inhibition of L-2 production at each concentration of the test compound was calculated. A test compound concentration necessary for inhibiting 50% of L-2 production ($IC_{50}$ value) was calculated from the concentration of the added test compound and the rate of inhibition of IL-2 production by the test compound by using EXSUS (version 8.1.0, manufactured by CAC Exicare Corp.).

In this test, the compounds of the present invention exhibited excellent IL-2 production inhibitory activity. For example, the $IC_{50}$ values of compound Nos. IV-3, IV-21, IV-113, IV-127, IV-161, IV-215, IV-299, IV-361, IV-379, IV-669, and IV-1049 were 100 nM or lower.

Test Example 7

Human Keratinocyte Growth Inhibition Assay

The measurement of a human keratinocyte growth inhibitory effect was carried out by modifying the method of Schafer et al. (British Journal of Pharmacology, 159, 842 (2011)).

Human keratinocytes (NHEK-Neo Pooled, manufactured by Lonza Group AG) were cultured in KGM-Gold keratinocyte growth medium Bullet Kit (manufactured by Lonza Group AG) and inoculated at $2 \times 10^3$ cells/well to a 96-well plate. After overnight culture in a carbon dioxide incubator, a test compound dissolved in DMSO (final DMSO concentration: 0.1%) was added thereto and left standing in a carbon dioxide incubator. After culture for 2 days, the absorbance thereof was measured by using Cell Counting Kit-8 (manufactured by Dojindo Laboratories).

The rate of inhibition of cell growth at each concentration was calculated from the test compound concentration and the absorbance of Cell Counting Kit-8, and the concentration of the test compound necessary for inhibiting 50% of cell growth ($GI_{50}$ value) was calculated by using EXSUS (version 8.1.0, manufactured by CAC Exicare Corp.).

In this test, the compounds of the present invention exhibited excellent human keratinocyte growth inhibitory activity, and, for example, the $GI_{50}$ values of compound Nos. IV-129, IV-215, IV-247, IV-361, and IV-379 were 500 nM or lower.

Test Example 8

Ear Thickening Suppression Test Using Mouse Imiquimod-Induced Psoriasis Model

An imiquimod-induced psoriasis model test was carried out by modifying the method of Leslie van der Fits et al. (J. Immunol. 182, 5836 (2009)).

Female BALB/c mice (supplied by Charles River Laboratories Japan, Inc.) were used as laboratory animals. On the start day of the test, the thicknesses of the right auricles of the mice were measured with a thickness gauge (manufactured by TECLOCK Corp.). A test compound or a solvent was applied or orally administered thereto, and after a certain time, a certain amount of Beselna Cream 5% (containing 5% imiquimod, manufactured by Mochida Pharmaceutical Co., Ltd.) was applied to the insides of the right auricles. The test compound or solvent application or oral administration and the imiquimod application were carried out for a certain period, and the thicknesses of the right auricles were measured again on the final day. The thicknesses of the right auricles were compared between the solvent-administered group and the test compound group, and the rate of inhibition was calculated. When increase in the thicknesses of the ears of the solvent-administered group on the final day was defined as 100%, the rate of inhibition of increase (%) at each dose of the test compound was calculated.

In this test, the compounds of the present invention exhibited excellent ear thickening suppressive activity, and, for example, compound Nos. IV-129, IV-137, IV-169, IV-199, IV-215, IV-247, IV-299, and IV-389 exhibited 50% or more rate of inhibition by the application of a 0.01% solution in methanol,

Test Example 9

Human Breast Cancer (MCF-7) Cell Growth Inhibition Test

The measurement of a human breast cancer cell growth inhibitory effect is carried out by modifying the method of Simak et al. (Cancer Research, 69, 6208 (2009)).

A human breast cancer cell line (MCF-7, obtained from DS Pharma Biomedical Co., Ltd.) is cultured in a MEM medium containing 10% FBS and nonessential amino acids and inoculated at $3 \times 10^3$ cells/well to a 96-well plate. After overnight culture in a carbon dioxide incubator, the medium is replaced with a fresh MEM medium containing 10% FBS and nonessential amino acids on the next day, and a test compound dissolved in DMSO (final DMSO concentration: 0.1%) is added thereto and left standing in a carbon dioxide incubator. After culture for 3 days, the absorbance thereof is measured by using In Vitro Toxicology Assay Kit Sulforhodamine B based (manufactured by Sigma-Aldrich Co. LLC.).

The rate of inhibition of cell growth at each concentration is calculated from the test compound concentration and the absorbance of sulforhodamine B, and the concentration of the test compound necessary for inhibiting 50% of cell growth ($GI_{50}$ value) is calculated by using EXSUS (version 8.1.0, manufactured by CAC Exicare Corp.).

Test Example 10

Test on Reduction in Abundance Ratio of Human Large Intestine Cancer Stem Cell (CD44/CD133-Positive Cell).

The measurement of human large intestine cancer stem cells was carried out by modifying the method of Youzhi et al. (Proceedings of the National Academy of Sciences, 112, 6, 1839 (2015)).

A human large intestine cancer cell line (HCT-116) was cultured in a McCoy's 5A medium containing 10% FBS and 1% penicillin/streptomycin/amphotericin B and inoculated at $1 \times 10^6$ cells/well to a 6-well plate. After overnight culture in a carbon dioxide incubator, a test compound dissolved in DMSO (final DMSO concentration: 0.1%) was added thereto and left standing in a carbon dioxide incubator. After culture for 7 days, the cells were collected by using trypsin/EDTA and treated with a single cell strainer, and then, a FITC-labeled CD44 antibody (Miltenyi Biotec K.K.) and a PE-labeled CD133 antibody (Miltenyi Biotec K.K.) were added thereto and reacted at room temperature for 15 minutes in the dark. The abundance ratio of cells positive to both CD44 and CD133 at each concentration was measured by using flow cytometry. When the abundance ratio of cells positive to both CD44 and CD133 in the solvent treated sample was defined as 100, the test compound concentration and the rate of reduction in the abundance ratio of cells positive to both CD44 and CD133 were calculated, and the concentration of the test compound necessary for inhibiting 50% of the abundance ratio ($GI_{50}$ value) was calculated by using EXSUS (version 8.1.0, manufactured by CAC Exicare Corp.).

In this test, the compounds of the present invention exhibited an excellent rate of reduction in the abundance ratio of CD44/CD133-positive cells, and, for example, the 1 μM solutions of compound Nos. IV-199, IV-215, IV-299, IV-361, and IV-379 exhibited 50% or more rate of reduction.

Test Example 11

Test on Inhibition of Ability of Human Large Intestine Cancer Stem Cell to Self-Renew The spheroid culture of human large intestine cancer stem cells is carried out by modifying the method of Youzhi et al. (Proceedings of the National Academy of Sciences, 112, 6, 1839 (2015)).

A human large intestine cancer cell line (HCT-116) was cultured in a McCoy's 5A medium containing 10% FBS and 1% penicillin/streptomycin/amphotericin B. The cells are collected from the flask, resuspended in Cancer Stem Premium medium (manufactured by ProMab Biotechnologies, Inc.), and inoculated at 1 to $10 \times 10^3$ cells/well to an ultralow attachment 96-well plate. After culture for 2 to 7 days in a carbon dioxide incubator, a test compound dissolved in DMSO (final DMSO concentration: 0.1%) is added thereto and left standing in a carbon dioxide incubator. After culture for 1 to 3 days, the absorbance thereof is measured by using Cell Counting kit-8 (manufactured by Dojindo Laboratories).

The rate of inhibition of cell growth at each concentration is calculated from the test compound concentration and the absorbance of Cell Counting kit-8, and the concentration of the test compound necessary for inhibiting 50% of cell growth ($IC_{50}$ value) is calculated by using EXSUS (version 8.1.0, manufactured by CAC Exicare Corp.).

Test Example 12

Human PBMC Various-Stimulant Cocktail-Induced IL-17 Production Inhibition Test

PBMC was separated and collected by using Ficoll-Paque (manufactured by GE Healthcare Japan Corp.) from blood collected from a healthy human adult in the presence of heparin. The collected PBMC was further cultured in a flask for a certain time, and then, non-adherent cells in the supernatant were collected and used as a T-cell suspension.

A RPMI1640 medium containing 10% FBS, 1% penicillin/streptomycin/amphotericin B, essential amino acids, and pyruvic acid and containing a test compound dissolved in DMSO, a human CD28 antibody, a human IFN-γ antibody, a human IL-4 antibody, human IL-6, human IL-23, human IL-1β, and human TGF-β was added at 100 µL/well to T cell Activation Plate Anti-Human CD3 96-well plate. Subsequently, 100 µL of a T-cell suspension adjusted to $2 \times 10^5$ cells/mL was added to each well (final DMSO concentration: 0.1%). Only DMSO was added to wells not supplemented with the test compound. After culture for 5 days in a carbon dioxide incubator, the culture supernatant was collected and stored at -20° C. until IL-17 content measurement.

In the measurement of an IL-17 content in the culture supernatant, a sandwich ELISA kit (Quantikine Human IL-17, manufactured by R&D Systems, Inc.) was used. The IL-17 content of each sample was calculated from the calibration curve of Standard IL-17 included in the kit. When the amount of IL-17 produced by the cocktail of various stimulants in the case of the addition of only DMSO was defined as 100%, the rate of inhibition of IL-17 production at each concentration of the test compound was calculated. The concentration of the test compound necessary for inhibiting 50% of IL-17 production ($IC_{50}$ value) was calculated from the concentration of the added test compound and the rate of inhibition of IL-17 production by the test compound by using EXSUS (version 8.1.0, manufactured by CAC Exicare Corp.).

In this test, the compounds of the present invention exhibited excellent IL-17 production inhibitory activity. For example, the $IC_{50}$ values of compound Nos. IV-3, IV-129, IV-137, IV-199, IV-215, IV-247, IV-299, IV-361, IV-379, IV-389, IV-669, and IV-1049 were 100 nM or lower.

Test Example 13

Paw Edema Suppression Test in Rat Adjuvant Arthritis Model

Female LEW rats (supplied by Charles River Laboratories Japan, Inc.) are used as laboratory animals. An adjuvant prepared from heat-killed bacteria of *Mycobacterium butyricum* (manufactured by Difco Laboratories Ltd.) and liquid paraffin (manufactured by Wako Pure Chemical Industries, Ltd.) is subcutaneously administered as a phlogogenic material to the right hind leg footpads of the rats under inhalation anesthesia with isoflurane (manufactured by Wako Pure Chemical Industries, Ltd.) to prepare arthritis models. Also, liquid paraffin not containing the killed bacteria is administered by a similar method to obtain an untreated group. A test compound is suspended in a 0.5 w/v % aqueous methylcellulose solution (0.5% MC) (manufactured by Wako Pure Chemical Industries, Ltd.) and orally administered at 10 mL/kg in a repeated manner from the adjuvant injection day. Also, only a solvent is administered instead of the test compound to the arthritis rat models in a control group. The volumes of the right hind legs and the left hind legs are measured several times after the adjuvant administration with a paw volume meter (TK-101CMP manufactured by Unicom Co., Ltd.), and the rate of edema is calculated according to the following expression:

Rate of edema (%)=[{(Footpad volume at the time of measurement)-(Footpad volume before the start of the test)}/(Footpad volume before the start of the test)]×100

The rate of suppression of edema in the control group is further calculated according to the following expression:

Rate of suppression of edema (%)=[1-{(Rate of edema of the test compound-administered group)-(Rate of edema of the untreated group)}/{(Rate of edema of the control group)-(Rate of edema of the untreated group)}]×100

Test Example

Swelling Suppression Test Using Mouse Collagen-Induced Arthritis Model

A mouse collagen-induced arthritis model test was carried out by modifying the method of Mihara et al. (British Journal of Pharmacology, 154, 153 (2008)).

Male DBA/1J mice (supplied by Japan SLC, Inc.) were used as laboratory animals. An adjuvant prepared from a type II collagen solution (Collagen Research Center) and Adjuvant Complete Freund (manufactured by Difco Laboratories Ltd.) was intracutaneously administered twice to the bases of the tails of the mice under inhalation anesthesia with isoflurane (manufactured by Wako Pure Chemical Industries, Ltd.) for sensitization to prepare arthritis models.

Also, Adjuvant Complete Freund (manufactured by Difco Laboratories Ltd.) not containing type II collagen was administered by a similar method to obtain a control group. A test compound was suspended in a 0.5 w/v % aqueous methylcellulose solution (0.5% MC) (manufactured by Wako Pure Chemical Industries, Ltd.) and orally administered at 10 mL/kg in a repeated manner starting at the booster day after a certain period from the injection day for the initial sensitization. Also, only a solvent was administered instead of the test compound to a comparative group.

During the test period, the swelling scoring of limbs (score 0: no disease, score 1: swelling and redness or weak swelling in the small joint of only one of the toes and the fingers, score 2: moderate swelling in the small joints of two or more of the toes and the fingers, score 3: strong swelling in the ankle or the forefoot wrist, score 4: overall strong swelling) was carried out to evaluate the drug efficacy of the test compound. When the total score of the solvent-administered group on the final day was defined as 100%, the rate of reduction in score (%) at each dose of the test compound was calculated.

In this test, the compounds of the present invention exhibited excellent swelling inhibitory activity, and, for example, compound No. IV-361 exhibited 50% or more rate of inhibition at a dose of 100 mg/kg.

Test Example 15

Paralysis Suppression Test Using Mouse $MOG_{35-55}$-Induced Experimental Autoimmune Encephalomyelitis (Repeated Administration)

A mouse $MOG_{35-55}$-induced experimental autoimmune encephalomyelitis (EAE) model test is carried out on the basis of the method of Namiki et al. (The Journal of Biological Chemistry, 287, 29, 24228-24238 (2012)).

Male C57BL/6J mice (supplied by Charles River Laboratories Japan, Inc.) are used as laboratory animals. An adjuvant prepared from a liquid of *M. Tuberculosis* H37RA (manufactured by Difco Laboratories Ltd.) ground and suspended in Adjuvant Incomplete Freund (manufactured by Difco Laboratories Ltd.), and a solution of synthetic $MOG_{35-55}$ peptide is subcutaneously administered to 4 flanks of limbs of the mice, and a pertussis toxin solution (manufactured by List Biological Laboratories, Inc.) is administered to the jugular veins (initial sensitization) to prepare EAE mouse models.

On the day following the preparation of the EAE mouse models, a pertussis toxin solution was administered to the jugular veins again. A test compound is suspended in a 0.5 w/v % aqueous methylcellulose solution (0.5% MC) (manufactured by Wako Pure Chemical Industries, Ltd.) and orally administered at 10 mL/kg in a repeated manner from the injection day for the initial sensitization. Also, only a solvent is administered instead of the test compound to the EAE mouse models in a control group.

During the test period, the scoring based on the pathological conditions of EAE (score 0: no disease, score 0.5: partial tail paralysis, score 1.0: complete tail paralysis, score 1.5: decline in righting reflex, score 2.0: impairment of righting reflex, score 2.5: hindlimb weakness, score 3.0: paralysis of a hindlimb, score 3.5: paralysis of both hindlimbs, score 4.0: paralysis of one forelimb, score 4.5: paralysis of both forelimbs, score 5: moribund or dead) was carried out to evaluate the drug efficacy of the test compound. When the total score of the solvent-administered group on the final day is defined as 100%, the rate of suppression in score (%) at each dose of the test compound is calculated.

Test Example 16

Various Human Cancer Cell Growth Inhibition Test

A breast cancer cell line BT-549 (obtained from American Type Culture Collection (ATCC)), a uterus cancer cell line C-33A (obtained from ATCC), an ovary cancer cell line PA-1 (obtained from ATCC), a large-cell lung cancer cell line NCI-H460 (obtained from ATCC), a small-cell lung cancer cell line NCI-H82 (obtained from ATCC), a kidney cancer cell line ACHN (obtained from ATCC), a pancreatic cancer cell line BxPC-3 (obtained from ATCC), a malignant melanoma cell line A375 (obtained from ATCC), a throat cancer cell line FaDu (obtained from ATCC), a medulloblastoma cell line Daoy (obtained from ATCC), a cutaneous epithelioid sarcoma cell line VA-ES-BJ (obtained from ATCC), a rhabdomyosarcoma cell line A-204 (obtained from ATCC), a prostate cancer cell line DU145 (obtained from ATCC), a bladder cancer cell line T24 (obtained from ATCC), a lymphoma cell line SR (obtained from ATCC), a neuroblastoma cell line SH-SY5Y (obtained from DS Pharma Biomedical Co., Ltd.), a liver cancer cell line HepG2 (obtained from DS Pharma Biomedical Co., Ltd.), a stomach cancer cell line HGC-27 (obtained from DS Pharma Biomedical Co., Ltd.), and a multiple myeloma cell line NCI-H929 (obtained from DS Pharma Biomedical Co., Ltd.) were used as human cancer cell lines.

Each cell line was cultured in a cell culture medium recommended by ATCC or DS Pharma Biomedical Co., Ltd. and inoculated at 0.3 to $5.0\times10^3$ cells/well to a 96-well plate. The cells were cultured overnight in a carbon dioxide incubator of 37° C. containing 5% carbon dioxide. The medium was replaced with a fresh medium on the next day, then replaced with a mixed solution of a DMSO solution of a test compound with varying concentrations and a culture medium (final DMSO concentration: 0.1%), and left standing in a carbon dioxide incubator (day 0). IV-361, IV-379, IV-3, IV-215, IV-299, IV-669, IV-1049, and palbociclib (for comparison) were used as test compounds. For a control group, DMSO was added instead of the DMSO solution of the test compound to a cell culture medium (final DMSO concentration: 0.1%).

After culture for a predetermined period, the ATP activity of BT-549, C-33A, PA-1, NCI-H460, NCI-H82, ACHN, BxPC-3, A375, FaDu, Daoy, VA-ES-BJ, A-204, DU145, T24, and SR was measured by using ATPlite (manufactured by PerkinElmer, Inc.). The ATP activity of SH-SY5Y, HepG2, HGC-27, and NCI-H929 was measured by using CellTiter-Glo (manufactured by Promega Corp.).

The rate of inhibition of cell growth (%) was calculated according to the expression given below. Specifically, in the case where the difference between the ATP activity before culture (day 0) and the ATP activity after culture in the test compound-administered group is the same as the difference between the ATP activity before culture (day 0) and the ATP activity after culture in the control group, the rate of inhibition of cell growth is 0%.

Rate of inhibition of cell growth=(1−((ATP activity of the test compound-administered group after culture)−(ATP activity of the test compound-administered group on day 0))/((ATP activity of the control group after culture)−(ATP activity of the control group on day 0)))×100

The concentration of the test compound necessary for inhibiting 50% of cell growth ($GI_{50}$ value) was calculated by using EXSUS (version 8.1.0, manufactured by CAC Exicare Corp.).

In this test, the compounds of the present invention exhibited excellent cell growth inhibitory activity. Also, the $GI_{50}$ values of compound Nos. IV-3, IV-215, IV-299, IV-361, IV-379, IV-669, and IV-1049 are as shown in Table 50.

TABLE 50

|  | Palbociclib | IV-361 | IV-379 | IV-3 | IV-215 | IV-299 | IV-669 | IV-1049 |
| --- | --- | --- | --- | --- | --- | --- | --- | --- |
| BT-549 | C | A | A | A | A | A | A | A |
| C-33 A | C | A | A | A | A | A | A | A |
| PA-1 | A | A | A | A | A | A | A | A |

TABLE 50-continued

| | Palbociclib | IV-361 | IV-379 | IV-3 | IV-215 | IV-299 | IV-669 | IV-1049 |
|---|---|---|---|---|---|---|---|---|
| NCI-H460 | A | A | A | A | A | A | A | A |
| NCI-H82 | C | A | A | A | A | A | A | A |
| ACHN | A | A | A | A | A | A | A | A |
| BxPC-3 | A | A | A | A | A | A | A | A |
| A375 | A | A | A | A | A | A | A | A |
| FaDu | C | A | A | A | A | A | A | A |
| Daoy | N.T. | A | A | A | A | A | A | A |
| VA-ES-BJ | N.T. | A | A | A | A | A | A | A |
| A-204 | C | A | A | A | A | A | A | A |
| DU 145 | N.T. | A | A | A | A | A | A | A |
| T24 | N.T. | A | A | A | A | A | A | A |
| SR | A | A | A | A | A | A | A | A |
| HCT-116 | B | A | A | A | A | A | A | A |
| HEPG2 | N.T. | B | A | B | A | B | A | A |
| HGC-27 | N.T. | A | A | A | A | A | A | A |
| NCI-H929 | N.T. | A | A | A | A | A | A | A |

A = lower than 300 nM;
B = 300 nM or higher and lower than 1000 nM;
C = 1000 nM or higher;
N.T. = not tested Test Example 17

Rat LPS Inhalation-Induced Pulmonary Neutrophil Infiltration Inhibition Test (Single Administration)

A pulmonary neutrophil infiltration inhibition test using rats was conducted by partially modifying the method of Spond et al. (Pulmonary Pharmacology and Therapeutics, 14, 157 (2001)). Five male SD rats (supplied by Charles River Laboratories Japan, Inc.) fasted for approximately 16 hours were used in each of a test compound-administered group and a control group.

A test compound solution for administration was prepared by dissolving or suspending a test compound in a 0.5 w/v % aqueous methylcellulose solution (0.5% MC) (manufactured by Wako Pure Chemical Industries, Ltd.).

The prepared test compound solution was orally administered at 10 mL/kg to the test compound-administered group, and 0.5% MC was administered at 10 mL/kg to the control group. 15 minutes after the administration, a solution of lipopolysaccharide (LPS) (manufactured by Sigma-Aldrich Co. LLC.) (concentration: 0.5 mg/mL) was administered to the rats in each group by inhalation for 30 minutes. In the administration by inhalation, a two fluid atomizer was used, and a small air compressor (P0-0.4LES, manufactured by Hitachi Industrial Equipment Systems Co., Ltd.) and an air supply unit (AP-678, manufactured by Shibata Scientific Technology Ltd.) were used for mist generation.

4 hours after the LPS administration, bronchoalveolar lavage was carried out as described below, and the bronchoalveolar lavage fluid (hereinafter, abbreviated to BALF) was collected.

Bronchoalveolar Lavage Method:

The rats were anesthetized with isoflurane and subsequently killed due to exsanguination by incision in the inferior vena cava. The trachea was exposed, and an oral sonde for mice (manufactured by Fuchigami Kikai Co., Ltd.) connected with a disposable syringe (5 mL, manufactured by Terumo Corp.) was inserted thereto, followed by the ligation of the trachea. 3.5 mL of saline containing BSA (final concentration: 1%) was injected thereto, and then, the injected saline was immediately collected to obtain BALF. BALF obtained by further repeating this operation four times was centrifuged (420×g, 10 min., 4° C.), then the supernatant was removed until the liquid volume became 1.5 mL, and precipitated cells were suspended to obtain BALF cell suspension.

Next, the number of neutrophils in the BALF cell suspension was measured by using an automatic multi-item blood cell counter (XT-2000iV, manufactured by Sysmex Corp.). The rate of inhibition of neutrophil infiltration (%) by the test compound administration was calculated according to the following expression:

Rate of inhibition of neutrophil infiltration (%)=100−[(NEUTc)/(NEUTv)]×100

NEUTv: the number of neutrophils in the BALF cell suspension of the control group NEUTc: the number of neutrophils in the BALF cell suspension of the test compound-administered group In this test, the compounds of the present invention exhibited an excellent pulmonary neutrophil infiltration inhibitory effect, and, for example, compound Nos. IV-215, IV-299, and IV-379 exhibited 50% or more rate of inhibition at a dose of 100 mg/kg.

Test Example 18

Swelling Suppression Test Using Oxazolone (OXA)-Induced Mouse Delayed-Type Hypersensitivity Dermatitis Model 0.05 mL of an ethanol solution of OXA (manufactured by Sigma-Aldrich Co. LLC.) adjusted to 2% was applied for 2 consecutive days to the abdomens of female BALB/c mice (supplied by Japan SLC, Inc.) shaved with a shaving cream to prepare sensitized animals. Also, mice to which ethanol was applied instead of 2% OXA was used as non-sensitized animals.

5 days after the application, 0.01 mL of an ethanol solution of a test compound adjusted to 1% was applied to each of both sides (front and back surfaces of auricles) of the right ears of the sensitized animals in the test compound-applied group. Also, 0.01 mL of ethanol was applied to each of both sides of the right ears of the non-sensitized animals in the control group. For a vehicle group, 0.01 mL of ethanol was applied to each of both sides of the right ears of the sensitized animals. One hour later, 0.015 mL of an ethanol solution of 2% OXA was applied to each of both sides of the right ears of the mice in each group. On the next day, the thicknesses of the right ears were measured with a thickness gauge (manufactured by TECLOCK Corp.), and the rate of suppression (%) was calculated according to the following expression:

Rate of suppression (%)=(1−(Ear thickness of the test compound-applied group)−(Ear thickness of the control group))/((Ear thickness of the vehicle group)−(Ear thickness of the control group)))×100

In this test, the compounds of the present invention exhibited an excellent swelling suppressive effect, and, for example, compound Nos. IV-215, IV-299, IV-379, and IV-1049 exhibited 50% or more suppression in the 1% solution.

Test Example 19

Evaluation of In Vitro Cell Growth Inhibitory Activity Against Human Large Intestine Cancer Line by Combined Use with Chemotherapeutic A human large intestine cancer cell line HCT-116 (obtained from DS Pharma Biomedical Co., Ltd.) was cultured in a McCoy's 5A medium (manufactured by Thermo Fisher Scientific, Inc.) containing 10% fetal bovine serum (FBS) (manufactured by Thermo Fisher Scientific, Inc.) and 1% penicillin/streptomycin/amphotericin B (manufactured by Thermo Fisher Scientific, Inc.) and inoculated at 0.5 to 2.0×10$^3$ cells/well to a 96-well plate. The cells were cultured overnight in a carbon dioxide incubator of 37° C. containing 5% carbon dioxide. The medium was replaced with a fresh medium on the next day, and then, a mixed solution of a DMSO solution of a test compound (IV-361, 5-FU or SN-38) with varying concentrations and a cell culture medium (final DMSO concentration: 0.2%) was added thereto. The concentration of the test compound was 10 nM, the concentration of 5-FU (manufactured by Wako Pure Chemical Industries, Ltd.) was 1000 nM, and the concentration of SN-38 (manufactured by Tocris Bioscience) was adjusted to 1 nM to carry out the test. For a control group, a mixed solution of DMSO and a cell culture medium (final DMSO concentration: 0.2%) was used instead of the DMSO solution of the test compound.

After the addition of the DMSO solution of the test compound, the cells were cultured for 3 days in a carbon dioxide incubator. Then, the absorbance (measurement wavelength: 565 nm) of the medium in each group was measured by using In Vitro Toxicology Assay Kit Sulforhodamine B based (manufactured by Sigma-Aldrich Co. LLC.).

The rate of inhibition of growth (%) was calculated according to the expression given below. Specifically, in the case where the difference between the average absorbance before culture (day 0) and the average absorbance after culture in the test compound-administered group is the same as the difference between the average absorbance before culture (day 0) and the average absorbance after culture in the control group, the rate of inhibition of cell growth is 0%.

Rate of inhibition of growth=(1−((Average absorbance of the test compound-administered group after culture)−(Average absorbance of the test compound-administered group on day 0))/((Average absorbance of the control group after culture)−(Average absorbance of the control group on day 0)))×100

In this test, the compound of the present invention exhibited an excellent cancer cell growth inhibitory effect in combined use with a chemotherapeutic, and, for example, compound No. IV-361 exhibited a synergistic cancer cell growth inhibitory effect, as shown in Table 51, when used in combination with the chemotherapeutic (5-FU or SN-38).

TABLE 51

| Test compound | Rate of inhibition of growth (%) |
|---|---|
| Compound No. IV-361(10 nM) Single-agent treatment | 11 |
| 5-FU(1000 nM) Single-agent treatment | 25 |
| SN-38(1 nM) Single-agent treatment | 12 |
| Compound No. IV-361(10 nM) + 5-FU(1000 nM) Combined treatment | 63 |
| Compound No. IV-361(10 nM) + SN-38(1 nM) Combined treatment | 66 |

Test Example 20

In Vivo Tumor Growth Inhibition Test for Human Large Intestine Cancer Cell Line by Combined Use with Chemotherapeutic A human large intestine cancer cell line (HCT-116) was cultured in a McCoy's 5A medium (manufactured by Thermo Fisher Scientific, Inc.) containing 10% fetal bovine serum (FBS) (manufactured by Thermo Fisher Scientific, Inc.) and 1% penicillin/streptomycin/amphotericin B (manufactured by Thermo Fisher Scientific, Inc.) and adjusted to 1.0×10$^8$ cells/mL with PBS or Hanks solution (HBSS(−)). The prepared cell suspension was subcutaneously injected at 0.1 mL/mouse to the right abdomens of female BALB nude mice (supplied by Charles River Laboratories Japan, Inc.). After rearing for a certain period, the long diameter (mm) and short diameter (mm) of tumor were measured with electronic calipers (manufactured by Mitsutoyo Corp., Cat. 500-712-10), and the tumor volume was calculated according to the following expression:

Tumor volume (mm$^3$)=(Long diameter)×(Short diameter)×(Short diameter)×0.5

Individuals whose tumor volume was within the range of 50 to 200 mm$^3$ were selected and grouped such that the tumor volume was almost equivalent. After the grouping, a test compound or only a solvent was administered in a repeated manner to the mice of each group as follows:

Single-agent administration group:
Control group: solvent (administered once a day)
IV-361-alone administration group: 25 mg/kg IV-361 (administered once a day)
5-Fluorouracil (5-FU)-alone administration group: 15 mg/kg 5-FU (administered twice a week)
Oxaliplatin-alone administration group: 3 mg/kg oxaliplatin (administered once a day)
Irinotecan-alone administration group: 12.5 mg/kg irinotecan (administered once a week)
Combined use group:
25 mg/kg compound No. IV-361+15 mg/kg 5-FU
25 mg/kg compound No. IV-361+3 mg/kg oxaliplatin
25 mg/kg compound No. IV-361+12.5 mg/kg irinotecan
Compound No. IV-361 was forcedly orally administered (10 mL/kg). 5-FU, oxaliplatin, and irinotecan were intraperitoneally administered (5 mL/kg).

After a lapse of a predetermined period, the body weights of the mice of each group and the long diameter and short diameter of tumor were measured, and the tumor volume of the test compound-administered group with respect to the tumor volume of the control group was calculated as the rate of suppression of tumor volume (%).

In this test, the compound of the present invention exhibited excellent tumor growth inhibitory activity in combined use with a chemotherapeutic, and, for example, compound No. IV-361 exhibited an excellent rate of suppression of tumor volume, as shown in Tables 52 to 54, when used in combination with the chemotherapeutic (5-FU, oxaliplatin or irinotecan).

TABLE 52

| Dose (mg/kg/day) | | Rate of suppression |
|---|---|---|
| IV-361 | 5-FU | of tumor volume |
| 25 | 0 | 46% |
| 0 | 15 | 21% |
| 25 | 15 | 63% |

TABLE 53

| Dose (mg/kg/day) | | Rate of suppression |
|---|---|---|
| IV-361 | Oxaliplatin | of tumor volume |
| 25 | 0 | 46% |
| 0 | 3 | 44% |
| 25 | 3 | 73% |

TABLE 54

| Dose (mg/kg/day) | | Rate of suppression |
|---|---|---|
| IV-361 | Irinotecan | of tumor volume |
| 25 | 0 | 20% |
| 0 | 12.5 | 92% |
| 25 | 12.5 | 103% |

From the results of Test Examples 1 to 20, it is concluded that the compound of the present invention has excellent CDK7 inhibitory activity and high selectivity and is useful as, for example, a therapeutic drug and/or a prophylactic drug for a cancer, an inflammatory disease, an allergic disease or a chronic respiratory disease. Also, the compound of the present invention exerts excellent therapeutic effects when used in combination with an additional existing therapeutic drug.

The invention claimed is:

1. A method for producing a compound represented by the formula (Ia):

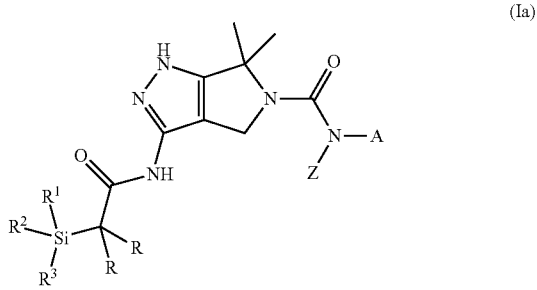

(Ia)

wherein two R moieties each independently are a $C_{1-3}$ alkyl group or are groups bonded to each other to form a $C_{2-5}$ alkylene group, A is an optionally substituted $C_{6-10}$ aryl group or an optionally substituted heteroaryl group, and Z is a hydrogen atom or an optionally substituted $C_{1-6}$ alkyl group, or a group represented by Z—N-A forms an optionally substituted bicyclic fused heterocyclic group through the bonding between A and Z, and $R^1$, $R^2$ and $R^3$ each independently are an optionally substituted linear or branched $C_{1-4}$ alkyl group, or a pharmacologically acceptable salt thereof, the method comprising a step of reacting a compound represented by the formula (1):

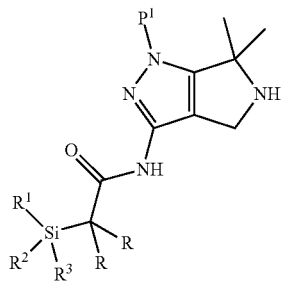

(1)

wherein R, $R^1$, $R^2$ and $R^3$ are defined as above and $P^1$ is a protecting group for an amino group, with an acylating agent to obtain a compound represented by the formula (2):

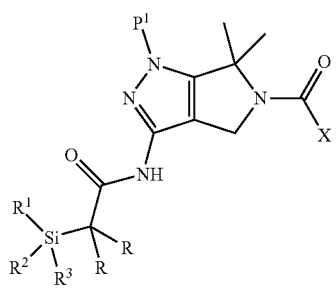

(2)

wherein R, $R^1$, $R^2$, $R^3$ and $P^1$ are defined as above and X is a leaving group;

a step of reacting the compound represented by the formula (2) with a compound represented by the formula (3a):

(3a)

wherein A and Z are defined as above;

to obtain a compound represented by the formula (4a):

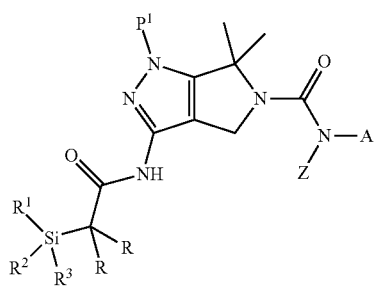

(4a)

wherein R, $R^1$, $R^2$, $R^3$, A, Z and $P^1$ are defined as above; and a step of removing the protecting group $P^1$ from the compound represented by the formula (4a) to obtain a compound represented by the formula (Ia).

2. The method according to claim 1, further comprising a step of reacting a compound represented by the formula (8):

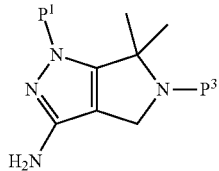
(8)

wherein P¹ and P³ are each independently a protecting group for an amino group,
with a compound represented by the formula (9):

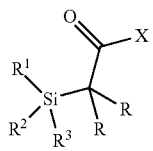
(9)

wherein $R^1$, $R^2$, $R^3$, and R are defined as above and X is a leaving group,
to obtain a compound represented by the formula (10):

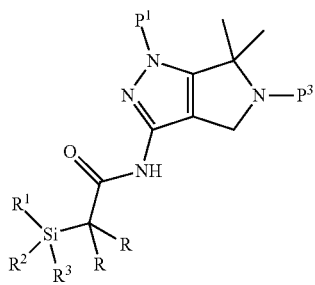
(10)

wherein R, $R^1$, $R^2$, $R^3$, $P^1$ and $P^3$ are defined as above; and
a step of removing the protecting group $P^3$ from the compound represented by the formula (10) to obtain the compound represented by the formula (1).

3. The method according to claim 2, further comprising
a step of reacting methyl 2-amino-2-methylpropanoate with acrylonitrile to obtain methyl 2-[(2-cyanoethyl)amino]-2-methylpropanoate;
a step of protecting methyl 2-[(2-cyanoethyl)amino]-2-methylpropanoate with a protecting group $P^3$ to obtain a compound represented by the formula (13):

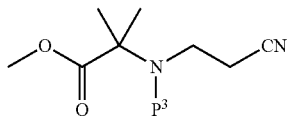
(13)

wherein $P^3$ is defined as above;
a step of cyclizing the compound represented by the formula (13) to obtain the compound represented by the formula (14):

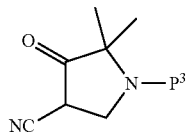
(14)

wherein $P^3$ is defined as above,
a step of reacting the compound represented by the formula (14) with hydrazine to obtain a compound represented by the formula (15):

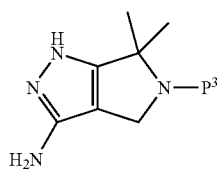
(15)

wherein $P^3$ is defined as above; and
a step of protecting the compound represented by the formula (15) with a protecting group $P^1$ to obtain a compound represented by the formula (8).

4. A method for producing a compound represented by the formula (I):

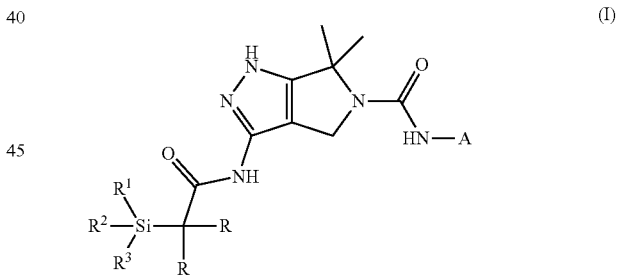
(I)

wherein
two R moieties each independently are a $C_{1-3}$ alkyl group or are groups bonded to each other to form a $C_{2-5}$ alkylene group,
A is an optionally substituted $C_{6-10}$ aryl group or an optionally substituted heteroaryl group, and
$R^1$, $R^2$ and $R^3$ each independently are an optionally substituted linear or branched $C_{1-4}$ alkyl group,
or a pharmacologically acceptable salt thereof, the method comprising
a step of reacting a compound represented by the formula (1):

(1)

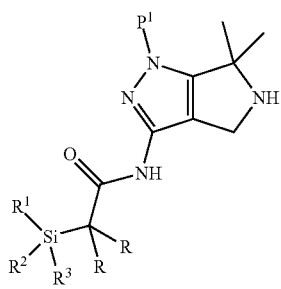

wherein R, R¹, R² and R³ are defined as above and P¹ is a protecting group for an amino group,
with a compound represented by the formula (6):

OCN-A    (6)

wherein A is defined as above,
to obtain a compound represented by the formula (4):

(8)

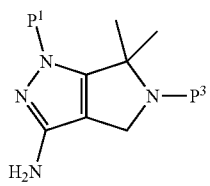

wherein R, R¹, R², R³, A and P¹ are defined as above; and
a step of removing the protecting group P¹ from the compound represented by the formula (4) to obtain a compound represented by the formula (I).

5. The method according to claim 4, further comprising a step of reacting a compound represented by the formula (8):

(4)

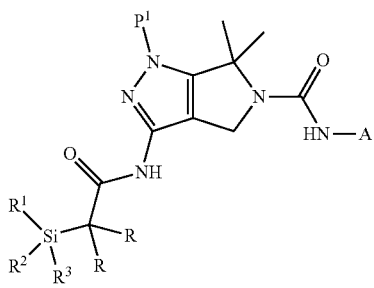

wherein P¹ and P³ are each independently a protecting group for an amino group,
with a compound represented by the formula (9):

(9)

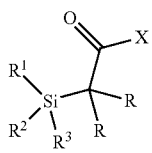

wherein R¹, R², R are defined as above and X is a leaving group,
to obtain a compound represented by the formula (10):

(10)

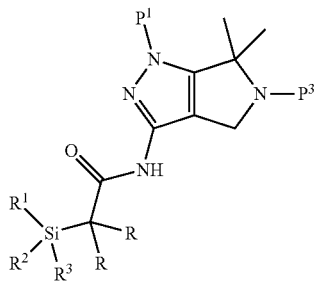

wherein R, R¹, R², R³, P¹ and P³ are defined as above; and
a step of removing the protecting group P³ from the compound represented by the formula (10) to obtain the compound represented by the formula (1).

6. The method according to claim 5, further comprising
a step of reacting methyl 2-amino-2-methylpropanoate with acrylonitrile to obtain methyl 2-[(2-cyanoethyl)amino]-2-methylpropanoate;
a step of protecting methyl 2-[(2-cyanoethyl)amino]-2-methylpropanoate with a protecting group P³ to obtain a compound represented by the formula (13):

(13)

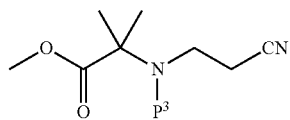

wherein P³ is defined as above,
a step of cyclizing the compound represented by the formula (13) to obtain a compound represented by the formula (14):

(14)

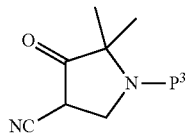

wherein P³ is defined as above;
a step of reacting the compound represented by the formula (14) with hydrazine to obtain a compound represented by the formula (15):

(15)

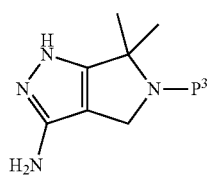

wherein P³ is defined as above; and
a step of protecting the compound represented by the formula (15) with a protecting group P¹ to obtain a compound represented by the formula (8).

7. A method for producing a compound represented by the formula (I):

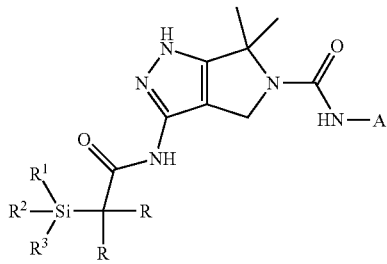

(I)

wherein
two R moieties each independently are a $C_{1-3}$ alkyl group or are groups bonded to each other to form a $C_{2-5}$ alkylene group,
A is an optionally substituted $C_{6-10}$ aryl group or an optionally substituted heteroaryl group, and
$R^1$, $R^2$ and $R^3$ each independently are an optionally substituted linear or branched $C_{1-4}$ alkyl group,
or a pharmacologically acceptable salt thereof, the method comprising
a step of reacting a compound represented by the formula (5):

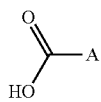

(5)

wherein A is defined as above,
with diphenylphosphorylazide and a base to obtain a compound represented by the formula (6):

OCN-A  (6)

wherein A is defined as above;
a step of reacting the compound represented by the formula (6) with a compound represented by the formula (1):

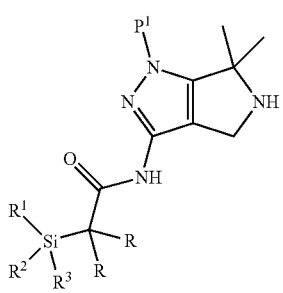

(1)

wherein R, $R^1$, $R^2$ and $R^3$ are defined as above, and $P^1$ is a protecting group for an amino group, to obtain a compound represented by the formula (4):

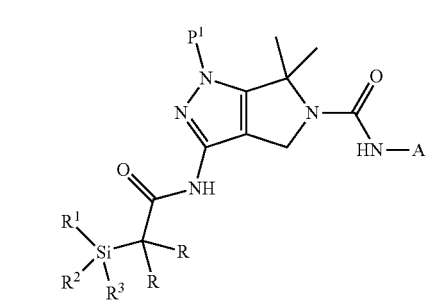

(4)

wherein R, $R^1$, $R^2$, $R^3$, A and $P^1$ are defined as above; and
a step of removing the protecting group $P^1$ from the compound represented by the formula (4) to obtain a compound represented by the formula (I).

8. The method according to claim 7, further comprising a step of reacting a compound represented by the formula (8):

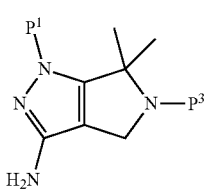

(8)

wherein $P^1$ and $P^3$ are each independently a protecting group for an amino group,
with a compound represented by the formula (9):

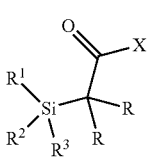

(9)

wherein R, $R^1$, $R^2$ and $R^3$ are defined as above and X is a leaving group,
to obtain a compound represented by the formula (10):

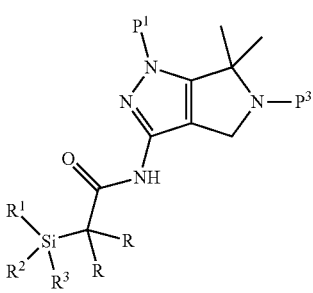

(10)

wherein R, $R^1$, $R^2$, $R^3$, $P^1$ and $P^3$ are defined as above; and
a step of removing the protecting group $P^3$ from the compound represented by the formula (10) to obtain the compound represented by the formula (1).

9. The method according to claim 8, further comprising
a step of reacting methyl 2-amino-2-methylpropanoate with acrylonitrile to obtain methyl 2-[(2-cyanoethyl)amino]-2-methylpropanoate;
a step of protecting methyl 2-[(2-cyanoethyl)amino]-2-methylpropanoate with a protecting group $P^3$ to obtain a compound represented by the formula (13):

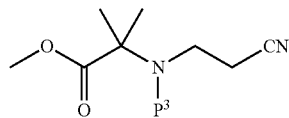
(13)

wherein $P^3$ is defined as above;
a step of cyclizing the compound represented by the formula (13) to obtain a compound represented by the formula (14):

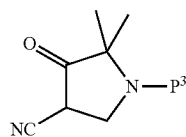
(14)

wherein $P^3$ is defined as above;
a step of reacting the compound represented by the formula (14) with hydrazine to obtain a compound represented by the formula (15):

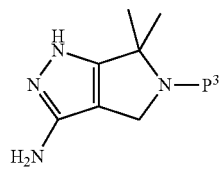
(15)

wherein $P^3$ is defined as above; and
a step of protecting the compound represented by the formula (15) with a protecting group $P^1$ to obtain a compound represented by the formula (8).

10. A method for producing a compound represented by the formula (I):

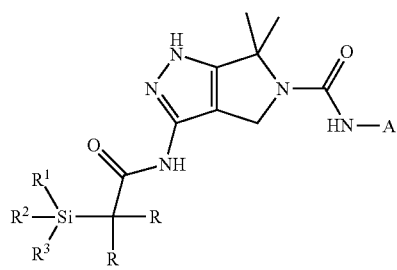
(I)

wherein
two R moieties each independently are a $C_{1-3}$ alkyl group or are groups bonded to each other to form a $C_{2-5}$ alkylene group, A is an optionally substituted $C_{6-10}$ aryl group or an optionally substituted heteroaryl group, and
$R^1$, $R^2$ and $R^3$ each independently are an optionally substituted linear or branched $C_{1-4}$ alkyl group,
or a pharmacologically acceptable salt thereof, the method comprising
a step of reacting a compound represented by the formula (7):

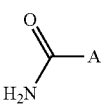
(7)

wherein A is defined as above,
with an oxidizing agent to obtain the compound represented by the formula (6):

OCN-A     (6)

wherein A is defined as above;
a step for reacting the compound represented by the formula (6) with a compound represented by the formula (1):

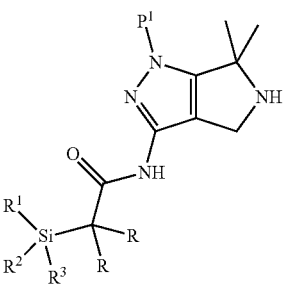
(1)

wherein R, $R^1$, $R^2$ and $R^3$ are defined as above, and $P^1$ is a protecting group for an amino group,
to obtain a compound represented by the formula (4):

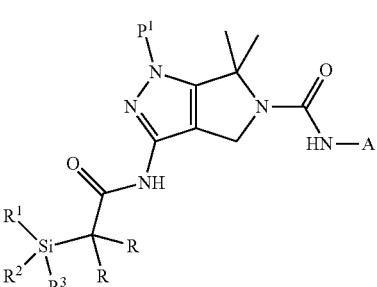
(4)

wherein R, $R^1$, $R^2$, $R^3$, A and $P^1$ are defined as above; and
a step of removing the protecting group $P^1$ from the compound represented by the formula (4) to obtain a compound represented by the formula (I).

11. The method according to claim 10, further comprising
a step of reacting a compound represented by the formula (8):

(8)

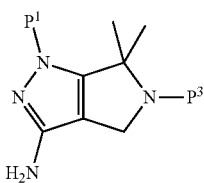

wherein P¹ and P³ are each independently a protecting group for an amino group,
with a compound represented by the formula (9):

(9)

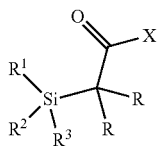

wherein R, R¹, R² and R³ are defined as above and X is a leaving group,
to obtain a compound represented by the formula (10):

(10)

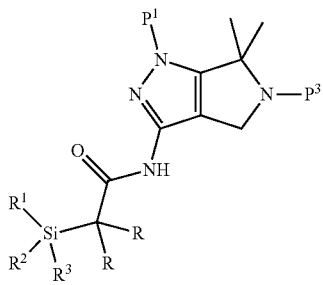

wherein R, R¹, R², R³, P¹ and P³ are defined as above; and
a step of removing the protecting group and P³ from the compound represented by the formula (10) to obtain the compound represented by the formula (1).

12. The method according to claim 11, further comprising
a step of reacting methyl 2-amino-2-methylpropanoate with acrylonitrile to obtain methyl 2-[(2-cyanoethyl)amino]-2-methylpropanoate;
a step of protecting methyl 2-[(2-cyanoethyl)amino]-2-methylpropanoate with a protecting group P³ to obtain a compound represented by the formula (13):

(13)

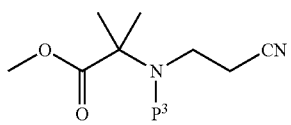

wherein P³ is defined as above;
a step of cyclizing the compound represented by the formula (13) to obtain a compound represented by the formula (14):

(14)

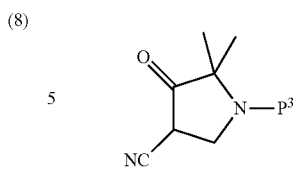

wherein P³ is defined as above;
a step of reacting the compound represented by the formula (14) with hydrazine to obtain a compound represented by the formula (15):

(15)

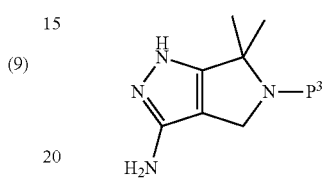

wherein P³ is defined as above; and
a step of protecting the compound represented by the formula (15) with a protecting group P¹ to obtain a compound represented by the formula (8).

13. A compound represented by the formula (4):

(4)

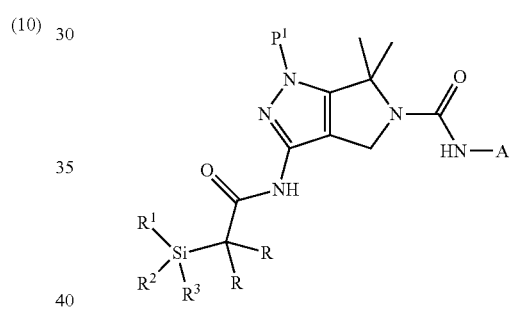

wherein
two R moieties each independently are a $C_{1-3}$ alkyl group or are groups bonded to each other to form a $C_{2-5}$ alkylene group;
A is an optionally substituted $C_{6-10}$ aryl group or an optionally substituted heteroaryl group;
R¹, R² and R³ each independently are an optionally substituted linear or branched $C_{1-4}$ alkyl group; and
P¹ is a protecting group for an amino group.

14. A compound represented by the formula (4a):

(4a)

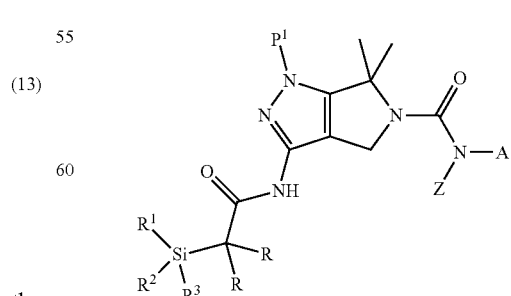

wherein
- two R moieties each independently are a $C_{1-3}$ alkyl group or are groups bonded to each other to form a $C_{2-5}$ alkylene group;
- A is an optionally substituted $C_{6-10}$ aryl group or an optionally substituted heteroaryl group, and Z is a hydrogen atom or an optionally substituted $C_{1-6}$ alkyl group, or a group represented by Z—N-A forms an optionally substituted bicyclic fused heterocyclic group through the bonding between A and Z;
- $R^1$, $R^2$ and $R^3$ each independently are an optionally substituted linear or branched $C_{1-4}$ alkyl group; and
- $P^1$ is a protecting group for an amino group.

* * * * *

UNITED STATES PATENT AND TRADEMARK OFFICE
CERTIFICATE OF CORRECTION

PATENT NO. : 10,894,798 B2
APPLICATION NO. : 16/373840
DATED : January 19, 2021
INVENTOR(S) : Iwase et al.

It is certified that error appears in the above-identified patent and that said Letters Patent is hereby corrected as shown below:

In the Claims

Column 293, Lines 21-31, Claim 4, replace:
--to obtain a compound represented by the formula (4):

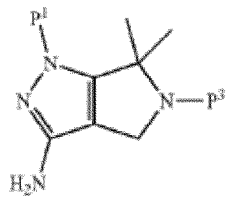

(8)

--

With the following:
"to obtain a compound represented by the formula (4):

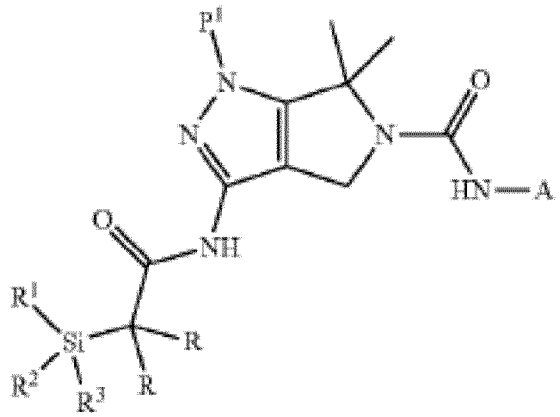

(4)

"

Column 293, Lines 38-53, Claim 5, replace:
--a step of reacting a compound represented by the formula (8):

Signed and Sealed this
Thirtieth Day of August, 2022

Katherine Kelly Vidal
*Director of the United States Patent and Trademark Office*

CERTIFICATE OF CORRECTION (continued)
U.S. Pat. No. 10,894,798 B2

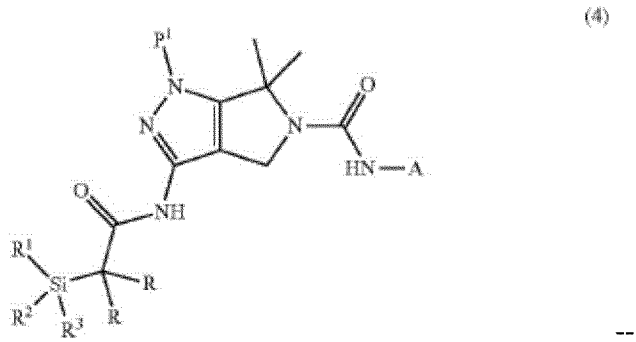

(4)

With the following:
"a step of reacting a compound represented by the formula (8):

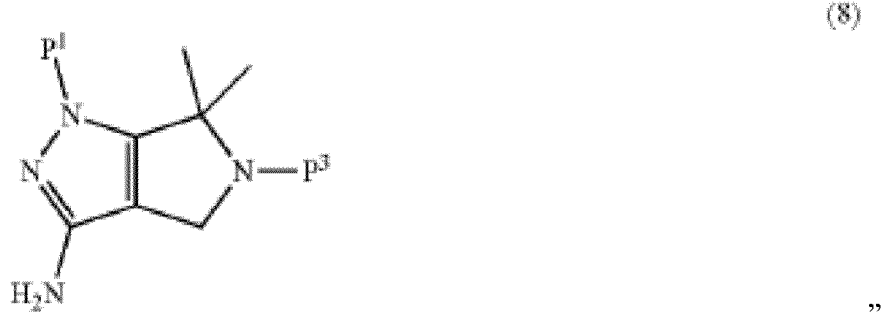

(8)

--

"